US011939363B2

(12) United States Patent
Limphong et al.

(10) Patent No.: US 11,939,363 B2
(45) Date of Patent: *Mar. 26, 2024

(54) TRANSLATABLE MOLECULES AND SYNTHESIS THEREOF

(71) Applicant: ARCTURUS THERAPEUTICS, INC., San Diego, CA (US)

(72) Inventors: Pattraranee Limphong, San Diego, CA (US); Kiyoshi Tachikawa, San Diego, CA (US); Padmanabh Chivukula, San Diego, CA (US); Daiki Matsuda, San Diego, CA (US); Arisa Cale, San Diego, CA (US)

(73) Assignee: ARCTURUS THERAPEUTICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/812,576

(22) Filed: Jul. 14, 2022

(65) Prior Publication Data

US 2023/0059111 A1 Feb. 23, 2023

Related U.S. Application Data

(63) Continuation of application No. 15/907,123, filed on Feb. 27, 2018, now Pat. No. 11,407,800.

(60) Provisional application No. 62/465,073, filed on Feb. 28, 2017.

(51) Int. Cl.

| | |
|---|---|
| ***C07K 14/505*** | (2006.01) |
| ***A61K 31/7115*** | (2006.01) |
| ***A61K 38/17*** | (2006.01) |
| ***A61K 38/18*** | (2006.01) |
| ***A61K 38/48*** | (2006.01) |
| ***C07K 14/575*** | (2006.01) |
| ***C07K 14/745*** | (2006.01) |
| ***C07K 14/81*** | (2006.01) |
| *A61K 38/00* | (2006.01) |
| *C12Q 1/68* | (2018.01) |

(52) U.S. Cl.

CPC ........ *C07K 14/505* (2013.01); *A61K 31/7115* (2013.01); *A61K 38/1709* (2013.01); *A61K 38/1816* (2013.01); *A61K 38/482* (2013.01); *A61K 38/4846* (2013.01); *C07K 14/575* (2013.01); *C07K 14/745* (2013.01); *C07K 14/81* (2013.01); *A61K 38/00* (2013.01)

(58) Field of Classification Search

None

See application file for complete search history.

(56) References Cited

U.S. PATENT DOCUMENTS

| | | | |
|---|---|---|---|
| 7,659,391 | B2 | 2/2010 | De et al. |
| 8,093,367 | B2 | 1/2012 | Kore et al. |
| 8,304,529 | B2 | 11/2012 | Kore et al. |
| 8,748,089 | B2 | 6/2014 | Kariko et al. |
| 9,149,506 | B2 | 10/2015 | Chakraborty et al. |
| 9,751,925 | B2 | 9/2017 | Hoge et al. |
| 10,072,057 | B2 | 9/2018 | Hoge et al. |
| 11,407,800 | B2 | 8/2022 | Limphong et al. |
| 2009/0226906 | A1 | 9/2009 | Xie et al. |
| 2013/0123481 | A1 | 5/2013 | De Fougerolles et al. |
| 2014/0147454 | A1 | 5/2014 | Chakraborty et al. |
| 2015/0064235 | A1 | 3/2015 | Bancel et al. |
| 2015/0104476 | A1 | 4/2015 | Von Der Mulbe et al. |
| 2015/0246139 | A1 | 9/2015 | Bancel et al. |
| 2016/0237134 | A1 | 8/2016 | Hoge et al. |
| 2017/0362627 | A1 | 12/2017 | Reynders, III et al. |
| 2018/0327471 | A1 | 11/2018 | Limphong et al. |
| 2019/0382774 | A1 | 12/2019 | Hoge et al. |

FOREIGN PATENT DOCUMENTS

| | | | |
|---|---|---|---|
| JP | 2015534817 | A | 12/2015 |
| JP | 2015535430 | A | 12/2015 |
| JP | 2016527908 | A | 9/2016 |
| WO | 2014071219 | A1 | 5/2014 |
| WO | 2015024667 | A1 | 2/2015 |
| WO | 2015051169 | A2 | 4/2015 |
| WO | 2015061491 | A1 | 4/2015 |
| WO | 2015124935 | A1 | 8/2015 |
| WO | 2016070166 | A2 | 5/2016 |
| WO | 2016077125 | A1 | 5/2016 |
| WO | 2018160592 | A1 | 9/2018 |

OTHER PUBLICATIONS

Li et al. (Feb. 24, 2016) "Effects of Chemically Modified Messenger RNA on Protein Expression", Bioconjugate Chemistry, 27(3):849-853.

International Search Report and Written Opinion received for PCT Application No. PCT/US2018/020018, dated Jul. 26, 2018, 18 pages.

Beckert et al. (2011) "Synthesis of RNA by In Vitro Transcription", Methods in Molecular Biology, 703:29-41.

Kozak, Marilyn. (Nov. 1990) "Downstream Secondary Structure Facilitates Recognition of Initiator Codons by Eukaryotic Ribosomes", Proceedings of the National Academy of Sciences, 87(21):8301-8305.

(Continued)

*Primary Examiner* — Sean McGarry

(74) *Attorney, Agent, or Firm* — Mintz, Levin, Cohn, Ferris, Glovsky and Popeo, P.C.

(57) ABSTRACT

A range of therapeutic mRNA molecules expressible to provide a target polypeptide or protein. The RNA molecules can contain one or more 5-methoxyuridines and 5-methylcytidines. Further provided are DNA templates, which can be transcribed to provide a target mRNA, and can have altered nucleotides, such as reduced deoxyadenosines. Also provided are processes for making the therapeutic mRNA molecules. The RNA molecules can be translated in vitro or in vivo to provide an active polypeptide or protein. The RNA molecules can be included in a composition used for preventing, treating, or ameliorating at least one symptom of a disease or condition in a subject in need thereof.

20 Claims, 21 Drawing Sheets

Specification includes a Sequence Listing.

(56) References Cited

OTHER PUBLICATIONS

Kozak, Marilyn. (Jul. 1988) "Leader Length and Secondary Structure Modulate mRNA Function Under Conditions of Stress.", Molecular and Cellular Biology, 8(7):2737-2744.

Kozak, Marilyn. (1991) "Structural Features in Eukaryotic mRNAs That Modulate The Initiation of Translation", Journal of Biological Chemistry, Oct. 25, 266(30): 19867-19870.

Kozak, Marilyn. ( Feb. 1989) "The Scanning Model for Translation: An Update", Journal of Cell Biology, 108 (2):229-241.

Wu et al. (Mar. 2020) "Synthesis of Low Immunogenicity RNA With High-temperature in Vitro Transcription", RNA, 26(3):345-360.

European Search Report issued in European Application No. 18761078.7, dated Nov. 26, 2020, 7 pages.

TRANSLATABLE MOLECULES AND SYNTHESIS THEREOF

CROSS-REFERENCES TO RELATED APPLICATIONS

This application is a continuation of U.S. patent application Ser. No. 15/907,123, filed Feb. 27, 2018, which claims the benefit of U.S. Provisional Application No. 62/465,073, filed Feb. 28, 2017; each of which are incorporated herein by reference in their entirety and for all purposes.

SEQUENCE LISTING

This application includes a Sequence Listing submitted electronically as an ASCII file created on Jul. 7, 2022, named 049386-511C01US_SL_ST26.xml, which is 463,872 bytes in size.

BACKGROUND OF THE INVENTION

The use of RNA molecules in therapeutics is a promising goal. Among other things, RNA molecules could be manipulated to affect or treat rare diseases that are not as readily approached by other means. It would be useful to utilize synthetic RNA to control or enhance the production and purity of a polypeptide or protein, especially one directly associated with a disease. However, realizing the potential of RNA therapeutics has long been difficult.

Drawbacks of using RNA molecules as medicinal agents include the general lack of control or ability to vary the structure to enhance therapeutic properties. There is a general lack of predictability for modifications or changes in chemical structures to modulate properties that are pertinent to drug success.

For example, increasing the level of a therapeutic moiety in vivo is a significant factor in drug success. Thus, compositions and methods to increase the translation efficiency of an RNA, and specifically increase the amount of a translated polypeptide or protein is a desirable result.

Further, structural modification that increases the efficiency of generating a translatable RNA, can improve the apparent and/or inherent activity of the RNA, thus contributing new therapeutic effects.

There is an urgent need for molecules, structures and compositions having translational activity to provide active polypeptides and proteins, both in vitro and in vivo. Such new molecules having functional cytoplasmic half-life for producing active peptides and proteins can yield new drug molecules and therapeutic modalities.

What is needed are translatable molecules, and methods of synthesis thereof, that can have increased specific activity, lifetime or other properties over native mRNA, to be used in methods and compositions for producing and delivering active polypeptides and proteins in medicines.

BRIEF SUMMARY

This invention relates to the fields of molecular biology, biopharmaceuticals and therapeutics generated with translatable molecules. More particularly, this invention relates to methods, structures and compositions for synthesis of molecules having translational activity for making active polypeptides or proteins, for use in vivo and as therapeutics.

This invention provides methods and compositions for a wide reaching platform to design and implement RNA agents for rare diseases, and other therapeutic modalities.

This disclosure includes methods and compositions for novel molecules having translational activity, which can be used to provide active polypeptides, proteins, or fragments thereof, in various settings.

In some aspects, this invention provides processes for making an RNA including steps for providing a DNA molecule that can be transcribed to provide the RNA. In the DNA, certain codons in an open reading frame of the DNA can be replaced with alternative codons, and codon in-frame position in a reading frame. The DNA molecule can be transcribed in the presence of nucleoside triphosphates, a 5' cap, and one or more chemically-modified nucleoside triphosphates to form a product mixture. An RNA can be isolated and purified from the mixture. The RNA may contain natural and chemically-modified nucleotides.

In certain aspects, this invention provides methods for synthesis of an RNA. Processes for making an RNA can include steps for providing a DNA molecule that can be transcribed to provide the RNA. In the DNA, certain deoxyadenosine nucleotides in an open reading frame of the DNA can be replaced with non-deoxyadenosine nucleotides. The DNA may further comprise a promoter for transcribing the non-coding strand. The DNA molecule can be transcribed in the presence of nucleoside triphosphates, a 5' cap, and one or more chemically-modified nucleoside triphosphates to form a product mixture. An RNA can be isolated and purified from the mixture. The RNA may contain natural and chemically-modified nucleotides.

The RNA product molecules made by a process of this invention can have functional cytoplasmic half-life for producing polypeptides and proteins. The peptides and proteins can be active for therapeutic modalities, as well as for use in vaccines and immunotherapies.

The RNA molecules made by a process of this invention can be translatable messenger molecules, which can have long half-life, particularly in the cytoplasm of a cell. The longer duration of the translatable messenger molecules of this invention can be significant for providing a translation product that is active for ameliorating, preventing or treating disease.

This disclosure provides a range of structures for translatable molecules having increased specific activity and/or lifetime over a native mRNA. The translatable molecules of this invention can be used in medicines, and for methods and compositions for producing and delivering active peptides and proteins.

This invention further provides processes for making translatable RNA molecules having enhanced properties for providing and delivering polypeptides and proteins.

Embodiments of this disclosure can provide a wide range of novel, translatable messenger RNA molecules. The translatable messenger molecules can contain various chemically modified nucleotides.

The translatable molecules of this invention can be used to provide polypeptides or proteins in vitro, ex vivo, or in vivo.

The translatable messenger molecules of this invention can be designed to provide high-efficiency expression of an expression product, polypeptide, protein, or fragment thereof. The expression can be in vitro, ex vivo, or in vivo.

In some embodiments, the messenger molecules of this invention have increased cytoplasmic half-life over a native, mature mRNA that provides the same expression product. The structures and compositions of this invention can provide increased functional half-life with respect to native, mature mRNAs.

In further aspects, a translatable messenger molecule of this invention can provide increased activity as a drug providing a polypeptide or protein product, as compared to a native, mature mRNA. In some embodiments, a translatable molecule can reduce the expected dose level that would be required for efficacious therapy.

In additional embodiments, this invention provides methods for ameliorating, preventing or treating a disease or condition in a subject comprising administering to the subject a composition containing a translatable molecule of this invention.

The disease or condition can be a rare disease, a chronic disease, a liver disease, or a cancer, among others.

In certain embodiments, this invention provides methods for producing a polypeptide or protein in vivo, by administering to a mammal a composition containing a translatable RNA molecule. The polypeptide or protein may be deficient in a disease or condition of a subject or mammal.

This invention further provides methods for producing a therapeutic polypeptide or protein in vitro, or in vivo, by transfecting a cell with a translatable molecule. The polypeptide or protein can be deficient in a disease or condition of a subject or mammal.

Embodiments of this invention include the following:

A RNA that is expressible to provide a target polypeptide or protein, wherein the occurrence of uridines in a coding sequence region of the RNA is reduced by at least 20% as compared to a wild type mRNA that is expressible to provide the target polypeptide or protein, and wherein the RNA contains one or more 5-methoxyuridines.

The RNA above, wherein 10-100% of the uridines in the RNA are 5-methoxyuridines. The RNA above, wherein the RNA contains one or more 5-methylcytidines. The RNA above, wherein 10-100% of the cytidines in the RNA are 5-methylcytidines.

The RNA above, wherein the occurrence of uridines in a coding sequence region of the RNA is reduced by at least 35% as compared to a wild type mRNA that is expressible to provide the target polypeptide or protein.

The RNA above, wherein the RNA is translatable for expression of a polypeptide or protein having at least 75% identity to the target polypeptide or protein. The RNA above, wherein the RNA is translatable for expression of a polypeptide or protein having at least 85% identity, or 90% identity, or 95% identity to the target polypeptide or protein.

The RNA above, wherein the RNA comprises a 5' cap, a 5' untranslated region, a coding region, a 3' untranslated region, and a tail region. The RNA above, wherein the RNA comprises a translation enhancer in a 5' or 3' untranslated region.

The RNA above, wherein the RNA is translatable in vitro, ex vivo, or in vivo. The RNA above, wherein the RNA comprises from 50 to 15,000 nucleotides. The RNA above, wherein the target polypeptide or protein is a polypeptide, a protein, a protein fragment, an antibody, an antibody fragment, a vaccine immunogen, or a vaccine toxoid.

The RNA above, wherein the RNA has at least 2-fold increased translation efficiency in vivo as compared to a native mRNA that expresses the target polypeptide or protein. The RNA above, wherein the RNA has at least 5-fold reduced immunogenicity as compared to a native mRNA that expresses the target polypeptide or protein.

The RNA above, wherein the target polypeptide or protein is an expression product, or a fragment thereof, of a gene selected from EPO, AAT, ADIPOQ, F9, TTR, and BIRC5.

Embodiments of this invention further contemplate a DNA encoding the RNA above.

In some aspects, this invention provides a composition comprising an RNA above and a pharmaceutically acceptable carrier. The carrier may comprise a transfection reagent, a nanoparticle, or a liposome.

This invention includes methods for preventing, treating, or ameliorating at least one symptom of a disease or condition in a subject in need thereof, the method comprising administering to the subject a composition above. The composition can be used in medical therapy, or in the treatment of the human or animal body.

In further embodiments, this invention includes a range of DNA templates that can be transcribable for expression of a target polypeptide or protein, the DNA template comprising a non-coding sequence template region, wherein deoxyadenosine nucleotides in the non-coding sequence template region are replaced with non-deoxyadenosine nucleotides, and wherein the occurrence of deoxyadenosines in the template region is reduced by at least 20% as compared to a wild type gene that is transcribable for expression of the target polypeptide or protein.

A DNA template may be double stranded, and comprise a coding non-template strand complementary to a non-coding template strand. A DNA template may have the occurrence of deoxyadenosines in the template region reduced by at least 35% as compared to a wild type gene that is transcribable for expression of the target polypeptide or protein. A DNA template may be transcribable for expression of a polypeptide or protein having at least 75% identity to the target polypeptide or protein. A DNA template can be transcribable for expression of a polypeptide or protein having at least 85% identity, or 90% identity, or 95% identity to the target polypeptide or protein. A DNA template may have a target polypeptide or protein being an expression product, or a fragment thereof, of a gene selected from EPO, AAT, ADIPOQ, F9, TTR, and BIRC5. A DNA template may comprise a plasmid, a linear polynucleotide, a PCR product, a synthetic oligonucleotide, a cloned oligonucleotide, or a reverse transcribed RNA.

This invention further contemplates processes for making an RNA, the RNA having an RNA coding region for expressing a target polypeptide or protein, the process comprising:

- providing a DNA molecule comprising a non-coding template region encoding the RNA, wherein deoxyadenosine nucleotides in the portion of the non-coding template region that encodes the RNA coding region are replaced with non-deoxyadenosine nucleotides, and wherein the DNA further comprises a promoter for transcribing the template region;
- transcribing the template region in the presence of nucleoside triphosphates and one or more chemically-modified nucleoside triphosphates to form a product mixture;
- isolating the RNA, wherein the RNA comprises natural and chemically-modified nucleotides.

In a process above, the chemically-modified nucleosides can be 5-methoxyuridines. The chemically-modified nucleosides may be 5-methoxyuridines and 5-methylcytidines.

In some embodiments, the chemically-modified nucleosides can be selected from 5-hydroxyuridine, 5-methyluridine, 5,6-dihydro-5-methyluridine, 2'-O-methyluridine, 2'-O-methyl-5-methyluridine, 2'-fluoro-2'-deoxyuridine, 2'-amino-2'-deoxyuridine, 2'-azido-2'-deoxyuridine, 4-thiouridine, 5-hydroxymethyluridine, 5-carboxyuridine, 5-carboxymethylesteruridine, 5-formyluridine, 5-methoxyuridine, 5-propynyluridine, 5-bromouridine, 5-iodouridine, 5-fluorouridine, pseudouridine, 2'-O-methyl-pseudouridine, $N^1$-hydroxypseudouridine, $N^1$-methylpseudouridine, 2'-O-methyl-$N^1$-methylpseudouridine, $N^1$-ethylpseudouridine, $N^1$-hydroxymethylpseudouridine, and Arauridine.

In a process above, the chemically-modified nucleosides can replace 10-100% of the same, but non-chemically-modified nucleotides in the RNA, or 50-100% of the same, but non-chemically-modified nucleotides in the RNA, or 10-80% of the same, but non-chemically-modified nucleotides in the RNA, or 50-80% of the same, but non-chemically-modified nucleotides in the RNA.

In a process above, the occurrence of deoxyadenosines in the template region can be reduced by at least 20% as compared to a wild type gene that is transcribable for expression of the target polypeptide or protein. In a process above, the occurrence of deoxyadenosines in the template region is reduced by at least 35% as compared to a wild type gene that is transcribable for expression of the target polypeptide or protein.

In certain embodiments, the step of transcribing the DNA can be performed along with a 5' cap. The RNA may comprise a 5' cap, a 5' untranslated region, a coding region, a 3' untranslated region, and a tail region. The step of transcribing may be performed with an RNA polymerase, such as SP6, T7, or T3 phage RNA polymerase. The promoter can be double stranded.

In a process above, the level of double-stranded RNA impurities in the product mixture can be reduced at least 2-fold as compared to the same process without replacing the deoxyadenosine nucleotides. The level of double-stranded RNA impurities in the product mixture may be less than 5%, or less than 1%, or less than 0.1% of the total RNA.

Embodiments of this invention also contemplate a synthetic RNA comprising a product of a process above.

This invention includes compositions comprising an RNA above and a pharmaceutically acceptable carrier. The carrier can comprise a transfection reagent, a nanoparticle, or a liposome.

In some aspects, this invention includes methods for preventing, treating, or ameliorating at least one symptom of a disease or condition in a subject in need thereof, by administering to the subject a composition of an RNA above.

A composition may be used for medical therapy, or in the treatment of the human or animal body. A composition may be used for preparing or manufacturing a medicament for preventing, ameliorating, delaying onset or treating a disease or condition in a subject in need.

BRIEF DESCRIPTION OF THE DRAWINGS

As shown in FIG. 1, certain deoxyadenosine nucleotides may be replaced in the template by non-deoxyadenosine nucleotides, while codon assignment to a target product may be preserved (S101). The double stranded DNA further includes a double stranded promoter for transcribing the template strand, such as a T7 promoter. The DNA can be transcribed in the presence of nucleoside triphosphates, including optionally a 5' cap (shown), and along with one or more chemically modified nucleoside triphosphates to form a product mixture (S103). The ARC-RNA product can be isolated and purified from the product mixture (S105). The ARC-RNA product is a translatable molecule that contains natural and chemically modified nucleotides, with enhanced translational efficiency and properties.

As shown in FIG. 2, certain deoxyadenosine nucleotides may be replaced by non-deoxyadenosine nucleotides in the template, while codon assignment to a target product may be preserved (S101). The DNA further includes a promoter. The DNA can be transcribed in the presence of nucleoside triphosphates, including optionally a 5' cap, and along with one or more chemically modified nucleoside triphosphates to form a product mixture (S103). The ARC-RNA product can be isolated and purified from the product mixture (S105).

FIG. 4 shows surprisingly high translational efficiency of the ARC-RNA (5MeOU) compared to the wild type hEPO mRNA (UTP).

FIG. 5 shows surprisingly high translational efficiency of the ARC-RNA (5MeOU) compared to the wild type hF9 mRNA (UTP).

FIG. 6 shows the results of a dot blot for detecting double strand RNA impurity in the synthesis mixture (nitro cellulose membrane, J2 antibody to detect dsRNA). The ARC-RNA (5MeOU) synthesis product, which was translatable for hF9, showed surprisingly reduced dot blot intensity as compared to a wild type mRNA synthesis product, without 5MeOU, and with similarly reduced T. Thus, the ARC-RNA (5MeOU) synthesis process, with template reduced T composition, surprisingly reduced double strand RNA impurity levels in the synthesis mixture. The process for synthesizing the ARC-RNA (5MeOU) molecules of this invention provided a surprisingly reduced level of double strand RNA impurity.

FIG. 7 shows the results of a dot blot for detecting double strand RNA impurity in the synthesis mixture (nitro cellulose membrane, J2 antibody to detect dsRNA). The ARC-RNA (5MeOU) synthesis product, which was translatable for hAAT, showed surprisingly reduced dot blot intensity as compared to a wild type mRNA synthesis product, without 5MeOU, and with similarly reduced T. Thus, the ARC-RNA (5MeOU) synthesis process, with template reduced T composition, surprisingly reduced double strand RNA impurity levels in the synthesis mixture. The process for synthesizing the ARC-RNA (5MeOU) molecules of this invention provided a surprisingly reduced level of double strand RNA impurity.

FIG. 8 shows surprisingly high translational efficiency of the ARC-RNA (5MeOU) compared to the wild type human adiponectin mRNA (UTP). The translational efficiency of the ARC-RNA (5MeOU) was also surprisingly higher as compared to human adiponectin mRNA (N1MPU), a similar RNA made with $N^1$-methylpseudouridine (100%).

FIG. 9 shows the results of a dot blot for detecting double strand RNA impurity in the synthesis mixture (nitro cellulose membrane, J2 antibody to detect dsRNA). The ARC-RNA (5MeOU) synthesis product, which was translatable for human adiponectin, showed surprisingly reduced dot blot intensity as compared to a wild type mRNA synthesis product, without 5MeOU, and with similarly reduced T. Thus, the ARC-RNA (5MeOU) synthesis process, with template reduced T composition, surprisingly reduced double strand RNA impurity levels in the synthesis mixture. The process for synthesizing the ARC-RNA (5MeOU) molecules of this invention provided a surprisingly reduced level of double strand RNA impurity.

FIG. 10 shows surprisingly high translational efficiency of the ARC-RNA (5MeOU) compared to the wild type cynomolgus monkey cmEPO mRNA (UTP). The translational efficiency of the ARC-RNA (5MeOU) was also surprisingly higher as compared to cmEPO mRNA (N1MPU), a similar RNA made with $N^1$-methylpseudouridine (100%).

FIG. 11 shows the results of a dot blot for detecting double strand RNA impurity in the synthesis mixture (nitro cellulose membrane, J2 antibody to detect dsRNA). The ARC-RNA (5MeOU) synthesis product, which was translatable for mouse EPO, showed surprisingly reduced dot blot intensity as compared to a wild type mRNA synthesis product, without 5MeOU, and with similarly reduced T. Under the same conditions and synthesis, the ARC-RNA (5MC/5MeOU) synthesis product, which was translatable for mouse EPO, also showed surprisingly further reduced dot blot intensity as compared to a wild type mRNA synthesis product, without 5MC/5MeOU. Thus, the ARC-RNA (5MC/5MeOU) synthesis process, with template reduced T composition, surprisingly reduced double strand RNA impurity levels in the synthesis mixture. As shown in FIG. 11, similar advantageously reduced double strand RNA impurity levels were found in synthesis mixtures for monkey mAdipo mRNA and mfEPO mRNA.

FIG. 12 shows the results of a cytokine assay for IFN-a as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of IFN-a.

FIG. 13 shows the results of a cytokine assay for RANTES as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of RANTES.

FIG. 14 shows the results of a cytokine assay for IL-6 as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of IL-6.

FIG. 15 shows the results of a cytokine assay for MIP-1a as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of MIP-1a.

FIG. 16 shows the results for hEPO protein expression after hEPO ARC-mRNA was injected into mice at 0.3 mg/kg dose. hEPO in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

FIG. 17 shows the results for cmEPO protein expression after cmEPO ARC-mRNA was injected into mice at 0.3 mg/kg dose. cmEPO in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased greater than 3-fold.

FIG. 18 shows the results for hF9 protein expression after hF9 ARC-mRNA was injected into mice at 0.3 mg/kg dose. hF9 in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

FIG. 19 shows the results for hAdipo protein expression after hAdipo ARC-mRNA was injected into mice at 0.3 mg/kg dose. hAdipo in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

FIG. 20 shows the results for hAAT protein expression after hAAT ARC-mRNA was injected into mice at 0.3 mg/kg dose. hAAT in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased upto about 4-fold.

FIG. 21 shows the results of a cytokine assay as generated in mouse using an hEPO ARC-RNA (5MeOU) of this invention, detected in serum 6 hrs post injection. The ARC-RNAs synthesized with 5MeOU and a reduced T composition template showed markedly reduced immunogenicity as compared to a synthetic mRNA with the same sequence and containing only natural nucleotides. The hEPO ARC-RNA (5MeOU) did not stimulate cytokine responses in vivo as compared to the UTP control.

DESCRIPTION OF THE INVENTION

Figure 1:
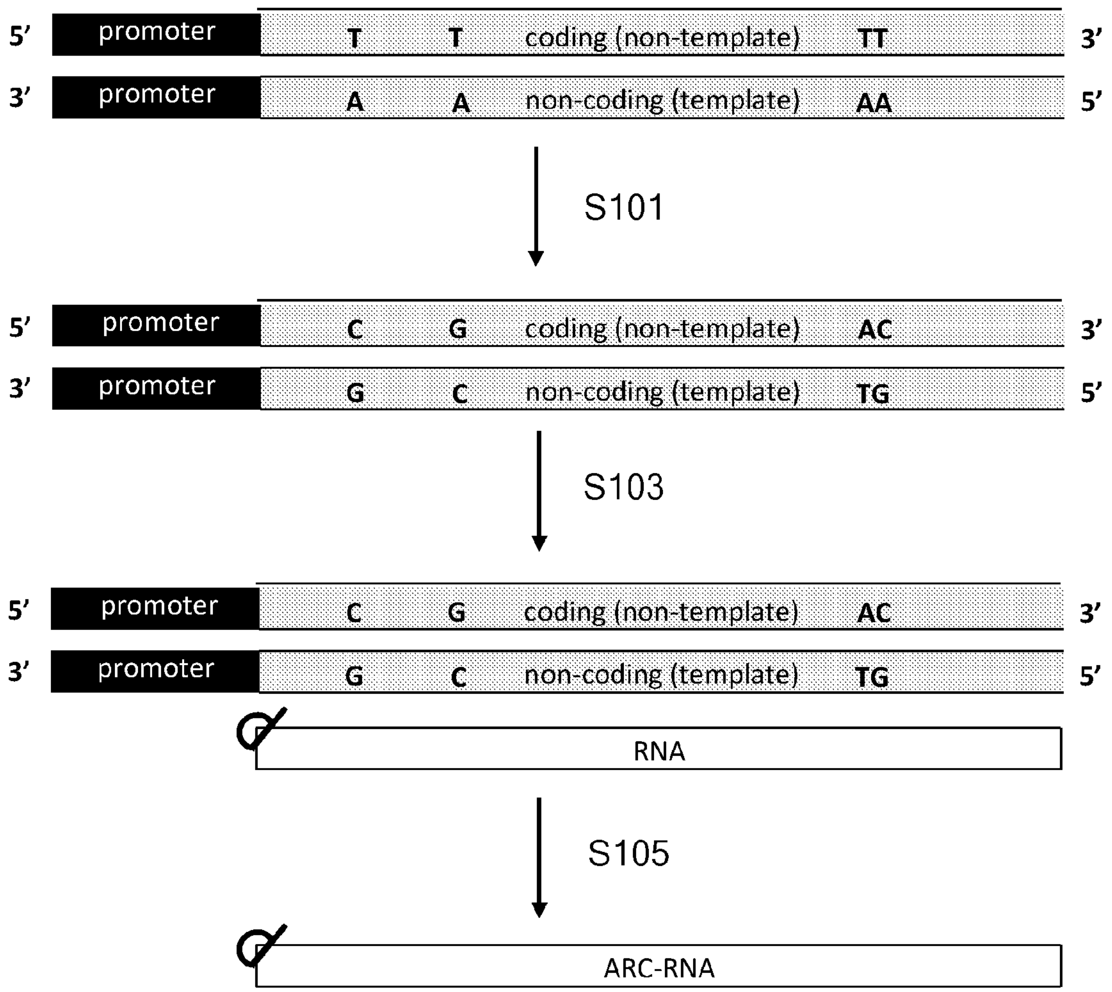
FIG. 1 shows a process for production of a translatable ARC-RNA molecule of this invention. A double stranded DNA molecule is provided having a non-coding template strand of nucleotides that can be transcribed to provide a targeted product RNA. The double stranded DNA contains an open reading frame in the template strand, which template is an alternative variation from a wild type or native version.

This invention provides a range of novel agents and compositions to be used for therapeutic applications. The molecules and compositions of this invention can be used for ameliorating, preventing or treating a disease, including, for example, rare diseases, and chronic diseases, among others.

In some embodiments, this invention encompasses synthetic, purified, and/or isolated translatable polynucleotide molecules for expressing a human polypeptide, protein, or fragment thereof, wherein the polynucleotide molecules comprise natural and chemically-modified nucleotides and encode the polypeptide, protein, or fragment.

Embodiments of this invention can provide nucleic acids that, when introduced into cells, can have improved properties such as increased expression levels, reduced immune response, and increased lifetime as compared to wild type nucleic acids.

In some embodiments, a translatable molecule of this invention can provide a modified mRNA. A modified mRNA can encode one or more biologically active peptides, polypeptides, or proteins. A modified mRNA can comprise one or more modifications as compared to wild type mRNA. Modifications of an mRNA may be located in any region of the molecule, including a coding region, an untranslated region, or a cap or tail region.

As used herein, the term "translatable" may be used interchangeably with the term "expressible." These terms can refer to the ability of polynucleotide, or a portion thereof, to provide a polypeptide, by transcription and/or translation events in a process using biological molecules, or in a cell, or in a natural biological setting. In some settings, translation is a process that can occur when a ribosome creates a polypeptide in a cell. In translation, a messenger RNA (mRNA) can be decoded by a ribosome to produce a specific amino acid chain, or polypeptide. A translatable oligomer or polynucleotide can provide a coding sequence region (usually, CDS), or portion thereof, that can be processed to provide a polypeptide, protein, or fragment thereof.

A translatable oligomer or polynucleotide of this invention can provide a coding sequence region, and can comprise various untranslated sequences, such as a 5' cap, a 5' untranslated region (5' UTR), a 3' untranslated region (3' UTR), and a tail region.

In some embodiments, a translatable molecule may include a 5' cap, a 5' UTR, a translation initiation sequence such as a Kozak sequence, a CDS, a 3' UTR, and a tail region.

In certain embodiments, a translatable molecule may include a 5' cap (m7GpppGm), a 5' UTR of tobacco etch virus (TEV), a Kozak sequence, a human CDS, a 3' UTR of xenopus beta-globin (XbG), and a tail region.

In additional embodiments, a human CDS may comprise a codon-modified sequence.

In certain embodiments, the level of G or C nucleotides of a region of a modified mRNA may be increased as compared to the level in the same region of the wild type mRNA, while codon assignment of the modified mRNA and the encoded amino acid sequence may be preserved. The increased level of G or C may be in any region of the molecule, including a coding region.

The level of GC content of a modified mRNA may be increased by at least 1%, or by at least 2%, or by at least 3%, or by at least 4%, or by at least 5%, or by at least 6%, or by at least 7%, or by at least 8%, or by at least 9%, or by at least 10%, or by at least 11%, or by at least 12%, or by at least 13%, or by at least 14%, or by at least 15%, or by at least 16%, or by at least 17%, or by at least 18%, as compared to the wild type mRNA.

The level of GC content of a modified mRNA may be increased by 1-3%, or by 4-6%, or by 7-9%, or by 10-12%, or by 13-15%, or by 16-20%, as compared to the wild type mRNA.

In further embodiments, the level of U nucleotides of a region of a modified mRNA may be decreased as compared to the level in the same region of the wild type mRNA, while codon assignment of the modified mRNA and the encoded amino acid sequence may be preserved. The decreased level of U may be in any region of the molecule, including a coding region.

The level of U content of a modified mRNA may be decreased by at least 1%, or by at least 2%, or by at least 3%, or by at least 4%, or by at least 5%, or by at least 6%, or by at least 7%, or by at least 8%, or by at least 9%, or by at least 10%, or by at least 12%, as compared to the wild type mRNA.

The level of U content of a modified mRNA may be decreased by 1%, or by 2%, or by 3%, or by 4%, or by 5%, or by 6%, or by 7%, or by 8%, or by 9%, or by 10%, as compared to the wild type mRNA.

In some embodiments, a translatable molecule of this invention may comprise a coding sequence that is at least 80%, 85%, 90%, 91%, 92%, 93%, 94%, 95%, 96%, 97%, 98%, 99% or more identical to a portion of a reference mRNA sequence, such as a human wild type mRNA sequence.

In some embodiments, a translatable molecule of this invention may comprise a coding sequence that has one, or two, or three, or four, or five, or six, or seven, or eight, or nine, or ten, or fifteen, or twenty or more synonymous or non-synonymous codon replacements as compared to a reference mRNA sequence, such as a human wild type mRNA sequence.

In some embodiments, a non-coding template sequence that is transcribable to provide a translatable molecule of this invention, when transcribed may provide a translatable molecule that is at least 80%, or 85%, or 90%, or 91%, or 92%, or 93%, or 94%, or 95%, or 96%, or 97%, or 98%, or 99% identical to a portion of a reference mRNA sequence, such as a human wild type mRNA sequence.

In some embodiments, a non-coding template sequence that is transcribable to provide a translatable molecule of this invention, when transcribed may provide a translatable molecule that has one, or two, or three, or four, or five, or six, or seven, or eight, or nine, or ten, or fifteen, or twenty or more synonymous or non-synonymous codon replacements as compared to a reference mRNA sequence, such as a human wild type mRNA sequence.

In some embodiments, a translatable molecule of this invention may be used to express a polypeptide that is at least 80%, 85%, 90%, 91%, 92%, 93%, 94%, 95%, 96%, 97%, 98%, 99% or more identical to a portion of a reference polypeptide or protein sequence, such as a human wild type protein sequence.

In some embodiments, a translatable molecule of this invention may be used to express a polypeptide that has one, or two, or three, or four, or five, or six, or seven, or eight, or nine, or ten, or fifteen, or twenty or more variant amino acid residues as compared to a reference polypeptide or protein sequence, such as a human wild type protein sequence.

In some embodiments, a translatable molecule of the invention may encode a fusion protein comprising a full length, or fragment or portion of a native human protein fused to another sequence, for example by N or C terminal fusion. In some embodiments, the N or C terminal sequence can be a signal sequence or a cellular targeting sequence.

A translatable molecule may comprise one or more LNA monomers.

The translatable molecules of this invention can be used in methods for ameliorating, preventing or treating a disease or condition associated with a polypeptide or protein. The translation efficiency of a translatable molecule of this invention can be increased as compared to a native mRNA.

A translatable molecule of this invention, which has one or more chemically modified nucleotides, can have reduced immunogenicity as compared to a native mRNA, or a synthetic mRNA with the same sequence and containing only natural nucleotides.

In some embodiments, a translatable molecule of this invention can have reduced immunogenicity as compared to a native mRNA. A translatable molecule can be less immunogenic than a synthetic RNA molecule with the same sequence and containing only natural nucleotides. Some methods for measuring immunogenicity include secretion of cytokines, for example, IL-12, IFN-a, TNF-a, RANTES, MIP-1a or b, IL-6, IFN-b, IFN-g or IL-8, and measuring expression of DC activation markers, for example, CD83, HLA-DR, CD80 and CD86.

In certain embodiments, the immunogenicity of a translatable molecule can be reduced by 2-fold, or 3-fold, or 5-fold, or 10-fold, or 20-fold, or more, as compared to a native mRNA, or as compared to a synthetic RNA molecule with the same sequence and containing only natural nucleotides.

A translatable molecule of this invention, which has one or more chemically modified nucleotides, can have increased translation efficiency as compared to a native mRNA, or a synthetic mRNA with the same sequence and containing only natural nucleotides.

In certain embodiments, the translation efficiency of a translatable molecule can be increased by 30%, or 50%, or 70%, or 100%, or 150%, or 200%, or more, as compared to a native mRNA, or as compared to a synthetic RNA molecule with the same sequence and containing only natural nucleotides. The translation efficiency may be performed in vitro, ex vivo, or in vivo.

Embodiments of this invention further encompass processes for making an RNA molecule for expressing a polypeptide or protein, wherein the RNA molecule comprises natural and chemically-modified nucleotides, and encodes the polypeptide or protein, or a fragment thereof. The processes can include transcribing a DNA template in the presence of chemically-modified nucleoside triphosphates to form a product mixture, and purifying the product mixture to isolate the RNA product. These processes may advantageously reduce the level of double-stranded RNA impurities in the product.

In a process of this invention, a translatable molecule of this invention can be synthesized with UTP replaced by 5-methoxy-UTP. The level of replacement can be 30% of UTP replaced by 5-methoxy-UTP, or 40% of UTP replaced by 5-methoxy-UTP, or 50% of UTP replaced by 5-methoxy-UTP, or 60% of UTP replaced by 5-methoxy-UTP, or 70% of UTP replaced by 5-methoxy-UTP, or 80% of UTP replaced by 5-methoxy-UTP, or 90% of UTP replaced by 5-methoxy-UTP, or 100% of UTP replaced by 5-methoxy-UTP.

In a process of this invention, a translatable molecule of this invention can be synthesized with CTP replaced by 5-methyl-CTP. The level of replacement can be 30% of CTP replaced by 5-methyl-CTP, or 40% of CTP replaced by 5-methyl-CTP, or 50% of CTP replaced by 5-methyl-CTP, or 60% of CTP replaced by 5-methyl-CTP, or 70% of CTP replaced by 5-methyl-CTP, or 80% of CTP replaced by 5-methyl-CTP, or 90% of CTP replaced by 5-methyl-CTP, or or 100% of CTP replaced by 5-methyl-CTP.

The molecules of this invention can be translatable messenger RNA molecules. In some embodiments, the RNA agents can have long half-life, particularly in the cytoplasm. The long duration messenger molecules can be used for ameliorating, preventing, or treating disease associated with a polypeptide or protein level in a subject.

In some aspects, this invention provides processes for production of a translatable product RNA molecule. A double stranded DNA molecule can be provided having a non-coding template strand of nucleotides that can be transcribed to provide the product RNA. The double stranded DNA may contain an open reading frame in the template strand, which template is an alternative variation from a wild type or native version. In the template, certain deoxyadenosine nucleotides may be replaced by non-deoxyadenosine nucleotides, while codon assignment to a target RNA product may be preserved. The double stranded DNA may further include a double stranded promoter for transcribing the template strand, such as a T7 promoter. The DNA can be transcribed in the presence of nucleoside triphosphates, including optionally a 5' cap, and along with one or more chemically modified nucleoside triphosphates to form a product mixture. The product RNA product can be isolated and purified from the product mixture.

The product RNA can be a translatable molecule that contains natural and chemically modified nucleotides, and enhanced translational efficiency and resulting activity.

In further aspects, this invention provides processes for production of a translatable RNA molecule. A single stranded DNA molecule can be provided having a non-coding template strand of nucleotides that can be transcribed to provide the product RNA. The DNA may contain an open reading frame in the template strand, which template is an alternative variation from a wild type or native version. In the template, certain deoxyadenosine nucleotides may be replaced by non-deoxyadenosine nucleotides, while codon assignment to a target RNA product may be preserved. The DNA may further include a promoter. The DNA can be transcribed in the presence of nucleoside triphosphates, including optionally a 5' cap, and along with one or more chemically modified nucleoside triphosphates to form a product mixture. The product RNA can be isolated and purified from the product mixture.

The properties of the translatable compounds of this invention arise according to their molecular structure, and the structure of the molecule in its entirety, as a whole, can provide significant benefits based on those properties. Embodiments of this invention can provide translatable molecules having one or more properties that advantageously provide enhanced effectiveness in regulating protein expression or concentration, or modulating protein activity. The molecules and compositions of this invention can provide formulations for therapeutic agents for various diseases and conditions, which can provide clinical agents.

This invention provides a range of translatable molecules that are surprisingly translatable to provide active peptide or protein, in vitro and in vivo.

The translatable structures and compositions can have increased translational activity and cytoplasmic half-life. In these embodiments, the translatable structures and compositions can provide increased functional half-life in the cytoplasm of mammalian cells over native mRNA molecules. The inventive translatable molecules can have increased half-life of activity with respect to a corresponding native mRNA.

A wide range of novel translatable molecules are provided herein, each of which can incorporate specialized linker groups. The linker groups can be attached in a chain in the translatable molecule. Each linker group can also be attached to a nucleobase.

Processes for production of a translatable RNA molecule of this invention are illustrated in FIG. 1. A double stranded DNA molecule is provided having a non-coding template strand of nucleotides that can be transcribed to provide a targeted product RNA. The double stranded DNA contains an open reading frame in the template strand, which template is an alternative variation from a wild type or native version. As shown in FIG. 1, certain deoxyadenosine nucleotides may be replaced by non-deoxyadenosine nucleotides, while codon assignment to a target product may be preserved. The double stranded DNA further includes a double stranded promoter for transcribing the template strand, such as a T7 promoter. The DNA can be transcribed in the presence of nucleoside triphosphates, including optionally a 5' cap, and along with one or more chemically modified nucleoside triphosphates to form a product mixture. The RNA product can be isolated and purified from the product mixture. The RNA product is a translatable molecule that contains natural and chemically modified nucleotides, and enhanced translational efficiency and resulting activity.

Figure 2:
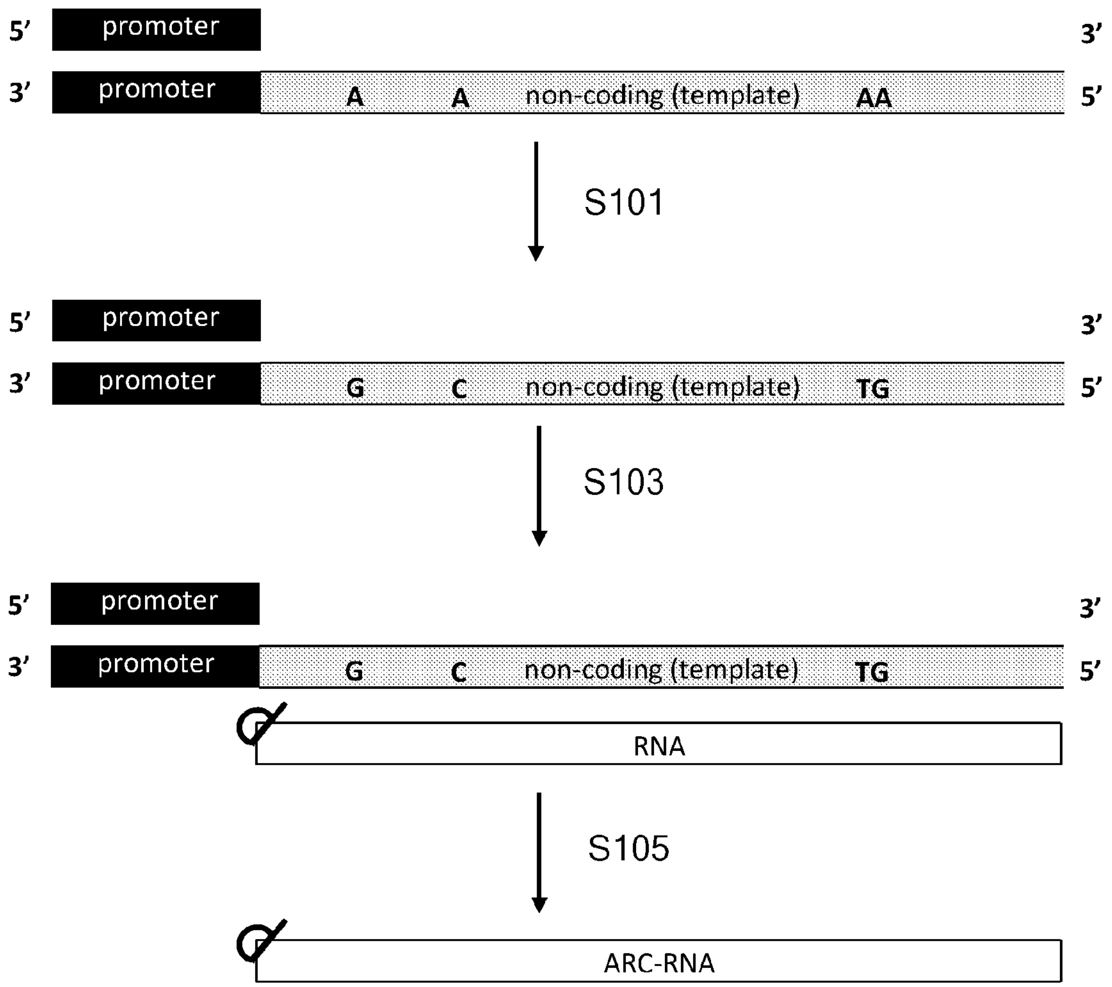
FIG. 2 shows a process for production of a translatable ARC-RNA molecule of this invention. A single stranded DNA molecule is provided having a non-coding template strand of nucleotides that can be transcribed to provide the product RNA. The DNA contains an open reading frame in the template strand, which template is an alternative variation from a wild type or native version.

Processes for production of a translatable RNA molecule of this invention are illustrated in FIG. 2. A single stranded DNA molecule is provided having a non-coding template strand of nucleotides that can be transcribed to provide the product RNA. The DNA contains an open reading frame in the template strand, which template is an alternative variation from a wild type or native version. As shown in FIG. 2, certain deoxyadenosine nucleotides may be replaced by non-deoxyadenosine nucleotides in the template, while codon assignment to a target product may be preserved. The DNA further includes a promoter. The DNA can be transcribed in the presence of nucleoside triphosphates, including optionally a 5' cap, and along with one or more chemically modified nucleoside triphosphates to form a product mixture. The RNA product can be isolated and purified from the product mixture.

Figure 3:
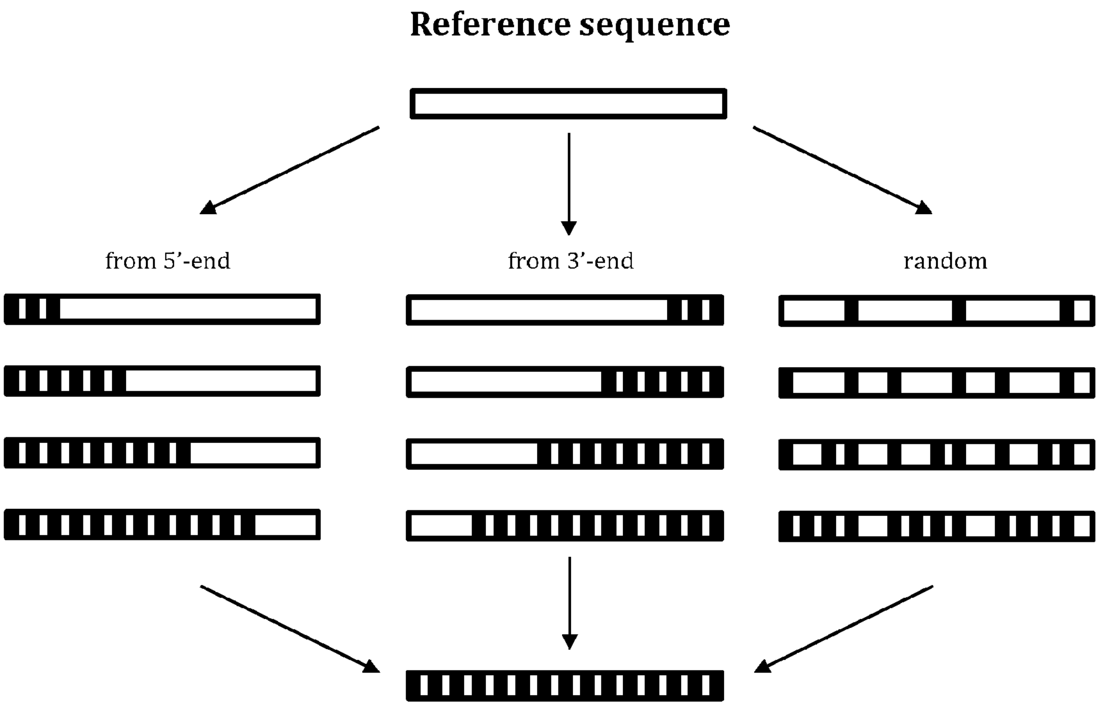
FIG. 3 shows embodiments of methods for providing templates for translatable molecules of this invention. Based on a reference sequence of an ORF of a template, certain deoxyadenosine nucleotides may be replaced in the template by non-deoxyadenosine nucleotides, while codon assignment to a target product may be preserved. In some methods, the deoxyadenosine nucleotides may be replaced beginning from the 5' end of the ORF. In further methods, the deoxyadenosine nucleotides may be replaced beginning from the 3' end of the ORF. In additional methods, the deoxyadenosine nucleotides may be replaced randomly throughout the ORF.

FIG. 3 shows embodiments of methods for providing templates for translatable molecules of this invention. Based on a reference sequence of an ORF of a template, certain deoxyadenosine nucleotides may be replaced in the template by non-deoxyadenosine nucleotides, while codon assignment to a target product may be preserved. In some methods, the deoxyadenosine nucleotides may be replaced beginning from the 5' end of the ORF. In further methods, the deoxyadenosine nucleotides may be replaced beginning from the 3' end of the ORF. In additional methods, the deoxyadenosine nucleotides may be replaced randomly throughout the ORF.

In some aspects, a linker group can be a monomer. Monomers can be attached to form a chain molecule. In a chain molecule of this invention, a linker group monomer can be attached at any point in the chain.

In certain aspects, linker group monomers can be attached in a chain molecule of this invention so that the linker group monomers reside near the ends of the chain, or at any position in the chain.

As used herein, a chain molecule can also be referred to as an oligomer.

In further aspects, the linker groups of a chain molecule can each be attached to a nucleobase. The presence of nucleobases in the chain molecule can provide a sequence of nucleobases in the chain molecule.

In certain embodiments, this invention provides translatable oligomer molecules having chain structures that incorporate novel combinations of the linker group monomers, along with certain natural nucleotides, or non-natural nucleotides, or modified nucleotides, or chemically-modified nucleotides.

The oligomer molecules of this invention can display a sequence of nucleobases, and can be designed to express a polypeptide or protein, in vitro, ex vivo, or in vivo. The expressed polypeptide or protein can have activity in various forms, including activity corresponding to protein expressed from natural mRNA, or activity corresponding to a negative or dominant negative protein.

In some aspects, this invention can provide active, translatable oligomer molecules having a base sequence that is complementary to at least a fragment of a native nucleic acid molecule of a cell.

In some embodiments, the cell can be a eukaryotic cell, a mammalian cell, or a human cell.

This invention provides structures, methods and compositions for translatable oligomeric agents that incorporate the linker group monomers. The oligomeric molecules of this invention can be used as active agents in formulations for therapeutics.

This invention provides a range of translatable molecules that are useful for providing therapeutic effects because of their longevity of activity in providing an expressed peptide or protein.

In certain embodiments, a translatable molecule can be structured as an oligomer composed of monomers. The oligomeric structures of this invention may contain one or more linker group monomers, along with certain nucleotides.

In certain embodiments, a translatable molecule may contain a sequence of nucleobases, and can be designed to express a peptide or protein of any isoform, in part by having sufficient homology with a native polynucleotide sequence.

In some embodiments, a translatable molecule can be from about 200 to about 12,000 monomers in length, or more. In certain embodiments, a translatable molecule can be from 200 to 12,000 monomers in length, or 200 to 10,000 monomers, or 200 to 8,000 monomers, or 200 to 6000 monomers, or 200 to 5000 monomers, or 200 to 4000 monomers, or 200 to 3600 monomers, or 200 to 3200 monomers, or 200 to 3000 monomers, or 200 to 2800 monomers, or 200 to 2600 monomers, or 200 to 2400 monomers, or 200 to 2200 monomers, or 600 to 3200 monomers, or 600 to 3000 monomers, or 600 to 2600 monomers.

In some embodiments, a translatable molecule can be from about 200 to about 12,000 bases in length, or more. In certain embodiments, a translatable molecule can be from 200 to 12,000 bases in length, or 200 to 10,000 bases, or 200 to 8,000 bases, or 200 to 6000 bases, or 200 to 5000 bases, or 200 to 4000 bases, or 200 to 3600 bases, or 200 to 3200 bases, or 200 to 3000 bases, or 200 to 2800 bases, or 200 to 2600 bases, or 200 to 2400 bases, or 200 to 2200 bases, or 600 to 3200 bases, or 600 to 3000 bases, or 600 to 2600 bases.

A translatable molecule of this invention may comprise a 5' cap, a 5' untranslated region of monomers, a coding region of monomers, a 3' untranslated region of monomers, and a tail region of monomers.

A translatable molecule of this invention may comprise regions of sequences or structures that are operable for translation in a cell, or which have the functionality of regions of an mRNA including, for example, a 5' cap, a 5' untranslated region, a coding region, a 3' untranslated region, and a polyA tail.

This invention further contemplates methods for delivering one or more vectors, or one or more translatable molecules to a cell.

In some embodiments, one or more translatable molecules can be delivered to a cell, in vitro, ex vivo, or in vivo. Viral and non-viral transfer methods as are known in the art can be used to introduce translatable molecules in mammalian cells. Translatable molecules can be delivered with a pharmaceutically acceptable vehicle, or for example, encapsulated in a liposome.

In some embodiments, translatable structures and compositions of this invention can reduce the number and frequency of transfections required for cell-fate manipulation in culture as compared to utilizing native compositions.

In additional aspects, this invention provides increased activity for mRNA-based drugs as compared to utilizing native compositions, and can reduce the dose levels required for efficacious therapy.

In further aspects, this invention provides increased activity for translatable or mRNA-based molecules, as compared to utilizing a native mRNA as active agent.

In some aspects, this invention can provide translatable molecules that may reduce the cellular innate immune response, as compared to that induced by a natural nucleic acid, peptide or protein.

This invention can provide synthetic translatable molecules that are refractory to deadenylation as compared to native molecules.

In certain embodiments, this invention can provide synthetic translatable molecules with increased specific activity and longer functional half-life as compared to native molecules. The synthetic translatable molecules of this invention can provide increased levels of ectopic protein expression. When using a translatable molecule as a vector, cellular-delivery can be at increased levels, and cytotoxic innate immune responses can be restrained so that higher levels of ectopic protein expression can be achieved. The translatable molecules of this invention can have increased specific activity and longer functional half-life than mRNAs.

In certain aspects, a translatable molecule may have a number of mutations from a native mRNA, or from a disease associated mRNA.

In further embodiments, this invention can provide translatable molecules having cleavable delivery and targeting moieties attached at a 3' end.

In general, the specific activity for a synthetic translatable molecule delivered by transfection can be viewed as the number of molecules of protein expressed per delivered transcript per unit time.

As used herein, translation efficiency refers to a measure of the production of a protein or polypeptide by translation of a messenger molecule in vitro or in vivo.

This invention provides a range of translatable molecules, which can contain one or more UNA monomers, and a number of nucleic acid monomers, wherein the translatable molecule can be translated to express a polypeptide or protein. UNA monomers are described in WO/2016/070166. In some embodiments, this invention includes a range of translatable molecules, which may contain one or more UNA monomers in a tail region, wherein the translatable molecule can be translated to express a polypeptide or protein. In some embodiments, a translatable molecule may comprise a 3' polyA tail containing one or more UNA monomers. In some embodiments, a 3' polyA tail may contain 2, 3, 4, 5, 10, or more UNA monomers.

In some embodiments, a translatable molecule can contain a modified 5' cap.

In further embodiments, a translatable molecule can contain a translation enhancing 5' untranslated region of monomers.

In additional embodiments, a translatable molecule can contain a translation enhancing 3' untranslated region of monomers.

A translatable molecule of this invention can exhibit increased translation efficiency in vivo as compared to a native mRNA that encodes the same translation product. For example, the translation efficiency can be increased by 10%, or 20%, or 30%, or 40%, or 50% or 100%, or more, as compared to a reference mRNA such as a native mRNA or human wild type mRNA.

In another aspect, a translatable molecule of this invention can exhibit at least 2-fold, 3-fold, 5-fold, or 10-fold increased translation efficiency in vivo as compared to a reference mRNA such as a native mRNA or human wild type mRNA.

In further aspects, a translatable molecule can provide increased levels of a polypeptide or protein in vivo as compared to a native mRNA that encodes the same polypeptide or protein. For example, the level of a polypeptide or protein can be increased by 10%, or 20%, or 30%, or 40%, or 50% or 100%, or more in vivo as compared to a reference mRNA such as a native mRNA or human wild type mRNA.

In a further aspect, a translatable molecule can produce at least 2-fold, 3-fold, 5-fold, or 10-fold increased levels of a polypeptide or protein in vivo as compared to a native mRNA or reference mRNA.

In additional embodiments, this invention provides methods for treating a disease or condition in a subject by administering to the subject a composition containing a translatable molecule.

Variant Templates in Processes for Translatable Molecules

A variant DNA template of this disclosure may exhibit advantages in processes for making a translatable molecule, and the efficiency of the translatable molecule. Variation of the template can be utilized to enhance incorporation of modified nucleotides or monomers in an RNA product of this invention. In certain aspects, variation of the template can be utilized to enhance the structural features of the translatable molecule. The enhanced structural features of the translatable molecule can provide unexpectedly advantageous properties, including translation efficiency to provide a polypeptide or protein product.

In some aspects of this invention, variation of the template may include reducing the occurrence or frequency of appearance of certain nucleotides in the template strand. Reducing the occurrence of a certain nucleotide can alter the structures and processes of this disclosure to provide forms, which achieve surprisingly improved properties of a translatable RNA product.

Aspects of this invention may require a variant DNA template in processes for making a translatable molecule. A DNA molecule can have a non-coding template strand of nucleotides that can be transcribed to provide a target RNA.

A target RNA can be any RNA, whether native or unknown, synthetic or derived from a natural source.

In some embodiments, a variant DNA template can be used for which an open reading frame of the template strand is transformed to an alternative form.

In certain embodiments, a DNA template can be used for which alternative nucleotides are used based on codon degeneracy.

In additional embodiments, a DNA template may have deoxyadenosine nucleotides replaced with non-deoxyadenosine nucleotides, while codon assignment may be preserved.

Embodiments of this invention advantageously utilize alternative codons in a DNA template of this invention to be used in processes for making a translatable RNA molecule. The variations that can be achieved in a DNA template of this invention can be far greater in scope than for cells and organisms, which may require preferred codons in many processes. In this invention, a wide range of alternative codons and positions can be used in a DNA template for transcribing an RNA molecule.

In further aspects of this invention, variation of the template may include reducing the occurrence or frequency of appearance of certain nucleotides in the template strand. For example, the occurrence of deoxyadenosine in a template may be reduced to a level below 25% of nucleotides in the template. In further examples, the occurrence of deoxyadenosine in a template may be reduced to a level below 20% of nucleotides in the template. In some examples, the occurrence of deoxyadenosine in a template may be reduced to a level below 16%, or 14% of nucleotides in the template. In certain examples, the occurrence of deoxyadenosine in a template may be reduced to a level below 12% of nucleotides in the template.

Inherent codon redundancy allows up to six different codons for a single amino acid. However, synonymous codons may not have equivalent preference in cells and organisms. Further, codon preference can vary among different genes, and may have functional effects. Codon degeneracy is in general poorly understood, with unpredictable effects on nucleic acid structures and processes. It is not generally known how codon alternatives affect ribosomes, protein folding, translation, and degradation of an RNA.

In some embodiments, the level of T can be reduced in a non-template strand, i.e. a coding strand, by replacing a triplet codon containing more than one T to another synonymous codon containing less T than the original triplet. For example, valine encoded by GTT can be replaced by GTC, GTA, or GTG. Serine encoded by TCT, TCC, TCA, TCG, AGT can be replaced by AGC. Complementary changes would be made in the template strand.

In certain embodiments, the level of T can be reduced in a non-template strand, i.e. a coding strand, by replacing all codons with synonymous codons where each replacement reduces the level of T.

In some aspects, in order to increase expression levels, a variant template can have a reduced number of rare codons. See, e.g. Mauro, A critical analysis of codon optimization in human therapeutics, Trends Mol Med 2014, Vol. 20(11), pp. 604-613.

In some aspects, any combination of synonymous codon replacements can be made in a variant template of this invention.

Various additional or synonymous codon replacements can be made as are known in the art.

Some examples of codon replacements in a coding non-template strand are shown in Table 1. For a variant template, complementary replacements are made in the template strand.

TABLE 1

| Amino acid codons | |
|---|---|
| AA | Codons |
| Ala | GCA, GCC, GCG, GCT |
| Asx | AAC, AAT, GAC, GAT |
| Cys | TGC, TGT |
| Asp | GAC, GAT |
| Glu | GAA, GAG |
| Phe | TTC, TTT |
| Gly | GGA, GGC, GGG, GGT |
| His | CAC, CAT |
| Ile | ATA, ATC, ATT |
| Lys | AAA, AAG |
| Leu | CTA, CTC, CTG, CTT, TTA, TTG |
| Met | ATG |
| Asn | AAC, AAT |
| Pro | CCA, CCC, CCG, CCT |
| Gln | CAA, CAG |
| Arg | AGA, AGG, CGA, CGC, CGG, CGT |
| Ser | AGC, AGT, TCA, TCC, TCG, TCT |
| Thr | ACA, ACC, ACG, ACT |
| Val | GTA, GTC, GTG, GTT |
| Trp | TGG |
| Tyr | TAC, TAT |
| Glx | CAA, CAG, GAA, GAG |

Functional Variant Templates for Translatable Molecules

A functional variant DNA template of this disclosure may have a structure reflecting enhanced arrangement of alternative codons.

A functional variant template of this invention can be utilized to enhance incorporation of modified nucleotides or monomers in an RNA product.

In certain aspects, a functional variant template can be utilized to enhance the structural features of a translatable molecule. Examples of enhanced structural features of a translatable molecule include translation efficiency.

In some embodiments, a functional variant template may have reduced occurrence or frequency of appearance of certain nucleotides in the non-coding template strand. Reducing the occurrence of a certain nucleotide can alter the structures and processes of this disclosure to provide forms, which achieve surprisingly improved properties of a translatable RNA product.

In certain aspects, a functional variant template of this invention may have reduced occurrence or frequency of appearance of deoxyadenosine nucleotides in a non-coding template strand, where the deoxyadenosine nucleotides are reduced beginning at the 5' end of the template, and extending toward the 3' end.

In further aspects, a functional variant template of this invention may have reduced occurrence or frequency of appearance of deoxyadenosine nucleotides in a non-coding template strand, where the deoxyadenosine nucleotides are reduced beginning at the 3' end of the template, and extending toward the 5' end.

In additional aspects, a functional variant template of this invention may have reduced occurrence or frequency of appearance of deoxyadenosine nucleotides in a non-coding template strand, where the deoxyadenosine nucleotides are randomly reduced in the template structure.

In certain embodiments, a functional variant template of this invention may have all deoxyadenosine nucleotides in a non-coding template strand replaced by non-deoxyadenosine nucleotides in the template structure.

A DNA template that is transcribable for expression of a target polypeptide or protein can have a non-coding sequence template region, in which deoxyadenosine nucleotides in the non-coding sequence template region are replaced with non-deoxyadenosine nucleotides while codon assignment may be preserved, and in which the occurrence of deoxyadenosines in the template region is reduced by at least 20% as compared to a wild type gene that is transcribable for expression of the target polypeptide or protein. In some embodiments, the occurrence of deoxyadenosines in the template region is reduced by at least 25% as compared to a wild type gene that is transcribable for expression of the target polypeptide or protein. In further embodiments, the occurrence of deoxyadenosines in the template region is reduced by at least 30% as compared to a wild type gene that is transcribable for expression of the target polypeptide or protein. In additional embodiments, the occurrence of deoxyadenosines in the template region is reduced by at least 35% as compared to a wild type gene that is transcribable for expression of the target polypeptide or protein. The occurrence of deoxyadenosines in the template region may be reduced by at least 40%, or 45%, or 50% as compared to a wild type gene that is transcribable for expression of the target polypeptide or protein.

In some aspects, the occurrence of deoxythymidine in a non-template sequence region may be reduced by at least 20%, or 25%, or 30%, or 35%, or 40%, or 45%, or 50% as compared to a wild type gene that is transcribable for expression of the target polypeptide or protein.

Some examples of codon replacements in a coding non-template strand are shown in Table 2. For a functional variant template, complementary replacements are made in the template strand.

TABLE 2

| Amino acid codons | | |
|---|---|---|
| AA | From | To |
| Asn | AAT | AAC |
| Thr | ACT | ACC |
| Ser | AGT | AGC |
| Ile | ATT | ATC |
| His | CAT | CAC |
| Pro | CCT | CCC |
| Arg | CGT | CGG |
| Lue | CTT | CTG |
| Asp | GAT | GAC |
| Ala | GCT | GCC |
| Gly | GGT | GGC |
| Val | GTT | GTG |
| Tyr | TAT | TAC |
| Ser | TCA | AGC |
| Ser | TCC | AGC |

TABLE 2-continued

| Amino acid codons | | |
|---|---|---|
| AA | From | To |
| Ser | TCG | AGC |
| Ser | TCT | AGC |
| Cys | TGT | TGC |
| Leu | TTA | CTG |
| Leu | TTG | CTG |
| Phe | TTT | TTC |

Processes and Polynucleotides with Chemically-Modified Nucleotides

Embodiments of this invention can provide processes for production of translatable molecules, wherein the translatable molecules can comprise one or more kinds of chemically-modified nucleotides.

Embodiments of this invention contemplate processes for production of translatable molecules, where the translatable molecules incorporate one or more kinds of chemically-modified nucleotides, and the translatable molecules are produced with reduced levels of impurities, such as double stranded impurities.

In certain embodiments, the level of double stranded impurities in a process of this invention can be reduced by 2-fold, or 3-fold, or 5-fold, or 10-fold, or 20-fold, or more, as compared to a process using only natural NTPs.

In certain embodiments, this invention can provide processes for production of translatable molecules, where the translatable molecules incorporate one or more kinds of chemically-modified nucleotides, and the translatable molecules are produced with advantageously reduced levels of impurities, such as double stranded impurities, so that the product translatable molecules can be utilized without further purification.

Translatable molecules of this invention having chemically-modified nucleotides can provide enhanced properties for therapeutic use of the translatable molecules.

A translatable molecule of this invention having chemically-modified nucleotides can provide advantageously increased expression levels in vitro, ex vivo, or in vivo, as compared to a reference such as wild type mRNA.

In some aspects, a translatable molecule of this invention having chemically-modified nucleotides can provide advantageously reduced immune response in vitro, ex vivo, or in vivo, as compared to a reference such as wild type mRNA.

In certain aspects, a translatable molecule of this invention having chemically-modified nucleotides can provide advantageously increased intracellular lifetime in vitro, ex vivo, or in vivo, as compared to a reference such as wild type mRNA.

Examples of chemically-modified nucleotides include 5-methoxyuridine (5MeOU).

In certain embodiments, a translatable molecule of this invention can have uridines replaced by 5-methoxyuridines. The level of replacement can be 30% of uridines replaced by 5-methoxyuridine, or 40% of uridines replaced by 5-methoxyuridine, or 50% of uridines replaced by 5-methoxyuridine, or 60% of uridines replaced by 5-methoxyuridine, or 70% of uridines replaced by 5-methoxyuridine, or 80% of uridines replaced by 5-methoxyuridine, or 90% of uridines replaced by 5-methoxyuridine, or 100% of uridines replaced by 5-methoxyuridine.

Examples of combinations of chemically-modified nucleotides include the combination of 5-methoxyuridine (5MeOU) and 5-methylcytidine (5MC). In a combination of chemically-modified nucleotides, both kinds of chemically-modified nucleotides are incorporated into the same polynucleotide.

As used herein, in the context of oligomer sequences, the symbol N can represent any natural nucleotide monomer, or any modified nucleotide monomer.

As used herein, in the context of oligomer sequences, the symbol Q represents a non-natural, modified, or chemically-modified nucleotide monomer.

Additional examples of chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Additional examples of chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine, 5-propynyluridine, 5-bromouridine, 5-fluorouridine, 5-iodouridine, 2-thiouridine, and 6-methyluridine.

Additional examples of chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'-O-methyluridine, and 3,2'-O-dimethyluridine.

Additional examples of chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, $N^4$-alkylcytidines, $N^4$-aminocytidines, $N^4$-acetylcytidines, and $N^4$,$N^4$-dialkylcytidines.

Additional examples of chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; $N^4$-methylcytidine, $N^4$-aminocytidine, $N^4$-acetylcytidine, and $N^4$,$N^4$-dimethylcytidine.

Additional examples of chemically-modified nucleotides include $N^6$-methyladenosine, 2-aminoadenosine, 3-methyladenosine, 8-azaadenosine, 7-deazaadenosine, 8-oxoadenosine, 8-bromoadenosine, 2-methylthio-$N^6$-methyladenosine, $N^6$-isopentenyladenosine, 2-methylthio-$N^6$-isopentenyladenosine, $N^6$-(cis-hydroxyisopentenyl) adenosine, 2-methylthio-$N^6$-(cis-hydroxyisopentenyl) adenosine, $N^6$-glycinylcarbamoyladenosine, N6-threonylcarbamoyl-adenosine, $N^6$-methyl-$N^6$-threonylcarbamoyl-adenosine, 2-methylthio-$N^6$-threonylcarbamoyladenosine, $N^6$,$N^6$-dimethyladenosine, N6-hydroxynorvalylcarbamoyladenosine, 2-methylthio-$N^6$-hydroxynorvalylcarbamoyladenosine, $N^6$-acetyl-adenosine, 7-methyl-adenine, 2-methylthio-adenine, 2-methoxy-adenine, alpha-thio-adenosine, 2'-O-methyl-adenosine, $N^6$,2'-O-dimethyl-adenosine, $N^6$,$N^6$,2'-O-trimethyl-adenosine, 1,2'-O-dimethyl-adenosine, 2'-O-ribosyladenosine, 2-amino-$N^6$-methyl-purine, 1-thio-adenosine, 2'-F-ara-adenosine, 2'-F-adenosine, 2'-OH-ara-adenosine, and $N^6$-(19-amino-pentaoxanonadecyl)-adenosine.

Additional examples of modified or chemically-modified nucleotides include $N^1$-alkylguanosines, $N^2$-alkylguanosines, thienoguanosines, 7-deazaguanosines, 8-oxoguanosines, 8-bromoguanosines, $O^6$-alkylguanosines, xanthosines, inosines, and $N^1$-alkylinosines.

Additional examples of chemically-modified nucleotides include $N^1$-methylguanosine, $N^2$-methylguanosine, thienoguanosine, 7-deazaguanosine, 8-oxoguanosine, 8-bromoguanosine, $O^6$-methylguanosine, xanthosine, inosine, and $N^1$-methylinosine.

Additional examples of chemically-modified nucleotides include pseudouridines. Examples of pseudouridines include $N^1$-alkylpseudouridines, $N^1$-cycloalkylpseudouridines, $N^1$-hydroxypseudouridines, $N^1$-hydroxyalkylpseudouridines, $N^1$-phenylpseudouridines, $N^1$-phenylalkylpseudouridines, $N^1$-aminoalkylpseudouridines, $N^3$-alkylpseudouridines, $N^6$-alkylpseudouridines, $N^6$-alkoxypseudouridines, $N^6$-hydroxypseudouridines, $N^6$-hydroxyalkylpseudouridines, $N^6$-morpholinopseudouridines, $N^6$-phenylpseudouridines, and $N^6$-halopseudouridines. Examples of pseudouridines include $N^1$-alkyl-$N^6$-alkylpseudouridines, $N^1$-alkyl-$N^6$-alkoxypseudouridines, $N^1$-alkyl-$N^6$-hydroxypseudouridines, $N^1$-alkyl-$N^6$-hydroxyalkylpseudouridines, $N^1$-alkyl-$N^6$-morpholinopseudouridines, $N^1$-alkyl-$N^6$-phenylpseudouridines, and $N^1$-alkyl-$N^6$-halopseudouridines. In these examples, the alkyl, cycloalkyl, and phenyl substituents may be unsubstituted, or further substituted with alkyl, halo, haloalkyl, amino, or nitro substituents.

Additional examples of pseudouridines include $N^1$-methylpseudouridine, $N^1$-ethylpseudouridine, $N^1$-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, and $N^1$-hydroxymethylpseudouridine.

Additional examples of chemically-modified nucleotides include 5-hydroxyuridine, 5-methyluridine, 5,6-dihydro-5-methyluridine, 2'-O-methyluridine, 2'-O-methyl-5-methyluridine, 2'-fluoro-2'-deoxyuridine, 2'-amino-2'-deoxyuridine, 2'-azido-2'-deoxyuridine, 5-hydroxymethyluridine, 5-carboxyuridine, 5-carboxymethylesteruridine, 5-formyluridine, 5-methoxyuridine, 5-propynyluridine, 5-bromouridine, 5-iodouridine, 5-fluorouridine, pseudouridine, 2'-O-methylpseudouridine, $N^1$-hydroxypseudouridine, $N^1$-methylpseudouridine, 2'-O-methyl-$N^1$-methylpseudouridine, $N^1$-ethylpseudouridine, $N^1$-hydroxymethylpseudouridine, and Arauridine.

Additional examples of non-natural, modified, and chemically-modified nucleotide monomers include any such nucleotides known in the art, for example, 2' methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Additional examples of non-natural, modified, and chemically-modified nucleotide monomers include 3'-end stabilized nucleotides, 3'-glyceryl nucleotides, 3'-inverted abasic nucleotides, and 3'-inverted thymidine.

Additional examples of non-natural, modified, and chemically-modified nucleotide monomers include locked nucleic acid nucleotides (LNA), glycol nucleic acids (GNA), 2'-O, 4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides.

Additional examples of non-natural, modified, and chemically-modified nucleotide monomers include 2',4'-Constrained 2'-O-Methoxyethyl (cMOE) and 2'-O-Ethyl (cEt) Modified DNAs.

Additional examples of non-natural, modified, and chemically-modified nucleotide monomers include 2'-amino nucleotides, 2'-O-amino nucleotides, 2'-C-allyl nucleotides, and 2'-O-allyl nucleotides.

Additional examples of non-natural, modified, and chemically-modified nucleotide monomers include nucleotide monomers with modified bases, such as 5-(3-amino)propyluridine and 5-(2-mercapto)ethyluridine.

Additional examples of non-natural, modified, and chemically-modified nucleotide monomers include 2'-O-aminopropyl substituted nucleotides.

Additional examples of non-natural, modified, and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Additional examples of nucleotide monomers include pseudouridine (psi-Uridine) and 1-methylpseudouridine.

Additional examples of chemically-modified nucleotide monomers include nucleotides having base modifications, nucleoside or nucleotide structure modifications, sugar modifications, or linkage modifications.

Examples of nucleic acid monomers include non-natural, modified, and chemically-modified nucleotides, including any such nucleotides known in the art.

Some examples of modified nucleotides are given in Saenger, Principles of Nucleic Acid Structure, Springer-Verlag, 1984; Rozenski J., Crain P. F., McCloskey J. A., The RNA Modification Database: 1999 update, Nucleic Acids Res., 1999; Vol. 27, pp. 196-197.

Modalities for Peptides and Proteins

An RNA molecule of this invention may be used for ameliorating, preventing or treating a disease through protein or enzyme modulation or replacement. An RNA molecule of this invention can be administered to regulate, modulate, increase, or decrease the concentration or effectiveness of a natural enzyme in a subject.

In some aspects, the protein can be an unmodified, natural enzyme for which the subject has an abnormal quantity.

In further embodiments, an RNA molecule can be delivered to cells or subjects, and translated to supply increased levels of a natural polypeptide or protein.

An RNA molecule of this invention may be used for ameliorating, preventing or treating a disease through modulation or introduction of a polypeptide or protein. In such embodiments, a translatable molecule of this invention can be administered to regulate, modulate, increase, or decrease the concentration or effectiveness of a peptide or protein in a subject, where the peptide or protein is non-natural or mutated, as compared to a native peptide or protein.

A polypeptide or protein delivered by an RNA molecule of this disclosure can be a modified, non-natural, exogenous, or synthetic polypeptide or protein, which has a pharmacological effect in a subject.

In some embodiments, an RNA molecule can be delivered to cells or subjects, and translated to supply a secretion or concentration of a peptide or protein.

A subject can be a human subject, a human patient, or a mammal.

Base sequences shown herein are from left to right, 5' to 3', unless stated otherwise.

A polypeptide, protein, or protein fragment provided by a polynucleotide of this disclosure can be a variant of a polypeptide or protein of interest. A variant of a polypeptide or protein can have at least about 50%, or 60%, or 70%, or 80%, or 90%, or 95% sequence identity to the polypeptide or protein of interest.

In some embodiments, a translatable molecule of this invention may encode a homolog, variant, or fragment thereof, of a human protein. A homolog or variant may have one or more amino acid substitutions, deletions, and/or insertions as compared to a wild type or naturally-occurring human protein, while retaining protein activity.

In further embodiments, a translatable molecule of this invention may encode a protein that is identical to human protein, or nearly identical.

For example, a translatable molecule may encode an amino acid sequence that is at least 80%, or 85%, or 90%, or 91%, or 92%, or 93%, or 94%, or 95%, or 96%, or 97%, or 98%, or 99% or more identical to the amino acid sequence of a reference polypeptide or protein, such as a human wild type protein.

In further examples, a translatable molecule may encode an amino acid sequence that may have one, or two, or three, or four, or five, or six, or seven, or eight, or nine, or ten, or fifteen, or twenty or more amino acid substitutions, deletions, and/or insertions as compared to the amino acid sequence of a reference polypeptide or protein, such as a human wild type protein.

Examples of polypeptides and proteins of this disclosure include human EPO, human Factor IX (hF9), human alpha-1-antitrypsin (hAAT), and human adiponectin (hAdipo), among others.

Diseases

Examples of diseases for enzyme modulation include lysosomal diseases, for example, Gaucher disease, Fabry disease, Mucopolysaccharidoses (MPS) and related diseases including MPS I, MPS II (Hunter syndrome), and MPS VI, as well as Glycogen storage disease type II.

Examples of diseases for enzyme modulation include hematologic diseases, for example, sickle-cell disease, thalassemia, methemoglobinemia, anemia due to deficiency of hemoglobin or $B_{12}$ intrinsic factor, spherocytosis, glucose-6-phosphate dehydrogenase deficiency, and pyruvate kinase deficiency.

Examples of diseases for enzyme modulation include hemophilia, Von Willebrand disease, Protein S deficiency, age-related macular degeneration, trinucleotide repeat disorders, muscular dystrophy, insertion mutation diseases, DNA repair-deficiency disorders, and deletion mutation diseases.

Examples of diseases and/or conditions for which the translatable molecules of this invention can be translatable to provide an active agent include those in Table 3.

TABLE 3

Rare diseases

| RARE DISEASE | DEFICIENCY |
|---|---|
| Aminoacylase 1 deficiency | Aminoacylase 1 |
| Apo A-I deficiency | Apo A-I |
| Carbamoyl phosphate synthetase 1 deficiency | Carbamoyl phosphate synthetase 1 |
| Ornithine transcarbamylase deficiency | Ornithine transcarbamylase |
| Plasminogen activator inhibitor type 1 deficiency | Plasminogen activator inhibitor type 1 |
| Flaujeac factor deficiency | Flaujeac factor (High-molecular-weight kininogen) |
| High-molecular-weight kininogen deficiency congenital | High-molecular-weight kininogen (Flaujeac factor) |
| PEPCK 1 deficiency | PEPCK 1 |
| Pyruvate kinase deficiency liver type | Pyruvate kinase liver type |
| Alpha 1-antitrypsin deficiency | Alpha 1-antitrypsin |
| Anti-plasmin deficiency congenital | Anti-plasmin |
| Apolipoprotein C 2I deficiency | Apolipoprotein C 2I |
| Butyrylcholinesterase deficiency | Butyrylcholinesterase |
| Complement component 2 deficiency | Complement component 2 |
| Complement component 8 deficiency type 2 | Complement component 8 type 2 |
| Congenital antithrombin deficiency type 1 | Antithrombin |
| Congenital antithrombin deficiency type 2 | Antithrombin, type 2 |
| Congenital antithrombin deficiency type 3 | Antithrombin, type 3 |
| Cortisone reductase deficiency 1 | Cortisone reductase |
| Factor VII deficiency | Factor VII |
| Factor X deficiency | Factor X |
| Factor XI deficiency | Factor XI |
| Factor XII deficiency | Factor XII |
| Factor XIII deficiency | Factor XIII |
| Fibrinogen deficiency congenital | Fibrinogen |
| Fructose-1 6-bisphosphatase deficiency | Fructose-1 6-bisphosphatase |
| Gamma aminobutyric acid transaminase deficiency | Gamma aminobutyric acid transaminase |

TABLE 3-continued

| Rare diseases | |
|---|---|
| RARE DISEASE | DEFICIENCY |
| Gamma-cystathionase deficiency | Gamma-cystathionase |
| Glut2 deficiency | Glut2 |
| GTP cyclohydrolase I deficiency | GTP cyclohydrolase I |
| Isolated growth hormone deficiency type 1B | Isolated growth hormone type 1B |
| Molybdenum cofactor deficiency | Molybdenum cofactor |
| Prekallikrein deficiency congenital | Prekallikrein |
| Proconvertin deficiency congenital | Proconvertin |
| Protein S deficiency | Protein S |
| Pseudocholinesterase deficiency | Pseudocholinesterase |
| Stuart factor deficiency congenital | Stuart factor |
| Tetrahydrobiopterin deficiency | Tetrahydrobiopterin |
| Type 1 plasminogen deficiency | Plasminogen |
| Urocanase deficiency | Urocanase |
| Chondrodysplasia punctata with steroid sulfatase deficiency | Chondrodysplasia punctata with steroid sulfatase/X-linked chondrodysplasia punctata 1 |
| Homocystinuria due to CBS deficiency | CBS |
| Guanidinoacetate methyltransferase deficiency | Guanidinoacetate methyltransferase |
| Pulmonary surfactant protein B deficiency | Pulmonary surfactant protein B |
| Aminoacylase 1 deficiency | Aminoacylase 1 |
| Acid Sphingomyelinase Deficiency | Enzyme found in lysosomes, responsible for conversion of lipid sphingomyelin into lipid ceramide |
| Adenylosuccinate Lyase Deficiency | Neurological disorder, brain dysfunction (encephalopathy) and to delayed development of mental and movement abilities, autistic behaviors and seizures |
| Aggressive Angiomyxoma | Myxoid tumor involving the blood vessels, may be a non-metastasizing benign tumor |
| Albrights Hereditary Osteodystrophy | Inherited in an autosomal dominant pattern, lack of responsiveness to parathyroid hormone, low serum calcium, high serum phosphate |
| Carney Stratakis Syndrome | Very rare syndrome characterized by gastrointestinal stromal tumors and paragangliomas. |
| Carney Triad Syndrome | Characterized by the coexistence of 3 types of neoplasms, mainly in young women, including gastric gastrointestinal stromal tumor, pulmonary chondroma, and extra-adrenal paraganglioma |
| CDKL5 Mutation | Results in severe neurodevelopmental impairment and early onset, difficult to control seizures |
| CLOVES Syndrome | Complex vascular anomalies: Congenital, Lipomatous Overgrowth, Vascular malformations, Epidermal nevi and Scoliosis/Skeletal/Spinal anomalies |
| Cockayne Syndrome | Characterized by short stature and an appearance of premature aging, failure to gain weight, abnormally small head size, and impaired development of the nervous system |
| Congenital Disorder of Glycosylation type 1R | Rare inborn errors of metabolism involving deficient or defective glycosylation |
| Cowden Syndrome | Characterized by multiple noncancerous, tumor-like growths called hamartomas and an increased risk of developing certain cancers |
| DEND Syndrome | Generally severe form of neonatal diabetes mellitus characterized by a triad of developmental delay, epilepsy, and neonatal diabetes |
| Dercum's Disease | Characterized by multiple, and painful lipomas. These lipomas mainly occur on the trunk, the upper arms and upper legs |
| Febrile Infection-Related Epilepsy Syndrome | Explosive-onset, potentially fatal acute epileptic encephalopathy, develops in previously healthy children and adolescents following the onset of a non-specific febrile illness |
| Fibular Aplasia Tibial Campomelia Oligosyndactyly Syndrome | Unknown genetic basis and inheritance with variable expressivity and penetrance |
| Food Protein-Induced Enterocolitis Syndrome | A non-IgE mediated immune reaction in the gastrointestinal system to one or more specific foods, commonly characterized by profuse vomiting and diarrhea |
| Foreign Body Giant Cell Reactive Tissue Disease | Collection of fused macrophages which are generated in response to the presence of a large foreign body; particularly evident with implants that cause the body chronic inflammation and foreign body response |

TABLE 3-continued

| Rare diseases | |
|---|---|
| RARE DISEASE | DEFICIENCY |
| Galloway-Mowat | Physical features may include an unusually small head and additional abnormalities of the head and facial area; damage to clusters of capillaries in the kidneys resulting in abnormal kidney function; and, in many cases, protrusion of part of the stomach through an abnormal opening in the diaphragm |
| Gitelman syndrome | Autosomal recessive kidney disorder characterized by hypokalemic metabolic alkalosis with hypocalciuria, and hypomagnesemia. |
| Glycerol Kinase Deficiency | X-linked recessive enzyme defect that is heterozygous in nature, responsible gene in a region containing genes in which deletions can cause DMD and adrenal hypoplasia congenita |
| Glycogen Storage Disease type 9 | Caused by the inability to break down glycogen. The different forms of the condition can affect glycogen breakdown in liver cells, muscle cells or both |
| gm1 gangliosidosis | Autosomal recessive lysosomal storage disease characterized by accumulation of ganglioside substrates in lysosomes |
| Hereditary spherocytosis | Affects red blood cells, shortage of red blood cells, yellowing of the eyes and skin, and an enlarged spleen |
| Hidradenitis Suppurativa Stage III | Disorder of the terminal follicular epithelium in the apocrine gland-bearing skin, frequently causing keloids, contractures, and immobility. Stage III is defined as multiple lesions, with more extensive sinus tracts and scarring |
| Horizonatal Gaze Palsy with Progressive Scoliosis | Disorder that affects vision and also causes an abnormal curvature of the spine |
| IMAGe syndrome | The combination of intrauterine growth restriction, metaphyseal dysplasia, adrenal hypoplasia congenita, and genital anomalies (only about 20 cases reported in the medical literature) |
| Isodicentric 15 | Chromosome abnormality in which a child is born with extra genetic material from chromosome 15 |
| isolated hemihyperplasia | One side of the body grows more than other, causing asymmetry |
| Juvenile Xanthogranuloma | Usually benign and self-limiting. It occurs most often in the skin of the head, neck, and trunk but can also occur in the arms, legs, feet, and buttocks |
| Kasabach-Merritt Syndrome | A vascular tumor leads to decreased platelet counts and sometimes other bleeding problems |
| Kniest Dysplasia | Disorder of bone growth characterized by short stature (dwarfism) with other skeletal abnormalities and problems with vision and hearing |
| Koolen de-Vries Syndrome | Disorder characterized by developmental delay and mild to moderate intellectual disability. They usually have weak muscle tone in childhood. About half have recurrent seizures |
| Lennox-Gastaut syndrome | Type of epilepsy with multiple different types of seizures, particularly tonic (stiffening) and atonic (drop) seizures. Intellectual development is usually, but not always, impaired |
| Lymphangiomatosis | Congenital and can affect any of the body's systems except the central nervous system (including the brain) |
| Lymphangiomiomytosis | Can occur either sporadically or in association with the tuberous sclerosis complex (TSC) and is often considered a forme fruste of TSC |
| MASA Syndrome | X-linked recessive neurological disorder |
| Mast Cell Activation disorder | Condition with signs and symptoms involving the skin, gastrointestinal, cardiovascular, respiratory, and neurologic systems |
| Mecp2 Duplication Syndrome | Genetic neurodevelopmental disorder characterized by low muscle tone, potentially severe intellectual disability, developmental delays, recurrent respiratory infections, speech abnormalities, seizures, and progressive spasticity |
| Mucha Habermann | Skin disorder |
| Neonatal Hemochromatosis | Severe liver disease of fetal or perinatal onset, associated with deposition of stainable iron in extrahepatic sites, disordered iron handling due to injury to the perinatal liver, as a form of fulminant hepatic failure |
| N-glycanase deficiency | The encoded enzyme may play a role in the proteasome-mediated degradation of misfolded glycoproteins |
| Opsoclonus Myoclonus Syndrome | Neurological disorder of unknown causes which appears to be the result of an autoimmune process involving the nervous system |

TABLE 3-continued

| Rare diseases | |
|---|---|
| RARE DISEASE | DEFICIENCY |
| Persistent genital arousal disorder | Results in a spontaneous, persistent, and uncontrollable genital arousal, with or without orgasm or genital engorgement, unrelated to any feelings of sexual desire |
| Pompe Disease | Inherited disorder caused by the buildup of glycogen in the body's cells. The accumulation of glycogen in certain organs and tissues, especially muscles, impairs their ability to function normally |
| Progressive Familial Intrahepatic Cholestasis | Disorder that causes progressive liver disease, which typically leads to liver failure. In people with PFIC, liver cells are less able to secrete a digestive fluid called bile. The buildup of bile in liver cells causes liver disease in affected individuals |
| Pseudohypoparathyroidism type 1a | Characterized by renal resistance to parathyroid hormone, resulting in hypocalcemia, hyperphosphatemia, and elevated PTH; resistance to other hormones including thydroid stimulating hormone, gonadotropins and growth-hormone-releasing hormone |
| PTEN Hamartoma Tumor Syndrome | The gene was identified as a tumor suppressor that is mutated in a large number of cancers at high frequency |
| Schnitzler syndrome | Characterised by chronic hives and periodic fever, bone pain and joint pain (sometimes with joint inflammation), weight loss, malaise, fatigue, swollen lymph glands and enlarged spleen and liver |
| Scleroderma | Chronic hardening and tightening of the skin and connective tissues |
| Semi Lobar Holoprosencephany | Holoprosencephany: birth defect of the brain, which often can also affect facial features, including closely spaced eyes, small head size, and sometimes clefts of the lip and roof of the mouth. Semilobar holoprosencephaly is a subtype of holoprosencephaly characterised by an incomplete forebrain division |
| Sjogren's Syndrome | Immune system disorder characterized by dry eyes and dry mouth |
| Specific Antibody Deficiency Disease | Immune |
| SYNGAP 1 | A ras GTPase-activating protein that is critical for the development of cognition and proper synapse function |
| Trigeminal Trophic Syndrome | This is the wing of tissue at the end of the nose above the nostril. Trigeminal trophic syndrome is due to damage to the trigeminal nerve |
| Undiffentiated Connective Tissue Disease | Systemic autoimmune disease |
| X-linked hypophosphatemia | X-linked dominant form of rickets (or osteomalacia) that differs from most cases of rickets in that ingestion of vitamin D is relatively ineffective. It can cause bone deformity including short stature and genu varum |

Modalities for Immune Modulation

The RNA molecules of this invention can be translatable to provide an active protein. In certain embodiments, a translatable RNA molecule can provide an active RNA immunization agent, or an RNA vaccine component.

Embodiments of this invention can provide vaccination with RNA molecules that encode a target antigen. The RNA molecules can induce immune response following capture by antigen-presenting cells. Synthetic, isolated RNA molecules of this invention can provide control of immunogenic response parameters, as well as pharmacokinetic properties.

In certain aspects, this disclosure provides methods for RNA vaccines. Synthetic, isolated RNA molecules of this invention can be delivered to cells or subjects in molecular form, or in various carriers. Examples of carriers include liposomes, coated nanoparticles, or cells transfected with RNA agents. In certain embodiments, a RNA agent can be used as an adjuvant, or for stimulating an innate immune response.

The RNA agents of this invention can provide therapeutics effective at a low dose.

An RNA vaccine of this disclosure can advantageously provide a safe and efficacious genetic vaccine by inducing an immune response having both cellular and humoral components. In general, protein can be expressed using an RNA vaccine of this invention.

In some embodiments, an RNA vaccine can advantageously provide protein synthesis in the cytoplasm. In certain embodiments, an RNA vaccine of this invention can provide internalization, release and transport of an exogenous translatable RNA in the cytoplasm.

In certain aspects, an RNA vaccine of this invention can encode for a protein antigen that can be translated by host cells.

In further aspects, some RNA vaccines of this disclosure can encode for tumor antigens, viral antigens, or allergens.

Modalities for administering an RNA vaccine of this invention can include intravenous, intranodal, intradermal, subcutaneous and intrasplenic.

Embodiments of this invention further provide RNA vaccines having increased half-life of translation, which can be used to reduce the necessary dose and exposure to antigen, and reduce the risk of inducing tolerance.

An RNA vaccine of this invention can provide an immunological effect without the risk of integration of a component into the genome, and may reduce the risk of mutagenesis as compared to other genetic vaccines.

Additional embodiments of this disclosure include RNA molecules having translational activity, where the translational activity can be described by a cytoplasmic half-life in a mammalian cell. The half-life can be determined by the time required for 50% of the translatable molecule to be degraded in the cell.

A translatable molecule of this invention can be a precursor of an active molecule, which can be used in the treatment of a condition or disease in a subject.

In some embodiments, a translatable molecule of this invention can be a pharmacologically active molecule having increased half-life in the cytoplasm of mammalian cells.

Aspects of this invention provide structures and compositions for translatable molecules that are oligomeric compounds. The translatable compounds can be active agents for pharmaceutical compositions. Oligomeric molecules of this invention can be used as active agents in formulations for supplying peptide and protein therapeutics.

Oligomeric compounds of this invention can have a length of from about 200 to about 12,000 bases in length. Translatable oligomeric compounds of this invention can have a length of about 1800, or about 1900, or about 2000, or about 2100, or about 2200, or about 2300, or about 2400, or about 2500 bases.

In further aspects, the oligomeric, translatable compounds of this invention can be pharmacologically active molecules. A translatable molecule can be used as an active pharmaceutical ingredient for generating a peptide or protein active agent in vitro, in vivo, or ex vivo.

In some aspects, a translatable molecule of this invention can have any number of phosphorothioate intermonomer linkages in any intermonomer location.

In some embodiments, any one or more of the intermonomer linkages of a translatable molecule can be a phosphodiester, a phosphorothioate including dithioates, a chiral phosphorothioate, and other chemically modified forms.

Enhanced Translation

A translatable molecule of this invention can incorporate a region that enhances the translational efficiency of the molecule.

In general, translational enhancer regions as known in the art can be incorporated into the structure of a translatable molecule to increase peptide or protein yields.

A translatable molecule containing a translation enhancer region can provide increased production of peptide or protein.

In some embodiments, a translation enhancer region can comprise, or be located in a 5' or 3' untranslated region of a translatable molecule.

Examples of translation enhancer regions include naturally-occurring enhancer regions from TEV 5'UTR and Xenopus beta-globin 3'UTR.

Molecular Structure and Sequences

A translatable molecule can be designed to express a target peptide or protein. In some embodiments, the target peptide or protein can be associated with a condition or disease in a subject.

In some aspects, the base sequence of a translatable molecule can include a portion that is identical to at least an effective portion or domain of a base sequence of an mRNA, where an effective portion is sufficient to impart a therapeutic activity to a translation product of the translatable molecule.

In some aspects, this invention provides active translatable oligomer molecules having a base sequence identical to at least a fragment of a native nucleic acid molecule of a cell.

In certain embodiments, the base sequence of a translatable molecule can include a portion that is identical to a base sequence of an mRNA, except for one or more base mutations. The number of mutations for the translatable molecule should not exceed an amount that would produce a translation product of the translatable molecule having substantially less activity than the mRNA.

The oligomeric, translatable molecules of this invention can display a sequence of nucleobases, and can be designed to express a peptide or protein, in vitro, ex vivo, or in vivo. The expressed peptide or protein can have activity in various forms, including activity corresponding to protein expressed from a native or natural mRNA.

In some embodiments, a translatable molecule of this invention may have a chain length of about 200 to 15,000 monomers.

Molecular Cap Structure

A translatable molecule of this invention may have a 5'-end capped with one of various groups as are known in the art.

In some embodiments, a 5' cap may be a m7GpppGm cap.

In further embodiments, a 5' cap may be selected from m7GpppA, m7GpppC; unmethylated cap analogs (e.g., GpppG); dimethylated cap analog (e.g., m2,7GpppG), a trimethylated cap analog (e.g., m2,2,7GpppG), dimethylated symmetrical cap analogs (e.g., m7Gpppm7G), or anti reverse cap analogs (e.g., ARCA; m7, 2'OmeGpppG, m72'dGpppG, m7,3'OmeGpppG, m7,3'dGpppG and their tetraphosphate derivatives) (see, e.g., Jemielity, J. et al., RNA 9: 1108-1122 (2003).

In additional embodiments, a 5' cap may be an ARCA cap (3'-OMe-m7G(5')pppG).

The 5' cap may be an mCAP (m7G(5')ppp(5')G, $N^7$-Methyl-Guanosine-5'-Triphosphate-5'-Guanosine).

The 5' cap may be resistant to hydrolysis.

Some examples of 5' cap structures are given in WO2015/051169, WO2015/061491, U.S. Pat. Nos. 8,093,367, and 8,304,529.

Untranslated Regions

In some embodiments, a translatable molecule may comprise a 5' untranslated region (5' UTR) and/or a 3' untranslated region (3' UTR).

In some embodiments, a translatable molecule may comprise a 5' UTR that is at least about 25, 50, 75, 100, 125, 150, 175, 200, 300, 400, or 500 nucleotides in length. In further embodiments, a 5' UTR may contain about 50 to 300 nucleotides, for example about 75 to 250 nucleotides, or about 100 to 200 nucleotides, or about 120 to 150 nucleotides, or about 135 nucleotides.

In some embodiments, a 5' UTR may be derived from a reference mRNA.

In some examples, a 5' UTR can be derived from an mRNA for a histone, a tubulin, a globin, a GAPDH, an actin, or a citric acid cycle enzyme.

In other embodiments, a 5' UTR sequence may include a partial sequence of a CMV immediate-early 1 (IE1) gene.

In some embodiments, a 5' UTR may comprise a sequence selected from the 5' UTR of human IL-6, alanine aminotransferase 1, human apolipoprotein E, human fibrinogen alpha chain, human transthyretin, human haptoglobin, human alpha antichymotrypsin, human antithrombin, human alpha-1-antitrypsin, human albumin, human beta globin, human complement C3, human complement C5, SynK, AT1G58420, mouse beta globin, mouse albumin, and a tobacco etch virus, or fragments of any of the foregoing.

In further embodiments, a 5' UTR may be derived from a tobacco etch virus (TEV).

In some embodiments, the translatable oligomeric molecule may comprise an internal ribosome entry site (IRES). An IRES can allow for translation initiation in an end-independent manner. In certain embodiments, an IRES can be in a 5' UTR. In other embodiments, an IRES may be outside a 5' UTR.

In some embodiments, a translatable molecule may comprise a 3' UTR that is at least about 25, 50, 75, 100, 125, 150, 175, 200, 300, 400, or 500 nucleotides in length. In some embodiments, a 3' UTR may contain about 50 to 300 nucleotides, for example, about 75 to 250 nucleotides, or about 100 to 200 nucleotides, or about 140 to 175 nucleotides, or about 160 nucleotides.

In some embodiments, a 3' UTR can comprise a sequence selected from a 3' UTR of alanine aminotransferase 1, human apolipoprotein E, human fibrinogen alpha chain, human haptoglobin, human antithrombin, human alpha globin, human beta globin, human complement C3, human growth factor, human hepcidin, MALAT-1, mouse beta globin, mouse albumin, and xenopus beta globin, or fragments of any of the foregoing.

In some embodiments, a 3' UTR can be derived from xenopus beta globin.

Some examples of UTRs may be found in U.S. Pat. No. 9,149,506.

Stop Codon

In some embodiments, a translatable molecule may comprise a sequence downstream of a CDS that creates a triple stop codon. In some embodiments, a transatable molecule may comprise the sequence AUAAGUGAA (SEQ ID NO: 1) downstream of a CDS.

Translation Initiation

In some embodiments, a translatable molecule may comprise a translation initiation site.

In certain embodiments, a translation initiation site can be a Kozak sequence. Some examples are found in Kozak, Marilyn (1988) Mol. and Cell Biol., 8:2737-2744; Kozak, Marilyn (1991) J. Biol. Chem., 266:19867-19870; Kozak, Marilyn (1990) Proc Natl. Acad. Sci. USA, 87:8301-8305; and Kozak, Marilyn (1989) J. Cell Biol., 108:229-241.

In some embodiments, a translation initiation site can be inserted upstream of a CDS.

In further embodiments, a translation initiation site can be inserted downstream of a 5' UTR.

Molecular Tail Structure

In some embodiments, a translatable molecule can comprise a tail region, which can serve to protect the molecule from exonuclease degradation.

In some embodiments, the tail region can be a polyA tail.

A PolyA tail can be connected to a translatable molecule using a variety of methods known in the art. For example, using poly A polymerase to add tails to synthetic or in vitro transcribed RNA. Other methods include the use of a transcription vector to encode poly A tails or the use of a ligase (e.g., via splint ligation using a T4 RNA ligase and/or T4 DNA ligase), wherein polyA may be ligated to the 3' end of a sense RNA. In some embodiments, a combination of any of the above methods can be utilized.

In some embodiments, a translatable molecule can comprise a 3' polyA tail structure. The length of a polyA tail can be 5, 10, 15, 20, 25, 30, 35, 40, 45, 50, 100, 200, or 300 nucleotides, or longer. In some embodiments, a 3' polyA tail can contain about 5 to 300 adenosine nucleotides, e.g., about 30 to 250 adenosine nucleotides, or about 60 to 220 adenosine nucleotides, or about 80 to 200 adenosine nucleotides, or about 90 to about 150 adenosine nucleotides, or about 100 to about 120 adenosine nucleotides. In some examples, a 3' polyA tail can be about 100 nucleotides in length, or 115 nucleotides in length.

In some embodiments, a translatable molecule may comprise a 3' polyC tail structure. In some embodiments, the length of the polyC tail can be at least about 5, 10, 15, 20, 25, 30, 35, 40, 45, 50, 100, 200, or 300 nucleotides, or more. In some embodiments, a 3' polyC tail may contain about 5 to 300 cytosine nucleotides, for example, about 30 to 250 cytosine nucleotides, or about 60 to 220 cytosine nucleotides, or about 80 to about 200 cytosine nucleotides, or about 90 to 150 cytosine nucleotides, or about 100 to about 120 cytosine nucleotides. In some embodiments, a 3' polyC tail can be about 100 nucleotides in length, or 115 nucleotides in length.

In further aspects, a polyC tail may be connected to a polyA tail. A polyC tail may connect to the 5' end of a polyA tail, or to the 3' end of a polyA tail.

In some embodiments, the length of the poly A and/or poly C tail can be varied to affect the stability of a translatable molecule.

Genetic Basis for Translatable Molecules

In some embodiments, the translatable molecules of this invention can be structured to provide peptides or proteins that are nominally expressed by any portion of a genome. Examples of genes for which a translatable molecule can be used to express the corresponding peptide or protein are set forth below.

Examples of genes for which a translatable molecule can be used to express the corresponding peptide or protein include: Neoplasia, PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc.

Examples of genes for which a translatable molecule can be used to express the corresponding peptide or protein include: Age-related Macular Degeneration, Schizophrenia, Aber; Ccl2; Cc2; cp (ceruloplasmin); Timp3; cathepsinD; Vld1r; Ccr2 Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b.

Examples of genes for which a translatable molecule can be used to express the corresponding peptide or protein include: 5-HTT (Slc6a4); COMT; DRD (Drd1a); SLC6A3; DAOA; DTNBP1; Dao (Dao1).

Examples of genes for which a translatable molecule can be used to express the corresponding peptide or protein include: Trinucleotide Repeat Disorders, HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn 1 (DRPLA Dx); CBP (Creb-BP-global instability); VLDLR (Alzheimer's); Atxn7; Atxn10.

Examples of genes for which a translatable molecule can be used to express the corresponding peptide or protein include: Fragile X Syndrome, FMR2; FXR1; FXR2; mGLUR5.

Examples of genes for which a translatable molecule can be used to express the corresponding peptide or protein include: Secretase Related Disorders, APH-1 (alpha and beta); Presenilin (Psen1); nicastrin (Ncstn); PEN-2.

Examples of genes for which a translatable molecule can be used to express the corresponding peptide or protein include: Nos1.

Examples of genes for which a translatable molecule can be used to express the corresponding peptide or protein include: Parp1.

Examples of genes for which a translatable molecule can be used to express the corresponding peptide or protein include: Nat1; Nat2.

Examples of genes for which a translatable molecule can be used to express the corresponding peptide or protein include: Prion-related disorders, Prp.

Examples of genes for which a translatable molecule can be used to express the corresponding peptide or protein include: ALS disease, SOD1; ALS2; STEX; FUS; TARDBP; VEGF (VEGF-a; VEGF-b; VEGF-c).

Examples of genes for which a translatable molecule can be used to express the corresponding peptide or protein include: Drug addiction, Prkce (alcohol); Drd2; Drd4; ABAT (alcohol); GRIA2; Grm5; Grin1; Htr1b; Grin2a; Drd3; Pdyn; Gria1 (alcohol).

Examples of genes for which a translatable molecule can be used to express the corresponding peptide or protein include: Autism, Mecp2; BZRAP1; MDGA2; Sema5A; Neurexin 1; Fragile X (FMR2 (AFF2); FXR1; FXR2; Mglur5).

Examples of genes for which a translatable molecule can be used to express the corresponding peptide or protein include: Alzheimer's Disease, E1; CHIP; UCH; UBB; Tau; LRP; PICALM; Clusterin; PS1; SORL1; CR1; Vld1r; Uba1; Uba3; CHIP28 (Aqp1, Aquaporin 1); Uchl1; Uchl3; APP.

Examples of genes for which a translatable molecule can be used to express the corresponding peptide or protein include: Inflammation, IL-10; IL-1 (IL-1a; IL-1b); IL-13; IL-17 (IL-17a (CTLA8); IL-17b; IL-17c; IL-17d; IL-17f); II-23; Cx3er1; ptpn22; TNFa; NOD2/CARD15 for IBD; IL-6; IL-12 (IL-12a; IL-12b); CTLA4; Cx3cl1.

Examples of genes for which a translatable molecule can be used to express the corresponding peptide or protein include: Parkinson's Disease, x-Synuclein; DJ-1; LRRK2; Parkin; PINK1.

Examples of genes for which a translatable molecule can be used to express the corresponding peptide or protein include: Blood and coagulation diseases and disorders, Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9 Factor IX, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1).

Examples of genes for which a translatable molecule can be used to express the corresponding peptide or protein include: Cell dysregulation and oncology diseases and disorders, B-cell non-Hodgkin lymphoma (BCL7A, BCL7); Leukemia (TAL1 TCL5, SCL, TAL2, FLT3, NBS1, NBS, ZNFN1A1, IK 1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STATSB, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN).

Examples of genes for which a translatable molecule can be used to express the corresponding peptide or protein include: Inflammation and immune related diseases and disorders, AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immuno-deficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immuno-deficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f, II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs) (JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4).

Examples of genes for which a translatable molecule can be used to express the corresponding peptide or protein include: Metabolic, liver, kidney and protein diseases and disorders, Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, BG213071, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SC01), Hepatic lipase deficiency (LIPC), Hepato-blastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63).

Examples of genes for which a translatable molecule can be used to express the corresponding peptide or protein include: Lipoprotein lipase, APOA1, APOC3 and APOA4.

Examples of genes for which a translatable molecule can be used to express the corresponding peptide or protein include: Muscular/skeletal diseases and disorders, Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facio-scapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1).

Examples of genes for which a translatable molecule can be used to express the corresponding peptide or protein include: Neurological and neuronal diseases and disorders, ALS (SOD1, ALS2, STEX, FUS, TARDBP, VEGF (VEGF-a, VEGF-b, VEGF-c); Alzheimer's Disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizo-phrenia (Neuregulin1 (Nrg1), Erb4 (receptor for Neuregulin), Complexin1 (Cplx1), Tph1 Trypto-phan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Dis-orders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP-global instability), VLDLR (Alzheimer's), Atxn7, Atxn10).

Examples of genes for which a translatable molecule can be used to express the corresponding peptide or protein include: Occular diseases and disorders, Age-related macular degeneration (Aber, Ccl2, Cc2, cp (ceruloplasmin), Timp3, cathepsinD, Vld1r, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2).

Examples of genes for which a translatable molecule can be used to express the corresponding peptide or protein include: Epilepsy, myoclonic, EPM2A, MELF, EPM2 Lafora type, 254780 Epilepsy, myoclonic, NHLRC1, EPM2A, EPM2B Lafora type, 254780.

Examples of genes for which a translatable molecule can be used to express the corresponding peptide or protein include: Duchenne muscular DMD, BMD dystrophy, 310200 (3) AIDS, delayed/rapid KIR3DL1, NKAT3, NKB1, AMB11, KIR3DS1 progression to (3).

Examples of genes for which a translatable molecule can be used to express the corresponding peptide or protein include: AIDS, delayed/rapid KIR3DL1, NKAT3, NKB1, AMB11, KIR3DS1 progression to (3) AIDS, rapid IFNG progression to, 609423 (3) AIDS, resistance to CXCL12, SDF1 (3).

Examples of genes for which a translatable molecule can be used to express the corresponding peptide or protein include: Alpha-1-Antitrypsin Deficiency, SERPINA1 [serpin peptidase inhibitor, clade A (alpha-1 antiproteinase, antitrypsin), member 1]; SERPINA2 [serpin peptidase inhibitor, clade A (alpha-1 antiproteinase, antitrypsin), member 2]; SERPINA3 [serpin peptidase inhibitor, clade A (alpha-1 antiproteinase, antitrypsin), member 3]; SERPINA5 [serpin peptidase inhibitor, clade A (alpha-1 antiproteinase, antitrypsin), member 5]; SERPINA6 [serpin peptidase inhibitor, clade A (alpha-1 antiproteinase, antitrypsin), member 6]; SERPINA7 [serpin peptidase inhibitor, clade A (alpha-1 antiproteinase, antitrypsin), member 7]; "AND" SERPLNA6 (serpin peptidase inhibitor, clade A (alpha-1 antiproteinase, antitrypsin), member 6).

Examples of genes for which a translatable molecule can be used to express the corresponding peptide or protein include: PI3K/AKT Signaling, PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1.

Examples of genes for which a translatable molecule can be used to express the corresponding peptide or protein include: ERK/MAPK Signaling, PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1;

PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK.

Examples of genes for which a translatable molecule can be used to express the corresponding peptide or protein include: Serine/Threonine-Protein Kinase, CDK16; PCTK1; CDK5R1.

Examples of genes for which a translatable molecule can be used to express the corresponding peptide or protein include: Glucocorticoid Receptor Signaling, RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1.

Examples of genes for which a translatable molecule can be used to express the corresponding peptide or protein include: Axonal Guidance Signaling, PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKC1; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA.

Examples of genes for which a translatable molecule can be used to express the corresponding peptide or protein include: Ephrin Receptor Signaling, PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4, AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK.

Examples of genes for which a translatable molecule can be used to express the corresponding peptide or protein include: Actin Cytoskeleton Signaling, ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK.

Examples of genes for which a translatable molecule can be used to express the corresponding peptide or protein include: Huntington's Disease Signaling, PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3.

Examples of genes for which a translatable molecule can be used to express the corresponding peptide or protein include: Apoptosis Signaling, PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1.

Examples of genes for which a translatable molecule can be used to express the corresponding peptide or protein include: B Cell Receptor Signaling, RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1.

Examples of genes for which a translatable molecule can be used to express the corresponding peptide or protein include: Leukocyte Extravasation Signaling, ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9.

Examples of genes for which a translatable molecule can be used to express the corresponding peptide or protein include: Integrin Signaling, ACTN4; ITGAM; ROCK1; ITGA5; RAC1; PTEN; RAP1A; TLN1; ARHGEF7; MAPK1; RAC2; CAPNS1; AKT2; CAPN2; P1K3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3.

Examples of genes for which a translatable molecule can be used to express the corresponding peptide or protein include: Acute Phase Response Signaling, IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6.

Examples of genes for which a translatable molecule can be used to express the corresponding peptide or protein include: PTEN Signaling, ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1.

Examples of genes for which a translatable molecule can be used to express the corresponding peptide or protein include: p53 Signaling, PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; RIK3R1; RRM2B; APAF1; CTNNB1; SIRT1; CCND1; PRKDC; ATM; SFN; CDKN2A; JUN; SNAI2; GSK3B; BAX; AKT3.

Examples of genes for which a translatable molecule can be used to express the corresponding peptide or protein include: Aryl Hydrocarbon Receptor Signaling, HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1.

Examples of genes for which a translatable molecule can be used to express the corresponding peptide or protein include: Xenobiotic Metabolism Signaling, PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1.

Examples of genes for which a translatable molecule can be used to express the corresponding peptide or protein include: SAPK/JNK Signaling, PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK.

Examples of genes for which a translatable molecule can be used to express the corresponding peptide or protein include: PPAr/RXR Signaling, PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ.

Examples of genes for which a translatable molecule can be used to express the corresponding peptide or protein include: NF-KB Signaling, IRAK1; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4: TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1.

Examples of genes for which a translatable molecule can be used to express the corresponding peptide or protein include: Neuregulin Signaling, ERBB4; PRKCE; ITGAM; ITGA5: PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1.

Examples of genes for which a translatable molecule can be used to express the corresponding peptide or protein include: Wnt & Beta catenin Signaling, CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2: ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2.

Examples of genes for which a translatable molecule can be used to express the corresponding peptide or protein include: Insulin Receptor Signaling, PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1.

Examples of genes for which a translatable molecule can be used to express the corresponding peptide or protein include: IL-6 Signaling, HSPB1; TRAF6; MAPKAPK2; ELK1; MAPK1; PTPN11; IKBKB; FOS; NFKB2: MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6.

Examples of genes for which a translatable molecule can be used to express the corresponding peptide or protein include: Hepatic Cholestasis, PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6.

Examples of genes for which a translatable molecule can be used to express the corresponding peptide or protein include: IGF-1 Signaling, IGF1; PRKCZ; ELK1; MAPK1; PTPN11; NEDD4; AKT2; PIK3CA; PRKC1; PTK2; FOS; PIK3CB; PIK3C3; MAPK8; 1GF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1.

Examples of genes for which a translatable molecule can be used to express the corresponding peptide or protein include: NRF2-mediated Oxidative Stress Response, PRKCE; EP300; SOD2; PRKCZ; MAPK1; SQSTM1; NQO1; PIK3CA; PRKC1; FOS; PIK3CB; P1K3C3; MAPK8; PRKD1; MAPK3; KRAS; PRKCD; GSTP1; MAPK9; FTL; NFE2L2; PIK3C2A; MAPK14; RAF1;

MAP3K7; CREBBP; MAP2K2; AKT1; PIK3R1; MAP2K1; PPIB; JUN; KEAP1; GSK3B; ATF4; PRKCA; EIF2AK3; HSP90AA1.

Examples of genes for which a translatable molecule can be used to express the corresponding peptide or protein include: Hepatic, Fibrosis/Hepatic Stellate Cell Activation, EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; TNF; RELB; IL8; PDGFRA; NFKB1; TGFBR1; SMAD4; VEGFA; BAX; IL1R1; CCL2; HGF; MMP1; STAT1; IL6; CTGF; MMP9.

Examples of genes for which a translatable molecule can be used to express the corresponding peptide or protein include: PPAR Signaling, EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; TNF; INSR; RAF1; IKBKG; RELB; MAP3K7; CREBBP; MAP2K2; CHUK; PDGFRA; MAP2K1; NFKB1; JUN; IL1R1; HSP90AA1.

Examples of genes for which a translatable molecule can be used to express the corresponding peptide or protein include: Fc Epsilon RI Signaling, PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA.

Examples of genes for which a translatable molecule can be used to express the corresponding peptide or protein include: G-Protein Coupled Receptor Signaling, PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA.

Examples of genes for which a translatable molecule can be used to express the corresponding peptide or protein include: Inositol Phosphate Metabolism, PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK.

Examples of genes for which a translatable molecule can be used to express the corresponding peptide or protein include: PDGF Signaling, EIF2AK2; ELK1; ABL2; MAPK1; PIK3CA; FOS; PIK3CB; PIK3C3; MAPK8; CAV1; ABL1; MAPK3; KRAS; SRC; PIK3C2A; RAF1; MAP2K2; JAK1; JAK2; PIK3R1; PDGFRA; STAT3; SPHK1; MAP2K1; MYC; JUN; CRKL; PRKCA; SRF; STAT1; SPHK2.

Examples of genes for which a translatable molecule can be used to express the corresponding peptide or protein include: VEGF Signaling, ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA.

Examples of genes for which a translatable molecule can be used to express the corresponding peptide or protein include: Natural Killer Cell Signaling, PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA.

Examples of genes for which a translatable molecule can be used to express the corresponding peptide or protein include: Cell Cycle: G1/S Checkpoint Regulation, HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6.

Examples of genes for which a translatable molecule can be used to express the corresponding peptide or protein include: T Cell Receptor Signaling, RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB, FYN; MAP2K2; PIK3R1; CHUK; MAP2K1; NFKB1; ITK; BCL10; JUN; VAV3.

Examples of genes for which a translatable molecule can be used to express the corresponding peptide or protein include: Death Receptor Signaling, CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3.

Examples of genes for which a translatable molecule can be used to express the corresponding peptide or protein include: FGF Signaling RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF.

Examples of genes for which a translatable molecule can be used to express the corresponding peptide or protein include: GM-CSF Signaling, LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1.

Examples of genes for which a translatable molecule can be used to express the corresponding peptide or protein include: Amyotrophic Lateral Sclerosis Signaling, BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3.

Examples of genes for which a translatable molecule can be used to express the corresponding peptide or protein include: JAK/Stat Signaling, PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1.

Examples of genes for which a translatable molecule can be used to express the corresponding peptide or protein include: Nicotinate and Nicotinamide Metabolism, PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK.

Examples of genes for which a translatable molecule can be used to express the corresponding peptide or protein include: Chemokine Signaling, CXCR4; ROCK2; MAPK1; PTK2; FOS; CFL1; GNAQ; CAMK2A; CXCL12; MAPK8;

MAPK3; KRAS; MAPK13; RHOA; CCR3; SRC; PPP1CC; MAPK14; NOX1; RAF1; MAP2K2; MAP2K1; JUN; CCL2; PRKCA.

Examples of genes for which a translatable molecule can be used to express the corresponding peptide or protein include: IL-2 Signaling, ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A: LCK; RAF1; MAP2K2; JAK1; AKT1; PIK3R1; MAP2K1; JUN; AKT3.

Examples of genes for which a translatable molecule can be used to express the corresponding peptide or protein include: Synaptic Long Term Depression, PRKCE; IGF1; PRKCZ; PRDX6; LYN; MAPK1; GNAS; PRKC1; GNAQ; PPP2R1A; IGF1R; PRKID1; MAPK3; KRAS; GRN; PRKCD; NOS3; NOS2A; PPP2CA; YWHAZ; RAF1; MAP2K2; PPP2R5C; MAP2K1; PRKCA.

Examples of genes for which a translatable molecule can be used to express the corresponding peptide or protein include: Estrogen Receptor Signaling, TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2.

Examples of genes for which a translatable molecule can be used to express the corresponding peptide or protein include: Protein Ubiquitination Pathway, TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3.

Examples of genes for which a translatable molecule can be used to express the corresponding peptide or protein include: IL-10 Signaling, TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6.

Examples of genes for which a translatable molecule can be used to express the corresponding peptide or protein include: VDR/RXR Activation, PRKCE; EP300; PRKCZ; RXRA; GADD45A; HES1; NCOR2; SP1; PRKC1; CDKN1B; PRKD1; PRKCD; RUNX2; KLF4; YY1; NCOA3; CDKN1A; NCOA2; SPP1; LRP5; CEBPB; FOXO1; PRKCA.

Examples of genes for which a translatable molecule can be used to express the corresponding peptide or protein include: TGF-beta Signaling, EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5.

Examples of genes for which a translatable molecule can be used to express the corresponding peptide or protein include: Toll-like Receptor Signaling, IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN.

Examples of genes for which a translatable molecule can be used to express the corresponding peptide or protein include: p38 MAPK Signaling, HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1.

Examples of genes for which a translatable molecule can be used to express the corresponding peptide or protein include: Neurotrophin/TRK Signaling, NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4.

Examples of genes for which a translatable molecule can be used to express the corresponding peptide or protein include: FXR/RXR Activation, INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1.

Examples of genes for which a translatable molecule can be used to express the corresponding peptide or protein include: Synaptic Long Term Potentiation, PRKCE; RAP1A; EP300; PRKCZ; MAPK1; CREB1; PRKC1; GNAQ; CAMK2A; PRKD1; MAPK3; KRAS; PRKCD; PPP1CC; RAF1; CREBBP; MAP2K2; MAP2K1; ATF4; PRKCA.

Examples of genes for which a translatable molecule can be used to express the corresponding peptide or protein include: Calcium Signaling, RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6.

Examples of genes for which a translatable molecule can be used to express the corresponding peptide or protein include: EGF Signaling, ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1.

Examples of genes for which a translatable molecule can be used to express the corresponding peptide or protein include: Hypoxia Signaling in the Cardiovascular System, EDN1; PTEN; EP300; NQO1; UBE21; CREB1; ARNT; HIF1A; SLC2A4; NOS3; TP53; LDHA; AKT1; ATM; VEGFA; JUN; ATF4; VHL; HSP90AA1.

Examples of genes for which a translatable molecule can be used to express the corresponding peptide or protein include: LPS/IL-1 Mediated Inhibition of RXR Function, IRAK1; MYD88; TRAF6; PPARA; RXRA; ABCA1, MAPK8; ALDH1A1; GSTP1; MAPK9; ABCB1; TRAF2; TLR4; TNF; MAP3K7; NR1H2; SREBF1; JUN; IL1R1.

Examples of genes for which a translatable molecule can be used to express the corresponding peptide or protein include: LXR/RXR Activation, FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9.

Examples of genes for which a translatable molecule can be used to express the corresponding peptide or protein include: Amyloid Processing, PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP.

Examples of genes for which a translatable molecule can be used to express the corresponding peptide or protein include: IL-4 Signaling, AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1.

Examples of genes for which a translatable molecule can be used to express the corresponding peptide or protein include: Cell Cycle: G2/M DNA Damage Checkpoint Regulation, EP300; PCAF; BRCA1; GADD45A; PLK1; BTRC; CHEK1; ATR; CHEK2; YWHAZ; TP53; CDKN1A; PRKDC; ATM; SFN; CDKN2A.

Examples of genes for which a translatable molecule can be used to express the corresponding peptide or protein include: Nitric Oxide Signaling in the Cardiovascular System, KDR; FLT1; PGF; AKT2; PIK3CA; PIK3CB; PIK3C3;

CAV1; PRKCD; NOS3; PIK3C2A; AKT1; PIK3R1; VEGFA; AKT3; HSP90AA1.

Examples of genes for which a translatable molecule can be used to express the corresponding peptide or protein include: Purine Metabolism NME2; SMARCA4; MYH9; RRM2; ADAR; EIF2AK4; PKM2; ENTPD1; RAD51; RRM2B; TJP2; RAD51C; NT5E; POLD1; NME1.

Examples of genes for which a translatable molecule can be used to express the corresponding peptide or protein include: cAMP-mediated Signaling, RAP1A; MAPK1; GNAS; CREB1; CAMK2A; MAPK3; SRC; RAF1; MAP2K2; STAT3; MAP2K1; BRAF; ATF4.

Examples of genes for which a translatable molecule can be used to express the corresponding peptide or protein include: Mitochondrial Dysfunction Notch Signaling, SOD2; MAPK8; CASP8; MAPK10; MAPK9; CASP9; PARK7; PSEN1; PARK2; APP; CASP3 HES1; JAG1; NUMB; NOTCH4; ADAM17; NOTCH2; PSEN1; NOTCH3; NOTCH1; DLL4.

Examples of genes for which a translatable molecule can be used to express the corresponding peptide or protein include: Endoplasmic Reticulum Stress Pathway, HSPA5; MAPK8; XBP1; TRAF2; ATF6; CASP9; ATF4; EIF2AK3; CASP3.

Examples of genes for which a translatable molecule can be used to express the corresponding peptide or protein include: Pyrimidine Metabolism, NME2; AICDA; RRM2; EIF2AK4; ENTPD1; RRM2B; NT5E; POLD1; NME1.

Examples of genes for which a translatable molecule can be used to express the corresponding peptide or protein include: Parkinson's Signaling, UCHL1; MAPK8; MAPK13; MAPK14; CASP9; PARK7; PARK2; CASP3.

Examples of genes for which a translatable molecule can be used to express the corresponding peptide or protein include: Cardiac & Beta Adrenergic Signaling, GNAS; GNAQ; PPP2R1A; GNB2L1; PPP2CA; PPP1CC; PPP2R5C.

Examples of genes for which a translatable molecule can be used to express the corresponding peptide or protein include: Glycolysis/Gluco-neogenesis, HK2; GCK; GPI; ALDH1A1; PKM2; LDHA; HK1.

Examples of genes for which a translatable molecule can be used to express the corresponding peptide or protein include: Interferon Signaling, IRF1; SOCS1; JAK1; JAK2; IFITM1; STAT1; IFIT3.

Examples of genes for which a translatable molecule can be used to express the corresponding peptide or protein include: Sonic Hedgehog Signaling, ARRB2; SMO; GLI2; DYRK1A; GLI1; GSK3B; DYRKIB.

Examples of genes for which a translatable molecule can be used to express the corresponding peptide or protein include: Glycerophospholipid Metabolism, PLD1; GRN; GPAM; YWHAZ; SPHK1; SPHK2.

Examples of genes for which a translatable molecule can be used to express the corresponding peptide or protein include: Phospholipid Degradation, PRDX6; PLD1; GRN; YWHAZ; SPHK1; SPHK2.

Examples of genes for which a translatable molecule can be used to express the corresponding peptide or protein include: Tryptophan Metabolism, SIAH2; PRMT5; NEDD4; ALDH1A1; CYP1B1; SIAH1.

Examples of genes for which a translatable molecule can be used to express the corresponding peptide or protein include: Lysine Degradation, SUV39H1; EHMT2; NSD1; SETD7; PPP2R5C.

Examples of genes for which a translatable molecule can be used to express the corresponding peptide or protein include: Nucleotide Excision, ERCC5; ERCC4; XPA; XPC; ERCC1.

Examples of genes for which a translatable molecule can be used to express the corresponding peptide or protein include: Repair Pathway Starch and Sucrose Metabolism, UCHL1; HK2; GCK; GPI; HK1.

Examples of genes for which a translatable molecule can be used to express the corresponding peptide or protein include: Aminosugars Metabolism, NQO1; HK2; GCK; HK1.

Examples of genes for which a translatable molecule can be used to express the corresponding peptide or protein include: Arachidonic Acid Metabolism, PRDX6; GRN; YWHAZ; CYP1B1.

Examples of genes for which a translatable molecule can be used to express the corresponding peptide or protein include: Circadian Rhythm Signaling, CSNK1E; CREB1; ATF4; NR1D1.

Examples of genes for which a translatable molecule can be used to express the corresponding peptide or protein include: Coagulation System, BDKRB1; F2R; SERPINE1; F3.

Examples of genes for which a translatable molecule can be used to express the corresponding peptide or protein include: Dopamine Receptor Signaling, PPP2R1A; PPP2CA; PPP1CC; PPP2R5C.

Examples of genes for which a translatable molecule can be used to express the corresponding peptide or protein include: Glutathione Metabolism, IDH2; GSTP1; ANPEP; IDH1.

Examples of genes for which a translatable molecule can be used to express the corresponding peptide or protein include: Glycerolipid Metabolism, ALDH1A1; GPAM; SPHK1; SPHK2.

Examples of genes for which a translatable molecule can be used to express the corresponding peptide or protein include: Linoleic Acid Metabolism, PRDX6; GRN; YWHAZ; CYP1B1.

Examples of genes for which a translatable molecule can be used to express the corresponding peptide or protein include: Methionine Metabolism, DNMT1; DNMT3B; AHCY; DNMT3A.

Examples of genes for which a translatable molecule can be used to express the corresponding peptide or protein include: Pyruvate Metabolism, GLO1; ALDH1A1; PKM2; LDHA.

Examples of genes for which a translatable molecule can be used to express the corresponding peptide or protein include: Arginine and Proline Metabolism, ALDH1A1; NOS3; NOS2A.

Examples of genes for which a translatable molecule can be used to express the corresponding peptide or protein include: Eicosanoid Signaling, PRDX6; GRN; YWHAZ.

Examples of genes for which a translatable molecule can be used to express the corresponding peptide or protein include: Fructose and Mannose Metabolism, HK2; GCK; HK1.

Examples of genes for which a translatable molecule can be used to express the corresponding peptide or protein include: Galactose Metabolism, HK2; GCK; HK1.

Examples of genes for which a translatable molecule can be used to express the corresponding peptide or protein include: Stilbene, Coumarine and Lignin Biosynthesis, PRDX6; PRDX1; TYR.

Examples of genes for which a translatable molecule can be used to express the corresponding peptide or protein include: Antigen Presentation Pathway, CALR; B2M.

Examples of genes for which a translatable molecule can be used to express the corresponding peptide or protein include: Biosynthesis of Steroids, NQO1; DHCR7.

Examples of genes for which a translatable molecule can be used to express the corresponding peptide or protein include: Butanoate Metabolism, ALDH1A1; NLGN1.

Examples of genes for which a translatable molecule can be used to express the corresponding peptide or protein include: Citrate Cycle, IDH2; IDH1.

Examples of genes for which a translatable molecule can be used to express the corresponding peptide or protein include: Fatty Acid Metabolism, ALDH1A1; CYP1B1.

Examples of genes for which a translatable molecule can be used to express the corresponding peptide or protein include: Glycerophospholipid Metabolism, PRDX6; CHKA.

Examples of genes for which a translatable molecule can be used to express the corresponding peptide or protein include: Histidine Metabolism, PRMT5; ALDH1A1.

Examples of genes for which a translatable molecule can be used to express the corresponding peptide or protein include: Inositol Metabolism, ERO1L; APEX1.

Examples of genes for which a translatable molecule can be used to express the corresponding peptide or protein include: Metabolism of Xenobiotics by Cytochrome p450, GSTP1; CYP1B1.

Examples of genes for which a translatable molecule can be used to express the corresponding peptide or protein include: Methane Metabolism, PRDX6; PRDX1.

Examples of genes for which a translatable molecule can be used to express the corresponding peptide or protein include: Phenylalanine Metabolism, PRDX6; PRDX1.

Examples of genes for which a translatable molecule can be used to express the corresponding peptide or protein include: Propanoate Metabolism, ALDH1A1; LDHA.

Examples of genes for which a translatable molecule can be used to express the corresponding peptide or protein include: Selenoamino Acid Metabolism, PRMT5; AHCY.

Examples of genes for which a translatable molecule can be used to express the corresponding peptide or protein include: Sphingolipid Metabolism, SPHK1; SPHK2.

Examples of genes for which a translatable molecule can be used to express the corresponding peptide or protein include: Aminophosphonate Metabolism, PRMT5.

Examples of genes for which a translatable molecule can be used to express the corresponding peptide or protein include: Androgen and Estrogen Metabolism, PRMT5.

Examples of genes for which a translatable molecule can be used to express the corresponding peptide or protein include: Ascorbate and Aldarate Metabolism, ALDH1A1.

Examples of genes for which a translatable molecule can be used to express the corresponding peptide or protein include: Bile Acid Biosynthesis, ALDH1A1.

Examples of genes for which a translatable molecule can be used to express the corresponding peptide or protein include: Cysteine Metabolism, LDHA.

Examples of genes for which a translatable molecule can be used to express the corresponding peptide or protein include: Fatty Acid Biosynthesis, FASN.

Examples of genes for which a translatable molecule can be used to express the corresponding peptide or protein include: Glutamate Receptor Signaling, GNB2L 1.

Examples of genes for which a translatable molecule can be used to express the corresponding peptide or protein include: NRF2-mediated Oxidative Stress Response, PRDX1.

Examples of genes for which a translatable molecule can be used to express the corresponding peptide or protein include: Pentose Phosphate Pathway, GPI.

Examples of genes for which a translatable molecule can be used to express the corresponding peptide or protein include: Pentose and Glucuronate Interconversions, UCHL1.

Examples of genes for which a translatable molecule can be used to express the corresponding peptide or protein include: Retinol Metabolism, ALDH1A1.

Examples of genes for which a translatable molecule can be used to express the corresponding peptide or protein include: Riboflavin Metabolism, TYR.

Examples of genes for which a translatable molecule can be used to express the corresponding peptide or protein include: Tyrosine Metabolism, PRMT5, TYR.

Examples of genes for which a translatable molecule can be used to express the corresponding peptide or protein include: Ubiquinone Biosynthesis, PRMT5.

Examples of genes for which a translatable molecule can be used to express the corresponding peptide or protein include: Valine, Leucine and Isoleucine Degradation, ALDH1A1.

Examples of genes for which a translatable molecule can be used to express the corresponding peptide or protein include: Glycine, Serine and Threonine Metabolism, CHKA.

Examples of genes for which a translatable molecule can be used to express the corresponding peptide or protein include: Lysine Degradation, ALDH1A1.

Examples of genes for which a translatable molecule can be used to express the corresponding peptide or protein include: Pain/Taste, TRPM5; TRPA1.

Examples of genes for which a translatable molecule can be used to express the corresponding peptide or protein include: Pain, TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a.

Examples of genes for which a translatable molecule can be used to express the corresponding peptide or protein include: Mitochondrial Function, AIF; CytC; SMAC (Diablo); Aifm-1; Aifm-2.

Examples of genes for which a translatable molecule can be used to express the corresponding peptide or protein include: Developmental Neurology, BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln.

Additional Synthesis Methods

In various aspects, this invention provides methods for synthesis of translatable molecules.

Translatable molecules of this invention can be synthesized and isolated using methods disclosed herein, as well as any pertinent techniques known in the art.

Some methods for preparing nucleic acids are given in, for example, Merino, Chemical Synthesis of Nucleoside Analogues, (2013); Gait, Oligonucleotide synthesis: a practical approach (1984); Herdewijn, Oligonucleotide Synthesis, Methods in Molecular Biology, Vol. 288 (2005).

In some embodiments, a translatable molecule can be made by in vitro transcription (IVT) reaction. A mix of nucleoside triphosphates (NTP) can be polymerized using T7 reagents, for example, to yield RNA from a DNA template. The DNA template can be degraded with RNase-free DNase, and the RNA column-separated.

In some embodiments, a ligase can be used to link a synthetic oligomer to the 3' end of an RNA molecule or an RNA transcript to form a translatable molecule. The synthetic oligomer that is ligated to the 3' end can provide the functionality of a polyA tail, and advantageously provide resistance to its removal by 3'-exoribonucleases. The ligated product translatable molecule can have increased specific activity and provide increased levels of ectopic protein expression.

In certain embodiments, ligated product translatable molecules of this invention can be made with an RNA transcript that has native specificity. The ligated product can be a synthetic molecule that retains the structure of the RNA transcript at the 5' end to ensure compatibility with the native specificity.

In further embodiments, ligated product translatable molecules of this invention can be made with an exogenous RNA transcript or non-natural RNA. The ligated product can be a synthetic molecule that retains the structure of the RNA.

In general, the canonical mRNA degradation pathway in cells includes the steps: (i) the polyA tail is gradually cut back to a stub by 3' exonucleases, shutting down the looping interaction required for efficient translation and leaving the cap open to attack; (ii) decapping complexes remove the 5' cap; (iii) the unprotected and translationally incompetent residuum of the transcript is degraded by 5' and 3' exonuclease activity.

Embodiments of this invention involve new translatable structures which can have increased translational activity over a native transcript. The translatable molecules can prevent exonucleases from trimming back the polyA tail in the process of de-adenylation.

Embodiments of this invention provide structures, compositions and methods for translatable molecules. Embodiments of this invention can provide translatable molecules containing one or more chemically modified monomers, as well as natural nucleotides, and having increased functional half-life.

Pharmaceutical Compositions

In some aspects, this invention provides pharmaceutical compositions containing a translatable compound and a pharmaceutically acceptable carrier.

A pharmaceutical composition can be capable of local or systemic administration. In some aspects, a pharmaceutical composition can be capable of any modality of administration. In certain aspects, the administration can be intravenous, subcutaneous, pulmonary, intramuscular, intraperitoneal, dermal, oral, or nasal administration.

Embodiments of this invention include pharmaceutical compositions containing a translatable compound in a lipid formulation.

In some embodiments, a pharmaceutical composition may comprise one or more lipids selected from cationic lipids, anionic lipids, sterols, pegylated lipids, and any combination of the foregoing.

In certain embodiments, a pharmaceutical composition can be substantially free of liposomes.

In further embodiments, a pharmaceutical composition can include liposomes or nanoparticles.

Some examples of lipids and lipid compositions for delivery of an active molecule of this invention are given in WO/2015/074085, which is hereby incorporated by reference in its entirety.

In additional embodiments, a pharmaceutical composition can contain an oligomeric compound within a viral or bacterial vector.

A pharmaceutical composition of this disclosure may include carriers, diluents or excipients as are known in the art. Examples of pharmaceutical compositions and methods are described, for example, in Remington's Pharmaceutical Sciences, Mack Publishing Co. (A. R. Gennaro ed. 1985), and Remington, The Science and Practice of Pharmacy, 21st Edition (2005).

Examples of excipients for a pharmaceutical composition include antioxidants, suspending agents, dispersing agents, preservatives, buffering agents, tonicity agents, and surfactants.

An effective dose of an agent or pharmaceutical formulation of this invention can be an amount that is sufficient to cause translation of a translatable molecule in a cell.

A therapeutically effective dose can be an amount of an agent or formulation that is sufficient to cause a therapeutic effect. A therapeutically effective dose can be administered in one or more separate administrations, and by different routes.

A therapeutically effective dose, upon administration, can result in serum levels of an active agent of 1-1000 pg/ml, or 1-1000 ng/ml, or 1-1000 μg/ml, or more.

A therapeutically effective dose of an active agent in vivo can be a dose of 0.001-0.01 mg/kg body weight, or 0.01-0.1 mg/kg, or 0.1-1 mg/kg, or 1-10 mg/kg, or 10-100 mg/kg.

A therapeutically effective dose of an active agent in vivo can be a dose of 0.001 mg/kg body weight, or 0.01 mg/kg, or 0.1 mg/kg, or 1 mg/kg, or 2 mg/kg, or 3 mg/kg, or 4 mg/kg, or 5 mg/kg, or more.

In Vitro Transcription (IVT) for Synthesis

The following protocol is for a 200 ul IVT reaction using NEB HiScribe T7 reagents, that should yield about 1 mg of RNA. 2.5×NTP mix was prepared as required by thawing individual 100 mM NTP stocks (ATP, GTP, CTP, and UTP nucleotides, or chemically modified counterparts) and pooling them together. For the IVT reaction, about 2-4 ug of the template was used for a 200 ul reaction. The 10×IVT reaction buffer, the 2.5× dNTP mix, the template DNA and the T7 RNA polymerase were mixed well by pipetting and incubated at 37° C. for 4 hours. To degrade the DNA template, the IVT reaction was diluted with 700 ul of nuclease-free water and then 10× DNase I buffer and 20 ul of the RNase-free DNase I are added to the IVT mix and incubated at 37° C. for 15 minutes. The diluted (to 1 ml) and DNase treated reaction was then purified by a Qiagen RNeasy Maxi columns as per the manufacturer's instructions with a final elution in RNase-free water. The purified RNA was then quantified by UV absorbance where the A260/A280 should be about 1.8-2.2, depending on the resuspension buffer used.

Enzymatic capping of IVT mRNA

For enzymatic capping, a 50× scaled-up version of NEB's one-step capping and 2'O-methylation reaction was used, that is suitable for treating up to 1 mg of IVT transcripts. A 10 ug RNA in a 20 ul reaction was recommended, based on the assumption that transcript length would be as short as 100 nt. However, a higher substrate-to-reaction volume was acceptable for mRNA transcripts, which were generally longer (about 300-600 nt) in length. Before initiating the capping reaction, the RNA was denatured at 65° C. for 5 minutes and then snap chilled to relieve any secondary conformations. For the total 1 ml capping reaction, 1 mg denatured RNA in 700 ul of nuclease-free water was used along with 100 ul (10×) capping buffer, 50 ul (10 mM) GTP, 50 ul (4 mM) SAM, 50 ul of (10 U/ul) Vaccinia capping enzyme and 50 ul of mRNA cap 2'-O-methyltransferase at (50 U/ul) were combined and incubated at 37° C. for 1 hour. The resulting capped mRNA was eluted using RNASE free water, re-purified on an RNeasy column, quantified by nanodrop. The mRNA was also visualized on the gel by running 500 ng of the purified product per lane in a denaturing gel after denaturation and snap-chill to remove secondary structures.

Dot Blots mRNA samples (100 ng) were doted on of each mRNA Biodyne® pre-cut modified nylon membrane (Thermo Scientific, Catalog #77016) (0.45 μm, 8×12 cm). The membrane was blocked by incubating 5% non-fat dried milk in TBS-T buffer (50 mM Tris HCl, 150 mM NaCl (pH 7.4) and 0.05% Tween20) for 1 hour, and then was incubated with primary antibody anti ds-RNA mAB J2 (English and Scientific Consulting K ft., Hungary, J2 monoclonal antibody (mAb), mouse, IgG2a, Batch #J2-1507, 1.0 mg/mL). After 1 hr incubation time, the membrane was washed using TBS-T buffer, each for 7 mins (4×7 min). Then the membrane was incubated with secondary antibody (Life Technologies, Goat anti-mouse IgG, (H+L), HRP Conjugate, Catalog #16066) for 1 hour at room temperature, following by washing 6 times with TBS-T (6×5 min), then once with TBS (5 min). The resulted membrane was incubated with ECL reagent (SUPERSIGNAL WEST PICO AND FEMTO MIX, Thermo Scientific, Catalog #34080 and 34095) for 3-4 min and exposed under white light inside Chemidoc-It$^2$ Imaging System

EXAMPLES

Example A: Cloning Example for Templates pIDT-SMART(Kan) (1962 bps, IDT DNA) was modified by point mutations to remove NotI and MluI restriction sites. At EcoRV site, the resulting plasmid was inserted with a 1226 bp DNA fragment containing the following DNA elements: stuffer DNA+T7 RNA promoter, 5' UTR from Tobacco Etch Virus (TEV), human EPO ORF, sequence containing 3' UTR from Xenopus beta globin (XbG) gene, polyA120, and BspQI restriction enzyme site+T7 terminator+stuffer DNA.

The resulting parental plasmid (pIDT-SMART-T7-TEV-hEPO-XbG-pA120) had total length of 3188 bps. The parental plasmid was used to clone the alternative ORFs.

Constructs containing TEV 5'UTR were constructed as follows. For Fluc, hEPO, and cmEPO constructs, the plasmid was linearized with NcoI and XhoI, and the synthesized ORF DNA fragments with NcoI and XhoI site were inserted by T4 DNA ligase. For hAdipo, hAAT, and F9 constructs, the synthesized ORF DNA fragments contained 20-25 bp of plasmid sequences flanking the designed ORFs, and cloned into the same linearized plasmid via a seamless cloning method.

SynK-cmEPO-XbG plasmid constructs were generated with synthesized DNA fragments containing SynK 5'UTR and cmEPO ORF with AflII and XhoI site. These fragments were cloned by T4 DNA ligase into the parental plasmid linearized with AflII and XhoI.

An example construct for hEPO is shown in Table 4.

TABLE 4

Cloning construct for hEPO

| DNA element | DNA Sequence |
|---|---|
| stuffer DNA + T7 RNA promoter | (SEQ ID NO: 2)<br>CGACACTGCTCGATCCGCTCGCACCGGGCTGGCAAGCCA<br>CGTTTGGTGTTGGACCCTCGTACAGAAGC**TAATACGACT**<br>**CACTATA** |
| TEV 5′ UTR | (SEQ ID NO: 3)<br>AGGAAACTTAAGTCAACACAACATATACAAAACAAACGA<br>ATCTCAAGCAATCAAGCATTCTACTTCTATTGCAGCAATT<br>TAAATCATTTCTTTTAAAGCAAAAGCAATTTTCTGAAAAT<br>TTTCACCATTTACGAACGATAGCC |
| human EPO ORF | (SEQ ID NO: 4)<br>ATGGGGGTGCACGAATGTCCTGCCTGGCTGTGGCTTCTCC<br>TGTCCCTGCTGTCGCTCCCTCTGGGCCTCCCAGTCCTGGG<br>CGCCCCACCACGCCTCATCTGTGACAGCCGAGTCCTGGAG<br>AGGTACCTCTTGGAGGCCAAGGAGGCCGAGAATATCACG<br>ACGGGCTGTGCTGAACACTGCAGCTTGAATGAGAATATC<br>ACTGTCCCAGACACCAAAGTTAATTTCTATGCCTGGAAGA<br>GGATGGAGGTCGGGCAGCAGGCCGTAGAAGTCTGGCAGG<br>GCCTGGCCCTGCTGTCGGAAGCTGTCCTGCGGGGCCAGGC<br>CCTGTTGGTCAACTCTTCCCAGCCGTGGGAGCCCCTGCAG<br>CTGCATGTGGATAAAGCCGTCAGTGGCCTTCGCAGCCTCA<br>CCACTCTGCTTCGGGCTCTGGGAGCCCAGAAGGAAGCCA<br>TCTCCCCTCCAGATGCGGCCTCAGCTGCTCCACTCCGAAC<br>AATCACTGCTGACACTTTCCGCAAACTCTTCCGAGTCTAC<br>TCCAATTTCCTCCGGGGAAAGCTGAAGCTGTACACAGGG<br>GAGGCCTGCAGGACAGGGGACAGATGA |
| XbG3' UTR | (SEQ ID NO: 5)<br>ATAAGTGAACTCGAGCTAGTGACTGACTAGGATCTGGTTA<br>CCACTAAACCAGCCTCAAGAACACCCGAATGGAGTCTCT<br>AAGCTACATAATACCAACTTACACTTACAAAATGTTGTCC<br>CCCAAAATGTAGCCATTCGTATCTGCTCCTAATAAAAAGA<br>AAGTTTCTTCACATTCTAG |

TABLE 4-continued

| Cloning construct for hEPO | |
|---|---|
| DNA element | DNA Sequence |
| polyA120 | (SEQ ID NO: 6)<br>AAAAAAAAAAAAAAAAAAAAAAAAAAAAAAAAAAAAA<br>AAAAAAAAAAAAAAAAAAAAAAAAAAAAAAAAAAAAA<br>AAAAAAAAAAAAAAAAAAAAAAAAAAAAAAAAAAAAA<br>AAAAAAAAA |
| BspQI site + T7 terminator + stuffer DNA | (SEQ ID NO: 7)<br>**GAAGAGC**GCTAGCGTCTTCAGCTGCACATAACCCCTTGG<br>GGCCTCTAAACGGGTCTTGAGGGGTTTTTTGCCTCTGACA<br>CATGCAGCTCCCGGGGATCGACGAGAGCAGCGCGACTGG |

The nucleotide T and GC compositions of wildtype protein coding sequences are shown in Table 5.

TABLE 5

| Nucleotide T compositions of wildtype protein coding sequences | | |
|---|---|---|
| Protein | T % | GC % |
| Fluc plus pGL3 | 25.8 | 47 |
| Human Adiponectin | 22.0 | 54 |
| Human AAT | 21.6 | 52 |
| Human F9 | 27.6 | 41 |
| Human EPO | 20.3 | 60 |
| Cynomolgus Monkey EPO | 20.4 | 60 |

Example B: Templates and mRNAs for hEPO

Figure 4:
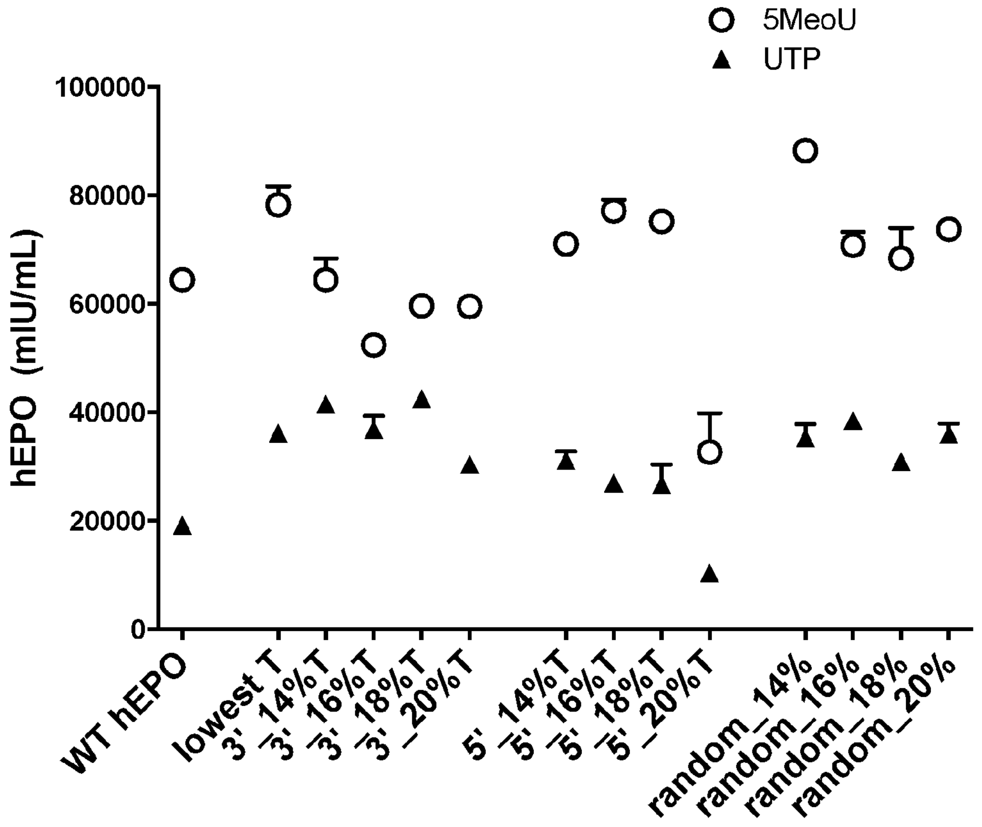
FIG. 4 shows the results of surprisingly increased human EPO protein production for a translatable molecule of this invention. Human EPO ARC-RNA was synthesized using a DNA template having reduced deoxyadenosine nucleotides in an open reading frame of the template strand, as well as reduced deoxythymidine nucleotides in the complementary non-template strand (reduced T). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 4 shows the results of surprisingly increased human EPO protein production for a translatable molecule of this invention. Human EPO ARC-RNA was synthesized using a DNA template having reduced deoxyadenosine nucleotides in an open reading frame of the template strand, as well as reduced complementary deoxythymidine nucleotides in the non-template strand (reduced T). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 4 shows surprisingly high translational efficiency of the ARC-mRNA (5MeOU) compared to the wild type hEPO mRNA (UTP). First, the ARC-mRNA (5MeOU) exhibited superior expression efficiency at all levels of template T composition as compared to the hEPO mRNA (UTP).

Further, FIG. 4 shows that ARC-mRNA (5MeOU) products exhibited unexpectedly superior expression efficiency at levels of template T composition of 13-16%, as compared to either wild type or "reduced T" hEPO mRNA (UTP).

Moreover, the ARC-mRNA (5MeOU) exhibited unexpectedly superior expression efficiency at 14% template T composition, when codon replacement was done randomly.

The compositions of the templates for hEPO are shown in Table 6.

TABLE 6

| Non-Template Nucleotide T compositions for hEPO | |
|---|---|
| hEPO | T % |
| hEPO_lowest_T | 13.1 |
| hEPO_3'_14% T | 13.9 |
| hEPO_3'_16% T | 16.0 |
| hEPO_3'_18% T | 17.9 |
| hEPO_3'_20% T | 19.9 |
| hEPO_5'_14% T | 13.9 |
| hEPO_5'_16% T | 16.0 |
| hEPO_5'_18% T | 17.9 |
| hEPO_5'_20% T | 19.9 |
| hEPO_random_14% | 13.9 |
| hEPO_random_16% | 16.0 |
| hEPO_random_18% | 17.9 |
| hEPO_random_20% | 19.9 |

Human EPO ORF reference. Sense strand, non-template. NM_000799.3:182-763 CDS Homo sapiens erythropoietin.

(SEQ ID NO: 8)

atgggggtgcacgaatgtcctgcctggctgtggcttctcctgtccctgctgtcgctccc tctgggcctcccagtcctgggcgccccaccacgcctcatctgtgacagccgagtcctgg agaggtacctcttggaggccaaggaggccgagaatatcacgacgggctgtgctgaacac tgcagcttgaatgagaatatcactgtcccagacaccaaagttaatttctatgcctggaa gaggatggaggtcgggcagcaggccgtagaagtctggcagggcctggccctgctgtcgg aagctgtcctgcggggccaggccctgttggtcaactcttcccagccgtgggagcccctg cagctgcatgtggataaagccgtcagtggccttcgcagcctcaccactctgcttcggc -continued tctgggagcccagaaggaagccatctcccctccagatgcggcctcagctgctccactcc gaacaatcactgctgacactttccgcaaactcttccgagtctactccaatttcctccgg ggaaagctgaagctgtacacaggggaggcctgcaggacaggggacagatga hEPO sense strand, non-template. 3'_lowest_T.

(SEQ ID NO: 9)

ATGGGGGTGCACGAATGCCCCGCCTGGCTGTGGCTGCTCCTGAGCCTGC

TGAGCCTCCCCCTGGGCCTCCCAGTCCTGGGCGCCCCACCACGCCTCATCTGCGACAGC

CGAGTCCTGGAGAGGTACCTCCTGGAGGCCAAGGAGGCCGAGAACATCACGACGGGCTG

CGCCGAACACTGGAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGCTGGTCAACAGCAGCCAGCCGTG

GGAGCCCCTGCAGCTGCACGTGGACAAAGCCGTCAGCGGCCTGCGCAGCCTCACCACCC

TGCTGCGGGCCCTGGGAGCCCAGAAGGAAGCCATCAGCCCCCCAGACGCGGCCAGCGCC

GCCCCACTCCGAACAATCACCGCCGACACCTTCCGCAAACTCTTCCGAGTCTACAGCAA

CTTCCTCCGGGGAAAGCTGAAGCTGTACACAGGGGAGGCCTGCAGGACAGGGGACAGAT

GA hEPO sense strand, non-template. 3'_14%_T.

(SEQ ID NO: 10)

ATGGGGGTGCACGAATGTCCTGCCTGGCTGTGGCTTCTCCTGTCCCTGC

TGTCGCTCCCCCTGGGCCTCCCAGTCCTGGGCGCCCCACCACGCCTCATCTGCGACAGC

CGAGTCCTGGAGAGGTACCTCCTGGAGGCCAAGGAGGCCGAGAACATCACGACGGGCTG

CGCCGAACACTGCAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGCTGGTCAACAGCAGCCAGCCGTG

GGAGCCCCTGCAGCTGCACGTGGACAAAGCCGTCAGCGGCCTGCGCAGCCTCACCACCC

TGCTGCGGGCCCTGGGAGCCCAGAAGGAAGCCATCAGCCCCCCAGACGCGGCCAGCGCC

GCCCCACTCCGAACAATCACCGCCGACACCTTCCGCAAACTCTTCCGAGTCTACAGCAA

CTTCCTCCGGGGAAAGCTGAAGCTGTACACAGGGGAGGCCTGCAGGACAGGGGACAGAT

GA hEPO sense strand, non-template. 3'_16%_T.

(SEQ ID NO: 11)

ATGGGGGTGCACGAATGTCCTGCCTGGCTGTGGCTTCTCCTGTCCCTGC

TGTCGCTCCCTCTGGGCCTCCCAGTCCTGGGCGCCCCACCACGCCTCATCTGTGACAGC

CGAGTCCTGGAGAGGTACCTCTTGGAGGCCAAGGAGGCCGAGAATATCACGACGGGCTG

TGCTGAACACTGGAGCTTGAATGAGAATATCACTGTCCCAGACACCAAAGTTAATTTCT

ACGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGCTGGTCAACAGCAGCCAGCCGTG

GGAGCCCCTGCAGCTGCACGTGGACAAAGCCGTCAGCGGCCTGCGCAGCCTCACCACCC

TGCTGCGGGCCCTGGGAGCCCAGAAGGAAGCCATCAGCCCCCCAGACGCGGCCAGCGCC

GCCCCACTCCGAACAATCACCGCCGACACCTTCCGCAAACTCTTCCGAGTCTACAGCAA

CTTCCTCCGGGGAAAGCTGAAGCTGTACACAGGGGAGGCCTGCAGGACAGGGGACAGAT

GA

-continued hEPO sense strand, non-template. 3'_18%_T.
(SEQ ID NO: 12)
ATGGGGGTGCACGAATGTCCTGCCTGGCTGTGGCTTCTCCTGTCCCTGC
TGTCGCTCCCTCTGGGCCTCCCAGTCCTGGGCGCCCCACCACGCCTCATCTGTGACAGC
CGAGTCCTGGAGAGGTACCTCTTGGAGGCCAAGGAGGCCGAGAATATCACGACGGGCTG
TGCTGAACACTGCAGCTTGAATGAGAATATCACTGTCCCAGACACCAAAGTTAATTTCT
ATGCCTGGAAGAGGATGGAGGTCGGGCAGCAGGCCGTAGAAGTCTGGCAGGGCCTGGCC
CTGCTGTCGGAAGCTGTCCTGCGGGGCCAGGCCCTGTTGGTCAACTCTTCCCAGCCGTG
GGAGCCCCTGCAGCTGCATGTGGATAAAGCCGTCAGTGGCCTTCGCAGCCTCACCACCC
TGCTGCGGGCCCTGGGAGCCCAGAAGGAAGCCATCAGCCCCCCAGACGCGGCCAGCGCC
GCCCCACTCCGAACAATCACCGCCGACACCTTCCGCAAACTCTTCCGAGTCTACAGCAA
CTTCCTCCGGGGAAAGCTGAAGCTGTACACAGGGGAGGCCTGCAGGACAGGGGACAGAT
GA hEPO sense strand, non-template. 3'_20%_T.
(SEQ ID NO: 13)
ATGGGGGTGCACGAATGTCCTGCCTGGCTGTGGCTTCTCCTGTCCCTGC
TGTCGCTCCCTCTGGGCCTCCCAGTCCTGGGCGCCCCACCACGCCTCATCTGTGACAGC
CGAGTCCTGGAGAGGTACCTCTTGGAGGCCAAGGAGGCCGAGAATATCACGACGGGCTG
TGCTGAACACTGCAGCTTGAATGAGAATATCACTGTCCCAGACACCAAAGTTAATTTCT
ATGCCTGGAAGAGGATGGAGGTCGGGCAGCAGGCCGTAGAAGTCTGGCAGGGCCTGGCC
CTGCTGTCGGAAGCTGTCCTGCGGGGCCAGGCCCTGTTGGTCAACTCTTCCCAGCCGTG
GGAGCCCCTGCAGCTGCATGTGGATAAAGCCGTCAGTGGCCTTCGCAGCCTCACCACTC
TGCTTCGGGCTCTGGGAGCCCAGAAGGAAGCCATCTCCCCTCCAGATGCGGCCTCAGCT
GCTCCACTCCGAACAATCACTGCTGACACTTTCCGCAAACTCTTCCGAGTCTACAGCAA
CTTCCTCCGGGGAAAGCTGAAGCTGTACACAGGGGAGGCCTGCAGGACAGGGGACAGAT
GA hEPO sense strand, non-template. 5'_14%_T.
(SEQ ID NO: 14)
ATGGGGGTGCACGAATGCCCCGCCTGGCTGTGGCTGCTCCTGAGCCTGC
TGAGCCTCCCCCTGGGCCTCCCAGTCCTGGGCGCCCCACCACGCCTCATCTGCGACAGC
CGAGTCCTGGAGAGGTACCTCCTGGAGGCCAAGGAGGCCGAGAACATCACGACGGGCTG
CGCCGAACACTGCAGCCTGAACGAGAACATCACCGTCCCAGACACCAAAGTGAACTTCT
ACGCCTGGAAGAGGATGGAGGTCGGGCAGCAGGCCGTAGAAGTCTGGCAGGGCCTGGCC
CTGCTGAGCGAAGCCGTCCTGCGGGGCCAGGCCCTGCTGGTCAACAGCAGCCAGCCGTG
GGAGCCCCTGCAGCTGCACGTGGACAAAGCCGTCAGCGGCCTGCGCAGCCTCACCACCC
TGCTGCGGGCCCTGGGAGCCCAGAAGGAAGCCATCAGCCCCCCAGACGCGGCCAGCGCC
GCCCCACTCCGAACAATCACTGCTGACACTTTCCGCAAACTCTTCCGAGTCTACTCCAA
TTTCCTCCGGGGAAAGCTGAAGCTGTACACAGGGGAGGCCTGCAGGACAGGGGACAGAT
GA hEPO sense strand, non-template. 5'_16%_T.
(SEQ ID NO: 15)
ATGGGGGTGCACGAATGCCCCGCCTGGCTGTGGCTGCTCCTGAGCCTGC
TGAGCCTCCCCCTGGGCCTCCCAGTCCTGGGCGCCCCACCACGCCTCATCTGCGACAGC
CGAGTCCTGGAGAGGTACCTCCTGGAGGCCAAGGAGGCCGAGAACATCACGACGGGCTG -continued

CGCCGAACACTGGAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGCTGGTCAACAGCAGCCAGCCGTG

GGAGCCCCTGCAGCTGCACGTGGATAAAGCCGTCAGTGGCCTTCGCAGCCTCACCACTC

TGCTTCGGGCTCTGGGAGCCCAGAAGGAAGCCATCTCCCCTCCAGATGCGGCCTCAGCT

GCTCCACTCCGAACAATCACTGCTGACACTTTCCGCAAACTCTTCCGAGTCTACTCCAA

TTTCCTCCGGGGAAAGCTGAAGCTGTACACAGGGGAGGCCTGCAGGACAGGGGACAGAT

GA hEPO sense strand, non-template. 5'_18%_T.

(SEQ ID NO: 16)

ATGGGGGTGCACGAATGCCCCGCCTGGCTGTGGCTGCTCCTGAGCCTGC

TGAGCCTCCCCCTGGGCCTCCCAGTCCTGGGCGCCCCACCACGCCTCATCTGCGACAGC

CGAGTCCTGGAGAGGTACCTCCTGGAGGCCAAGGAGGCCGAGAACATCACGACGGGCTG

CGCCGAACACTGCAGCCTGAACGAGAACATCACTGTCCCAGACACCAAAGTTAATTTCT

ATGCCTGGAAGAGGATGGAGGTCGGGCAGCAGGCCGTAGAAGTCTGGCAGGGCCTGGCC

CTGCTGTCGGAAGCTGTCCTGCGGGGCCAGGCCCTGTTGGTCAACTCTTCCCAGCCGTG

GGAGCCCCTGCAGCTGCATGTGGATAAAGCCGTCAGTGGCCTTCGCAGCCTCACCACTC

TGCTTCGGGCTCTGGGAGCCCAGAAGGAAGCCATCTCCCCTCCAGATGCGGCCTCAGCT

GCTCCACTCCGAACAATCACTGCTGACACTTTCCGCAAACTCTTCCGAGTCTACTCCAA

TTTCCTCCGGGGAAAGCTGAAGCTGTACACAGGGGAGGCCTGCAGGACAGGGGACAGAT

GA hEPO sense strand, non-template. 5'_20%_T.

(SEQ ID NO: 17)

ATGGGGGTGCACGAATGCCCCGCCTGGCTGTGGCTTCTCCTGTCCCTGC

TGTCGCTCCCTCTGGGCCTCCCAGTCCTGGGCGCCCCACCACGCCTCATCTGTGACAGC

CGAGTCCTGGAGAGGTACCTCTTGGAGGCCAAGGAGGCCGAGAATATCACGACGGGCTG

TGCTGAACACTGCAGCTTGAATGAGAATATCACTGTCCCAGACACCAAAGTTAATTTCT

ATGCCTGGAAGAGGATGGAGGTCGGGCAGCAGGCCGTAGAAGTCTGGCAGGGCCTGGCC

CTGCTGTCGGAAGCTGTCCTGCGGGGCCAGGCCCTGTTGGTCAACTCTTCCCAGCCGTG

GGAGCCCCTGCAGCTGCATGTGGATAAAGCCGTCAGTGGCCTTCGCAGCCTCACCACTC

TGCTTCGGGCTCTGGGAGCCCAGAAGGAAGCCATCTCCCCTCCAGATGCGGCCTCAGCT

GCTCCACTCCGAACAATCACTGCTGACACTTTCCGCAAACTCTTCCGAGTCTACTCCAA

TTTCCTCCGGGGAAAGCTGAAGCTGTACACAGGGGAGGCCTGCAGGACAGGGGACAGAT

GA hEPO sense strand, non-template. random_14%_T.

(SEQ ID NO: 18)

ATGGGGGTGCACGAATGCCCTGCCTGGCTGTGGCTGCTCCTGAGCCTGC

TGAGCCTCCCCCTGGGCCTCCCAGTCCTGGGCGCCCCACCACGCCTCATCTGCGACAGC

CGAGTCCTGGAGAGGTACCTCCTGGAGGCCAAGGAGGCCGAGAACATCACGACGGGCTG

CGCCGAACACTGGAGCTTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGCTGGTCAACAGCTCCCAGCCGTG

GGAGCCCCTGCAGCTGCACGTGGACAAAGCCGTCAGCGGCCTGCGCAGCCTCACCACCC

TGCTGCGGGCCCTGGGAGCCCAGAAGGAAGCCATCAGCCCCCCAGACGCGGCCAGCGCC

-continued

GCCCCACTCCGAACAATCACCGCTGACACCTTCCGCAAACTCTTCCGAGTCTACTCCAA

CTTCCTCCGGGGAAAGCTGAAGCTGTACACAGGGGAGGCCTGCAGGACAGGGGACAGAT

GA hEPO sense strand, non-template. random_16%_T.
(SEQ ID NO: 19)
ATGGGGGTGCACGAATGTCCCGCCTGGCTGTGGCTGCTCCTGAGCCTGC

TGAGCCTCCCTCTGGGCCTCCCAGTCCTGGGCGCCCCACCACGCCTCATCTGCGACAGC

CGAGTCCTGGAGAGGTACCTCCTGGAGGCCAAGGAGGCCGAGAATATCACGACGGGCTG

TGCCGAACACTGCAGCTTGAACGAGAATATCACCGTCCCAGACACCAAAGTTAATTTCT

ATGCCTGGAAGAGGATGGAGGTCGGGCAGCAGGCCGTAGAAGTCTGGCAGGGCCTGGCC

CTGCTGTCGGAAGCTGTCCTGCGGGGCCAGGCCCTGCTGGTCAACAGCAGCCAGCCGTG

GGAGCCCCTGCAGCTGCACGTGGATAAAGCCGTCAGCGGCCTGCGCAGCCTCACCACCC

TGCTGCGGGCTCTGGGAGCCCAGAAGGAAGCCATCAGCCCTCCAGATGCGGCCAGCGCC

GCTCCACTCCGAACAATCACCGCCGACACTTTCCGCAAACTCTTCCGAGTCTACAGCAA

CTTCCTCCGGGGAAAGCTGAAGCTGTACACAGGGGAGGCCTGCAGGACAGGGGACAGAT

GA hEPO sense strand, non-template. random_18%_T.
(SEQ ID NO: 20)
ATGGGGGTGCACGAATGTCCTGCCTGGCTGTGGCTTCTCCTGTCCCTGC

TGAGCCTCCCTCTGGGCCTCCCAGTCCTGGGCGCCCCACCACGCCTCATCTGTGACAGC

CGAGTCCTGGAGAGGTACCTCTTGGAGGCCAAGGAGGCCGAGAACATCACGACGGGCTG

CGCTGAACACTGCAGCCTGAATGAGAATATCACTGTCCCAGACACCAAAGTGAATTTCT

ATGCCTGGAAGAGGATGGAGGTCGGGCAGCAGGCCGTAGAAGTCTGGCAGGGCCTGGCC

CTGCTGAGCGAAGCCGTCCTGCGGGGCCAGGCCCTGTTGGTCAACAGCAGCCAGCCGTG

GGAGCCCCTGCAGCTGCATGTGGATAAAGCCGTCAGTGGCCTTCGCAGCCTCACCACTC

TGCTTCGGGCCCTGGGAGCCCAGAAGGAAGCCATCTCCCCTCCAGACGCGGCCTCAGCT

GCCCCACTCCGAACAATCACTGCTGACACTTTCCGCAAACTCTTCCGAGTCTACAGCAA

TTTCCTCCGGGGAAAGCTGAAGCTGTACACAGGGGAGGCCTGCAGGACAGGGGACAGAT

GA hEPO sense strand, non-template. random_20%_T.
(SEQ ID NO: 21)
ATGGGGGTGCACGAATGTCCTGCCTGGCTGTGGCTTCTCCTGTCCCTGC

TGTCGCTCCCTCTGGGCCTCCCAGTCCTGGGCGCCCCACCACGCCTCATCTGTGACAGC

CGAGTCCTGGAGAGGTACCTCTTGGAGGCCAAGGAGGCCGAGAATATCACGACGGGCTG

TGCTGAACACTGCAGCTTGAATGAGAATATCACTGTCCCAGACACCAAAGTTAACTTCT

ATGCCTGGAAGAGGATGGAGGTCGGGCAGCAGGCCGTAGAAGTCTGGCAGGGCCTGGCC

CTGCTGTCGGAAGCTGTCCTGCGGGGCCAGGCCCTGCTGGTCAACTCTTCCCAGCCGTG

GGAGCCCCTGCAGCTGCATGTGGATAAAGCCGTCAGTGGCCTTCGCAGCCTCACCACTC

TGCTTCGGGCTCTGGGAGCCCAGAAGGAAGCCATCTCCCCTCCAGATGCGGCCTCAGCT

GCTCCACTCCGAACAATCACTGCTGACACTTTCCGCAAACTCTTCCGAGTCTACTCCAA

TTTCCTCCGGGGAAAGCTGAAGCTGTACACAGGGGAGGCCTGCAGGACAGGGGACAGAT

GA

-continued

TEV-hEPO-XbG sense strand, non-template.
3'_lowest_T (1014 nt).
(SEQ ID NO: 22)

AGGAAACTTAAGTCAACACAACATATACAAAACAAACGAATCTCAAGGA

ATCAAGCATTCTAGTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCAGCCAGCCGTGGGAGCCCCTGCAGCTGCACGTGGACAAAGCCGTC

AGCGGCCTGCGCAGCCTCACCACCCTGCTGCGGGCCCTGGGAGCCCAGAAGGAAGCCAT

CAGCCCCCCAGACGCGGCCAGCGCCGCCCCACTCCGAACAATCACCGCCGACACCTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACGAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAA

TEV-hEPO-XbG sense strand, non-template.
3'_14%_T (1014 nt).
(SEQ ID NO: 23)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGTCGCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCAGCCAGCCGTGGGAGCCCCTGCAGCTGCACGTGGACAAAGCCGTC

AGCGGCCTGCGCAGCCTCACCACCCTGCTGCGGGCCCTGGGAGCCCAGAAGGAAGCCAT

CAGCCCCCCAGACGCGGCCAGCGCCGCCCCACTCCGAACAATCACCGCCGACACCTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAA

-continued

TEV-hEPO-XbG sense strand, non-template.
3'_16%_T (1014 nt).

(SEQ ID NO: 24)

AGGAAACTTAAGTCAACACAACATATACAAAACAAACGAATCTCAAGCA

ATCAAGCATTCTAGTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGTCGCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAATATCACGACGGGCTGTGCTGAACACTGCAGCTTGAATGAGAATATCACT

GTCCCAGACACCAAAGTTAATTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCAGCCAGCCGTGGGAGCCCCTGCAGCTGCACGTGGACAAAGCCGTC

AGCGGCCTGCGCAGCCTCACCACCCTGCTGCGGGCCCTGGGAGCCCAGAAGGAAGCCAT

CAGCCCCCCAGACGCGGCCAGCGCCGCCCCACTCCGAACAATCACCGCCGACACCTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACGAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAA

TEV-hEPO-XbG sense strand, non-template.
3'_18%_T (1014 nt).

(SEQ ID NO: 25)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGTCGCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAATATCACGACGGGCTGTGCTGAACACTGCAGCTTGAATGAGAATATCACT

GTCCCAGACACCAAAGTTAATTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGTTGGTCAACTCTTCCCAGCCGTGGGAGCCCCTGCAGCTGCATGTGGATAAAGCCGTC

AGTGGCCTTCGCAGCCTCACCACCCTGCTGCGGGCCCTGGGAGCCCAGAAGGAAGCCAT

CAGCCCCCCAGACGCGGCCAGCGCCGCCCCACTCCGAACAATCACCGCCGACACCTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAA

-continued

TEV-hEPO-XbG sense strand, non-template.
3'_20%_T (1014 nt).
(SEQ ID NO: 26)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGTCGCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAATATCACGACGGGCTGTGCTGAACACTGCAGCTTGAATGAGAATATCACT

GTCCCAGACACCAAAGTTAATTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGTTGGTCAACTCTTCCCAGCCGTGGGAGCCCCTGCAGCTGCATGTGGATAAAGCCGTC

AGTGGCCTTCGCAGCCTCACCACTCTGCTTCGGGCTCTGGGAGCCCAGAAGGAAGCCAT

CTCCCCTCCAGATGCGGCCTCAGCTGCTCCACTCCGAACAATCACTGCTGACACTTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACGAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAA

TEV-hEPO-XbG sense strand, non-template.
5'_14%_T (1014 nt).
(SEQ ID NO: 27)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCAGCCAGCCGTGGGAGCCCCTGCAGCTGCACGTGGACAAAGCCGTC

AGCGGCCTGCGCAGCCTCACCACCCTGCTGCGGGCCCTGGGAGCCCAGAAGGAAGCCAT

CAGCCCCCCAGACGCGGCCAGCGCCGCCCCACTCCGAACAATCACTGCTGACACTTTCC

GCAAACTCTTCCGAGTCTACTCCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAA

-continued

TEV-hEPO-XbG sense strand, non-template.
5'_16%_T (1014 nt).
(SEQ ID NO: 28)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCAGCCAGCCGTGGGAGCCCCTGCAGCTGCACGTGGATAAAGCCGTC

AGTGGCCTTCGCAGCCTCACCACTCTGCTTCGGGCTCTGGGAGCCCAGAAGGAAGCCAT

CTCCCCTCCAGATGCGGCCTCAGCTGCTCCACTCCGAACAATCACTGCTGACACTTTCC

GCAAACTCTTCCGAGTCTACTCCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACGAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAA

TEV-hEPO-XbG sense strand, non-template.
5'_18%_T (1014 nt).
(SEQ ID NO: 29)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCCTGAACGAGAACATCACT

GTCCCAGACACCAAAGTTAATTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGTTGGTCAACTCTTCCCAGCCGTGGGAGCCCCTGCAGCTGCATGTGGATAAAGCCGTC

AGTGGCCTTCGCAGCCTCACCACTCTGCTTCGGGCTCTGGGAGCCCAGAAGGAAGCCAT

CTCCCCTCCAGATGCGGCCTCAGCTGCTCCACTCCGAACAATCACTGCTGACACTTTCC

GCAAACTCTTCCGAGTCTACTCCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAA

-continued

TEV-hEPO-XbG sense strand, non-template.
5'_20%_T (1014 nt).

(SEQ ID NO: 30)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTTCTCCTGTCCCTGCTGTCGCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAATATCACGACGGGCTGTGCTGAACACTGCAGCTTGAATGAGAATATCACT

GTCCCAGACACCAAAGTTAATTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGTTGGTCAACTCTTCCCAGCCGTGGGAGCCCCTGCAGCTGCATGTGGATAAAGCCGTC

AGTGGCCTTCGCAGCCTCACCACTCTGCTTCGGGCTCTGGGAGCCCAGAAGGAAGCCAT

CTCCCCTCCAGATGCGGCCTCAGCTGCTCCACTCCGAACAATCACTGCTGACACTTTCC

GCAAACTCTTCCGAGTCTACTCCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACGAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAA

TEV-hEPO-XbG sense strand, non-template.
random_14%_T (1014 nt).

(SEQ ID NO: 31)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCTGCC

TGGCTGTGGCTGCTCCTGAGCCTGCTGAGCCTCCCCCTGGGCCTCCCAGTCCTGGGCGC

CCCACCACGCCTCATCTGCGACAGCCGAGTCCTGGAGAGGTACCTCCTGGAGGCCAAGG

AGGCCGAGAACATCACGACGGGCTGCGCCGAACACTGCAGCTTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGCTGGTCAACAGCTCCCAGCCGTGGGAGCCCCTGCAGCTGCACGTGGACAAAGCCGTC

AGCGGCCTGCGCAGCCTCACCACCCTGCTGCGGGCCCTGGGAGCCCAGAAGGAAGCCAT

CAGCCCCCCAGACGCGGCCAGCGCCGCCCCACTCCGAACAATCACCGCTGACACCTTCC

GCAAACTCTTCCGAGTCTACTCCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAA

-continued

TEV-hEPO-XbG sense strand, non-template.
random_16%_T (1014 nt).

(SEQ ID NO: 32)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCCGCC

TGGCTGTGGCTGCTCCTGAGCCTGCTGAGCCTCCCTCTGGGCCTCCCAGTCCTGGGCGC

CCCACCACGCCTCATCTGCGACAGCCGAGTCCTGGAGAGGTACCTCCTGGAGGCCAAGG

AGGCCGAGAATATCACGACGGGCTGTGCCGAACACTGCAGCTTGAACGAGAATATCACC

GTCCCAGACACCAAAGTTAATTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGCTGGTCAACAGCAGCCAGCCGTGGGAGCCCCTGCAGCTGCACGTGGATAAAGCCGTC

AGCGGCCTGCGCAGCCTCACCACCCTGCTGCGGGCTCTGGGAGCCCAGAAGGAAGCCAT

CAGCCCTCCAGATGCGGCCAGCGCCGCTCCACTCCGAACAATCACCGCCGACACTTTCC

GCAAACTCTTCCGAGTCTACAGCAACTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAA

AAAAAAAAAAAAAAAAAAAA

TEV-hEPO-XbG sense strand, non-template.
random_18% T (1014 nt).

(SEQ ID NO: 33)

AGGAAACTTAAGTCAACACAACATATACAAAACAAACGAATCTCAAGGA

ATCAAGCATTCTAGTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGAGCCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAACATCACGACGGGCTGCGCTGAACACTGCAGCCTGAATGAGAATATCACT

GTCCCAGACACCAAAGTGAATTTCTATGCCTGGAAGAGGATGGAGGTCGGGCAGCAGGC

CGTAGAAGTCTGGCAGGGCCTGGCCCTGCTGAGCGAAGCCGTCCTGCGGGGCCAGGCCC

TGTTGGTCAACAGCAGCCAGCCGTGGGAGCCCCTGCAGCTGCATGTGGATAAAGCCGTC

AGTGGCCTTCGCAGCCTCACCACTCTGCTTCGGGCCCTGGGAGCCCAGAAGGAAGCCAT

CTCCCCTCCAGACGCGGCCTCAGCTGCCCCACTCCGAACAATCACTGCTGACACTTTCC

GCAAACTCTTCCGAGTCTACAGCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACGAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAA

-continued

TEV-hEPO-XbG sense strand, non-template.
random_20%_T (1014 nt).

(SEQ ID NO: 34)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGTCCCTGCTGTCGCTCCCTCTGGGCCTCCCAGTCCTGGGCGC

CCCACCACGCCTCATCTGTGACAGCCGAGTCCTGGAGAGGTACCTCTTGGAGGCCAAGG

AGGCCGAGAATATCACGACGGGCTGTGCTGAACACTGCAGCTTGAATGAGAATATCACT

GTCCCAGACACCAAAGTTAACTTCTATGCCTGGAAGAGGATGGAGGTCGGGCAGCAGGC

CGTAGAAGTCTGGCAGGGCCTGGCCCTGCTGTCGGAAGCTGTCCTGCGGGGCCAGGCCC

TGCTGGTCAACTCTTCCCAGCCGTGGGAGCCCCTGCAGCTGCATGTGGATAAAGCCGTC

AGTGGCCTTCGCAGCCTCACCACTCTGCTTCGGGCTCTGGGAGCCCAGAAGGAAGCCAT

CTCCCCTCCAGATGCGGCCTCAGCTGCTCCACTCCGAACAATCACTGCTGACACTTTCC

GCAAACTCTTCCGAGTCTACTCCAATTTCCTCCGGGGAAAGCTGAAGCTGTACACAGGG

GAGGCCTGCAGGACAGGGGACAGATGACTCGAGCTAGTGACTGACTAGGATCTGGTTAC

CACTAAACCAGCCTCAAGAACACCCGAATGGAGTCTCTAAGCTACATAATACCAACTTA

CACTTACAAAATGTTGTCCCCCAAAATGTAGCCATTCGTATCTGCTCCTAATAAAAAGA

AAGTTTCTTCACATTCTAGAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAA

TEV-hEPO-XbG ARC-mRNA. 3'_lowest_T (1014 nt).

(SEQ ID NO: 35)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCCCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

CAUCACGACGGGCUGCGCCGAACACUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGCUGGUCAA

CAGCAGCCAGCCGUGGGAGCCCCUGCAGCUGCACGUGGACAAAGCCGUCAGCGGCCUGC

GCAGCCUCACCACCCUGCUGCGGGCCCUGGGAGCCCAGAAGGAAGCCAUCAGCCCCCCA

GACGCGGCCAGCGCCGCCCCACUCCGAACAAUCACCGCCGACACCUUCCGCAAACUCUU

CCGAGUCUACAGCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

-continued

AUGUUGUCGCCCAAAAUGUAGCCAUUCGUAUCUGCUCCUAAUAAAAAGAAAGUUUCUUC
ACAUUCUAGAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAA
AAAAAAAAAAA

TEV-hEPO-XbG ARC-mRNA. 3'_14%_T (1014 nt).
(SEQ ID NO: 36)
5'-cap-
AGGAAACUUAAGUCAACACAACAUAUACAAAACAAACGAAUCUCAAGCAAUCAAGCAUU
CUACUUCUAUUGCAGCAAUUUAAAUCAUUUCUUUUAAAGCAAAAGCAAUUUUCUGAAAA
UUUUCACCAUUUACGAACGAUAGCCAUGGGGGUGCACGAAUGUCCUGCCUGGCUGUGGC
UUCUCCUGUCCCUGCUGUCGCUCCCCCUGGGCCUCCCAGUCCUGGGCGCCCCACCACGC
CUCAUCUGCGACAGCCGAGUCCUGGAGAGGUACCUCCUGGAGGCCAAGGAGGCCGAGAA
CAUCACGACGGGCUGCGCCGAACACUGCAGCCUGAACGAGAACAUCACCGUCCCAGACA
CCAAAGUGAACUUCUACGCCUGGAAGAGGAUGGAGGUCGGGCAGCAGGCCGUAGAAGUC
UGGCAGGGCCUGGCCCUGCUGAGCGAAGCCGUCCUGCGGGGCCAGGCCCUGCUGGUCAA
CAGCAGCCAGCCGUGGGAGCCCCUGCAGCUGCACGUGGACAAAGCCGUCAGCGGCCUGC
GCAGCCUCACCACCCUGCUGCGGGCCCUGGGAGCCCAGAAGGAAGCCAUCAGCCCCCCA
GACGCGGCCAGCGCCGCCCCACUCCGAACAAUCACCGCCGACACCUUCCGCAAACUCUU
CCGAGUCUACAGCAACUUCCUCCGGGGAAAGCUGAAGCUGUACACAGGGGAGGCCUGCA
GGACAGGGGACAGAUGACUCGAGCUAGUGACUGACUAGGAUCUGGUUACCACUAAACCA
GCCUCAAGAACACCCGAAUGGAGUCUCUAAGCUACAUAAUACCAACUUACACUUACAAA
AUGUUGUCCCCCAAAAUGUAGCCAUUCGUAUCUGCUCCUAAUAAAAAGAAAGUUUCUUC
ACAUUCUAGAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAA
AAAAAAAAAAA TEV-hEPO-XbG ARC-mRNA. 3'_16%_T (1014 nt).
(SEQ ID NO: 37)
5'-cap-
AGGAAACUUAAGUCAACACAACAUAUACAAAACAAACGAAUCUCAAGCAAUCAAGCAUU
CUACUUCUAUUGCAGCAAUUUAAAUCAUUUCUUUUAAAGCAAAAGCAAUUUUCUGAAAA
UUUUCACCAUUUACGAACGAUAGCCAUGGGGGUGCACGAAUGUCCUGCCUGGCUGUGGC
UUCUCCUGUCCCUGCUGUCGCUCCCUCUGGGCCUCCCAGUCCUGGGCGCCCCACCACGC
CUCAUCUGUGACAGCCGAGUCCUGGAGAGGUACCUCUUGGAGGCCAAGGAGGCCGAGAA
UAUCACGACGGGCUGUGCUGAACACUGCAGCUUGAAUGAGAAUAUCACUGUCCCAGACA
CCAAAGUUAAUUUCUACGCCUGGAAGAGGAUGGAGGUCGGGCAGCAGGCCGUAGAAGUC
UGGCAGGGCCUGGCCCUGCUGAGCGAAGCCGUCCUGCGGGGCCAGGCCCUGCUGGUCAA
CAGCAGCCAGCCGUGGGAGCCCCUGCAGCUGCACGUGGACAAAGCCGUCAGCGGCCUGC
GCAGCCUCACCACCCUGCUGCGGGCCCUGGGAGCCCAGAAGGAAGCCAUCAGCCCCCCA
GACGCGGCCAGCGCCGCCCCACUCCGAACAAUCACCGCCGACACCUUCCGCAAACUCUU
CCGAGUCUACAGCAACUUCCUCCGGGGAAAGCUGAAGCUGUACACAGGGGAGGCCUGCA
GGACAGGGGACAGAUGACUCGAGCUAGUGACUGACUAGGAUCUGGUUACCACUAAACCA
GCCUCAAGAACACCCGAAUGGAGUCUCUAAGCUACAUAAUACCAACUUACACUUACAAA -continued

AUGUUGUCGCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAA

TEV-hEPO-XbG ARC-mRNA. 3'_18%_T (1014 nt).

(SEQ ID NO: 38)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGUCCCUGCUGUCGCUCCCUCUGGGCCUCCCAGUCCUGGGCGCCCCACCACGC

CUCAUCUGUGACAGCCGAGUCCUGGAGAGGUACCUCUUGGAGGCCAAGGAGGCCGAGAA

UAUCACGACGGGCUGUGCUGAACACUGCAGCUUGAAUGAGAAUAUCACUGUCCCAGACA

CCAAAGUUAAUUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGUUGGUCAA

CUCUUCCCAGCCGUGGGAGCCCCUGCAGCUGCAUGUGGAUAAAGCCGUCAGUGGCCUUC

GCAGCCUCACCACCCUGCUGCGGGCCCUGGGAGCCCAGAAGGAAGCCAUCAGCCCCCCA

GACGCGGCCAGCGCCGCCCCACUCCGAACAAUCACCGCCGACACCUUCCGCAAACUCUU

CCGAGUCUACAGCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAA

TEV-hEPO-XbG ARC-mRNA. 3'_20%_T (1014 nt).

(SEQ ID NO: 39)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGUCCCUGCUGUCGCUCCCUCUGGGCCUCCCAGUCCUGGGCGCCCCACCACGC

CUCAUCUGUGACAGCCGAGUCCUGGAGAGGUACCUCUUGGAGGCCAAGGAGGCCGAGAA

UAUCACGACGGGCUGUGCUGAACACUGCAGCUUGAAUGAGAAUAUCACUGUCCCAGACA

CCAAAGUUAAUUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGUUGGUCAA

CUCUUCCCAGCCGUGGGAGCCCCUGCAGCUGCAUGUGGAUAAAGCCGUCAGUGGCCUUC

GCAGCCUCACCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCGCAAACUCUU

CCGAGUCUACAGCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCGCCCAAAAUGUAGCCAUUCGUAUCUGCUCCUAAUAAAAAGAAAGUUUCUUC

-continued

ACAUUCUAGAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAA

TEV-hEPO-XbG ARC-mRNA. 5'_14%_T (1014 nt).

(SEQ ID NO: 40)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCCCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

CAUCACGACGGGCUGCGCCGAACACUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGCUGGUCAA

CAGCAGCCAGCCGUGGGAGCCCCUGCAGCUGCACGUGGACAAAGCCGUCAGCGGCCUGC

GCAGCCUCACCACCCUGCUGCGGGCCCUGGGAGCCCAGAAGGAAGCCAUCAGCCCCCCA

GACGCGGCCAGCGCCGCCCCACUCCGAACAAUCACUGCUGACACUUUCCGCAAACUCUU

CCGAGUCUACUCCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAA

TEV-hEPO-XbG ARC-mRNA. 5'_16%_T (1014 nt).

(SEQ ID NO: 41)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCCCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

CAUCACGACGGGCUGCGCCGAACACUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGCUGGUCAA

CAGCAGCCAGCCGUGGGAGCCCCUGCAGCUGCACGUGGAUAAAGCCGUCAGUGGCCUUC

GCAGCCUCACCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCGCAAACUCUU

CCGAGUCUACUCCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCCAAAAUGUAGCCAUUCGUAUCUGCUCCUAAUAAAAAGAAAGUUUCUUC

-continued

ACAUUCUAGAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAA

TEV-hEPO-XbG ARC-mRNA. 5'_18%_T (1014 nt).

(SEQ ID NO: 42)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCCCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

CAUCACGACGGGCUGCGCCGAACACUGCAGCCUGAACGAGAACAUCACUGUCCCAGACA

CCAAAGUUAAUUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGUUGGUCAA

CUCUUCCCAGCCGUGGGAGCCCCUGCAGCUGCAUGUGGAUAAAGCCGUCAGUGGCCUUC

GCAGCCUCACCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCGCAAACUCUU

CCGAGUCUACUCCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAA

TEV-hEPO-XbG ARC-mRNA. 5'_20%_T (1014 nt).

(SEQ ID NO: 43)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UUCUCCUGUCCCUGCUGUCGCUCCCUCUGGGCCUCCCAGUCCUGGGCGCCCCACCACGC

CUCAUCUGUGACAGCCGAGUCCUGGAGAGGUACCUCUUGGAGGCCAAGGAGGCCGAGAA

UAUCACGACGGGCUGUGCUGAACACUGCAGCUUGAAUGAGAAUAUCACUGUCCCAGACA

CCAAAGUUAAUUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGUUGGUCAA

CUCUUCCCAGCCGUGGGAGCCCCUGCAGCUGCAUGUGGAUAAAGCCGUCAGUGGCCUUC

GCAGCCUCACCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCGCAAACUCUU

CCGAGUCUACUCCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAAAAA

-continued

AAAAAAAAAAAAAAAAAAAAAAAAAAAAAAAAAAAAAAAAAAAAAAAAAAAAAAAAAAAA

AAAAAAAAAAA

TEV-hEPO-XbG ARC-mRNA. random_14%_T (1014 nt).

(SEQ ID NO: 44)

5′-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCUGCCUGGCUGUGGC

UGCUCCUGAGCCUGCUGAGCCUCCCCCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

CAUCACGACGGGCUGCGCCGAACACUGCAGCUUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGCUGGUCAA

CAGCUCCCAGCCGUGGGAGCCCCUGCAGCUGCACGUGGACAAAGCCGUCAGCGGCCUGC

GCAGCCUCACCACCCUGCUGCGGGCCCUGGGAGCCCAGAAGGAAGCCAUCAGCCCCCCA

GACGCGGCCAGCGCCGCCCCACUCCGAACAAUCACCGCUGACACCUUCCGCAAACUCUU

CCGAGUCUACUCCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCGCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAA

TEV-hEPO-XbG ARC-mRNA. random_16%_T (1014 nt).

(SEQ ID NO: 45)

5′-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCCGCCUGGCUGUGGC

UGCUCCUGAGCCUGCUGAGCCUCCCUCUGGGCCUCCCAGUCCUGGGCGCCCCACCACGC

CUCAUCUGCGACAGCCGAGUCCUGGAGAGGUACCUCCUGGAGGCCAAGGAGGCCGAGAA

UAUCACGACGGGCUGUGCCGAACACUGCAGCUUGAACGAGAAUAUCACCGUCCCAGACA

CCAAAGUUAAUUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGCUGGUCAA

CAGCAGCCAGCCGUGGGAGCCCCUGCAGCUGCACGUGGAUAAAGCCGUCAGCGGCCUGC

GCAGCCUCACCACCCUGCUGCGGGCUCUGGGAGCCCAGAAGGAAGCCAUCAGCCCUCCA

GAUGCGGCCAGCGCCGCUCCACUCCGAACAAUCACCGCCGACACUUUCCGCAAACUCUU

CCGAGUCUACAGCAACUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAAAA

-continued

AAAAAAAAAAAAAAAAAAAAAAAAAAAAAAAAAAAAAAAAAAAAAAAAAAAAAAAAAAAA

AAAAAAAAAAA

TEV-hEPO-XbG ARC-mRNA. random_18%_T (1014 nt).
(SEQ ID NO: 46)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGUCCCUGCUGAGCCUCCCUCUGGGCCUCCCAGUCCUGGGCGCCCCACCACGC

CUCAUCUGUGACAGCCGAGUCCUGGAGAGGUACCUCUUGGAGGCCAAGGAGGCCGAGAA

CAUCACGACGGGCUGCGCUGAACACUGCAGCCUGAAUGAGAAUAUCACUGUCCCAGACA

CCAAAGUGAAUUUCUAUGCCUGGAAGAGGAUGGAGGUCGGGCAGCAGGCCGUAGAAGUC

UGGCAGGGCCUGGCCCUGCUGAGCGAAGCCGUCCUGCGGGGCCAGGCCCUGUUGGUCAA

CAGCAGCCAGCCGUGGGAGCCCCUGCAGCUGCAUGUGGAUAAAGCCGUCAGUGGCCUUC

GCAGCCUCACCACUCUGCUUCGGGCCCUGGGAGCCCAGAAGGAAGCCAUCUCCCCUCCA

GACGCGGCCUCAGCUGCCCCACUCCGAACAAUCACUGCUGACACUUUCCGCAAACUCUU

CCGAGUCUACAGCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCGCCCAAAAUGUAGCCAUUCGUAUCUGCUCCUAAUAAAAAGAAAGUUUCUUC

ACAUUCUAGAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAA

TEV-hEPO-XbG ARC-mRNA. random_20%_T (1014 nt).
(SEQ ID NO: 47)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGUCCCUGCUGUCGCUCCCUCUGGGCCUCCCAGUCCUGGGCGCCCCACCACGC

CUCAUCUGUGACAGCCGAGUCCUGGAGAGGUACCUCUUGGAGGCCAAGGAGGCCGAGAA

UAUCACGACGGGCUGUGCUGAACACUGCAGCUUGAAUGAGAAUAUCACUGUCCCAGACA

CCAAAGUUAACUUCUAUGCCUGGAAGAGGAUGGAGGUCGGGCAGCAGGCCGUAGAAGUC

UGGCAGGGCCUGGCCCUGCUGUCGGAAGCUGUCCUGCGGGGCCAGGCCCUGCUGGUCAA

CUCUUCCCAGCCGUGGGAGCCCCUGCAGCUGCAUGUGGAUAAAGCCGUCAGUGGCCUUC

GCAGCCUCACCACUCUGCUUCGGGCUCUGGGAGCCCAGAAGGAAGCCAUCUCCCCUCCA

GAUGCGGCCUCAGCUGCUCCACUCCGAACAAUCACUGCUGACACUUUCCGCAAACUCUU

CCGAGUCUACUCCAAUUUCCUCCGGGGAAAGCUGAAGCUGUACACAGGGGAGGCCUGCA

GGACAGGGGACAGAUGACUCGAGCUAGUGACUGACUAGGAUCUGGUUACCACUAAACCA

GCCUCAAGAACACCCGAAUGGAGUCUCUAAGCUACAUAAUACCAACUUACACUUACAAA

AUGUUGUCCCCCAAAAUGUAGCCAUUCGUAUCUGCUCCUAAUAAAAAGAAAGUUUCUUC

-continued

```
ACAUUCUAGAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAA
```

Example C: Templates and mRNAs for hF9

Figure 5:
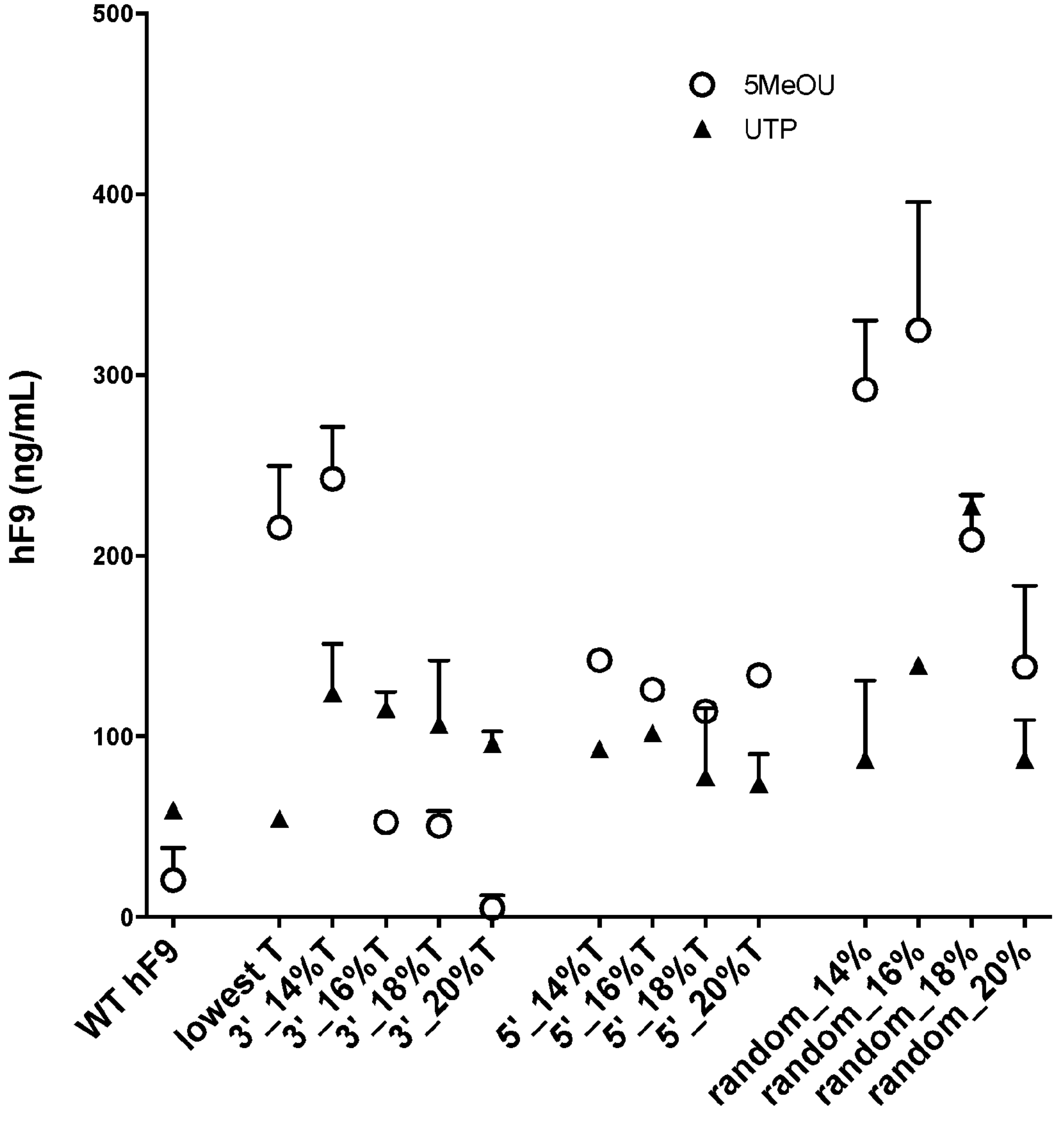
FIG. 5 shows the results of surprisingly increased human F9 protein production for a translatable molecule of this invention. Human F9 ARC-RNA was synthesized using a DNA template having reduced deoxyadenosine nucleotides in an open reading frame of the template strand, as well as reduced deoxythymidine nucleotides in the complementary non-template strand ("reduced T"). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 5 shows the results of surprisingly increased human F9 protein production for a translatable molecule of this invention. Human F9 ARC-RNA was synthesized using a DNA template having reduced deoxyadenosine nucleotides in an open reading frame of the template strand, as well as reduced complementary deoxythymidine nucleotides in the non-template strand ("reduced T"). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 5 shows surprisingly high translational efficiency of the ARC-mRNA (5MeOU) compared to the wild type hF9 mRNA (UTP). First, FIG. 5 shows that ARC-mRNA (5MeOU) products exhibited surprisingly superior expression efficiency at levels of template T composition of 13-14%. The increase of ARC-mRNA (5MeOU) expression efficiency at lower levels of template T composition of 13-14% is unexpectedly advantageous because neither the wild type nor "reduced T" hEPO mRNA (UTP) was increased at lower levels of template T composition.

Further, FIG. 5 shows that the ARC-mRNA (5MeOU) exhibited unexpectedly superior expression efficiency at 14-16% template T composition, when codon replacement was done randomly.

Figure 6:
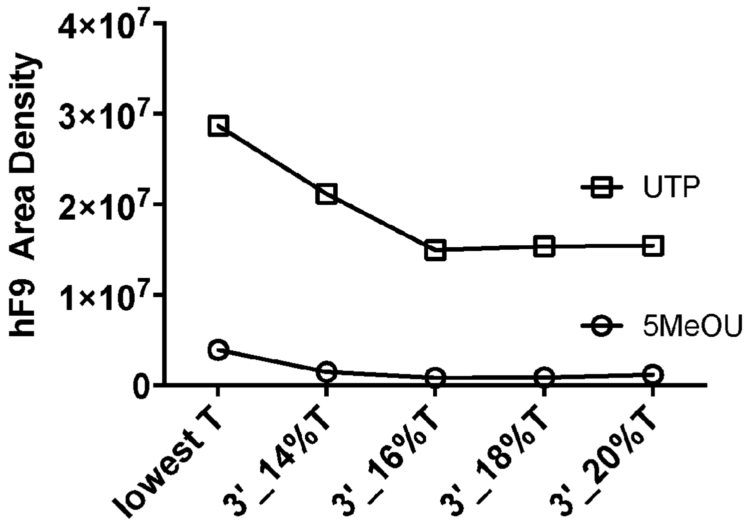
FIG. 6 shows the results of surprisingly reduced impurity levels in a process for synthesizing an hF9 translatable molecule of this invention.

FIG. 6 shows the results of surprisingly reduced impurity levels in a process for synthesizing an hF9 translatable molecule of this invention. FIG. 6 shows the results of a dot blot for detecting double strand RNA impurity in the synthesis mixture (nitro cellulose membrane, J2 antibody to detect dsRNA). The ARC-RNA (5MeOU) "reduced T" synthesis products, which were translatable for hF9, showed surprisingly reduced dot blot intensity as compared to similar "reduced T" mRNA (UTP) synthesis products. Thus, the ARC-RNA (5MeOU) synthesis process, with template reduced T composition, surprisingly reduced double strand RNA impurity levels in the synthesis mixture. The process for synthesizing the ARC-RNA (5MeOU) molecules of this invention with template reduced T composition provided a surprisingly reduced level of double strand RNA impurity. As shown in FIG. 6, this result is surprising because the "reduced T" mRNA (UTP) synthesis products exhibited increased levels of double strand RNA impurity at lower template T composition.

The compositions of the templates for hF9 are shown in Table 7.

TABLE 7

Non-Template Nucleotide T compositions for hF9

| hEPO | T % |
|---|---|
| hF9_lowest_T | 13.5 |
| hF9_3'_14% T | 14.1 |
| hF9_3'_16% T | 16.0 |
| hF9_3'_18% T | 18.0 |
| hF9_3'_20% T | 19.9 |
| hF9_5'_14% T | 14.1 |
| hF9_5'_16% T | 16.0 |
| hF9_5'_18% T | 18.0 |
| hF9_5'_20% T | 20.1 |
| hF9_random_14% | 14.1 |
| hF9_random_16% | 16.0 |
| hF9_random_18% | 18.0 |
| hF9_random_20% | 20.0 |

Human F9 ORF reference. Sense strand, non-template. NM_000133.3:30-1415 CDS Homo sapiens coagulation factor IX.

```
                                                  (SEQ ID NO: 48)
atgcagcgcgtgaacatgatcatggcagaatcaccaggcctcatcacca

tctgccttttaggatatctactcagtgctgaatgtacagtttttcttgatcatgaaaac

gccaacaaaattctgaatcggccaaagaggtataattcaggtaaattggaagagtttgt

tcaagggaaccttgagagagaatgtatggaagaaaagtgtagttttgaagaagcacgag

aagtttttgaaaacactgaaagaacaactgaattttggaagcagtatgttgatggagat

cagtgtgagtccaatccatgtttaaatggcggcagttgcaaggatgacattaattccta

tgaatgttggtgtccctttggatttgaaggaaagaactgtgaattagatgtaacatgta

acattaagaatggcagatgcgagcagttttgtaaaaatagtgctgataacaaggtggtt

tgctcctgtactgagggatatcgacttgcagaaaaccagaagtcctgtgaaccagcagt

gccatttccatgtggaagagtttctgtttcacaaacttctaagctcacccgtgctgaga

ctgtttttcctgatgtggactatgtaaattctactgaagctgaaaccattttggataac
```

-continued atcactcaaagcacccaatcatttaatgacttcactcgggttgttggtggagaagatgc
caaaccaggtcaattcccttggcaggttgttttgaatggtaaagttgatgcattctgtg
gaggctctatcgttaatgaaaaatggattgtaactgctgcccactgtgttgaaactggt
gttaaaattacagttgtcgcaggtgaacataatattgaggagacagaacatacagagca
aaagcgaaatgtgattcgaattattcctcaccacaactacaatgcagctattaataagt
acaaccatgacattgcccttctggaactggacgaacccttagtgctaaacagctacgtt
acacctatttgcattgctgacaaggaatacacgaacatcttcctcaaatttggatctgg
ctatgtaagtggctggggaagagtcttccacaaagggagatcagctttagttcttcagt
accttagagttccacttgttgaccgagccacatgtcttcgatctacaaagttcaccatc
tataacaacatgttctgtgctggcttccatgaaggaggtagagattcatgtcaaggaga
tagtgggggaccccatgttactgaagtggaagggaccagtttcttaactggaattatta
gctggggtgaagagtgtgcaatgaaaggcaaatatggaatatataccaaggtatcccgg
tatgtcaactggattaaggaaaaaacaaagctcacttaa hF9 sense strand, non-template. 3'_lowest_T.
(SEQ ID NO: 49)
ATGGGGGTGCACGAATGCCCCGCCTGGCTGTGGCTGCTCCTGAGCCTGC
TGAGCCTCCCCCTGGGCCTCCCAGTCCTGGGCGCCCCACCACGCCTCATCTGCGACAGC
CGAGTCCTGGAGAGGTACCTCCTGGAGGCCAAGGAGGCCGAGAACATCACGACGGGCTG
CGCCGAACACTGGAGCCTGAACGAGAACATCACCGTCCCAGACACCAAAGTGAACTTCT
ACGCCTGGAAGAGGATGGAGGTCGGGCAGCAGGCCGTAGAAGTCTGGCAGGGCCTGGCC
CTGCTGAGCGAAGCCGTCCTGCGGGGCCAGGCCCTGCTGGTCAACAGCAGCCAGCCGTG
GGAGCCCCTGCAGCTGCACGTGGACAAAGCCGTCAGCGGCCTGCGCAGCCTCACCACCC
TGCTGCGGGCCCTGGGAGCCCAGAAGGAAGCCATCAGCCCCCCAGACGCGGCCAGCGCC
GCCCCACTCCGAACAATCACCGCCGACACCTTCCGCAAACTCTTCCGAGTCTACAGCAA
CTTCCTCCGGGGAAAGCTGAAGCTGTACACAGGGGAGGCCTGCAGGACAGGGGACAGAT
GA hF9 sense strand, non-template. 3'_lowest_T.
(SEQ ID NO: 50)
ATGCAGCGCGTGAACATGATCATGGCAGAAAGCCCAGGCCTCATCACCA
TCTGCCTGCTGGGATACCTACTCAGCGCCGAATGCACAGTGTTCCTGGACCACGAAAAC
GCCAACAAAATCCTGAACCGGCCAAAGAGGTACAACAGCGGCAAACTGGAAGAGTTCGT
GCAAGGGAACCTGGAGAGAGAATGCATGGAAGAAAAGTGCAGCTTCGAAGAAGCACGAG
AAGTGTTCGAAAACACCGAAAGAACAACCGAATTCTGGAAGCAGTACGTGGACGGAGAC
CAGTGCGAGAGCAACCCATGCCTGAACGGCGGCAGCTGCAAGGACGACATCAACAGCTA
CGAATGCTGGTGCCCCTTCGGATTCGAAGGAAAGAACTGCGAACTGGACGTAACATGCA
ACATCAAGAACGGCAGATGCGAGCAGTTCTGCAAAAACAGCGCCGACAACAAGGTGGTG
TGCAGCTGCACCGAGGGATACCGACTGGCAGAAAACCAGAAGTCCTGCGAACCAGCAGT
GCCATTCCCATGCGGAAGAGTGAGCGTGAGCCAAACCAGCAAGCTCACCCGGGCCGAGA
CCGTGTTCCCCGACGTGGACTACGTAAACAGCACCGAAGCCGAAACCATCCTGGACAAC
ATCACCCAAAGCACCCAAAGCTTCAACGACTTCACCCGGGTGGTGGGCGGAGAAGACGC
CAAACCAGGCCAATTCCCCTGGCAGGTGGTGCTGAACGGCAAAGTGGACGCATTCTGCG
GAGGCAGCATCGTGAACGAAAAATGGATCGTAACCGCCGCCCACTGCGTGGAAACCGGC
GTGAAAATCACAGTGGTCGCAGGCGAACACAACATCGAGGAGACAGAACACACAGAGCA -continued AAAGCGAAACGTGATCCGAATCATCCCCCACCACAACTACAACGCAGCCATCAACAAGT
ACAACCACGACATCGCCCTGCTGGAACTGGACGAACCCCTGGTGCTAAACAGCTACGTG
ACACCCATCTGCATCGCCGACAAGGAATACACGAACATCTTCCTCAAATTCGGAAGCGG
CTACGTAAGCGGCTGGGGAAGAGTCTTCCACAAAGGGAGAAGCGCCCTGGTGCTGCAGT
ACCTGAGAGTGCCACTGGTGGACCGAGCCACATGCCTGCGAAGCACAAAGTTCACCATC
TACAACAACATGTTCTGCGCCGGCTTCCACGAAGGAGGCAGAGACAGCTGCCAAGGAGA
CAGCGGGGGACCCCACGTGACCGAAGTGGAAGGGACCAGCTTCCTGACCGGAATCATCA
GCTGGGGCGAAGAGTGCGCAATGAAAGGCAAATACGGAATATACACCAAGGTAAGCCGG
TACGTCAACTGGATCAAGGAAAAAACAAAGCTCACCTAA hF9 sense strand, non-template. 3′_14%_T.

(SEQ ID NO: 51)

ATGCAGCGCGTGAACATGATCATGGCAGAATCACCAGGCCTCATCACCA
TCTGCCTTTTAGGATATCTACTCAGTGCTGAATGTACAGTTTTCCTGGACCACGAAAAC
GCCAACAAAATCCTGAACCGGCCAAAGAGGTACAACAGCGGCAAACTGGAAGAGTTCGT
GCAAGGGAACCTGGAGAGAGAATGCATGGAAGAAAAGTGCAGCTTCGAAGAAGCACGAG
AAGTGTTCGAAAACACCGAAAGAACAACCGAATTCTGGAAGCAGTACGTGGACGGAGAC
CAGTGCGAGAGCAACCCATGCCTGAACGGCGGCAGCTGCAAGGACGACATCAACAGCTA
CGAATGCTGGTGCCCCTTCGGATTCGAAGGAAAGAACTGCGAACTGGACGTAACATGCA
ACATCAAGAACGGCAGATGCGAGCAGTTCTGCAAAAACAGCGCCGACAACAAGGTGGTG
TGCAGCTGCACCGAGGGATACCGACTGGCAGAAAACCAGAAGTCCTGCGAACCAGCAGT
GCCATTCCCATGCGGAAGAGTGAGCGTGAGCCAAACCAGCAAGCTCACCCGGGCCGAGA
CCGTGTTCCCCGACGTGGACTACGTAAACAGCACCGAAGCCGAAACCATCCTGGACAAC
ATCACCCAAAGCACCCAAAGCTTCAACGACTTCACCCGGGTGGTGGGCGGAGAAGACGC
CAAACCAGGCCAATTCCCCTGGCAGGTGGTGCTGAACGGCAAAGTGGACGCATTCTGCG
GAGGCAGCATCGTGAACGAAAAATGGATCGTAACCGCCGCCCACTGCGTGGAAACCGGC
GTGAAAATCACAGTGGTCGCAGGCGAACACAACATCGAGGAGACAGAACACACAGAGCA
AAAGCGAAACGTGATCCGAATCATCCCCCACCACAACTAGAACGCAGCCATCAACAAGT
ACAACCACGACATCGCCCTGCTGGAACTGGACGAACCCCTGGTGCTAAACAGCTACGTG
ACACCCATCTGCATCGCCGACAAGGAATACACGAACATCTTCCTCAAATTCGGAAGCGG
CTACGTAAGCGGCTGGGGAAGAGTCTTCCACAAAGGGAGAAGCGCCCTGGTGCTGCAGT
ACCTGAGAGTGCCACTGGTGGACCGAGCCACATGCCTGCGAAGCACAAAGTTCACCATC
TACAACAACATGTTCTGCGCCGGCTTCCACGAAGGAGGCAGAGACAGCTGCCAAGGAGA
CAGCGGGGGACCCCACGTGACCGAAGTGGAAGGGACCAGCTTCCTGACCGGAATCATCA
GCTGGGGCGAAGAGTGCGCAATGAAAGGCAAATACGGAATATACACCAAGGTAAGCCGG
TACGTCAACTGGATCAAGGAAAAAACAAAGCTCACCTAA hF9 sense strand, non-template. 3′_16%_T.

(SEQ ID NO: 52)

ATGCAGCGCGTGAACATGATCATGGCAGAATCACCAGGCCTCATCACCA
TCTGCCTTTTAGGATATCTACTCAGTGCTGAATGTACAGTTTTTCTTGATCATGAAAAC
GCCAACAAAATTCTGAATCGGCCAAAGAGGTATAATTCAGGTAAATTGGAAGAGTTTGT
TCAAGGGAACCTTGAGAGAGAATGTATGGAAGAAAAGTGTAGTTTTGAAGAAGCACGAG
AAGTTTTTGAAAACACTGAAAGAACAACTGAATTTTGGAAGCAGTATGTTGATGGAGAT

-continued

CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTGAACGAAAAATGGATCGTAACCGCCGCCCACTGCGTGGAAACCGGC

GTGAAAATCACAGTGGTCGCAGGCGAACACAACATCGAGGAGACAGAACACACAGAGCA

AAAGCGAAACGTGATCCGAATCATCCCCCACCACAACTACAACGGAGCCATCAACAAGT

ACAACCACGACATCGCCCTGCTGGAACTGGACGAACCCCTGGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTGCTGCAGT

ACCTGAGAGTGCCACTGGTGGACCGAGCCACATGCCTGCGAAGCACAAAGTTCACCATC

TACAACAACATGTTCTGCGCCGGCTTCCACGAAGGAGGCAGAGACAGCTGCCAAGGAGA

CAGCGGGGGACCCCACGTGACCGAAGTGGAAGGGACCAGCTTCCTGACCGGAATCATCA

GCTGGGGCGAAGAGTGCGCAATGAAAGGCAAATACGGAATATACACCAAGGTAAGCCGG

TACGTCAACTGGATCAAGGAAAAAACAAAGCTCACCTAA hF9 sense strand, non-template. 3'_18%_T.

(SEQ ID NO: 53)

ATGCAGCGCGTGAACATGATCATGGCAGAATCACCAGGCCTCATCACCA

TCTGCCTTTTAGGATATCTACTCAGTGCTGAATGTACAGTTTTTCTTGATCATGAAAAC

GCCAACAAAATTCTGAATCGGCCAAAGAGGTATAATTCAGGTAAATTGGAAGAGTTTGT

TCAAGGGAACCTTGAGAGAGAATGTATGGAAGAAAAGTGTAGTTTTGAAGAAGCACGAG

AAGTTTTTGAAAACACTGAAAGAACAACTGAATTTTGGAAGCAGTATGTTGATGGAGAT

CAGTGTGAGTCCAATCCATGTTTAAATGGCGGCAGTTGCAAGGATGACATTAATTCCTA

TGAATGTTGGTGTCCCTTTGGATTTGAAGGAAAGAACTGTGAATTAGATGTAACATGTA

ACATTAAGAATGGCAGATGCGAGCAGTTTTGTAAAAATAGTGCTGATAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTGAACGAAAAATGGATCGTAACCGCCGCCCACTGCGTGGAAACCGGC

GTGAAAATCACAGTGGTCGCAGGCGAACACAACATCGAGGAGACAGAACACACAGAGCA

AAAGCGAAACGTGATCCGAATCATCCCCCACCACAACTAGAACGCAGCCATCAACAAGT

ACAACCACGACATCGCCCTGCTGGAACTGGACGAACCCCTGGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTGCTGCAGT

ACCTGAGAGTGCCACTGGTGGACCGAGCCACATGCCTGCGAAGCACAAAGTTCACCATC

TACAACAACATGTTCTGCGCCGGCTTCCACGAAGGAGGCAGAGACAGCTGCCAAGGAGA

-continued

CAGCGGGGGACCCCACGTGACCGAAGTGGAAGGGACCAGCTTCCTGACCGGAATCATCA
GCTGGGGCGAAGAGTGCGCAATGAAAGGCAAATACGGAATATACACCAAGGTAAGCCGG
TACGTCAACTGGATCAAGGAAAAAACAAAGCTCACCTAA hF9 sense strand, non-template. 3'_20%_T.

(SEQ ID NO: 54)

ATGCAGCGCGTGAACATGATCATGGCAGAATCACCAGGCCTCATCACCA
TCTGCCTTTTAGGATATCTACTCAGTGCTGAATGTACAGTTTTTCTTGATCATGAAAAC
GCCAACAAAATTCTGAATCGGCCAAAGAGGTATAATTCAGGTAAATTGGAAGAGTTTGT
TCAAGGGAACCTTGAGAGAGAATGTATGGAAGAAAAGTGTAGTTTTGAAGAAGCACGAG
AAGTTTTTGAAAACACTGAAAGAACAACTGAATTTTGGAAGCAGTATGTTGATGGAGAT
CAGTGTGAGTCCAATCCATGTTTAAATGGCGGCAGTTGCAAGGATGACATTAATTCCTA
TGAATGTTGGTGTCCCTTTGGATTTGAAGGAAAGAACTGTGAATTAGATGTAACATGTA
ACATTAAGAATGGCAGATGCGAGCAGTTTTGTAAAAATAGTGCTGATAACAAGGTGGTT
TGCTCCTGTACTGAGGGATATCGACTTGCAGAAAACCAGAAGTCCTGTGAACCAGCAGT
GCCATTTCCATGTGGAAGAGTTTCTGTTTCACAAACTTCTAAGCTCACCCGTGCTGAGA
CTGTTTTTCCTGATGTGGACTATGTAAATAGCACCGAAGCCGAAACCATCCTGGACAAC
ATCACCCAAAGCACCCAAAGCTTCAACGACTTCACCCGGGTGGTGGGCGGAGAAGACGC
CAAACCAGGCCAATTCCCCTGGCAGGTGGTGCTGAACGGCAAAGTGGACGCATTCTGCG
GAGGCAGCATCGTGAACGAAAAATGGATCGTAACCGCCGCCCACTGCGTGGAAACCGGC
GTGAAAATCACAGTGGTCGCAGGCGAACACAACATCGAGGAGACAGAACACACAGAGCA
AAAGCGAAACGTGATCCGAATCATCCCCCACCACAACTACAACGGAGCCATCAACAAGT
ACAACCACGACATCGCCCTGCTGGAACTGGACGAACCCCTGGTGCTAAACAGCTACGTG
ACACCCATCTGCATCGCCGACAAGGAATACACGAACATCTTCCTCAAATTCGGAAGCGG
CTACGTAAGCGGCTGGGGAAGAGTCTTCCACAAAGGGAGAAGCGCCCTGGTGCTGCAGT
ACCTGAGAGTGCCACTGGTGGACCGAGCCACATGCCTGCGAAGCACAAAGTTCACCATC
TACAACAACATGTTCTGCGCCGGCTTCCACGAAGGAGGCAGAGACAGCTGCCAAGGAGA
CAGCGGGGGACCCCACGTGACCGAAGTGGAAGGGACCAGCTTCCTGACCGGAATCATCA
GCTGGGGCGAAGAGTGCGCAATGAAAGGCAAATACGGAATATACACCAAGGTAAGCCGG
TACGTCAACTGGATCAAGGAAAAAACAAAGCTCACCTAA hF9 sense strand, non-template. 5'_14%_T.

(SEQ ID NO: 55)

ATGCAGCGCGTGAACATGATCATGGCAGAAAGCCCAGGCCTCATCACCA
TCTGCCTGCTGGGATACCTACTCAGCGCCGAATGCACAGTGTTCCTGGACCACGAAAAC
GCCAACAAAATCCTGAACCGGCCAAAGAGGTACAACAGCGGCAAACTGGAAGAGTTCGT
GCAAGGGAACCTGGAGAGAGAATGCATGGAAGAAAAGTGCAGCTTCGAAGAAGCACGAG
AAGTGTTCGAAAACACCGAAAGAACAACCGAATTCTGGAAGCAGTACGTGGACGGAGAC
CAGTGCGAGAGCAACCCATGCCTGAACGGCGGCAGCTGCAAGGACGACATCAACAGCTA
CGAATGCTGGTGCCCCTTCGGATTCGAAGGAAAGAACTGCGAACTGGACGTAACATGCA
ACATCAAGAACGGCAGATGCGAGCAGTTCTGCAAAAACAGCGCCGACAACAAGGTGGTG
TGCAGCTGCACCGAGGGATACCGACTGGCAGAAAACCAGAAGTCCTGCGAACCAGCAGT
GCCATTCCCATGCGGAAGAGTGAGCGTGAGCCAAACCAGCAAGCTCACCCGGGCCGAGA
CCGTGTTCCCCGACGTGGACTACGTAAACAGCACCGAAGCCGAAACCATCCTGGACAAC

-continued

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTGAACGAAAAATGGATCGTAACCGCCGCCCACTGCGTGGAAACCGGC

GTGAAAATCACAGTGGTCGCAGGCGAACACAACATCGAGGAGACAGAACACACAGAGCA

AAAGCGAAACGTGATCCGAATCATCCCCCACCACAACTAGAACGCAGCCATCAACAAGT

ACAACCACGACATCGCCCTGCTGGAACTGGACGAACCCCTGGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTGCTGCAGT

ACCTGAGAGTGCCACTGGTGGACCGAGCCACATGCCTGCGAAGCACAAAGTTCACCATC

TACAACAACATGTTCTGCGCCGGCTTCCACGAAGGAGGCAGAGACAGCTGCCAAGGAGA

CAGCGGGGGACCCCACGTGACCGAAGTGGAAGGGACCAGCTTCCTGACCGGAATCATCA

GCTGGGGTGAAGAGTGTGCAATGAAAGGCAAATATGGAATATATACCAAGGTATCCCGG

TATGTCAACTGGATTAAGGAAAAAACAAAGCTCACTTAA hF9 sense strand, non-template. 5'_16%_T.

(SEQ ID NO: 56)

ATGCAGCGCGTGAACATGATCATGGCAGAAAGCCCAGGCCTCATCACCA

TCTGCCTGCTGGGATACCTACTCAGCGCCGAATGCACAGTGTTCCTGGACCACGAAAAC

GCCAACAAAATCCTGAACCGGCCAAAGAGGTACAACAGCGGCAAACTGGAAGAGTTCGT

GCAAGGGAACCTGGAGAGAGAATGCATGGAAGAAAAGTGCAGCTTCGAAGAAGCACGAG

AAGTGTTCGAAAACACCGAAAGAACAACCGAATTCTGGAAGGAGTACGTGGACGGAGAC

CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTGAACGAAAAATGGATCGTAACCGCCGCCCACTGCGTGGAAACCGGC

GTGAAAATCACAGTGGTCGCAGGCGAACACAACATCGAGGAGACAGAACACACAGAGCA

AAAGCGAAACGTGATCCGAATCATCCCCCACCACAACTACAACGCAGCCATCAACAAGT

ACAACCACGACATCGCCCTGCTGGAACTGGACGAACCCCTGGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTGCTTCAGT

ACCTTAGAGTTCCACTTGTTGACCGAGCCACATGTCTTCGATCTACAAAGTTCACCATC

TATAACAACATGTTCTGTGCTGGCTTCCATGAAGGAGGTAGAGATTCATGTCAAGGAGA

TAGTGGGGGACCCCATGTTACTGAAGTGGAAGGGACCAGTTTCTTAACTGGAATTATTA

GCTGGGGTGAAGAGTGTGCAATGAAAGGCAAATATGGAATATATACCAAGGTATCCCGG

TATGTCAACTGGATTAAGGAAAAAACAAAGCTCACTTAA hF9 sense strand, non-template. 5'_18%_T.

(SEQ ID NO: 57)

ATGCAGCGCGTGAACATGATCATGGCAGAAAGCCCAGGCCTCATCACCA

TCTGCCTGCTGGGATACCTACTCAGCGCCGAATGCACAGTGTTCCTGGACCACGAAAAC

-continued

GCCAACAAAATCCTGAACCGGCCAAAGAGGTACAACAGCGGCAAACTGGAAGAGTTCGT

GCAAGGGAACCTGGAGAGAGAATGCATGGAAGAAAAGTGCAGCTTCGAAGAAGCACGAG

AAGTGTTCGAAAACACCGAAAGAACAACCGAATTCTGGAAGCAGTACGTGGACGGAGAC

CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTGAACGAAAAATGGATCGTAACCGCCGCCCACTGCGTGGAAACCGGC

GTGAAAATCACAGTGGTCGCAGGCGAACACAACATCGAGGAGACAGAACATACAGAGCA

AAAGCGAAATGTGATTCGAATTATTCCTCACCACAACTACAATGCAGCTATTAATAAGT

ACAACCATGACATTGCCCTTCTGGAACTGGACGAACCCTTAGTGCTAAACAGCTACGTT

ACACCTATTTGCATTGCTGACAAGGAATACACGAACATCTTCCTCAAATTTGGATCTGG

CTATGTAAGTGGCTGGGGAAGAGTCTTCCACAAAGGGAGATCAGCTTTAGTTCTTCAGT

ACCTTAGAGTTCCACTTGTTGACCGAGCCACATGTCTTCGATCTACAAAGTTCACCATC

TATAACAACATGTTCTGTGCTGGCTTCCATGAAGGAGGTAGAGATTCATGTCAAGGAGA

TAGTGGGGGACCCCATGTTACTGAAGTGGAAGGGACCAGTTTCTTAACTGGAATTATTA

GCTGGGGTGAAGAGTGTGCAATGAAAGGCAAATATGGAATATATACCAAGGTATCCCGG

TATGTCAACTGGATTAAGGAAAAAACAAAGCTCACTTAA hF9 sense strand, non-template. 5'_20%_T.

(SEQ ID NO: 58)

ATGCAGCGCGTGAACATGATCATGGCAGAAAGCCCAGGCCTCATCACCA

TCTGCCTGCTGGGATACCTACTCAGCGCCGAATGCACAGTGTTCCTGGACCACGAAAAC

GCCAACAAAATCCTGAACCGGCCAAAGAGGTACAACAGCGGCAAACTGGAAGAGTTCGT

GCAAGGGAACCTGGAGAGAGAATGCATGGAAGAAAAGTGCAGCTTCGAAGAAGCACGAG

AAGTGTTCGAAAACACCGAAAGAACAACCGAATTCTGGAAGGAGTACGTGGACGGAGAC

CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTGGCAGAAAACCAGAAGTCCTGCGAACCAGCAGT

GCCATTCCCATGCGGAAGAGTGAGCGTGAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGTCAATTCCCTTGGCAGGTTGTTTTGAATGGTAAAGTTGATGCATTCTGTG

GAGGCTCTATCGTTAATGAAAAATGGATTGTAACTGCTGCCCACTGTGTTGAAACTGGT

GTTAAAATTAGAGTTGTCGCAGGTGAACATAATATTGAGGAGACAGAACATACAGAGCA

AAAGCGAAATGTGATTCGAATTATTCCTCACCACAACTAGAATGCAGCTATTAATAAGT

ACAACCATGACATTGCCCTTCTGGAACTGGACGAACCCTTAGTGCTAAACAGCTACGTT

-continued

ACACCTATTTGCATTGCTGACAAGGAATACACGAACATCTTCCTCAAATTTGGATCTGG

CTATGTAAGTGGCTGGGGAAGAGTCTTCCACAAAGGGAGATCAGCTTTAGTTCTTCAGT

ACCTTAGAGTTCCACTTGTTGACCGAGCCACATGTCTTCGATCTACAAAGTTCACCATC

TATAACAACATGTTCTGTGCTGGCTTCCATGAAGGAGGTAGAGATTCATGTCAAGGAGA

TAGTGGGGGACCCCATGTTACTGAAGTGGAAGGGACCAGTTTCTTAACTGGAATTATTA

GCTGGGGTGAAGAGTGTGCAATGAAAGGCAAATATGGAATATATACCAAGGTATCCCGG

TATGTCAACTGGATTAAGGAAAAAACAAAGCTCACTTAA hF9 sense strand, non-template. random_14%_T.

(SEQ ID NO: 59)

ATGCAGCGCGTGAACATGATCATGGCAGAAAGCCCAGGCCTCATCACCA

TCTGCCTGCTGGGATATCTACTCAGCGCCGAATGCACAGTGTTCCTGGACCACGAAAAC

GCCAACAAAATCCTGAACCGGCCAAAGAGGTACAACAGCGGTAAACTGGAAGAGTTCGT

GCAAGGGAACCTGGAGAGAGAATGCATGGAAGAAAAGTGCAGCTTCGAAGAAGCACGAG

AAGTGTTCGAAAACACCGAAAGAACAACCGAATTCTGGAAGCAGTACGTGGACGGAGAC

CAGTGCGAGAGCAACCCATGCCTGAACGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTCTGCAAAAACAGCGCCGACAACAAGGTGGTG

TGCAGCTGCACCGAGGGATACCGACTTGCAGAAAACCAGAAGTCCTGCGAACCAGCAGT

GCCATTCCCATGCGGAAGAGTGAGCGTTAGCCAAACCAGCAAGCTCACCCGGGCCGAGA

CCGTGTTCCCCGACGTGGACTACGTAAACAGCACCGAAGCCGAAACCATCCTGGACAAC

ATCACCCAAAGCACCCAAAGCTTCAACGACTTCACCCGGGTGGTGGGCGGAGAAGACGC

CAAACCAGGCCAATTCCCCTGGCAGGTGGTGCTGAACGGCAAAGTGGACGCATTCTGCG

GAGGCAGCATCGTTAACGAAAAATGGATCGTAACCGCCGCCCACTGCGTGGAAACCGGC

GTGAAAATCACAGTGGTCGCAGGCGAACACAACATCGAGGAGACAGAACACACAGAGCA

AAAGCGAAACGTGATCCGAATCATCCCTCACCACAACTAGAACGCAGCCATCAACAAGT

ACAACCACGACATCGCCCTGCTGGAACTGGACGAACCCTTAGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTGCTGCAGT

ACCTGAGAGTGCCACTGGTGGACCGAGCCACATGCCTGCGAAGCACAAAGTTCACCATC

TACAACAACATGTTCTGCGCCGGCTTCCACGAAGGAGGCAGAGACAGCTGCCAAGGAGA

CAGCGGGGGACCCCACGTGACCGAAGTGGAAGGGACCAGCTTCCTGACCGGAATCATCA

GCTGGGGCGAAGAGTGTGCAATGAAAGGCAAATACGGAATATACACCAAGGTAAGCCGG

TACGTCAACTGGATCAAGGAAAAAACAAAGCTCACCTAA hF9 sense strand, non-template random_16%_T.

(SEQ ID NO: 60)

ATGCAGCGCGTGAACATGATCATGGCAGAAAGCCCAGGCCTCATCACCA

TCTGCCTGCTGGGATACCTACTCAGTGCCGAATGTACAGTGTTCCTGGACCACGAAAAC

GCCAACAAAATCCTGAACCGGCCAAAGAGGTACAACTCAGGCAAACTGGAAGAGTTCGT

GCAAGGGAACCTGGAGAGAGAATGCATGGAAGAAAAGTGCAGCTTCGAAGAAGCACGAG

AAGTGTTTGAAAACACTGAAAGAACAACCGAATTTTGGAAGCAGTACGTGGATGGAGAT

CAGTGCGAGAGCAACCCATGCCTGAATGGCGGCAGCTGCAAGGACGACATCAACAGCTA

CGAATGCTGGTGCCCCTTCGGATTCGAAGGAAAGAACTGCGAACTGGACGTAACATGCA

ACATCAAGAACGGCAGATGCGAGCAGTTTTGTAAAAACAGCGCCGACAACAAGGTGGTG

-continued

TGCAGCTGCACCGAGGGATACCGACTGGCAGAAAACCAGAAGTCCTGCGAACCAGCAGT

GCCATTCCCATGCGGAAGAGTGTCTGTGTCACAAACCAGCAAGCTCACCCGGGCCGAGA

CCGTGTTCCCCGACGTGGACTACGTAAACAGCACCGAAGCCGAAACCATCCTGGATAAC

ATCACCCAAAGCACCCAAAGCTTCAATGACTTCACCCGGGTGGTGGGCGGAGAAGACGC

CAAACCAGGCCAATTCCCCTGGCAGGTTGTGCTGAACGGCAAAGTTGACGCATTCTGCG

GAGGCAGCATCGTGAACGAAAAATGGATCGTAACCGCTGCCCACTGCGTTGAAACCGGC

GTGAAAATCACAGTGGTCGCAGGCGAACACAACATTGAGGAGACAGAACACACAGAGCA

AAAGCGAAACGTGATCCGAATTATCCCCCACCACAACTAGAACGCAGCCATTAATAAGT

ACAACCATGACATCGCCCTGCTGGAACTGGACGAACCCTTAGTGCTAAACAGCTACGTG

ACACCCATCTGCATCGCCGACAAGGAATACACGAACATCTTCCTCAAATTCGGAAGCGG

CTACGTAAGCGGCTGGGGAAGAGTCTTCCACAAAGGGAGAAGCGCCCTGGTTCTGCAGT

ACCTGAGAGTGCCACTGGTTGACCGAGCCACATGCCTGCGAAGCACAAAGTTCACCATC

TACAACAACATGTTCTGCGCCGGCTTCCATGAAGGAGGTAGAGACAGCTGTCAAGGAGA

CAGCGGGGGACCCCACGTTACTGAAGTGGAAGGGACCAGCTTCCTGACCGGAATCATCA

GCTGGGGCGAAGAGTGCGCAATGAAAGGCAAATACGGAATATATACCAAGGTAAGCCGG

TACGTCAACTGGATCAAGGAAAAAACAAAGCTCACTTAA hF9 sense strand, non-template. random_18%_T.

(SEQ ID NO: 61)

ATGCAGCGCGTGAACATGATCATGGCAGAATCACCAGGCCTCATCACCA

TCTGCCTGTTAGGATACCTACTCAGCGCCGAATGTACAGTGTTTCTTGACCACGAAAAC

GCCAACAAAATCCTGAATCGGCCAAAGAGGTATAACTCAGGTAAACTGGAAGAGTTTGT

GCAAGGGAACCTGGAGAGAGAATGCATGGAAGAAAAGTGCAGCTTCGAAGAAGCACGAG

AAGTGTTCGAAAACACTGAAAGAACAACCGAATTTTGGAAGCAGTATGTGGATGGAGAC

CAGTGCGAGTCCAACCCATGCTTAAACGGCGGCAGTTGCAAGGACGACATCAACAGCTA

TGAATGCTGGTGCCCCTTCGGATTTGAAGGAAAGAACTGCGAACTGGACGTAACATGTA

ACATCAAGAATGGCAGATGCGAGCAGTTCTGTAAAAATAGCGCCGACAACAAGGTGGTG

TGCAGCTGTACCGAGGGATACCGACTGGCAGAAAACCAGAAGTCCTGCGAACCAGCAGT

GCCATTCCCATGCGGAAGAGTTAGCGTGAGCCAAACCAGCAAGCTCACCCGGGCCGAGA

CCGTGTTCCCTGACGTGGACTACGTAAACTCTACCGAAGCTGAAACCATCCTGGACAAC

ATCACTCAAAGCACCCAATCATTCAACGACTTCACCCGGGTGGTGGGCGGAGAAGATGC

CAAACCAGGTCAATTCCCTTGGCAGGTGGTGTTGAACGGCAAAGTGGACGCATTCTGTG

GAGGCAGCATCGTGAACGAAAAATGGATCGTAACTGCCGCCCACTGCGTGGAAACCGGC

GTGAAAATCACAGTGGTCGCAGGCGAACACAATATTGAGGAGACAGAACACACAGAGCA

AAAGCGAAATGTGATCCGAATTATCCCTCACCACAACTACAACGGAGCTATTAACAAGT

ACAACCACGACATTGCCCTGCTGGAACTGGACGAACCCCTGGTGCTAAACAGCTACGTT

ACACCTATCTGCATCGCCGACAAGGAATACACGAACATCTTCCTCAAATTCGGATCTGG

CTACGTAAGCGGCTGGGGAAGAGTCTTCCACAAAGGGAGATCAGCCCTGGTGCTTCAGT

ACCTTAGAGTGCCACTTGTGGACCGAGCCACATGCCTGCGAAGCACAAAGTTCACCATC

TACAACAACATGTTCTGTGCTGGCTTCCACGAAGGAGGTAGAGACAGCTGTCAAGGAGA

-continued

TAGCGGGGGACCCCACGTTACCGAAGTGGAAGGGACCAGCTTCTTAACTGGAATCATCA

GCTGGGGCGAAGAGTGCGCAATGAAAGGCAAATACGGAATATACACCAAGGTATCCCGG

TATGTCAACTGGATCAAGGAAAAAACAAAGCTCACCTAA hF9 sense strand, non-template random_20%_T.

(SEQ ID NO: 62)

ATGCAGCGCGTGAACATGATCATGGCAGAAAGCCCAGGCCTCATCACCA

TCTGCCTTCTGGGATATCTACTCAGCGCCGAATGCACAGTTTTCCTTGACCACGAAAAC

GCCAACAAAATCCTGAATCGGCCAAAGAGGTATAATTCAGGTAAACTGGAAGAGTTTGT

TCAAGGGAACCTTGAGAGAGAATGCATGGAAGAAAAGTGTAGTTTTGAAGAAGCACGAG

AAGTGTTCGAAAACACCGAAAGAACAACCGAATTTTGGAAGCAGTATGTGGATGGAGAC

CAGTGCGAGAGCAATCCATGCTTAAATGGCGGCAGCTGCAAGGACGACATTAATTCCTA

TGAATGCTGGTGCCCCTTTGGATTCGAAGGAAAGAACTGCGAATTAGACGTAACATGCA

ACATCAAGAACGGCAGATGCGAGCAGTTTTGTAAAAATAGTGCTGACAACAAGGTGGTT

TGCAGCTGCACCGAGGGATACCGACTGGCAGAAAACCAGAAGTCCTGCGAACCAGCAGT

GCCATTCCCATGTGGAAGAGTTTCTGTGAGCCAAACTTCTAAGCTCACCCGTGCCGAGA

CCGTTTTCCCTGACGTGGACTATGTAAATTCTACCGAAGCCGAAACCATTTTGGATAAC

ATCACCCAAAGCACCCAAAGCTTTAACGACTTCACTCGGGTGGTTGGCGGAGAAGACGC

CAAACCAGGCCAATTCCCTTGGCAGGTGGTTCTGAATGGCAAAGTGGATGCATTCTGTG

GAGGCTCTATCGTGAACGAAAAATGGATCGTAACTGCCGCCCACTGCGTTGAAACCGGC

GTTAAAATTACAGTGGTCGCAGGCGAACACAATATTGAGGAGACAGAACACACAGAGCA

AAAGCGAAACGTGATTCGAATTATCCCTCACCACAACTACAATGCAGCCATTAACAAGT

ACAACCATGACATCGCCCTGCTGGAACTGGACGAACCCCTGGTGCTAAACAGCTACGTT

ACACCTATTTGCATCGCCGACAAGGAATACACGAACATCTTCCTCAAATTTGGATCTGG

CTATGTAAGCGGCTGGGGAAGAGTCTTCCACAAAGGGAGAAGCGCCCTGGTGCTTCAGT

ACCTGAGAGTGCCACTTGTGGACCGAGCCACATGTCTGCGAAGCACAAAGTTCACCATC

TACAACAACATGTTCTGCGCCGGCTTCCACGAAGGAGGTAGAGACTCATGCCAAGGAGA

TAGCGGGGGACCCCACGTGACCGAAGTGGAAGGGACCAGCTTCCTGACTGGAATTATTA

GCTGGGGCGAAGAGTGCGCAATGAAAGGCAAATATGGAATATACACCAAGGTAAGCCGG

TATGTCAACTGGATCAAGGAAAAAACAAAGCTCACCTAA

TEV-hF9-XbG sense strand, non-template.
3'_lowest_T. (1818 nt)

(SEQ ID NO: 63)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGCGCCGAATG

CACAGTGTTCCTGGACCACGAAAACGCCAACAAAATCCTGAACCGGCCAAAGAGGTACA

ACAGCGGCAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

-continued

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

GGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGCGCAATGAAAGGCAAATA

CGGAATATACACCAAGGTAAGCCGGTACGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTAGACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

TEV-hF9-XbG sense strand, non-template. 3’_14%_T (1818 nt)
(SEQ ID NO: 64)

AGGAAACTTAAGTCAACACAACATATACAAAACAAACGAATCTCAAGCA

ATCAAGCATTCTAGTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAATCACCAGGCCTCATCACCATCTGCCTTTTAGGATATCTACTCAGTGCTGAATG

TACAGTTTTCCTGGACCACGAAAACGCCAACAAAATCCTGAACCGGCCAAAGAGGTACA

ACAGCGGCAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

-continued

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGCGCAATGAAAGGCAAATA

CGGAATATACACCAAGGTAAGCCGGTACGTCAACTGGATCAAGGAAAAAACAAAGCTCA

GCTAACTCGAGCTAGTGACTGACTAGGATCTGGTTACCACTAAACGAGCCTCAAGAACA

CCCGAATGGAGTCTCTAAGCTACATAATACCAACTTAGACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

TEV-hF9-XbG sense strand, non-template. 3'_16%_T (1818 nt)
(SEQ ID NO: 65)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAATCACCAGGCCTCATCACCATCTGCCTTTTAGGATATCTACTCAGTGCTGAATG

TACAGTTTTTCTTGATCATGAAAACGCCAACAAAATTCTGAATCGGCCAAAGAGGTATA

ATTCAGGTAAATTGGAAGAGTTTGTTCAAGGGAACCTTGAGAGAGAATGTATGGAAGAA

AAGTGTAGTTTTGAAGAAGCACGAGAAGTTTTTGAAAACACTGAAAGAACAACTGAATT

TTGGAAGCAGTATGTTGATGGAGATCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGCGCAATGAAAGGCAAATA

CGGAATATACACCAAGGTAAGCCGGTACGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

-continued

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

TEV-hF9-XbG sense strand, non-template. 3'_18%_T (1818 nt)
(SEQ ID NO: 66)

AGGAAACTTAAGTCAACACAACATATACAAAACAAACGAATCTCAAGGA

ATCAAGCATTCTAGTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAATCACCAGGCCTCATCACCATCTGCCTTTTAGGATATCTACTCAGTGCTGAATG

TACAGTTTTTCTTGATCATGAAAACGCCAACAAAATTCTGAATCGGCCAAAGAGGTATA

ATTCAGGTAAATTGGAAGAGTTTGTTCAAGGGAACCTTGAGAGAGAATGTATGGAAGAA

AAGTGTAGTTTTGAAGAAGCACGAGAAGTTTTTGAAAACACTGAAAGAACAACTGAATT

TTGGAAGCAGTATGTTGATGGAGATCAGTGTGAGTCCAATCCATGTTTAAATGGCGGCA

GTTGCAAGGATGACATTAATTCCTATGAATGTTGGTGTCCCTTTGGATTTGAAGGAAAG

AACTGTGAATTAGATGTAACATGTAACATTAAGAATGGCAGATGCGAGCAGTTTTGTAA

AAATAGTGCTGATAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGCGCAATGAAAGGCAAATA

CGGAATATACACCAAGGTAAGCCGGTACGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTAGACTTAGAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

TEV-hF9-XbG sense strand, non-template. 3'_20%_T (1818 nt)
(SEQ ID NO: 67)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAATCACCAGGCCTCATCACCATCTGCCTTTTAGGATATCTACTCAGTGCTGAATG

-continued

TACAGTTTTTCTTGATCATGAAAACGCCAACAAAATTCTGAATCGGCCAAAGAGGTATA

ATTCAGGTAAATTGGAAGAGTTTGTTCAAGGGAACCTTGAGAGAGAATGTATGGAAGAA

AAGTGTAGTTTTGAAGAAGCACGAGAAGTTTTTGAAAACACTGAAAGAACAACTGAATT

TTGGAAGCAGTATGTTGATGGAGATCAGTGTGAGTCCAATCCATGTTTAAATGGCGGCA

GTTGCAAGGATGACATTAATTCCTATGAATGTTGGTGTCCCTTTGGATTTGAAGGAAAG

AACTGTGAATTAGATGTAACATGTAACATTAAGAATGGCAGATGCGAGCAGTTTTGTAA

AAATAGTGCTGATAACAAGGTGGTTTGCTCCTGTACTGAGGGATATCGACTTGCAGAAA

ACCAGAAGTCCTGTGAACCAGCAGTGCCATTTCCATGTGGAAGAGTTTCTGTTTCACAA

ACTTCTAAGCTCACCCGTGCTGAGACTGTTTTTCCTGATGTGGACTATGTAAATAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGCGCAATGAAAGGCAAATA

CGGAATATACACCAAGGTAAGCCGGTACGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTAGACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAA

TEV-hF9-XbG sense strand, non-template. 5'_14%_T (1818 nt)
(SEQ ID NO: 68)

AGGAAACTTAAGTCAACACAACATATACAAAACAAACGAATCTCAAGCA

ATCAAGCATTCTAGTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGCGCCGAATG

CACAGTGTTCCTGGACCACGAAAACGCCAACAAAATCCTGAACCGGCCAAAGAGGTACA

ACAGCGGCAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

-continued

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGTGAAGAGTGTGCAATGAAAGGCAAATA

TGGAATATATACCAAGGTATCCCGGTATGTCAACTGGATTAAGGAAAAAACAAAGCTCA

CTTAACTCGAGCTAGTGACTGACTAGGATCTGGTTACCACTAAACGAGCCTCAAGAACA

CCCGAATGGAGTCTCTAAGCTACATAATACCAACTTAGACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

TEV-hF9-XbG sense strand, non-template. 5’_16%_T (1818 nt)
(SEQ ID NO: 69)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGCGCCGAATG

CACAGTGTTCCTGGACCACGAAAACGCCAACAAAATCCTGAACCGGCCAAAGAGGTACA

ACAGCGGCAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCCCACCAC

AACTACAACGCAGCCATCAACAAGTACAACCACGACATCGCCCTGCTGGAACTGGACGA

ACCCCTGGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

-continued

GGGAGAAGCGCCCTGGTGCTTCAGTACCTTAGAGTTCCACTTGTTGACCGAGCCACATG

TCTTCGATCTACAAAGTTCACCATCTATAACAACATGTTCTGTGCTGGCTTCCATGAAG

GAGGTAGAGATTCATGTCAAGGAGATAGTGGGGGACCCCATGTTACTGAAGTGGAAGGG

ACCAGTTTCTTAACTGGAATTATTAGCTGGGGTGAAGAGTGTGCAATGAAAGGCAAATA

TGGAATATATACCAAGGTATCCCGGTATGTCAACTGGATTAAGGAAAAAACAAAGCTCA

CTTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

TEV-hF9-XbG sense strand, non-template. 5'_18%_T (1818 nt)
(SEQ ID NO: 70)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGCGCCGAATG

CACAGTGTTCCTGGACCACGAAAACGCCAACAAAATCCTGAACCGGCCAAAGAGGTACA

ACAGCGGCAAACTGGAAGAGTTCGTGCAAGGGAACCTGGAGAGAGAATGCATGGAAGAA

AAGTGGAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTGAACGAAAAATGGATCGTAAC

CGCCGCCCACTGCGTGGAAACCGGCGTGAAAATCACAGTGGTCGCAGGCGAACACAACA

TCGAGGAGACAGAACATACAGAGCAAAAGCGAAATGTGATTCGAATTATTCCTCACCAC

AACTACAATGCAGCTATTAATAAGTACAACCATGACATTGCCCTTCTGGAACTGGACGA

ACCCTTAGTGCTAAACAGCTACGTTACACCTATTTGCATTGCTGACAAGGAATACACGA

ACATCTTCCTCAAATTTGGATCTGGCTATGTAAGTGGCTGGGGAAGAGTCTTCCACAAA

GGGAGATCAGCTTTAGTTCTTCAGTACCTTAGAGTTCCACTTGTTGACCGAGCCACATG

TCTTCGATCTACAAAGTTCACCATCTATAACAACATGTTCTGTGCTGGCTTCCATGAAG

GAGGTAGAGATTCATGTCAAGGAGATAGTGGGGGACCCCATGTTACTGAAGTGGAAGGG

ACCAGTTTCTTAACTGGAATTATTAGCTGGGGTGAAGAGTGTGCAATGAAAGGCAAATA

TGGAATATATACCAAGGTATCCCGGTATGTCAACTGGATTAAGGAAAAAACAAAGCTCA

CTTAACTCGAGCTAGTGACTGACTAGGATCTGGTTACCACTAAACCAGCCTCAAGAACA

CCCGAATGGAGTCTCTAAGCTACATAATACCAACTTAGACTTACAAAATGTTGTCCCCC

-continued

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

TEV-hF9-XbG sense strand, non-template. 5'_20%_T (1818 nt)
(SEQ ID NO: 71)

AGGAAACTTAAGTCAACACAACATATACAAAACAAACGAATCTCAAGCA

ATCAAGCATTCTAGTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGCGCCGAATG

CACAGTGTTCCTGGACCACGAAAACGCCAACAAAATCCTGAACCGGCCAAAGAGGTACA

ACAGCGGCAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGAGCGTGAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGTCAATTCCCTTGGCAGGTTGTTTTG

AATGGTAAAGTTGATGCATTCTGTGGAGGCTCTATCGTTAATGAAAAATGGATTGTAAC

TGCTGCCCACTGTGTTGAAACTGGTGTTAAAATTACAGTTGTCGCAGGTGAACATAATA

TTGAGGAGACAGAACATACAGAGCAAAAGCGAAATGTGATTCGAATTATTCCTCACCAC

AACTACAATGCAGCTATTAATAAGTACAACCATGACATTGCCCTTCTGGAACTGGACGA

ACCCTTAGTGCTAAACAGCTACGTTACACCTATTTGCATTGCTGACAAGGAATACACGA

ACATCTTCCTCAAATTTGGATCTGGCTATGTAAGTGGCTGGGGAAGAGTCTTCCACAAA

GGGAGATCAGCTTTAGTTCTTCAGTACCTTAGAGTTCCACTTGTTGACCGAGCCACATG

TCTTCGATCTACAAAGTTCACCATCTATAACAACATGTTCTGTGCTGGCTTCCATGAAG

GAGGTAGAGATTCATGTCAAGGAGATAGTGGGGGACCCCATGTTACTGAAGTGGAAGGG

ACCAGTTTCTTAACTGGAATTATTAGCTGGGGTGAAGAGTGTGCAATGAAAGGCAAATA

TGGAATATATACCAAGGTATCCCGGTATGTCAACTGGATTAAGGAAAAAACAAAGCTCA

CTTAACTCGAGCTAGTGACTGACTAGGATCTGGTTACCACTAAACGAGCCTCAAGAACA

CCCGAATGGAGTCTCTAAGCTACATAATACCAACTTAGACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

TEV-hF9-XbG sense strand, non-template.
random_14%_T. (1818 nt)
(SEQ ID NO: 72)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATATCTACTCAGCGCCGAATG

-continued

CACAGTGTTCCTGGACCACGAAAACGCCAACAAAATCCTGAACCGGCCAAAGAGGTACA

ACAGCGGTAAACTGGAAGAGTTCGTGCAAGGGAACCTGGAGAGAGAATGCATGGAAGAA

AAGTGCAGCTTCGAAGAAGCACGAGAAGTGTTCGAAAACACCGAAAGAACAACCGAATT

CTGGAAGCAGTACGTGGACGGAGACCAGTGCGAGAGCAACCCATGCCTGAACGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTCTGCAA

AAACAGCGCCGACAACAAGGTGGTGTGCAGCTGCACCGAGGGATACCGACTTGCAGAAA

ACCAGAAGTCCTGCGAACCAGCAGTGCCATTCCCATGCGGAAGAGTGAGCGTTAGCCAA

ACCAGCAAGCTCACCCGGGCCGAGACCGTGTTCCCCGACGTGGACTACGTAAACAGCAC

CGAAGCCGAAACCATCCTGGACAACATCACCCAAAGCACCCAAAGCTTCAACGACTTCA

CCCGGGTGGTGGGCGGAGAAGACGCCAAACCAGGCCAATTCCCCTGGCAGGTGGTGCTG

AACGGCAAAGTGGACGCATTCTGCGGAGGCAGCATCGTTAACGAAAAATGGATCGTAAC

CGCCGCCCACTGCGTGGAAACCGGCGTGAAAATCACAGTGGTCGCAGGCGAACACAACA

TCGAGGAGACAGAACACACAGAGCAAAAGCGAAACGTGATCCGAATCATCCCTCACCAC

AACTACAACGCAGCCATCAACAAGTACAACCACGACATCGCCCTGCTGGAACTGGACGA

ACCCTTAGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTGCTGCAGTACCTGAGAGTGCCACTGGTGGACCGAGCCACATG

CCTGCGAAGCACAAAGTTCACCATCTACAACAACATGTTCTGCGCCGGCTTCCACGAAG

GAGGCAGAGACAGCTGCCAAGGAGACAGCGGGGGACCCCACGTGACCGAAGTGGAAGGG

ACCAGCTTCCTGACCGGAATCATCAGCTGGGGCGAAGAGTGTGCAATGAAAGGCAAATA

CGGAATATACACCAAGGTAAGCCGGTACGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTACATAATACCAACTTACACTTACAAAATGTTGTCCCCC

AAAATGTAGCCATTCGTATCTGCTCCTAATAAAAAGAAAGTTTCTTCACATTCTAGAAA

TEV-hF9-XbG sense strand, non-template.
random_16%_T. (1818 nt)

(SEQ ID NO: 73)

AGGAAACTTAAGTCAACACAACATATACAAAACAAACGAATCTCAAGCA

ATCAAGCATTCTAGTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTGCTGGGATACCTACTCAGTGCCGAATG

TACAGTGTTCCTGGACCACGAAAACGCCAACAAAATCCTGAACCGGCCAAAGAGGTACA

ACTCAGGCAAACTGGAAGAGTTCGTGCAAGGGAACCTGGAGAGAGAATGCATGGAAGAA

AAGTGCAGCTTCGAAGAAGCACGAGAAGTGTTTGAAAACACTGAAAGAACAACCGAATT

TTGGAAGCAGTACGTGGATGGAGATCAGTGCGAGAGCAACCCATGCCTGAATGGCGGCA

GCTGCAAGGACGACATCAACAGCTACGAATGCTGGTGCCCCTTCGGATTCGAAGGAAAG

AACTGCGAACTGGACGTAACATGCAACATCAAGAACGGCAGATGCGAGCAGTTTTGTAA

AAACAGCGCCGACAACAAGGTGGTGTGCAGCTGCACCGAGGGATACCGACTGGCAGAAA

ACCAGAAGTCCTGCGAACCAGCAGTGCCATTCCCATGCGGAAGAGTGTCTGTGTCACAA

ACCAGCAAGCTCACCCGGGCCGAGACCGTGTTCCCCGACGTGGACTACGTAAACAGCAC

CGAAGCCGAAACCATCCTGGATAACATCACCCAAAGCACCCAAAGCTTCAATGACTTCA

-continued

CCCGGGTGGTGGGCGGAGAAGACGCCAAACCAGGCCAATTCCCCTGGCAGGTTGTGCTG

AACGGCAAAGTTGACGCATTCTGCGGAGGCAGCATCGTGAACGAAAAATGGATCGTAAC

CGCTGCCCACTGCGTTGAAACCGGCGTGAAAATCACAGTGGTCGCAGGCGAACACAACA

TTGAGGAGACAGAACACACAGAGCAAAAGCGAAACGTGATCCGAATTATCCCCCACCAC

AACTACAACGCAGCCATTAATAAGTACAACCATGACATCGCCCTGCTGGAACTGGACGA

ACCCTTAGTGCTAAACAGCTACGTGACACCCATCTGCATCGCCGACAAGGAATACACGA

ACATCTTCCTCAAATTCGGAAGCGGCTACGTAAGCGGCTGGGGAAGAGTCTTCCACAAA

GGGAGAAGCGCCCTGGTTCTGCAGTACCTGAGAGTGCCACTGGTTGACCGAGCCACATG

CCTGCGAAGCACAAAGTTCACCATCTACAACAACATGTTCTGCGCCGGCTTCCATGAAG

GAGGTAGAGACAGCTGTCAAGGAGACAGCGGGGGACCCCACGTTACTGAAGTGGAAGGG

ACCAGCTTCCTGACCGGAATCATCAGCTGGGGCGAAGAGTGCGCAATGAAAGGCAAATA

CGGAATATATACCAAGGTAAGCCGGTACGTCAACTGGATCAAGGAAAAAACAAAGCTCA

CTTAACTCGAGCTAGTGACTGACTAGGATCTGGTTACCACTAAACCAGCCTCAAGAACA

CCCGAATGGAGTCTCTAAGCTAGATAATACCAACTTAGACTTACAAAATGTTGTCCCCC

AAAATGTAGCCATTCGTATCTGCTCCTAATAAAAGAAAGTTTCTTCACATTCTAGAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

TEV-hF9-XbG sense strand, non-template.
random_18%_T. (1818 nt)

(SEQ ID NO: 74)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAATCACCAGGCCTCATCACCATCTGCCTGTTAGGATACCTACTCAGCGCCGAATG

TACAGTGTTTCTTGACCACGAAAACGCCAACAAAATCCTGAATCGGCCAAAGAGGTATA

ACTCAGGTAAACTGGAAGAGTTTGTGCAAGGGAACCTGGAGAGAGAATGCATGGAAGAA

AAGTGCAGCTTCGAAGAAGCACGAGAAGTGTTCGAAAACACTGAAAGAACAACCGAATT

TTGGAAGCAGTATGTGGATGGAGACCAGTGCGAGTCCAACCCATGCTTAAACGGCGGCA

GTTGCAAGGACGACATCAACAGCTATGAATGCTGGTGCCCCTTCGGATTTGAAGGAAAG

AACTGCGAACTGGACGTAACATGTAACATCAAGAATGGCAGATGCGAGCAGTTCTGTAA

AAATAGCGCCGACAACAAGGTGGTGTGCAGCTGTACCGAGGGATACCGACTGGCAGAAA

ACCAGAAGTCCTGCGAACCAGCAGTGCCATTCCCATGCGGAAGAGTTAGCGTGAGCCAA

ACCAGCAAGCTCACCCGGGCCGAGACCGTGTTCCCTGACGTGGACTACGTAAACTCTAC

CGAAGCTGAAACCATCCTGGACAACATCACTCAAAGCACCCAATCATTCAACGACTTCA

CCCGGGTGGTGGGCGGAGAAGATGCCAAACCAGGTCAATTCCCTTGGCAGGTGGTGTTG

AACGGCAAAGTGGACGCATTCTGTGGAGGCAGCATCGTGAACGAAAAATGGATCGTAAC

TGCCGCCCACTGCGTGGAAACCGGCGTGAAAATCACAGTGGTCGCAGGCGAACACAATA

TTGAGGAGACAGAACACACAGAGCAAAAGCGAAATGTGATCCGAATTATCCCTCACCAC

AACTACAACGCAGCTATTAACAAGTACAACCACGACATTGCCCTGCTGGAACTGGACGA

ACCCCTGGTGCTAAACAGCTACGTTACACCTATCTGCATCGCCGACAAGGAATACACGA

ACATCTTCCTCAAATTCGGATCTGGCTACGTAAGCGGCTGGGGAAGAGTCTTCCACAAA

GGGAGATCAGCCCTGGTGCTTCAGTACCTTAGAGTGCCACTTGTGGACCGAGCCACATG

-continued

CCTGCGAAGCACAAAGTTCACCATCTACAACAACATGTTCTGTGCTGGCTTCCACGAAG

GAGGTAGAGACAGCTGTCAAGGAGATAGCGGGGGACCCCACGTTACCGAAGTGGAAGGG

ACCAGCTTCTTAACTGGAATCATCAGCTGGGGCGAAGAGTGCGCAATGAAAGGCAAATA

CGGAATATACACCAAGGTATCCCGGTATGTCAACTGGATCAAGGAAAAAACAAAGCTCA

CCTAACTCGAGCTAGTGACTGACTAGGATCTGGTTACCACTAAACCAGCCTCAAGAACA

CCCGAATGGAGTCTCTAAGCTAGATAATACCAACTTAGACTTACAAAATGTTGTCCCCC

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

TEV-hF9-XbG sense strand, non-template.
random_20%_T. (1818 nt)

(SEQ ID NO: 75)

AGGAAACTTAAGTCAACACAACATATACAAAACAAACGAATCTCAAGCA

ATCAAGCATTCTAGTTCTATTGCAGCAATTTAAATCATTTCTTTTAAAGCAAAAGCAAT

TTTCTGAAAATTTTCACCATTTACGAACGATAGCCATGCAGCGCGTGAACATGATCATG

GCAGAAAGCCCAGGCCTCATCACCATCTGCCTTCTGGGATATCTACTCAGCGCCGAATG

CACAGTTTTCCTTGACCACGAAAACGCCAACAAAATCCTGAATCGGCCAAAGAGGTATA

ATTCAGGTAAACTGGAAGAGTTTGTTCAAGGGAACCTTGAGAGAGAATGCATGGAAGAA

AAGTGTAGTTTTGAAGAAGCACGAGAAGTGTTCGAAAACACCGAAAGAACAACCGAATT

TTGGAAGCAGTATGTGGATGGAGACCAGTGCGAGAGCAATCCATGCTTAAATGGCGGCA

GCTGCAAGGACGACATTAATTCCTATGAATGCTGGTGCCCCTTTGGATTCGAAGGAAAG

AACTGCGAATTAGACGTAACATGCAACATCAAGAACGGCAGATGCGAGCAGTTTTGTAA

AAATAGTGCTGACAACAAGGTGGTTTGCAGCTGCACCGAGGGATACCGACTGGCAGAAA

ACCAGAAGTCCTGCGAACCAGCAGTGCCATTCCCATGTGGAAGAGTTTCTGTGAGCCAA

ACTTCTAAGCTCACCCGTGCCGAGACCGTTTTCCCTGACGTGGACTATGTAAATTCTAC

CGAAGCCGAAACCATTTTGGATAACATCACCCAAAGCACCCAAAGCTTTAACGACTTCA

CTCGGGTGGTTGGCGGAGAAGACGCCAAACCAGGCCAATTCCCTTGGCAGGTGGTTCTG

AATGGCAAAGTGGATGCATTCTGTGGAGGCTCTATCGTGAACGAAAAATGGATCGTAAC

TGCCGCCCACTGCGTTGAAACCGGCGTTAAAATTACAGTGGTCGCAGGCGAACACAATA

TTGAGGAGACAGAACACACAGAGCAAAAGCGAAACGTGATTCGAATTATCCCTCACCAC

AACTACAATGCAGCCATTAACAAGTACAACCATGACATCGCCCTGCTGGAACTGGACGA

ACCCCTGGTGCTAAACAGCTACGTTACACCTATTTGCATCGCCGACAAGGAATACACGA

ACATCTTCCTCAAATTTGGATCTGGCTATGTAAGCGGCTGGGGAAGAGTCTTCCACAAA

GGGAGAAGCGCCCTGGTGCTTCAGTACCTGAGAGTGCCACTTGTGGACCGAGCCACATG

TCTGCGAAGCACAAAGTTCACCATCTACAACAACATGTTCTGCGCCGGCTTCCACGAAG

GAGGTAGAGACTCATGCCAAGGAGATAGCGGGGGACCCCACGTGACCGAAGTGGAAGGG

ACCAGCTTCCTGACTGGAATTATTAGCTGGGGCGAAGAGTGCGCAATGAAAGGCAAATA

TGGAATATACACCAAGGTAAGCCGGTATGTCAACTGGATCAAGGAAAAAACAAAGCTCA

GCTAACTCGAGCTAGTGAGTGAGTAGGATCTGGTTACCACTAAACGAGCCTCAAGAACA

CCCGAATGGAGTCTCTAAGCTACATAATACCAACTTAGACTTACAAAATGTTGTCCCCC

-continued

AAAATGTAGCCATTCGTATCTGCTCCTAATAAAAAGAAAGTTTCTTCACATTCTAGAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAA

TEV-hF9-XbG ARC-mRNA. 3'_lowest_T. (1818 nt)
(SEQ ID NO: 76)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGCGCCGAAUGCACAGUGUUC

CUGGACCACGAAAACGCCAACAAAAUCCUGAACCGGCCAAAGAGGUACAACAGCGGCAA

ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUCUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAACUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGCGAAGAGUGCGCAAUGAAAGGCAAAUACGGAAUAUAC

ACCAAGGUAAGCCGGUACGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

TEV-hF9-XbG ARC-mRNA. 3'_14%_T. (1818 nt)
(SEQ ID NO: 77)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

-continued

UUUUCACCAUUUACGAACGAUAGCCAUGCAGCGCGUGAACAUGAUCAUGGCAGAAUCAC
CAGGCCUCAUCACCAUCUGCCUUUUAGGAUAUCUACUCAGUGCUGAAUGUACAGUUUUC
CUGGACCACGAAAACGCCAACAAAAUCCUGAACCGGCCAAAGAGGUACAACAGCGGCAA
ACUGGAAGAGUUCGUGCAAGGGAACCUGGAGAGAGAAUGCAUGGAAGAAAAGUGCAGCU
UCGAAGAAGCACGAGAAGUGUUCGAAAACACCGAAAGAACAACCGAAUUCUGGAAGCAG
UACGUGGACGGAGACCAGUGCGAGAGCAACCCAUGCCUGAACGGCGGCAGCUGCAAGGA
CGACAUCAACAGCUACGAAUGCUGGUGCCCCUUCGGAUUCGAAGGAAAGAACUGCGAAC
UGGACGUAACAUGCAACAUCAAGAACGGCAGAUGCGAGCAGUUCUGCAAAAACAGCGCC
GACAACAAGGUGGUGUGCAGCUGCACCGAGGGAUACCGACUGGCAGAAAACCAGAAGUC
CUGCGAACCAGCAGUGCCAUUCCCAUGCGGAAGAGUGAGCGUGAGCCAAACCAGCAAGC
UCACCCGGGCCGAGACCGUGUUCCCCGACGUGGACUACGUAAACAGCACCGAAGCCGAA
ACCAUCCUGGACAACAUCACCCAAAGCACCCAAAGCUUCAACGACUUCACCCGGGUGGU
GGGCGGAGAAGACGCCAAACCAGGCCAAUUCCCCUGGCAGGUGGUGCUGAACGGCAAAG
UGGACGCAUUCUGCGGAGGCAGCAUCGUGAACGAAAAAUGGAUCGUAACCGCCGCCCAC
UGCGUGGAAACCGGCGUGAAAAUCACAGUGGUCGCAGGCGAACACAACAUCGAGGAGAC
AGAACACACAGAGCAAAAGCGAAACGUGAUCCGAAUCAUCCCCCACCACAACUACAACG
CAGCCAUCAACAAGUACAACCACGACAUCGCCCUGCUGGAACUGGACGAACCCCUGGUG
CUAAACAGCUACGUGACACCCAUCUGCAUCGCCGACAAGGAAUACACGAACAUCUUCCU
CAAAUUCGGAAGCGGCUACGUAAGCGGCUGGGGAAGAGUCUUCCACAAAGGGAGAAGCG
CCCUGGUGCUGCAGUACCUGAGAGUGCCACUGGUGGACCGAGCCACAUGCCUGCGAAGC
ACAAAGUUCACCAUCUACAACAACAUGUUCUGCGCCGGCUUCCACGAAGGAGGCAGAGA
CAGCUGCCAAGGAGACAGCGGGGGACCCCACGUGACCGAAGUGGAAGGGACCAGCUUCC
UGACCGGAAUCAUCAGCUGGGGCGAAGAGUGCGCAAUGAAAGGCAAAUACGGAAUAUAC
ACCAAGGUAAGCCGGUACGUCAACUGGAUCAAGGAAAAAACAAAGCUCACCUAACUCGA
GCUAGUGACUGACUAGGAUCUGGUUACCACUAAACCAGCCUCAAGAACACCCGAAUGGA
GUCUCUAAGCUACAUAAUACCAACUUACACUUACAAAAUGUUGUCCCCCAAAAUGUAGC
CAUUCGUAUCUGCUCCUAAUAAAAAGAAAGUUUCUUCACAUUCUAGAAAAAAAAAAAAA
AAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAA

TEV-hF9-XbG ARC-mRNA. 3'_16%_T. (1818 nt)
(SEQ ID NO: 78)
5'-cap-
AGGAAACUUAAGUCAACACAACAUAUACAAAACAAACGAAUCUCAAGCAAUCAAGCAUU
CUACUUCUAUUGCAGCAAUUUAAAUCAUUUCUUUUAAAGCAAAAGCAAUUUUCUGAAAA
UUUUCACCAUUUACGAACGAUAGCCAUGCAGCGCGUGAACAUGAUCAUGGCAGAAUCAC
CAGGCCUCAUCACCAUCUGCCUUUUAGGAUAUCUACUCAGUGCUGAAUGUACAGUUUUU
CUUGAUCAUGAAAACGCCAACAAAAUUCUGAAUCGGCCAAAGAGGUAUAAUUCAGGUAA
AUUGGAAGAGUUUGUUCAAGGGAACCUUGAGAGAGAAUGUAUGGAAGAAAAGUGUAGUU
UUGAAGAAGCACGAGAAGUUUUUGAAAACACUGAAAGAACAACUGAAUUUUGGAAGCAG
UAUGUUGAUGGAGAUCAGUGCGAGAGCAACCCAUGCCUGAACGGCGGCAGCUGCAAGGA
CGACAUCAACAGCUACGAAUGCUGGUGCCCCUUCGGAUUCGAAGGAAAGAACUGCGAAC
UGGACGUAACAUGCAACAUCAAGAACGGCAGAUGCGAGCAGUUCUGCAAAAACAGCGCC -continued

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAAGUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGCGAAGAGUGCGCAAUGAAAGGCAAAUACGGAAUAUAC

ACCAAGGUAAGCCGGUACGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAA

TEV-hF9-XbG ARC-mRNA. 3'_18%_T. (1818 nt)

(SEQ ID NO: 79)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAUCAC

CAGGCCUCAUCACCAUCUGCCUUUUAGGAUAUCUACUCAGUGCUGAAUGUACAGUUUUU

CUUGAUCAUGAAAACGCCAACAAAAUUCUGAAUCGGCCAAAGAGGUAUAAUUCAGGUAA

AUUGGAAGAGUUUGUUCAAGGGAACCUUGAGAGAGAAUGUAUGGAAGAAAAGUGUAGUU

UUGAAGAAGCACGAGAAGUUUUUGAAAACACUGAAAGAACAACUGAAUUUUGGAAGCAG

UAUGUUGAUGGAGAUCAGUGUGAGUCCAAUCCAUGUUUAAAUGGCGGCAGUUGCAAGGA

UGACAUUAAUUCCUAUGAAUGUUGGUGUCCCUUUGGAUUUGAAGGAAAGAACUGUGAAU

UAGAUGUAACAUGUAACAUUAAGAAUGGCAGAUGCGAGCAGUUUUGUAAAAAUAGUGCU

GAUAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

-continued

AGAACACACAGAGCAAAAGCGAAACGUGAUCCGAAUCAUCCCCCACCACAAGUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGCGAAGAGUGCGCAAUGAAAGGCAAAUACGGAAUAUAC

ACCAAGGUAAGCCGGUACGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

TEV-hF9-XbG ARC-mRNA. 3'_20%_T. (1818 nt)
(SEQ ID NO: 80)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAUCAC

CAGGCCUCAUCACCAUCUGCCUUUUAGGAUAUCUACUCAGUGCUGAAUGUACAGUUUUU

CUUGAUCAUGAAAACGCCAACAAAAUUCUGAAUCGGCCAAAGAGGUAUAAUUCAGGUAA

AUUGGAAGAGUUUGUUCAAGGGAACCUUGAGAGAGAAUGUAUGGAAGAAAAGUGUAGUU

UUGAAGAAGCACGAGAAGUUUUUGAAAACACUGAAAGAACAACUGAAUUUUGGAAGCAG

UAUGUUGAUGGAGAUCAGUGUGAGUCCAAUCCAUGUUUAAAUGGCGGCAGUUGCAAGGA

UGACAUUAAUUCCUAUGAAUGUUGGUGUCCCUUUGGAUUUGAAGGAAAGAACUGUGAAU

UAGAUGUAACAUGUAACAUUAAGAAUGGCAGAUGCGAGCAGUUUUGUAAAAAUAGUGCU

GAUAACAAGGUGGUUUGCUCCUGUACUGAGGGAUAUCGACUUGCAGAAAACCAGAAGUC

CUGUGAACCAGCAGUGCCAUUUCCAUGUGGAAGAGUUUCUGUUUCACAAACUUCUAAGC

UCACCCGUGCUGAGACUGUUUUUCCUGAUGUGGACUAUGUAAAUAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAAGUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGCGAAGAGUGCGCAAUGAAAGGCAAAUACGGAAUAUAC

-continued

ACCAAGGUAAGCCGGUACGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

TEV-hF9-XbG ARC-mRNA. 5'_14%_T. (1818 nt)
(SEQ ID NO: 81)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGCGCCGAAUGCACAGUGUUC

CUGGACCACGAAAACGCCAACAAAAUCCUGAACCGGCCAAAGAGGUACAACAGCGGCAA

ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUGUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAAGUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGUGAAGAGUGUGCAAUGAAAGGCAAAUAUGGAAUAUAU

ACCAAGGUAUCCCGGUAUGUCAACUGGAUUAAGGAAAAAACAAAGCUCACUUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

-continued

TEV-hF9-XbG ARC-mRNA. 5'_16%_T. (1818 nt)
(SEQ ID NO: 82)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGCGCCGAAUGCACAGUGUUC

CUGGACCACGAAAACGCCAACAAAAUCCUGAACCGGCCAAAGAGGUACAACAGCGGCAA

ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUGUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCCCACCACAAGUACAACG

CAGCCAUCAACAAGUACAACCACGACAUCGCCCUGCUGGAACUGGACGAACCCCUGGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUGCUUCAGUACCUUAGAGUUCCACUUGUUGACCGAGCCACAUGUCUUCGAUCU

ACAAAGUUCACCAUCUAUAACAACAUGUUCUGUGCUGGCUUCCAUGAAGGAGGUAGAGA

UUCAUGUCAAGGAGAUAGUGGGGGACCCCAUGUUACUGAAGUGGAAGGGACCAGUUUCU

UAACUGGAAUUAUUAGCUGGGGUGAAGAGUGUGCAAUGAAAGGCAAAUAUGGAAUAUAU

ACCAAGGUAUCCCGGUAUGUCAACUGGAUUAAGGAAAAAACAAAGCUCACUUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

TEV-hF9-XbG ARC-mRNA. 5'_18%_T. (1818 nt)
(SEQ ID NO: 83)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGCGCCGAAUGCACAGUGUUC

CUGGACCACGAAAACGCCAACAAAAUCCUGAACCGGCCAAAGAGGUACAACAGCGGCAA

-continued

ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUCUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUGAACGAAAAAUGGAUCGUAACCGCCGCCCAC

UGCGUGGAAACCGGCGUGAAAAUCACAGUGGUCGCAGGCGAACACAACAUCGAGGAGAC

AGAACAUACAGAGCAAAAGCGAAAUGUGAUUCGAAUUAUUCCUCACCACAACUACAAUG

CAGCUAUUAAUAAGUACAACCAUGACAUUGCCCUUCUGGAACUGGACGAACCCUUAGUG

CUAAACAGCUACGUUACACCUAUUUGCAUUGCUGACAAGGAAUACACGAACAUCUUCCU

CAAAUUUGGAUCUGGCUAUGUAAGUGGCUGGGGAAGAGUCUUCCACAAAGGGAGAUCAG

CUUUAGUUCUUCAGUACCUUAGAGUUCCACUUGUUGACCGAGCCACAUGUCUUCGAUCU

ACAAAGUUCACCAUCUAUAACAACAUGUUCUGUGCUGGCUUCCAUGAAGGAGGUAGAGA

UUCAUGUCAAGGAGAUAGUGGGGGACCCCAUGUUACUGAAGUGGAAGGGACCAGUUUCU

UAACUGGAAUUAUUAGCUGGGGUGAAGAGUGUGCAAUGAAAGGCAAAUAUGGAAUAUAU

ACCAAGGUAUCCCGGUAUGUCAACUGGAUUAAGGAAAAAACAAAGCUCACUUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAA

TEV-hF9-XbG ARC-mRNA. 5'_20%_T. (1818 nt)

(SEQ ID NO: 84)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGCGCCGAAUGCACAGUGUUC

CUGGACCACGAAAACGCCAACAAAAUCCUGAACCGGCCAAAGAGGUACAACAGCGGCAA

ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUGUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGAGCGUGAGCCAAACCAGCAAGC

UCACCCGGGCCGAGACCGUGUUCCCCGACGUGGACUACGUAAACAGCACCGAAGCCGAA

-continued

ACCAUCCUGGACAACAUCACCCAAAGCACCCAAAGCUUCAACGACUUCACCCGGGUGGU

GGGCGGAGAAGACGCCAAACCAGGUCAAUUCCCUUGGCAGGUUGUUUUGAAUGGUAAAG

UUGAUGCAUUCUGUGGAGGCUCUAUCGUUAAUGAAAAAUGGAUUGUAACUGCUGCCCAC

UGUGUUGAAACUGGUGUUAAAAUUACAGUUGUCGCAGGUGAACAUAAUAUUGAGGAGAC

AGAACAUACAGAGCAAAAGCGAAAUGUGAUUCGAAUUAUUCCUCACCACAACUACAAUG

CAGCUAUUAAUAAGUACAACCAUGACAUUGCCCUUCUGGAACUGGACGAACCCUUAGUG

CUAAACAGCUACGUUACACCUAUUUGCAUUGCUGACAAGGAAUACACGAACAUCUUCCU

CAAAUUUGGAUCUGGCUAUGUAAGUGGCUGGGGAAGAGUCUUCCACAAAGGGAGAUCAG

CUUUAGUUCUUCAGUACCUUAGAGUUCCACUUGUUGACCGAGCCACAUGUCUUCGAUCU

ACAAAGUUCACCAUCUAUAACAACAUGUUCUGUGCUGGCUUCCAUGAAGGAGGUAGAGA

UUCAUGUCAAGGAGAUAGUGGGGGACCCCAUGUUACUGAAGUGGAAGGGACCAGUUUCU

UAACUGGAAUUAUUAGCUGGGGUGAAGAGUGUGCAAUGAAAGGCAAAUAUGGAAUAUAU

ACCAAGGUAUCCCGGUAUGUCAACUGGAUUAAGGAAAAAACAAAGCUCACUUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAA

TEV-hF9-XbG ARC-mRNA. random_14%_T. (1818 nt)

(SEQ ID NO: 85)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUAUCUACUCAGCGCCGAAUGCACAGUGUUC

CUGGACCACGAAAACGCCAACAAAAUCCUGAACCGGCCAAAGAGGUACAACAGCGGUAA

ACUGGAAGAGUUCGUGCAAGGGAACCUGGAGAGAGAAUGCAUGGAAGAAAAGUGCAGCU

UCGAAGAAGCACGAGAAGUGUUCGAAAACACCGAAAGAACAACCGAAUUGUGGAAGCAG

UACGUGGACGGAGACCAGUGCGAGAGCAACCCAUGCCUGAACGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUCUGCAAAAACAGCGCC

GACAACAAGGUGGUGUGCAGCUGCACCGAGGGAUACCGACUUGCAGAAAACCAGAAGUC

CUGCGAACCAGCAGUGCCAUUCCCAUGCGGAAGAGUGAGCGUUAGCCAAACCAGCAAGC

UCACCCGGGCCGAGACCGUGUUCCCCGACGUGGACUACGUAAACAGCACCGAAGCCGAA

ACCAUCCUGGACAACAUCACCCAAAGCACCCAAAGCUUCAACGACUUCACCCGGGUGGU

GGGCGGAGAAGACGCCAAACCAGGCCAAUUCCCCUGGCAGGUGGUGCUGAACGGCAAAG

UGGACGCAUUCUGCGGAGGCAGCAUCGUUAACGAAAAAUGGAUCGUAACCGCCGCCCAC

UGCGUGGAAACCGGCGUGAAAAUCACAGUGGUCGCAGGCGAACACAACAUCGAGGAGAC

AGAACACACAGAGCAAAAGCGAAACGUGAUCCGAAUCAUCCCUCACCACAAGUACAACG

CAGCCAUCAACAAGUACAACCACGACAUCGCCCUGCUGGAACUGGACGAACCCUUAGUG

CUAAACAGCUACGUGACACCCAUCUGCAUCGCCGACAAGGAAUACACGAACAUCUUCCU

-continued

CAAAUUCGGAAGCGGCUACGUAAGCGGCUGGGGAAGAGUCUUCCACAAAGGGAGAAGCG

CCCUGGUGCUGCAGUACCUGAGAGUGCCACUGGUGGACCGAGCCACAUGCCUGCGAAGC

ACAAAGUUCACCAUCUACAACAACAUGUUCUGCGCCGGCUUCCACGAAGGAGGCAGAGA

CAGCUGCCAAGGAGACAGCGGGGGACCCCACGUGACCGAAGUGGAAGGGACCAGCUUCC

UGACCGGAAUCAUCAGCUGGGGCGAAGAGUGUGCAAUGAAAGGCAAAUACGGAAUAUAC

ACCAAGGUAAGCCGGUACGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAA

TEV-hF9-XbG ARC-mRNA. random_16%_T. (1818 nt)

(SEQ ID NO: 86)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAAGCC

CAGGCCUCAUCACCAUCUGCCUGCUGGGAUACCUACUCAGUGCCGAAUGUACAGUGUUC

CUGGACCACGAAAACGCCAACAAAAUCCUGAACCGGCCAAAGAGGUACAACUCAGGCAA

ACUGGAAGAGUUCGUGCAAGGGAACCUGGAGAGAGAAUGCAUGGAAGAAAAGUGCAGCU

UCGAAGAAGCACGAGAAGUGUUUGAAAACACUGAAAGAACAACCGAAUUUUGGAAGCAG

UACGUGGAUGGAGAUCAGUGCGAGAGCAACCCAUGCCUGAAUGGCGGCAGCUGCAAGGA

CGACAUCAACAGCUACGAAUGCUGGUGCCCCUUCGGAUUCGAAGGAAAGAACUGCGAAC

UGGACGUAACAUGCAACAUCAAGAACGGCAGAUGCGAGCAGUUUUGUAAAAACAGCGCC

GACAACAAGGUGGUGUGCAGCUGCACCGAGGGAUACCGACUGGCAGAAAACCAGAAGUC

CUGCGAACCAGCAGUGCCAUUCCCAUGCGGAAGAGUGUCUGUGUCACAAACCAGCAAGC

UCACCCGGGCCGAGACCGUGUUCCCCGACGUGGACUACGUAAACAGCACCGAAGCCGAA

ACCAUCCUGGAUAACAUCACCCAAAGCACCCAAAGCUUCAAUGACUUCACCCGGGUGGU

GGGCGGAGAAGACGCCAAACCAGGCCAAUUCCCCUGGCAGGUUGUGCUGAACGGCAAAG

UUGACGCAUUCUGCGGAGGCAGCAUCGUGAACGAAAAAUGGAUCGUAACCGCUGCCCAC

UGCGUUGAAACCGGCGUGAAAAUCACAGUGGUCGCAGGCGAACACAACAUUGAGGAGAC

AGAACACACAGAGCAAAAGCGAAACGUGAUCCGAAUUAUCCCCCACCACAAGUACAACG

CAGCCAUUAAUAAGUACAACCAUGACAUCGCCCUGCUGGAACUGGACGAACCCUUAGUG

CUAAACAGCUACGUGACACCCAUCUGCAUCGCCGACAAGGAAUACACGAACAUCUUCCU

CAAAUUCGGAAGCGGCUACGUAAGCGGCUGGGGAAGAGUCUUCCACAAAGGGAGAAGCG

CCCUGGUUCUGCAGUACCUGAGAGUGCCACUGGUUGACCGAGCCACAUGCCUGCGAAGC

ACAAAGUUCACCAUCUACAACAACAUGUUCUGCGCCGGCUUCCAUGAAGGAGGUAGAGA

CAGCUGUCAAGGAGACAGCGGGGGACCCCACGUUACUGAAGUGGAAGGGACCAGCUUCC

UGACCGGAAUCAUCAGCUGGGGCGAAGAGUGCGCAAUGAAAGGCAAAUACGGAAUAUAU

ACCAAGGUAAGCCGGUACGUCAACUGGAUCAAGGAAAAAACAAAGCUCACUUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

-continued

CAUUCGUAUCUGCUCCUAAUAAAAAGAAAGUUUCUUCACAUUCUAGAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

TEV-hF9-XbG ARC-mRNA. random_18%_T. (1818 nt)
(SEQ ID NO: 87)
5′-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCAGCGCGUGAACAUGAUCAUGGCAGAAUCAC

CAGGCCUCAUCACCAUCUGCCUGUUAGGAUACCUACUCAGCGCCGAAUGUACAGUGUUU

CUUGACCACGAAAACGCCAACAAAAUCCUGAAUCGGCCAAAGAGGUAUAACUCAGGUAA

ACUGGAAGAGUUUGUGCAAGGGAACCUGGAGAGAGAAUGCAUGGAAGAAAAGUGCAGCU

UCGAAGAAGCACGAGAAGUGUUCGAAAACACUGAAAGAACAACCGAAUUUUGGAAGCAG

UAUGUGGAUGGAGACCAGUGCGAGUCCAACCCAUGCUUAAACGGCGGCAGUUGCAAGGA

CGACAUCAACAGCUAUGAAUGCUGGUGCCCCUUCGGAUUUGAAGGAAAGAACUGCGAAC

UGGACGUAACAUGUAACAUCAAGAAUGGCAGAUGCGAGCAGUUCUGUAAAAAUAGCGCC

GACAACAAGGUGGUGUGCAGCUGUACCGAGGGAUACCGACUGGCAGAAAACCAGAAGUC

CUGCGAACCAGCAGUGCCAUUCCCAUGCGGAAGAGUUAGCGUGAGCCAAACCAGCAAGC

UCACCCGGGCCGAGACCGUGUUCCCUGACGUGGACUACGUAAACUCUACCGAAGCUGAA

ACCAUCCUGGACAACAUCACUCAAAGCACCCAAUCAUUCAACGACUUCACCCGGGUGGU

GGGCGGAGAAGAUGCCAAACCAGGUCAAUUCCCUUGGCAGGUGGUGUUGAACGGCAAAG

UGGACGCAUUCUGUGGAGGCAGCAUCGUGAACGAAAAAUGGAUCGUAACUGCCGCCCAC

UGCGUGGAAACCGGCGUGAAAAUCACAGUGGUCGCAGGCGAACACAAUAUUGAGGAGAC

AGAACACACAGAGCAAAAGCGAAAUGUGAUCCGAAUUAUCCCUCACCACAAGUACAACG

CAGCUAUUAACAAGUACAACCACGACAUUGCCCUGCUGGAACUGGACGAACCCCUGGUG

CUAAACAGCUACGUUACACCUAUCUGCAUCGCCGACAAGGAAUACACGAACAUCUUCCU

CAAAUUCGGAUCUGGCUACGUAAGCGGCUGGGGAAGAGUCUUCCACAAAGGGAGAUCAG

CCCUGGUGCUUCAGUACCUUAGAGUGCCACUUGUGGACCGAGCCACAUGCCUGCGAAGC

ACAAAGUUCACCAUCUACAACAACAUGUUCUGUGCUGGCUUCCACGAAGGAGGUAGAGA

CAGCUGUCAAGGAGAUAGCGGGGGACCCCACGUUACCGAAGUGGAAGGGACCAGCUUCU

UAACUGGAAUCAUCAGCUGGGGCGAAGAGUGCGCAAUGAAAGGCAAAUACGGAAUAUAC

ACCAAGGUAUCCCGGUAUGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

TEV-hF9-XbG ARC-mRNA. random_20%_T. (1818 nt)
(SEQ ID NO: 88)
5′-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

-continued

UUUUCACCAUUUACGAACGAUAGCCAUGCAGCGCGUGAACAUGAUCAUGGCAGAAAGCC

CAGGCCUCAUCACCAUCUGCCUUCUGGGAUAUCUACUCAGCGCCGAAUGCACAGUUUUC

CUUGACCACGAAAACGCCAACAAAAUCCUGAAUCGGCCAAAGAGGUAUAAUUCAGGUAA

ACUGGAAGAGUUUGUUCAAGGGAACCUUGAGAGAGAAUGCAUGGAAGAAAAGUGUAGUU

UUGAAGAAGCACGAGAAGUGUUCGAAAACACCGAAAGAACAACCGAAUUUUGGAAGGAG

UAUGUGGAUGGAGACCAGUGCGAGAGCAAUCCAUGCUUAAAUGGCGGCAGCUGCAAGGA

CGACAUUAAUUCCUAUGAAUGCUGGUGCCCCUUUGGAUUCGAAGGAAAGAACUGCGAAU

UAGACGUAACAUGCAACAUCAAGAACGGCAGAUGCGAGCAGUUUUGUAAAAAUAGUGCU

GACAACAAGGUGGUUUGCAGCUGCACCGAGGGAUACCGACUGGCAGAAAACCAGAAGUC

CUGCGAACCAGCAGUGCCAUUCCCAUGUGGAAGAGUUUCUGUGAGCCAAACUUCUAAGC

UCACCCGUGCCGAGACCGUUUUCCCUGACGUGGACUAUGUAAAUUCUACCGAAGCCGAA

ACCAUUUUGGAUAACAUCACCCAAAGCACCCAAAGCUUUAACGACUUCACUCGGGUGGU

UGGCGGAGAAGACGCCAAACCAGGCCAAUUCCCUUGGCAGGUGGUUCUGAAUGGCAAAG

UGGAUGCAUUCUGUGGAGGCUCUAUCGUGAACGAAAAAUGGAUCGUAACUGCCGCCCAC

UGCGUUGAAACCGGCGUUAAAAUUACAGUGGUCGCAGGCGAACACAAUAUUGAGGAGAC

AGAACACACAGAGCAAAAGCGAAACGUGAUUCGAAUUAUCCCUCACCACAACUACAAUG

CAGCCAUUAACAAGUACAACCAUGACAUCGCCCUGCUGGAACUGGACGAACCCCUGGUG

CUAAACAGCUACGUUACACCUAUUUGCAUCGCCGACAAGGAAUACACGAACAUCUUCCU

CAAAUUUGGAUCUGGCUAUGUAAGCGGCUGGGGAAGAGUCUUCCACAAAGGGAGAAGCG

CCCUGGUGCUUCAGUACCUGAGAGUGCCACUUGUGGACCGAGCCACAUGUCUGCGAAGC

ACAAAGUUCACCAUCUACAACAACAUGUUCUGCGCCGGCUUCCACGAAGGAGGUAGAGA

CUCAUGCCAAGGAGAUAGCGGGGGACCCCACGUGACCGAAGUGGAAGGGACCAGCUUCC

UGACUGGAAUUAUUAGCUGGGGCGAAGAGUGCGCAAUGAAAGGCAAAUAUGGAAUAUAC

ACCAAGGUAAGCCGGUAUGUCAACUGGAUCAAGGAAAAAACAAAGCUCACCUAACUCGA

GCUAGUGACUGACUAGGAUCUGGUUACCACUAAACCAGCCUCAAGAACACCCGAAUGGA

GUCUCUAAGCUACAUAAUACCAACUUACACUUACAAAAUGUUGUCCCCCAAAAUGUAGC

CAUUCGUAUCUGCUCCUAAUAAAAAGAAAGUUUCUUCACAUUCUAGAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAA

Example D: Templates and mRNAs for Human Alpha-1-Antitrypsin (hAAT)

Figure 7:
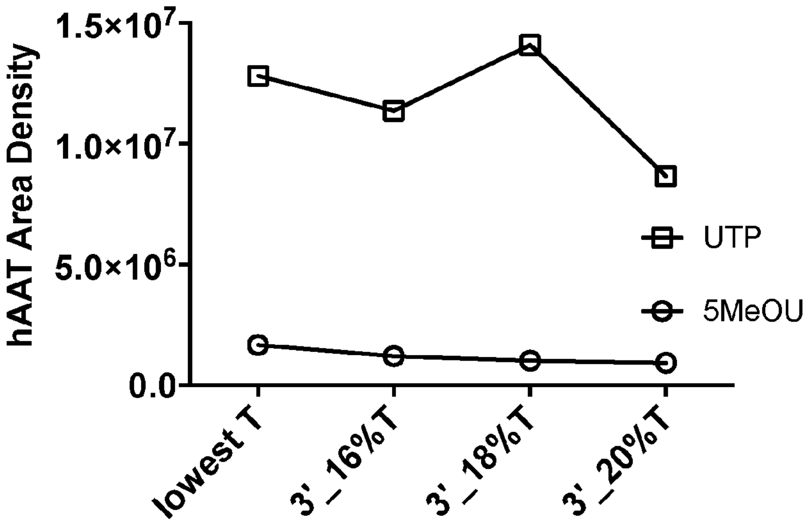
FIG. 7 shows the results of surprisingly reduced impurity levels in a process for synthesizing an hAAT translatable molecule of this invention.

FIG. 7 shows the results of surprisingly reduced impurity levels in a process for synthesizing an hAAT translatable molecule of this invention. FIG. 7 shows the results of a dot blot for detecting double strand RNA impurity in the synthesis mixture (nitro cellulose membrane, J2 antibody to detect dsRNA). The ARC-RNA (5MeOU) "reduced T" synthesis products, which were translatable for hAAT, showed surprisingly reduced dot blot intensity as compared to similar "reduced T" mRNA (UTP) synthesis products. Thus, the ARC-RNA (5MeOU) synthesis process, with template reduced T composition, surprisingly reduced double strand RNA impurity levels in the synthesis mixture. The process for synthesizing the ARC-RNA (5MeOU) molecules of this invention with template reduced T composition provided a surprisingly reduced level of double strand RNA impurity. As shown in FIG. 7, this result is surprising because the "reduced T" mRNA (UTP) synthesis products exhibited increased levels of double strand RNA impurity at lower template T composition.

The compositions of the templates for hAAT are shown in Table 8.

TABLE 8

| Non-Template Nucleotide T compositions for hAAT | |
|---|---|
| hEPO | T % |
| hAAT__lowest__T | 14.0 |
| hAAT__3'__16% T | 16.1 |
| hAAT__3'__18% T | 18.1 |
| hAAT__3'__20% T | 20.0 |
| hAAT__5'__16% T | 16.1 |
| hAAT__5'__18% T | 18.1 |
| hAAT__5'__20% T | 20.0 |
| hAAT__random__16% | 16.1 |
| hAAT__random__18% | 18.1 |
| hAAT__random__20% | 20.0 |

Human AAT ORF reference. Sense strand, non-template. NM_000295.4:262-1518 Homo sapiens serpin family A member 1 (SERPINA1).

(SEQ ID NO: 89)

atgccgtcttctgtctcgtggggcatcctcctgctggcaggcctgtgct gcctggtccctgtctccctggctgaggatccccagggagatgctgcccagaagacagat acatcccaccatgatcaggatcacccaaccttcaacaagatcacccccaacctggctga gttcgccttcagcctataccgccagctggcacaccagtccaacagcaccaatatcttct tctccccagtgagcatcgctacagcctttgcaatgetctccctggggaccaaggctgac actcacgatgaaatcctggagggcctgaatttcaacctcacggagattccggaggctca gatccatgaaggcttccaggaactcctccgtaccctcaaccagccagacagccagctcc agctgaccaccggcaatggcctgttcctcagcgagggcctgaagctagtggataagttt ttggaggatgttaaaaagttgtaccactcagaagccttcactgtcaacttcggggacac cgaagaggccaagaaacagatcaacgattacgtggagaagggtactcaagggaaaattg tggatttggtcaaggagcttgacagagacacagtttttgctctggtgaattacatcttc tttaaaggcaaatgggagagaccctttgaagtcaaggacaccgaggaagaggacttcca cgtggaccaggtgaccaccgtgaaggtgcctatgatgaagcgtttaggcatgtttaaca tccagcactgtaagaagctgtccagctgggtgctgctgatgaaatacctgggcaatgcc accgccatcttcttcctgcctgatgaggggaaactacagcacctggaaaatgaactcac ccacgatatcatcaccaagttcctggaaaatgaagacagaaggtctgccagcttacatt tacccaaactgtccattactggaacctatgatctgaagagcgtcctgggtcaactgggc atcactaaggtcttcagcaatggggctgacctctccggggtcacagaggaggcacccct gaagctctccaaggccgtgcataaggctgtgctgaccatcgacgagaaagggactgaag ctgctggggccatgtttttagaggccatacccatgtctatccccccgaggtcaagttc aacaaaccctttgtcttcttaatgattgaacaaaataccaagtctcccctcttcatggg aaaagtggtgaatcccacccaaaaataa hAAT sense strand, non-template. 3'_lowest_T.

(SEQ ID NO: 90)

ATGCCGAGCAGCGTCAGCTGGGGCATCCTCCTGCTGGCAGGCCTGTGCT

GCCTGGTCCCCGTCAGCCTGGCCGAGGACCCCCAGGGAGACGCCGCCCAGAAGACAGAC

ACAAGCCACCACGAGGAGGAGCACCCAACCTTCAACAAGATCACCCCCAACCTGGCCGA

GTTCGCCTTCAGCCTATACCGCCAGCTGGCACACCAGAGCAACAGCACCAACATCTTCT

TCAGCCCAGTGAGCATCGCCACAGCCTTCGCAATGCTCAGCCTGGGGACCAAGGCCGAC

ACCCACGACGAAATCCTGGAGGGCCTGAACTTCAACCTCACGGAGATCCCGGAGGCCCA

GATCCACGAAGGCTTCCAGGAACTCCTCCGGACCCTCAACCAGCCAGACAGCCAGCTCC

AGCTGACCACCGGCAACGGCCTGTTCCTCAGCGAGGGCCTGAAGCTAGTGGACAAGTTC

CTGGAGGACGTGAAAAAGCTGTACCACAGCGAAGCCTTCACCGTCAACTTCGGGGACAC

-continued

CGAAGAGGCCAAGAAACAGATCAACGACTACGTGGAGAAGGGCACCCAAGGGAAAATCG

TGGACCTGGTCAAGGAGCTGGACAGAGACACAGTGTTCGCCCTGGTGAACTACATCTTC

TTCAAAGGCAAATGGGAGAGACCCTTCGAAGTCAAGGACACCGAGGAAGAGGACTTCCA

CGTGGACCAGGTGACCACCGTGAAGGTGCCCATGATGAAGCGGCTGGGCATGTTCAACA

TCCAGCACTGCAAGAAGCTGAGCAGCTGGGTGCTGCTGATGAAATACCTGGGCAACGCC

ACCGCCATCTTCTTCCTGCCCGACGAGGGGAAACTACAGCACCTGGAAAACGAACTCAC

CCACGACATCATCACCAAGTTCCTGGAAAACGAAGACAGAAGGAGCGCCAGCCTGCACC

TGCCCAAACTGAGCATCACCGGAACCTACGACCTGAAGTCCGTGCTGGGCCAACTGGGC

ATCACCAAGGTCTTCAGCAACGGGGCCGACCTCAGCGGGGTCACAGAGGAGGCACCCCT

GAAGCTCAGCAAGGCCGTGCACAAGGCCGTGCTGACCATCGACGAGAAAGGGACCGAAG

CCGCCGGGGCCATGTTCCTGGAGGCCATACCCATGAGCATCCCCCCCGAGGTCAAGTTC

AACAAACCCTTCGTCTTCCTGATGATCGAACAAAACACCAAGAGCCCCCTCTTCATGGG

AAAAGTGGTGAACCCCACCCAAAAATAA hAAT sense strand, non-template. 3'_16%_T.

(SEQ ID NO: 91)

ATGCCGTCTTCTGTCTCGTGGGGCATCCTCCTGCTGGCAGGCCTGTGCT

GCCTGGTCCCTGTCTCCCTGGCTGAGGATCCCCAGGGAGATGCTGCCCAGAAGACAGAT

ACATCCCACCATGATCAGGATCACCCAACCTTCAACAAGATCACCCCCAACCTGGCTGA

GTTCGCCTTCAGCCTATACCGCCAGCTGGCACACCAGTCCAACAGCACCAATATCTTCT

TCTCCCCAGTGAGCATCGCTACAGCCTTTGCAATGCTCTCCCTGGGGACCAAGGCTGAC

ACTCACGATGAAATCCTGGAGGGCCTGAACTTCAACCTCACGGAGATCCCGGAGGCCCA

GATCCACGAAGGCTTCCAGGAACTCCTCCGGACCCTCAACCAGCCAGACAGCCAGCTCC

AGCTGACCACCGGCAACGGCCTGTTCCTCAGCGAGGGCCTGAAGCTAGTGGACAAGTTC

CTGGAGGACGTGAAAAAGCTGTACCACAGCGAAGCCTTCACCGTCAACTTCGGGGACAC

CGAAGAGGCCAAGAAACAGATCAACGACTACGTGGAGAAGGGCACCCAAGGGAAAATCG

TGGACCTGGTCAAGGAGCTGGACAGAGACACAGTGTTCGCCCTGGTGAACTACATCTTC

TTCAAAGGCAAATGGGAGAGACCCTTCGAAGTCAAGGACACCGAGGAAGAGGACTTCCA

CGTGGACCAGGTGACCACCGTGAAGGTGCCCATGATGAAGCGGCTGGGCATGTTCAACA

TCCAGCACTGCAAGAAGCTGAGCAGCTGGGTGCTGCTGATGAAATACCTGGGCAACGCC

ACCGCCATCTTCTTCCTGCCCGACGAGGGGAAACTACAGCACCTGGAAAACGAACTCAC

CCACGACATCATCACCAAGTTCCTGGAAAACGAAGACAGAAGGAGCGCCAGCCTGCACC

TGCCCAAACTGAGCATCACCGGAACCTACGACCTGAAGTCCGTGCTGGGCCAACTGGGC

ATCACCAAGGTCTTCAGCAACGGGGCCGACCTCAGCGGGGTCACAGAGGAGGCACCCCT

GAAGCTCAGCAAGGCCGTGCACAAGGCCGTGCTGACCATCGACGAGAAAGGGACCGAAG

CCGCCGGGGCCATGTTCCTGGAGGCCATACCCATGAGCATCCCCCCCGAGGTCAAGTTC

AACAAACCCTTCGTCTTCCTGATGATCGAACAAAACACCAAGAGCCCCCTCTTCATGGG

AAAAGTGGTGAACCCCACCCAAAAATAA hAAT sense strand, non-template. 3'_18%_T.

(SEQ ID NO: 92)

ATGCCGTCTTCTGTCTCGTGGGGCATCCTCCTGCTGGCAGGCCTGTGCT

GCCTGGTCCCTGTCTCCCTGGCTGAGGATCCCCAGGGAGATGCTGCCCAGAAGACAGAT

ACATCCCACCATGATCAGGATCACCCAACCTTCAACAAGATCACCCCCAACCTGGCTGA

GTTCGCCTTCAGCCTATACCGCCAGCTGGCACACCAGTCCAACAGCACCAATATCTTCT

-continued

TCTCCCCAGTGAGCATCGCTACAGCCTTTGCAATGCTCTCCCTGGGGACCAAGGCTGAC

ACTCACGATGAAATCCTGGAGGGCCTGAATTTCAACCTCACGGAGATTCCGGAGGCTCA

GATCCATGAAGGCTTCCAGGAACTCCTCCGTACCCTCAACCAGCCAGACAGCCAGCTCC

AGCTGACCACCGGCAATGGCCTGTTCCTCAGCGAGGGCCTGAAGCTAGTGGATAAGTTT

TTGGAGGATGTTAAAAAGTTGTACCACTCAGAAGCCTTCACTGTCAACTTCGGGGACAC

CGAAGAGGCCAAGAAACAGATCAACGATTACGTGGAGAAGGGTACTCAAGGGAAAATTG

TGGATTTGGTCAAGGAGCTTGACAGAGACACAGTTTTTGCTCTGGTGAATTACATCTTC

TTCAAAGGCAAATGGGAGAGACCCTTCGAAGTCAAGGACACCGAGGAAGAGGACTTCCA

CGTGGACCAGGTGACCACCGTGAAGGTGCCCATGATGAAGCGGCTGGGCATGTTCAACA

TCCAGCACTGCAAGAAGCTGAGCAGCTGGGTGCTGCTGATGAAATACCTGGGCAACGCC

ACCGCCATCTTCTTCCTGCCCGACGAGGGGAAACTACAGCACCTGGAAAACGAACTCAC

CCACGACATCATCACCAAGTTCCTGGAAAACGAAGACAGAAGGAGCGCCAGCCTGCACC

TGCCCAAACTGAGCATCACCGGAACCTACGACCTGAAGTCCGTGCTGGGCCAACTGGGC

ATCACCAAGGTCTTCAGCAACGGGGCCGACCTCAGCGGGGTCACAGAGGAGGCACCCCT

GAAGCTCAGCAAGGCCGTGCACAAGGCCGTGCTGACCATCGACGAGAAAGGGACCGAAG

CCGCCGGGGCCATGTTCCTGGAGGCCATACCCATGAGCATCCCCCCCGAGGTCAAGTTC

AACAAACCCTTCGTCTTCCTGATGATCGAACAAAACACCAAGAGCCCCCTCTTCATGGG

AAAAGTGGTGAACCCCACCCAAAAATAA hAAT sense strand, non-template. 3'_20%_T.

(SEQ ID NO: 93)

ATGCCGTCTTCTGTCTCGTGGGGCATCCTCCTGCTGGCAGGCCTGTGCT

GCCTGGTCCCTGTCTCCCTGGCTGAGGATCCCCAGGGAGATGCTGCCCAGAAGACAGAT

ACATCCCACCATGATCAGGATCACCCAACCTTCAACAAGATCACCCCCAACCTGGCTGA

GTTCGCCTTCAGCCTATACCGCCAGCTGGCACACCAGTCCAACAGCACCAATATCTTCT

TCTCCCCAGTGAGCATCGCTACAGCCTTTGCAATGCTCTCCCTGGGGACCAAGGCTGAC

ACTCACGATGAAATCCTGGAGGGCCTGAATTTCAACCTCACGGAGATTCCGGAGGCTCA

GATCCATGAAGGCTTCCAGGAACTCCTCCGTACCCTCAACCAGCCAGACAGCCAGCTCC

AGCTGACCACCGGCAATGGCCTGTTCCTCAGCGAGGGCCTGAAGCTAGTGGATAAGTTT

TTGGAGGATGTTAAAAAGTTGTACCACTCAGAAGCCTTCACTGTCAACTTCGGGGACAC

CGAAGAGGCCAAGAAACAGATCAACGATTACGTGGAGAAGGGTACTCAAGGGAAAATTG

TGGATTTGGTCAAGGAGCTTGACAGAGACACAGTTTTTGCTCTGGTGAATTACATCTTC

TTTAAAGGCAAATGGGAGAGACCCTTTGAAGTCAAGGACACCGAGGAAGAGGACTTCCA

CGTGGACCAGGTGACCACCGTGAAGGTGCCTATGATGAAGCGTTTAGGCATGTTTAACA

TCCAGCACTGTAAGAAGCTGTCCAGCTGGGTGCTGCTGATGAAATACCTGGGCAATGCC

ACCGCCATCTTCTTCCTGCCTGATGAGGGGAAACTACAGCACCTGGAAAATGAACTCAC

CCACGATATCATCACCAAGTTCCTGGAAAATGAAGACAGAAGGTCTGCCAGCTTACATT

TACCCAAACTGTCCATTACTGGAACCTATGATCTGAAGTCCGTGCTGGGTCAACTGGGC

ATCACCAAGGTCTTCAGCAACGGGGCCGACCTCAGCGGGGTCACAGAGGAGGCACCCCT

GAAGCTCAGCAAGGCCGTGCACAAGGCCGTGCTGACCATCGACGAGAAAGGGACCGAAG

-continued

CCGCCGGGGCCATGTTCCTGGAGGCCATACCCATGAGCATCCCCCCCGAGGTCAAGTTC

AACAAACCCTTCGTCTTCCTGATGATCGAACAAAACACCAAGAGCCCCCTCTTCATGGG

AAAAGTGGTGAACCCCACCCAAAAATAA hAAT sense strand, non-template. 5'_16%_T.

(SEQ ID NO: 94)

ATGCCGAGCAGCGTCAGCTGGGGCATCCTCCTGCTGGCAGGCCTGTGCT

GCCTGGTCCCCGTCAGCCTGGCCGAGGACCCCCAGGGAGACGCCGCCCAGAAGACAGAC

ACAAGCCACCACGACCAGGACCACCCAACCTTCAACAAGATCACCCCCAACCTGGCCGA

GTTCGCCTTCAGCCTATACCGCCAGCTGGCACACCAGAGCAACAGCACCAACATCTTCT

TCAGCCCAGTGAGCATCGCCACAGCCTTCGCAATGCTCAGCCTGGGGACCAAGGCCGAC

ACCCACGACGAAATCCTGGAGGGCCTGAACTTCAACCTCACGGAGATCCCGGAGGCCCA

GATCCACGAAGGCTTCCAGGAACTCCTCCGGACCCTCAACCAGCCAGACAGCCAGCTCC

AGCTGACCACCGGCAACGGCCTGTTCCTCAGCGAGGGCCTGAAGCTAGTGGACAAGTTC

CTGGAGGACGTGAAAAAGCTGTACCACAGCGAAGCCTTCACCGTCAACTTCGGGGACAC

CGAAGAGGCCAAGAAACAGATCAACGACTACGTGGAGAAGGGCACCCAAGGGAAAATCG

TGGACCTGGTCAAGGAGCTGGACAGAGACACAGTGTTCGCCCTGGTGAACTACATCTTC

TTCAAAGGCAAATGGGAGAGACCCTTCGAAGTCAAGGACACCGAGGAAGAGGACTTCCA

CGTGGACCAGGTGACCACCGTGAAGGTGCCCATGATGAAGCGGCTGGGCATGTTCAACA

TCCAGCACTGCAAGAAGCTGAGCAGCTGGGTGCTGCTGATGAAATACCTGGGCAACGCC

ACCGCCATCTTCTTCCTGCCCGACGAGGGGAAACTACAGCACCTGGAAAACGAACTCAC

CCACGACATCATCACCAAGTTCCTGGAAAACGAAGACAGAAGGAGCGCCAGCCTGCACC

TGCCCAAACTGAGCATTACTGGAACCTATGATCTGAAGTCCGTGCTGGGTCAACTGGGC

ATCACTAAGGTCTTCAGCAATGGGGCTGACCTCTCCGGGGTCACAGAGGAGGCACCCCT

GAAGCTCTCCAAGGCCGTGCATAAGGCTGTGCTGACCATCGACGAGAAAGGGACTGAAG

CTGCTGGGGCCATGTTTTTAGAGGCCATACCCATGTCTATCCCCCCCGAGGTCAAGTTC

AACAAACCCTTTGTCTTCTTAATGATTGAACAAAATACCAAGTCTCCCCTCTTCATGGG

AAAAGTGGTGAATCCCACCCAAAAATAA hAAT sense strand, non-template. 5'_18%_T.

(SEQ ID NO: 95)

ATGCCGAGCAGCGTCAGCTGGGGCATCCTCCTGCTGGCAGGCCTGTGCT

GCCTGGTCCCCGTCAGCCTGGCCGAGGACCCCCAGGGAGACGCCGCCCAGAAGACAGAC

ACAAGCCACCACGACCAGGACCACCCAACCTTCAACAAGATCACCCCCAACCTGGCCGA

GTTCGCCTTCAGCCTATACCGCCAGCTGGCACACCAGAGCAACAGCACCAACATCTTCT

TCAGCCCAGTGAGCATCGCCACAGCCTTCGCAATGCTCAGCCTGGGGACCAAGGCCGAC

ACCCACGACGAAATCCTGGAGGGCCTGAACTTCAACCTCACGGAGATCCCGGAGGCCCA

GATCCACGAAGGCTTCCAGGAACTCCTCCGGACCCTCAACCAGCCAGACAGCCAGCTCC

AGCTGACCACCGGCAACGGCCTGTTCCTCAGCGAGGGCCTGAAGCTAGTGGACAAGTTC

CTGGAGGACGTGAAAAAGCTGTACCACAGCGAAGCCTTCACCGTCAACTTCGGGGACAC

CGAAGAGGCCAAGAAACAGATCAACGACTACGTGGAGAAGGGCACCCAAGGGAAAATCG

TGGACCTGGTCAAGGAGCTTGACAGAGACACAGTTTTTGCTCTGGTGAATTACATCTTC

TTTAAAGGCAAATGGGAGAGACCCTTTGAAGTCAAGGACACCGAGGAAGAGGACTTCCA

CGTGGACCAGGTGACCACCGTGAAGGTGCCTATGATGAAGCGTTTAGGCATGTTTAACA

-continued

TCCAGCACTGTAAGAAGCTGTCCAGCTGGGTGCTGCTGATGAAATACCTGGGCAATGCC

ACCGCCATCTTCTTCCTGCCTGATGAGGGGAAACTACAGCACCTGGAAAATGAACTCAC

CCACGATATCATCACCAAGTTCCTGGAAAATGAAGACAGAAGGTCTGCCAGCTTACATT

TACCCAAACTGTCCATTACTGGAACCTATGATCTGAAGTCCGTGCTGGGTCAACTGGGC

ATCACTAAGGTCTTCAGCAATGGGGCTGACCTCTCCGGGGTCACAGAGGAGGCACCCCT

GAAGCTCTCCAAGGCCGTGCATAAGGCTGTGCTGACCATCGACGAGAAAGGGACTGAAG

CTGCTGGGGCCATGTTTTTAGAGGCCATACCCATGTCTATCCCCCCCGAGGTCAAGTTC

AACAAACCCTTTGTCTTCTTAATGATTGAACAAAATACCAAGTCTCCCCTCTTCATGGG

AAAAGTGGTGAATCCCACCCAAAAATAA hAAT sense strand, non-template. 5'_20%_T.

(SEQ ID NO: 96)

ATGCCGAGCAGCGTCAGCTGGGGCATCCTCCTGCTGGCAGGCCTGTGCT

GCCTGGTCCCCGTCAGCCTGGCCGAGGACCCCCAGGGAGACGCCGCCCAGAAGACAGAC

ACAAGCCACCACGACCAGGACCACCCAACCTTCAACAAGATCACCCCCAACCTGGCCGA

GTTCGCCTTCAGCCTATACCGCCAGCTGGCACACCAGAGCAACAGCACCAACATCTTCT

TCAGCCCAGTGAGCATCGCCACAGCCTTTGCAATGCTCTCCCTGGGGACCAAGGCTGAC

ACTCACGATGAAATCCTGGAGGGCCTGAATTTCAACCTCACGGAGATTCCGGAGGCTCA

GATCCATGAAGGCTTCCAGGAACTCCTCCGTACCCTCAACCAGCCAGACAGCCAGCTCC

AGCTGACCACCGGCAATGGCCTGTTCCTCAGCGAGGGCCTGAAGCTAGTGGATAAGTTT

TTGGAGGATGTTAAAAAGTTGTACCACTCAGAAGCCTTCACTGTCAACTTCGGGGACAC

CGAAGAGGCCAAGAAACAGATCAACGATTACGTGGAGAAGGGTACTCAAGGGAAAATTG

TGGATTTGGTCAAGGAGCTTGACAGAGACACAGTTTTTGCTCTGGTGAATTACATCTTC

TTTAAAGGCAAATGGGAGAGACCCTTTGAAGTCAAGGACACCGAGGAAGAGGACTTCCA

CGTGGACCAGGTGACCACCGTGAAGGTGCCTATGATGAAGCGTTTAGGCATGTTTAACA

TCCAGCACTGTAAGAAGCTGTCCAGCTGGGTGCTGCTGATGAAATACCTGGGCAATGCC

ACCGCCATCTTCTTCCTGCCTGATGAGGGGAAACTACAGCACCTGGAAAATGAACTCAC

CCACGATATCATCACCAAGTTCCTGGAAAATGAAGACAGAAGGTCTGCCAGCTTACATT

TACCCAAACTGTCCATTACTGGAACCTATGATCTGAAGTCCGTGCTGGGTCAACTGGGC

ATCACTAAGGTCTTCAGCAATGGGGCTGACCTCTCCGGGGTCACAGAGGAGGCACCCCT

GAAGCTCTCCAAGGCCGTGCATAAGGCTGTGCTGACCATCGACGAGAAAGGGACTGAAG

CTGCTGGGGCCATGTTTTTAGAGGCCATACCCATGTCTATCCCCCCCGAGGTCAAGTTC

AACAAACCCTTTGTCTTCTTAATGATTGAACAAAATACCAAGTCTCCCCTCTTCATGGG

AAAAGTGGTGAATCCCACCCAAAAATAA hAAT sense strand, non-template. random_16%_T.

(SEQ ID NO: 97)

ATGCCGAGCAGCGTCTCGTGGGGCATCCTCCTGCTGGCAGGCCTGTGCT

GCCTGGTCCCCGTCAGCCTGGCCGAGGACCCCCAGGGAGATGCTGCCCAGAAGACAGAC

ACATCCCACCACGACCAGGACCACCCAACCTTCAACAAGATCACCCCCAACCTGGCTGA

GTTCGCCTTCAGCCTATACCGCCAGCTGGCACACCAGAGCAACAGCACCAATATCTTCT

TCAGCCCAGTGAGCATCGCTACAGCCTTCGCAATGCTCAGCCTGGGGACCAAGGCCGAC

ACCCACGATGAAATCCTGGAGGGCCTGAATTTCAACCTCACGGAGATCCCGGAGGCTCA

GATCCACGAAGGCTTCCAGGAACTCCTCCGGACCCTCAACCAGCCAGACAGCCAGCTCC

AGCTGACCACCGGCAACGGCCTGTTCCTCAGCGAGGGCCTGAAGCTAGTGGACAAGTTC

-continued

CTGGAGGACGTTAAAAAGCTGTACCACAGCGAAGCCTTCACCGTCAACTTCGGGGACAC

CGAAGAGGCCAAGAAACAGATCAACGATTACGTGGAGAAGGGCACCCAAGGGAAAATCG

TGGACCTGGTCAAGGAGCTTGACAGAGACACAGTGTTTGCCCTGGTGAACTACATCTTC

TTCAAAGGCAAATGGGAGAGACCCTTCGAAGTCAAGGACACCGAGGAAGAGGACTTCCA

CGTGGACCAGGTGACCACCGTGAAGGTGCCCATGATGAAGCGGTTAGGCATGTTCAACA

TCCAGCACTGCAAGAAGCTGAGCAGCTGGGTGCTGCTGATGAAATACCTGGGCAACGCC

ACCGCCATCTTCTTCCTGCCCGACGAGGGGAAACTACAGCACCTGGAAAACGAACTCAC

CCACGACATCATCACCAAGTTCCTGGAAAACGAAGACAGAAGGAGCGCCAGCCTGCATC

TGCCCAAACTGAGCATTACTGGAACCTACGATCTGAAGTCCGTGCTGGGTCAACTGGGC

ATCACCAAGGTCTTCAGCAATGGGGCCGACCTCAGCGGGGTCACAGAGGAGGCACCCCT

GAAGCTCAGCAAGGCCGTGCACAAGGCTGTGCTGACCATCGACGAGAAAGGGACCGAAG

CCGCTGGGGCCATGTTCCTGGAGGCCATACCCATGAGCATCCCCCCCGAGGTCAAGTTC

AACAAACCCTTTGTCTTCCTGATGATCGAACAAAACACCAAGTCTCCCCTCTTCATGGG

AAAAGTGGTGAACCCCACCCAAAAATAA hAAT sense strand, non-template. random_18%_T.

(SEQ ID NO: 98)

ATGCCGTCTTCTGTCTCGTGGGGCATCCTCCTGCTGGCAGGCCTGTGCT

GCCTGGTCCCCGTCTCCCTGGCTGAGGACCCCCAGGGAGATGCCGCCCAGAAGACAGAC

ACATCCCACCATGACCAGGACCACCCAACCTTCAACAAGATCACCCCCAACCTGGCCGA

GTTCGCCTTCAGCCTATACCGCCAGCTGGCACACCAGAGCAACAGCACCAACATCTTCT

TCTCCCCAGTGAGCATCGCCACAGCCTTTGCAATGCTCTCCCTGGGGACCAAGGCCGAC

ACCCACGACGAAATCCTGGAGGGCCTGAATTTCAACCTCACGGAGATCCCGGAGGCTCA

GATCCATGAAGGCTTCCAGGAACTCCTCCGGACCCTCAACCAGCCAGACAGCCAGCTCC

AGCTGACCACCGGCAATGGCCTGTTCCTCAGCGAGGGCCTGAAGCTAGTGGATAAGTTC

CTGGAGGATGTTAAAAAGCTGTACCACAGCGAAGCCTTCACCGTCAACTTCGGGGACAC

CGAAGAGGCCAAGAAACAGATCAACGATTACGTGGAGAAGGGCACCCAAGGGAAAATCG

TGGACCTGGTCAAGGAGCTTGACAGAGACACAGTGTTTGCTCTGGTGAATTACATCTTC

TTTAAAGGCAAATGGGAGAGACCCTTTGAAGTCAAGGACACCGAGGAAGAGGACTTCCA

CGTGGACCAGGTGACCACCGTGAAGGTGCCTATGATGAAGCGGTTAGGCATGTTTAACA

TCCAGCACTGCAAGAAGCTGAGCAGCTGGGTGCTGCTGATGAAATACCTGGGCAATGCC

ACCGCCATCTTCTTCCTGCCTGATGAGGGGAAACTACAGCACCTGGAAAACGAACTCAC

CCACGACATCATCACCAAGTTCCTGGAAAATGAAGACAGAAGGTCTGCCAGCTTACACT

TACCCAAACTGAGCATTACTGGAACCTACGATCTGAAGTCCGTGCTGGGCCAACTGGGC

ATCACTAAGGTCTTCAGCAACGGGGCTGACCTCTCCGGGGTCACAGAGGAGGCACCCCT

GAAGCTCAGCAAGGCCGTGCACAAGGCTGTGCTGACCATCGACGAGAAAGGGACCGAAG

CTGCCGGGGCCATGTTTCTGGAGGCCATACCCATGTCTATCCCCCCCGAGGTCAAGTTC

AACAAACCCTTTGTCTTCCTGATGATCGAACAAAATACCAAGAGCCCCCTCTTCATGGG

AAAAGTGGTGAACCCCACCCAAAAATAA hAAT sense strand, non-template. random_20%_T.

(SEQ ID NO: 99)

ATGCCGAGCAGCGTCAGCTGGGGCATCCTCCTGCTGGCAGGCCTGTGCT

GCCTGGTCCCTGTCTCCCTGGCTGAGGATCCCCAGGGAGATGCTGCCCAGAAGACAGAT

-continued

ACATCCCACCATGATCAGGATCACCCAACCTTCAACAAGATCACCCCCAACCTGGCTGA

GTTCGCCTTCAGCCTATACCGCCAGCTGGCACACCAGTCCAACAGCACCAATATCTTCT

TCTCCCCAGTGAGCATCGCTACAGCCTTCGCAATGCTCTCCCTGGGGACCAAGGCTGAC

ACTCACGATGAAATCCTGGAGGGCCTGAATTTCAACCTCACGGAGATTCCGGAGGCCCA

GATCCATGAAGGCTTCCAGGAACTCCTCCGTACCCTCAACCAGCCAGACAGCCAGCTCC

AGCTGACCACCGGCAATGGCCTGTTCCTCAGCGAGGGCCTGAAGCTAGTGGATAAGTTT

TTGGAGGATGTTAAAAAGCTGTACCACAGCGAAGCCTTCACTGTCAACTTCGGGGACAC

CGAAGAGGCCAAGAAACAGATCAACGATTACGTGGAGAAGGGTACTCAAGGGAAAATTG

TGGATTTGGTCAAGGAGCTTGACAGAGACACAGTTTTTGCTCTGGTGAATTACATCTTC

TTCAAAGGCAAATGGGAGAGACCCTTTGAAGTCAAGGACACCGAGGAAGAGGACTTCCA

CGTGGACCAGGTGACCACCGTGAAGGTGCCTATGATGAAGCGGTTAGGCATGTTCAACA

TCCAGCACTGTAAGAAGCTGTCCAGCTGGGTGCTGCTGATGAAATACCTGGGCAATGCC

ACCGCCATCTTCTTCCTGCCTGATGAGGGGAAACTACAGCACCTGGAAAATGAACTCAC

CCACGATATCATCACCAAGTTCCTGGAAAATGAAGACAGAAGGAGCGCCAGCTTACATT

TACCCAAACTGAGCATTACTGGAACCTACGATCTGAAGTCCGTGCTGGGTCAACTGGGC

ATCACTAAGGTCTTCAGCAACGGGGCTGACCTCTCCGGGGTCACAGAGGAGGCACCCCT

GAAGCTCTCCAAGGCCGTGCATAAGGCTGTGCTGACCATCGACGAGAAAGGGACTGAAG

CTGCTGGGGCCATGTTTTTAGAGGCCATACCCATGTCTATCCCCCCCGAGGTCAAGTTC

AACAAACCCTTTGTCTTCCTGATGATCGAACAAAATACCAAGAGCCCCCTCTTCATGGG

AAAAGTGGTGAATCCCACCCAAAAATAA

TEV-hAAT-XbG sense strand, non-template.
3'_lowest_T. (1689 nt)

(SEQ ID NO: 100)

AGGAAACTTAAGTCAACACAACATATACAAAACAAACGAATCTCAAGGA

ATCAAGCATTCTAGTTCTATTGCAGCAATTTAAATCATTTCTTTTAAAGCAAAAGCAAT

TTTCTGAAAATTTTCACCATTTACGAACGATAGCCATGCCGAGCAGCGTCAGCTGGGGC

ATCCTCCTGCTGGCAGGCCTGTGCTGCCTGGTCCCCGTCAGCCTGGCCGAGGACCCCCA

GGGAGACGCCGCCCAGAAGACAGACACAAGCCACCACGACCAGGACCACCCAACCTTCA

ACAAGATCACCCCCAACCTGGCCGAGTTCGCCTTCAGCCTATACCGCCAGCTGGCACAC

CAGAGCAACAGCACCAACATCTTCTTCAGCCCAGTGAGCATCGCCACAGCCTTCGCAAT

GCTCAGCCTGGGGACCAAGGCCGACACCCACGACGAAATCCTGGAGGGCCTGAACTTCA

ACCTCACGGAGATCCCGGAGGCCCAGATCCACGAAGGCTTCCAGGAACTCCTCCGGACC

CTCAACCAGCCAGACAGCCAGCTCCAGCTGACCACCGGCAACGGCCTGTTCCTCAGCGA

GGGCCTGAAGCTAGTGGACAAGTTCCTGGAGGACGTGAAAAAGCTGTACCACAGCGAAG

CCTTCACCGTCAACTTCGGGGACACCGAAGAGGCCAAGAAACAGATCAACGACTACGTG

GAGAAGGGCACCCAAGGGAAAATCGTGGACCTGGTCAAGGAGCTGGACAGAGACACAGT

GTTCGCCCTGGTGAACTACATCTTCTTCAAAGGCAAATGGGAGAGACCCTTCGAAGTCA

AGGACACCGAGGAAGAGGACTTCCACGTGGACCAGGTGACCACCGTGAAGGTGCCCATG

ATGAAGCGGCTGGGCATGTTCAACATCCAGCACTGCAAGAAGCTGAGCAGCTGGGTGCT

GCTGATGAAATACCTGGGCAACGCCACCGCCATCTTCTTCCTGCCCGACGAGGGGAAAC

TACAGCACCTGGAAAACGAACTCACCCACGACATCATCACCAAGTTCCTGGAAAACGAA

GACAGAAGGAGCGCCAGCCTGCACCTGCCCAAACTGAGCATCACCGGAACCTACGACCT

-continued

GAAGTCCGTGCTGGGCCAACTGGGCATCACCAAGGTCTTCAGCAACGGGGCCGACCTCA

GCGGGGTCACAGAGGAGGCACCCCTGAAGCTCAGCAAGGCCGTGCACAAGGCCGTGCTG

ACCATCGACGAGAAAGGGACCGAAGCCGCCGGGGCCATGTTCCTGGAGGCCATACCCAT

GAGCATCCCCCCCGAGGTCAAGTTCAACAAACCCTTCGTCTTCCTGATGATCGAACAAA

ACACCAAGAGCCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAA

TEV-hAAT-XbG sense strand, non-template.
3'_16%_T. (1689 nt)

(SEQ ID NO: 101)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGTCTTCTGTCTCGTGGGGC

ATCCTCCTGCTGGCAGGCCTGTGCTGCCTGGTCCCTGTCTCCCTGGCTGAGGATCCCCA

GGGAGATGCTGCCCAGAAGACAGATACATCCCACCATGATCAGGATCACCCAACCTTCA

ACAAGATCACCCCCAACCTGGCTGAGTTCGCCTTCAGCCTATACCGCCAGCTGGCACAC

CAGTCCAACAGCACCAATATCTTCTTCTCCCCAGTGAGCATCGCTACAGCCTTTGCAAT

GCTCTCCCTGGGGACCAAGGCTGACACTCACGATGAAATCCTGGAGGGCCTGAACTTCA

ACCTCACGGAGATCCCGGAGGCCCAGATCCACGAAGGCTTCCAGGAACTCCTCCGGACC

CTCAACCAGCCAGACAGCCAGCTCCAGCTGACCACCGGCAACGGCCTGTTCCTCAGCGA

GGGCCTGAAGCTAGTGGACAAGTTCCTGGAGGACGTGAAAAAGCTGTACCACAGCGAAG

CCTTCACCGTCAACTTCGGGGACACCGAAGAGGCCAAGAAACAGATCAACGACTACGTG

GAGAAGGGCACCCAAGGGAAAATCGTGGACCTGGTCAAGGAGCTGGACAGAGACACAGT

GTTCGCCCTGGTGAACTACATCTTCTTCAAAGGCAAATGGGAGAGACCCTTCGAAGTCA

AGGACACCGAGGAAGAGGACTTCCACGTGGACCAGGTGACCACCGTGAAGGTGCCCATG

ATGAAGCGGCTGGGCATGTTCAACATCCAGCACTGCAAGAAGCTGAGCAGCTGGGTGCT

GCTGATGAAATACCTGGGCAACGCCACCGCCATCTTCTTCCTGCCCGACGAGGGGAAAC

TACAGCACCTGGAAAACGAACTCACCCACGACATCATCACCAAGTTCCTGGAAAACGAA

GACAGAAGGAGCGCCAGCCTGCACCTGCCCAAACTGAGCATCACCGGAACCTACGACCT

GAAGTCCGTGCTGGGCCAACTGGGCATCACCAAGGTCTTCAGCAACGGGGCCGACCTCA

GCGGGGTCACAGAGGAGGCACCCCTGAAGCTCAGCAAGGCCGTGCACAAGGCCGTGCTG

ACCATCGACGAGAAAGGGACCGAAGCCGCCGGGGCCATGTTCCTGGAGGCCATACCCAT

GAGCATCCCCCCCGAGGTCAAGTTCAACAAACCCTTCGTCTTCCTGATGATCGAACAAA

ACACCAAGAGCCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAA

-continued

TEV-hAAT-XbG sense strand, non-template.
3'_18%_T. (1689 nt)
(SEQ ID NO: 102)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGTCTTCTGTCTCGTGGGGC

ATCCTCCTGCTGGCAGGCCTGTGCTGCCTGGTCCCTGTCTCCCTGGCTGAGGATCCCCA

GGGAGATGCTGCCCAGAAGACAGATACATCCCACCATGATCAGGATCACCCAACCTTCA

ACAAGATCACCCCCAACCTGGCTGAGTTCGCCTTCAGCCTATACCGCCAGCTGGCACAC

CAGTCCAACAGCACCAATATCTTCTTCTCCCCAGTGAGCATCGCTACAGCCTTTGCAAT

GCTCTCCCTGGGGACCAAGGCTGACACTCACGATGAAATCCTGGAGGGCCTGAATTTCA

ACCTCACGGAGATTCCGGAGGCTCAGATCCATGAAGGCTTCCAGGAACTCCTCCGTACC

CTCAACCAGCCAGACAGCCAGCTCCAGCTGACCACCGGCAATGGCCTGTTCCTCAGCGA

GGGCCTGAAGCTAGTGGATAAGTTTTTGGAGGATGTTAAAAAGTTGTACCACTCAGAAG

CCTTCACTGTCAACTTCGGGGACACCGAAGAGGCCAAGAAACAGATCAACGATTACGTG

GAGAAGGGTACTCAAGGGAAAATTGTGGATTTGGTCAAGGAGCTTGACAGAGACACAGT

TTTTGCTCTGGTGAATTACATCTTCTTCAAAGGCAAATGGGAGAGACCCTTCGAAGTCA

AGGACACCGAGGAAGAGGACTTCCACGTGGACCAGGTGACCACCGTGAAGGTGCCCATG

ATGAAGCGGCTGGGCATGTTCAACATCCAGCACTGCAAGAAGCTGAGCAGCTGGGTGCT

GCTGATGAAATACCTGGGCAACGCCACCGCCATCTTCTTCCTGCCCGACGAGGGGAAAC

TACAGCACCTGGAAAACGAACTCACCCACGACATCATCACCAAGTTCCTGGAAAACGAA

GACAGAAGGAGCGCCAGCCTGCACCTGCCCAAACTGAGCATCACCGGAACCTACGACCT

GAAGTCCGTGCTGGGCCAACTGGGCATCACCAAGGTCTTCAGCAACGGGGCCGACCTCA

GCGGGGTCACAGAGGAGGCACCCCTGAAGCTCAGCAAGGCCGTGCACAAGGCCGTGCTG

ACCATCGACGAGAAAGGGACCGAAGCCGCCGGGGCCATGTTCCTGGAGGCCATACCCAT

GAGCATCCCCCCCGAGGTCAAGTTCAACAAACCCTTCGTCTTCCTGATGATCGAACAAA

ACACCAAGAGCCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAA

TEV-hAAT-XbG sense strand, non-template.
3'_20%_T. (1689 nt)
(SEQ ID NO: 103)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGTCTTCTGTCTCGTGGGGC

ATCCTCCTGCTGGCAGGCCTGTGCTGCCTGGTCCCTGTCTCCCTGGCTGAGGATCCCCA

GGGAGATGCTGCCCAGAAGACAGATACATCCCACCATGATCAGGATCACCCAACCTTCA

ACAAGATCACCCCCAACCTGGCTGAGTTCGCCTTCAGCCTATACCGCCAGCTGGCACAC

CAGTCCAACAGCACCAATATCTTCTTCTCCCCAGTGAGCATCGCTACAGCCTTTGCAAT

GCTCTCCCTGGGGACCAAGGCTGACACTCACGATGAAATCCTGGAGGGCCTGAATTTCA

-continued

ACCTCACGGAGATTCCGGAGGCTCAGATCCATGAAGGCTTCCAGGAACTCCTCCGTACC

CTCAACCAGCCAGACAGCCAGCTCCAGCTGACCACCGGCAATGGCCTGTTCCTCAGCGA

GGGCCTGAAGCTAGTGGATAAGTTTTTGGAGGATGTTAAAAAGTTGTACCACTCAGAAG

CCTTCACTGTCAACTTCGGGGACACCGAAGAGGCCAAGAAACAGATCAACGATTACGTG

GAGAAGGGTACTCAAGGGAAAATTGTGGATTTGGTCAAGGAGCTTGACAGAGACACAGT

TTTTGCTCTGGTGAATTACATCTTCTTTAAAGGCAAATGGGAGAGACCCTTTGAAGTCA

AGGACACCGAGGAAGAGGACTTCCACGTGGACCAGGTGACCACCGTGAAGGTGCCTATG

ATGAAGCGTTTAGGCATGTTTAACATCCAGCACTGTAAGAAGCTGTCCAGCTGGGTGCT

GCTGATGAAATACCTGGGCAATGCCACCGCCATCTTCTTCCTGCCTGATGAGGGGAAAC

TACAGCACCTGGAAAATGAACTCACCCACGATATCATCACCAAGTTCCTGGAAAATGAA

GACAGAAGGTCTGCCAGCTTACATTTACCCAAACTGTCCATTACTGGAACCTATGATCT

GAAGTCCGTGCTGGGTCAACTGGGCATCACCAAGGTCTTCAGCAACGGGGCCGACCTCA

GCGGGGTCACAGAGGAGGCACCCCTGAAGCTCAGCAAGGCCGTGCACAAGGCCGTGCTG

ACCATCGACGAGAAAGGGACCGAAGCCGCCGGGGCCATGTTCCTGGAGGCCATACCCAT

GAGCATCCCCCCCGAGGTCAAGTTCAACAAACCCTTCGTCTTCCTGATGATCGAACAAA

ACACCAAGAGCCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAA

TEV-hAAT-XbG sense strand, non-template.
5'_16%_T. (1689 nt)

(SEQ ID NO: 104)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGAGCAGCGTCAGCTGGGGC

ATCCTCCTGCTGGCAGGCCTGTGCTGCCTGGTCCCCGTCAGCCTGGCCGAGGACCCCCA

GGGAGACGCCGCCCAGAAGACAGACACAAGCCACCACGACCAGGACCACCCAACCTTCA

ACAAGATCACCCCCAACCTGGCCGAGTTCGCCTTCAGCCTATACCGCCAGCTGGCACAC

CAGAGCAACAGCACCAACATCTTCTTCAGCCCAGTGAGCATCGCCACAGCCTTCGCAAT

GCTCAGCCTGGGGACCAAGGCCGACACCCACGACGAAATCCTGGAGGGCCTGAACTTCA

ACCTCACGGAGATCCCGGAGGCCCAGATCCACGAAGGCTTCCAGGAACTCCTCCGGACC

CTCAACCAGCCAGACAGCCAGCTCCAGCTGACCACCGGCAACGGCCTGTTCCTCAGCGA

GGGCCTGAAGCTAGTGGACAAGTTCCTGGAGGACGTGAAAAAGCTGTACCACAGCGAAG

CCTTCACCGTCAACTTCGGGGACACCGAAGAGGCCAAGAAACAGATCAACGACTACGTG

GAGAAGGGCACCCAAGGGAAAATCGTGGACCTGGTCAAGGAGCTGGACAGAGACACAGT

GTTCGCCCTGGTGAACTACATCTTCTTCAAAGGCAAATGGGAGAGACCCTTCGAAGTCA

AGGACACCGAGGAAGAGGACTTCCACGTGGACCAGGTGACCACCGTGAAGGTGCCCATG

ATGAAGCGGCTGGGCATGTTCAACATCCAGCACTGCAAGAAGCTGAGCAGCTGGGTGCT

GCTGATGAAATACCTGGGCAACGCCACCGCCATCTTCTTCCTGCCCGACGAGGGGAAAC

TACAGCACCTGGAAAACGAACTCACCCACGACATCATCACCAAGTTCCTGGAAAACGAA

-continued

GACAGAAGGAGCGCCAGCCTGCACCTGCCCAAACTGAGCATTACTGGAACCTATGATCT

GAAGTCCGTGCTGGGTCAACTGGGCATCACTAAGGTCTTCAGCAATGGGGCTGACCTCT

CCGGGGTCACAGAGGAGGCACCCCTGAAGCTCTCCAAGGCCGTGCATAAGGCTGTGCTG

ACCATCGACGAGAAAGGGACTGAAGCTGCTGGGGCCATGTTTTTAGAGGCCATACCCAT

GTCTATCCCCCCCGAGGTCAAGTTCAACAAACCCTTTGTCTTCTTAATGATTGAACAAA

ATACCAAGTCTCCCCTCTTCATGGGAAAAGTGGTGAATCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAA

TEV-hAAT-XbG sense strand, non-template.
5'_18%_T. (1689 nt)

(SEQ ID NO: 105)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGAGCAGCGTCAGCTGGGGC

ATCCTCCTGCTGGCAGGCCTGTGCTGCCTGGTCCCCGTCAGCCTGGCCGAGGACCCCCA

GGGAGACGCCGCCCAGAAGACAGACACAAGCCACCACGACCAGGACCACCCAACCTTCA

ACAAGATCACCCCCAACCTGGCCGAGTTCGCCTTCAGCCTATACCGCCAGCTGGCACAC

CAGAGCAACAGCACCAACATCTTCTTCAGCCCAGTGAGCATCGCCACAGCCTTCGCAAT

GCTCAGCCTGGGGACCAAGGCCGACACCCACGACGAAATCCTGGAGGGCCTGAACTTCA

ACCTCACGGAGATCCCGGAGGCCCAGATCCACGAAGGCTTCCAGGAACTCCTCCGGACC

CTCAACCAGCCAGACAGCCAGCTCCAGCTGACCACCGGCAACGGCCTGTTCCTCAGCGA

GGGCCTGAAGCTAGTGGACAAGTTCCTGGAGGACGTGAAAAAGCTGTACCACAGCGAAG

CCTTCACCGTCAACTTCGGGGACACCGAAGAGGCCAAGAAACAGATCAACGACTACGTG

GAGAAGGGCACCCAAGGGAAAATCGTGGACCTGGTCAAGGAGCTTGACAGAGACACAGT

TTTTGCTCTGGTGAATTACATCTTCTTTAAAGGCAAATGGGAGAGACCCTTTGAAGTCA

AGGACACCGAGGAAGAGGACTTCCACGTGGACCAGGTGACCACCGTGAAGGTGCCTATG

ATGAAGCGTTTAGGCATGTTTAACATCCAGCACTGTAAGAAGCTGTCCAGCTGGGTGCT

GCTGATGAAATACCTGGGCAATGCCACCGCCATCTTCTTCCTGCCTGATGAGGGGAAAC

TACAGCACCTGGAAAATGAACTCACCCACGATATCATCACCAAGTTCCTGGAAAATGAA

GACAGAAGGTCTGCCAGCTTACATTTACCCAAACTGTCCATTACTGGAACCTATGATCT

GAAGTCCGTGCTGGGTCAACTGGGCATCACTAAGGTCTTCAGCAATGGGGCTGACCTCT

CCGGGGTCACAGAGGAGGCACCCCTGAAGCTCTCCAAGGCCGTGCATAAGGCTGTGCTG

ACCATCGACGAGAAAGGGACTGAAGCTGCTGGGGCCATGTTTTTAGAGGCCATACCCAT

GTCTATCCCCCCCGAGGTCAAGTTCAACAAACCCTTTGTCTTCTTAATGATTGAACAAA

ATACCAAGTCTCCCCTCTTCATGGGAAAAGTGGTGAATCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

-continued

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAA

TEV-hAAT-XbG sense strand, non-template.
5'_20%_T. (1689 nt)

(SEQ ID NO: 106)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGAGCAGCGTCAGCTGGGGC

ATCCTCCTGCTGGCAGGCCTGTGCTGCCTGGTCCCCGTCAGCCTGGCCGAGGACCCCCA

GGGAGACGCCGCCCAGAAGACAGACACAAGCCACCACGACCAGGACCACCCAACCTTCA

ACAAGATCACCCCCAACCTGGCCGAGTTCGCCTTCAGCCTATACCGCCAGCTGGCACAC

CAGAGCAACAGCACCAACATCTTCTTCAGCCCAGTGAGCATCGCCACAGCCTTTGCAAT

GCTCTCCCTGGGGACCAAGGCTGACACTCACGATGAAATCCTGGAGGGCCTGAATTTCA

ACCTCACGGAGATTCCGGAGGCTCAGATCCATGAAGGCTTCCAGGAACTCCTCCGTACC

CTCAACCAGCCAGACAGCCAGCTCCAGCTGACCACCGGCAATGGCCTGTTCCTCAGCGA

GGGCCTGAAGCTAGTGGATAAGTTTTTGGAGGATGTTAAAAAGTTGTACCACTCAGAAG

CCTTCACTGTCAACTTCGGGGACACCGAAGAGGCCAAGAAACAGATCAACGATTACGTG

GAGAAGGGTACTCAAGGGAAAATTGTGGATTTGGTCAAGGAGCTTGACAGAGACACAGT

TTTTGCTCTGGTGAATTACATCTTCTTTAAAGGCAAATGGGAGAGACCCTTTGAAGTCA

AGGACACCGAGGAAGAGGACTTCCACGTGGACCAGGTGACCACCGTGAAGGTGCCTATG

ATGAAGCGTTTAGGCATGTTTAACATCCAGCACTGTAAGAAGCTGTCCAGCTGGGTGCT

GCTGATGAAATACCTGGGCAATGCCACCGCCATCTTCTTCCTGCCTGATGAGGGGAAAC

TACAGCACCTGGAAAATGAACTCACCCACGATATCATCACCAAGTTCCTGGAAAATGAA

GACAGAAGGTCTGCCAGCTTACATTTACCCAAACTGTCCATTACTGGAACCTATGATCT

GAAGTCCGTGCTGGGTCAACTGGGCATCACTAAGGTCTTCAGCAATGGGGCTGACCTCT

CCGGGGTCACAGAGGAGGCACCCCTGAAGCTCTCCAAGGCCGTGCATAAGGCTGTGCTG

ACCATCGACGAGAAAGGGACTGAAGCTGCTGGGGCCATGTTTTTAGAGGCCATACCCAT

GTCTATCCCCCCCGAGGTCAAGTTCAACAAACCCTTTGTCTTCTTAATGATTGAACAAA

ATACCAAGTCTCCCCTCTTCATGGGAAAAGTGGTGAATCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAA

TEV-hAAT-XbG sense strand, non-template.
random_16%_T. (1689 nt)

(SEQ ID NO: 107)

AGGAAACTTAAGTCAACACAACATATACAAAACAAACGAATCTCAAGCA

ATCAAGCATTCTAGTTCTATTGCAGCAATTTAAATCATTTCTTTTAAAGCAAAAGCAAT

TTTCTGAAAATTTTCACCATTTACGAACGATAGCCATGCCGAGCAGCGTCTCGTGGGGC

ATCCTCCTGCTGGCAGGCCTGTGCTGCCTGGTCCCCGTCAGCCTGGCCGAGGACCCCCA

GGGAGATGCTGCCCAGAAGACAGACACATCCCACCACGACCAGGACCACCCAACCTTCA

-continued

ACAAGATCACCCCCAACCTGGCTGAGTTCGCCTTCAGCCTATACCGCCAGCTGGCACAC

CAGAGCAACAGCACCAATATCTTCTTCAGCCCAGTGAGCATCGCTACAGCCTTCGCAAT

GCTCAGCCTGGGGACCAAGGCCGACACCCACGATGAAATCCTGGAGGGCCTGAATTTCA

ACCTCACGGAGATCCCGGAGGCTCAGATCCACGAAGGCTTCCAGGAACTCCTCCGGACC

CTCAACCAGCCAGACAGCCAGCTCCAGCTGACCACCGGCAACGGCCTGTTCCTCAGCGA

GGGCCTGAAGCTAGTGGACAAGTTCCTGGAGGACGTTAAAAAGCTGTACCACAGCGAAG

CCTTCACCGTCAACTTCGGGGACACCGAAGAGGCCAAGAAACAGATCAACGATTACGTG

GAGAAGGGCACCCAAGGGAAAATCGTGGACCTGGTCAAGGAGCTTGACAGAGACACAGT

GTTTGCCCTGGTGAACTACATCTTCTTCAAAGGCAAATGGGAGAGACCCTTCGAAGTCA

AGGACACCGAGGAAGAGGACTTCCACGTGGACCAGGTGACCACCGTGAAGGTGCCCATG

ATGAAGCGGTTAGGCATGTTCAACATCCAGCACTGCAAGAAGCTGAGCAGCTGGGTGCT

GCTGATGAAATACCTGGGCAACGCCACCGCCATCTTCTTCCTGCCCGACGAGGGGAAAC

TACAGCACCTGGAAAACGAACTCACCCACGACATCATCACCAAGTTCCTGGAAAACGAA

GACAGAAGGAGCGCCAGCCTGCATCTGCCCAAACTGAGCATTACTGGAACCTACGATCT

GAAGTCCGTGCTGGGTCAACTGGGCATCACCAAGGTCTTCAGCAATGGGGCCGACCTCA

GCGGGGTCACAGAGGAGGCACCCCTGAAGCTCAGCAAGGCCGTGCACAAGGCTGTGCTG

ACCATCGACGAGAAAGGGACCGAAGCCGCTGGGGCCATGTTCCTGGAGGCCATACCCAT

GAGCATCCCCCCCGAGGTCAAGTTCAACAAACCCTTTGTCTTCCTGATGATCGAACAAA

ACACCAAGTCTCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAA

TEV-hAAT-XbG sense strand, non-template.
random_18%_T. (1689 nt)

(SEQ ID NO: 108)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGTCTTCTGTCTCGTGGGGC

ATCCTCCTGCTGGCAGGCCTGTGCTGCCTGGTCCCCGTCTCCCTGGCTGAGGACCCCCA

GGGAGATGCCGCCCAGAAGACAGACACATCCCACCATGACCAGGACCACCCAACCTTCA

ACAAGATCACCCCCAACCTGGCCGAGTTCGCCTTCAGCCTATACCGCCAGCTGGCACAC

CAGAGCAACAGCACCAACATCTTCTTCTCCCCAGTGAGCATCGCCACAGCCTTTGCAAT

GCTCTCCCTGGGGACCAAGGCCGACACCCACGACGAAATCCTGGAGGGCCTGAATTTCA

ACCTCACGGAGATCCCGGAGGCTCAGATCCATGAAGGCTTCCAGGAACTCCTCCGGACC

CTCAACCAGCCAGACAGCCAGCTCCAGCTGACCACCGGCAATGGCCTGTTCCTCAGCGA

GGGCCTGAAGCTAGTGGATAAGTTCCTGGAGGATGTTAAAAAGCTGTACCACAGCGAAG

CCTTCACCGTCAACTTCGGGGACACCGAAGAGGCCAAGAAACAGATCAACGATTACGTG

GAGAAGGGCACCCAAGGGAAAATCGTGGACCTGGTCAAGGAGCTTGACAGAGACACAGT

GTTTGCTCTGGTGAATTACATCTTCTTTAAAGGCAAATGGGAGAGACCCTTTGAAGTCA

AGGACACCGAGGAAGAGGACTTCCACGTGGACCAGGTGACCACCGTGAAGGTGCCTATG

-continued

ATGAAGCGGTTAGGCATGTTTAACATCCAGCACTGCAAGAAGCTGAGCAGCTGGGTGCT

GCTGATGAAATACCTGGGCAATGCCACCGCCATCTTCTTCCTGCCTGATGAGGGGAAAC

TACAGCACCTGGAAAACGAACTCACCCACGACATCATCACCAAGTTCCTGGAAAATGAA

GACAGAAGGTCTGCCAGCTTACACTTACCCAAACTGAGCATTACTGGAACCTACGATCT

GAAGTCCGTGCTGGGCCAACTGGGCATCACTAAGGTCTTCAGCAACGGGGCTGACCTCT

CCGGGGTCACAGAGGAGGCACCCCTGAAGCTCAGCAAGGCCGTGCACAAGGCTGTGCTG

ACCATCGACGAGAAAGGGACCGAAGCTGCCGGGGCCATGTTTCTGGAGGCCATACCCAT

GTCTATCCCCCCCGAGGTCAAGTTCAACAAACCCTTTGTCTTCCTGATGATCGAACAAA

ATACCAAGAGCCCCCTCTTCATGGGAAAAGTGGTGAACCCCACCCAAAAATAACTCGAG

CTAGTGACTGACTAGGATCTGGTTACCACTAAACCAGCCTCAAGAACACCCGAATGGAG

TCTCTAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAA

TEV-hAAT-XbG sense strand, non-template.
random_20%_T. (1689 nt)

(SEQ ID NO: 109)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCCGAGCAGCGTCAGCTGGGGC

ATCCTCCTGCTGGCAGGCCTGTGCTGCCTGGTCCCTGTCTCCCTGGCTGAGGATCCCCA

GGGAGATGCTGCCCAGAAGACAGATACATCCCACCATGATCAGGATCACCCAACCTTCA

ACAAGATCACCCCCAACCTGGCTGAGTTCGCCTTCAGCCTATACCGCCAGCTGGCACAC

CAGTCCAACAGCACCAATATCTTCTTCTCCCCAGTGAGCATCGCTACAGCCTTCGCAAT

GCTCTCCCTGGGGACCAAGGCTGACACTCACGATGAAATCCTGGAGGGCCTGAATTTCA

ACCTCACGGAGATTCCGGAGGCCCAGATCCATGAAGGCTTCCAGGAACTCCTCCGTACC

CTCAACCAGCCAGACAGCCAGCTCCAGCTGACCACCGGCAATGGCCTGTTCCTCAGCGA

GGGCCTGAAGCTAGTGGATAAGTTTTTGGAGGATGTTAAAAAGCTGTACCACAGCGAAG

CCTTCACTGTCAACTTCGGGGACACCGAAGAGGCCAAGAAACAGATCAACGATTACGTG

GAGAAGGGTACTCAAGGGAAAATTGTGGATTTGGTCAAGGAGCTTGACAGAGACACAGT

TTTTGCTCTGGTGAATTACATCTTCTTCAAAGGCAAATGGGAGAGACCCTTTGAAGTCA

AGGACACCGAGGAAGAGGACTTCCACGTGGACCAGGTGACCACCGTGAAGGTGCCTATG

ATGAAGCGGTTAGGCATGTTCAACATCCAGCACTGTAAGAAGCTGTCCAGCTGGGTGCT

GCTGATGAAATACCTGGGCAATGCCACCGCCATCTTCTTCCTGCCTGATGAGGGGAAAC

TACAGCACCTGGAAAATGAACTCACCCACGATATCATCACCAAGTTCCTGGAAAATGAA

GACAGAAGGAGCGCCAGCTTACATTTACCCAAACTGAGCATTACTGGAACCTACGATCT

GAAGTCCGTGCTGGGTCAACTGGGCATCACTAAGGTCTTCAGCAACGGGGCTGACCTCT

CCGGGGTCACAGAGGAGGCACCCCTGAAGCTCTCCAAGGCCGTGCATAAGGCTGTGCTG

ACCATCGACGAGAAAGGGACTGAAGCTGCTGGGGCCATGTTTTTAGAGGCCATACCCAT

GTCTATCCCCCCCGAGGTCAAGTTCAACAAACCCTTTGTCTTCCTGATGATCGAACAAA

ATACCAAGAGCCCCCTCTTCATGGGAAAAGTGGTGAATCCCACCCAAAAATAACTCGAG

CTAGTGACTGACTAGGATCTGGTTACCACTAAACCAGCCTCAAGAACACCCGAATGGAG

-continued

TCTCTAAGCTACATAATACCAACTTAGACTTACAAAATGTTGTCCCCCAAAATGTAGCC

ATTCGTATCTGCTCCTAATAAAAAGAAAGTTTCTTCACATTCTAGAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAA

TEV-hAAT-XbG ARC-mRNA. 3'_lowest_T. (1689 nt)

(SEQ ID NO: 110)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGAGCAGCGUCAGCUGGGGCAUCCUCCUGC

UGGCAGGCCUGUGCUGCCUGGUCCCCGUCAGCCUGGCCGAGGACCCCCAGGGAGACGCC

GCCCAGAAGACAGACACAAGCCACCACGACCAGGACCACCCAACCUUCAACAAGAUCAC

CCCCAACCUGGCCGAGUUCGCCUUCAGCCUAUACCGCCAGCUGGCACACCAGAGCAACA

GCACCAACAUCUUCUUCAGCCCAGUGAGCAUCGCCACAGCCUUCGCAAUGCUCAGCCUG

GGGACCAAGGCCGACACCCACGACGAAAUCCUGGAGGGCCUGAACUUCAACCUCACGGA

GAUCCCGGAGGCCCAGAUCCACGAAGGCUUCCAGGAACUCCUCCGGACCCUCAACCAGC

CAGACAGCCAGCUCCAGCUGACCACCGGCAACGGCCUGUUCCUCAGCGAGGGCCUGAAG

CUAGUGGACAAGUUCCUGGAGGACGUGAAAAAGCUGUACCACAGCGAAGCCUUCACCGU

CAACUUCGGGGACACCGAAGAGGCCAAGAAACAGAUCAACGACUACGUGGAGAAGGGCA

CCCAAGGGAAAAUCGUGGACCUGGUCAAGGAGCUGGACAGAGACACAGUGUUCGCCCUG

GUGAACUACAUCUUCUUCAAAGGCAAAUGGGAGAGACCCUUCGAAGUCAAGGACACCGA

GGAAGAGGACUUCCACGUGGACCAGGUGACCACCGUGAAGGUGCCCAUGAUGAAGCGGC

UGGGCAUGUUCAACAUCCAGCACUGCAAGAAGCUGAGCAGCUGGGUGCUGCUGAUGAAA

UACCUGGGCAACGCCACCGCCAUCUUCUUCCUGCCCGACGAGGGGAAACUACAGCACCU

GGAAAACGAACUCACCCACGACAUCAUCACCAAGUUCCUGGAAAACGAAGACAGAAGGA

GCGCCAGCCUGCACCUGCCCAAACUGAGCAUCACCGGAACCUACGACCUGAAGUCCGUG

CUGGGCCAACUGGGCAUCACCAAGGUCUUCAGCAACGGGGCCGACCUCAGCGGGGUCAC

AGAGGAGGCACCCCUGAAGCUCAGCAAGGCCGUGCACAAGGCCGUGCUGACCAUCGACG

AGAAAGGGACCGAAGCCGCCGGGGCCAUGUUCCUGGAGGCCAUACCCAUGAGCAUCCCC

CCCGAGGUCAAGUUCAACAAACCCUUCGUCUUCCUGAUGAUCGAACAAAACACCAAGAG

CCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAA

TEV-hAAT-XbGARC-mRNA. 3'_16%_T. (1689 nt)

(SEQ ID NO: 111)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGUCUUCUGUCUCGUGGGGCAUCCUCCUGC

UGGCAGGCCUGUGCUGCCUGGUCCCUGUCUCCCUGGCUGAGGAUCCCCAGGGAGAUGCU

-continued

GCCCAGAAGACAGAUACAUCCCACCAUGAUCAGGAUCACCCAACCUUCAACAAGAUCAC

CCCCAACCUGGCUGAGUUCGCCUUCAGCCUAUACCGCCAGCUGGCACACCAGUCCAACA

GCACCAAUAUCUUCUUCUCCCCAGUGAGCAUCGCUACAGCCUUUGCAAUGCUCUCCCUG

GGGACCAAGGCUGACACUCACGAUGAAAUCCUGGAGGGCCUGAACUUCAACCUCACGGA

GAUCCCGGAGGCCCAGAUCCACGAAGGCUUCCAGGAACUCCUCCGGACCCUCAACCAGC

CAGACAGCCAGCUCCAGCUGACCACCGGCAACGGCCUGUUCCUCAGCGAGGGCCUGAAG

CUAGUGGACAAGUUCCUGGAGGACGUGAAAAAGCUGUACCACAGCGAAGCCUUCACCGU

CAACUUCGGGGACACCGAAGAGGCCAAGAAACAGAUCAACGACUACGUGGAGAAGGGCA

CCCAAGGGAAAAUCGUGGACCUGGUCAAGGAGCUGGACAGAGACACAGUGUUCGCCCUG

GUGAACUACAUCUUCUUCAAAGGCAAAUGGGAGAGACCCUUCGAAGUCAAGGACACCGA

GGAAGAGGACUUCCACGUGGACCAGGUGACCACCGUGAAGGUGCCCAUGAUGAAGCGGC

UGGGCAUGUUCAACAUCCAGCACUGCAAGAAGCUGAGCAGCUGGGUGCUGCUGAUGAAA

UACCUGGGCAACGCCACCGCCAUCUUCUUCCUGCCCGACGAGGGGAAACUACAGCACCU

GGAAAACGAACUCACCCACGACAUCAUCACCAAGUUCCUGGAAAACGAAGACAGAAGGA

GCGCCAGCCUGCACCUGCCCAAACUGAGCAUCACCGGAACCUACGACCUGAAGUCCGUG

CUGGGCCAACUGGGCAUCACCAAGGUCUUCAGCAACGGGGCCGACCUCAGCGGGGUCAC

AGAGGAGGCACCCCUGAAGCUCAGCAAGGCCGUGCACAAGGCCGUGCUGACCAUCGACG

AGAAAGGGACCGAAGCCGCCGGGGCCAUGUUCCUGGAGGCCAUACCCAUGAGCAUCCCC

CCCGAGGUCAAGUUCAACAAACCCUUCGUCUUCCUGAUGAUCGAACAAAACACCAAGAG

CCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAA

TEV-hAAT-XbGARC-mRNA. 3'_18%_T. (1689 nt)
(SEQ ID NO: 112)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGUCUUCUGUCUCGUGGGGCAUCCUCCUGC

UGGCAGGCCUGUGCUGCCUGGUCCCUGUCUCCCUGGCUGAGGAUCCCCAGGGAGAUGCU

GCCCAGAAGACAGAUACAUCCCACCAUGAUCAGGAUCACCCAACCUUCAACAAGAUCAC

CCCCAACCUGGCUGAGUUCGCCUUCAGCCUAUACCGCCAGCUGGCACACCAGUCCAACA

GCACCAAUAUCUUCUUCUCCCCAGUGAGCAUCGCUACAGCCUUUGCAAUGCUCUCCCUG

GGGACCAAGGCUGACACUCACGAUGAAAUCCUGGAGGGCCUGAAUUUCAACCUCACGGA

GAUUCCGGAGGCUCAGAUCCAUGAAGGCUUCCAGGAACUCCUCCGUACCCUCAACCAGC

CAGACAGCCAGCUCCAGCUGACCACCGGCAAUGGCCUGUUCCUCAGCGAGGGCCUGAAG

CUAGUGGAUAAGUUUUUGGAGGAUGUUAAAAAGUUGUACCACUCAGAAGCCUUCACUGU

CAACUUCGGGGACACCGAAGAGGCCAAGAAACAGAUCAACGAUUACGUGGAGAAGGGUA

CUCAAGGGAAAAUUGUGGAUUUGGUCAAGGAGCUUGACAGAGACACAGUUUUUGCUCUG

-continued

GUGAAUUACAUCUUCUUCAAAGGCAAAUGGGAGAGACCCUUCGAAGUCAAGGACACCGA

GGAAGAGGACUUCCACGUGGACCAGGUGACCACCGUGAAGGUGCCCAUGAUGAAGCGGC

UGGGCAUGUUCAACAUCCAGCACUGCAAGAAGCUGAGCAGCUGGGUGCUGCUGAUGAAA

UACCUGGGCAACGCCACCGCCAUCUUCUUCCUGCCCGACGAGGGGAAACUACAGCACCU

GGAAAACGAACUCACCCACGACAUCAUCACCAAGUUCCUGGAAAACGAAGACAGAAGGA

GCGCCAGCCUGCACCUGCCCAAACUGAGCAUCACCGGAACCUACGACCUGAAGUCCGUG

CUGGGCCAACUGGGCAUCACCAAGGUCUUCAGCAACGGGGCCGACCUCAGCGGGGUCAC

AGAGGAGGCACCCCUGAAGCUCAGCAAGGCCGUGCACAAGGCCGUGCUGACCAUCGACG

AGAAAGGGACCGAAGCCGCCGGGGCCAUGUUCCUGGAGGCCAUACCCAUGAGCAUCCCC

CCCGAGGUCAAGUUCAACAAACCCUUCGUCUUCCUGAUGAUCGAACAAAACACCAAGAG

CCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAA

TEV-hAAT-XbGARC-mRNA. 3'20%_T. (1689 nt)

(SEQ ID NO: 113)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGUCUUCUGUCUCGUGGGGCAUCCUCCUGC

UGGCAGGCCUGUGCUGCCUGGUCCCUGUCUCCCUGGCUGAGGAUCCCCAGGGAGAUGCU

GCCCAGAAGACAGAUACAUCCCACCAUGAUCAGGAUCACCCAACCUUCAACAAGAUCAC

CCCCAACCUGGCUGAGUUCGCCUUCAGCCUAUACCGCCAGCUGGCACACCAGUCCAACA

GCACCAAUAUCUUCUUCUCCCCAGUGAGCAUCGCUACAGCCUUUGCAAUGCUCUCCCUG

GGGACCAAGGCUGACACUCACGAUGAAAUCCUGGAGGGCCUGAAUUUCAACCUCACGGA

GAUUCCGGAGGCUCAGAUCCAUGAAGGCUUCCAGGAACUCCUCCGUACCCUCAACCAGC

CAGACAGCCAGCUCCAGCUGACCACCGGCAAUGGCCUGUUCCUCAGCGAGGGCCUGAAG

CUAGUGGAUAAGUUUUUGGAGGAUGUUAAAAAGUUGUACCACUCAGAAGCCUUCACUGU

CAACUUCGGGGACACCGAAGAGGCCAAGAAACAGAUCAACGAUUACGUGGAGAAGGGUA

CUCAAGGGAAAAUUGUGGAUUUGGUCAAGGAGCUUGACAGAGACACAGUUUUUGCUCUG

GUGAAUUACAUCUUCUUUAAAGGCAAAUGGGAGAGACCCUUUGAAGUCAAGGACACCGA

GGAAGAGGACUUCCACGUGGACCAGGUGACCACCGUGAAGGUGCCUAUGAUGAAGCGUU

UAGGCAUGUUUAACAUCCAGCACUGUAAGAAGCUGUCCAGCUGGGUGCUGCUGAUGAAA

UACCUGGGCAAUGCCACCGCCAUCUUCUUCCUGCCUGAUGAGGGGAAACUACAGCACCU

GGAAAAUGAACUCACCCACGAUAUCAUCACCAAGUUCCUGGAAAAUGAAGACAGAAGGU

CUGCCAGCUUACAUUUACCCAAACUGUCCAUUACUGGAACCUAUGAUCUGAAGUCCGUG

CUGGGUCAACUGGGCAUCACCAAGGUCUUCAGCAACGGGGCCGACCUCAGCGGGGUCAC

AGAGGAGGCACCCCUGAAGCUCAGCAAGGCCGUGCACAAGGCCGUGCUGACCAUCGACG

AGAAAGGGACCGAAGCCGCCGGGGCCAUGUUCCUGGAGGCCAUACCCAUGAGCAUCCCC

CCCGAGGUCAAGUUCAACAAACCCUUCGUCUUCCUGAUGAUCGAACAAAACACCAAGAG

-continued

CCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAA

TEV-hAAT-XbG ARC-mRNA. 5'_16%_T. (1689 nt)

(SEQ ID NO: 114)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGAGCAGCGUCAGCUGGGGCAUCCUCCUGC

UGGCAGGCCUGUGCUGCCUGGUCCCCGUCAGCCUGGCCGAGGACCCCCAGGGAGACGCC

GCCCAGAAGACAGACACAAGCCACCACGACGAGGACCACCCAACCUUCAACAAGAUCAC

CCCCAACCUGGCCGAGUUCGCCUUCAGCCUAUACCGCCAGCUGGCACACCAGAGCAACA

GCACCAACAUCUUCUUCAGCCCAGUGAGCAUCGCCACAGCCUUCGCAAUGCUCAGCCUG

GGGACCAAGGCCGACACCCACGACGAAAUCCUGGAGGGCCUGAACUUCAACCUCACGGA

GAUCCCGGAGGCCCAGAUCCACGAAGGCUUCCAGGAACUCCUCCGGACCCUCAACCAGC

CAGACAGCCAGCUCCAGCUGACCACCGGCAACGGCCUGUUCCUCAGCGAGGGCCUGAAG

CUAGUGGACAAGUUCCUGGAGGACGUGAAAAAGCUGUACCACAGCGAAGCCUUCACCGU

CAACUUCGGGGACACCGAAGAGGCCAAGAAACAGAUCAACGACUACGUGGAGAAGGGCA

CCCAAGGGAAAAUCGUGGACCUGGUCAAGGAGCUGGACAGAGACACAGUGUUCGCCCUG

GUGAACUACAUCUUCUUCAAAGGCAAAUGGGAGAGACCCUUCGAAGUCAAGGACACCGA

GGAAGAGGACUUCCACGUGGACCAGGUGACCACCGUGAAGGUGCCCAUGAUGAAGCGGC

UGGGCAUGUUCAACAUCCAGCACUGCAAGAAGCUGAGCAGCUGGGUGCUGCUGAUGAAA

UACCUGGGCAACGCCACCGCCAUCUUCUUCCUGCCCGACGAGGGGAAACUACAGCACCU

GGAAAACGAACUCACCCACGACAUCAUCACCAAGUUCCUGGAAAACGAAGACAGAAGGA

GCGCCAGCCUGCACCUGCCCAAACUGAGCAUUACUGGAACCUAUGAUCUGAAGUCCGUG

CUGGGUCAACUGGGCAUCACUAAGGUCUUCAGCAAUGGGGCUGACCUCUCCGGGGUCAC

AGAGGAGGCACCCCUGAAGCUCUCCAAGGCCGUGCAUAAGGCUGUGCUGACCAUCGACG

AGAAAGGGACUGAAGCUGCUGGGGCCAUGUUUUUAGAGGCCAUACCCAUGUCUAUCCCC

CCCGAGGUCAAGUUCAACAAACCCUUUGUCUUCUUAAUGAUUGAACAAAAUACCAAGUC

UCCCCUCUUCAUGGGAAAAGUGGUGAAUCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAA

-continued

TEV-hAAT-XbGARC-mRNA. 5'_18%_T. (1689 nt)
(SEQ ID NO: 115)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGAGCAGCGUCAGCUGGGGCAUCCUCCUGC

UGGCAGGCCUGUGCUGCCUGGUCCCCGUCAGCCUGGCCGAGGACCCCCAGGGAGACGCC

GCCCAGAAGACAGACACAAGCCACCACGACCAGGACCACCCAACCUUCAACAAGAUCAC

CCCCAACCUGGCCGAGUUCGCCUUCAGCCUAUACCGCCAGCUGGCACACCAGAGCAACA

GCACCAACAUCUUCUUCAGCCCAGUGAGCAUCGCCACAGCCUUCGCAAUGCUCAGCCUG

GGGACCAAGGCCGACACCCACGACGAAAUCCUGGAGGGCCUGAACUUCAACCUCACGGA

GAUCCCGGAGGCCCAGAUCCACGAAGGCUUCCAGGAACUCCUCCGGACCCUCAACCAGC

CAGACAGCCAGCUCCAGCUGACCACCGGCAACGGCCUGUUCCUCAGCGAGGGCCUGAAG

CUAGUGGACAAGUUCCUGGAGGACGUGAAAAAGCUGUACCACAGCGAAGCCUUCACCGU

CAACUUCGGGGACACCGAAGAGGCCAAGAAACAGAUCAACGACUACGUGGAGAAGGGCA

CCCAAGGGAAAAUCGUGGACCUGGUCAAGGAGCUUGACAGAGACACAGUUUUUGCUCUG

GUGAAUUACAUCUUCUUUAAAGGCAAAUGGGAGAGACCCUUUGAAGUCAAGGACACCGA

GGAAGAGGACUUCCACGUGGACCAGGUGACCACCGUGAAGGUGCCUAUGAUGAAGCGUU

UAGGCAUGUUUAACAUCCAGCACUGUAAGAAGCUGUCCAGCUGGGUGCUGCUGAUGAAA

UACCUGGGCAAUGCCACCGCCAUCUUCUUCCUGCCUGAUGAGGGGAAACUACAGCACCU

GGAAAAUGAACUCACCGAGGAUAUCAUCACCAAGUUCCUGGAAAAUGAAGACAGAAGGU

CUGCCAGCUUACAUUUACCCAAACUGUCCAUUACUGGAACCUAUGAUCUGAAGUCCGUG

CUGGGUCAACUGGGCAUCACUAAGGUCUUCAGCAAUGGGGCUGACCUCUCCGGGGUCAC

AGAGGAGGCACCCCUGAAGCUCUCCAAGGCCGUGCAUAAGGCUGUGCUGACCAUCGACG

AGAAAGGGACUGAAGCUGCUGGGGCCAUGUUUUUAGAGGCCAUACCCAUGUCUAUCCCC

CCCGAGGUCAAGUUCAACAAACCCUUUGUCUUCUUAAUGAUUGAACAAAAUACCAAGUC

UCCCCUCUUCAUGGGAAAAGUGGUGAAUCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAA

TEV-hAAT-XbGARC-mRNA. 5'_20%_T. (1689 nt)
(SEQ ID NO: 116)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGAGCAGCGUCAGCUGGGGCAUCCUCCUGC

UGGCAGGCCUGUGCUGCCUGGUCCCCGUCAGCCUGGCCGAGGACCCCCAGGGAGACGCC

GCCCAGAAGACAGACACAAGCCACCACGACCAGGACCACCCAACCUUCAACAAGAUCAC

CCCCAACCUGGCCGAGUUCGCCUUCAGCCUAUACCGCCAGCUGGCACACCAGAGCAACA

GCACCAACAUCUUCUUCAGCCCAGUGAGCAUCGCCACAGCCUUUGCAAUGCUCUCCCUG

-continued

GGGACCAAGGCUGACACUCACGAUGAAAUCCUGGAGGGCCUGAAUUUCAACCUCACGGA

GAUUCCGGAGGCUCAGAUCCAUGAAGGCUUCCAGGAACUCCUCCGUACCCUCAACCAGC

CAGACAGCCAGCUCCAGCUGACCACCGGCAAUGGCCUGUUCCUCAGCGAGGGCCUGAAG

CUAGUGGAUAAGUUUUUGGAGGAUGUUAAAAAGUUGUACCACUCAGAAGCCUUCACUGU

CAACUUCGGGGACACCGAAGAGGCCAAGAAACAGAUCAACGAUUACGUGGAGAAGGGUA

CUCAAGGGAAAAUUGUGGAUUUGGUCAAGGAGCUUGACAGAGACACAGUUUUUGCUCUG

GUGAAUUACAUCUUCUUUAAAGGCAAAUGGGAGAGACCCUUUGAAGUCAAGGACACCGA

GGAAGAGGACUUCCACGUGGACCAGGUGACCACCGUGAAGGUGCCUAUGAUGAAGCGUU

UAGGCAUGUUUAACAUCCAGCACUGUAAGAAGCUGUCCAGCUGGGUGCUGCUGAUGAAA

UACCUGGGCAAUGCCACCGCCAUCUUCUUCCUGCCUGAUGAGGGGAAACUACAGCACCU

GGAAAAUGAACUCACCCACGAUAUCAUCACCAAGUUCCUGGAAAAUGAAGACAGAAGGU

CUGCCAGCUUACAUUUACCCAAACUGUCCAUUACUGGAACCUAUGAUCUGAAGUCCGUG

CUGGGUCAACUGGGCAUCACUAAGGUCUUCAGCAAUGGGGCUGACCUCUCCGGGGUCAC

AGAGGAGGCACCCCUGAAGCUCUCCAAGGCCGUGCAUAAGGCUGUGCUGACCAUCGACG

AGAAAGGGACUGAAGCUGCUGGGGCCAUGUUUUUAGAGGCCAUACCCAUGUCUAUCCCC

CCCGAGGUCAAGUUCAACAAACCCUUUGUCUUCUUAAUGAUUGAACAAAAUACCAAGUC

UCCCCUCUUCAUGGGAAAAGUGGUGAAUCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAA

TEV-hAAT-XbG ARC-mRNA.
random_16%_T. (1689 nt)

(SEQ ID NO: 117)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGAGCAGCGUCUCGUGGGGCAUCCUCCUGC

UGGCAGGCCUGUGCUGCCUGGUCCCCGUCAGCCUGGCCGAGGACCCCCAGGGAGAUGCU

GCCCAGAAGACAGACACAUCCCACGAGGAGCAGGACCACCCAACCUUCAACAAGAUCAC

CCCCAACCUGGCUGAGUUCGCCUUCAGCCUAUACCGCCAGCUGGCACACCAGAGCAACA

GCACCAAUAUCUUCUUCAGCCCAGUGAGCAUCGCUACAGCCUUCGCAAUGCUCAGCCUG

GGGACCAAGGCCGACACCCACGAUGAAAUCCUGGAGGGCCUGAAUUUCAACCUCACGGA

GAUCCCGGAGGCUCAGAUCCACGAAGGCUUCCAGGAACUCCUCCGGACCCUCAACCAGC

CAGACAGCCAGCUCCAGCUGACCACCGGCAACGGCCUGUUCCUCAGCGAGGGCCUGAAG

CUAGUGGACAAGUUCCUGGAGGACGUUAAAAAGCUGUACCACAGCGAAGCCUUCACCGU

CAACUUCGGGGACACCGAAGAGGCCAAGAAACAGAUCAACGAUUACGUGGAGAAGGGCA

CCCAAGGGAAAAUCGUGGACCUGGUCAAGGAGCUUGACAGAGACACAGUGUUUGCCCUG

GUGAACUACAUCUUCUUCAAAGGCAAAUGGGAGAGACCCUUCGAAGUCAAGGACACCGA

GGAAGAGGACUUCCACGUGGACCAGGUGACCACCGUGAAGGUGCCCAUGAUGAAGCGGU

UAGGCAUGUUCAACAUCCAGCACUGCAAGAAGCUGAGCAGCUGGGUGCUGCUGAUGAAA

-continued

UACCUGGGCAACGCCACCGCCAUCUUCUUCCUGCCCGACGAGGGGAAACUACAGCACCU

GGAAAACGAACUCACCCACGACAUCAUCACCAAGUUCCUGGAAAACGAAGACAGAAGGA

GCGCCAGCCUGCAUCUGCCCAAACUGAGCAUUACUGGAACCUACGAUCUGAAGUCCGUG

CUGGGUCAACUGGGCAUCACCAAGGUCUUCAGCAAUGGGGCCGACCUCAGCGGGGUCAC

AGAGGAGGCACCCCUGAAGCUCAGCAAGGCCGUGCACAAGGCUGUGCUGACCAUCGACG

AGAAAGGGACCGAAGCCGCUGGGGCCAUGUUCCUGGAGGCCAUACCCAUGAGCAUCCCC

CCCGAGGUCAAGUUCAACAAACCCUUUGUCUUCCUGAUGAUCGAACAAAACACCAAGUC

UCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAA

TEV-hAAT-XbG ARC-mRNA. random_18%_T. (1689 nt)
(SEQ ID NO: 118)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGUCUUCUGUCUCGUGGGGCAUCCUCCUGC

UGGCAGGCCUGUGCUGCCUGGUCCCCGUCUCCCUGGCUGAGGACCCCCAGGGAGAUGCC

GCCCAGAAGACAGACACAUCCCACCAUGACCAGGACCACCCAACCUUCAACAAGAUCAC

CCCCAACCUGGCCGAGUUCGCCUUCAGCCUAUACCGCCAGCUGGCACACCAGAGCAACA

GCACCAACAUCUUCUUCUCCCCAGUGAGCAUCGCCACAGCCUUUGCAAUGCUCUCCCUG

GGGACCAAGGCCGACACCCACGACGAAAUCCUGGAGGGCCUGAAUUUCAACCUCACGGA

GAUCCCGGAGGCUCAGAUCCAUGAAGGCUUCCAGGAACUCCUCCGGACCCUCAACCAGC

CAGACAGCCAGCUCCAGCUGACCACCGGCAAUGGCCUGUUCCUCAGCGAGGGCCUGAAG

CUAGUGGAUAAGUUCCUGGAGGAUGUUAAAAAGCUGUACCACAGCGAAGCCUUCACCGU

CAACUUCGGGGACACCGAAGAGGCCAAGAAACAGAUCAACGAUUACGUGGAGAAGGGCA

CCCAAGGGAAAAUCGUGGACCUGGUCAAGGAGCUUGACAGAGACACAGUGUUUGCUCUG

GUGAAUUACAUCUUCUUUAAAGGCAAAUGGGAGAGACCCUUUGAAGUCAAGGACACCGA

GGAAGAGGACUUCCACGUGGACCAGGUGACCACCGUGAAGGUGCCUAUGAUGAAGCGGU

UAGGCAUGUUUAACAUCCAGCACUGCAAGAAGCUGAGCAGCUGGGUGCUGCUGAUGAAA

UACCUGGGCAAUGCCACCGCCAUCUUCUUCCUGCCUGAUGAGGGGAAACUACAGCACCU

GGAAAACGAACUCACCCACGACAUCAUCACCAAGUUCCUGGAAAAUGAAGACAGAAGGU

CUGCCAGCUUACACUUACCCAAACUGAGCAUUACUGGAACCUACGAUCUGAAGUCCGUG

CUGGGCCAACUGGGCAUCACUAAGGUCUUCAGCAACGGGGCUGACCUCUCCGGGGUCAC

AGAGGAGGCACCCCUGAAGCUCAGCAAGGCCGUGCACAAGGCUGUGCUGACCAUCGACG

AGAAAGGGACCGAAGCUGCCGGGGCCAUGUUUCUGGAGGCCAUACCCAUGUCUAUCCCC

CCCGAGGUCAAGUUCAACAAACCCUUUGUCUUCCUGAUGAUCGAACAAAAUACCAAGAG

CCCCCUCUUCAUGGGAAAAGUGGUGAACCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

-continued

```
GCUCCUAAUAAAAAGAAAGUUUCUUCACAUUCUAGAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAA

TEV-hAAT-XbGARC-mRNA. random_20%_T. (1689 nt)
                                                    (SEQ ID NO: 119)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCCGAGCAGCGUCAGCUGGGGCAUCCUCCUGC

UGGCAGGCCUGUGCUGCCUGGUCCCUGUCUCCCUGGCUGAGGAUCCCCAGGGAGAUGCU

GCCCAGAAGACAGAUACAUCCCACCAUGAUCAGGAUCACCCAACCUUCAACAAGAUCAC

CCCCAACCUGGCUGAGUUCGCCUUCAGCCUAUACCGCCAGCUGGCACACCAGUCCAACA

GCACCAAUAUCUUCUUCUCCCCAGUGAGCAUCGCUACAGCCUUCGCAAUGCUCUCCCUG

GGGACCAAGGCUGACACUCACGAUGAAAUCCUGGAGGGCCUGAAUUUCAACCUCACGGA

GAUUCCGGAGGCCCAGAUCCAUGAAGGCUUCCAGGAACUCCUCCGUACCCUCAACCAGC

CAGACAGCCAGCUCCAGCUGACCACCGGCAAUGGCCUGUUCCUCAGCGAGGGCCUGAAG

CUAGUGGAUAAGUUUUUGGAGGAUGUUAAAAAGCUGUACCACAGCGAAGCCUUCACUGU

CAACUUCGGGGACACCGAAGAGGCCAAGAAACAGAUCAACGAUUACGUGGAGAAGGGUA

CUCAAGGGAAAAUUGUGGAUUUGGUCAAGGAGCUUGACAGAGACACAGUUUUUGCUCUG

GUGAAUUACAUCUUCUUCAAAGGCAAAUGGGAGAGACCCUUUGAAGUCAAGGACACCGA

GGAAGAGGACUUCCACGUGGACCAGGUGACCACCGUGAAGGUGCCUAUGAUGAAGCGGU

UAGGCAUGUUCAACAUCCAGCACUGUAAGAAGCUGUCCAGCUGGGUGCUGCUGAUGAAA

UACCUGGGCAAUGCCACCGCCAUCUUCUUCCUGCCUGAUGAGGGGAAACUACAGCACCU

GGAAAAUGAACUCACCCACGAUAUCAUCACCAAGUUCCUGGAAAAUGAAGACAGAAGGA

GCGCCAGCUUACAUUUACCCAAACUGAGCAUUACUGGAACCUACGAUCUGAAGUCCGUG

CUGGGUCAACUGGGCAUCACUAAGGUCUUCAGCAACGGGGCUGACCUCUCCGGGGUCAC

AGAGGAGGCACCCCUGAAGCUCUCCAAGGCCGUGCAUAAGGCUGUGCUGACCAUCGACG

AGAAAGGGACUGAAGCUGCUGGGGCCAUGUUUUUAGAGGCCAUACCCAUGUCUAUCCCC

CCCGAGGUCAAGUUCAACAAACCCUUUGUCUUCCUGAUGAUCGAACAAAAUACCAAGAG

CCCCCUCUUCAUGGGAAAAGUGGUGAAUCCCACCCAAAAAUAACUCGAGCUAGUGACUG

ACUAGGAUCUGGUUACCACUAAACCAGCCUCAAGAACACCCGAAUGGAGUCUCUAAGCU

ACAUAAUACCAACUUACACUUACAAAAUGUUGUCCCCCAAAAUGUAGCCAUUCGUAUCU

GCUCCUAAUAAAAAGAAAGUUUCUUCACAUUCUAGAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAA
```

Example E: Templates and mRNAs for Human Adiponectin (hAdipo)

Figure 8:
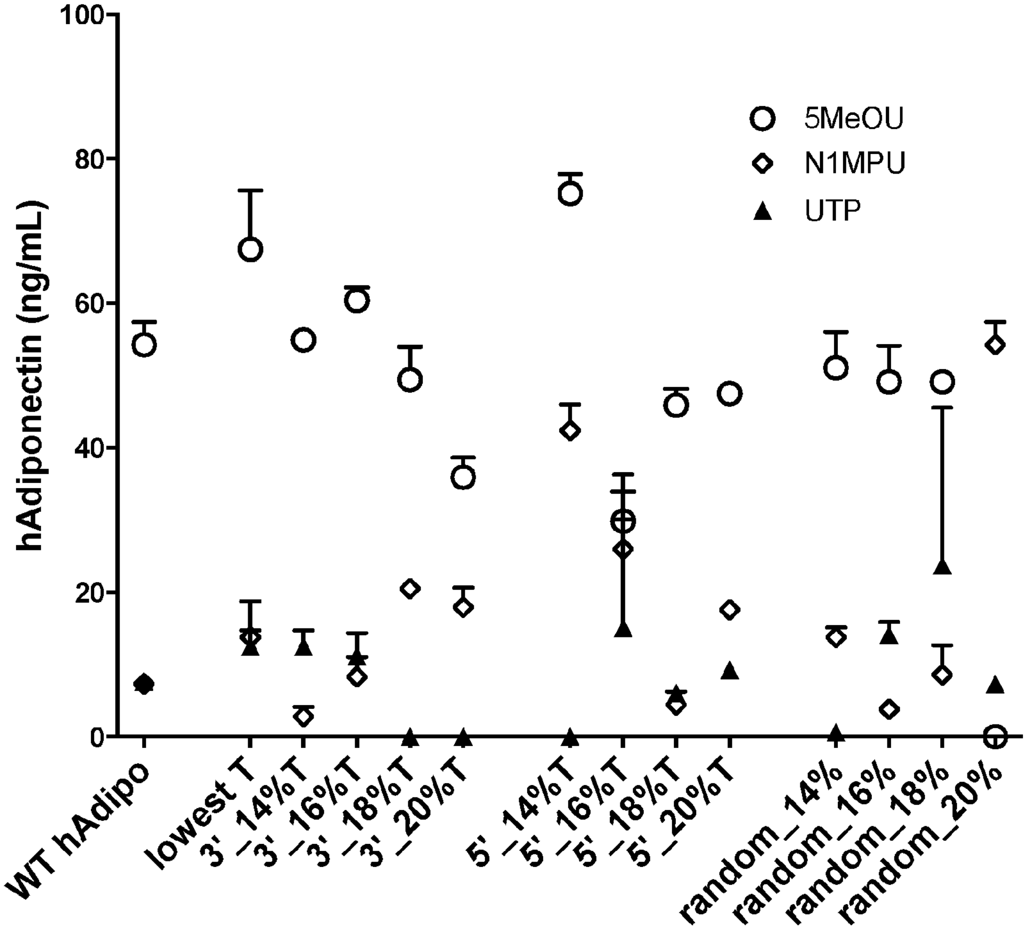
FIG. 8 shows the results of surprisingly increased human adiponectin protein production for a translatable molecule of this invention. Human adiponectin ARC-RNA was synthesized using a DNA template having reduced deoxyadenosine nucleotides in an open reading frame of the template strand, as well as reduced deoxythymidine nucleotides in the complementary non-template strand ("reduced T"). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 8 shows the results of surprisingly increased human adiponectin protein production for a translatable molecule of this invention. Human adiponectin ARC-RNA was synthesized using a DNA template having reduced deoxyadenosine nucleotides in an open reading frame of the template strand, as well as reduced complementary deoxythymidine nucleotides in the non-template strand ("reduced T"). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 8 shows surprisingly high translational efficiency of the ARC-mRNA (5MeOU) compared to the wild type hAdipo mRNA (UTP). First, the ARC-mRNA (5MeOU)

exhibited superior expression efficiency at all levels of template T composition as compared to the hAdipo mRNA (UTP). Further, the ARC-mRNA (5MeOU) exhibited unexpectedly superior expression efficiency at all levels of template T composition as compared to the hAdipo mRNA (N1MPU).

Moreover, FIG. 8 shows that ARC-mRNA (5MeOU) products exhibited superior expression efficiency at levels of template T composition of 12-14%. The increase of ARC-mRNA (5MeOU) expression efficiency at lower levels of template T composition of 12-14% was unexpectedly advantageous because the "reduced T" hAdipo mRNA (UTP) was not increased at lower levels of template T composition.

In addition, FIG. 8 shows that the translational efficiency of the ARC-RNA (5MeOU) was also surprisingly higher as compared to WT human adiponectin mRNA (N1MPU), a similar RNA made with $N^1$-methylpseudouridine (100%).

Figure 9:
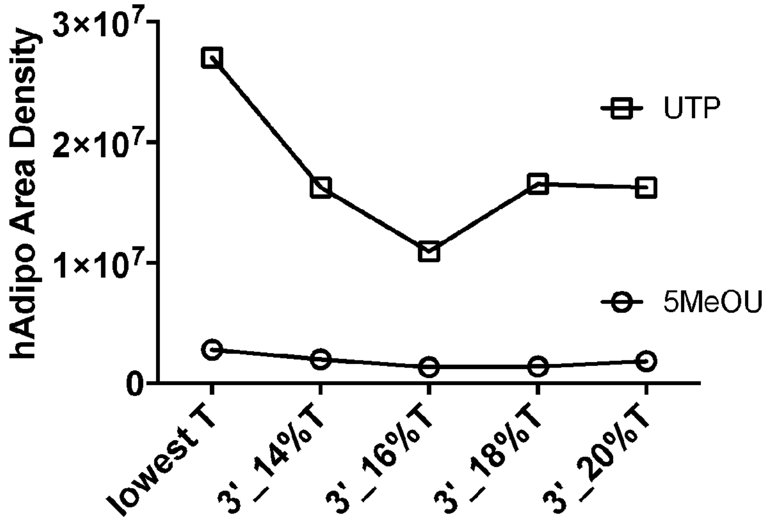
FIG. 9 shows the results of surprisingly reduced impurity levels in a process for synthesizing a human adiponectin translatable molecule of this invention.

FIG. 9 shows the results of surprisingly reduced impurity levels in a process for synthesizing an hAdipo translatable molecule of this invention. FIG. 9 shows the results of a dot blot for detecting double strand RNA impurity in the synthesis mixture (nitro cellulose membrane, J2 antibody to detect dsRNA). The ARC-RNA (5MeOU) "reduced T" synthesis products, which were translatable for hAdipo, showed surprisingly reduced dot blot intensity as compared to similar "reduced T" mRNA (UTP) synthesis products. Thus, the ARC-RNA (5MeOU) synthesis process, with template reduced T composition, surprisingly reduced double strand RNA impurity levels in the synthesis mixture.

The process for synthesizing the ARC-RNA (5MeOU) molecules of this invention with template reduced T composition provided a surprisingly reduced level of double strand RNA impurity. As shown in FIG. 9, this result is surprising because the "reduced T" mRNA (UTP) synthesis products exhibited increased levels of double strand RNA impurity at lower template T composition.

The compositions of the templates for hAdipo are shown in Table 9.

TABLE 9

Non-Template Nucleotide T compositions for hAdipo

| hEPO | T % |
|---|---|
| hAdipo_lowest_T | 12.2 |
| hAdipo_3'_14% T | 13.9 |
| hAdipo_3'_16% T | 15.9 |
| hAdipo_3'_18% T | 18.0 |
| hAdipo_3'_20% T | 20.0 |
| hAdipo_5'_14% T | 13.9 |
| hAdipo_5'_16% T | 15.9 |
| hAdipo_5'_18% T | 18.0 |
| hAdipo_5'_20% T | 20.0 |
| hAdipo_random_14% | 13.9 |
| hAdipo_random_16% | 15.9 |
| hAdipo_random_18% | 18.0 |
| hAdipo_random_20% | 20.0 |

Human Adipo ORF reference. Sense strand, non-template. NM_001177800.1:136-870 Homo sapiens adiponectin, C1Q and collagen domain containing (ADIPOQ).

(SEQ ID NO: 120)

```
atgctgttgctgggagctgttctactgctattagctctgcccggtcatg

accaggaaaccacgactcaagggcccggagtcctgcttcccctgcccaagggggcctgc

acaggttggatggcgggcatcccagggcatccgggccataatggggccccaggccgtga

tggcagagatggcacccctggtgagaagggtgagaaaggagatccaggtcttattggtc

ctaagggagacatcggtgaaaccggagtacccggggctgaaggtccccgaggctttccg

ggaatccaaggcaggaaaggagaacctggagaaggtgcctatgtataccgctcagcatt

cagtgtgggattggagacttacgttactatccccaacatgcccattcgctttaccaaga

tcttctacaatcagcaaaaccactatgatggctccactggtaaattccactgcaacatt

cctgggctgtactactttgcctaccacatcacagtctatatgaaggatgtgaaggtcag

cctcttcaagaaggacaaggctatgctcttcacctatgatcagtaccaggaaaataatg

tggaccaggcctccggctctgtgctcctgcatctggaggtgggcgaccaagtctggctc

caggtgtatggggaaggagagcgtaatggactctatgctgataatgacaatgactccac

cttcacaggctttcttctctaccatgacaccaactga
```

hAdipo sense strand, non-template. 3'_lowest_T.

(SEQ ID NO: 121)

```
ATGCTGCTGCTGGGAGCCGTGCTACTGCTACTGGCCCTGCCCGGCCACG

ACCAGGAAACCACGACCCAAGGGCCCGGAGTCCTGCTGCCCCTGCCCAAGGGGGCCTGC

ACAGGCTGGATGGCGGGCATCCCAGGGCACCCGGGCCACAACGGGGCCCCAGGCCGGGA

CGGCAGAGACGGCACCCCCGGCGAGAAGGGCGAGAAAGGAGACCCAGGCCTGATCGGCC

CCAAGGGAGACATCGGCGAAACCGGAGTACCCGGGGCCGAAGGCCCCCGAGGCTTCCCG

GGAATCCAAGGCAGGAAAGGAGAACCCGGAGAAGGCGCCTACGTATACCGCAGCGCATT

CAGCGTGGGACTGGAGACCTACGTGACCATCCCCAACATGCCCATCCGCTTCACCAAGA
```

-continued

TCTTCTACAACCAGCAAAACCACTACGACGGCAGCACCGGCAAATTCCACTGCAACATC

CCCGGGCTGTACTACTTCGCCTACCACATCACAGTCTACATGAAGGACGTGAAGGTCAG

CCTCTTCAAGAAGGACAAGGCCATGCTGTTCACCTACGACCAGTACCAGGAAAACAACG

TGGACCAGGCCAGCGGCAGCGTGCTCCTGCACCTGGAGGTGGGCGACCAAGTCTGGCTC

CAGGTGTACGGGGAAGGAGAGCGGAACGGACTCTACGCCGACAACGACAACGACAGCAC

CTTCACAGGCTTCCTGCTCTACCACGAGACCAACTGA hAdipo sense strand, non-template. 3'_14%_T.

(SEQ ID NO: 122)

ATGCTGTTGCTGGGAGCTGTTCTACTGCTATTAGCTCTGCCCGGTCATG

ACCAGGAAACCACGACTCAAGGGCCCGGAGTCCTGCTTCCCCTGCCCAAGGGGGCCTGC

ACAGGTTGGATGGCGGGCATCCCAGGGCATCCGGGCCATAACGGGGCCCCAGGCCGGGA

CGGCAGAGACGGCACCCCCGGCGAGAAGGGCGAGAAAGGAGACCCAGGCCTGATCGGCC

CCAAGGGAGACATCGGCGAAACCGGAGTACCCGGGGCCGAAGGCCCCCGAGGCTTCCCG

GGAATCCAAGGCAGGAAAGGAGAACCCGGAGAAGGCGCCTACGTATACCGCAGCGCATT

CAGCGTGGGACTGGAGACCTACGTGACCATCCCCAACATGCCCATCCGCTTCACCAAGA

TCTTCTACAACCAGCAAAACCACTACGACGGCAGCACCGGCAAATTCCACTGCAACATC

CCCGGGCTGTACTACTTCGCCTACCACATCACAGTCTACATGAAGGACGTGAAGGTCAG

CCTCTTCAAGAAGGACAAGGCCATGCTGTTCACCTACGACCAGTACCAGGAAAACAACG

TGGACCAGGCCAGCGGCAGCGTGCTCCTGCACCTGGAGGTGGGCGACCAAGTCTGGCTC

CAGGTGTACGGGGAAGGAGAGCGGAACGGACTCTACGCCGACAACGACAACGACAGCAC

CTTCACAGGCTTCCTGCTCTACCACGACACCAACTGA hAdipo sense strand, non-template. 3'_16%_T.

(SEQ ID NO: 123)

ATGCTGTTGCTGGGAGCTGTTCTACTGCTATTAGCTCTGCCCGGTCATG

ACCAGGAAACCACGACTCAAGGGCCCGGAGTCCTGCTTCCCCTGCCCAAGGGGGCCTGC

ACAGGTTGGATGGCGGGCATCCCAGGGCATCCGGGCCATAATGGGGCCCCAGGCCGTGA

TGGCAGAGATGGCACCCCTGGTGAGAAGGGTGAGAAAGGAGATCCAGGTCTTATTGGTC

CTAAGGGAGACATCGGTGAAACCGGAGTACCCGGGGCTGAAGGCCCCCGAGGCTTCCCG

GGAATCCAAGGCAGGAAAGGAGAACCCGGAGAAGGCGCCTACGTATACCGCAGCGCATT

CAGCGTGGGACTGGAGACCTACGTGACCATCCCCAACATGCCCATCCGCTTCACCAAGA

TCTTCTACAACCAGCAAAACCACTACGACGGCAGCACCGGCAAATTCCACTGCAACATC

CCCGGGCTGTACTACTTCGCCTACCACATCACAGTCTACATGAAGGACGTGAAGGTCAG

CCTCTTCAAGAAGGACAAGGCCATGCTGTTCACCTACGACCAGTACCAGGAAAACAACG

TGGACCAGGCCAGCGGCAGCGTGCTCCTGCACCTGGAGGTGGGCGACCAAGTCTGGCTC

CAGGTGTACGGGGAAGGAGAGCGGAACGGACTCTACGCCGACAACGACAACGACAGCAC

CTTCACAGGCTTCCTGCTCTACCACGACACCAACTGA hAdipo sense strand, non-template. 3'_18%_T.

(SEQ ID NO: 124)

ATGCTGTTGCTGGGAGCTGTTCTACTGCTATTAGCTCTGCCCGGTCATG

ACCAGGAAACCACGACTCAAGGGCCCGGAGTCCTGCTTCCCCTGCCCAAGGGGGCCTGC

ACAGGTTGGATGGCGGGCATCCCAGGGCATCCGGGCCATAATGGGGCCCCAGGCCGTGA

TGGCAGAGATGGCACCCCTGGTGAGAAGGGTGAGAAAGGAGATCCAGGTCTTATTGGTC

CTAAGGGAGACATCGGTGAAACCGGAGTACCCGGGGCTGAAGGTCCCCGAGGCTTTCCG

GGAATCCAAGGCAGGAAAGGAGAACCTGGAGAAGGTGCCTATGTATACCGCTCAGCATT

-continued

CAGTGTGGGATTGGAGACTTACGTTACTATCCCCAACATGCCCATTCGCTTTACCAAGA
TCTTCTACAATCAGCAAAACCACTATGACGGCAGCACCGGCAAATTCCACTGCAACATC
CCCGGGCTGTACTACTTCGCCTACCACATCACAGTCTACATGAAGGACGTGAAGGTCAG
CCTCTTCAAGAAGGACAAGGCCATGCTGTTCACCTACGACCAGTACCAGGAAAACAACG
TGGACCAGGCCAGCGGCAGCGTGCTCCTGCACCTGGAGGTGGGCGACCAAGTCTGGCTC
CAGGTGTACGGGGAAGGAGAGCGGAACGGACTCTACGCCGACAACGACAACGACAGCAC
CTTCACAGGCTTCCTGCTCTACCACGACACCAACTGA hAdipo sense strand, non-template. 3'_20%_T.
(SEQ ID NO: 125)
ATGCTGTTGCTGGGAGCTGTTCTACTGCTATTAGCTCTGCCCGGTCATG
ACCAGGAAACCACGACTCAAGGGCCCGGAGTCCTGCTTCCCCTGCCCAAGGGGGCCTGC
ACAGGTTGGATGGCGGGCATCCCAGGGCATCCGGGCCATAATGGGGCCCCAGGCCGTGA
TGGCAGAGATGGCACCCCTGGTGAGAAGGGTGAGAAAGGAGATCCAGGTCTTATTGGTC
CTAAGGGAGACATCGGTGAAACCGGAGTACCCGGGGCTGAAGGTCCCCGAGGCTTTCCG
GGAATCCAAGGCAGGAAAGGAGAACCTGGAGAAGGTGCCTATGTATACCGCTCAGCATT
CAGTGTGGGATTGGAGACTTACGTTACTATCCCCAACATGCCCATTCGCTTTACCAAGA
TCTTCTACAATCAGCAAAACCACTATGATGGCTCCACTGGTAAATTCCACTGCAACATT
CCTGGGCTGTACTACTTTGCCTACCACATCACAGTCTATATGAAGGATGTGAAGGTCAG
CCTCTTCAAGAAGGACAAGGCTATGCTGTTCACCTATGATCAGTACCAGGAAAATAATG
TGGACCAGGCCTCCGGCAGCGTGCTCCTGCACCTGGAGGTGGGCGACCAAGTCTGGCTC
CAGGTGTACGGGGAAGGAGAGCGGAACGGACTCTACGCCGACAACGACAACGACAGCAC
CTTCACAGGCTTCCTGCTCTACCACGAGACCAACTGA hAdipo sense strand, non-template. 5'_14%_T.
(SEQ ID NO: 126)
ATGCTGCTGCTGGGAGCCGTGCTACTGCTACTGGCCCTGCCCGGCCACG
ACCAGGAAACCACGACCCAAGGGCCCGGAGTCCTGCTGCCCCTGCCCAAGGGGGCCTGC
ACAGGCTGGATGGCGGGCATCCCAGGGCACCCGGGCCACAACGGGGCCCCAGGCCGGGA
CGGCAGAGACGGCACCCCCGGCGAGAAGGGCGAGAAAGGAGACCCAGGCCTGATCGGCC
CCAAGGGAGACATCGGCGAAACCGGAGTACCCGGGGCCGAAGGCCCCCGAGGCTTCCCG
GGAATCCAAGGCAGGAAAGGAGAACCCGGAGAAGGCGCCTACGTATACCGCAGCGCATT
CAGCGTGGGACTGGAGACCTACGTGACCATCCCCAACATGCCCATCCGCTTCACCAAGA
TCTTCTACAACCAGCAAAACCACTACGACGGCAGCACCGGCAAATTCCACTGCAACATC
CCCGGGCTGTACTACTTCGCCTACCACATCACAGTCTACATGAAGGACGTGAAGGTCAG
CCTCTTCAAGAAGGACAAGGCCATGCTGTTCACCTACGACCAGTACCAGGAAAACAACG
TGGACCAGGCCAGCGGCAGCGTGCTCCTGCACCTGGAGGTGGGCGACCAAGTCTGGCTC
CAGGTGTATGGGGAAGGAGAGCGTAATGGACTCTATGCTGATAATGACAATGACTCCAC
CTTCACAGGCTTTCTTCTCTACCATGACACCAACTGA hAdipo sense strand, non-template. 5'_16%_T.
(SEQ ID NO: 127)
ATGCTGCTGCTGGGAGCCGTGCTACTGCTACTGGCCCTGCCCGGCCACG
ACCAGGAAACCACGACCCAAGGGCCCGGAGTCCTGCTGCCCCTGCCCAAGGGGGCCTGC
ACAGGCTGGATGGCGGGCATCCCAGGGCACCCGGGCCACAACGGGGCCCCAGGCCGGGA
CGGCAGAGACGGCACCCCCGGCGAGAAGGGCGAGAAAGGAGACCCAGGCCTGATCGGCC -continued

CCAAGGGAGACATCGGCGAAACCGGAGTACCCGGGGCCGAAGGCCCCCGAGGCTTCCCG

GGAATCCAAGGCAGGAAAGGAGAACCCGGAGAAGGCGCCTACGTATACCGCAGCGCATT

CAGCGTGGGACTGGAGACCTACGTGACCATCCCCAACATGCCCATCCGCTTCACCAAGA

TCTTCTACAACCAGCAAAACCACTACGACGGCAGCACCGGTAAATTCCACTGCAACATT

CCTGGGCTGTACTACTTTGCCTACCACATCACAGTCTATATGAAGGATGTGAAGGTCAG

CCTCTTCAAGAAGGACAAGGCTATGCTGTTCACCTATGATCAGTACCAGGAAAATAATG

TGGACCAGGCCTCCGGCTCTGTGCTCCTGCATCTGGAGGTGGGCGACCAAGTCTGGCTC

CAGGTGTATGGGGAAGGAGAGCGTAATGGACTCTATGCTGATAATGACAATGACTCCAC

CTTCACAGGCTTTCTTCTCTACCATGACACCAACTGA hAdipo sense strand, non-template. 5'_18%_T.

(SEQ ID NO: 128)

ATGCTGCTGCTGGGAGCCGTGCTACTGCTACTGGCCCTGCCCGGCCACG

ACCAGGAAACCACGACCCAAGGGCCCGGAGTCCTGCTGCCCCTGCCCAAGGGGGCCTGC

ACAGGCTGGATGGCGGGCATCCCAGGGCACCCGGGCCACAACGGGGCCCCAGGCCGGGA

CGGCAGAGACGGCACCCCCGGCGAGAAGGGCGAGAAAGGAGACCCAGGCCTGATCGGCC

CCAAGGGAGACATCGGCGAAACCGGAGTACCCGGGGCCGAAGGCCCCCGAGGCTTCCCG

GGAATCCAAGGCAGGAAAGGAGAACCCGGAGAAGGTGCCTATGTATACCGCTCAGCATT

CAGTGTGGGATTGGAGACTTACGTTACTATCCCCAACATGCCCATTCGCTTTACCAAGA

TCTTCTACAATCAGCAAAACCACTATGATGGCTCCACTGGTAAATTCCACTGCAACATT

CCTGGGCTGTACTACTTTGCCTACCACATCACAGTCTATATGAAGGATGTGAAGGTCAG

CCTCTTCAAGAAGGACAAGGCTATGCTGTTCACCTATGATCAGTACCAGGAAAATAATG

TGGACCAGGCCTCCGGCTCTGTGCTCCTGCATCTGGAGGTGGGCGACCAAGTCTGGCTC

CAGGTGTATGGGGAAGGAGAGCGTAATGGACTCTATGCTGATAATGACAATGACTCCAC

CTTCACAGGCTTTCTTCTCTACCATGACACCAACTGA hAdipo sense strand, non-template. 5'_20%_T.

(SEQ ID NO: 129)

ATGCTGCTGCTGGGAGCCGTGCTACTGCTACTGGCCCTGCCCGGCCACG

ACCAGGAAACCACGACCCAAGGGCCCGGAGTCCTGCTGCCCCTGCCCAAGGGGGCCTGC

ACAGGCTGGATGGCGGGCATCCCAGGGCACCCGGGCCACAACGGGGCCCCAGGCCGGGA

CGGCAGAGATGGCACCCCTGGTGAGAAGGGTGAGAAAGGAGATCCAGGTCTTATTGGTC

CTAAGGGAGACATCGGTGAAACCGGAGTACCCGGGGCTGAAGGTCCCCGAGGCTTTCCG

GGAATCCAAGGCAGGAAAGGAGAACCTGGAGAAGGTGCCTATGTATACCGCTCAGCATT

CAGTGTGGGATTGGAGACTTACGTTACTATCCCCAACATGCCCATTCGCTTTACCAAGA

TCTTCTACAATCAGCAAAACCACTATGATGGCTCCACTGGTAAATTCCACTGCAACATT

CCTGGGCTGTACTACTTTGCCTACCACATCACAGTCTATATGAAGGATGTGAAGGTCAG

CCTCTTCAAGAAGGACAAGGCTATGCTGTTCACCTATGATCAGTACCAGGAAAATAATG

TGGACCAGGCCTCCGGCTCTGTGCTCCTGCATCTGGAGGTGGGCGACCAAGTCTGGCTC

CAGGTGTATGGGGAAGGAGAGCGTAATGGACTCTATGCTGATAATGACAATGACTCCAC

CTTCACAGGCTTTCTTCTCTACCATGACACCAACTGA hAdipo sense strand, non-template. random_14%_T.

(SEQ ID NO: 130)

ATGCTGTTGCTGGGAGCCGTGCTACTGCTACTGGCCCTGCCCGGCCACG

ACCAGGAAACCACGACTCAAGGGCCCGGAGTCCTGCTGCCCCTGCCCAAGGGGGCCTGC

ACAGGTTGGATGGCGGGCATCCCAGGGCACCCGGGCCACAATGGGGCCCCAGGCCGGGA

```
TGGCAGAGACGGCACCCCCGGCGAGAAGGGCGAGAAAGGAGATCCAGGCCTGATCGGTC

CCAAGGGAGACATCGGCGAAACCGGAGTACCCGGGGCCGAAGGCCCCCGAGGCTTCCCG

GGAATCCAAGGCAGGAAAGGAGAACCCGGAGAAGGCGCCTATGTATACCGCAGCGCATT

CAGTGTGGGATTGGAGACCTACGTGACCATCCCCAACATGCCCATCCGCTTCACCAAGA

TCTTCTACAACCAGCAAAACCACTACGACGGCAGCACCGGCAAATTCCACTGCAACATC

CCCGGGCTGTACTACTTTGCCTACCACATCACAGTCTACATGAAGGACGTGAAGGTCAG

CCTCTTCAAGAAGGACAAGGCCATGCTGTTCACCTACGACCAGTACCAGGAAAACAACG

TGGACCAGGCCAGCGGCAGCGTGCTCCTGCACCTGGAGGTGGGCGACCAAGTCTGGCTC

CAGGTGTACGGGGAAGGAGAGCGTAACGGACTCTACGCCGACAACGACAACGACAGCAC

CTTCACAGGCTTCCTGCTCTACCACGAGACCAACTGA
```

hAdipo sense strand, non-template. random_16%_T.
(SEQ ID NO: 131)
```
ATGCTGCTGCTGGGAGCCGTGCTACTGCTACTGGCTCTGCCCGGTCACG

ACCAGGAAACCACGACTCAAGGGCCCGGAGTCCTGCTGCCCCTGCCCAAGGGGGCCTGC

ACAGGTTGGATGGCGGGCATCCCAGGGCATCCGGGCCATAACGGGGCCCCAGGCCGGGA

TGGCAGAGACGGCACCCCTGGCGAGAAGGGTGAGAAAGGAGACCCAGGCCTGATCGGCC

CTAAGGGAGACATCGGCGAAACCGGAGTACCCGGGGCCGAAGGCCCCCGAGGCTTCCCG

GGAATCCAAGGCAGGAAAGGAGAACCCGGAGAAGGCGCCTATGTATACCGCAGCGCATT

CAGTGTGGGATTGGAGACTTACGTTACCATCCCCAACATGCCCATTCGCTTCACCAAGA

TCTTCTACAACCAGCAAAACCACTACGACGGCAGCACCGGTAAATTCCACTGCAACATC

CCTGGGCTGTACTACTTTGCCTACCACATCACAGTCTATATGAAGGATGTGAAGGTCAG

CCTCTTCAAGAAGGACAAGGCTATGCTGTTCACCTACGATCAGTACCAGGAAAATAATG

TGGACCAGGCCAGCGGCAGCGTGCTCCTGCACCTGGAGGTGGGCGACCAAGTCTGGCTC

CAGGTGTACGGGGAAGGAGAGCGGAACGGACTCTACGCCGACAACGACAATGACAGCAC

CTTCACAGGCTTCCTGCTCTACCATGACACCAACTGA
```

hAdipo sense strand, non-template. random_18%_T.
(SEQ ID NO: 132)
```
ATGCTGTTGCTGGGAGCCGTTCTACTGCTACTGGCTCTGCCCGGCCATG

ACCAGGAAACCACGACCCAAGGGCCCGGAGTCCTGCTTCCCCTGCCCAAGGGGGCCTGC

ACAGGTTGGATGGCGGGCATCCCAGGGCACCCGGGCCATAATGGGGCCCCAGGCCGTGA

TGGCAGAGACGGCACCCCCGGCGAGAAGGGTGAGAAAGGAGATCCAGGTCTGATCGGTC

CTAAGGGAGACATCGGCGAAACCGGAGTACCCGGGGCTGAAGGTCCCCGAGGCTTTCCG

GGAATCCAAGGCAGGAAAGGAGAACCTGGAGAAGGCGCCTACGTATACCGCAGCGCATT

CAGCGTGGGACTGGAGACCTACGTGACCATCCCCAACATGCCCATCCGCTTTACCAAGA

TCTTCTACAATCAGCAAAACCACTATGACGGCTCCACTGGCAAATTCCACTGCAACATT

CCCGGGCTGTACTACTTTGCCTACCACATCACAGTCTATATGAAGGATGTGAAGGTCAG

CCTCTTCAAGAAGGACAAGGCCATGCTGTTCACCTACGATCAGTACCAGGAAAACAATG

TGGACCAGGCCAGCGGCTCTGTGCTCCTGCATCTGGAGGTGGGCGACCAAGTCTGGCTC

CAGGTGTACGGGGAAGGAGAGCGTAACGGACTCTATGCCGATAATGACAATGACTCCAC

CTTCACAGGCTTTCTTCTCTACCATGACACCAACTGA
```

-continued hAdipo sense strand, non-template. random_20%_T.
(SEQ ID NO: 133)
ATGCTGTTGCTGGGAGCCGTTCTACTGCTATTAGCTCTGCCCGGTCATG

ACCAGGAAACCACGACTCAAGGGCCCGGAGTCCTGCTGCCCCTGCCCAAGGGGGCCTGC

ACAGGTTGGATGGCGGGCATCCCAGGGCATCCGGGCCATAATGGGGCCCCAGGCCGTGA

CGGCAGAGATGGCACCCCCGGTGAGAAGGGTGAGAAAGGAGACCCAGGTCTTATTGGCC

CTAAGGGAGACATCGGTGAAACCGGAGTACCCGGGGCTGAAGGCCCCCGAGGCTTTCCG

GGAATCCAAGGCAGGAAAGGAGAACCTGGAGAAGGCGCCTATGTATACCGCAGCGCATT

CAGTGTGGGATTGGAGACTTACGTTACTATCCCCAACATGCCCATTCGCTTTACCAAGA

TCTTCTACAATCAGCAAAACCACTATGATGGCAGCACCGGTAAATTCCACTGCAACATC

CCTGGGCTGTACTACTTTGCCTACCACATCACAGTCTATATGAAGGATGTGAAGGTCAG

CCTCTTCAAGAAGGACAAGGCTATGCTGTTCACCTATGACCAGTACCAGGAAAATAATG

TGGACCAGGCCTCCGGCTCTGTGCTCCTGCATCTGGAGGTGGGCGACCAAGTCTGGCTC

CAGGTGTATGGGGAAGGAGAGCGTAATGGACTCTACGCTGATAATGACAATGACTCCAC

CTTCACAGGCTTTCTGCTCTACCATGACACCAACTGA

TEV-hAdipo-XbG sense strand, non-template.
3'_lowest_T. (1167 nt)
(SEQ ID NO: 134)
AGGAAACTTAAGTCAACACAACATATACAAAACAAACGAATCTCAAGGA

ATCAAGCATTCTAGTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCCCTGCCCGGCCACGACCAGGAAACCACGACCCAAGGGCCCGGAGTCCT

GCTGCCCCTGCCCAAGGGGGCCTGCACAGGCTGGATGGCGGGCATCCCAGGGCACCCGG

GCCACAACGGGGCCCCAGGCCGGGACGGCAGAGACGGCACCCCCGGCGAGAAGGGCGAG

AAAGGAGACCCAGGCCTGATCGGCCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTACGTATACCGCAGCGCATTCAGCGTGGGACTGGAGACCTACGTGACCATCCCC

AACATGCCCATCCGCTTCACCAAGATCTTCTACAACCAGCAAAACCACTACGACGGCAG

CACCGGCAAATTCCACTGCAACATCCCCGGGCTGTACTACTTCGCCTACCACATCACAG

TCTACATGAAGGACGTGAAGGTCAGCCTCTTCAAGAAGGACAAGGCCATGCTGTTCACC

TACGACCAGTACCAGGAAAACAACGTGGACCAGGCCAGCGGCAGCGTGCTCCTGCACCT

GGAGGTGGGCGACCAAGTCTGGCTCCAGGTGTACGGGGAAGGAGAGCGGAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACGAGCCTCAAGAACACC

CGAATGGAGTCTCTAAGCTACATAATACCAACTTAGACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAA

TEV-hAdipo-XbG sense strand, non-template.
3'_14%_T. (1167 nt)
(SEQ ID NO: 135)
AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCTGTTCTA

-continued

CTGCTATTAGCTCTGCCCGGTCATGACCAGGAAACCACGACTCAAGGGCCCGGAGTCCT

GCTTCCCCTGCCCAAGGGGGCCTGCACAGGTTGGATGGCGGGCATCCCAGGGCATCCGG

GCCATAACGGGGCCCCAGGCCGGGACGGCAGAGACGGCACCCCCGGCGAGAAGGGCGAG

AAAGGAGACCCAGGCCTGATCGGCCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTACGTATACCGCAGCGCATTCAGCGTGGGACTGGAGACCTACGTGACCATCCCC

AACATGCCCATCCGCTTCACCAAGATCTTCTACAACCAGCAAAACCACTACGACGGCAG

CACCGGCAAATTCCACTGCAACATCCCCGGGCTGTACTACTTCGCCTACCACATCACAG

TCTACATGAAGGACGTGAAGGTCAGCCTCTTCAAGAAGGACAAGGCCATGCTGTTCACC

TACGACCAGTACCAGGAAAACAACGTGGACCAGGCCAGCGGCAGCGTGCTCCTGCACCT

GGAGGTGGGCGACCAAGTCTGGCTCCAGGTGTACGGGGAAGGAGAGCGGAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

TEV-hAdipo-XbG sense strand, non-template.
3'_16%_T. (1167 nt)

(SEQ ID NO: 136)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCTGTTCTA

CTGCTATTAGCTCTGCCCGGTCATGACCAGGAAACCACGACTCAAGGGCCCGGAGTCCT

GCTTCCCCTGCCCAAGGGGGCCTGCACAGGTTGGATGGCGGGCATCCCAGGGCATCCGG

GCCATAATGGGGCCCCAGGCCGTGATGGCAGAGATGGCACCCCTGGTGAGAAGGGTGAG

AAAGGAGATCCAGGTCTTATTGGTCCTAAGGGAGACATCGGTGAAACCGGAGTACCCGG

GGCTGAAGGCCCCCGAGGCTTCCCGGGAATCCAAGGCAGGAAAGGAGAACCCGGAGAAG

GCGCCTACGTATACCGCAGCGCATTCAGCGTGGGACTGGAGACCTACGTGACCATCCCC

AACATGCCCATCCGCTTCACCAAGATCTTCTACAACCAGCAAAACCACTACGACGGCAG

CACCGGCAAATTCCACTGCAACATCCCCGGGCTGTACTACTTCGCCTACCACATCACAG

TCTACATGAAGGACGTGAAGGTCAGCCTCTTCAAGAAGGACAAGGCCATGCTGTTCACC

TACGACCAGTACCAGGAAAACAACGTGGACCAGGCCAGCGGCAGCGTGCTCCTGCACCT

GGAGGTGGGCGACCAAGTCTGGCTCCAGGTGTACGGGGAAGGAGAGCGGAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACGAGCCTCAAGAACACC

CGAATGGAGTCTCTAAGCTACATAATACCAACTTAGACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

-continued

TEV-hAdipo-XbG sense strand, non-template.
3'_18%_T. (1167 nt)

(SEQ ID NO: 137)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCTGTTCTA

CTGCTATTAGCTCTGCCCGGTCATGACCAGGAAACCACGACTCAAGGGCCCGGAGTCCT

GCTTCCCCTGCCCAAGGGGGCCTGCACAGGTTGGATGGCGGGCATCCCAGGGCATCCGG

GCCATAATGGGGCCCCAGGCCGTGATGGCAGAGATGGCACCCCTGGTGAGAAGGGTGAG

AAAGGAGATCCAGGTCTTATTGGTCCTAAGGGAGACATCGGTGAAACCGGAGTACCCGG

GGCTGAAGGTCCCCGAGGCTTTCCGGGAATCCAAGGCAGGAAAGGAGAACCTGGAGAAG

GTGCCTATGTATACCGCTCAGCATTCAGTGTGGGATTGGAGACTTACGTTACTATCCCC

AACATGCCCATTCGCTTTACCAAGATCTTCTACAATCAGCAAAACCACTATGACGGCAG

CACCGGCAAATTCCACTGCAACATCCCCGGGCTGTACTACTTCGCCTACCACATCACAG

TCTACATGAAGGACGTGAAGGTCAGCCTCTTCAAGAAGGACAAGGCCATGCTGTTCACC

TACGACCAGTACCAGGAAAACAACGTGGACCAGGCCAGCGGCAGCGTGCTCCTGCACCT

GGAGGTGGGCGACCAAGTCTGGCTCCAGGTGTACGGGGAAGGAGAGCGGAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAA

TEV-hAdipo-XbG sense strand, non-template.
3'_20%_T. (1167 nt)

(SEQ ID NO: 138)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCTGTTCTA

CTGCTATTAGCTCTGCCCGGTCATGACCAGGAAACCACGACTCAAGGGCCCGGAGTCCT

GCTTCCCCTGCCCAAGGGGGCCTGCACAGGTTGGATGGCGGGCATCCCAGGGCATCCGG

GCCATAATGGGGCCCCAGGCCGTGATGGCAGAGATGGCACCCCTGGTGAGAAGGGTGAG

AAAGGAGATCCAGGTCTTATTGGTCCTAAGGGAGACATCGGTGAAACCGGAGTACCCGG

GGCTGAAGGTCCCCGAGGCTTTCCGGGAATCCAAGGCAGGAAAGGAGAACCTGGAGAAG

GTGCCTATGTATACCGCTCAGCATTCAGTGTGGGATTGGAGACTTACGTTACTATCCCC

AACATGCCCATTCGCTTTACCAAGATCTTCTACAATCAGCAAAACCACTATGATGGCTC

CACTGGTAAATTCCACTGCAACATTCCTGGGCTGTACTACTTTGCCTACCACATCACAG

TCTATATGAAGGATGTGAAGGTCAGCCTCTTCAAGAAGGACAAGGCTATGCTGTTCACC

TATGATCAGTACCAGGAAAATAATGTGGACCAGGCCTCCGGCAGCGTGCTCCTGCACCT

GGAGGTGGGCGACCAAGTCTGGCTCCAGGTGTACGGGGAAGGAGAGCGGAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACGAGCCTCAAGAACACC

CGAATGGAGTCTCTAAGCTACATAATACCAACTTAGACTTACAAAATGTTGTCCCCCAA

-continued

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAA

TEV-hAdipo-XbG sense strand, non-template.
5'_14%_T. (1167 nt)

(SEQ ID NO: 139)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCCCTGCCCGGCCACGACCAGGAAACCACGACCCAAGGGCCCGGAGTCCT

GCTGCCCCTGCCCAAGGGGGCCTGCACAGGCTGGATGGCGGGCATCCCAGGGCACCCGG

GCCACAACGGGGCCCCAGGCCGGGACGGCAGAGACGGCACCCCCGGCGAGAAGGGCGAG

AAAGGAGACCCAGGCCTGATCGGCCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTACGTATACCGCAGCGCATTCAGCGTGGGACTGGAGACCTACGTGACCATCCCC

AACATGCCCATCCGCTTCACCAAGATCTTCTACAACCAGCAAAACCACTACGACGGCAG

CACCGGCAAATTCCACTGCAACATCCCCGGGCTGTACTACTTCGCCTACCACATCACAG

TCTACATGAAGGACGTGAAGGTCAGCCTCTTCAAGAAGGACAAGGCCATGCTGTTCACC

TACGACCAGTACCAGGAAAACAACGTGGACCAGGCCAGCGGCAGCGTGCTCCTGCACCT

GGAGGTGGGCGACCAAGTCTGGCTCCAGGTGTATGGGGAAGGAGAGCGTAATGGACTCT

ATGCTGATAATGACAATGACTCCACCTTCACAGGCTTTCTTCTCTACCATGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAA

TEV-hAdipo-XbG sense strand, non-template.
5'_16%_T. (1167 nt)

(SEQ ID NO: 140)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCCCTGCCCGGCCACGACCAGGAAACCACGACCCAAGGGCCCGGAGTCCT

GCTGCCCCTGCCCAAGGGGGCCTGCACAGGCTGGATGGCGGGCATCCCAGGGCACCCGG

GCCACAACGGGGCCCCAGGCCGGGACGGCAGAGACGGCACCCCCGGCGAGAAGGGCGAG

AAAGGAGACCCAGGCCTGATCGGCCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTACGTATACCGCAGCGCATTCAGCGTGGGACTGGAGACCTACGTGACCATCCCC

AACATGCCCATCCGCTTCACCAAGATCTTCTACAACCAGCAAAACCACTACGACGGCAG

CACCGGTAAATTCCACTGCAACATTCCTGGGCTGTACTACTTTGCCTACCACATCACAG

TCTATATGAAGGATGTGAAGGTCAGCCTCTTCAAGAAGGACAAGGCTATGCTGTTCACC

TATGATCAGTACCAGGAAAATAATGTGGACCAGGCCTCCGGCTCTGTGCTCCTGCATCT

GGAGGTGGGCGACCAAGTCTGGCTCCAGGTGTATGGGGAAGGAGAGCGTAATGGACTCT

ATGCTGATAATGACAATGACTCCACCTTCACAGGCTTTCTTCTCTACCATGACACCAAC

-continued

TGACTCGAGCTAGTGACTGACTAGGATCTGGTTACCACTAAACGAGCCTCAAGAACACC

CGAATGGAGTCTCTAAGCTACATAATACCAACTTAGACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

TEV-hAdipo-XbG sense strand, non-template.
5'_18%_T. (1167 nt)

(SEQ ID NO: 141)

AGGAAACTTAAGTCAACACAACATATACAAAACAAACGAATCTCAAGCA

ATCAAGCATTCTAGTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCCCTGCCCGGCCACGACCAGGAAACCACGACCCAAGGGCCCGGAGTCCT

GCTGCCCCTGCCCAAGGGGGCCTGCACAGGCTGGATGGCGGGCATCCCAGGGCACCCGG

GCCACAACGGGGCCCCAGGCCGGGACGGCAGAGACGGCACCCCCGGCGAGAAGGGCGAG

AAAGGAGACCCAGGCCTGATCGGCCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GTGCCTATGTATACCGCTCAGCATTCAGTGTGGGATTGGAGACTTACGTTACTATCCCC

AACATGCCCATTCGCTTTACCAAGATCTTCTACAATCAGCAAAACCACTATGATGGCTC

CACTGGTAAATTCCACTGCAACATTCCTGGGCTGTACTACTTTGCCTACCACATCACAG

TCTATATGAAGGATGTGAAGGTCAGCCTCTTCAAGAAGGACAAGGCTATGCTGTTCACC

TATGATCAGTACCAGGAAAATAATGTGGACCAGGCCTCCGGCTCTGTGCTCCTGCATCT

GGAGGTGGGCGACCAAGTCTGGCTCCAGGTGTATGGGGAAGGAGAGCGTAATGGACTCT

ATGCTGATAATGACAATGACTCCACCTTCACAGGCTTTCTTCTCTACCATGACACCAAC

TGACTCGAGCTAGTGACTGACTAGGATCTGGTTACCACTAAACCAGCCTCAAGAACACC

CGAATGGAGTCTCTAAGCTAGATAATACCAACTTAGACTTAGAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

TEV-hAdipo-XbG sense strand, non-template.
5'_20%_T. (1167 nt)

(SEQ ID NO: 142)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCCCTGCCCGGCCACGACCAGGAAACCACGACCCAAGGGCCCGGAGTCCT

GCTGCCCCTGCCCAAGGGGGCCTGCACAGGCTGGATGGCGGGCATCCCAGGGCACCCGG

GCCACAACGGGGCCCCAGGCCGGGACGGCAGAGATGGCACCCCTGGTGAGAAGGGTGAG

AAAGGAGATCCAGGTCTTATTGGTCCTAAGGGAGACATCGGTGAAACCGGAGTACCCGG

GGCTGAAGGTCCCCGAGGCTTTCCGGGAATCCAAGGCAGGAAAGGAGAACCTGGAGAAG

GTGCCTATGTATACCGCTCAGCATTCAGTGTGGGATTGGAGACTTACGTTACTATCCCC

AACATGCCCATTCGCTTTACCAAGATCTTCTACAATCAGCAAAACCACTATGATGGCTC

CACTGGTAAATTCCACTGCAACATTCCTGGGCTGTACTACTTTGCCTACCACATCACAG

TCTATATGAAGGATGTGAAGGTCAGCCTCTTCAAGAAGGACAAGGCTATGCTGTTCACC

-continued

TATGATCAGTACCAGGAAAATAATGTGGACCAGGCCTCCGGCTCTGTGCTCCTGCATCT

GGAGGTGGGCGACCAAGTCTGGCTCCAGGTGTATGGGGAAGGAGAGCGTAATGGACTCT

ATGCTGATAATGACAATGACTCCACCTTCACAGGCTTTCTTCTCTACCATGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

TEV-hAdipo-XbG sense strand, non-template.
random_14%_T. (1167 nt)

(SEQ ID NO: 143)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCCGTGCTA

CTGCTACTGGCCCTGCCCGGCCACGACCAGGAAACCACGACTCAAGGGCCCGGAGTCCT

GCTGCCCCTGCCCAAGGGGGCCTGCACAGGTTGGATGGCGGGCATCCCAGGGCACCCGG

GCCACAATGGGGCCCCAGGCCGGGATGGCAGAGACGGCACCCCCGGCGAGAAGGGCGAG

AAAGGAGATCCAGGCCTGATCGGTCCCAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTATGTATACCGCAGCGCATTCAGTGTGGGATTGGAGACCTACGTGACCATCCCC

AACATGCCCATCCGCTTCACCAAGATCTTCTACAACCAGCAAAACCACTACGACGGCAG

CACCGGCAAATTCCACTGCAACATCCCCGGGCTGTACTACTTTGCCTACCACATCACAG

TCTACATGAAGGACGTGAAGGTCAGCCTCTTCAAGAAGGACAAGGCCATGCTGTTCACC

TACGACCAGTACCAGGAAAACAACGTGGACCAGGCCAGCGGCAGCGTGCTCCTGCACCT

GGAGGTGGGCGACCAAGTCTGGCTCCAGGTGTACGGGGAAGGAGAGCGTAACGGACTCT

ACGCCGACAACGACAACGACAGCACCTTCACAGGCTTCCTGCTCTACCACGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

TEV-hAdipo-XbG sense strand, non-template.
random_16%_T. (1167 nt)

(SEQ ID NO: 144)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGCTGCTGGGAGCCGTGCTA

CTGCTACTGGCTCTGCCCGGTCACGACCAGGAAACCACGACTCAAGGGCCCGGAGTCCT

GCTGCCCCTGCCCAAGGGGGCCTGCACAGGTTGGATGGCGGGCATCCCAGGGCATCCGG

GCCATAACGGGGCCCCAGGCCGGGATGGCAGAGACGGCACCCCTGGCGAGAAGGGTGAG

AAAGGAGACCCAGGCCTGATCGGCCCTAAGGGAGACATCGGCGAAACCGGAGTACCCGG

GGCCGAAGGCCCCCGAGGCTTCCCGGGAATCCAAGGCAGGAAAGGAGAACCCGGAGAAG

GCGCCTATGTATACCGCAGCGCATTCAGTGTGGGATTGGAGACTTACGTTACCATCCCC

AACATGCCCATTCGCTTCACCAAGATCTTCTACAACCAGCAAAACCACTACGACGGCAG

-continued

CACCGGTAAATTCCACTGCAACATCCCTGGGCTGTACTACTTTGCCTACCACATCACAG

TCTATATGAAGGATGTGAAGGTCAGCCTCTTCAAGAAGGACAAGGCTATGCTGTTCACC

TACGATCAGTACCAGGAAAATAATGTGGACCAGGCCAGCGGCAGCGTGCTCCTGCACCT

GGAGGTGGGCGACCAAGTCTGGCTCCAGGTGTACGGGGAAGGAGAGCGGAACGGACTCT

ACGCCGACAACGACAATGACAGCACCTTCACAGGCTTCCTGCTCTACCATGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

TEV-hAdipo-XbG sense strand, non-template.
random_18%_T. (1167 nt)

(SEQ ID NO: 145)

AGGAAACTTAAGTCAACACAACATATACAAAACAAACGAATCTCAAGGA

ATCAAGCATTCTAGTTCTATTGCAGCAATTTAAATCATTTCTTTTAAAGCAAAAGCAAT

TTTCTGAAAATTTTCACCATTTACGAACGATAGCCATGCTGTTGCTGGGAGCCGTTCTA

CTGCTACTGGCTCTGCCCGGCCATGACCAGGAAACCACGACCCAAGGGCCCGGAGTCCT

GCTTCCCCTGCCCAAGGGGGCCTGCACAGGTTGGATGGCGGGCATCCCAGGGCACCCGG

GCCATAATGGGGCCCCAGGCCGTGATGGCAGAGACGGCACCCCCGGCGAGAAGGGTGAG

AAAGGAGATCCAGGTCTGATCGGTCCTAAGGGAGACATCGGCGAAACCGGAGTACCCGG

GGCTGAAGGTCCCCGAGGCTTTCCGGGAATCCAAGGCAGGAAAGGAGAACCTGGAGAAG

GCGCCTACGTATACCGCAGCGCATTCAGCGTGGGACTGGAGACCTACGTGACCATCCCC

AACATGCCCATCCGCTTTACCAAGATCTTCTACAATCAGCAAAACCACTATGACGGCTC

CACTGGCAAATTCCACTGCAACATTCCCGGGCTGTACTACTTTGCCTACCACATCACAG

TCTATATGAAGGATGTGAAGGTCAGCCTCTTCAAGAAGGACAAGGCCATGCTGTTCACC

TACGATCAGTACCAGGAAAACAATGTGGACCAGGCCAGCGGCTCTGTGCTCCTGCATCT

GGAGGTGGGCGACCAAGTCTGGCTCCAGGTGTACGGGGAAGGAGAGCGTAACGGACTCT

ATGCCGATAATGACAATGACTCCACCTTCACAGGCTTTCTTCTCTACCATGACACCAAC

TGACTCGAGCTAGTGACTGACTAGGATCTGGTTACCACTAAACCAGCCTCAAGAACACC

CGAATGGAGTCTCTAAGCTAGATAATACCAACTTACACTTACAAAATGTTGTCCCCCAA

AATGTAGCCATTCGTATCTGCTCCTAATAAAAAGAAAGTTTCTTCACATTCTAGAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAA

TEV-hAdipo-XbG sense strand, non-template.
random_20%_T. (1167 nt)

(SEQ ID NO: 146)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGCTGTTGCTGGGAGCCGTTCTA

CTGCTATTAGCTCTGCCCGGTCATGACCAGGAAACCACGACTCAAGGGCCCGGAGTCCT

GCTGCCCCTGCCCAAGGGGGCCTGCACAGGTTGGATGGCGGGCATCCCAGGGCATCCGG

GCCATAATGGGGCCCCAGGCCGTGACGGCAGAGATGGCACCCCCGGTGAGAAGGGTGAG

AAAGGAGACCCAGGTCTTATTGGCCCTAAGGGAGACATCGGTGAAACCGGAGTACCCGG

-continued

GGCTGAAGGCCCCCGAGGCTTTCCGGGAATCCAAGGCAGGAAAGGAGAACCTGGAGAAG

GCGCCTATGTATACCGCAGCGCATTCAGTGTGGGATTGGAGACTTACGTTACTATCCCC

AACATGCCCATTCGCTTTACCAAGATCTTCTACAATCAGCAAAACCACTATGATGGCAG

CACCGGTAAATTCCACTGCAACATCCCTGGGCTGTACTACTTTGCCTACCACATCACAG

TCTATATGAAGGATGTGAAGGTCAGCCTCTTCAAGAAGGACAAGGCTATGCTGTTCACC

TATGACCAGTACCAGGAAAATAATGTGGACCAGGCCTCCGGCTCTGTGCTCCTGCATCT

GGAGGTGGGCGACCAAGTCTGGCTCCAGGTGTATGGGGAAGGAGAGCGTAATGGACTCT

ACGCTGATAATGACAATGACTCCACCTTCACAGGCTTTCTGCTCTACCATGACACCAAC

TGACTCGAGCTAGTGACTGACTAGGATCTGGTTACCACTAAACCAGCCTCAAGAACACC

CGAATGGAGTCTCTAAGCTACATAATACCAACTTACACTTACAAAATGTTGTCCCCCAA

AATGTAGCCATTCGTATCTGCTCCTAATAAAAAGAAAGTTTCTTCACATTCTAGAAAAA

TEV-hAdipo-XbG ARC-mRNA. 3'_lowest_T. (1167 nt)
(SEQ ID NO: 147)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGCUGCUGGGAGCCGUGCUACUGCUACUGG

CCCUGCCCGGCCACGACCAGGAAACCACGACCCAAGGGCCCGGAGUCCUGCUGCCCCUG

CCCAAGGGGGCCUGCACAGGCUGGAUGGCGGGCAUCCCAGGGCACCCGGGCCACAACGG

GGCCCCAGGCCGGGACGGCAGAGACGGCACCCCCGGCGAGAAGGGCGAGAAAGGAGACC

CAGGCCUGAUCGGCCCCAAGGGAGACAUCGGCGAAACCGGAGUACCCGGGGCCGAAGGC

CCCCGAGGCUUCCCGGGAAUCCAAGGCAGGAAAGGAGAACCCGGAGAAGGCGCCUACGU

AUACCGCAGCGCAUUCAGCGUGGGACUGGAGACCUACGUGACCAUCCCCAACAUGCCCA

UCCGCUUCACCAAGAUCUUCUACAACCAGCAAAACCACUACGACGGCAGCACCGGCAAA

UUCCACUGCAACAUCCCCGGGCUGUACUACUUCGCCUACCACAUCACAGUCUACAUGAA

GGACGUGAAGGUCAGCCUCUUCAAGAAGGACAAGGCCAUGCUGUUCACCUACGACCAGU

ACCAGGAAAACAACGUGGACCAGGCCAGCGGCAGCGUGCUCCUGCACCUGGAGGUGGGC

GACCAAGUCUGGCUCCAGGUGUACGGGGAAGGAGAGCGGAACGGACUCUACGCCGACAA

CGACAACGACAGCACCUUCACAGGCUUCCUGCUCUACCACGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAA

TEV-hAdipo-XbGARC-mRNA. 3'_14%_T. (1167 nt)
(SEQ ID NO: 148)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGUUGCUGGGAGCUGUUCUACUGCUAUUAG

CUCUGCCCGGUCAUGACCAGGAAACCACGACUCAAGGGCCCGGAGUCCUGCUUCCCCUG

CCCAAGGGGGCCUGCACAGGUUGGAUGGCGGGCAUCCCAGGGCAUCCGGGCCAUAACGG

GGCCCCAGGCCGGGACGGCAGAGACGGCACCCCCGGCGAGAAGGGCGAGAAAGGAGACC

-continued

CAGGCCUGAUCGGCCCCAAGGGAGACAUCGGCGAAACCGGAGUACCCGGGGCCGAAGGC

CCCCGAGGCUUCCCGGGAAUCCAAGGCAGGAAAGGAGAACCCGGAGAAGGCGCCUACGU

AUACCGCAGCGCAUUCAGCGUGGGACUGGAGACCUACGUGACCAUCCCCAACAUGCCCA

UCCGCUUCACCAAGAUCUUCUACAACCAGCAAAACCACUACGACGGCAGCACCGGCAAA

UUCCACUGCAACAUCCCCGGGCUGUACUACUUCGCCUACCACAUCACAGUCUACAUGAA

GGACGUGAAGGUCAGCCUCUUCAAGAAGGACAAGGCCAUGCUGUUCACCUACGACCAGU

ACCAGGAAAACAACGUGGACCAGGCCAGCGGCAGCGUGCUCCUGCACCUGGAGGUGGGC

GACCAAGUCUGGCUCCAGGUGUACGGGGAAGGAGAGCGGAACGGACUCUACGCCGACAA

CGACAACGACAGCACCUUCACAGGCUUCCUGCUCUACCACGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAA

TEV-hAdipo-XbG ARC-mRNA. 3'_16%_T. (1167 nt)
(SEQ ID NO: 149)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGUUGCUGGGAGCUGUUCUACUGCUAUUAG

CUCUGCCCGGUCAUGACCAGGAAACCACGACUCAAGGGCCCGGAGUCCUGCUUCCCCUG

CCCAAGGGGGCCUGCACAGGUUGGAUGGCGGGCAUCCCAGGGCAUCCGGGCCAUAAUGG

GGCCCCAGGCCGUGAUGGCAGAGAUGGCACCCCUGGUGAGAAGGGUGAGAAAGGAGAUC

CAGGUCUUAUUGGUCCUAAGGGAGACAUCGGUGAAACCGGAGUACCCGGGGCUGAAGGC

CCCCGAGGCUUCCCGGGAAUCCAAGGCAGGAAAGGAGAACCCGGAGAAGGCGCCUACGU

AUACCGCAGCGCAUUCAGCGUGGGACUGGAGACCUACGUGACCAUCCCCAACAUGCCCA

UCCGCUUCACCAAGAUCUUCUACAACCAGCAAAACCACUACGACGGCAGCACCGGCAAA

UUCCACUGCAACAUCCCCGGGCUGUACUACUUCGCCUACCACAUCACAGUCUACAUGAA

GGACGUGAAGGUCAGCCUCUUCAAGAAGGACAAGGCCAUGCUGUUCACCUACGACCAGU

ACCAGGAAAACAACGUGGACCAGGCCAGCGGCAGCGUGCUCCUGCACCUGGAGGUGGGC

GACCAAGUCUGGCUCCAGGUGUACGGGGAAGGAGAGCGGAACGGACUCUACGCCGACAA

CGACAACGACAGCACCUUCACAGGCUUCCUGCUCUACCACGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAA

TEV-hAdipo-XbGARC-mRNA. 3'_18%_T. (1167 nt)
(SEQ ID NO: 150)
5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGUUGCUGGGAGCUGUUCUACUGCUAUUAG

-continued

CUCUGCCCGGUCAUGACCAGGAAACCACGACUCAAGGGCCCGGAGUCCUGCUUCCCCUG

CCCAAGGGGGCCUGCACAGGUUGGAUGGCGGGCAUCCCAGGGCAUCCGGGCCAUAAUGG

GGCCCCAGGCCGUGAUGGCAGAGAUGGCACCCCUGGUGAGAAGGGUGAGAAAGGAGAUC

CAGGUCUUAUUGGUCCUAAGGGAGACAUCGGUGAAACCGGAGUACCCGGGGCUGAAGGU

CCCCGAGGCUUUCCGGGAAUCCAAGGCAGGAAAGGAGAACCUGGAGAAGGUGCCUAUGU

AUACCGCUCAGCAUUCAGUGUGGGAUUGGAGACUUACGUUACUAUCCCCAACAUGCCCA

UUCGCUUUACCAAGAUCUUCUACAAUCAGCAAAACCACUAUGACGGCAGCACCGGCAAA

UUCCACUGCAACAUCCCCGGGCUGUACUACUUCGCCUACCACAUCACAGUCUACAUGAA

GGACGUGAAGGUCAGCCUCUUCAAGAAGGACAAGGCCAUGCUGUUCACCUACGACCAGU

ACCAGGAAAACAACGUGGACCAGGCCAGCGGCAGCGUGCUCCUGCACCUGGAGGUGGGC

GACCAAGUCUGGCUCCAGGUGUACGGGGAAGGAGAGCGGAACGGACUCUACGCCGACAA

CGACAACGACAGCACCUUCACAGGCUUCCUGCUCUACCACGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAA

TEV-hAdipo-XbG ARC-mRNA. 3' 20%_T. (1167 nt)

(SEQ ID NO: 151)

5'-cap-
AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGUUGCUGGGAGCUGUUCUACUGCUAUUAG

CUCUGCCCGGUCAUGACCAGGAAACCACGACUCAAGGGCCCGGAGUCCUGCUUCCCCUG

CCCAAGGGGGCCUGCACAGGUUGGAUGGCGGGCAUCCCAGGGCAUCCGGGCCAUAAUGG

GGCCCCAGGCCGUGAUGGCAGAGAUGGCACCCCUGGUGAGAAGGGUGAGAAAGGAGAUC

CAGGUCUUAUUGGUCCUAAGGGAGACAUCGGUGAAACCGGAGUACCCGGGGCUGAAGGU

CCCCGAGGCUUUCCGGGAAUCCAAGGCAGGAAAGGAGAACCUGGAGAAGGUGCCUAUGU

AUACCGCUCAGCAUUCAGUGUGGGAUUGGAGACUUACGUUACUAUCCCCAACAUGCCCA

UUCGCUUUACCAAGAUCUUCUACAAUCAGCAAAACCACUAUGAUGGCUCCACUGGUAAA

UUCCACUGCAACAUUCCUGGGCUGUACUACUUUGCCUACCACAUCACAGUCUAUAUGAA

GGAUGUGAAGGUCAGCCUCUUCAAGAAGGACAAGGCUAUGCUGUUCACCUAUGAUCAGU

ACCAGGAAAAUAAUGUGGACCAGGCCUCCGGCAGCGUGCUCCUGCACCUGGAGGUGGGC

GACCAAGUCUGGCUCCAGGUGUACGGGGAAGGAGAGCGGAACGGACUCUACGCCGACAA

CGACAACGACAGCACCUUCACAGGCUUCCUGCUCUACCACGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAA

-continued

TEV-hAdipo-XbGARC-mRNA. 5'_14%_T. (1167 nt)
(SEQ ID NO: 152)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGCUGCUGGGAGCCGUGCUACUGCUACUGG

CCCUGCCCGGCCACGACCAGGAAACCACGACCCAAGGGCCCGGAGUCCUGCUGCCCCUG

CCCAAGGGGGCCUGCACAGGCUGGAUGGCGGGCAUCCCAGGGCACCCGGGCCACAACGG

GGCCCCAGGCCGGGACGGCAGAGACGGCACCCCCGGCGAGAAGGGCGAGAAAGGAGACC

CAGGCCUGAUCGGCCCCAAGGGAGACAUCGGCGAAACCGGAGUACCCGGGGCCGAAGGC

CCCCGAGGCUUCCCGGGAAUCCAAGGCAGGAAAGGAGAACCCGGAGAAGGCGCCUACGU

AUACCGCAGCGCAUUCAGCGUGGGACUGGAGACCUACGUGACCAUCCCCAACAUGCCCA

UCCGCUUCACCAAGAUCUUCUACAACCAGCAAAACCACUACGACGGCAGCACCGGCAAA

UUCCACUGCAACAUCCCCGGGCUGUACUACUUCGCCUACCACAUCACAGUCUACAUGAA

GGACGUGAAGGUCAGCCUCUUCAAGAAGGACAAGGCCAUGCUGUUCACCUACGACCAGU

ACCAGGAAAACAACGUGGACCAGGCCAGCGGCAGCGUGCUCCUGCACCUGGAGGUGGGC

GACCAAGUCUGGCUCCAGGUGUAUGGGGAAGGAGAGCGUAAUGGACUCUAUGCUGAUAA

UGACAAUGACUCCACCUUCACAGGCUUUCUUCUCUACCAUGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAA

TEV-hAdipo-XbG ARC-mRNA. 5'_16%_T. (1167 nt)
(SEQ ID NO: 153)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGCUGCUGGGAGCCGUGCUACUGCUACUGG

CCCUGCCCGGCCACGACCAGGAAACCACGACCCAAGGGCCCGGAGUCCUGCUGCCCCUG

CCCAAGGGGGCCUGCACAGGCUGGAUGGCGGGCAUCCCAGGGCACCCGGGCCACAACGG

GGCCCCAGGCCGGGACGGCAGAGACGGCACCCCCGGCGAGAAGGGCGAGAAAGGAGACC

CAGGCCUGAUCGGCCCCAAGGGAGACAUCGGCGAAACCGGAGUACCCGGGGCCGAAGGC

CCCCGAGGCUUCCCGGGAAUCCAAGGCAGGAAAGGAGAACCCGGAGAAGGCGCCUACGU

AUACCGCAGCGCAUUCAGCGUGGGACUGGAGACCUACGUGACCAUCCCCAACAUGCCCA

UCCGCUUCACCAAGAUCUUCUACAACCAGCAAAACCACUACGACGGCAGCACCGGUAAA

UUCCACUGCAACAUUCCUGGGCUGUACUACUUUGCCUACCACAUCACAGUCUAUAUGAA

GGAUGUGAAGGUCAGCCUCUUCAAGAAGGACAAGGCUAUGCUGUUCACCUAUGAUCAGU

ACCAGGAAAAUAAUGUGGACCAGGCCUCCGGCUCUGUGCUCCUGCAUCUGGAGGUGGGC

GACCAAGUCUGGCUCCAGGUGUAUGGGGAAGGAGAGCGUAAUGGACUCUAUGCUGAUAA

UGACAAUGACUCCACCUUCACAGGCUUUCUUCUCUACCAUGACACCAACUGACUCGAGC

UAGUGACUGACUAGGAUCUGGUUACCACUAAACCAGCCUCAAGAACACCCGAAUGGAGU

-continued

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAA

TEV-hAdipo-XbGARC-mRNA. 5'_18%_T. (1167 nt)

(SEQ ID NO: 154)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGCUGCUGGGAGCCGUGCUACUGCUACUGG

CCCUGCCCGGCCACGACCAGGAAACCACGACCCAAGGGCCCGGAGUCCUGCUGCCCCUG

CCCAAGGGGGCCUGCACAGGCUGGAUGGCGGGCAUCCCAGGGCACCCGGGCCACAACGG

GGCCCCAGGCCGGGACGGCAGAGACGGCACCCCCGGCGAGAAGGGCGAGAAAGGAGACC

CAGGCCUGAUCGGCCCCAAGGGAGACAUCGGCGAAACCGGAGUACCCGGGGCCGAAGGC

CCCCGAGGCUUCCCGGGAAUCCAAGGCAGGAAAGGAGAACCCGGAGAAGGUGCCUAUGU

AUACCGCUCAGCAUUCAGUGUGGGAUUGGAGACUUACGUUACUAUCCCCAACAUGCCCA

UUCGCUUUACCAAGAUCUUCUACAAUCAGCAAAACCACUAUGAUGGCUCCACUGGUAAA

UUCCACUGCAACAUUCCUGGGCUGUACUACUUUGCCUACCACAUCACAGUCUAUAUGAA

GGAUGUGAAGGUCAGCCUCUUCAAGAAGGACAAGGCUAUGCUGUUCACCUAUGAUCAGU

ACCAGGAAAAUAAUGUGGACCAGGCCUCCGGCUCUGUGCUCCUGCAUCUGGAGGUGGGC

GACCAAGUCUGGCUCCAGGUGUAUGGGGAAGGAGAGCGUAAUGGACUCUAUGCUGAUAA

UGACAAUGACUCCACCUUCACAGGCUUUCUUCUCUACCAUGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAA

TEV-hAdipo-XbG ARC-mRNA. 5'_20%_T. (1167 nt)

(SEQ ID NO: 155)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGCUGCUGGGAGCCGUGCUACUGCUACUGG

CCCUGCCCGGCCACGACCAGGAAACCACGACCCAAGGGCCCGGAGUCCUGCUGCCCCUG

CCCAAGGGGGCCUGCACAGGCUGGAUGGCGGGCAUCCCAGGGCACCCGGGCCACAACGG

GGCCCCAGGCCGGGACGGCAGAGAUGGCACCCCUGGUGAGAAGGGUGAGAAAGGAGAUC

CAGGUCUUAUUGGUCCUAAGGGAGACAUCGGUGAAACCGGAGUACCCGGGGCUGAAGGU

CCCCGAGGCUUUCCGGGAAUCCAAGGCAGGAAAGGAGAACCUGGAGAAGGUGCCUAUGU

AUACCGCUCAGCAUUCAGUGUGGGAUUGGAGACUUACGUUACUAUCCCCAACAUGCCCA

UUCGCUUUACCAAGAUCUUCUACAAUCAGCAAAACCACUAUGAUGGCUCCACUGGUAAA

UUCCACUGCAACAUUCCUGGGCUGUACUACUUUGCCUACCACAUCACAGUCUAUAUGAA

GGAUGUGAAGGUCAGCCUCUUCAAGAAGGACAAGGCUAUGCUGUUCACCUAUGAUCAGU

ACCAGGAAAAUAAUGUGGACCAGGCCUCCGGCUCUGUGCUCCUGCAUCUGGAGGUGGGC

-continued

GACCAAGUCUGGCUCCAGGUGUAUGGGGAAGGAGAGCGUAAUGGACUCUAUGCUGAUAA

UGACAAUGACUCCACCUUCACAGGCUUUCUUCUCUACCAUGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAA

TEV-hAdipo-XbGARC-mRNA. random_14%_T. (1167 nt)

(SEQ ID NO: 156)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGUUGCUGGGAGCCGUGCUACUGCUACUGG

CCCUGCCCGGCCACGACCAGGAAACCACGACUCAAGGGCCCGGAGUCCUGCUGCCCCUG

CCCAAGGGGGCCUGCACAGGUUGGAUGGCGGGCAUCCCAGGGCACCCGGGCCACAAUGG

GGCCCCAGGCCGGGAUGGCAGAGACGGCACCCCCGGCGAGAAGGGCGAGAAAGGAGAUC

CAGGCCUGAUCGGUCCCAAGGGAGACAUCGGCGAAACCGGAGUACCCGGGGCCGAAGGC

CCCCGAGGCUUCCCGGGAAUCCAAGGCAGGAAAGGAGAACCCGGAGAAGGCGCCUAUGU

AUACCGCAGCGCAUUCAGUGUGGGAUUGGAGACCUACGUGACCAUCCCCAACAUGCCCA

UCCGCUUCACCAAGAUCUUCUACAACCAGCAAAACCACUACGACGGCAGCACCGGCAAA

UUCCACUGCAACAUCCCCGGGCUGUACUACUUUGCCUACCACAUCACAGUCUACAUGAA

GGACGUGAAGGUCAGCCUCUUCAAGAAGGACAAGGCCAUGCUGUUCACCUACGACCAGU

ACCAGGAAAACAACGUGGACCAGGCCAGCGGCAGCGUGCUCCUGCACCUGGAGGUGGGC

GACCAAGUCUGGCUCCAGGUGUACGGGGAAGGAGAGCGUAACGGACUCUACGCCGACAA

CGACAACGACAGCACCUUCACAGGCUUCCUGCUCUACCACGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAA

TEV-hAdipo-XbG ARC-mRNA. random_16%_T. (1167 nt)

(SEQ ID NO: 157)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGCUGCUGCUGGGAGCCGUGCUACUGCUACUGG

CUCUGCCCGGUCACGACCAGGAAACCACGACUCAAGGGCCCGGAGUCCUGCUGCCCCUG

CCCAAGGGGGCCUGCACAGGUUGGAUGGCGGGCAUCCCAGGGCAUCCGGGCCAUAACGG

GGCCCCAGGCCGGGAUGGCAGAGACGGCACCCCUGGCGAGAAGGGUGAGAAAGGAGACC

CAGGCCUGAUCGGCCCUAAGGGAGACAUCGGCGAAACCGGAGUACCCGGGGCCGAAGGC

CCCCGAGGCUUCCCGGGAAUCCAAGGCAGGAAAGGAGAACCCGGAGAAGGCGCCUAUGU

AUACCGCAGCGCAUUCAGUGUGGGAUUGGAGACUUACGUUACCAUCCCCAACAUGCCCA

-continued
UUCGCUUCACCAAGAUCUUCUACAACCAGCAAAACCACUACGACGGCAGCACCGGUAAA
UUCCACUGCAACAUCCCUGGGCUGUACUACUUUGCCUACCACAUCACAGUCUAUAUGAA
GGAUGUGAAGGUCAGCCUCUUCAAGAAGGACAAGGCUAUGCUGUUCACCUACGAUCAGU
ACCAGGAAAAUAAUGUGGACCAGGCCAGCGGCAGCGUGCUCCUGCACCUGGAGGUGGGC
GACCAAGUCUGGCUCCAGGUGUACGGGGAAGGAGAGCGGAACGGACUCUACGCCGACAA
CGACAAUGACAGCACCUUCACAGGCUUCCUGCUCUACCAUGACACCAACUGACUCGAGC
UAGUGACUGACUAGGAUCUGGUUACCACUAAACCAGCCUCAAGAACACCCGAAUGGAGU
CUCUAAGCUACAUAAUACCAACUUACACUUACAAAAUGUUGUCCCCCAAAAUGUAGCCA
UUCGUAUCUGCUCCUAAUAAAAAGAAAGUUUCUUCACAUUCUAGAAAAAAAAAAAAAAA
AAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAA TEV-hAdipo-XbGARC-mRNA. random_18%_T. (1167 nt)
(SEQ ID NO: 158)
5'-cap-
AGGAAACUUAAGUCAACACAACAUAUACAAAACAAACGAAUCUCAAGCAAUCAAGCAUU
CUACUUCUAUUGCAGCAAUUUAAAUCAUUUCUUUUAAAGCAAAAGCAAUUUUCUGAAAA
UUUUCACCAUUUACGAACGAUAGCCAUGCUGUUGCUGGGAGCCGUUCUACUGCUACUGG
CUCUGCCCGGCCAUGACCAGGAAACCACGACCCAAGGGCCCGGAGUCCUGCUUCCCCUG
CCCAAGGGGGCCUGCACAGGUUGGAUGGCGGGCAUCCCAGGGCACCCGGGCCAUAAUGG
GGCCCCAGGCCGUGAUGGCAGAGACGGCACCCCCGGCGAGAAGGGUGAGAAAGGAGAUC
CAGGUCUGAUCGGUCCUAAGGGAGACAUCGGCGAAACCGGAGUACCCGGGGCUGAAGGU
CCCCGAGGCUUUCCGGGAAUCCAAGGCAGGAAAGGAGAACCUGGAGAAGGCGCCUACGU
AUACCGCAGCGCAUUCAGCGUGGGACUGGAGACCUACGUGACCAUCCCCAACAUGCCCA
UCCGCUUUACCAAGAUCUUCUACAAUCAGCAAAACCACUAUGACGGCUCCACUGGCAAA
UUCCACUGCAACAUUCCCGGGCUGUACUACUUUGCCUACCACAUCACAGUCUAUAUGAA
GGAUGUGAAGGUCAGCCUCUUCAAGAAGGACAAGGCCAUGCUGUUCACCUACGAUCAGU
ACCAGGAAAACAAUGUGGACCAGGCCAGCGGCUCUGUGCUCCUGCAUCUGGAGGUGGGC
GACCAAGUCUGGCUCCAGGUGUACGGGGAAGGAGAGCGUAACGGACUCUAUGCCGAUAA
UGACAAUGACUCCACCUUCACAGGCUUUCUUCUCUACCAUGACACCAACUGACUCGAGC
UAGUGACUGACUAGGAUCUGGUUACCACUAAACCAGCCUCAAGAACACCCGAAUGGAGU
CUCUAAGCUACAUAAUACCAACUUACACUUACAAAAUGUUGUCCCCCAAAAUGUAGCCA
UUCGUAUCUGCUCCUAAUAAAAAGAAAGUUUCUUCACAUUCUAGAAAAAAAAAAAAAAA
AAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAA TEV-hAdipo-XbG ARC-mRNA. random_20%_T. (1167 nt)
(SEQ ID NO: 159)
5'-cap-
AGGAAACUUAAGUCAACACAACAUAUACAAAACAAACGAAUCUCAAGCAAUCAAGCAUU
CUACUUCUAUUGCAGCAAUUUAAAUCAUUUCUUUUAAAGCAAAAGCAAUUUUCUGAAAA
UUUUCACCAUUUACGAACGAUAGCCAUGCUGUUGCUGGGAGCCGUUCUACUGCUAUUAG
CUCUGCCCGGUCAUGACCAGGAAACCACGACUCAAGGGCCCGGAGUCCUGCUGCCCCUG
CCCAAGGGGGCCUGCACAGGUUGGAUGGCGGGCAUCCCAGGGCAUCCGGGCCAUAAUGG
GGCCCCAGGCCGUGACGGCAGAGAUGGCACCCCCGGUGAGAAGGGUGAGAAAGGAGACC -continued

```
CAGGUCUUAUUGGCCCUAAGGGAGACAUCGGUGAAACCGGAGUACCCGGGGCUGAAGGC

CCCCGAGGCUUUCCGGGAAUCCAAGGCAGGAAAGGAGAACCUGGAGAAGGCGCCUAUGU

AUACCGCAGCGCAUUCAGUGUGGGAUUGGAGACUUACGUUACUAUCCCCAACAUGCCCA

UUCGCUUUACCAAGAUCUUCUACAAUCAGCAAAACCACUAUGAUGGCAGCACCGGUAAA

UUCCACUGCAACAUCCCUGGGCUGUACUACUUUGCCUACCACAUCACAGUCUAUAUGAA

GGAUGUGAAGGUCAGCCUCUUCAAGAAGGACAAGGCUAUGCUGUUCACCUAUGACCAGU

ACCAGGAAAAUAAUGUGGACCAGGCCUCCGGCUCUGUGCUCCUGCAUCUGGAGGUGGGC

GACCAAGUCUGGCUCCAGGUGUAUGGGGAAGGAGAGCGUAAUGGACUCUACGCUGAUAA

UGACAAUGACUCCACCUUCACAGGCUUUCUGCUCUACCAUGACACCAACUGACUCGAGC

UAGUGACUGACUAGGAUCUGGUUACCACUAAACCAGCCUCAAGAACACCCGAAUGGAGU

CUCUAAGCUACAUAAUACCAACUUACACUUACAAAAUGUUGUCCCCCAAAAUGUAGCCA

UUCGUAUCUGCUCCUAAUAAAAAGAAAGUUUCUUCACAUUCUAGAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAA
```

Example F: Templates and mRNAs for Cynomolgus Monkey EPO (cmEPO)

Figure 10:
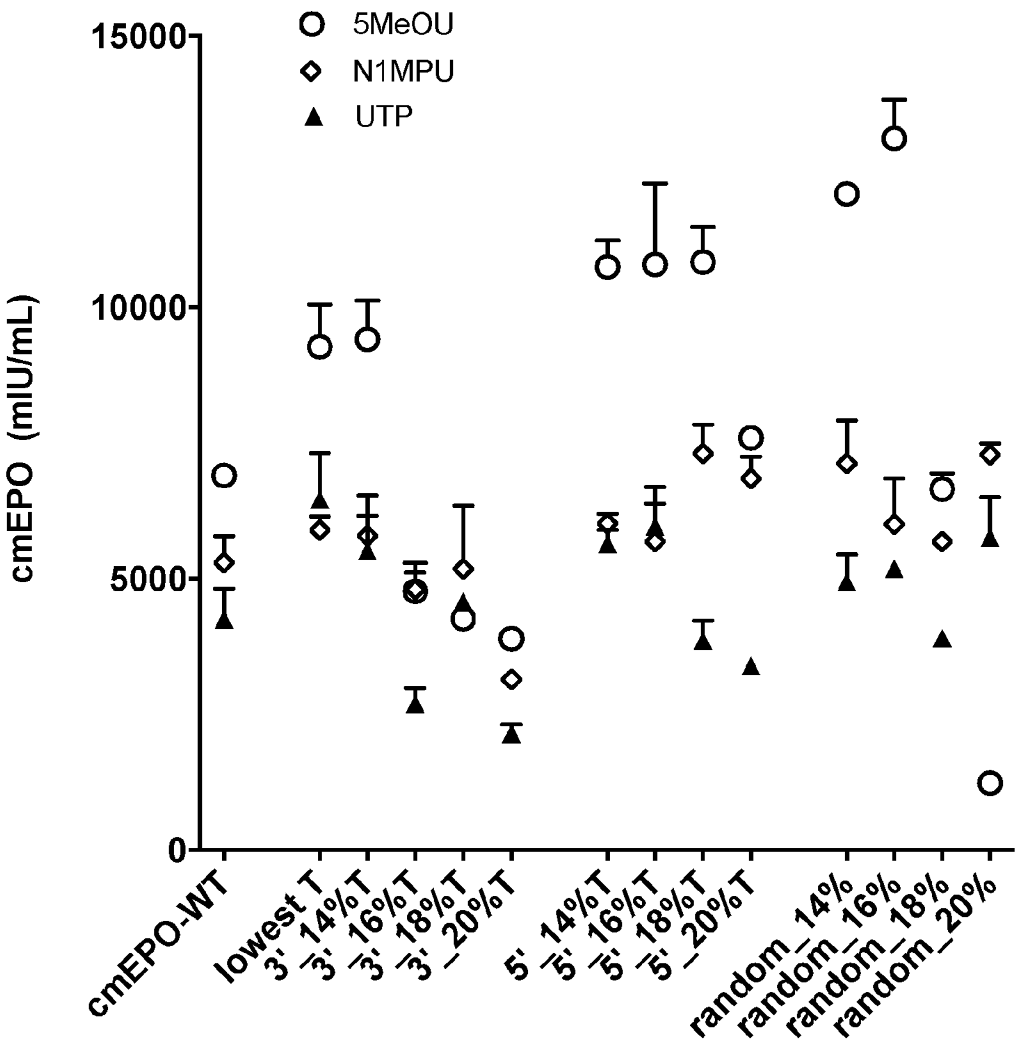
FIG. 10 shows the results of surprisingly increased cynomolgus monkey EPO protein production for a translatable molecule of this invention. Cynomolgus monkey cmEPO ARC-RNA was synthesized using a DNA template having reduced deoxyadenosine nucleotides in an open reading frame of the template strand, as well as reduced complementary deoxythymidine nucleotides in the non-template strand ("reduced T"). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 10 shows the results of surprisingly increased cynomolgus monkey EPO protein production for a translatable molecule of this invention. Cynomolgus monkey EPO ARC-RNA was synthesized using a DNA template having reduced deoxyadenosine nucleotides in an open reading frame of the template strand, as well as reduced complementary deoxythymidine nucleotides in the non-template strand ("reduced T"). The synthesis was also carried out with 5-methoxyuridines (5MeOU, 100%). The ARC-RNA was transfected into HEPA1-6 cells using MESSENGERMAX transfection reagents. The cell culture medium was collected 24 hrs after transfection. ELISA was used to detect the protein production with the ARC-RNA (5MeOU) as compared to wild type mRNA with similarly reduced T.

FIG. 10 shows surprisingly high translational efficiency of the ARC-mRNA (5MeOU) compared to the wild type cmEPO mRNA (UTP). First, FIG. 10 shows that ARC-mRNA (5MeOU) products exhibited surprisingly superior expression efficiency at levels of template T composition of 13-16%. Further, FIG. 10 shows that ARC-mRNA (5MeOU) products exhibited surprisingly superior expression efficiency at levels of template T composition of 13-16% as compared to cmEPO mRNA (N1MPU).

Further, FIG. 10 shows that the ARC-mRNA (5MeOU) exhibited unexpectedly superior expression efficiency at 14-16% template T composition, when codon replacement was done randomly.

In addition, FIG. 10 shows that the translational efficiency of the ARC-RNA (5MeOU) was also surprisingly higher as compared to WT cmEPO mRNA (N1MPU), a similar RNA made with $N^1$-methylpseudouridine (100%).

The compositions of the templates for cmEPO are shown in Table 10.

TABLE 10

| Non-Template Nucleotide T compositions for cmEPO | |
|---|---|
| hEPO | T % |
| mEPO__lowest__T | 13.5 |
| mEPO__3'__14% T | 14.0 |
| mEPO__3'__16% T | 15.9 |
| mEPO__3'__18% T | 18.0 |
| mEPO__3'__20% T | 19.9 |
| mEPO__5'__14% T | 14.0 |
| mEPO__5'__16% T | 15.9 |
| mEPO__5'__18% T | 18.0 |
| mEPO__5'__20% T | 19.9 |
| mEPO__random__14% | 14.0 |
| mEPO__random__16% | 15.9 |
| mEPO__random__18% | 18.0 |
| mEPO__random__20% | 19.9 |

Cynomolgus Monkey EPO ORF reference. Sense strand, non-template. NM_001284561.1:220-798 Macaca fascicularis erythropoietin (cmEPO).

(SEQ ID NO: 160)

```
atgggggtgcacgaatgtcctgcctggctgtggcttctcctgtctctgc

tgtcgctccctctgggcctcccagtcccgggcgccccaccacgcctcatctgtgacagc

cgagtcctggagaggtacctcttggaggccaaggaggccgagaatgtcacgatgggctg

ttccgaaagctgcagcttgaatgagaatatcaccgtcccagacaccaaagttaacttct

atgcctggaagaggatggaggtcgggcagcaggctgtagaagtctggcagggcctggcc

ctgctctcagaagctgtcctgcggggccaggccgtgttggccaactcttcccagcctt
```

-continued
cgagcccctgcagctgcacatggataaagccatcagtggccttcgcagcatcaccactc tgcttcgggcgctgggagcccaggaagccatctccctcccagatgcggcctcggctgct ccactccgaaccatcactgctgacactttctgcaaactcttccgagtctactccaattt cctccggggaaagctgaagctgtacacgggggaggcctgcaggagaggggacagatga cmEPO sense strand, non-template. 3'_lowest_T.
(SEQ ID NO: 161)
ATGGGGGTGCACGAATGCCCCGCCTGGCTGTGGCTGCTCCTGAGCCTGC

TGAGCCTCCCCCTGGGCCTCCCAGTCCCGGGCGCCCCACCACGCCTCATCTGCGACAGC

CGAGTCCTGGAGAGGTACCTCCTGGAGGCCAAGGAGGCCGAGAACGTCACGATGGGCTG

GAGCGAAAGCTGGAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTCAGCGAAGCCGTCCTGCGGGGCCAGGCCGTGCTGGCCAACAGCAGCCAGCCCTT

CGAGCCCCTGCAGCTGCACATGGACAAAGCCATCAGCGGCCTGCGCAGCATCACCACCC

TGCTGCGGGCGCTGGGAGCCCAGGAAGCCATCAGCCTCCCAGACGCGGCCAGCGCCGCC

CCACTCCGAACCATCACCGCCGACACCTTCTGCAAACTCTTCCGAGTCTACAGCAACTT

CCTCCGGGGAAAGCTGAAGCTGTACACGGGGGAGGCCTGCAGGAGAGGGGACAGATGA cmEPO sense strand, non-template. 3'_14%_T.
(SEQ ID NO: 162)
ATGGGGGTGCACGAATGTCCTGCCTGGCTGTGGCTTCTCCTGAGCCTGC

TGAGCCTCCCCCTGGGCCTCCCAGTCCCGGGCGCCCCACCACGCCTCATCTGCGACAGC

CGAGTCCTGGAGAGGTACCTCCTGGAGGCCAAGGAGGCCGAGAACGTCACGATGGGCTG

CAGCGAAAGCTGCAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTCAGCGAAGCCGTCCTGCGGGGCCAGGCCGTGCTGGCCAACAGCAGCCAGCCCTT

CGAGCCCCTGCAGCTGCACATGGACAAAGCCATCAGCGGCCTGCGCAGCATCACCACCC

TGCTGCGGGCGCTGGGAGCCCAGGAAGCCATCAGCCTCCCAGACGCGGCCAGCGCCGCC

CCACTCCGAACCATCACCGCCGACACCTTCTGCAAACTCTTCCGAGTCTACAGCAACTT

CCTCCGGGGAAAGCTGAAGCTGTACACGGGGGAGGCCTGCAGGAGAGGGGACAGATGA cmEPO sense strand, non-template. 3'_16%_T.
(SEQ ID NO: 163)
ATGGGGGTGCACGAATGTCCTGCCTGGCTGTGGCTTCTCCTGTCTCTGC

TGTCGCTCCCTCTGGGCCTCCCAGTCCCGGGCGCCCCACCACGCCTCATCTGTGACAGC

CGAGTCCTGGAGAGGTACCTCTTGGAGGCCAAGGAGGCCGAGAATGTCACGATGGGCTG

TTCCGAAAGCTGGAGCTTGAATGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTCAGCGAAGCCGTCCTGCGGGGCCAGGCCGTGCTGGCCAACAGCAGCCAGCCCTT

CGAGCCCCTGCAGCTGCACATGGACAAAGCCATCAGCGGCCTGCGCAGCATCACCACCC

TGCTGCGGGCGCTGGGAGCCCAGGAAGCCATCAGCCTCCCAGACGCGGCCAGCGCCGCC

CCACTCCGAACCATCACCGCCGACACCTTCTGCAAACTCTTCCGAGTCTACAGCAACTT

CCTCCGGGGAAAGCTGAAGCTGTACACGGGGGAGGCCTGCAGGAGAGGGGACAGATGA cmEPO sense strand, non-template. 3'_18%_T.
(SEQ ID NO: 164)
ATGGGGGTGCACGAATGTCCTGCCTGGCTGTGGCTTCTCCTGTCTCTGC

TGTCGCTCCCTCTGGGCCTCCCAGTCCCGGGCGCCCCACCACGCCTCATCTGTGACAGC

CGAGTCCTGGAGAGGTACCTCTTGGAGGCCAAGGAGGCCGAGAATGTCACGATGGGCTG

-continued

TTCCGAAAGCTGCAGCTTGAATGAGAATATCACCGTCCCAGACACCAAAGTTAACTTCT

ATGCCTGGAAGAGGATGGAGGTCGGGCAGCAGGCTGTAGAAGTCTGGCAGGGCCTGGCC

CTGCTCTCAGAAGCTGTCCTGCGGGGCCAGGCCGTGTTGGCCAACTCTTCCCAGCCTTT

CGAGCCCCTGCAGCTGCACATGGATAAAGCCATCAGCGGCCTGCGCAGCATCACCACCC

TGCTGCGGGCGCTGGGAGCCCAGGAAGCCATCAGCCTCCCAGACGCGGCCAGCGCCGCC

CCACTCCGAACCATCACCGCCGACACCTTCTGCAAACTCTTCCGAGTCTACAGCAACTT

CCTCCGGGGAAAGCTGAAGCTGTACACGGGGGAGGCCTGCAGGAGAGGGGACAGATGA cmEPO sense strand, non-template. 3'_20%_T.

(SEQ ID NO: 165)

ATGGGGGTGCACGAATGTCCTGCCTGGCTGTGGCTTCTCCTGTCTCTGC

TGTCGCTCCCTCTGGGCCTCCCAGTCCCGGGCGCCCCACCACGCCTCATCTGTGACAGC

CGAGTCCTGGAGAGGTACCTCTTGGAGGCCAAGGAGGCCGAGAATGTCACGATGGGCTG

TTCCGAAAGCTGCAGCTTGAATGAGAATATCACCGTCCCAGACACCAAAGTTAACTTCT

ATGCCTGGAAGAGGATGGAGGTCGGGCAGCAGGCTGTAGAAGTCTGGCAGGGCCTGGCC

CTGCTCTCAGAAGCTGTCCTGCGGGGCCAGGCCGTGTTGGCCAACTCTTCCCAGCCTTT

CGAGCCCCTGCAGCTGCACATGGATAAAGCCATCAGTGGCCTTCGCAGCATCACCACTC

TGCTTCGGGCGCTGGGAGCCCAGGAAGCCATCTCCCTCCCAGATGCGGCCTCGGCTGCT

CCACTCCGAACCATCACTGCTGACACCTTCTGCAAACTCTTCCGAGTCTACAGCAACTT

CCTCCGGGGAAAGCTGAAGCTGTACACGGGGGAGGCCTGCAGGAGAGGGGACAGATGA cmEPO sense strand, non-template. 5'_14%_T.

(SEQ ID NO: 166)

ATGGGGGTGCACGAATGCCCCGCCTGGCTGTGGCTGCTCCTGAGCCTGC

TGAGCCTCCCCCTGGGCCTCCCAGTCCCGGGCGCCCCACCACGCCTCATCTGCGACAGC

CGAGTCCTGGAGAGGTACCTCCTGGAGGCCAAGGAGGCCGAGAACGTCACGATGGGCTG

CAGCGAAAGCTGCAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTCAGCGAAGCCGTCCTGCGGGGCCAGGCCGTGCTGGCCAACAGCAGCCAGCCCTT

CGAGCCCCTGCAGCTGCACATGGACAAAGCCATCAGCGGCCTGCGCAGCATCACCACCC

TGCTGCGGGCGCTGGGAGCCCAGGAAGCCATCAGCCTCCCAGACGCGGCCAGCGCCGCC

CCACTCCGAACCATCACCGCCGACACTTTCTGCAAACTCTTCCGAGTCTACTCCAATTT

CCTCCGGGGAAAGCTGAAGCTGTACACGGGGGAGGCCTGCAGGAGAGGGGACAGATGA cmEPO sense strand, non-template. 5'_16%_T.

(SEQ ID NO: 167)

ATGGGGGTGCACGAATGCCCCGCCTGGCTGTGGCTGCTCCTGAGCCTGC

TGAGCCTCCCCCTGGGCCTCCCAGTCCCGGGCGCCCCACCACGCCTCATCTGCGACAGC

CGAGTCCTGGAGAGGTACCTCCTGGAGGCCAAGGAGGCCGAGAACGTCACGATGGGCTG

GAGCGAAAGCTGGAGCCTGAACGAGAACATCACCGTCCCAGACACCAAAGTGAACTTCT

ACGCCTGGAAGAGGATGGAGGTCGGGCAGCAGGCCGTAGAAGTCTGGCAGGGCCTGGCC

CTGCTCAGCGAAGCCGTCCTGCGGGGCCAGGCCGTGCTGGCCAACAGCAGCCAGCCCTT

CGAGCCCCTGCAGCTGCACATGGACAAAGCCATCAGTGGCCTTCGCAGCATCACCACTC

TGCTTCGGGCGCTGGGAGCCCAGGAAGCCATCTCCCTCCCAGATGCGGCCTCGGCTGCT

CCACTCCGAACCATCACTGCTGACACTTTCTGCAAACTCTTCCGAGTCTACTCCAATTT

CCTCCGGGGAAAGCTGAAGCTGTACACGGGGGAGGCCTGCAGGAGAGGGGACAGATGA

-continued cmEPO sense strand, non-template. 5'_18%_T.
(SEQ ID NO: 168)
ATGGGGGTGCACGAATGCCCCGCCTGGCTGTGGCTGCTCCTGAGCCTGC
TGAGCCTCCCCCTGGGCCTCCCAGTCCCGGGCGCCCCACCACGCCTCATCTGCGACAGC
CGAGTCCTGGAGAGGTACCTCCTGGAGGCCAAGGAGGCCGAGAACGTCACGATGGGCTG
CAGCGAAAGCTGCAGCCTGAACGAGAATATCACCGTCCCAGACACCAAAGTTAACTTCT
ATGCCTGGAAGAGGATGGAGGTCGGGCAGCAGGCTGTAGAAGTCTGGCAGGGCCTGGCC
CTGCTCTCAGAAGCTGTCCTGCGGGGCCAGGCCGTGTTGGCCAACTCTTCCCAGCCTTT
CGAGCCCCTGCAGCTGCACATGGATAAAGCCATCAGTGGCCTTCGCAGCATCACCACTC
TGCTTCGGGCGCTGGGAGCCCAGGAAGCCATCTCCCTCCCAGATGCGGCCTCGGCTGCT
CCACTCCGAACCATCACTGCTGACACTTTCTGCAAACTCTTCCGAGTCTACTCCAATTT
CCTCCGGGGAAAGCTGAAGCTGTACACGGGGGAGGCCTGCAGGAGAGGGGACAGATGA cmEPO sense strand, non-template. 5'_20%_T.
(SEQ ID NO: 169)
ATGGGGGTGCACGAATGCCCCGCCTGGCTGTGGCTGCTCCTGTCTCTGC
TGTCGCTCCCTCTGGGCCTCCCAGTCCCGGGCGCCCCACCACGCCTCATCTGTGACAGC
CGAGTCCTGGAGAGGTACCTCTTGGAGGCCAAGGAGGCCGAGAATGTCACGATGGGCTG
TTCCGAAAGCTGCAGCTTGAATGAGAATATCACCGTCCCAGACACCAAAGTTAACTTCT
ATGCCTGGAAGAGGATGGAGGTCGGGCAGCAGGCTGTAGAAGTCTGGCAGGGCCTGGCC
CTGCTCTCAGAAGCTGTCCTGCGGGGCCAGGCCGTGTTGGCCAACTCTTCCCAGCCTTT
CGAGCCCCTGCAGCTGCACATGGATAAAGCCATCAGTGGCCTTCGCAGCATCACCACTC
TGCTTCGGGCGCTGGGAGCCCAGGAAGCCATCTCCCTCCCAGATGCGGCCTCGGCTGCT
CCACTCCGAACCATCACTGCTGACACTTTCTGCAAACTCTTCCGAGTCTACTCCAATTT
CCTCCGGGGAAAGCTGAAGCTGTACACGGGGGAGGCCTGCAGGAGAGGGGACAGATGA cmEPO sense strand, non-template. random_14%_T.
(SEQ ID NO: 170)
ATGGGGGTGCACGAATGCCCCGCCTGGCTGTGGCTGCTCCTGAGCCTGC
TGAGCCTCCCTCTGGGCCTCCCAGTCCCGGGCGCCCCACCACGCCTCATCTGCGACAGC
CGAGTCCTGGAGAGGTACCTCCTGGAGGCCAAGGAGGCCGAGAACGTCACGATGGGCTG
CAGCGAAAGCTGCAGCCTGAACGAGAATATCACCGTCCCAGACACCAAAGTGAACTTCT
ACGCCTGGAAGAGGATGGAGGTCGGGCAGCAGGCCGTAGAAGTCTGGCAGGGCCTGGCC
CTGCTCAGCGAAGCCGTCCTGCGGGGCCAGGCCGTGCTGGCCAACAGCAGCCAGCCTTT
CGAGCCCCTGCAGCTGCACATGGACAAAGCCATCAGCGGCCTGCGCAGCATCACCACCC
TGCTGCGGGCGCTGGGAGCCCAGGAAGCCATCAGCCTCCCAGACGCGGCCAGCGCCGCC
CCACTCCGAACCATCACCGCCGACACCTTCTGCAAACTCTTCCGAGTCTACAGCAACTT
CCTCCGGGGAAAGCTGAAGCTGTACACGGGGGAGGCCTGCAGGAGAGGGGACAGATGA cmEPO sense strand, non-template. random_16%_T.
(SEQ ID NO: 171)
ATGGGGGTGCACGAATGCCCCGCCTGGCTGTGGCTTCTCCTGAGCCTGC
TGTCGCTCCCCCTGGGCCTCCCAGTCCCGGGCGCCCCACCACGCCTCATCTGCGACAGC
CGAGTCCTGGAGAGGTACCTCCTGGAGGCCAAGGAGGCCGAGAACGTCACGATGGGCTG
CTCCGAAAGCTGGAGCTTGAATGAGAACATCACCGTCCCAGACACCAAAGTGAACTTCT
ACGCCTGGAAGAGGATGGAGGTCGGGCAGCAGGCCGTAGAAGTCTGGCAGGGCCTGGCC
CTGCTCTCAGAAGCCGTCCTGCGGGGCCAGGCCGTGCTGGCCAACAGCAGCCAGCCTTT
CGAGCCCCTGCAGCTGCACATGGATAAAGCCATCAGCGGCCTTCGCAGCATCACCACTC -continued

TGCTGCGGGCGCTGGGAGCCCAGGAAGCCATCTCCCTCCCAGATGCGGCCAGCGCTGCC

CCACTCCGAACCATCACTGCCGACACCTTCTGCAAACTCTTCCGAGTCTACAGCAACTT

CCTCCGGGGAAAGCTGAAGCTGTACACGGGGGAGGCCTGCAGGAGAGGGGACAGATGA cmEPO sense strand, non-template. random_18%_T.
(SEQ ID NO: 172)
ATGGGGGTGCACGAATGCCCCGCCTGGCTGTGGCTTCTCCTGTCTCTGC

TGAGCCTCCCTCTGGGCCTCCCAGTCCCGGGCGCCCCACCACGCCTCATCTGTGACAGC

CGAGTCCTGGAGAGGTACCTCTTGGAGGCCAAGGAGGCCGAGAACGTCACGATGGGCTG

TTCCGAAAGCTGCAGCTTGAACGAGAATATCACCGTCCCAGACACCAAAGTGAACTTCT

ATGCCTGGAAGAGGATGGAGGTCGGGCAGCAGGCTGTAGAAGTCTGGCAGGGCCTGGCC

CTGCTCAGCGAAGCCGTCCTGCGGGGCCAGGCCGTGTTGGCCAACAGCTCCCAGCCCTT

CGAGCCCCTGCAGCTGCACATGGACAAAGCCATCAGTGGCCTGCGCAGCATCACCACTC

TGCTTCGGGCGCTGGGAGCCCAGGAAGCCATCTCCCTCCCAGATGCGGCCAGCGCTGCT

CCACTCCGAACCATCACTGCTGACACTTTCTGCAAACTCTTCCGAGTCTACTCCAATTT

CCTCCGGGGAAAGCTGAAGCTGTACACGGGGGAGGCCTGCAGGAGAGGGGACAGATGA cmEPO sense strand, non-template. random_20%_T.
(SEQ ID NO: 173)
ATGGGGGTGCACGAATGCCCTGCCTGGCTGTGGCTTCTCCTGTCTCTGC

TGTCGCTCCCTCTGGGCCTCCCAGTCCCGGGCGCCCCACCACGCCTCATCTGTGACAGC

CGAGTCCTGGAGAGGTACCTCTTGGAGGCCAAGGAGGCCGAGAATGTCACGATGGGCTG

TTCCGAAAGCTGCAGCCTGAATGAGAATATCACCGTCCCAGACACCAAAGTTAACTTCT

ATGCCTGGAAGAGGATGGAGGTCGGGCAGCAGGCTGTAGAAGTCTGGCAGGGCCTGGCC

CTGCTCTCAGAAGCTGTCCTGCGGGGCCAGGCCGTGTTGGCCAACTCTTCCCAGCCTTT

CGAGCCCCTGCAGCTGCACATGGATAAAGCCATCAGTGGCCTTCGCAGCATCACCACTC

TGCTGCGGGCGCTGGGAGCCCAGGAAGCCATCTCCCTCCCAGATGCGGCCTCGGCTGCT

CCACTCCGAACCATCACTGCTGACACTTTCTGCAAACTCTTCCGAGTCTACTCCAATTT

CCTCCGGGGAAAGCTGAAGCTGTACACGGGGGAGGCCTGCAGGAGAGGGGACAGATGA

SynK-cmEPO-XbG sense strand, non-template.
3'_lowest_T. (913 nt)
(SEQ ID NO: 174)
AGGAAACTTAAGAACTTAAAAAAAAAAATCAAAATGGCCGCCACCATGG

GGGTGCACGAATGCCCCGCCTGGCTGTGGCTGCTCCTGAGCCTGCTGAGCCTCCCCCTG

GGCCTCCCAGTCCCGGGCGCCCCACCACGCCTCATCTGCGACAGCCGAGTCCTGGAGAG

GTACCTCCTGGAGGCCAAGGAGGCCGAGAACGTCACGATGGGCTGCAGCGAAAGCTGCA

GCCTGAACGAGAACATCACCGTCCCAGACACCAAAGTGAACTTCTACGCCTGGAAGAGG

ATGGAGGTCGGGCAGCAGGCCGTAGAAGTCTGGCAGGGCCTGGCCCTGCTCAGCGAAGC

CGTCCTGCGGGGCCAGGCCGTGCTGGCCAACAGCAGCCAGCCCTTCGAGCCCCTGCAGC

TGCACATGGACAAAGCCATCAGCGGCCTGCGCAGCATCACCACCCTGCTGCGGGCGCTG

GGAGCCCAGGAAGCCATCAGCCTCCCAGACGCGGCCAGCGCCGCCCCACTCCGAACCAT

CACCGCCGACACCTTCTGCAAACTCTTCCGAGTCTACAGCAACTTCCTCCGGGGAAAGC

TGAAGCTGTACACGGGGGAGGCCTGCAGGAGAGGGGACAGATGACTCGAGCTAGTGACT

GACTAGGATCTGGTTACCACTAAACCAGCCTCAAGAACACCCGAATGGAGTCTCTAAGC

TACATAATACCAACTTACACTTACAAAATGTTGTCCCCCAAAATGTAGCCATTCGTATC

TGCTCCTAATAAAAAGAAAGTTTCTTCACATTCTAGAAAAAAAAAAAAAAAAAAAAAAA

-continued

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAA

SynK-cmEPO-XbG sense strand, non-template.
3'_14%_T. (913 nt)
(SEQ ID NO: 175)
AGGAAACTTAAGAACTTAAAAAAAAAAATCAAAATGGCCGCCACCATGG

GGGTGCACGAATGTCCTGCCTGGCTGTGGCTTCTCCTGAGCCTGCTGAGCCTCCCCCTG

GGCCTCCCAGTCCCGGGCGCCCCACCACGCCTCATCTGCGACAGCCGAGTCCTGGAGAG

GTACCTCCTGGAGGCCAAGGAGGCCGAGAACGTCACGATGGGCTGCAGCGAAAGCTGCA

GCCTGAACGAGAACATCACCGTCCCAGACACCAAAGTGAACTTCTACGCCTGGAAGAGG

ATGGAGGTCGGGCAGCAGGCCGTAGAAGTCTGGCAGGGCCTGGCCCTGCTCAGCGAAGC

CGTCCTGCGGGGCCAGGCCGTGCTGGCCAACAGCAGCCAGCCCTTCGAGCCCCTGCAGC

TGCACATGGACAAAGCCATCAGCGGCCTGCGCAGCATCACCACCCTGCTGCGGGCGCTG

GGAGCCCAGGAAGCCATCAGCCTCCCAGACGCGGCCAGCGCCGCCCCACTCCGAACCAT

CACCGCCGACACCTTCTGCAAACTCTTCCGAGTCTACAGCAACTTCCTCCGGGGAAAGC

TGAAGCTGTACACGGGGGAGGCCTGCAGGAGAGGGGACAGATGACTCGAGCTAGTGACT

GACTAGGATCTGGTTACCACTAAACCAGCCTCAAGAACACCCGAATGGAGTCTCTAAGC

TAGATAATACCAACTTACACTTACAAAATGTTGTCCCCCAAAATGTAGCCATTCGTATC

TGCTCCTAATAAAAAGAAAGTTTCTTCACATTCTAGAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAA

SynK-cmEPO-XbG sense strand, non-template.
5'_14%_T. (913 nt)
(SEQ ID NO: 176)
AGGAAACTTAAGAACTTAAAAAAAAAAATCAAAATGGCCGCCACCATGG

GGGTGCACGAATGCCCCGCCTGGCTGTGGCTGCTCCTGAGCCTGCTGAGCCTCCCCCTG

GGCCTCCCAGTCCCGGGCGCCCCACCACGCCTCATCTGCGACAGCCGAGTCCTGGAGAG

GTACCTCCTGGAGGCCAAGGAGGCCGAGAACGTCACGATGGGCTGCAGCGAAAGCTGCA

GCCTGAACGAGAACATCACCGTCCCAGACACCAAAGTGAACTTCTACGCCTGGAAGAGG

ATGGAGGTCGGGCAGCAGGCCGTAGAAGTCTGGCAGGGCCTGGCCCTGCTCAGCGAAGC

CGTCCTGCGGGGCCAGGCCGTGCTGGCCAACAGCAGCCAGCCCTTCGAGCCCCTGCAGC

TGCACATGGACAAAGCCATCAGCGGCCTGCGCAGCATCACCACCCTGCTGCGGGCGCTG

GGAGCCCAGGAAGCCATCAGCCTCCCAGACGCGGCCAGCGCCGCCCCACTCCGAACCAT

CACCGCCGACACTTTCTGCAAACTCTTCCGAGTCTACTCCAATTTCCTCCGGGGAAAGC

TGAAGCTGTACACGGGGGAGGCCTGCAGGAGAGGGGACAGATGACTCGAGCTAGTGACT

GACTAGGATCTGGTTACCACTAAACCAGCCTCAAGAACACCCGAATGGAGTCTCTAAGC

TACATAATACCAACTTACACTTACAAAATGTTGTCCCCCAAAATGTAGCCATTCGTATC

TGCTCCTAATAAAAAGAAAGTTTCTTCACATTCTAGAAAAAAAAAAAAAAAAAAAAAAA

AAAAAAAAAAAAAAAAAAAAAAAAAAAAAAAAAAAAAAA

SynK-cmEPO-XbG sense strand, non-template.
random_14%_T. (913 nt)
(SEQ ID NO: 177)
AGGAAACTTAAGAACTTAAAAAAAAAAATCAAAATGGCCGCCACCATGG

GGGTGCACGAATGCCCCGCCTGGCTGTGGCTGCTCCTGAGCCTGCTGAGCCTCCCTCTG

GGCCTCCCAGTCCCGGGCGCCCCACCACGCCTCATCTGCGACAGCCGAGTCCTGGAGAG

-continued

GTACCTCCTGGAGGCCAAGGAGGCCGAGAACGTCACGATGGGCTGCAGCGAAAGCTGCA

GCCTGAACGAGAATATCACCGTCCCAGACACCAAAGTGAACTTCTACGCCTGGAAGAGG

ATGGAGGTCGGGCAGCAGGCCGTAGAAGTCTGGCAGGGCCTGGCCCTGCTCAGCGAAGC

CGTCCTGCGGGGCCAGGCCGTGCTGGCCAACAGCAGCCAGCCTTTCGAGCCCCTGCAGC

TGCACATGGACAAAGCCATCAGCGGCCTGCGCAGCATCACCACCCTGCTGCGGGCGCTG

GGAGCCCAGGAAGCCATCAGCCTCCCAGACGCGGCCAGCGCCGCCCCACTCCGAACCAT

CACCGCCGACACCTTCTGCAAACTCTTCCGAGTCTACAGCAACTTCCTCCGGGGAAAGC

TGAAGCTGTACACGGGGGAGGCCTGCAGGAGAGGGGACAGATGACTCGAGCTAGTGACT

GACTAGGATCTGGTTACCACTAAACCAGCCTCAAGAACACCCGAATGGAGTCTCTAAGC

TACATAATACCAACTTAGACTTACAAAATGTTGTCCCCCAAAATGTAGCCATTCGTATC

TGCTCCTAATAAAAAGAAAGTTTCTTCACATTCTAGAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAA

SynK-cmEPO-XbG ARC-mRNA. 3'_lowest_T. (913 nt)
(SEQ ID NO: 178)
5'-cap-

AGGAAACUUAAGAACUUAAAAAAAAAAAUCAAAAUGGCCGCCACCAUGGGGGUGCACGA

AUGCCCCGCCUGGCUGUGGCUGCUCCUGAGCCUGCUGAGCCUCCCCCUGGGCCUCCCAG

UCCCGGGCGCCCCACCACGCCUCAUCUGCGACAGCCGAGUCCUGGAGAGGUACCUCCUG

GAGGCCAAGGAGGCCGAGAACGUCACGAUGGGCUGCAGCGAAAGCUGCAGCCUGAACGA

GAACAUCACCGUCCCAGACACCAAAGUGAACUUCUACGCCUGGAAGAGGAUGGAGGUCG

GGCAGCAGGCCGUAGAAGUCUGGCAGGGCCUGGCCCUGCUCAGCGAAGCCGUCCUGCGG

GGCCAGGCCGUGCUGGCCAACAGCAGCCAGCCCUUCGAGCCCCUGCAGCUGCACAUGGA

CAAAGCCAUCAGCGGCCUGCGCAGCAUCACCACCCUGCUGCGGGCGCUGGGAGCCCAGG

AAGCCAUCAGCCUCCCAGACGCGGCCAGCGCCGCCCCACUCCGAACCAUCACCGCCGAC

ACCUUCUGCAAACUCUUCCGAGUCUACAGCAACUUCCUCCGGGGAAAGCUGAAGCUGUA

CACGGGGGAGGCCUGCAGGAGAGGGGACAGAUGACUCGAGCUAGUGACUGACUAGGAUC

UGGUUACCACUAAACCAGCCUCAAGAACACCCGAAUGGAGUCUCUAAGCUACAUAAUAC

CAACUUACACUUACAAAAUGUUGUCCCCCAAAAUGUAGCCAUUCGUAUCUGCUCCUAAU

AAAAAGAAAGUUUCUUCACAUUCUAGAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAA

SynK-cmEPO-XbG ARC-mRNA. 3'_14%_T. (913 nt)
(SEQ ID NO: 179)
5'-cap-

AGGAAACUUAAGAACUUAAAAAAAAAAAUCAAAAUGGCCGCCACCAUGGGGGUGCACGA

AUGUCCUGCCUGGCUGUGGCUUCUCCUGAGCCUGCUGAGCCUCCCCCUGGGCCUCCCAG

UCCCGGGCGCCCCACCACGCCUCAUCUGCGACAGCCGAGUCCUGGAGAGGUACCUCCUG

GAGGCCAAGGAGGCCGAGAACGUCACGAUGGGCUGCAGCGAAAGCUGCAGCCUGAACGA

GAACAUCACCGUCCCAGACACCAAAGUGAACUUCUACGCCUGGAAGAGGAUGGAGGUCG

GGCAGCAGGCCGUAGAAGUCUGGCAGGGCCUGGCCCUGCUCAGCGAAGCCGUCCUGCGG

GGCCAGGCCGUGCUGGCCAACAGCAGCCAGCCCUUCGAGCCCCUGCAGCUGCACAUGGA

-continued

CAAAGCCAUCAGCGGCCUGCGCAGCAUCACCACCCUGCUGCGGGCGCUGGGAGCCCAGG

AAGCCAUCAGCCUCCCAGACGCGGCCAGCGCCGCCCCACUCCGAACCAUCACCGCCGAC

ACCUUCUGCAAACUCUUCCGAGUCUACAGCAACUUCCUCCGGGGAAAGCUGAAGCUGUA

CACGGGGGAGGCCUGCAGGAGAGGGGACAGAUGACUCGAGCUAGUGACUGACUAGGAUC

UGGUUACCACUAAACCAGCCUCAAGAACACCCGAAUGGAGUCUCUAAGCUACAUAAUAC

CAACUUACACUUACAAAAUGUUGUCCCCCAAAAUGUAGCCAUUCGUAUCUGCUCCUAAU

AAAAAGAAAGUUUCUUCACAUUCUAGAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAA

SynK-cmEPO-XbG ARC-mRNA. 5'_14%_T. (913 nt)
(SEQ ID NO: 180)

5'-cap-

AGGAAACUUAAGAACUUAAAAAAAAAAAUCAAAAUGGCCGCCACCAUGGGGGUGCACGA

AUGCCCCGCCUGGCUGUGGCUGCUCCUGAGCCUGCUGAGCCUCCCCCUGGGCCUCCCAG

UCCCGGGCGCCCCACCACGCCUCAUCUGCGACAGCCGAGUCCUGGAGAGGUACCUCCUG

GAGGCCAAGGAGGCCGAGAACGUCACGAUGGGCUGCAGCGAAAGCUGCAGCCUGAACGA

GAACAUCACCGUCCCAGACACCAAAGUGAACUUCUACGCCUGGAAGAGGAUGGAGGUCG

GGCAGCAGGCCGUAGAAGUCUGGCAGGGCCUGGCCCUGCUCAGCGAAGCCGUCCUGCGG

GGCCAGGCCGUGCUGGCCAACAGCAGCCAGCCCUUCGAGCCCCUGCAGCUGCACAUGGA

CAAAGCCAUCAGCGGCCUGCGCAGCAUCACCACCCUGCUGCGGGCGCUGGGAGCCCAGG

AAGCCAUCAGCCUCCCAGACGCGGCCAGCGCCGCCCCACUCCGAACCAUCACCGCCGAC

ACUUUCUGCAAACUCUUCCGAGUCUACUCCAAUUUCCUCCGGGGAAAGCUGAAGCUGUA

CACGGGGGAGGCCUGCAGGAGAGGGGACAGAUGACUCGAGCUAGUGACUGACUAGGAUC

UGGUUACCACUAAACCAGCCUCAAGAACACCCGAAUGGAGUCUCUAAGCUACAUAAUAC

CAACUUACACUUACAAAAUGUUGUCCCCCAAAAUGUAGCCAUUCGUAUCUGCUCCUAAU

AAAAAGAAAGUUUCUUCACAUUCUAGAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAAAAAAAAAAAAAAAAAAAAAA

SynK-cmEPO-XbG ARC-mRNA. random_14%_T. (913 nt)
(SEQ ID NO: 181)

5'-cap-

AGGAAACUUAAGAACUUAAAAAAAAAAAUCAAAAUGGCCGCCACCAUGGGGGUGCACGA

AUGCCCCGCCUGGCUGUGGCUGCUCCUGAGCCUGCUGAGCCUCCCUCUGGGCCUCCCAG

UCCCGGGCGCCCCACCACGCCUCAUCUGCGACAGCCGAGUCCUGGAGAGGUACCUCCUG

GAGGCCAAGGAGGCCGAGAACGUCACGAUGGGCUGCAGCGAAAGCUGCAGCCUGAACGA

GAAUAUCACCGUCCCAGACACCAAAGUGAACUUCUACGCCUGGAAGAGGAUGGAGGUCG

GGCAGCAGGCCGUAGAAGUCUGGCAGGGCCUGGCCCUGCUCAGCGAAGCCGUCCUGCGG

GGCCAGGCCGUGCUGGCCAACAGCAGCCAGCCUUUCGAGCCCCUGCAGCUGCACAUGGA

CAAAGCCAUCAGCGGCCUGCGCAGCAUCACCACCCUGCUGCGGGCGCUGGGAGCCCAGG

AAGCCAUCAGCCUCCCAGACGCGGCCAGCGCCGCCCCACUCCGAACCAUCACCGCCGAC

ACCUUCUGCAAACUCUUCCGAGUCUACAGCAACUUCCUCCGGGGAAAGCUGAAGCUGUA

CACGGGGGAGGCCUGCAGGAGAGGGGACAGAUGACUCGAGCUAGUGACUGACUAGGAUC

UGGUUACCACUAAACCAGCCUCAAGAACACCCGAAUGGAGUCUCUAAGCUACAUAAUAC

CAACUUACACUUACAAAAUGUUGUCCCCCAAAAUGUAGCCAUUCGUAUCUGCUCCUAAU

AAAAAGAAAGUUUCUUCACAUUCUAGAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAA

TEV-cmEPO-XbG sense strand, non-template.
3'_lowest_T. (1011 nt)

(SEQ ID NO: 182)

AGGAAACTTAAGTCAACACAACATATACAAAACAAACGAATCTCAAGGA

ATCAAGCATTCTAGTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCCCTGGGCCTCCCAGTCCCGGGCGC

CCCACCACGCCTCATCTGCGACAGCCGAGTCCTGGAGAGGTACCTCCTGGAGGCCAAGG

AGGCCGAGAACGTCACGATGGGCTGCAGCGAAAGCTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTCAGCGAAGCCGTCCTGCGGGGCCAGGCCG

TGCTGGCCAACAGCAGCCAGCCCTTCGAGCCCCTGCAGCTGCACATGGACAAAGCCATC

AGCGGCCTGCGCAGCATCACCACCCTGCTGCGGGCGCTGGGAGCCCAGGAAGCCATCAG

CCTCCCAGACGCGGCCAGCGCCGCCCCACTCCGAACCATCACCGCCGACACCTTCTGCA

AACTCTTCCGAGTCTACAGCAACTTCCTCCGGGGAAAGCTGAAGCTGTACACGGGGGAG

GCCTGCAGGAGAGGGGACAGATGACTCGAGCTAGTGACTGACTAGGATCTGGTTACCAC

TAAACGAGCCTCAAGAACACCCGAATGGAGTCTCTAAGCTACATAATACCAACTTACAC

TTACAAAATGTTGTCCCCCAAAATGTAGCCATTCGTATCTGCTCCTAATAAAAAGAAAG

TTTCTTCACATTCTAGAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAA

TEV-cmEPO-XbG sense strand, non-template.
3'_14%_T. (1011 nt)

(SEQ ID NO: 183)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGTCCTGCC

TGGCTGTGGCTTCTCCTGAGCCTGCTGAGCCTCCCCCTGGGCCTCCCAGTCCCGGGCGC

CCCACCACGCCTCATCTGCGACAGCCGAGTCCTGGAGAGGTACCTCCTGGAGGCCAAGG

AGGCCGAGAACGTCACGATGGGCTGCAGCGAAAGCTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTCAGCGAAGCCGTCCTGCGGGGCCAGGCCG

TGCTGGCCAACAGCAGCCAGCCCTTCGAGCCCCTGCAGCTGCACATGGACAAAGCCATC

AGCGGCCTGCGCAGCATCACCACCCTGCTGCGGGCGCTGGGAGCCCAGGAAGCCATCAG

CCTCCCAGACGCGGCCAGCGCCGCCCCACTCCGAACCATCACCGCCGACACCTTCTGCA

AACTCTTCCGAGTCTACAGCAACTTCCTCCGGGGAAAGCTGAAGCTGTACACGGGGGAG

GCCTGCAGGAGAGGGGACAGATGACTCGAGCTAGTGACTGACTAGGATCTGGTTACCAC

TAAACCAGCCTCAAGAACACCCGAATGGAGTCTCTAAGCTACATAATACCAACTTACAC

TTACAAAATGTTGTCCCCCAAAATGTAGCCATTCGTATCTGCTCCTAATAAAAAGAAAG

-continued

TTTCTTCACATTCTAGAAAAAAAAAAAAAAAAAAAAAAAAAAAAAAAAAAAAAAAAAAAA

AAAAAAAAAAAAAAAAAA

TEV-cmEPO-XbG sense strand, non-template.
5'_14%_T. (1011 nt)

(SEQ ID NO: 184)

AGGAAACTTAAGTCAACACAACATATACAAAACAAACGAATCTCAAGGA

ATCAAGCATTCTAGTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCCCTGGGCCTCCCAGTCCCGGGCGC

CCCACCACGCCTCATCTGCGACAGCCGAGTCCTGGAGAGGTACCTCCTGGAGGCCAAGG

AGGCCGAGAACGTCACGATGGGCTGCAGCGAAAGCTGCAGCCTGAACGAGAACATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTCAGCGAAGCCGTCCTGCGGGGCCAGGCCG

TGCTGGCCAACAGCAGCCAGCCCTTCGAGCCCCTGCAGCTGCACATGGACAAAGCCATC

AGCGGCCTGCGCAGCATCACCACCCTGCTGCGGGCGCTGGGAGCCCAGGAAGCCATCAG

CCTCCCAGACGCGGCCAGCGCCGCCCCACTCCGAACCATCACCGCCGACACTTTCTGCA

AACTCTTCCGAGTCTACTCCAATTTCCTCCGGGGAAAGCTGAAGCTGTACACGGGGGAG

GCCTGCAGGAGAGGGGACAGATGACTCGAGCTAGTGACTGACTAGGATCTGGTTACCAC

TAAACGAGCCTCAAGAACACCCGAATGGAGTCTCTAAGCTACATAATACCAACTTACAC

TTACAAAATGTTGTCCCCCAAAATGTAGCCATTCGTATCTGCTCCTAATAAAAAGAAAG

TTTCTTCACATTCTAGAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAA

TEV-cmEPO-XbG sense strand, non-template.
random_14%_T. (1011 nt)

(SEQ ID NO: 185)

AGGAAACTTAAGTCAACACAACATATACAAAACAAACGAATCTCAAGCA

ATCAAGCATTCTACTTCTATTGCAGCAATTTAAATCATTTCTTTTAAAGCAAAAGCAAT

TTTCTGAAAATTTTCACCATTTACGAACGATAGCCATGGGGGTGCACGAATGCCCCGCC

TGGCTGTGGCTGCTCCTGAGCCTGCTGAGCCTCCCTCTGGGCCTCCCAGTCCCGGGCGC

CCCACCACGCCTCATCTGCGACAGCCGAGTCCTGGAGAGGTACCTCCTGGAGGCCAAGG

AGGCCGAGAACGTCACGATGGGCTGCAGCGAAAGCTGCAGCCTGAACGAGAATATCACC

GTCCCAGACACCAAAGTGAACTTCTACGCCTGGAAGAGGATGGAGGTCGGGCAGCAGGC

CGTAGAAGTCTGGCAGGGCCTGGCCCTGCTCAGCGAAGCCGTCCTGCGGGGCCAGGCCG

TGCTGGCCAACAGCAGCCAGCCTTTCGAGCCCCTGCAGCTGCACATGGACAAAGCCATC

AGCGGCCTGCGCAGCATCACCACCCTGCTGCGGGCGCTGGGAGCCCAGGAAGCCATCAG

CCTCCCAGACGCGGCCAGCGCCGCCCCACTCCGAACCATCACCGCCGACACCTTCTGCA

AACTCTTCCGAGTCTACAGCAACTTCCTCCGGGGAAAGCTGAAGCTGTACACGGGGGAG

GCCTGCAGGAGAGGGGACAGATGACTCGAGCTAGTGACTGACTAGGATCTGGTTACCAC

TAAACCAGCCTCAAGAACACCCGAATGGAGTCTCTAAGCTACATAATACCAACTTACAC

TTACAAAATGTTGTCCCCCAAAATGTAGCCATTCGTATCTGCTCCTAATAAAAAGAAAG

TTTCTTCACATTCTAGAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAA

-continued

TEV-cmEPO-XbG ARC-mRNA. 3'_lowest_T. (1011 nt)
(SEQ ID NO: 186)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCCCUGGGCCUCCCAGUCCCGGGCGCCCCACCACGC

CUCAUCUGCGACAGCCGAGUCCUGGAGAGGUACCUCCUGGAGGCCAAGGAGGCCGAGAA

CGUCACGAUGGGCUGCAGCGAAAGCUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUCAGCGAAGCCGUCCUGCGGGGCCAGGCCGUGCUGGCCAA

CAGCAGCCAGCCCUUCGAGCCCCUGCAGCUGCACAUGGACAAAGCCAUCAGCGGCCUGC

GCAGCAUCACCACCCUGCUGCGGGCGCUGGGAGCCCAGGAAGCCAUCAGCCUCCCAGAC

GCGGCCAGCGCCGCCCCACUCCGAACCAUCACCGCCGACACCUUCUGCAAACUCUUCCG

AGUCUACAGCAACUUCCUCCGGGGAAAGCUGAAGCUGUACACGGGGGAGGCCUGCAGGA

GAGGGGACAGAUGACUCGAGCUAGUGACUGACUAGGAUCUGGUUACCACUAAACCAGCC

UCAAGAACACCCGAAUGGAGUCUCUAAGCUACAUAAUACCAACUUACACUUACAAAAUG

UUGUCGCCCAAAAUGUAGCCAUUCGUAUCUGCUCCUAAUAAAAAGAAAGUUUCUUCACA

UUCUAGAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAA

TEV-cmEPO-XbG ARC-mRNA. 3'_14%_T. (1011 nt)
(SEQ ID NO: 187)
5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGUCCUGCCUGGCUGUGGC

UUCUCCUGAGCCUGCUGAGCCUCCCCCUGGGCCUCCCAGUCCCGGGCGCCCCACCACGC

CUCAUCUGCGACAGCCGAGUCCUGGAGAGGUACCUCCUGGAGGCCAAGGAGGCCGAGAA

CGUCACGAUGGGCUGCAGCGAAAGCUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUCAGCGAAGCCGUCCUGCGGGGCCAGGCCGUGCUGGCCAA

CAGCAGCCAGCCCUUCGAGCCCCUGCAGCUGCACAUGGACAAAGCCAUCAGCGGCCUGC

GCAGCAUCACCACCCUGCUGCGGGCGCUGGGAGCCCAGGAAGCCAUCAGCCUCCCAGAC

GCGGCCAGCGCCGCCCCACUCCGAACCAUCACCGCCGACACCUUCUGCAAACUCUUCCG

AGUCUACAGCAACUUCCUCCGGGGAAAGCUGAAGCUGUACACGGGGGAGGCCUGCAGGA

GAGGGGACAGAUGACUCGAGCUAGUGACUGACUAGGAUCUGGUUACCACUAAACCAGCC

UCAAGAACACCCGAAUGGAGUCUCUAAGCUACAUAAUACCAACUUACACUUACAAAAUG

UUGUCCCCCAAAAUGUAGCCAUUCGUAUCUGCUCCUAAUAAAAAGAAAGUUUCUUCACA

UUCUAGAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAA

-continued

TEV-cmEPO-XbG ARC-mRNA. 5'_14%_T. (1011 nt)
(SEQ ID NO: 188)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCCCUGGGCCUCCCAGUCCCGGGCGCCCCACCACGC

CUCAUCUGCGACAGCCGAGUCCUGGAGAGGUACCUCCUGGAGGCCAAGGAGGCCGAGAA

CGUCACGAUGGGCUGCAGCGAAAGCUGCAGCCUGAACGAGAACAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUCAGCGAAGCCGUCCUGCGGGGCCAGGCCGUGCUGGCCAA

CAGCAGCCAGCCCUUCGAGCCCCUGCAGCUGCACAUGGACAAAGCCAUCAGCGGCCUGC

GCAGCAUCACCACCCUGCUGCGGGCGCUGGGAGCCCAGGAAGCCAUCAGCCUCCCAGAC

GCGGCCAGCGCCGCCCCACUCCGAACCAUCACCGCCGACACUUUCUGCAAACUCUUCCG

AGUCUACUCCAAUUUCCUCCGGGGAAAGCUGAAGCUGUACACGGGGGAGGCCUGCAGGA

GAGGGGACAGAUGACUCGAGCUAGUGACUGACUAGGAUCUGGUUACCACUAAACCAGCC

UCAAGAACACCCGAAUGGAGUCUCUAAGCUACAUAAUACCAACUUACACUUACAAAAUG

UUGUCGCCCAAAAUGUAGCCAUUCGUAUCUGCUCCUAAUAAAAAGAAAGUUUCUUCACA

UUCUAGAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAA

TEV-cmEPO-XbG ARC-mRNA. random_14%_T. (1011 nt)
(SEQ ID NO: 189)

5'-cap-

AGGAAACUUAAGUCAACACAACAUAUACAAAACAAACGAAUCUCAAGCAAUCAAGCAUU

CUACUUCUAUUGCAGCAAUUUAAAUCAUUUCUUUUAAAGCAAAAGCAAUUUUCUGAAAA

UUUUCACCAUUUACGAACGAUAGCCAUGGGGGUGCACGAAUGCCCCGCCUGGCUGUGGC

UGCUCCUGAGCCUGCUGAGCCUCCCUCUGGGCCUCCCAGUCCCGGGCGCCCCACCACGC

CUCAUCUGCGACAGCCGAGUCCUGGAGAGGUACCUCCUGGAGGCCAAGGAGGCCGAGAA

CGUCACGAUGGGCUGCAGCGAAAGCUGCAGCCUGAACGAGAAUAUCACCGUCCCAGACA

CCAAAGUGAACUUCUACGCCUGGAAGAGGAUGGAGGUCGGGCAGCAGGCCGUAGAAGUC

UGGCAGGGCCUGGCCCUGCUCAGCGAAGCCGUCCUGCGGGGCCAGGCCGUGCUGGCCAA

CAGCAGCCAGCCUUUCGAGCCCCUGCAGCUGCACAUGGACAAAGCCAUCAGCGGCCUGC

GCAGCAUCACCACCCUGCUGCGGGCGCUGGGAGCCCAGGAAGCCAUCAGCCUCCCAGAC

GCGGCCAGCGCCGCCCCACUCCGAACCAUCACCGCCGACACCUUCUGCAAACUCUUCCG

AGUCUACAGCAACUUCCUCCGGGGAAAGCUGAAGCUGUACACGGGGGAGGCCUGCAGGA

GAGGGGACAGAUGACUCGAGCUAGUGACUGACUAGGAUCUGGUUACCACUAAACCAGCC

UCAAGAACACCCGAAUGGAGUCUCUAAGCUACAUAAUACCAACUUACACUUACAAAAUG

UUGUCCCCCAAAAUGUAGCCAUUCGUAUCUGCUCCUAAUAAAAAGAAAGUUUCUUCACA

UUCUAGAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAA

AAAAAAAA

Example G: Templates and mRNAs for Fluc. Photinus Luciferase (Fluc+, Promega; Fluc)

The compositions of the templates for Fluc are shown in Table 11.

TABLE 11

| Non-Template Nucleotide T compositions for Fluc | |
|---|---|
| hEPO | T % |
| Fluc_lowest_T | 14.3 |
| Fluc_3'_16% T | 16.0 |
| Fluc_3'_18% T | 18.0 |
| Fluc_3'_20% T | 20.0 |

TABLE 11-continued

| Non-Template Nucleotide T compositions for Fluc | |
|---|---|
| hEPO | T % |
| Fluc_5'_16% T | 15.9 |
| Fluc_5'_18% T | 18.0 |
| Fluc_5'_20% T | 20.0 |
| Fluc_random_16% | 16.0 |
| Fluc_random_18% | 18.0 |
| Fluc_random_20% | 20.0 |

Fluc ORF reference. Sense strand, non-template. Fluc_plus_pGL3_Promega (U47295.2:88-1740 Cloning vector pGL3-Basic).

(SEQ ID NO: 190)

```
atggaagacgccaaaaacataaagaaaggcccggcgccattctatccgc

tggaagatggaaccgctggagagcaactgcataaggctatgaagagatacgccctggtt

cctggaacaattgcttttacagatgcacatatcgaggtggacatcacttacgctgagta

cttcgaaatgtccgttcggttggcagaagctatgaaacgatatgggctgaatacaaatc

acagaatcgtcgtatgcagtgaaaactctcttcaattctttatgccggtgttgggcgcg

ttatttatcggagttgcagttgcgcccgcgaacgacatttataatgaacgtgaattgct

caacagtatgggcatttcgcagcctaccgtggtgttcgtttccaaaaaggggttgcaaa

aaattttgaacgtgcaaaaaaagctcccaatcatccaaaaaattattatcatggattct

aaaacggattaccagggatttcagtcgatgtacacgttcgtcacatctcatctacctcc

cggttttaatgaatacgattttgtgccagagtccttcgatagggacaagacaattgcac

tgatcatgaactcctctggatctactggtctgcctaaaggtgtcgctctgcctcataga

actgcctgcgtgagattctcgcatgccagagatcctatttttggcaatcaaatcattcc

ggatactgcgattttaagtgttgttccattccatcacggttttggaatgtttactacac

tcggatatttgatatgtggatttcgagtcgtcttaatgtatagatttgaagaagagctg

tttctgaggagccttcaggattacaagattcaaagtgcgctgctggtgccaaccctatt

ctccttcttcgccaaaagcactctgattgacaaatacgatttatctaatttacacgaaa

ttgcttctggtggcgctcccctctctaaggaagtcggggaagcggttgccaagaggttc

catctgccaggtatcaggcaaggatatgggctcactgagactacatcagctattctgat

tacacccgagggggatgataaaccgggcgcggtcggtaaagttgttccattttttgaag

cgaaggttgtggatctggataccgggaaaacgctgggcgttaatcaaagaggcgaactg

tgtgtgagaggtcctatgattatgtccggttatgtaaacaatccggaagcgaccaacgc

cttgattgacaaggatggatggctacattctggagacatagcttactgggacgaagacg

aacacttcttcatcgttgaccgcctgaagtctctgattaagtacaaaggctatcaggtg

gctcccgctgaattggaatccatcttgctccaacaccccaacatcttcgacgcaggtgt

cgcaggtcttcccgacgatgacgccggtgaacttcccgccgccgttgttgttttggagc

acggaaagacgatgacggaaaaagagatcgtggattacgtcgccagtcaagtaacaacc

gcgaaaaagttgcgcggaggagttgtgtttgtggacgaagtaccgaaaggtcttaccgg

aaaactcgacgcaagaaaaatcagagagatcctcataaaggccaagaagggcggaaaga

tcgccgtgtaa
```

-continued

Fluc sense strand, non-template. lowest _T.

(SEQ ID NO: 191)

ATGGAAGACGCCAAAAACATAAAGAAAGGCCCGGCGCCATTCTACCCGC

TGGAAGACGGAACCGCCGGAGAGCAACTGCACAAGGCCATGAAGAGATACGCCCTGGTG

CCCGGAACAATCGCCTTCACAGACGCACACATCGAGGTGGACATCACCTACGCCGAGTA

CTTCGAAATGAGCGTGCGGCTGGCAGAAGCCATGAAACGATACGGGCTGAACACAAACC

ACAGAATCGTCGTATGCAGCGAAAACAGCCTGCAATTCTTCATGCCGGTGCTGGGCGCG

CTGTTCATCGGAGTGGCAGTGGCGCCCGCGAACGACATCTACAACGAACGGGAACTGCT

CAACAGCATGGGCATCAGCCAGCCCACCGTGGTGTTCGTGAGCAAAAAGGGGCTGCAAA

AAATCCTGAACGTGCAAAAAAAGCTCCCAATCATCCAAAAAATCATCATCATGGACAGC

AAAACGGACTACCAGGGATTCCAGAGCATGTACACGTTCGTCACAAGCCACCTACCCCC

CGGCTTCAACGAATACGACTTCGTGCCAGAGAGCTTCGACAGGGACAAGACAATCGCAC

TGATCATGAACAGCAGCGGAAGCACCGGCCTGCCCAAAGGCGTCGCCCTGCCCCACAGA

ACCGCCTGCGTGAGATTCAGCCACGCCAGAGACCCCATCTTCGGCAACCAAATCATCCC

GGACACCGCGATCCTGAGCGTGGTGCCATTCCACCACGGCTTCGGAATGTTCACCACAC

TCGGATACCTGATATGCGGATTCCGAGTCGTCCTGATGTACAGATTCGAGGAGGAGCTG

TTCCTGAGGAGCCTGCAGGACTACAAGATCCAAAGCGCGCTGCTGGTGCCAACCCTATT

CAGCTTCTTCGCCAAAAGCACCCTGATCGACAAATACGACCTGAGCAACCTGCACGAAA

TCGCCAGCGGCGGCGCCCCCCTCAGCAAGGAAGTCGGGGAAGCGGTGGCCAAGAGGTTC

CACCTGCCAGGCATCAGGCAAGGATACGGGCTCACCGAGACCACAAGCGCCATCCTGAT

CACACCCGAGGGGGACGACAAACCGGGCGCGGTCGGCAAAGTGGTGCCATTCTTCGAAG

CGAAGGTGGTGGACCTGGACACCGGGAAAACGCTGGGCGTGAACCAAAGAGGCGAACTG

TGCGTGAGAGGCCCCATGATCATGAGCGGCTACGTAAACAACCCGGAAGCGACCAACGC

CCTGATCGACAAGGACGGATGGCTACACAGCGGAGACATAGCCTACTGGGACGAAGACG

AACACTTCTTCATCGTGGACCGCCTGAAGTCCCTGATCAAGTACAAAGGCTACCAGGTG

GCCCCCGCCGAACTGGAAAGCATCCTGCTCCAACACCCCAACATCTTCGACGCAGGCGT

CGCAGGCCTGCCCGACGACGACGCCGGCGAACTGCCCGCCGCCGTGGTGGTGCTGGAGC

ACGGAAAGACGATGACGGAAAAAGAGATCGTGGACTACGTCGCCAGCCAAGTAACAACC

GCGAAAAAGCTGCGCGGAGGAGTGGTGTTCGTGGACGAAGTACCGAAAGGCCTGACCGG

AAAACTCGACGCAAGAAAAATCAGAGAGATCCTCATAAAGGCCAAGAAGGGCGGAAAGA

TCGCCGTGTAA

Fluc sense strand, non-template. 3'_16%_T.

(SEQ ID NO: 192)

ATGGAAGACGCCAAAAACATAAAGAAAGGCCCGGCGCCATTCTATCCGC

TGGAAGATGGAACCGCTGGAGAGCAACTGCATAAGGCTATGAAGAGATACGCCCTGGTT

CCTGGAACAATTGCTTTTACAGATGCACATATCGAGGTGGACATCACTTACGCTGAGTA

CTTCGAAATGTCCGTTCGGTTGGCAGAAGCTATGAAACGATATGGGCTGAATACAAATC

ACAGAATCGTCGTATGCAGTGAAAACTCTCTTCAATTCTTTATGCCGGTGTTGGGCGCG

TTATTTATCGGAGTGGCAGTGGCGCCCGCGAACGACATCTACAACGAACGGGAACTGCT

CAACAGCATGGGCATCAGCCAGCCCACCGTGGTGTTCGTGAGCAAAAAGGGGCTGCAAA

AAATCCTGAACGTGCAAAAAAAGCTCCCAATCATCCAAAAAATCATCATCATGGACAGC

AAAACGGACTACCAGGGATTCCAGAGCATGTACACGTTCGTCACAAGCCACCTACCCCC

-continued

CGGCTTCAACGAATACGACTTCGTGCCAGAGAGCTTCGACAGGGACAAGACAATCGCAC

TGATCATGAACAGCAGCGGAAGCACCGGCCTGCCCAAAGGCGTCGCCCTGCCCCACAGA

ACCGCCTGCGTGAGATTCAGCCACGCCAGAGACCCCATCTTCGGCAACCAAATCATCCC

GGACACCGCGATCCTGAGCGTGGTGCCATTCCACCACGGCTTCGGAATGTTCACCACAC

TCGGATACCTGATATGCGGATTCCGAGTCGTCCTGATGTACAGATTCGAGGAGGAGCTG

TTCCTGAGGAGCCTGCAGGACTACAAGATCCAAAGCGCGCTGCTGGTGCCAACCCTATT

CAGCTTCTTCGCCAAAAGCACCCTGATCGACAAATACGACCTGAGCAACCTGCACGAAA

TCGCCAGCGGCGGCGCCCCCCTCAGCAAGGAAGTCGGGGAAGCGGTGGCCAAGAGGTTC

CACCTGCCAGGCATCAGGCAAGGATACGGGCTCACCGAGACCACAAGCGCCATCCTGAT

CACACCCGAGGGGGACGACAAACCGGGCGCGGTCGGCAAAGTGGTGCCATTCTTCGAAG

CGAAGGTGGTGGACCTGGACACCGGGAAAACGCTGGGCGTGAACCAAAGAGGCGAACTG

TGCGTGAGAGGCCCCATGATCATGAGCGGCTACGTAAACAACCCGGAAGCGACCAACGC

CCTGATCGACAAGGACGGATGGCTACACAGCGGAGACATAGCCTACTGGGACGAAGACG

AACACTTCTTCATCGTGGACCGCCTGAAGTCCCTGATCAAGTACAAAGGCTACCAGGTG

GCCCCCGCCGAACTGGAAAGCATCCTGCTCCAACACCCCAACATCTTCGACGCAGGCGT

CGCAGGCCTGCCCGACGACGACGCCGGCGAACTGCCCGCCGCCGTGGTGGTGCTGGAGC

ACGGAAAGACGATGAGGGAAAAAGAGATCGTGGACTACGTCGCCAGCCAAGTAACAACC

GCGAAAAAGCTGCGCGGAGGAGTGGTGTTCGTGGACGAAGTACCGAAAGGCCTGACCGG

AAAACTCGACGCAAGAAAAATCAGAGAGATCCTCATAAAGGCCAAGAAGGGCGGAAAGA

TCGCCGTGTAA

Example H: Reduced Impurities in a Process for ARC-mRNA

Figure 11:
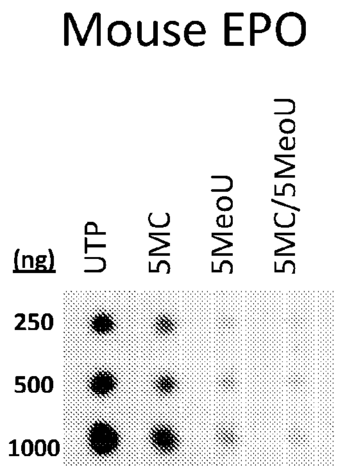
FIG. 11 shows the results of surprisingly reduced impurity levels in a process for synthesizing a mouse EPO translatable molecule of this invention.
Figure 11:
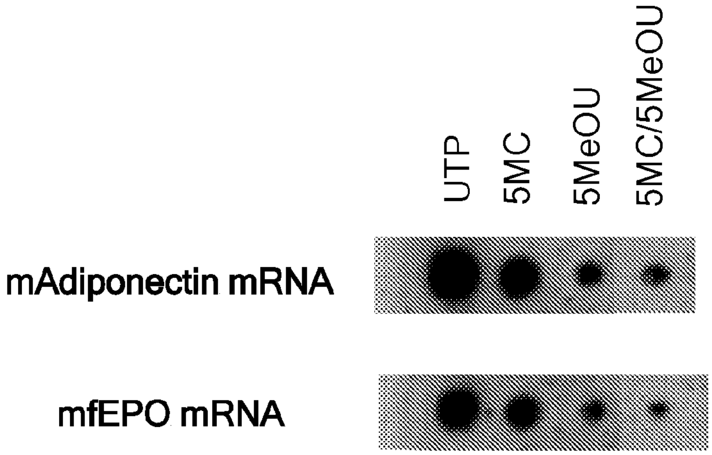

FIG. 11 shows the results of surprisingly reduced impurity levels in a process for synthesizing a mouse EPO translatable molecule of this invention. FIG. 11 shows the results of a dot blot for detecting double strand RNA impurity in the synthesis mixture (nitro cellulose membrane, J2 antibody to detect dsRNA). The ARC-RNA (5MeOU) synthesis product, which was translatable for mouse EPO, showed surprisingly reduced dot blot intensity as compared to a wild type mRNA synthesis product, without 5MeOU, and with similarly reduced T. Under the same conditions and synthesis, the ARC-RNA (5MC/5MeOU) synthesis product, which was translatable for mouse EPO, also showed surprisingly further reduced dot blot intensity as compared to a wild type mRNA synthesis product, without 5MC/5MeOU. Thus, the ARC-RNA (5MC/5MeOU) synthesis process, with template reduced T composition, surprisingly reduced double strand RNA impurity levels in the synthesis mixture. As shown in FIG. 11, similar advantageously reduced double strand RNA impurity levels were found in synthesis mixtures for monkey mAdipo mRNA and mfEPO mRNA.

The double strand RNA impurity levels for mouse EPO for FIG. 11 are shown in Table 12.

TABLE 12

| Area density | |
|---|---|
| Mouse EPO | Area density |
| UTP | 15,674 |
| 5MC | 7,663 |
| 5MeOU | 1,108 |
| 5MC/5MeOU | 506 |

The double strand RNA impurity levels for mfEPO for FIG. 11 are shown in Table 13.

TABLE 13

| Area density | |
|---|---|
| Mouse EPO | Area density |
| UTP | 17,874 |
| 5MC | 11,238 |
| 5MeOU | 4,801 |
| 5MC/5MeOU | 3,386 |

Example I: Reduced Immunogenicity for ARC-mRNA

Figure 12:
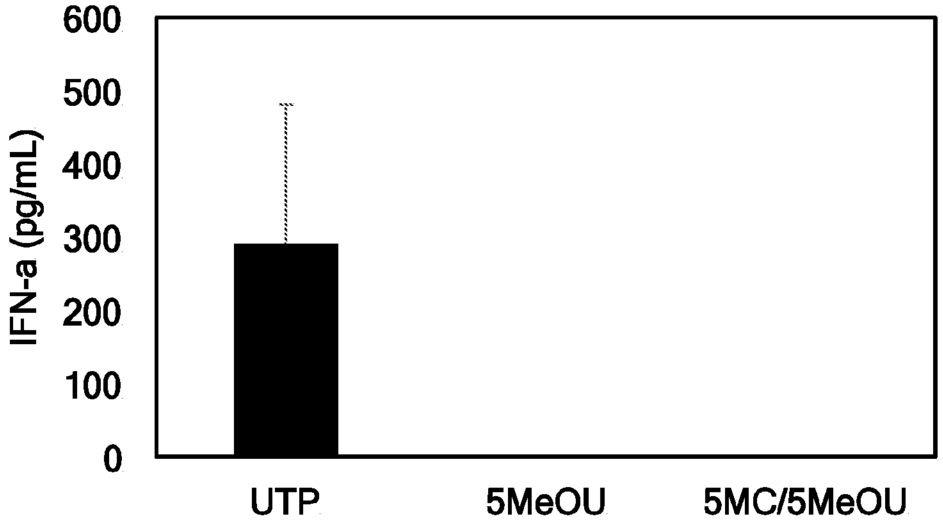
FIG. 12 shows the results of reduced immunogenicity for a translatable molecule of this invention.

FIG. 12 shows the results of reduced immunogenicity for a translatable molecule of this invention. FIG. 12 shows the results of a cytokine assay for IFN-a as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of IFN-a.

Figure 13:
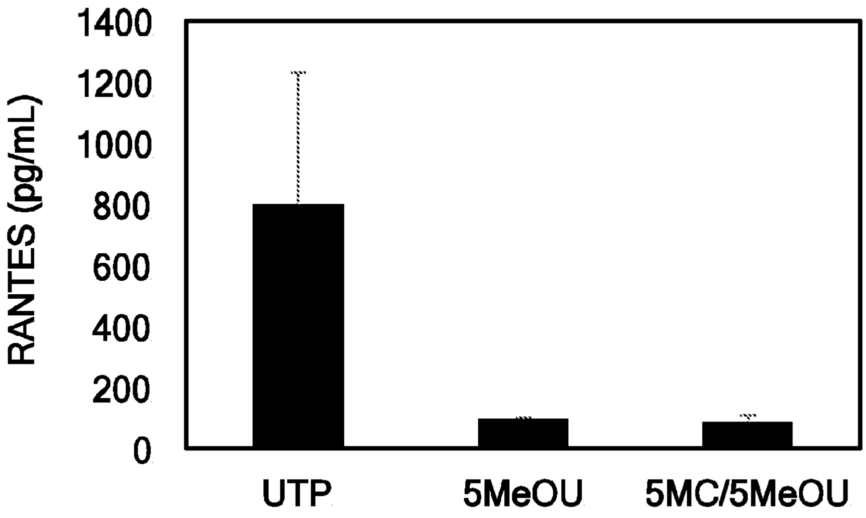
FIG. 13 shows the results of reduced immunogenicity for a translatable molecule of this invention.

FIG. 13 shows the results of reduced immunogenicity for a translatable molecule of this invention. FIG. 13 shows the results of a cytokine assay for RANTES as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of RANTES.

Figure 14:
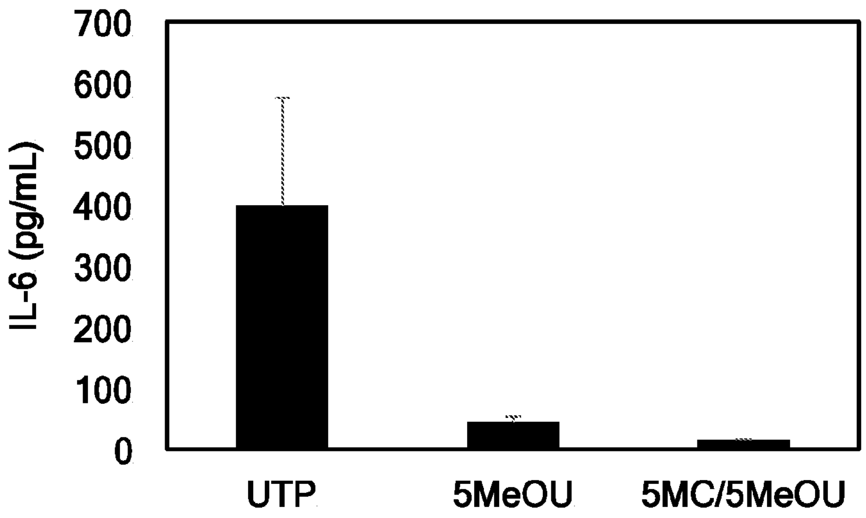
FIG. 14 shows the results of reduced immunogenicity for a translatable molecule of this invention.

FIG. 14 shows the results of reduced immunogenicity for a translatable molecule of this invention. FIG. 14 shows the results of a cytokine assay for IL-6 as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of IL-6.

Figure 15:
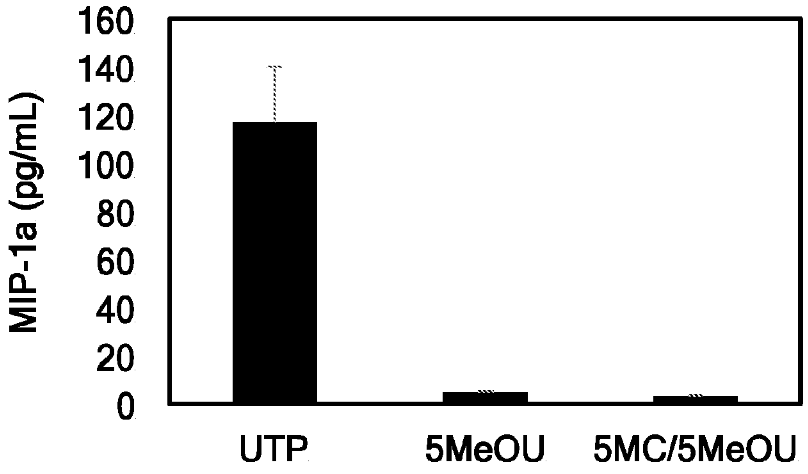
FIG. 15 shows the results of reduced immunogenicity for a translatable molecule of this invention.

FIG. 15 shows the results of reduced immunogenicity for a translatable molecule of this invention. FIG. 15 shows the results of a cytokine assay for MIP-1a as generated in human dendritic cells (DC) with cmEPO ARC-RNA of this invention. The ARC-RNA was synthesized with only UTP along with other NTPs, or with 5MeOU along with other NTPs, or with a combination of 5MC/5MeOU along with other NTPs. 5MC and 5MeOU were used at 100% in the synthesis. The ARC-RNAs synthesized with 5MeOU or with a combination of 5MC/5MeOU showed markedly reduced immunogenicity in generation of MIP-1a.

Example J: Enhanced Expression for ARC-mRNA

Figure 16:
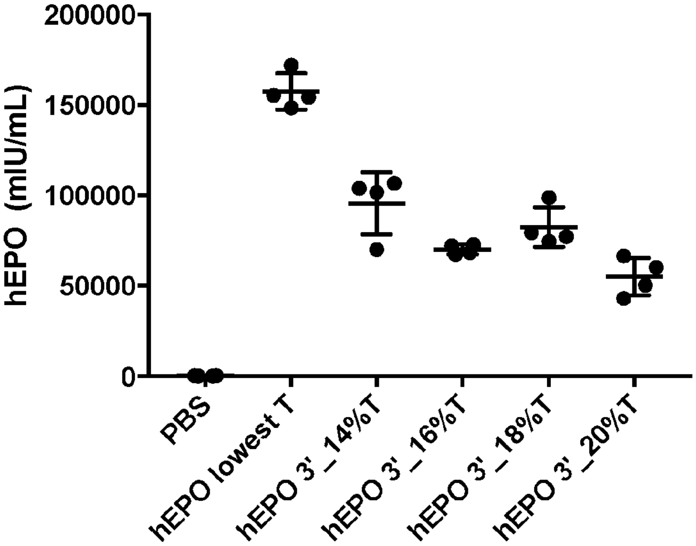
FIG. 16 shows the results of surprisingly increased human EPO protein production in vivo for a translatable molecule of this invention.

FIG. 16 shows the results of surprisingly increased human EPO protein production in vivo for a translatable molecule of this invention. FIG. 16 shows the results for hEPO protein expression after hEPO ARC-mRNA was injected into mice at 0.3 mg/kg dose. hEPO in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

Figure 17:
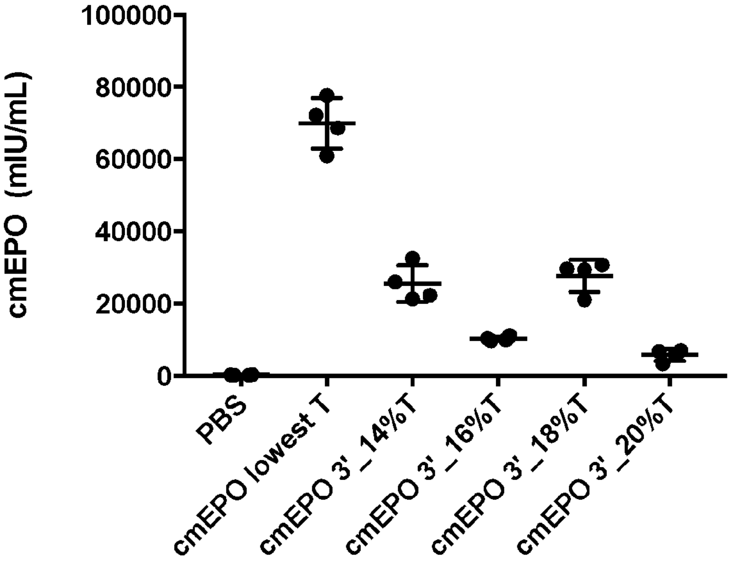
FIG. 17 shows the results of surprisingly increased cynomolgus monkey EPO protein production in vivo for a translatable molecule of this invention.

FIG. 17 shows the results of surprisingly increased cynomolgus monkey EPO protein production in vivo for a translatable molecule of this invention. FIG. 17 shows the results for cmEPO protein expression after cmEPO ARC-mRNA was injected into mice at 0.3 mg/kg dose. cmEPO in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased greater than 3-fold.

Figure 18:
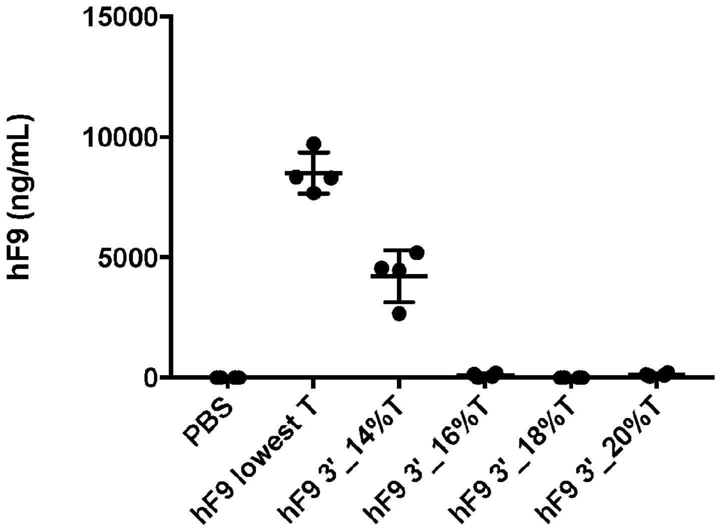
FIG. 18 shows the results of surprisingly increased human F9 protein production in vivo for a translatable molecule of this invention.

FIG. 18 shows the results of surprisingly increased human F9 protein production in vivo for a translatable molecule of this invention. FIG. 18 shows the results for hF9 protein expression after hF9 ARC-mRNA was injected into mice at 0.3 mg/kg dose. hF9 in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

Figure 19:
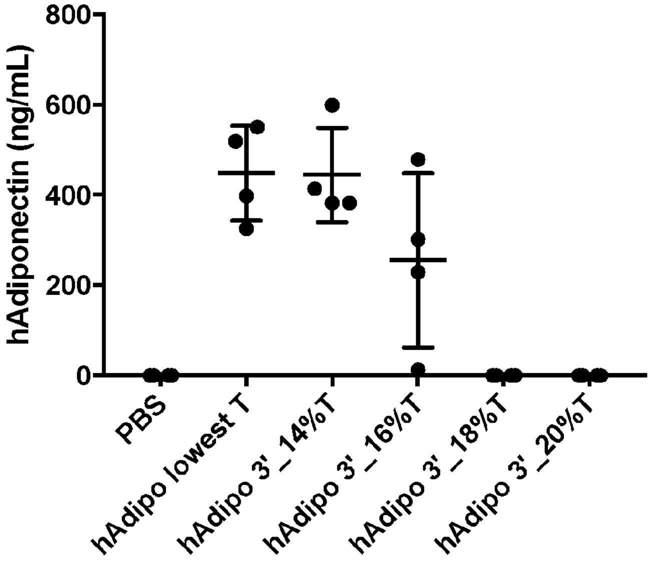
FIG. 19 shows the results of surprisingly increased human adiponectin protein production in vivo for a translatable molecule of this invention.

FIG. 19 shows the results of surprisingly increased human adiponectin protein production in vivo for a translatable molecule of this invention. FIG. 19 shows the results for hAdipo protein expression after hAdipo ARC-mRNA was injected into mice at 0.3 mg/kg dose. hAdipo in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased about 2-fold.

Figure 20:
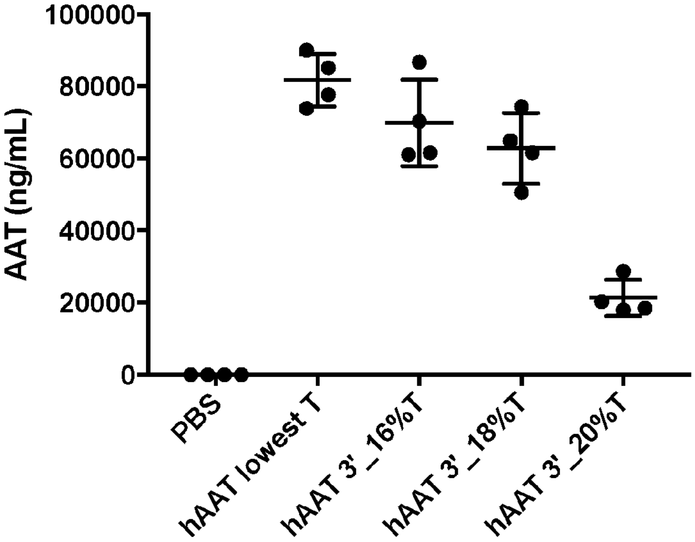
FIG. 20 shows the results of surprisingly increased human AAT protein production in vivo for a translatable molecule of this invention.

FIG. 20 shows the results of surprisingly increased human AAT protein production in vivo for a translatable molecule of this invention. FIG. 20 shows the results for hAAT protein expression after hAAT ARC-mRNA was injected into mice at 0.3 mg/kg dose. hAAT in mouse serum was measured by ELISA. The ARC-RNA was synthesized with reduced T composition templates, using 5MeOU along with other NTPs. 5MeOU was used at 100% in the synthesis. The ARC-RNAs synthesized with 5MeOU using a reduced T composition template showed markedly increased protein production in vivo, increased upto about 4-fold.

Example K: Reduced Immunogenicity for ARC-mRNA

Figure 21:
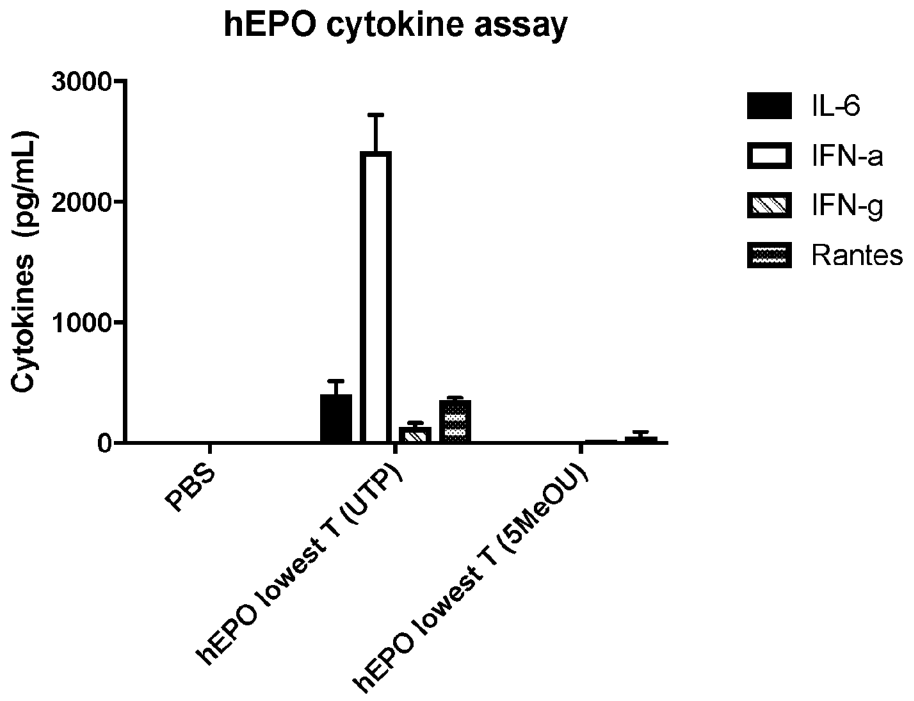
FIG. 21 shows the results of reduced immunogenicity for a translatable molecule of this invention in vivo.

FIG. 21 shows the results of reduced immunogenicity for a translatable molecule of this invention in vivo. FIG. 21 shows the results of a cytokine assay as generated in mouse using an hEPO ARC-RNA (5MeOU) of this invention, detected in serum 6 hrs post injection. The ARC-RNAs synthesized with 5MeOU and a reduced T composition template showed markedly reduced immunogenicity as compared to a synthetic mRNA with the same sequence and containing only natural nucleotides. The hEPO ARC-RNA (5MeOU) did not stimulate cytokine responses in vivo as compared to the UTP control.

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms “a”, “an”, and “the” include plural reference unless the context clearly dictates otherwise. As well, the terms “a” (or “an”), “one or more” and “at least one" can be used interchangeably herein. It is also to be noted that the terms "comprise," "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limiting of the remainder of the disclosure in any way.

All of the features disclosed in this specification may be combined in any combination. Each feature disclosed in this specification may be replaced by an alternative feature serving the same, equivalent, or similar purpose.

What is claimed is:

1. A composition comprising a modified messenger RNA (mRNA), wherein (i) the modified mRNA comprises a coding region of a wild-type mRNA that is expressible, wherein (a) one or more codons of the coding region have been replaced such that the occurrence of uridine monomers in the coding region is reduced by at least 20% as compared to the coding region of the wild type mRNA; and (b) the modified mRNA encodes a polypeptide or protein; and (ii) modified mRNA contains one or more 5-methoxyuridines, wherein the composition comprises an at least three-fold lower level of double stranded RNA as compared to a composition comprising an mRNA having the same coding region sequence with a similarly reduced occurrence of uridine monomers in the coding region as the modified mRNA and lacking 5-methoxyuridine, and wherein the composition is a synthesis mixture.

2. The composition of claim 1, wherein 10-100% of the uridine monomers in the modified mRNA are 5-methoxyuridines, or wherein 50-80% of the uridine monomers in the modified mRNA are 5-methoxyuridines.

3. The composition of claim 1, wherein the modified mRNA contains one or more 5-methylcytidines.

4. The composition of claim 1, wherein 10-100% of the cytidines in the modified mRNA are 5-methylcytidines.

5. The composition of claim 1, wherein one or more codons of the coding region have been replaced such that the occurrence of uridine monomers in the coding region of the modified mRNA is reduced by at least 35% as compared to the coding region of the wild type mRNA.

6. The composition of claim 1, wherein the uridine monomers are replaced beginning from the 5' end of the coding region, or beginning from the 3' end of the coding region, or randomly throughout the coding region.

7. The composition of claim 1, wherein the modified mRNA is selected from SEQ ID NOs:35-47, 76-88, 110-119, and 147-159, wherein one or more of the uridines are 5-methoxyuridines.

8. The composition of claim 1, wherein the modified mRNA encodes a polypeptide or protein having at least 75% identity to a target polypeptide or protein of interest.

9. The composition of claim 1, wherein the modified mRNA encodes a polypeptide or protein having at least 85% identity to a target polypeptide or protein of interest.

10. The composition of claim 1, wherein the modified mRNA comprises a 5' cap, a 5' untranslated region, a coding region, a 3' untranslated region, and a tail region.

11. The composition of claim 1, wherein the modified mRNA comprises a translation enhancer in a 5' or 3' untranslated region.

12. The composition of claim 1, wherein the modified mRNA is translatable in vitro, ex vivo, or in vivo.

13. The composition of claim 1, wherein the modified mRNA comprises from 50 to 15,000 nucleotides.

14. The composition of claim 1, wherein the modified mRNA is expressible to provide a polypeptide, a protein, a protein fragment, an antibody, an antibody fragment, a vaccine immunogen, or a vaccine toxoid.

15. The composition of claim 1, wherein the modified mRNA has at least 2-fold increased translation efficiency in vivo as compared to a native mRNA that expresses the polypeptide or protein.

16. The composition of claim 1, wherein the modified mRNA has at least 5-fold reduced immunogenicity as compared to a native mRNA that expresses the polypeptide or protein.

17. The composition of claim 1, wherein the polypeptide or protein is an expression product, or a fragment thereof, of a gene selected from EPO, AAT, ADIPOQ, F9, TTR, and BIRC5.

18. A composition comprising a DNA template encoding a modified mRNA, wherein (i) the modified mRNA comprises a coding region of a wild-type mRNA that is expressible, wherein (a) one or more codons of the coding region have been replaced such that the occurrence of uridine monomers in the coding region is reduced by at least 20% as compared to the coding region of the wild-type mRNA; and (b) the modified mRNA encodes a polypeptide or protein; and (ii) the modified mRNA contains one or more 5-methoxyuridines, wherein the composition comprises an at least three-fold lower level of double stranded RNA as compared to a composition comprising an mRNA having the same coding region sequence with a similarly reduced occurrence of uridine monomers in the coding region as the modified mRNA and lacking 5-methoxyuridine, and wherein the composition is a synthesis mixture.

19. The composition of claim 1, wherein the synthesis mixture is an in vitro transcription reaction.

20. The composition of claim 18, wherein the synthesis mixture is an in vitro transcription reaction.

* * * * *

SEQUENCE LISTING

```
Sequence total quantity: 192
SEQ ID NO: 1            moltype =   length =
SEQUENCE: 1
000

SEQ ID NO: 2            moltype = DNA  length = 85
FEATURE                 Location/Qualifiers
misc_feature            1..85
                        note = Description of Artificial Sequence:
                         Syntheticoligonucleotide
source                  1..85
                        mol_type = other DNA
                        organism = synthetic construct
SEQUENCE: 2
cgacactgct cgatccgctc gcaccgggct ggcaagccac gtttggtgtt ggaccctcgt  60
acagaagcta atacgactca ctata                                         85

SEQ ID NO: 3            moltype = DNA  length = 143
FEATURE                 Location/Qualifiers
source                  1..143
                        mol_type = other DNA
                        organism = Tobacco etch virus
SEQUENCE: 3
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gcc                                           143

SEQ ID NO: 4            moltype = DNA  length = 582
FEATURE                 Location/Qualifiers
source                  1..582
                        mol_type = genomic DNA
                        organism = Homo sapiens
SEQUENCE: 4
atgggggtgc acgaatgtcc tgcctggctg tggcttctcc tgtccctgct gtcgctccct  60
ctgggcctcc cagtcctggg cgccccacca cgcctcatct gtgacagccg agtcctggag  120
aggtacctct tggaggccaa ggaggccgag aatatcacga cgggctgtgc tgaacactgc  180
agcttgaatg agaatatcac tgtcccagac accaaagtta atttctatgc ctggaagagg  240
atggaggtcg ggcagcaggc cgtagaagtc tggcagggcc tggccctgct gtcggaagct  300
gtcctgcggg gccaggccct gttggtcaac tcttcccagc cgtgggagcc cctgcagctg  360
catgtggata aagccgtcag tggccttcgc agcctcacca ctctgcttcg ggctctggga  420
gcccagaagg aagccatctc ccctccagat gcggcctcag ctgctccact ccgaacaatc  480
actgctgaca ctttccgcaa actcttccga gtctactcca atttcctccg gggaaagctg  540
aagctgtaca caggggaggc ctgcaggaca ggggacagat ga                      582

SEQ ID NO: 5            moltype = DNA  length = 178
FEATURE                 Location/Qualifiers
source                  1..178
                        mol_type = genomic DNA
                        organism = Xenopus sp.
SEQUENCE: 5
ataagtgaac tcgagctagt gactgactag gatctggtta ccactaaacc agcctcaaga  60
acacccgaat ggagtctcta agctacataa taccaactta cacttacaaa atgttgtccc  120
ccaaaatgta gccattcgta tctgctccta ataaaaagaa agtttcttca cattctag    178

SEQ ID NO: 6            moltype = DNA  length = 120
FEATURE                 Location/Qualifiers
misc_feature            1..120
                        note = Description of Artificial Sequence:
                         Syntheticpolynucleotide
source                  1..120
                        mol_type = other DNA
                        organism = synthetic construct
SEQUENCE: 6
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120

SEQ ID NO: 7            moltype = DNA  length = 118
FEATURE                 Location/Qualifiers
```

```
misc_feature           1..118
                       note = Description of Artificial Sequence:
                        Syntheticpolynucleotide
source                 1..118
                       mol_type = other DNA
                       organism = synthetic construct
SEQUENCE: 7
gaagagcgct agcgtcttca gctgcacata acccccttggg gcctctaaac gggtcttgag  60
gggttttttg cctctgacac atgcagctcc cggggatcga cgagagcagc gcgactgg    118

SEQ ID NO: 8           moltype = DNA  length = 582
FEATURE                Location/Qualifiers
source                 1..582
                       mol_type = genomic DNA
                       organism = Homo sapiens
SEQUENCE: 8
atgggggtgc acgaatgtcc tgcctggctg tggcttctcc tgtccctgct gtcgctccct  60
ctgggcctcc cagtcctggg cgccccacca cgcctcatct gtgacagccg agtcctggag  120
aggtacctct tggaggccaa ggaggccgag aatatcacga cgggctgtgc tgaacactgc  180
agcttgaatg agaatatcac tgtcccagac accaaagtta atttctatgc ctggaagagg  240
atggaggtcg ggcagcaggc cgtagaagtc tggcagggcc tggccctgct gtcggaagct  300
gtcctgcggg gccaggccct gttggtcaac tcttcccagc cgtgggagcc cctgcagctg  360
catgtggata aagccgtcag tggccttcgc agcctcacca ctctgcttcg ggctctggga  420
gcccagaagg aagccatctc ccctccagat gcggcctcag ctgctccact ccgaacaatc  480
actgctgaca ctttccgcaa actcttccga gtctactcca atttcctccg gggaaagctg  540
aagctgtaca caggggaggc ctgcaggaca ggggacagat ga                      582

SEQ ID NO: 9           moltype = DNA  length = 582
FEATURE                Location/Qualifiers
misc_feature           1..582
                       note = Description of Artificial Sequence:
                        Syntheticpolynucleotide
source                 1..582
                       mol_type = other DNA
                       organism = synthetic construct
SEQUENCE: 9
atgggggtgc acgaatgccc cgcctggctg tggctgctcc tgagcctgct gagcctcccc  60
ctgggcctcc cagtcctggg cgccccacca cgcctcatct gcgacagccg agtcctggag  120
aggtacctcc tggaggccaa ggaggccgag aacatcacga cgggctgcgc cgaacactgc  180
agcctgaacg agaacatcac cgtcccagac accaaagtga acttctacgc ctggaagagg  240
atggaggtcg ggcagcaggc cgtagaagtc tggcagggcc tggccctgct gagcgaagcc  300
gtcctgcggg gccaggccct gctggtcaac agcagccagc cgtgggagcc cctgcagctg  360
cacgtggaca aagccgtcag cggcctgcgc agcctcacca ccctgctgcg ggccctggga  420
gcccagaagg aagccatcag ccccccagac gcggccagcg ccgcccccact ccgaacaatc  480
accgccgaca ccttccgcaa actcttccga gtctacagca acttcctccg gggaaagctg  540
aagctgtaca caggggaggc ctgcaggaca ggggacagat ga                      582

SEQ ID NO: 10          moltype = DNA  length = 582
FEATURE                Location/Qualifiers
misc_feature           1..582
                       note = Description of Artificial Sequence:
                        Syntheticpolynucleotide
source                 1..582
                       mol_type = other DNA
                       organism = synthetic construct
SEQUENCE: 10
atgggggtgc acgaatgtcc tgcctggctg tggcttctcc tgtccctgct gtcgctcccc  60
ctgggcctcc cagtcctggg cgccccacca cgcctcatct gcgacagccg agtcctggag  120
aggtacctcc tggaggccaa ggaggccgag aacatcacga cgggctgcgc cgaacactgc  180
agcctgaacg agaacatcac cgtcccagac accaaagtga acttctacgc ctggaagagg  240
atggaggtcg ggcagcaggc cgtagaagtc tggcagggcc tggccctgct gagcgaagcc  300
gtcctgcggg gccaggccct gctggtcaac agcagccagc cgtgggagcc cctgcagctg  360
cacgtggaca aagccgtcag cggcctgcgc agcctcacca ccctgctgcg ggccctggga  420
gcccagaagg aagccatcag ccccccagac gcggccagcg ccgcccccact ccgaacaatc  480
accgccgaca ccttccgcaa actcttccga gtctacagca acttcctccg gggaaagctg  540
aagctgtaca caggggaggc ctgcaggaca ggggacagat ga                      582

SEQ ID NO: 11          moltype = DNA  length = 582
FEATURE                Location/Qualifiers
misc_feature           1..582
                       note = Description of Artificial Sequence:
                        Syntheticpolynucleotide
source                 1..582
                       mol_type = other DNA
                       organism = synthetic construct
SEQUENCE: 11
atgggggtgc acgaatgtcc tgcctggctg tggcttctcc tgtccctgct gtcgctccct  60
ctgggcctcc cagtcctggg cgccccacca cgcctcatct gtgacagccg agtcctggag  120
aggtacctct tggaggccaa ggaggccgag aatatcacga cgggctgtgc tgaacactgc  180
```

```
agcttgaatg agaatatcac tgtcccagac accaaagtta atttctacgc ctggaagagg  240
atggaggtcg ggcagcaggc cgtagaagtc tggcagggcc tggccctgct gagcgaagcc  300
gtcctgcggg gccaggccct gctggtcaac agcagccagc cgtgggagcc cctgcagctg  360
cacgtggaca aagccgtcag cggcctgcgc agcctcacca ccctgctgcg ggccctggga  420
gcccagaagg aagccatcag ccccccagac gcggccagcg ccgcccccact ccgaacaatc  480
accgccgaca ccttccgcaa actcttccga gtctacagca acttcctccg gggaaagctg  540
aagctgtaca caggggaggc ctgcaggaca ggggacagat ga                      582

SEQ ID NO: 12          moltype = DNA  length = 582
FEATURE                Location/Qualifiers
misc_feature           1..582
                       note = Description of Artificial Sequence:
                        Syntheticpolynucleotide
source                 1..582
                       mol_type = other DNA
                       organism = synthetic construct
SEQUENCE: 12
atgggggtgc acgaatgtcc tgcctggctg tggcttctcc tgtccctgct gtcgctccct  60
ctgggcctcc cagtcctggg cgccccacca cgcctcatct gtgacagccg agtcctggag  120
aggtacctct tggaggccaa ggaggccgag aatatcacga cgggctgtgc tgaacactgc  180
agcttgaatg agaatatcac tgtcccagac accaaagtta atttctatgc ctggaagagg  240
atggaggtcg ggcagcaggc cgtagaagtc tggcagggcc tggccctgct gtcggaagct  300
gtcctgcggg gccaggccct gttggtcaac tcttcccagc cgtgggagcc cctgcagctg  360
catgtggata aagccgtcag tggccttcgc agcctcacca ccctgctgcg ggccctggga  420
gcccagaagg aagccatcag ccccccagac gcggccagcg ccgcccccact ccgaacaatc  480
accgccgaca ccttccgcaa actcttccga gtctacagca acttcctccg gggaaagctg  540
aagctgtaca caggggaggc ctgcaggaca ggggacagat ga                      582

SEQ ID NO: 13          moltype = DNA  length = 582
FEATURE                Location/Qualifiers
misc_feature           1..582
                       note = Description of Artificial Sequence:
                        Syntheticpolynucleotide
source                 1..582
                       mol_type = other DNA
                       organism = synthetic construct
SEQUENCE: 13
atgggggtgc acgaatgtcc tgcctggctg tggcttctcc tgtccctgct gtcgctccct  60
ctgggcctcc cagtcctggg cgccccacca cgcctcatct gtgacagccg agtcctggag  120
aggtacctct tggaggccaa ggaggccgag aatatcacga cgggctgtgc tgaacactgc  180
agcttgaatg agaatatcac tgtcccagac accaaagtta atttctatgc ctggaagagg  240
atggaggtcg ggcagcaggc cgtagaagtc tggcagggcc tggccctgct gtcggaagct  300
gtcctgcggg gccaggccct gttggtcaac tcttcccagc cgtgggagcc cctgcagctg  360
catgtggata aagccgtcag tggccttcgc agcctcacca ctctgcttcg ggctctggga  420
gcccagaagg aagccatctc ccctccagat gcggcctcag ctgctccact ccgaacaatc  480
actgctgaca ctttccgcaa actcttccga gtctacagca acttcctccg gggaaagctg  540
aagctgtaca caggggaggc ctgcaggaca ggggacagat ga                      582

SEQ ID NO: 14          moltype = DNA  length = 582
FEATURE                Location/Qualifiers
misc_feature           1..582
                       note = Description of Artificial Sequence:
                        Syntheticpolynucleotide
source                 1..582
                       mol_type = other DNA
                       organism = synthetic construct
SEQUENCE: 14
atgggggtgc acgaatgccc cgcctggctg tggctgctcc tgagcctgct gagcctcccc  60
ctgggcctcc cagtcctggg cgccccacca cgcctcatct gcgacagccg agtcctggag  120
aggtacctcc tggaggccaa ggaggccgag aacatcacga cgggctgcgc cgaacactgc  180
agcctgaacg agaacatcac cgtcccagac accaaagtga acttctacgc ctggaagagg  240
atggaggtcg ggcagcaggc cgtagaagtc tggcagggcc tggccctgct gagcgaagcc  300
gtcctgcggg gccaggccct gctggtcaac agcagccagc cgtgggagcc cctgcagctg  360
cacgtggaca aagccgtcag cggcctgcgc agcctcacca ccctgctgcg ggccctggga  420
gcccagaagg aagccatcag ccccccagac gcggccagcg ccgcccccact ccgaacaatc  480
actgctgaca ctttccgcaa actcttccga gtctactcca atttcctccg gggaaagctg  540
aagctgtaca caggggaggc ctgcaggaca ggggacagat ga                      582

SEQ ID NO: 15          moltype = DNA  length = 582
FEATURE                Location/Qualifiers
misc_feature           1..582
                       note = Description of Artificial Sequence:
                        Syntheticpolynucleotide
source                 1..582
                       mol_type = other DNA
                       organism = synthetic construct
SEQUENCE: 15
atgggggtgc acgaatgccc cgcctggctg tggctgctcc tgagcctgct gagcctcccc  60
ctgggcctcc cagtcctggg cgccccacca cgcctcatct gcgacagccg agtcctggag  120
```

-continued

```
aggtacctcc tggaggccaa ggaggccgag aacatcacga cgggctgcgc cgaacactgc  180
agcctgaacg agaacatcac cgtcccagac accaaagtga acttctacgc ctggaagagg  240
atggaggtcg ggcagcaggc cgtagaagtc tggcagggcc tggccctgct gagcgaagcc  300
gtcctgcggg gccaggccct gctggtcaac agcagccagc cgtgggagcc cctgcagctg  360
cacgtggata aagccgtcag tggccttcgc agcctcacca ctctgcttcg ggctctggga  420
gcccagaagg aagccatctc ccctccagat gcggcctcag ctgctccact ccgaacaatc  480
actgctgaca ctttccgcaa actcttccga gtctactcca atttcctccg gggaaagctg  540
aagctgtaca caggggaggc ctgcaggaca ggggacagat ga                    582

SEQ ID NO: 16           moltype = DNA  length = 582
FEATURE                 Location/Qualifiers
misc_feature            1..582
                        note = Description of Artificial Sequence:
                         Syntheticpolynucleotide
source                  1..582
                        mol_type = other DNA
                        organism = synthetic construct
SEQUENCE: 16
atgggggtgc acgaatgccc cgcctggctg tggctgctcc tgagcctgct gagcctcccc  60
ctgggcctcc cagtcctggg cgccccacca cgcctcatct gcgacagccg agtcctggag  120
aggtacctcc tggaggccaa ggaggccgag aacatcacga cgggctgcgc cgaacactgc  180
agcctgaacg agaacatcac tgtcccagac accaaagtta atttctatgc ctggaagagg  240
atggaggtcg ggcagcaggc cgtagaagtc tggcagggcc tggccctgct gtcggaagct  300
gtcctgcggg gccaggccct gttggtcaac tcttcccagc cgtgggagcc cctgcagctg  360
catgtggata aagccgtcag tggccttcgc agcctcacca ctctgcttcg ggctctggga  420
gcccagaagg aagccatctc ccctccagat gcggcctcag ctgctccact ccgaacaatc  480
actgctgaca ctttccgcaa actcttccga gtctactcca atttcctccg gggaaagctg  540
aagctgtaca caggggaggc ctgcaggaca ggggacagat ga                    582

SEQ ID NO: 17           moltype = DNA  length = 582
FEATURE                 Location/Qualifiers
misc_feature            1..582
                        note = Description of Artificial Sequence:
                         Syntheticpolynucleotide
source                  1..582
                        mol_type = other DNA
                        organism = synthetic construct
SEQUENCE: 17
atgggggtgc acgaatgccc cgcctggctg tggcttctcc tgtccctgct gtcgctccct  60
ctgggcctcc cagtcctggg cgccccacca cgcctcatct gtgacagccg agtcctggag  120
aggtacctct tggaggccaa ggaggccgag aatatcacga cgggctgtgc tgaacactgc  180
agcttgaatg agaatatcac tgtcccagac accaaagtta atttctatgc ctggaagagg  240
atggaggtcg ggcagcaggc cgtagaagtc tggcagggcc tggccctgct gtcggaagct  300
gtcctgcggg gccaggccct gttggtcaac tcttcccagc cgtgggagcc cctgcagctg  360
catgtggata aagccgtcag tggccttcgc agcctcacca ctctgcttcg ggctctggga  420
gcccagaagg aagccatctc ccctccagat gcggcctcag ctgctccact ccgaacaatc  480
actgctgaca ctttccgcaa actcttccga gtctactcca atttcctccg gggaaagctg  540
aagctgtaca caggggaggc ctgcaggaca ggggacagat ga                    582

SEQ ID NO: 18           moltype = DNA  length = 582
FEATURE                 Location/Qualifiers
misc_feature            1..582
                        note = Description of Artificial Sequence:
                         Syntheticpolynucleotide
source                  1..582
                        mol_type = other DNA
                        organism = synthetic construct
SEQUENCE: 18
atgggggtgc acgaatgccc tgcctggctg tggctgctcc tgagcctgct gagcctcccc  60
ctgggcctcc cagtcctggg cgccccacca cgcctcatct gcgacagccg agtcctggag  120
aggtacctcc tggaggccaa ggaggccgag aacatcacga cgggctgcgc cgaacactgc  180
agcttgaacg agaacatcac cgtcccagac accaaagtga acttctacgc ctggaagagg  240
atggaggtcg ggcagcaggc cgtagaagtc tggcagggcc tggccctgct gagcgaagcc  300
gtcctgcggg gccaggccct gctggtcaac agctcccagc cgtgggagcc cctgcagctg  360
cacgtggaca aagccgtcag cggcctgcgc agcctcacca ccctgctgcg ggccctggga  420
gcccagaagg aagccatcag ccccccagac gcggccagcg ccgcccccact ccgaacaatc  480
accgctgaca ccttccgcaa actcttccga gtctactcca acttcctccg gggaaagctg  540
aagctgtaca caggggaggc ctgcaggaca ggggacagat ga                    582

SEQ ID NO: 19           moltype = DNA  length = 582
FEATURE                 Location/Qualifiers
misc_feature            1..582
                        note = Description of Artificial Sequence:
                         Syntheticpolynucleotide
source                  1..582
                        mol_type = other DNA
                        organism = synthetic construct
SEQUENCE: 19
atgggggtgc acgaatgtcc cgcctggctg tggctgctcc tgagcctgct gagcctccct  60
```

```
ctgggcctcc cagtcctggg cgccccacca cgcctcatct gcgacagccg agtcctggag  120
aggtacctcc tggaggccaa ggaggccgag aatatcacga cgggctgtgc cgaacactgc  180
agcttgaacg agaatatcac cgtcccagac accaaagtta atttctatgc ctggaagagg  240
atggaggtcg ggcagcaggc cgtagaagtc tggcagggcc tggccctgct gtcggaagct  300
gtcctgcggg gccaggccct gctggtcaac agcagccagc cgtgggagcc cctgcagctg  360
cacgtggata aagccgtcag cggcctgcgc agcctcacca ccctgctgcg ggctctggga  420
gcccagaagg aagccatcag ccctccagat gcggccagcg ccgctccact ccgaacaatc  480
accgccgaca ctttccgcaa actcttccga gtctacagca acttcctccg gggaaagctg  540
aagctgtaca caggggaggc ctgcaggaca ggggacagat ga                    582

SEQ ID NO: 20          moltype = DNA  length = 582
FEATURE                Location/Qualifiers
misc_feature           1..582
                       note = Description of Artificial Sequence:
                        Syntheticpolynucleotide
source                 1..582
                       mol_type = other DNA
                       organism = synthetic construct
SEQUENCE: 20
atgggggtgc acgaatgtcc tgcctggctg tggcttctcc tgtccctgct gagcctccct  60
ctgggcctcc cagtcctggg cgccccacca cgcctcatct gtgacagccg agtcctggag  120
aggtacctct tggaggccaa ggaggccgag aacatcacga cgggctgcgc tgaacactgc  180
agcctgaatg agaatatcac tgtcccagac accaaagtga atttctatgc ctggaagagg  240
atggaggtcg ggcagcaggc cgtagaagtc tggcagggcc tggccctgct gagcgaagcc  300
gtcctgcggg gccaggccct gttggtcaac agcagccagc cgtgggagcc cctgcagctg  360
catgtggata aagccgtcag tggccttcgc agcctcacca ctctgcttcg ggccctggga  420
gcccagaagg aagccatctc ccctccagac gcggcctcag ctgccccact ccgaacaatc  480
actgctgaca ctttccgcaa actcttccga gtctacagca atttcctccg gggaaagctg  540
aagctgtaca caggggaggc ctgcaggaca ggggacagat ga                    582

SEQ ID NO: 21          moltype = DNA  length = 582
FEATURE                Location/Qualifiers
misc_feature           1..582
                       note = Description of Artificial Sequence:
                        Syntheticpolynucleotide
source                 1..582
                       mol_type = other DNA
                       organism = synthetic construct
SEQUENCE: 21
atgggggtgc acgaatgtcc tgcctggctg tggcttctcc tgtccctgct gtcgctccct  60
ctgggcctcc cagtcctggg cgccccacca cgcctcatct gtgacagccg agtcctggag  120
aggtacctct tggaggccaa ggaggccgag aatatcacga cgggctgtgc tgaacactgc  180
agcttgaatg agaatatcac tgtcccagac accaaagtta acttctatgc ctggaagagg  240
atggaggtcg ggcagcaggc cgtagaagtc tggcagggcc tggccctgct gtcggaagct  300
gtcctgcggg gccaggccct gctggtcaac tcttcccagc cgtgggagcc cctgcagctg  360
catgtggata aagccgtcag tggccttcgc agcctcacca ctctgcttcg ggctctggga  420
gcccagaagg aagccatctc ccctccagat gcggcctcag ctgctccact ccgaacaatc  480
actgctgaca ctttccgcaa actcttccga gtctactcca atttcctccg gggaaagctg  540
aagctgtaca caggggaggc ctgcaggaca ggggacagat ga                    582

SEQ ID NO: 22          moltype = DNA  length = 1014
FEATURE                Location/Qualifiers
misc_feature           1..1014
                       note = Description of Artificial Sequence:
                        Syntheticpolynucleotide
source                 1..1014
                       mol_type = other DNA
                       organism = synthetic construct
SEQUENCE: 22
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcctga acgagaacat caccgtccca gacaccaaag  360
tgaacttcta cgcctggaag aggatggagg tcgggcagca ggccgtagaa gtctggcagg  420
gcctggccct gctgagcgaa gccgtcctgc ggggccaggc cctgctggtc aacagcagcc  480
agccgtggga gcccctgcag ctgcacgtgg acaaagccgt cagcggcctg cgcagcctca  540
ccaccctgct gcgggccctg ggagcccaga aggaagccat cagcccccca gacgcggcca  600
gcgccgcccc actccgaaca atcaccgccg acaccttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 23          moltype = DNA  length = 1014
FEATURE                Location/Qualifiers
```

```
misc_feature            1..1014
                        note = Description of Artificial Sequence:
                         Syntheticpolynucleotide
source                  1..1014
                        mol_type = other DNA
                        organism = synthetic construct
SEQUENCE: 23
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgtcgctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcctga acgagaacat caccgtccca gacaccaaag  360
tgaacttcta cgcctggaag aggatggagg tcgggcagca ggccgtagaa gtctggcagg  420
gcctggccct gctgagcgaa gccgtcctgc ggggccaggc cctgctggtc aacagcagcc  480
agccgtggga gcccctgcag ctgcacgtgg acaaagccgt cagcggcctg cgcagcctca  540
ccaccctgct gcgggccctg ggagcccaga aggaagccat cagcccccca gacgcggcca  600
gcgccgcccc actccgaaca atcaccgccg acaccttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 24           moltype = DNA  length = 1014
FEATURE                 Location/Qualifiers
misc_feature            1..1014
                        note = Description of Artificial Sequence:
                         Syntheticpolynucleotide
source                  1..1014
                        mol_type = other DNA
                        organism = synthetic construct
SEQUENCE: 24
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgtcgctc cctctgggcc tcccagtcct gggcgcccca ccacgcctca  240
tctgtgacag ccgagtcctg gagaggtacc tcttggaggc caaggaggcc gagaatatca  300
cgacgggctg tgctgaacac tgcagcttga atgagaatat cactgtccca gacaccaaag  360
ttaatttcta cgcctggaag aggatggagg tcgggcagca ggccgtagaa gtctggcagg  420
gcctggccct gctgagcgaa gccgtcctgc ggggccaggc cctgctggtc aacagcagcc  480
agccgtggga gcccctgcag ctgcacgtgg acaaagccgt cagcggcctg cgcagcctca  540
ccaccctgct gcgggccctg ggagcccaga aggaagccat cagcccccca gacgcggcca  600
gcgccgcccc actccgaaca atcaccgccg acaccttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 25           moltype = DNA  length = 1014
FEATURE                 Location/Qualifiers
misc_feature            1..1014
                        note = Description of Artificial Sequence:
                         Syntheticpolynucleotide
source                  1..1014
                        mol_type = other DNA
                        organism = synthetic construct
SEQUENCE: 25
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgtcgctc cctctgggcc tcccagtcct gggcgcccca ccacgcctca  240
tctgtgacag ccgagtcctg gagaggtacc tcttggaggc caaggaggcc gagaatatca  300
cgacgggctg tgctgaacac tgcagcttga atgagaatat cactgtccca gacaccaaag  360
ttaatttcta tgcctggaag aggatggagg tcgggcagca ggccgtagaa gtctggcagg  420
gcctggccct gctgtcggaa gctgtcctgc ggggccaggc cctgttggtc aactcttccc  480
agccgtggga gcccctgcag ctgcatgtgg ataaagccgt cagtggcctt cgcagcctca  540
ccaccctgct gcgggccctg ggagcccaga aggaagccat cagcccccca gacgcggcca  600
gcgccgcccc actccgaaca atcaccgccg acaccttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014
```

```
SEQ ID NO: 26          moltype = DNA  length = 1014
FEATURE                Location/Qualifiers
misc_feature           1..1014
                       note = Description of Artificial Sequence:
                        Syntheticpolynucleotide
source                 1..1014
                       mol_type = other DNA
                       organism = synthetic construct
SEQUENCE: 26
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgtcgctc cctctgggcc tcccagtcct gggcgcccca ccacgcctca  240
tctgtgacag ccgagtcctg gagaggtacc tcttggaggc caaggaggcc gagaatatca  300
cgacgggctg tgctgaacac tgcagcttga atgagaatat cactgtccca gacaccaaag  360
ttaatttcta tgcctggaag aggatggagg tcgggcagca ggccgtagaa gtctggcagg  420
gcctggccct gctgtcggaa gctgtcctgc ggggccaggc cctgttggtc aactcttccc  480
agccgtggga gcccctgcag ctgcatgtgg ataaagccgt cagtggcctt cgcagcctca  540
ccactctgct tcgggctctg ggagcccaga aggaagccat ctcccctcca gatgcggcct  600
cagctgctcc actccgaaca atcactgctg acactttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 27          moltype = DNA  length = 1014
FEATURE                Location/Qualifiers
misc_feature           1..1014
                       note = Description of Artificial Sequence:
                        Syntheticpolynucleotide
source                 1..1014
                       mol_type = other DNA
                       organism = synthetic construct
SEQUENCE: 27
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcctga acgagaacat caccgtccca gacaccaaag  360
tgaacttcta cgcctggaag aggatggagg tcgggcagca ggccgtagaa gtctggcagg  420
gcctggccct gctgagcgaa gccgtcctgc ggggccaggc cctgctggtc aacagcagcc  480
agccgtggga gcccctgcag ctgcacgtgg acaaagccgt cagcggcctg cgcagcctca  540
ccaccctgct gcgggccctg ggagcccaga aggaagccat cagcccccca gacgcggcca  600
gcgccgcccc actccgaaca atcactgctg acactttccg caaactcttc cgagtctact  660
ccaatttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 28          moltype = DNA  length = 1014
FEATURE                Location/Qualifiers
misc_feature           1..1014
                       note = Description of Artificial Sequence:
                        Syntheticpolynucleotide
source                 1..1014
                       mol_type = other DNA
                       organism = synthetic construct
SEQUENCE: 28
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcctga acgagaacat caccgtccca gacaccaaag  360
tgaacttcta cgcctggaag aggatggagg tcgggcagca ggccgtagaa gtctggcagg  420
gcctggccct gctgagcgaa gccgtcctgc ggggccaggc cctgctggtc aacagcagcc  480
agccgtggga gcccctgcag ctgcacgtgg ataaagccgt cagtggcctt cgcagcctca  540
ccactctgct tcgggctctg ggagcccaga aggaagccat ctcccctcca gatgcggcct  600
cagctgctcc actccgaaca atcactgctg acactttccg caaactcttc cgagtctact  660
ccaatttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
```

```
aaaaaaaaaa aaaaaaaaaa aaaaaaaaaa aaaaaaaaaa aaaaaaaaaa aaaa        1014

SEQ ID NO: 29          moltype = DNA  length = 1014
FEATURE                Location/Qualifiers
misc_feature           1..1014
                       note = Description of Artificial Sequence:
                        Syntheticpolynucleotide
source                 1..1014
                       mol_type = other DNA
                       organism = synthetic construct
SEQUENCE: 29
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcctga acgagaacat cactgtccca gacaccaaag  360
ttaatttcta tgcctggaag aggatggagg tcgggcagca ggccgtagaa gtctggcagg  420
gcctggccct gctgtcggaa gctgtcctgc ggggccaggc cctgttggtc aactcttccc  480
agccgtggga gcccctgcag ctgcatgtgg ataaagccgt cagtggcctt cgcagcctca  540
ccactctgct tcgggctctg ggagcccaga aggaagccat ctcccctcca gatgcggcct  600
cagctgctcc actccgaaca atcactgctg acactttccg caaactcttc cgagtctact  660
ccaatttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 30          moltype = DNA  length = 1014
FEATURE                Location/Qualifiers
misc_feature           1..1014
                       note = Description of Artificial Sequence:
                        Syntheticpolynucleotide
source                 1..1014
                       mol_type = other DNA
                       organism = synthetic construct
SEQUENCE: 30
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggcttc  180
tcctgtccct gctgtcgctc cctctgggcc tcccagtcct gggcgcccca ccacgcctca  240
tctgtgacag ccgagtcctg gagaggtacc tcttggaggc caaggaggcc gagaatatca  300
cgacgggctg tgctgaacac tgcagcttga atgagaatat cactgtccca gacaccaaag  360
ttaatttcta tgcctggaag aggatggagg tcgggcagca ggccgtagaa gtctggcagg  420
gcctggccct gctgtcggaa gctgtcctgc ggggccaggc cctgttggtc aactcttccc  480
agccgtggga gcccctgcag ctgcatgtgg ataaagccgt cagtggcctt cgcagcctca  540
ccactctgct tcgggctctg ggagcccaga aggaagccat ctcccctcca gatgcggcct  600
cagctgctcc actccgaaca atcactgctg acactttccg caaactcttc cgagtctact  660
ccaatttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 31          moltype = DNA  length = 1014
FEATURE                Location/Qualifiers
misc_feature           1..1014
                       note = Description of Artificial Sequence:
                        Syntheticpolynucleotide
source                 1..1014
                       mol_type = other DNA
                       organism = synthetic construct
SEQUENCE: 31
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccctgcctgg ctgtggctgc  180
tcctgagcct gctgagcctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcttga acgagaacat caccgtccca gacaccaaag  360
tgaacttcta cgcctggaag aggatggagg tcgggcagca ggccgtagaa gtctggcagg  420
gcctggccct gctgagcgaa gccgtcctgc ggggccaggc cctgctggtc aacagctccc  480
agccgtggga gcccctgcag ctgcacgtgg acaaagccgt cagcggcctg cgcagcctca  540
ccaccctgct gcgggccctg ggagcccaga aggaagccat cagcccccca gacgcggcca  600
gcgccgcccc actccgaaca atcaccgctg acaccttccg caaactcttc cgagtctact  660
ccaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
```

```
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 32          moltype = DNA  length = 1014
FEATURE                Location/Qualifiers
misc_feature           1..1014
                       note = Description of Artificial Sequence:
                        Syntheticpolynucleotide
source                 1..1014
                       mol_type = other DNA
                       organism = synthetic construct
SEQUENCE: 32
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcccgcctgg ctgtggctgc  180
tcctgagcct gctgagcctc cctctgggcc tcccagtcct gggcgcccca ccacgcctca  240
tctgcgacag ccgagtcctg gagaggtacc tcctggaggc caaggaggcc gagaatatca  300
cgacgggctg tgccgaacac tgcagcttga acgagaatat caccgtccca gacaccaaag  360
ttaatttcta tgcctggaag aggatggagg tcgggcagca ggccgtagaa gtctggcagg  420
gcctggccct gctgtcggaa gctgtcctgc ggggccaggc cctgctggtc aacagcagcc  480
agccgtggga gcccctgcag ctgcacgtgg ataaagccgt cagcggcctg cgcagcctca  540
ccaccctgct gcgggctctg ggagcccaga aggaagccat cagccctcca gatgcggcca  600
gcgccgctcc actccgaaca atcaccgccg acactttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 33          moltype = DNA  length = 1014
FEATURE                Location/Qualifiers
misc_feature           1..1014
                       note = Description of Artificial Sequence:
                        Syntheticpolynucleotide
source                 1..1014
                       mol_type = other DNA
                       organism = synthetic construct
SEQUENCE: 33
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgagcctc cctctgggcc tcccagtcct gggcgcccca ccacgcctca  240
tctgtgacag ccgagtcctg gagaggtacc tcttggaggc caaggaggcc gagaacatca  300
cgacgggctg cgctgaacac tgcagcctga atgagaatat cactgtccca gacaccaaag  360
tgaatttcta tgcctggaag aggatggagg tcgggcagca ggccgtagaa gtctggcagg  420
gcctggccct gctgagcgaa gccgtcctgc ggggccaggc cctgttggtc aacagcagcc  480
agccgtggga gcccctgcag ctgcatgtgg ataaagccgt cagtggcctt cgcagcctca  540
ccactctgct ggagccctg ggagcccaga aggaagccat ctcccctcca gacgcggcct  600
cagctgcccc actccgaaca atcactgctg acactttccg caaactcttc cgagtctaca  660
gcaatttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 34          moltype = DNA  length = 1014
FEATURE                Location/Qualifiers
misc_feature           1..1014
                       note = Description of Artificial Sequence:
                        Syntheticpolynucleotide
source                 1..1014
                       mol_type = other DNA
                       organism = synthetic construct
SEQUENCE: 34
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgtcgctc cctctgggcc tcccagtcct gggcgcccca ccacgcctca  240
tctgtgacag ccgagtcctg gagaggtacc tcttggaggc caaggaggcc gagaatatca  300
cgacgggctg tgctgaacac tgcagcttga atgagaatat cactgtccca gacaccaaag  360
ttaacttcta tgcctggaag aggatggagg tcgggcagca ggccgtagaa gtctggcagg  420
gcctggccct gctgtcggaa gctgtcctgc ggggccaggc cctgctggtc aactcttccc  480
agccgtggga gcccctgcag ctgcatgtgg ataaagccgt cagtggcctt cgcagcctca  540
ccactctgct tcgggctctg ggagcccaga aggaagccat ctcccctcca gatgcggcct  600
cagctgctcc actccgaaca atcactgctg acactttccg caaactcttc cgagtctact  660
ccaatttcct ccggggaaag ctgaagctgt acacagggga ggcctgcagg acaggggaca  720
```

```
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 35          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 35
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcctga acgagaacat caccgtccca gacaccaaag  360
tgaacttcta cgcctggaag aggatggagg tcgggcagca ggccgtagaa gtctggcagg  420
gcctggccct gctgagcgaa gccgtcctgc ggggccaggc cctgctggtc aacagcagcc  480
agccgtggga gcccctgcag ctgcacgtgg acaaagccgt cagcggcctg cgcagcctca  540
ccaccctgct gcgggccctg ggagcccaga aggaagccat cagcccccca gacgcggcca  600
gcgccgcccc actccgaaca atcaccgccg acaccttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 36          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 36
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgtcgctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcctga acgagaacat caccgtccca gacaccaaag  360
tgaacttcta cgcctggaag aggatggagg tcgggcagca ggccgtagaa gtctggcagg  420
gcctggccct gctgagcgaa gccgtcctgc ggggccaggc cctgctggtc aacagcagcc  480
agccgtggga gcccctgcag ctgcacgtgg acaaagccgt cagcggcctg cgcagcctca  540
ccaccctgct gcgggccctg ggagcccaga aggaagccat cagcccccca gacgcggcca  600
gcgccgcccc actccgaaca atcaccgccg acaccttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 37          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 37
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgtcgctc cctctgggcc tcccagtcct gggcgcccca ccacgcctca  240
tctgtgacag ccgagtcctg gagaggtacc tcttggaggc caaggaggcc gagaatatca  300
cgacgggctg tgctgaacac tgcagcttga atgagaatat cactgtccca gacaccaaag  360
ttaatttcta cgcctggaag aggatggagg tcgggcagca ggccgtagaa gtctggcagg  420
gcctggccct gctgagcgaa gccgtcctgc ggggccaggc cctgctggtc aacagcagcc  480
agccgtggga gcccctgcag ctgcacgtgg acaaagccgt cagcggcctg cgcagcctca  540
ccaccctgct gcgggccctg ggagcccaga aggaagccat cagcccccca gacgcggcca  600
```

```
gcgccgcccc actccgaaca atcaccgccg acaccttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 38          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 38
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgtcgctc cctctgggcc tcccagtcct gggcgcccca ccacgcctca  240
tctgtgacag ccgagtcctg gagaggtacc tcttggaggc caaggaggcc gagaatatca  300
cgacgggctg tgctgaacac tgcagcttga atgagaatat cactgtccca gacaccaaag  360
ttaatttcta tgcctggaag aggatggagg tcgggcagca ggccgtagaa gtctggcagg  420
gcctggccct gctgtcggaa gctgtcctgc ggggccaggc cctgttggtc aactcttccc  480
agccgtggga gcccctgcag ctgcatgtgg ataaagccgt cagtggcctt cgcagcctca  540
ccaccctgct gcgggccctg ggagcccaga aggaagccat cagcccccca gacgcggcca  600
gcgccgcccc actccgaaca atcaccgccg acaccttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 39          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 39
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgtcgctc cctctgggcc tcccagtcct gggcgcccca ccacgcctca  240
tctgtgacag ccgagtcctg gagaggtacc tcttggaggc caaggaggcc gagaatatca  300
cgacgggctg tgctgaacac tgcagcttga atgagaatat cactgtccca gacaccaaag  360
ttaatttcta tgcctggaag aggatggagg tcgggcagca ggccgtagaa gtctggcagg  420
gcctggccct gctgtcggaa gctgtcctgc ggggccaggc cctgttggtc aactcttccc  480
agccgtggga gcccctgcag ctgcatgtgg ataaagccgt cagtggcctt cgcagcctca  540
ccactctgct tcgggctctg ggagcccaga aggaagccat ctcccctcca gatgcggcct  600
cagctgctcc actccgaaca atcactgctg acactttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 40          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 40
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcctga acgagaacat caccgtccca gacaccaaag  360
tgaacttcta cgcctggaag aggatggagg tcgggcagca ggccgtagaa gtctggcagg  420
gcctggccct gctgagcgaa gccgtcctgc ggggccaggc cctgctggtc aacagcagcc  480
```

```
agccgtggga gcccctgcag ctgcacgtgg acaaagccgt cagcggcctg cgcagcctca  540
ccaccctgct gcgggccctg ggagcccaga aggaagccat cagcccccca gacgcggcca  600
gcgccgcccc actccgaaca atcactgctg acactttccg caaactcttc cgagtctact  660
ccaatttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 41          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 41
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcctga acgagaacat caccgtccca gacaccaaag  360
tgaacttcta cgcctggaag aggatggagg tcgggcagca ggccgtagaa gtctggcagg  420
gcctggccct gctgagcgaa gccgtcctgc ggggccaggc cctgctggtc aacagcagcc  480
agccgtggga gcccctgcag ctgcacgtgg ataaagccgt cagtggcctt cgcagcctca  540
ccactctgct tcgggctctg ggagcccaga aggaagccat ctcccctcca gatgcggcct  600
cagctgctcc actccgaaca atcactgctg acactttccg caaactcttc cgagtctact  660
ccaatttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 42          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 42
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcctga acgagaacat cactgtccca gacaccaaag  360
ttaatttcta tgcctggaag aggatggagg tcgggcagca ggccgtagaa gtctggcagg  420
gcctggccct gctgtcggaa gctgtcctgc ggggccaggc cctgttggtc aactcttccc  480
agccgtggga gcccctgcag ctgcatgtgg ataaagccgt cagtggcctt cgcagcctca  540
ccactctgct tcgggctctg ggagcccaga aggaagccat ctcccctcca gatgcggcct  600
cagctgctcc actccgaaca atcactgctg acactttccg caaactcttc cgagtctact  660
ccaatttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 43          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 43
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggcttc  180
tcctgtccct gctgtcgctc cctctgggcc tcccagtcct gggcgcccca ccacgcctca  240
tctgtgacag ccgagtcctg gagaggtacc tcttggaggc caaggaggcc gagaatatca  300
cgacgggctg tgctgaacac tgcagcttga atgagaatat cactgtccca gacaccaaag  360
```

-continued

```
ttaatttcta tgcctggaag aggatggagg tcgggcagca ggccgtagaa gtctggcagg  420
gcctggccct gctgtcggaa gctgtcctgc ggggccaggc cctgttggtc aactcttccc  480
agccgtggga gcccctgcag ctgcatgtgg ataaagccgt cagtggcctt cgcagcctca  540
ccactctgct tcgggctctg ggagcccaga aggaagccat ctcccctcca gatgcggcct  600
cagctgctcc actccgaaca atcactgctg acactttccg caaactcttc cgagtctact  660
ccaatttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 44          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 44
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccctgcctgg ctgtggctgc  180
tcctgagcct gctgagcctc cccctgggcc tcccagtcct gggcgcccca ccacgcctca  240
tctgcgacag ccgagtcctg gagaggtacc tcctggaggc caaggaggcc gagaacatca  300
cgacgggctg cgccgaacac tgcagcttga acgagaacat caccgtccca gacaccaaag  360
tgaacttcta cgcctggaag aggatggagg tcgggcagca ggccgtagaa gtctggcagg  420
gcctggccct gctgagcgaa gccgtcctgc ggggccaggc cctgctggtc aacagctccc  480
agccgtggga gcccctgcag ctgcacgtgg acaaagccgt cagcggcctg cgcagcctca  540
ccaccctgct gcgggccctg ggagcccaga aggaagccat cagcccccca gacgcggcca  600
gcgccgcccc actccgaaca atcaccgctg acaccttccg caaactcttc cgagtctact  660
ccaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 45          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 45
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcccgcctgg ctgtggctgc  180
tcctgagcct gctgagcctc cctctgggcc tcccagtcct gggcgcccca ccacgcctca  240
tctgcgacag ccgagtcctg gagaggtacc tcctggaggc caaggaggcc gagaatatca  300
cgacgggctg tgccgaacac tgcagcttga acgagaatat caccgtccca gacaccaaag  360
ttaatttcta tgcctggaag aggatggagg tcgggcagca ggccgtagaa gtctggcagg  420
gcctggccct gctgtcggaa gctgtcctgc ggggccaggc cctgctggtc aacagcagcc  480
agccgtggga gcccctgcag ctgcacgtgg ataaagccgt cagcggcctg cgcagcctca  540
ccaccctgct gcgggctctg ggagcccaga aggaagccat cagccctcca gatgcggcca  600
gcgccgctcc actccgaaca atcaccgccg acactttccg caaactcttc cgagtctaca  660
gcaacttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaa        1014

SEQ ID NO: 46          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 46
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgagcctc cctctgggcc tcccagtcct gggcgcccca ccacgcctca  240
```

-continued

```
tctgtgacag ccgagtcctg gagaggtacc tcttggaggc caaggaggcc gagaacatca  300
cgacgggctg cgctgaacac tgcagcctga atgagaatat cactgtccca gacaccaaag  360
tgaatttcta tgcctggaag aggatggagg tcgggcagca ggccgtagaa gtctggcagg  420
gcctggccct gctgagcgaa gccgtcctgc ggggccaggc cctgttggtc aacagcagcc  480
agccgtggga gcccctgcag ctgcatgtgg ataaagccgt cagtggcctt cgcagcctca  540
ccactctgct tcgggccctg ggagcccaga aggaagccat ctcccctcca gacgcggcct  600
cagctgcccc actccgaaca atcactgctg acactttccg caaactcttc cgagtctaca  660
gcaatttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaa                   1014

SEQ ID NO: 47          moltype = RNA  length = 1014
FEATURE                Location/Qualifiers
misc_feature           1..1014
                       note = Description of Artificial Sequence:
                        Syntheticpolynucleotide
source                 1..1014
                       mol_type = other RNA
                       organism = synthetic construct
SEQUENCE: 47
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgtccct gctgtcgctc cctctgggcc tcccagtcct gggcgcccca ccacgcctca  240
tctgtgacag ccgagtcctg gagaggtacc tcttggaggc caaggaggcc gagaatatca  300
cgacgggctg tgctgaacac tgcagcttga atgagaatat cactgtccca gacaccaaag  360
ttaacttcta tgcctggaag aggatggagg tcgggcagca ggccgtagaa gtctggcagg  420
gcctggccct gctgtcggaa gctgtcctgc ggggccaggc cctgctggtc aactcttccc  480
agccgtggga gcccctgcag ctgcatgtgg ataaagccgt cagtggcctt cgcagcctca  540
ccactctgct tcgggctctg ggagcccaga aggaagccat ctcccctcca gatgcggcct  600
cagctgctcc actccgaaca atcactgctg acactttccg caaactcttc cgagtctact  660
ccaatttcct ccggggaaag ctgaagctgt acacagggga ggcctgcagg acaggggaca  720
gatgactcga gctagtgact gactaggatc tggttaccac taaaccagcc tcaagaacac  780
ccgaatggag tctctaagct acataatacc aacttacact tacaaaatgt tgtcccccaa  840
aatgtagcca ttcgtatctg ctcctaataa aaagaaagtt tcttcacatt ctagaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaa                   1014

SEQ ID NO: 48          moltype = DNA  length = 1386
FEATURE                Location/Qualifiers
source                 1..1386
                       mol_type = genomic DNA
                       organism = Homo sapiens
SEQUENCE: 48
atgcagcgcg tgaacatgat catggcagaa tcaccaggcc tcatcaccat ctgcctttta  60
ggatatctac tcagtgctga atgtacagtt tttcttgatc atgaaaacgc caacaaaatt  120
ctgaatcggc caaagaggta taattcaggt aaattggaag agtttgttca agggaacctt  180
gagagagaat gtatggaaga aaagtgtagt tttgaagaag cacgagaagt ttttgaaaac  240
actgaaagaa caactgaatt ttggaagcag tatgttgatg gagatcagtg tgagtccaat  300
ccatgtttaa atggcggcag ttgcaaggat gacattaatt cctatgaatg ttggtgtccc  360
tttggatttg aaggaaagaa ctgtgaatta gatgtaacat gtaacattaa gaatggcaga  420
tgcgagcagt tttgtaaaaa tagtgctgat aacaaggtgg tttgctcctg tactgaggga  480
tatcgacttg cagaaaacca gaagtcctgt gaaccagcag tgccatttcc atgtggaaga  540
gtttctgttt cacaaacttc taagctcacc cgtgctgaga ctgtttttcc tgatgtggac  600
tatgtaaatt ctactgaagc tgaaaccatt ttggataaca tcactcaaag cacccaatca  660
tttaatgact tcactcgggt tgttggtgga gaagatgcca aaccaggtca attcccttgg  720
caggttgttt tgaatggtaa agttgatgca ttctgtggag gctctatcgt taatgaaaaa  780
tggattgtaa ctgctgccca ctgtgttgaa actggtgtta aaattacagt tgtcgcaggt  840
gaacataata ttgaggagac agaacataca gagcaaaagc gaaatgtgat tcgaattatt  900
cctcaccaca actacaatgc agctattaat aagtacaacc atgacattgc ccttctggaa  960
ctggacgaac ccttagtgct aaacagctac gttacaccta tttgcattgc tgacaaggaa  1020
tacacgaaca tcttcctcaa atttggatct ggctatgtaa gtggctgggg aagagtcttc  1080
cacaaaggga gatcagcttt agttcttcag taccttagag ttccacttgt tgaccgagcc  1140
acatgtcttc gatctacaaa gttcaccatc tataacaaca tgttctgtgc tggcttccat  1200
gaaggaggta gagattcatg tcaaggagat agtgggggac cccatgttac tgaagtggaa  1260
gggaccagtt tcttaactgg aattattagc tggggtgaag agtgtgcaat gaaaggcaaa  1320
tatggaatat ataccaaggt atcccggtat gtcaactgga ttaaggaaaa aacaaagctc  1380
acttaa                                                             1386

SEQ ID NO: 49          moltype = DNA  length = 582
FEATURE                Location/Qualifiers
misc_feature           1..582
                       note = Description of Artificial Sequence:
                        Syntheticpolynucleotide
source                 1..582
                       mol_type = other DNA
```

```
                          organism = synthetic construct
SEQUENCE: 49
atgggggtgc acgaatgccc cgcctggctg tggctgctcc tgagcctgct gagcctcccc  60
ctgggcctcc cagtcctggg cgcccccacca cgcctcatct gcgacagccg agtcctggag  120
aggtacctcc tggaggccaa ggaggccgag aacatcacga cgggctgcgc cgaacactgc  180
agcctgaacg agaacatcac cgtcccagac accaaagtga acttctacgc ctggaagagg  240
atggaggtcg ggcagcaggc cgtagaagtc tggcagggcc tggccctgct gagcgaagcc  300
gtcctgcggg gccaggccct gctggtcaac agcagccagc cgtgggagcc cctgcagctg  360
cacgtggaca aagccgtcag cggcctgcgc agcctcacca ccctgctgcg ggccctggga  420
gcccagaagg aagccatcag ccccccagac gcggccagcg ccgcccccact ccgaacaatc  480
accgccgaca ccttccgcaa actcttccga gtctacagca acttcctccg gggaaagctg  540
aagctgtaca caggggaggc ctgcaggaca ggggacagat ga                    582

SEQ ID NO: 50             moltype = DNA  length = 1386
FEATURE                   Location/Qualifiers
misc_feature              1..1386
                          note = Description of Artificial Sequence:
                           Syntheticpolynucleotide
source                    1..1386
                          mol_type = other DNA
                          organism = synthetic construct
SEQUENCE: 50
atgcagcgcg tgaacatgat catggcagaa agcccaggcc tcatcaccat ctgcctgctg  60
ggatacctac tcagcgccga atgcacagtg ttcctggacc acgaaaacgc caacaaaatc  120
ctgaaccggc caaagaggta caacagcggc aaactggaag agttcgtgca agggaacctg  180
gagagagaat gcatggaaga aaagtgcagc ttcgaagaag cacgagaagt gttcgaaaac  240
accgaaagaa caaccgaatt ctggaagcag tacgtggacg gagaccagtg cgagagcaac  300
ccatgcctga acggcggcag ctgcaaggac gacatcaaca gctacgaatg ctggtgcccc  360
ttcggattcg aaggaaagaa ctgcgaactg gacgtaacat gcaacatcaa gaacggcaga  420
tgcgagcagt tctgcaaaaa cagcgccgac aacaaggtgg tgtgcagctg caccgaggga  480
taccgactgg cagaaaacca gaagtcctgc gaaccagcag tgccattccc atgcggaaga  540
gtgagcgtga gccaaaccag caagctcacc cgggccgaga ccgtgttccc cgacgtggac  600
tacgtaaaca gcaccgaagc cgaaaccatc ctggacaaca tcacccaaag cacccaaagc  660
ttcaacgact tcacccgggt ggtgggcgga gaagacgcca aaccaggcca attcccctgg  720
caggtggtgc tgaacggcaa agtggacgca ttctgcggag gcagcatcgt gaacgaaaaa  780
tggatcgtaa ccgccgccca ctgcgtggaa accggcgtga aaatcacagt ggtcgcaggc  840
gaacacaaca tcgaggagac agaacacaca gagcaaaagc gaaacgtgat ccgaatcatc  900
ccccaccaca actacaacgc agccatcaac aagtacaacc acgacatcgc cctgctggaa  960
ctggacgaac ccctggtgct aaacagctac gtgacaccca tctgcatcgc cgacaaggaa  1020
tacacgaaca tcttcctcaa attcggaagc ggctacgtaa gcggctgggg aagagtcttc  1080
cacaaaggga gaagcgccct ggtgctgcag tacctgagag tgccactggt ggaccgagcc  1140
acatgcctgc gaagcacaaa gttcaccatc tacaacaaca tgttctgcgc cggcttccac  1200
gaaggaggca gagacagctg ccaaggagac agcgggggac cccacgtgac cgaagtggaa  1260
gggaccagct tcctgaccgg aatcatcagc tggggcgaag agtgcgcaat gaaaggcaaa  1320
tacggaatat acaccaaggt aagccggtac gtcaactgga tcaaggaaaa aacaaagctc  1380
acctaa                                                            1386

SEQ ID NO: 51             moltype = DNA  length = 1386
FEATURE                   Location/Qualifiers
misc_feature              1..1386
                          note = Description of Artificial Sequence:
                           Syntheticpolynucleotide
source                    1..1386
                          mol_type = other DNA
                          organism = synthetic construct
SEQUENCE: 51
atgcagcgcg tgaacatgat catggcagaa tcaccaggcc tcatcaccat ctgcctttta  60
ggatatctac tcagtgctga atgtacagtt ttcctggacc acgaaaacgc caacaaaatc  120
ctgaaccggc caaagaggta caacagcggc aaactggaag agttcgtgca agggaacctg  180
gagagagaat gcatggaaga aaagtgcagc ttcgaagaag cacgagaagt gttcgaaaac  240
accgaaagaa caaccgaatt ctggaagcag tacgtggacg gagaccagtg cgagagcaac  300
ccatgcctga acggcggcag ctgcaaggac gacatcaaca gctacgaatg ctggtgcccc  360
ttcggattcg aaggaaagaa ctgcgaactg gacgtaacat gcaacatcaa gaacggcaga  420
tgcgagcagt tctgcaaaaa cagcgccgac aacaaggtgg tgtgcagctg caccgaggga  480
taccgactgg cagaaaacca gaagtcctgc gaaccagcag tgccattccc atgcggaaga  540
gtgagcgtga gccaaaccag caagctcacc cgggccgaga ccgtgttccc cgacgtggac  600
tacgtaaaca gcaccgaagc cgaaaccatc ctggacaaca tcacccaaag cacccaaagc  660
ttcaacgact tcacccgggt ggtgggcgga gaagacgcca aaccaggcca attcccctgg  720
caggtggtgc tgaacggcaa agtggacgca ttctgcggag gcagcatcgt gaacgaaaaa  780
tggatcgtaa ccgccgccca ctgcgtggaa accggcgtga aaatcacagt ggtcgcaggc  840
gaacacaaca tcgaggagac agaacacaca gagcaaaagc gaaacgtgat ccgaatcatc  900
ccccaccaca actacaacgc agccatcaac aagtacaacc acgacatcgc cctgctggaa  960
ctggacgaac ccctggtgct aaacagctac gtgacaccca tctgcatcgc cgacaaggaa  1020
tacacgaaca tcttcctcaa attcggaagc ggctacgtaa gcggctgggg aagagtcttc  1080
cacaaaggga gaagcgccct ggtgctgcag tacctgagag tgccactggt ggaccgagcc  1140
acatgcctgc gaagcacaaa gttcaccatc tacaacaaca tgttctgcgc cggcttccac  1200
gaaggaggca gagacagctg ccaaggagac agcgggggac cccacgtgac cgaagtggaa  1260
gggaccagct tcctgaccgg aatcatcagc tggggcgaag agtgcgcaat gaaaggcaaa  1320
tacggaatat acaccaaggt aagccggtac gtcaactgga tcaaggaaaa aacaaagctc  1380
```

```
acctaa                                                               1386

SEQ ID NO: 52          moltype = DNA  length = 1386
FEATURE                Location/Qualifiers
misc_feature           1..1386
                       note = Description of Artificial Sequence:
                        Syntheticpolynucleotide
source                 1..1386
                       mol_type = other DNA
                       organism = synthetic construct
SEQUENCE: 52
atgcagcgcg tgaacatgat catggcagaa tcaccaggcc tcatcaccat ctgcctttta  60
ggatatctac tcagtgctga atgtacagtt tttcttgatc atgaaaacgc caacaaaatt  120
ctgaatcggc caaagaggta taattcaggt aaattggaag agtttgttca agggaacctt  180
gagagagaat gtatggaaga aaagtgtagt tttgaagaag cacgagaagt tttgaaaac   240
actgaaagaa caactgaatt ttggaagcag tatgttgatg gagatcagtg cgagagcaac  300
ccatgcctga acggcggcag ctgcaaggac gacatcaaca gctacgaatg ctggtgcccc  360
ttcggattcg aaggaaagaa ctgcgaactg gacgtaacat gcaacatcaa gaacggcaga  420
tgcgagcagt tctgcaaaaa cagcgccgac aacaaggtgg tgtgcagctg caccgaggga  480
taccgactgg cagaaaacca gaagtcctgc gaaccagcag tgccattccc atgcggaaga  540
gtgagcgtga gccaaaccag caagctcacc cgggccgaga ccgtgttccc cgacgtggac  600
tacgtaaaca gcaccgaagc cgaaaccatc ctggacaaca tcacccaaag cacccaaagc  660
ttcaacgact tcacccgggt ggtgggcgga gaagacgcca aaccaggcca attcccctgg  720
caggtggtgc tgaacggcaa agtggacgca ttctgcggag gcagcatcgt gaacgaaaaa  780
tggatcgtaa ccgccgccca ctgcgtggaa accggcgtga aaatcacagt ggtcgcaggc  840
gaacacaaca tcgaggagac agaacacaca gagcaaaagc gaaacgtgat ccgaatcatc  900
ccccaccaca actacaacgc agccatcaac aagtacaacc acgacatcgc cctgctggaa  960
ctggacgaac ccctggtgct aaacagctac gtgacaccca tctgcatcgc cgacaaggaa  1020
tacacgaaca tcttcctcaa attcggaagc ggctacgtaa gcggctgggg aagagtcttc  1080
cacaaaggga gaagcgccct ggtgctgcag tacctgagag tgccactggt ggaccgagcc  1140
acatgcctgc gaagcacaaa gttcaccatc tacaacaaca tgttctgcgc cggcttccac  1200
gaaggaggca gagacagctg ccaaggagac agcgggggac cccacgtgac cgaagtggaa  1260
gggaccagct tcctgaccgg aatcatcagc tggggcgaag agtgcgcaat gaaaggcaaa  1320
tacggaatat acaccaaggt aagccggtac gtcaactgga tcaaggaaaa aacaaagctc  1380
acctaa                                                               1386

SEQ ID NO: 53          moltype = DNA  length = 1386
FEATURE                Location/Qualifiers
misc_feature           1..1386
                       note = Description of Artificial Sequence:
                        Syntheticpolynucleotide
source                 1..1386
                       mol_type = other DNA
                       organism = synthetic construct
SEQUENCE: 53
atgcagcgcg tgaacatgat catggcagaa tcaccaggcc tcatcaccat ctgcctttta  60
ggatatctac tcagtgctga atgtacagtt tttcttgatc atgaaaacgc caacaaaatt  120
ctgaatcggc caaagaggta taattcaggt aaattggaag agtttgttca agggaacctt  180
gagagagaat gtatggaaga aaagtgtagt tttgaagaag cacgagaagt tttgaaaac   240
actgaaagaa caactgaatt ttggaagcag tatgttgatg gagatcagtg tgagtccaat  300
ccatgtttaa atggcggcag ttgcaaggat gacattaatt cctatgaatg ttggtgtccc  360
tttggatttg aaggaaagaa ctgtgaatta gatgtaacat gtaacattaa gaatggcaga  420
tgcgagcagt tttgtaaaaa tagtgctgat aacaaggtgg tgtgcagctg caccgaggga  480
taccgactgg cagaaaacca gaagtcctgc gaaccagcag tgccattccc atgcggaaga  540
gtgagcgtga gccaaaccag caagctcacc cgggccgaga ccgtgttccc cgacgtggac  600
tacgtaaaca gcaccgaagc cgaaaccatc ctggacaaca tcacccaaag cacccaaagc  660
ttcaacgact tcacccgggt ggtgggcgga gaagacgcca aaccaggcca attcccctgg  720
caggtggtgc tgaacggcaa agtggacgca ttctgcggag gcagcatcgt gaacgaaaaa  780
tggatcgtaa ccgccgccca ctgcgtggaa accggcgtga aaatcacagt ggtcgcaggc  840
gaacacaaca tcgaggagac agaacacaca gagcaaaagc gaaacgtgat ccgaatcatc  900
ccccaccaca actacaacgc agccatcaac aagtacaacc acgacatcgc cctgctggaa  960
ctggacgaac ccctggtgct aaacagctac gtgacaccca tctgcatcgc cgacaaggaa  1020
tacacgaaca tcttcctcaa attcggaagc ggctacgtaa gcggctgggg aagagtcttc  1080
cacaaaggga gaagcgccct ggtgctgcag tacctgagag tgccactggt ggaccgagcc  1140
acatgcctgc gaagcacaaa gttcaccatc tacaacaaca tgttctgcgc cggcttccac  1200
gaaggaggca gagacagctg ccaaggagac agcgggggac cccacgtgac cgaagtggaa  1260
gggaccagct tcctgaccgg aatcatcagc tggggcgaag agtgcgcaat gaaaggcaaa  1320
tacggaatat acaccaaggt aagccggtac gtcaactgga tcaaggaaaa aacaaagctc  1380
acctaa                                                               1386

SEQ ID NO: 54          moltype = DNA  length = 1386
FEATURE                Location/Qualifiers
misc_feature           1..1386
                       note = Description of Artificial Sequence:
                        Syntheticpolynucleotide
source                 1..1386
                       mol_type = other DNA
                       organism = synthetic construct
SEQUENCE: 54
```

```
atgcagcgcg tgaacatgat catggcagaa tcaccaggcc tcatcaccat ctgcctttta  60
ggatatctac tcagtgctga atgtacagtt tttcttgatc atgaaaacgc caacaaaatt  120
ctgaatcggc caaagaggta taattcaggt aaattggaag agtttgttca agggaacctt  180
gagagagaat gtatggaaga aaagtgtagt tttgaagaag cacgagaagt ttttgaaaac  240
actgaaagaa caactgaatt ttggaagcag tatgttgatg gagatcagtg tgagtccaat  300
ccatgtttaa atggcggcag ttgcaaggat gacattaatt cctatgaatg ttggtgtccc  360
tttggatttg aaggaaagaa ctgtgaatta gatgtaacat gtaacattaa gaatggcaga  420
tgcgagcagt tttgtaaaaa tagtgctgat aacaaggtgg tttgctcctg tactgaggga  480
tatcgacttg cagaaaacca gaagtcctgt gaaccagcag tgccatttcc atgtggaaga  540
gtttctgttt cacaaacttc taagctcacc cgtgctgaga ctgtttttcc tgatgtggac  600
tatgtaaata gcaccgaagc cgaaaccatc ctggacaaca tcacccaaag cacccaaagc  660
ttcaacgact tcacccgggt ggtgggcgga gaagacgcca aaccaggcca attcccctgg  720
caggtggtgc tgaacggcaa agtggacgca ttctgcggag gcagcatcgt gaacgaaaaa  780
tggatcgtaa ccgccgccca ctgcgtggaa accggcgtga aaatcacagt ggtcgcaggc  840
gaacacaaca tcgaggagac agaacacaca gagcaaaagc gaaacgtgat ccgaatcatc  900
ccccaccaca actacaacgc agccatcaac aagtacaacc acgacatcgc cctgctggaa  960
ctggacgaac ccctggtgct aaacagctac gtgacaccca tctgcatcgc cgacaaggaa  1020
tacacgaaca tcttcctcaa attcggaagc ggctacgtaa gcggctgggg aagagtcttc  1080
cacaaaggga gaagcgccct ggtgctgcag tacctgagag tgccactggt ggaccgagcc  1140
acatgcctgc gaagcacaaa gttcaccatc tacaacaaca tgttctgcgc cggcttccac  1200
gaaggaggca gagacagctg ccaaggagac agcgggggac cccacgtgac cgaagtggaa  1260
gggaccagct tcctgaccgg aatcatcagc tggggcgaag agtgcgcaat gaaaggcaaa  1320
tacggaatat acaccaaggt aagccggtac gtcaactgga tcaaggaaaa aacaaagctc  1380
acctaa                                                              1386

SEQ ID NO: 55          moltype = DNA  length = 1386
FEATURE                Location/Qualifiers
misc_feature           1..1386
                       note = Description of Artificial Sequence:
                        Syntheticpolynucleotide
source                 1..1386
                       mol_type = other DNA
                       organism = synthetic construct
SEQUENCE: 55
atgcagcgcg tgaacatgat catggcagaa agcccaggcc tcatcaccat ctgcctgctg  60
ggatacctac tcagcgccga atgcacagtg ttcctggacc acgaaaacgc caacaaaatc  120
ctgaaccggc caaagaggta caacagcggc aaactggaag agttcgtgca agggaacctg  180
gagagagaat gcatggaaga aaagtgcagc ttcgaagaag cacgagaagt gttcgaaaac  240
accgaaagaa caaccgaatt ctggaagcag tacgtggacg gagaccagtg cgagagcaac  300
ccatgcctga acggcggcag ctgcaaggac gacatcaaca gctacgaatg ctggtgcccc  360
ttcggattcg aaggaaagaa ctgcgaactg gacgtaacat gcaacatcaa gaacggcaga  420
tgcgagcagt tctgcaaaaa cagcgccgac aacaaggtgg tgtgcagctg caccgaggga  480
taccgactgg cagaaaacca gaagtcctgc gaaccagcag tgccattccc atgcggaaga  540
gtgagcgtga gccaaaccag caagctcacc cgggccgaga ccgtgttccc cgacgtggac  600
tacgtaaaca gcaccgaagc cgaaaccatc ctggacaaca tcacccaaag cacccaaagc  660
ttcaacgact tcacccgggt ggtgggcgga gaagacgcca aaccaggcca attcccctgg  720
caggtggtgc tgaacggcaa agtggacgca ttctgcggag gcagcatcgt gaacgaaaaa  780
tggatcgtaa ccgccgccca ctgcgtggaa accggcgtga aaatcacagt ggtcgcaggc  840
gaacacaaca tcgaggagac agaacacaca gagcaaaagc gaaacgtgat ccgaatcatc  900
ccccaccaca actacaacgc agccatcaac aagtacaacc acgacatcgc cctgctggaa  960
ctggacgaac ccctggtgct aaacagctac gtgacaccca tctgcatcgc cgacaaggaa  1020
tacacgaaca tcttcctcaa attcggaagc ggctacgtaa gcggctgggg aagagtcttc  1080
cacaaaggga gaagcgccct ggtgctgcag tacctgagag tgccactggt ggaccgagcc  1140
acatgcctgc gaagcacaaa gttcaccatc tacaacaaca tgttctgcgc cggcttccac  1200
gaaggaggca gagacagctg ccaaggagac agcgggggac cccacgtgac cgaagtggaa  1260
gggaccagct tcctgaccgg aatcatcagc tggggtgaag agtgtgcaat gaaaggcaaa  1320
tatggaatat ataccaaggt atcccggtat gtcaactgga ttaaggaaaa aacaaagctc  1380
acttaa                                                              1386

SEQ ID NO: 56          moltype = DNA  length = 1386
FEATURE                Location/Qualifiers
misc_feature           1..1386
                       note = Description of Artificial Sequence:
                        Syntheticpolynucleotide
source                 1..1386
                       mol_type = other DNA
                       organism = synthetic construct
SEQUENCE: 56
atgcagcgcg tgaacatgat catggcagaa agcccaggcc tcatcaccat ctgcctgctg  60
ggatacctac tcagcgccga atgcacagtg ttcctggacc acgaaaacgc caacaaaatc  120
ctgaaccggc caaagaggta caacagcggc aaactggaag agttcgtgca agggaacctg  180
gagagagaat gcatggaaga aaagtgcagc ttcgaagaag cacgagaagt gttcgaaaac  240
accgaaagaa caaccgaatt ctggaagcag tacgtggacg gagaccagtg cgagagcaac  300
ccatgcctga acggcggcag ctgcaaggac gacatcaaca gctacgaatg ctggtgcccc  360
ttcggattcg aaggaaagaa ctgcgaactg gacgtaacat gcaacatcaa gaacggcaga  420
tgcgagcagt tctgcaaaaa cagcgccgac aacaaggtgg tgtgcagctg caccgaggga  480
taccgactgg cagaaaacca gaagtcctgc gaaccagcag tgccattccc atgcggaaga  540
gtgagcgtga gccaaaccag caagctcacc cgggccgaga ccgtgttccc cgacgtggac  600
tacgtaaaca gcaccgaagc cgaaaccatc ctggacaaca tcacccaaag cacccaaagc  660
```

```
ttcaacgact tcacccgggt ggtgggcgga gaagacgcca aaccaggcca attcccctgg  720
caggtggtgc tgaacggcaa agtggacgca ttctgcggag gcagcatcgt gaacgaaaaa  780
tggatcgtaa ccgccgccca ctgcgtggaa accggcgtga aaatcacagt ggtcgcaggc  840
gaacacaaca tcgaggagac agaacacaca gagcaaaagc gaaacgtgat ccgaatcatc  900
ccccaccaca actacaacgc agccatcaac aagtacaacc acgacatcgc cctgctggaa  960
ctggacgaac ccctggtgct aaacagctac gtgacaccca tctgcatcgc cgacaaggaa  1020
tacacgaaca tcttcctcaa attcggaagc ggctacgtaa gcggctgggg aagagtcttc  1080
cacaaaggga gaagcgccct ggtgcttcag taccttagag ttccacttgt tgaccgagcc  1140
acatgtcttc gatctacaaa gttcaccatc tataacaaca tgttctgtgc tggcttccat  1200
gaaggaggta gagattcatg tcaaggagat agtgggggac cccatgttac tgaagtggaa  1260
gggaccagtt tcttaactgg aattattagc tggggtgaag agtgtgcaat gaaaggcaaa  1320
tatggaatat ataccaaggt atcccggtat gtcaactgga ttaaggaaaa aacaaagctc  1380
acttaa                                                            1386

SEQ ID NO: 57          moltype = DNA  length = 1386
FEATURE                Location/Qualifiers
misc_feature           1..1386
                       note = Description of Artificial Sequence:
                        Syntheticpolynucleotide
source                 1..1386
                       mol_type = other DNA
                       organism = synthetic construct
SEQUENCE: 57
atgcagcgcg tgaacatgat catggcagaa agcccaggcc tcatcaccat ctgcctgctg  60
ggatacctac tcagcgccga atgcacagtg ttcctggacc acgaaaacgc caacaaaatc  120
ctgaaccggc caaagaggta caacagcggc aaactggaag agttcgtgca agggaacctg  180
gagagagaat gcatggaaga aaagtgcagc ttcgaagaag cacgagaagt gttcgaaaac  240
accgaaagaa caaccgaatt ctggaagcag tacgtggacg gagaccagtg cgagagcaac  300
ccatgcctga acggcggcag ctgcaaggac gacatcaaca gctacgaatg ctggtgcccc  360
ttcggattcg aaggaaagaa ctgcgaactg gacgtaacat gcaacatcaa gaacggcaga  420
tgcgagcagt tctgcaaaaa cagcgccgac aacaaggtgg tgtgcagctg caccgaggga  480
taccgactgg cagaaaacca gaagtcctgc gaaccagcag tgccattccc atgcggaaga  540
gtgagcgtga gccaaaccag caagctcacc cgggccgaga ccgtgttccc cgacgtggac  600
tacgtaaaca gcaccgaagc cgaaaccatc ctggacaaca tcacccaaag cacccaaagc  660
ttcaacgact tcacccgggt ggtgggcgga gaagacgcca aaccaggcca attcccctgg  720
caggtggtgc tgaacggcaa agtggacgca ttctgcggag gcagcatcgt gaacgaaaaa  780
tggatcgtaa ccgccgccca ctgcgtggaa accggcgtga aaatcacagt ggtcgcaggc  840
gaacacaaca tcgaggagac agaacataca gagcaaaagc gaaatgtgat tcgaattatt  900
cctcaccaca actacaatgc agctattaat aagtacaacc atgacattgc ccttctggaa  960
ctggacgaac ccttagtgct aaacagctac gttacaccta tttgcattgc tgacaaggaa  1020
tacacgaaca tcttcctcaa atttggatct ggctatgtaa gtggctgggg aagagtcttc  1080
cacaaaggga gatcagcttt agttcttcag taccttagag ttccacttgt tgaccgagcc  1140
acatgtcttc gatctacaaa gttcaccatc tataacaaca tgttctgtgc tggcttccat  1200
gaaggaggta gagattcatg tcaaggagat agtgggggac cccatgttac tgaagtggaa  1260
gggaccagtt tcttaactgg aattattagc tggggtgaag agtgtgcaat gaaaggcaaa  1320
tatggaatat ataccaaggt atcccggtat gtcaactgga ttaaggaaaa aacaaagctc  1380
acttaa                                                            1386

SEQ ID NO: 58          moltype = DNA  length = 1386
FEATURE                Location/Qualifiers
misc_feature           1..1386
                       note = Description of Artificial Sequence:
                        Syntheticpolynucleotide
source                 1..1386
                       mol_type = other DNA
                       organism = synthetic construct
SEQUENCE: 58
atgcagcgcg tgaacatgat catggcagaa agcccaggcc tcatcaccat ctgcctgctg  60
ggatacctac tcagcgccga atgcacagtg ttcctggacc acgaaaacgc caacaaaatc  120
ctgaaccggc caaagaggta caacagcggc aaactggaag agttcgtgca agggaacctg  180
gagagagaat gcatggaaga aaagtgcagc ttcgaagaag cacgagaagt gttcgaaaac  240
accgaaagaa caaccgaatt ctggaagcag tacgtggacg gagaccagtg cgagagcaac  300
ccatgcctga acggcggcag ctgcaaggac gacatcaaca gctacgaatg ctggtgcccc  360
ttcggattcg aaggaaagaa ctgcgaactg gacgtaacat gcaacatcaa gaacggcaga  420
tgcgagcagt tctgcaaaaa cagcgccgac aacaaggtgg tgtgcagctg caccgaggga  480
taccgactgg cagaaaacca gaagtcctgc gaaccagcag tgccattccc atgcggaaga  540
gtgagcgtga gccaaaccag caagctcacc cgggccgaga ccgtgttccc cgacgtggac  600
tacgtaaaca gcaccgaagc cgaaaccatc ctggacaaca tcacccaaag cacccaaagc  660
ttcaacgact tcacccgggt ggtgggcgga gaagacgcca aaccaggtca attcccttgg  720
caggttgttt tgaatggtaa agttgatgca ttctgtggag gctctatcgt taatgaaaaa  780
tggattgtaa ctgctgccca ctgtgttgaa actggtgtta aaattacagt tgtcgcaggt  840
gaacataata ttgaggagac agaacataca gagcaaaagc gaaatgtgat tcgaattatt  900
cctcaccaca actacaatgc agctattaat aagtacaacc atgacattgc ccttctggaa  960
ctggacgaac ccttagtgct aaacagctac gttacaccta tttgcattgc tgacaaggaa  1020
tacacgaaca tcttcctcaa atttggatct ggctatgtaa gtggctgggg aagagtcttc  1080
cacaaaggga gatcagcttt agttcttcag taccttagag ttccacttgt tgaccgagcc  1140
acatgtcttc gatctacaaa gttcaccatc tataacaaca tgttctgtgc tggcttccat  1200
gaaggaggta gagattcatg tcaaggagat agtgggggac cccatgttac tgaagtggaa  1260
gggaccagtt tcttaactgg aattattagc tggggtgaag agtgtgcaat gaaaggcaaa  1320
```

```
tatggaatat ataccaaggt atcccggtat gtcaactgga ttaaggaaaa aacaaagctc  1380
acttaa                                                              1386

SEQ ID NO: 59          moltype = DNA  length = 1386
FEATURE                Location/Qualifiers
misc_feature           1..1386
                       note = Description of Artificial Sequence:
                        Syntheticpolynucleotide
source                 1..1386
                       mol_type = other DNA
                       organism = synthetic construct
SEQUENCE: 59
atgcagcgcg tgaacatgat catggcagaa agcccaggcc tcatcaccat ctgcctgctg  60
ggatatctac tcagcgccga atgcacagtg ttcctggacc acgaaaacgc caacaaaatc  120
ctgaaccggc caaagaggta caacagcggt aaactggaag agttcgtgca agggaacctg  180
gagagagaat gcatggaaga aaagtgcagc ttcgaagaag cacgagaagt gttcgaaaac  240
accgaaagaa caaccgaatt ctggaagcag tacgtggacg gagaccagtg cgagagcaac  300
ccatgcctga acggcggcag ctgcaaggac gacatcaaca gctacgaatg ctggtgcccc  360
ttcggattcg aaggaaagaa ctgcgaactg gacgtaacat gcaacatcaa gaacggcaga  420
tgcgagcagt tctgcaaaaa cagcgccgac aacaaggtgg tgtgcagctg caccgaggga  480
taccgacttg cagaaaacca gaagtcctgc gaaccagcag tgccattccc atgcggaaga  540
gtgagcgtta gccaaaccag caagctcacc cgggccgaga ccgtgttccc cgacgtggac  600
tacgtaaaca gcaccgaagc cgaaaccatc ctggacaaca tcacccaaag cacccaaagc  660
ttcaacgact tcacccgggt ggtgggcgga gaagacgcca aaccaggcca attcccctgg  720
caggtggtgc tgaacggcaa agtggacgca ttctgcggag gcagcatcgt taacgaaaaa  780
tggatcgtaa ccgccgccca ctgcgtggaa accggcgtga aaatcacagt ggtcgcaggc  840
gaacacaaca tcgaggagac agaacacaca gagcaaaagc gaaacgtgat ccgaatcatc  900
cctcaccaca actacaacgc agccatcaac aagtacaacc acgacatcgc cctgctggaa  960
ctggacgaac ccttagtgct aaacagctac gtgacaccca tctgcatcgc cgacaaggaa  1020
tacacgaaca tcttcctcaa attcggaagc ggctacgtaa gcggctgggg aagagtcttc  1080
cacaaaggga gaagcgccct ggtgctgcag tacctgagag tgccactggt ggaccgagcc  1140
acatgcctgc gaagcacaaa gttcaccatc tacaacaaca tgttctgcgc cggcttccac  1200
gaaggaggca gagacagctg ccaaggagac agcgggggac cccacgtgac cgaagtggaa  1260
gggaccagct tcctgaccgg aatcatcagc tggggcgaag agtgtgcaat gaaaggcaaa  1320
tacggaatat acaccaaggt aagccggtac gtcaactgga tcaaggaaaa aacaaagctc  1380
acctaa                                                              1386

SEQ ID NO: 60          moltype = DNA  length = 1386
FEATURE                Location/Qualifiers
misc_feature           1..1386
                       note = Description of Artificial Sequence:
                        Syntheticpolynucleotide
source                 1..1386
                       mol_type = other DNA
                       organism = synthetic construct
SEQUENCE: 60
atgcagcgcg tgaacatgat catggcagaa agcccaggcc tcatcaccat ctgcctgctg  60
ggatacctac tcagtgccga atgtacagtg ttcctggacc acgaaaacgc caacaaaatc  120
ctgaaccggc caaagaggta caactcaggc aaactggaag agttcgtgca agggaacctg  180
gagagagaat gcatggaaga aaagtgcagc ttcgaagaag cacgagaagt gtttgaaaac  240
actgaaagaa caaccgaatt ttggaagcag tacgtggatg gagatcagtg cgagagcaac  300
ccatgcctga atggcggcag ctgcaaggac gacatcaaca gctacgaatg ctggtgcccc  360
ttcggattcg aaggaaagaa ctgcgaactg gacgtaacat gcaacatcaa gaacggcaga  420
tgcgagcagt tttgtaaaaa cagcgccgac aacaaggtgg tgtgcagctg caccgaggga  480
taccgactgg cagaaaacca gaagtcctgc gaaccagcag tgccattccc atgcggaaga  540
gtgtctgtgt cacaaaccag caagctcacc cgggccgaga ccgtgttccc cgacgtggac  600
tacgtaaaca gcaccgaagc cgaaaccatc ctggataaca tcacccaaag cacccaaagc  660
ttcaatgact tcacccgggt ggtgggcgga gaagacgcca aaccaggcca attcccctgg  720
caggttgtgc tgaacggcaa agttgacgca ttctgcggag gcagcatcgt gaacgaaaaa  780
tggatcgtaa ccgctgccca ctgcgttgaa accggcgtga aaatcacagt ggtcgcaggc  840
gaacacaaca ttgaggagac agaacacaca gagcaaaagc gaaacgtgat ccgaattatc  900
ccccaccaca actacaacgc agccattaat aagtacaacc atgacatcgc cctgctggaa  960
ctggacgaac ccttagtgct aaacagctac gtgacaccca tctgcatcgc cgacaaggaa  1020
tacacgaaca tcttcctcaa attcggaagc ggctacgtaa gcggctgggg aagagtcttc  1080
cacaaaggga gaagcgccct ggttctgcag tacctgagag tgccactggt tgaccgagcc  1140
acatgcctgc gaagcacaaa gttcaccatc tacaacaaca tgttctgcgc cggcttccat  1200
gaaggaggta gagacagctg tcaaggagac agcgggggac cccacgttac tgaagtggaa  1260
gggaccagct tcctgaccgg aatcatcagc tggggcgaag agtgcgcaat gaaaggcaaa  1320
tacggaatat ataccaaggt aagccggtac gtcaactgga tcaaggaaaa aacaaagctc  1380
acttaa                                                              1386

SEQ ID NO: 61          moltype = DNA  length = 1386
FEATURE                Location/Qualifiers
misc_feature           1..1386
                       note = Description of Artificial Sequence:
                        Syntheticpolynucleotide
source                 1..1386
                       mol_type = other DNA
                       organism = synthetic construct
```

SEQUENCE: 61
atgcagcgcg tgaacatgat catggcagaa tcaccaggcc tcatcaccat ctgcctgtta 60
ggatacctac tcagcgccga atgtacagtg tttcttgacc acgaaaacgc caacaaaatc 120
ctgaatcggc caaagaggta taactcaggt aaactggaag agtttgtgca agggaacctg 180
gagagagaat gcatggaaga aaagtgcagc ttcgaagaag cacgagaagt gttcgaaaac 240
actgaaagaa caaccgaatt ttggaagcag tatgtggatg gagaccagtg cgagtccaac 300
ccatgcttaa acggcggcag ttgcaaggac gacatcaaca gctatgaatg ctggtgcccc 360
ttcggatttg aaggaaagaa ctgcgaactg gacgtaacat gtaacatcaa gaatggcaga 420
tgcgagcagt tctgtaaaaa tagcgccgac aacaaggtgg tgtgcagctg taccgaggga 480
taccgactgg cagaaaacca gaagtcctgc gaaccagcag tgccattccc atgcggaaga 540
gttagcgtga gccaaaccag caagctcacc cgggccgaga ccgtgttccc tgacgtggac 600
tacgtaaact ctaccgaagc tgaaaccatc ctggacaaca tcactcaaag cacccaatca 660
ttcaacgact tcacccgggt ggtgggcgga gaagatgcca aaccaggtca attcccttgg 720
caggtggtgt tgaacggcaa agtggacgca ttctgtggag gcagcatcgt gaacgaaaaa 780
tggatcgtaa ctgccgccca ctgcgtggaa accggcgtga aaatcacagt ggtcgcaggc 840
gaacacaata ttgaggagac agaacacaca gagcaaaagc gaaatgtgat ccgaattatc 900
cctcaccaca actacaacgc agctattaac aagtacaacc acgacattgc cctgctggaa 960
ctggacgaac ccctggtgct aaacagctac gttacaccta tctgcatcgc cgacaaggaa 1020
tacacgaaca tcttcctcaa attcggatct ggctacgtaa gcggctgggg aagagtcttc 1080
cacaaaggga gatcagccct ggtgcttcag taccttagag tgccacttgt ggaccgagcc 1140
acatgcctgc gaagcacaaa gttcaccatc tacaacaaca tgttctgtgc tggcttccac 1200
gaaggaggta gagacagctg tcaaggagat agcgggggac cccacgttac cgaagtggaa 1260
gggaccagct tcttaactgg aatcatcagc tggggcgaag agtgcgcaat gaaaggcaaa 1320
tacggaatat acaccaaggt atcccggtat gtcaactgga tcaaggaaaa aacaaagctc 1380
acctaa 1386

SEQ ID NO: 62 moltype = DNA length = 1386
FEATURE Location/Qualifiers
misc_feature 1..1386
note = Description of Artificial Sequence:
Syntheticpolynucleotide
source 1..1386
mol_type = other DNA
organism = synthetic construct
SEQUENCE: 62
atgcagcgcg tgaacatgat catggcagaa agcccaggcc tcatcaccat ctgccttctg 60
ggatatctac tcagcgccga atgcacagtt ttccttgacc acgaaaacgc caacaaaatc 120
ctgaatcggc caaagaggta taattcaggt aaactggaag agtttgttca agggaacctt 180
gagagagaat gcatggaaga aaagtgtagt tttgaagaag cacgagaagt gttcgaaaac 240
accgaaagaa caaccgaatt ttggaagcag tatgtggatg gagaccagtg cgagagcaat 300
ccatgcttaa atggcggcag ctgcaaggac gacattaatt cctatgaatg ctggtgcccc 360
tttggattcg aaggaaagaa ctgcgaatta gacgtaacat gcaacatcaa gaacggcaga 420
tgcgagcagt tttgtaaaaa tagtgctgac aacaaggtgg tttgcagctg caccgaggga 480
taccgactgg cagaaaacca gaagtcctgc gaaccagcag tgccattccc atgtggaaga 540
gtttctgtga gccaaacttc taagctcacc cgtgccgaga ccgttttccc tgacgtggac 600
tatgtaaatt ctaccgaagc cgaaaccatt ttggataaca tcacccaaag cacccaaagc 660
tttaacgact tcactcgggt ggttggcgga gaagacgcca aaccaggcca attcccttgg 720
caggtggttc tgaatggcaa agtggatgca ttctgtggag gctctatcgt gaacgaaaaa 780
tggatcgtaa ctgccgccca ctgcgttgaa accggcgtta aaattacagt ggtcgcaggc 840
gaacacaata ttgaggagac agaacacaca gagcaaaagc gaaacgtgat tcgaattatc 900
cctcaccaca actacaatgc agccattaac aagtacaacc atgacatcgc cctgctggaa 960
ctggacgaac ccctggtgct aaacagctac gttacaccta tttgcatcgc cgacaaggaa 1020
tacacgaaca tcttcctcaa atttggatct ggctatgtaa gcggctgggg aagagtcttc 1080
cacaaaggga gaagcgccct ggtgcttcag tacctgagag tgccacttgt ggaccgagcc 1140
acatgtctgc gaagcacaaa gttcaccatc tacaacaaca tgttctgcgc cggcttccac 1200
gaaggaggta gagactcatg ccaaggagat agcgggggac cccacgtgac cgaagtggaa 1260
gggaccagct tcctgactgg aattattagc tggggcgaag agtgcgcaat gaaaggcaaa 1320
tatggaatat acaccaaggt aagccggtat gtcaactgga tcaaggaaaa aacaaagctc 1380
acctaa 1386

SEQ ID NO: 63 moltype = DNA length = 1818
FEATURE Location/Qualifiers
misc_feature 1..1818
note = Description of Artificial Sequence:
Syntheticpolynucleotide
source 1..1818
mol_type = other DNA
organism = synthetic construct
SEQUENCE: 63
aggaaactta agtcaacaca acatatacaa aacaaacgaa tctcaagcaa tcaagcattc 60
tacttctatt gcagcaattt aaatcatttc ttttaaagca aaagcaattt tctgaaaatt 120
ttcaccattt acgaacgata gccatgcagc gcgtgaacat gatcatggca gaaagcccag 180
gcctcatcac catctgcctg ctgggatacc tactcagcgc cgaatgcaca gtgttcctgg 240
accacgaaaa cgccaacaaa atcctgaacc ggccaaagag gtacaacagc ggcaaactgg 300
aagagttcgt gcaagggaac ctggagagag aatgcatgga agaaaagtgc agcttcgaag 360
aagcacgaga agtgttcgaa aacaccgaaa gaacaaccga attctggaag cagtacgtgg 420
acggagacca gtgcgagagc aacccatgcc tgaacggcgg cagctgcaag gacgacatca 480
acagctacga atgctggtgc cccttcggat tcgaaggaaa gaactgcgaa ctggacgtaa 540
catgcaacat caagaacggc agatgcgagc agttctgcaa aaacagcgcc gacaacaagg 600

```
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg ggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgcgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 64          moltype = DNA  length = 1818
FEATURE                Location/Qualifiers
misc_feature           1..1818
                       note = Description of Artificial Sequence:
                        Syntheticpolynucleotide
source                 1..1818
                       mol_type = other DNA
                       organism = synthetic construct
SEQUENCE: 64
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaatcaccag  180
gcctcatcac catctgcctt ttaggatatc tactcagtgc tgaatgtaca gttttcctgg  240
accacgaaaa cgccaacaaa atcctgaacc ggccaaagag gtacaacagc ggcaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg ggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgcgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 65          moltype = DNA  length = 1818
FEATURE                Location/Qualifiers
misc_feature           1..1818
                       note = Description of Artificial Sequence:
                        Syntheticpolynucleotide
source                 1..1818
                       mol_type = other DNA
                       organism = synthetic construct
SEQUENCE: 65
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaatcaccag  180
gcctcatcac catctgcctt ttaggatatc tactcagtgc tgaatgtaca gtttttcttg  240
atcatgaaaa cgccaacaaa attctgaatc ggccaaagag gtataattca ggtaaattgg  300
aagagtttgt tcaagggaac cttgagagag aatgtatgga agaaaagtgt agttttgaag  360
aagcacgaga agtttttgaa aacactgaaa gaacaactga attttggaag cagtatgttg  420
```

```
atggagatca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg ggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgcgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                               1818

SEQ ID NO: 66          moltype = DNA  length = 1818
FEATURE                Location/Qualifiers
misc_feature           1..1818
                       note = Description of Artificial Sequence:
                        Syntheticpolynucleotide
source                 1..1818
                       mol_type = other DNA
                       organism = synthetic construct
SEQUENCE: 66
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaatcaccag  180
gcctcatcac catctgcctt ttaggatatc tactcagtgc tgaatgtaca gtttttcttg  240
atcatgaaaa cgccaacaaa attctgaatc ggccaaagag gtataattca ggtaaattgg  300
aagagtttgt tcaagggaac cttgagagag aatgtatgga agaaaagtgt agttttgaag  360
aagcacgaga agtttttgaa aacactgaaa gaacaactga attttggaag cagtatgttg  420
atggagatca gtgtgagtcc aatccatgtt taaatggcgg cagttgcaag gatgacatta  480
attcctatga atgttggtgt ccctttggat ttgaaggaaa gaactgtgaa ttagatgtaa  540
catgtaacat taagaatggc agatgcgagc agttttgtaa aaatagtgct gataacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg ggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgcgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                               1818

SEQ ID NO: 67          moltype = DNA  length = 1818
FEATURE                Location/Qualifiers
misc_feature           1..1818
                       note = Description of Artificial Sequence:
                        Syntheticpolynucleotide
source                 1..1818
                       mol_type = other DNA
                       organism = synthetic construct
SEQUENCE: 67
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaatcaccag  180
gcctcatcac catctgcctt ttaggatatc tactcagtgc tgaatgtaca gtttttcttg  240
```

```
atcatgaaaa cgccaacaaa attctgaatc ggccaaagag gtataattca ggtaaattgg  300
aagagtttgt tcaagggaac cttgagagag aatgtatgga agaaaagtgt agttttgaag  360
aagcacgaga agtttttgaa aacactgaaa gaacaactga attttggaag cagtatgttg  420
atggagatca gtgtgagtcc aatccatgtt taaatggcgg cagttgcaag gatgacatta  480
attcctatga atgttggtgt ccctttggat ttgaaggaaa gaactgtgaa ttagatgtaa  540
catgtaacat taagaatggc agatgcgagc agttttgtaa aaatagtgct gataacaagg  600
tggtttgctc ctgtactgag ggatatcgac ttgcagaaaa ccagaagtcc tgtgaaccag  660
cagtgccatt tccatgtgga agagtttctg tttcacaaac ttctaagctc acccgtgctg  720
agactgtttt tcctgatgtg gactatgtaa atagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgcgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                               1818

SEQ ID NO: 68          moltype = DNA  length = 1818
FEATURE                Location/Qualifiers
misc_feature           1..1818
                       note = Description of Artificial Sequence:
                        Syntheticpolynucleotide
source                 1..1818
                       mol_type = other DNA
                       organism = synthetic construct
SEQUENCE: 68
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatacc tactcagcgc cgaatgcaca gtgttcctgg  240
accacgaaaa cgccaacaaa atcctgaacc ggccaaagag gtacaacagc ggcaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggtg  1440
aagagtgtgc aatgaaaggc aaatatggaa tatataccaa ggtatcccgg tatgtcaact  1500
ggattaagga aaaaacaaag ctcacttaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                               1818

SEQ ID NO: 69          moltype = DNA  length = 1818
FEATURE                Location/Qualifiers
misc_feature           1..1818
                       note = Description of Artificial Sequence:
                        Syntheticpolynucleotide
source                 1..1818
                       mol_type = other DNA
                       organism = synthetic construct
SEQUENCE: 69
aggaaactta agtcaacaca acatatacaa aacaaacgaa tctcaagcaa tcaagcattc  60
```

```
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatacc tactcagcgc cgaatgcaca gtgttcctgg  240
accacgaaaa cgccaacaaa atcctgaacc ggccaaagag gtacaacagc ggcaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggtgctt cagtacctta  1260
gagttccact tgttgaccga gccacatgtc ttcgatctac aaagttcacc atctataaca  1320
acatgttctg tgctggcttc catgaaggag gtagagattc atgtcaagga gatagtgggg  1380
gaccccatgt tactgaagtg gaagggacca gtttcttaac tggaattatt agctggggtg  1440
aagagtgtgc aatgaaaggc aaatatggaa tatataccaa ggtatcccgg tatgtcaact  1500
ggattaagga aaaaacaaag ctcacttaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 70          moltype = DNA  length = 1818
FEATURE                Location/Qualifiers
misc_feature           1..1818
                       note = Description of Artificial Sequence:
                        Syntheticpolynucleotide
source                 1..1818
                       mol_type = other DNA
                       organism = synthetic construct
SEQUENCE: 70
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatacc tactcagcgc cgaatgcaca gtgttcctgg  240
accacgaaaa cgccaacaaa atcctgaacc ggccaaagag gtacaacagc ggcaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacat acagagcaaa  1020
agcgaaatgt gattcgaatt attcctcacc acaactacaa tgcagctatt aataagtaca  1080
accatgacat tgcccttctg gaactggacg aacccttagt gctaaacagc tacgttacac  1140
ctatttgcat tgctgacaag gaatacacga acatcttcct caaatttgga tctggctatg  1200
taagtggctg gggaagagtc ttccacaaag ggagatcagc tttagttctt cagtacctta  1260
gagttccact tgttgaccga gccacatgtc ttcgatctac aaagttcacc atctataaca  1320
acatgttctg tgctggcttc catgaaggag gtagagattc atgtcaagga gatagtgggg  1380
gaccccatgt tactgaagtg gaagggacca gtttcttaac tggaattatt agctggggtg  1440
aagagtgtgc aatgaaaggc aaatatggaa tatataccaa ggtatcccgg tatgtcaact  1500
ggattaagga aaaaacaaag ctcacttaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 71          moltype = DNA  length = 1818
FEATURE                Location/Qualifiers
misc_feature           1..1818
                       note = Description of Artificial Sequence:
                        Syntheticpolynucleotide
source                 1..1818
                       mol_type = other DNA
```

```
                         organism = synthetic construct
SEQUENCE: 71
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatacc tactcagcgc cgaatgcaca gtgttcctgg  240
accacgaaaa cgccaacaaa atcctgaacc ggccaaagag gtacaacagc ggcaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg tcaattccct tggcaggttg ttttgaatgg taaagttgat gcattctgtg  900
gaggctctat cgttaatgaa aaatggattg taactgctgc ccactgtgtt gaaactggtg  960
ttaaaattac agttgtcgca ggtgaacata atattgagga gacagaacat acagagcaaa  1020
agcgaaatgt gattcgaatt attcctcacc acaactacaa tgcagctatt aataagtaca  1080
accatgacat tgcccttctg gaactggacg aacccttagt gctaaacagc tacgttacac  1140
ctatttgcat tgctgacaag gaatacacga acatcttcct caaatttgga tctggctatg  1200
taagtggctg gggaagagtc ttccacaaag ggagatcagc tttagttctt cagtacctta  1260
gagttccact tgttgaccga gccacatgtc ttcgatctac aaagttcacc atctataaca  1320
acatgttctg tgctggcttc catgaaggag gtagagattc atgtcaagga gatagtgggg  1380
gaccccatgt tactgaagtg gaagggacca gtttcttaac tggaattatt agctggggtg  1440
aagagtgtgc aatgaaaggc aaatatggaa tatataccaa ggtatcccgg tatgtcaact  1500
ggattaagga aaaaacaaag ctcacttaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 72            moltype = DNA  length = 1818
FEATURE                  Location/Qualifiers
misc_feature             1..1818
                         note = Description of Artificial Sequence:
                          Syntheticpolynucleotide
source                   1..1818
                         mol_type = other DNA
                         organism = synthetic construct
SEQUENCE: 72
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatatc tactcagcgc cgaatgcaca gtgttcctgg  240
accacgaaaa cgccaacaaa atcctgaacc ggccaaagag gtacaacagc ggtaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac ttgcagaaaa ccagaagtcc tgcgaaccag  660
cagtgccatt cccatgcgga agagtgagcg ttagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgttaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atccctcacc acaactacaa cgcagccatc aacaagtaca  1080
accacgacat cgccctgctg gaactggacg aacccttagt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgtgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 73            moltype = DNA  length = 1818
FEATURE                  Location/Qualifiers
misc_feature             1..1818
                         note = Description of Artificial Sequence:
```

-continued

```
                         Syntheticpolynucleotide
source                  1..1818
                        mol_type = other DNA
                        organism = synthetic construct
SEQUENCE: 73
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatacc tactcagtgc cgaatgtaca gtgttcctgg  240
accacgaaaa cgccaacaaa atcctgaacc ggccaaagag gtacaactca ggcaaactgg  300
aagagttcgt gcaagggaac ctggagagag aatgcatgga agaaaagtgc agcttcgaag  360
aagcacgaga agtgtttgaa aacactgaaa gaacaaccga attttggaag cagtacgtgg  420
atggagatca gtgcgagagc aacccatgcc tgaatggcgg cagctgcaag gacgacatca  480
acagctacga atgctggtgc cccttcggat tcgaaggaaa gaactgcgaa ctggacgtaa  540
catgcaacat caagaacggc agatgcgagc agttttgtaa aaacagcgcc gacaacaagg  600
tggtgtgcag ctgcaccgag ggataccgac tggcagaaaa ccagaagtcc tgcgaaccag  660
cagtgccatt cccatgcgga agagtgtctg tgtcacaaac cagcaagctc acccgggccg  720
agaccgtgtt ccccgacgtg gactacgtaa acagcaccga agccgaaacc atcctggata  780
acatcaccca aagcacccaa agcttcaatg acttcacccg ggtggtgggc ggagagaagacg  840
ccaaaccagg ccaattcccc tggcaggttg tgctgaacgg caaagttgac gcattctgcg  900
gaggcagcat cgtgaacgaa aaatggatcg taaccgctgc ccactgcgtt gaaaccggcg  960
tgaaaatcac agtggtcgca ggcgaacaca acattgagga gacagaacac acagagcaaa  1020
agcgaaacgt gatccgaatt atcccccacc acaactacaa cgcagccatt aataagtaca  1080
accatgacat cgccctgctg gaactggacg aacccttagt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggttctg cagtacctga  1260
gagtgccact ggttgaccga gccacatgcc tgcgaagcac aaagttcacc atctacaaca  1320
acatgttctg cgccggcttc catgaaggag gtagagacag ctgtcaagga gacagcgggg  1380
gaccccacgt tactgaagtg gaagggacca gcttcctgac cggaatcatc agctggggcg  1440
aagagtgcgc aatgaaaggc aaatacggaa tatataccaa ggtaagccgg tacgtcaact  1500
ggatcaagga aaaaacaaag ctcacttaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                              1818

SEQ ID NO: 74           moltype = DNA  length = 1818
FEATURE                 Location/Qualifiers
misc_feature            1..1818
                        note = Description of Artificial Sequence:
                         Syntheticpolynucleotide
source                  1..1818
                        mol_type = other DNA
                        organism = synthetic construct
SEQUENCE: 74
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaatcaccag  180
gcctcatcac catctgcctg ttaggatacc tactcagcgc cgaatgtaca gtgtttcttg  240
accacgaaaa cgccaacaaa atcctgaatc ggccaaagag gtataactca ggtaaactgg  300
aagagtttgt gcaagggaac ctggagagag aatgcatgga agaaaagtgc agcttcgaag  360
aagcacgaga agtgttcgaa aacactgaaa gaacaaccga attttggaag cagtatgtgg  420
atggagacca gtgcgagtcc aacccatgct taaacggcgg cagttgcaag gacgacatca  480
acagctatga atgctggtgc cccttcggat ttgaaggaaa gaactgcgaa ctggacgtaa  540
catgtaacat caagaatggc agatgcgagc agttctgtaa aaatagcgcc gacaacaagg  600
tggtgtgcag ctgtaccgag ggataccgac tggcagaaaa ccagaagtcc tgcgaaccag  660
cagtgccatt cccatgcgga agagttagcg tgagccaaac cagcaagctc acccgggccg  720
agaccgtgtt ccctgacgtg gactacgtaa actctaccga agctgaaacc atcctggaca  780
acatcactca aagcacccaa tcattcaacg acttcacccg ggtggtgggc ggagaagatg  840
ccaaaccagg tcaattccct tggcaggtgg tgttgaacgg caaagtggac gcattctgtg  900
gaggcagcat cgtgaacgaa aaatggatcg taactgccgc ccactgcgtg gaaaccggcg  960
tgaaaatcac agtggtcgca ggcgaacaca atattgagga gacagaacac acagagcaaa  1020
agcgaaatgt gatccgaatt atccctcacc acaactacaa cgcagctatt aacaagtaca  1080
accacgacat tgccctgctg gaactggacg aacccctggt gctaaacagc tacgttacac  1140
ctatctgcat cgccgacaag gaatacacga acatcttcct caaattcgga tctggctacg  1200
taagcggctg gggaagagtc ttccacaaag ggagatcagc cctggtgctt cagtacctta  1260
gagtgccact tgtggaccga gccacatgcc tgcgaagcac aaagttcacc atctacaaca  1320
acatgttctg tgctggcttc cacgaaggag gtagagacag ctgtcaagga gatagcgggg  1380
gaccccacgt taccgaagtg gaagggacca gcttcttaac tggaatcatc agctggggcg  1440
aagagtgcgc aatgaaaggc aaatacggaa tatacaccaa ggtatcccgg tatgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                              1818

SEQ ID NO: 75           moltype = DNA  length = 1818
```

-continued

```
FEATURE              Location/Qualifiers
misc_feature         1..1818
                     note = Description of Artificial Sequence:
                      Syntheticpolynucleotide
source               1..1818
                     mol_type = other DNA
                     organism = synthetic construct
SEQUENCE: 75
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctt ctgggatatc tactcagcgc cgaatgcaca gttttccttg  240
accacgaaaa cgccaacaaa atcctgaatc ggccaaagag gtataattca ggtaaactgg  300
aagagtttgt tcaagggaac cttgagagag aatgcatgga agaaaagtgt agttttgaag  360
aagcacgaga agtgttcgaa aacaccgaaa gaacaaccga attttggaag cagtatgtgg  420
atggagacca gtgcgagagc aatccatgct taaatggcgg cagctgcaag gacgacatta  480
attcctatga atgctggtgc ccctttggat tcgaaggaaa gaactgcgaa ttagacgtaa  540
catgcaacat caagaacggc agatgcgagc agttttgtaa aaatagtgct gacaacaagg  600
tggtttgcag ctgcaccgag ggataccgac tggcagaaaa ccagaagtcc tgcgaaccag  660
cagtgccatt cccatgtgga agagtttctg tgagccaaac ttctaagctc acccgtgccg  720
agaccgtttt ccctgacgtg gactatgtaa attctaccga agccgaaacc attttggata  780
acatcaccca aagcacccaa agctttaacg acttcactcg ggtggttggc ggagaagacg  840
ccaaaccagg ccaattccct tggcaggtgg ttctgaatgg caaagtggat gcattctgtg  900
gaggctctat cgtgaacgaa aaatggatcg taactgccgc ccactgcgtt gaaaccggcg  960
ttaaaattac agtggtcgca ggcgaacaca atattgagga gacagaacac acagagcaaa  1020
agcgaaacgt gattcgaatt atccctcacc acaactacaa tgcagccatt aacaagtaca  1080
accatgacat cgccctgctg gaactggacg aacccctggt gctaaacagc tacgttacac  1140
ctatttgcat cgccgacaag gaatacacga acatcttcct caaatttgga tctggctatg  1200
taagcggctg gggaagagtc ttccacaaag ggagaagcgc cctggtgctt cagtacctga  1260
gagtgccact tgtggaccga gccacatgtc tgcgaagcac aaagttcacc atctacaaca  1320
acatgttctg cgccggcttc cacgaaggag gtagagactc atgccaagga gatagcgggg  1380
gaccccacgt gaccgaagtg gaagggacca gcttcctgac tggaattatt agctggggcg  1440
aagagtgcgc aatgaaaggc aaatatggaa tatacaccaa ggtaagccgg tatgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 76        moltype = RNA  length = 1818
FEATURE              Location/Qualifiers
misc_feature         1..1818
                     note = Description of Artificial Sequence:
                      Syntheticpolynucleotide
source               1..1818
                     mol_type = other RNA
                     organism = synthetic construct
SEQUENCE: 76
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatacc tactcagcgc cgaatgcaca gtgttcctgg  240
accacgaaaa cgccaacaaa atcctgaacc ggccaaagag gtacaacagc ggcaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgcgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
```

```
aaaaaaaaaa aaaaaaaa                                              1818

SEQ ID NO: 77          moltype = RNA  length = 1818
FEATURE                Location/Qualifiers
misc_feature           1..1818
                       note = Description of Artificial Sequence:
                        Syntheticpolynucleotide
source                 1..1818
                       mol_type = other RNA
                       organism = synthetic construct
SEQUENCE: 77
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaatcaccag  180
gcctcatcac catctgcctt ttaggatatc tactcagtgc tgaatgtaca gttttcctgg  240
accacgaaaa cgccaacaaa atcctgaacc ggccaaagag gtacaacagc ggcaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgcgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                              1818

SEQ ID NO: 78          moltype = RNA  length = 1818
FEATURE                Location/Qualifiers
misc_feature           1..1818
                       note = Description of Artificial Sequence:
                        Syntheticpolynucleotide
source                 1..1818
                       mol_type = other RNA
                       organism = synthetic construct
SEQUENCE: 78
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaatcaccag  180
gcctcatcac catctgcctt ttaggatatc tactcagtgc tgaatgtaca gtttttcttg  240
atcatgaaaa cgccaacaaa attctgaatc ggccaaagag gtataattca ggtaaattgg  300
aagagtttgt tcaagggaac cttgagagag aatgtatgga agaaaagtgt agttttgaag  360
aagcacgaga agtttttgaa aacactgaaa gaacaactga attttggaag cagtatgttg  420
atggagatca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgcgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
```

-continued

```
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 79          moltype = RNA  length = 1818
FEATURE                Location/Qualifiers
misc_feature           1..1818
                       note = Description of Artificial Sequence:
                        Syntheticpolynucleotide
source                 1..1818
                       mol_type = other RNA
                       organism = synthetic construct
SEQUENCE: 79
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaatcaccag  180
gcctcatcac catctgcctt ttaggatatc tactcagtgc tgaatgtaca gtttttcttg  240
atcatgaaaa cgccaacaaa attctgaatc ggccaaagag gtataattca ggtaaattgg  300
aagagtttgt tcaagggaac cttgagagag aatgtatgga agaaaagtgt agttttgaag  360
aagcacgaga agtttttgaa aacactgaaa gaacaactga attttggaag cagtatgttg  420
atggagatca gtgtgagtcc aatccatgtt taaatggcgg cagttgcaag gatgacatta  480
attcctatga atgttggtgt ccctttggat ttgaaggaaa gaactgtgaa ttagatgtaa  540
catgtaacat taagaatggc agatgcgagc agttttgtaa aaatagtgct gataacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg ggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgcgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 80          moltype = RNA  length = 1818
FEATURE                Location/Qualifiers
misc_feature           1..1818
                       note = Description of Artificial Sequence:
                        Syntheticpolynucleotide
source                 1..1818
                       mol_type = other RNA
                       organism = synthetic construct
SEQUENCE: 80
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaatcaccag  180
gcctcatcac catctgcctt ttaggatatc tactcagtgc tgaatgtaca gtttttcttg  240
atcatgaaaa cgccaacaaa attctgaatc ggccaaagag gtataattca ggtaaattgg  300
aagagtttgt tcaagggaac cttgagagag aatgtatgga agaaaagtgt agttttgaag  360
aagcacgaga agtttttgaa aacactgaaa gaacaactga attttggaag cagtatgttg  420
atggagatca gtgtgagtcc aatccatgtt taaatggcgg cagttgcaag gatgacatta  480
attcctatga atgttggtgt ccctttggat ttgaaggaaa gaactgtgaa ttagatgtaa  540
catgtaacat taagaatggc agatgcgagc agttttgtaa aaatagtgct gataacaagg  600
tggtttgctc ctgtactgag ggatatcgac ttgcagaaaa ccagaagtcc tgtgaaccag  660
cagtgccatt tccatgtgga agagtttctg tttcacaaac ttctaagctc acccgtgctg  720
agactgtttt tcctgatgtg gactatgtaa atagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg ggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
```

```
aagagtgcgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 81          moltype = RNA  length = 1818
FEATURE                Location/Qualifiers
misc_feature           1..1818
                       note = Description of Artificial Sequence:
                        Syntheticpolynucleotide
source                 1..1818
                       mol_type = other RNA
                       organism = synthetic construct
SEQUENCE: 81
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatacc tactcagcgc cgaatgcaca gtgttcctgg  240
accacgaaaa cgccaacaaa atcctgaacc ggccaaagag gtacaacagc ggcaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggtg  1440
aagagtgtgc aatgaaaggc aaatatggaa tatataccaa ggtatcccgg tatgtcaact  1500
ggattaagga aaaaacaaag ctcacttaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 82          moltype = RNA  length = 1818
FEATURE                Location/Qualifiers
misc_feature           1..1818
                       note = Description of Artificial Sequence:
                        Syntheticpolynucleotide
source                 1..1818
                       mol_type = other RNA
                       organism = synthetic construct
SEQUENCE: 82
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatacc tactcagcgc cgaatgcaca gtgttcctgg  240
accacgaaaa cgccaacaaa atcctgaacc ggccaaagag gtacaacagc ggcaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atcccccacc acaactacaa cgcagccatc aacaagtaca  1080
accacgacat cgccctgctg gaactggacg aacccctggt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggtgctt cagtacctta  1260
```

-continued

```
gagttccact tgttgaccga gccacatgtc ttcgatctac aaagttcacc atctataaca  1320
acatgttctg tgctggcttc catgaaggag gtagagattc atgtcaagga gatagtgggg  1380
gaccccatgt tactgaagtg gaagggacca gtttcttaac tggaattatt agctggggtg  1440
aagagtgtgc aatgaaaggc aaatatggaa tatataccaa ggtatcccgg tatgtcaact  1500
ggattaagga aaaaacaaag ctcacttaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 83           moltype = RNA  length = 1818
FEATURE                 Location/Qualifiers
misc_feature            1..1818
                        note = Description of Artificial Sequence:
                         Syntheticpolynucleotide
source                  1..1818
                        mol_type = other RNA
                        organism = synthetic construct
SEQUENCE: 83
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatacc tactcagcgc cgaatgcaca gtgttcctgg  240
accacgaaaa cgccaacaaa atcctgaacc ggccaaagag gtacaacagc ggcaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgtgaacgaa aaatggatcg taaccgccgc ccactgcgtg gaaaccggcg  960
tgaaaatcac agtggtcgca ggcgaacaca acatcgagga gacagaacat acagagcaaa  1020
agcgaaatgt gattcgaatt attcctcacc acaactacaa tgcagctatt aataagtaca  1080
accatgacat tgcccttctg gaactggacg aacccttagt gctaaacagc tacgttacac  1140
ctatttgcat tgctgacaag gaatacacga acatcttcct caaatttgga tctggctatg  1200
taagtggctg ggggaagagtc ttccacaaag ggagatcagc tttagttctt cagtacctta  1260
gagttccact tgttgaccga gccacatgtc ttcgatctac aaagttcacc atctataaca  1320
acatgttctg tgctggcttc catgaaggag gtagagattc atgtcaagga gatagtgggg  1380
gaccccatgt tactgaagtg gaagggacca gtttcttaac tggaattatt agctggggtg  1440
aagagtgtgc aatgaaaggc aaatatggaa tatataccaa ggtatcccgg tatgtcaact  1500
ggattaagga aaaaacaaag ctcacttaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 84           moltype = RNA  length = 1818
FEATURE                 Location/Qualifiers
misc_feature            1..1818
                        note = Description of Artificial Sequence:
                         Syntheticpolynucleotide
source                  1..1818
                        mol_type = other RNA
                        organism = synthetic construct
SEQUENCE: 84
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatacc tactcagcgc cgaatgcaca gtgttcctgg  240
accacgaaaa cgccaacaaa atcctgaacc ggccaaagag gtacaacagc ggcaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac tggcagaaaa ccagaagtcc tgcgaaccag  660
cagtgccatt cccatgcgga agagtgagcg tgagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg tcaattccct tggcaggttg ttttgaatgg taaagttgat gcattctgtg  900
gaggctctat cgttaatgaa aaatggattg taactgctgc ccactgtgtt gaaactggtg  960
ttaaaattac agttgtcgca ggtgaacata atattgagga gacagaacat acagagcaaa  1020
agcgaaatgt gattcgaatt attcctcacc acaactacaa tgcagctatt aataagtaca  1080
```

```
accatgacat tgcccttctg gaactggacg aacccttagt gctaaacagc tacgttacac  1140
ctatttgcat tgctgacaag gaatacacga acatcttcct caaatttgga tctggctatg  1200
taagtggctg gggaagagtc ttccacaaag ggagatcagc tttagttctt cagtacctta  1260
gagttccact tgttgaccga gccacatgtc ttcgatctac aaagttcacc atctataaca  1320
acatgttctg tgctggcttc catgaaggag gtagagattc atgtcaagga gatagtgggg  1380
gaccccatgt tactgaagtg gaagggacca gtttcttaac tggaattatt agctggggtg  1440
aagagtgtgc aatgaaaggc aaatatggaa tatataccaa ggtatcccgg tatgtcaact  1500
ggattaagga aaaaacaaag ctcacttaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 85          moltype = RNA  length = 1818
FEATURE                Location/Qualifiers
misc_feature           1..1818
                       note = Description of Artificial Sequence:
                        Syntheticpolynucleotide
source                 1..1818
                       mol_type = other RNA
                       organism = synthetic construct
SEQUENCE: 85
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatatc tactcagcgc cgaatgcaca gtgttcctgg  240
accacgaaaa cgccaacaaa atcctgaacc ggccaaagag gtacaacagc ggtaaactgg  300
aagagttcgt gcaagggaac ctggagagag aatgcatgga agaaaagtgc agcttcgaag  360
aagcacgaga agtgttcgaa aacaccgaaa gaacaaccga attctggaag cagtacgtgg  420
acggagacca gtgcgagagc aacccatgcc tgaacggcgg cagctgcaag gacgacatca  480
acagctacga atgctggtgc cccttcggat tcgaaggaaa gaactgcgaa ctggacgtaa  540
catgcaacat caagaacggc agatgcgagc agttctgcaa aaacagcgcc gacaacaagg  600
tggtgtgcag ctgcaccgag ggataccgac ttgcagaaaa ccagaagtcc tgcgaaccag  660
cagtgccatt cccatgcgga agagtgagcg ttagccaaac cagcaagctc acccgggccg  720
agaccgtgtt ccccgacgtg gactacgtaa acagcaccga agccgaaacc atcctggaca  780
acatcaccca aagcacccaa agcttcaacg acttcacccg ggtggtgggc ggagaagacg  840
ccaaaccagg ccaattcccc tggcaggtgg tgctgaacgg caaagtggac gcattctgcg  900
gaggcagcat cgttaacgaa aaatggatcg taaccgccgc ccactgcgtg gaaaccggcg  960
tgaaaatcac agtggtcgca ggcgaacaca acatcgagga gacagaacac acagagcaaa  1020
agcgaaacgt gatccgaatc atccctcacc acaactacaa cgcagccatc aacaagtaca  1080
accacgacat cgccctgctg gaactggacg aacccttagt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggtgctg cagtacctga  1260
gagtgccact ggtggaccga gccacatgcc tgcgaagcac aaagttcacc atctacaaca  1320
acatgttctg cgccggcttc cacgaaggag gcagagacag ctgccaagga gacagcgggg  1380
gaccccacgt gaccgaagtg gaagggacca gcttcctgac cggaatcatc agctggggcg  1440
aagagtgtgc aatgaaaggc aaatacggaa tatacaccaa ggtaagccgg tacgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 86          moltype = RNA  length = 1818
FEATURE                Location/Qualifiers
misc_feature           1..1818
                       note = Description of Artificial Sequence:
                        Syntheticpolynucleotide
source                 1..1818
                       mol_type = other RNA
                       organism = synthetic construct
SEQUENCE: 86
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctg ctgggatacc tactcagtgc cgaatgtaca gtgttcctgg  240
accacgaaaa cgccaacaaa atcctgaacc ggccaaagag gtacaactca ggcaaactgg  300
aagagttcgt gcaagggaac ctggagagag aatgcatgga agaaaagtgc agcttcgaag  360
aagcacgaga agtgtttgaa aacactgaaa gaacaaccga attttggaag cagtacgtgg  420
atggagatca gtgcgagagc aacccatgcc tgaatggcgg cagctgcaag gacgacatca  480
acagctacga atgctggtgc cccttcggat tcgaaggaaa gaactgcgaa ctggacgtaa  540
catgcaacat caagaacggc agatgcgagc agttttgtaa aaacagcgcc gacaacaagg  600
tggtgtgcag ctgcaccgag ggataccgac tggcagaaaa ccagaagtcc tgcgaaccag  660
cagtgccatt cccatgcgga agagtgtctg tgtcacaaac cagcaagctc acccgggccg  720
agaccgtgtt ccccgacgtg gactacgtaa acagcaccga agccgaaacc atcctggata  780
acatcaccca aagcacccaa agcttcaatg acttcacccg ggtggtgggc ggagaagacg  840
ccaaaccagg ccaattcccc tggcaggttg tgctgaacgg caaagttgac gcattctgcg  900
```

```
gaggcagcat cgtgaacgaa aaatggatcg taaccgctgc ccactgcgtt gaaaccggcg  960
tgaaaatcac agtggtcgca ggcgaacaca acattgagga gacagaacac acagagcaaa  1020
agcgaaacgt gatccgaatt atcccccacc acaactacaa cgcagccatt aataagtaca  1080
accatgacat cgccctgctg gaactggacg aacccttagt gctaaacagc tacgtgacac  1140
ccatctgcat cgccgacaag gaatacacga acatcttcct caaattcgga agcggctacg  1200
taagcggctg gggaagagtc ttccacaaag ggagaagcgc cctggttctg cagtacctga  1260
gagtgccact ggttgaccga gccacatgcc tgcgaagcac aaagttcacc atctacaaca  1320
acatgttctg cgccggcttc catgaaggag gtagagacag ctgtcaagga gacagcgggg  1380
gaccccacgt tactgaagtg gaagggacca gcttcctgac cggaatcatc agctggggcg  1440
aagagtgcgc aatgaaaggc aaatacggaa tatataccaa ggtaagccgg tacgtcaact  1500
ggatcaagga aaaaacaaag ctcacttaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 87          moltype = RNA  length = 1818
FEATURE                Location/Qualifiers
misc_feature           1..1818
                       note = Description of Artificial Sequence:
                        Syntheticpolynucleotide
source                 1..1818
                       mol_type = other RNA
                       organism = synthetic construct
SEQUENCE: 87
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaatcaccag  180
gcctcatcac catctgcctg ttaggatacc tactcagcgc cgaatgtaca gtgtttcttg  240
accacgaaaa cgccaacaaa atcctgaatc ggccaaagag gtataactca ggtaaactgg  300
aagagtttgt gcaagggaac ctggagagag aatgcatgga agaaaagtgc agcttcgaag  360
aagcacgaga agtgttcgaa aacactgaaa gaacaaccga attttggaag cagtatgtgg  420
atggagacca gtgcgagtcc aacccatgct taaacggcgg cagttgcaag gacgacatca  480
acagctatga atgctggtgc cccttcggat ttgaaggaaa gaactgcgaa ctggacgtaa  540
catgtaacat caagaatggc agatgcgagc agttctgtaa aaatagcgcc gacaacaagg  600
tggtgtgcag ctgtaccgag ggataccgac tggcagaaaa ccagaagtcc tgcgaaccag  660
cagtgccatt cccatgcgga agagttagcg tgagccaaac cagcaagctc acccgggccg  720
agaccgtgtt ccctgacgtg gactacgtaa actctaccga agctgaaacc atcctggaca  780
acatcactca aagcacccaa tcattcaacg acttcacccg ggtggtgggc ggagaagatg  840
ccaaaccagg tcaattccct tggcaggtgg tgttgaacgg caaagtggac gcattctgtg  900
gaggcagcat cgtgaacgaa aaatggatcg taactgccgc ccactgcgtg gaaaccggcg  960
tgaaaatcac agtggtcgca ggcgaacaca atattgagga gacagaacac acagagcaaa  1020
agcgaaatgt gatccgaatt atccctcacc acaactacaa cgcagctatt aacaagtaca  1080
accacgacat tgccctgctg gaactggacg aacccctggt gctaaacagc tacgttacac  1140
ctatctgcat cgccgacaag gaatacacga acatcttcct caaattcgga tctggctacg  1200
taagcggctg gggaagagtc ttccacaaag ggagatcagc cctggtgctt cagtacctta  1260
gagtgccact tgtggaccga gccacatgcc tgcgaagcac aaagttcacc atctacaaca  1320
acatgttctg tgctggcttc cacgaaggag gtagagacag ctgtcaagga gatagcgggg  1380
gaccccacgt taccgaagtg gaagggacca gcttcttaac tggaatcatc agctggggcg  1440
aagagtgcgc aatgaaaggc aaatacggaa tatacaccaa ggtatcccgg tatgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 88          moltype = RNA  length = 1818
FEATURE                Location/Qualifiers
misc_feature           1..1818
                       note = Description of Artificial Sequence:
                        Syntheticpolynucleotide
source                 1..1818
                       mol_type = other RNA
                       organism = synthetic construct
SEQUENCE: 88
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgcagc gcgtgaacat gatcatggca gaaagcccag  180
gcctcatcac catctgcctt ctgggatatc tactcagcgc cgaatgcaca gttttccttg  240
accacgaaaa cgccaacaaa atcctgaatc ggccaaagag gtataattca ggtaaactgg  300
aagagtttgt tcaagggaac cttgagagag aatgcatgga agaaaagtgt agttttgaag  360
aagcacgaga agtgttcgaa aacaccgaaa gaacaaccga attttggaag cagtatgtgg  420
atggagacca gtgcgagagc aatccatgct taaatggcgg cagctgcaag gacgacatta  480
attcctatga atgctggtgc ccctttggat tcgaaggaaa gaactgcgaa ttagacgtaa  540
catgcaacat caagaacggc agatgcgagc agttttgtaa aaatagtgct gacaacaagg  600
tggtttgcag ctgcaccgag ggataccgac tggcagaaaa ccagaagtcc tgcgaaccag  660
cagtgccatt cccatgtgga agagtttctg tgagccaaac ttctaagctc acccgtgccg  720
```

```
agaccgtttt ccctgacgtg gactatgtaa attctaccga agccgaaacc attttggata  780
acatcaccca aagcacccaa agctttaacg acttcactcg ggtggttggc ggagaagacg  840
ccaaaccagg ccaattccct tggcaggtgg ttctgaatgg caaagtggat gcattctgtg  900
gaggctctat cgtgaacgaa aaatggatcg taactgccgc ccactgcgtt gaaaccggcg  960
ttaaaattac agtggtcgca ggcgaacaca atattgagga gacagaacac acagagcaaa  1020
agcgaaacgt gattcgaatt atccctcacc acaactacaa tgcagccatt aacaagtaca  1080
accatgacat cgccctgctg gaactggacg aacccctggt gctaaacagc tacgttacac  1140
ctatttgcat cgccgacaag gaatacacga acatcttcct caaatttgga tctggctatg  1200
taagcggctg ggaagagtc ttccacaaag ggagaagcgc cctggtgctt cagtacctga  1260
gagtgccact tgtggaccga gccacatgtc tgcgaagcac aaagttcacc atctacaaca  1320
acatgttctg cgccggcttc cacgaaggag gtagagactc atgccaagga gatagcgggg  1380
gaccccacgt gaccgaagtg gaagggacca gcttcctgac tggaattatt agctggggcg  1440
aagagtgcgc aatgaaaggc aaatatggaa tatacaccaa ggtaagccgg tatgtcaact  1500
ggatcaagga aaaaacaaag ctcacctaac tcgagctagt gactgactag gatctggtta  1560
ccactaaacc agcctcaaga acacccgaat ggagtctcta agctacataa taccaactta  1620
cacttacaaa atgttgtccc ccaaaatgta gccattcgta tctgctccta ataaaaagaa  1680
agtttcttca cattctagaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaa                                                1818

SEQ ID NO: 89          moltype = DNA  length = 1257
FEATURE                Location/Qualifiers
source                 1..1257
                       mol_type = genomic DNA
                       organism = Homo sapiens
SEQUENCE: 89
atgccgtctt ctgtctcgtg gggcatcctc ctgctggcag gcctgtgctg cctggtccct  60
gtctccctgg ctgaggatcc ccagggagat gctgcccaga agacagatac atcccaccat  120
gatcaggatc acccaacctt caacaagatc acccccaacc tggctgagtt cgccttcagc  180
ctataccgcc agctggcaca ccagtccaac agcaccaata tcttcttctc cccagtgagc  240
atcgctacag cctttgcaat gctctccctg gggaccaagg ctgacactca cgatgaaatc  300
ctggagggcc tgaatttcaa cctcacggag attccggagg ctcagatcca tgaaggcttc  360
caggaactcc tccgtaccct caaccagcca gacagccagc tccagctgac caccggcaat  420
ggcctgttcc tcagcgaggg cctgaagcta gtggataagt tttggagga tgttaaaaag  480
ttgtaccact cagaagcctt cactgtcaac ttcggggaca ccgaagaggc caagaaacag  540
atcaacgatt acgtggagaa gggtactcaa gggaaaattg tggatttggt caaggagctt  600
gacagagaca cagtttttgc tctggtgaat tacatcttct ttaaaggcaa atgggagaga  660
ccctttgaag tcaaggacac cgaggaagag gacttccacg tggaccaggt gaccaccgtg  720
aaggtgccta tgatgaagcg tttaggcatg tttaacatcc agcactgtaa gaagctgtcc  780
agctgggtgc tgctgatgaa atacctgggc aatgccaccg ccatcttctt cctgcctgat  840
gaggggaaac tacagcacct ggaaaatgaa ctcacccacg atatcatcac caagttcctg  900
gaaaatgaag acagaaggtc tgccagctta catttaccca aactgtccat tactggaacc  960
tatgatctga agagcgtcct gggtcaactg ggcatcacta aggtcttcag caatggggct  1020
gacctctccg gggtcacaga ggaggcaccc ctgaagctct ccaaggccgt gcataaggct  1080
gtgctgacca tcgacgagaa agggactgaa gctgctgggg ccatgttttt agaggccata  1140
cccatgtcta tccccccga ggtcaagttc aacaaaccct ttgtcttctt aatgattgaa  1200
caaaatacca agtctcccct cttcatggga aaagtggtga atcccaccca aaaataa     1257

SEQ ID NO: 90          moltype = DNA  length = 1257
FEATURE                Location/Qualifiers
misc_feature           1..1257
                       note = Description of Artificial Sequence:
                        Syntheticpolynucleotide
source                 1..1257
                       mol_type = other DNA
                       organism = synthetic construct
SEQUENCE: 90
atgccgagca gcgtcagctg gggcatcctc ctgctggcag gcctgtgctg cctggtcccc  60
gtcagcctgg ccgaggaccc ccagggagac gccgcccaga agacagacac aagccaccac  120
gaccaggacc acccaacctt caacaagatc acccccaacc tggccgagtt cgccttcagc  180
ctataccgcc agctggcaca ccagagcaac agcaccaaca tcttcttcag cccagtgagc  240
atcgccacag ccttcgcaat gctcagcctg gggaccaagg ccgacaccca cgacgaaatc  300
ctggagggcc tgaacttcaa cctcacggag atcccggagg cccagatcca cgaaggcttc  360
caggaactcc tccggaccct caaccagcca gacagccagc tccagctgac caccggcaac  420
ggcctgttcc tcagcgaggg cctgaagcta gtggacaagt tcctggagga cgtgaaaaag  480
ctgtaccaca gcgaagcctt caccgtcaac ttcggggaca ccgaagaggc caagaaacag  540
atcaacgact acgtggagaa gggcacccaa gggaaaatcg tggacctggt caaggagctg  600
gacagagaca cagtgttcgc cctggtgaac tacatcttct tcaaaggcaa atgggagaga  660
cccttcgaag tcaaggacac cgaggaagag gacttccacg tggaccaggt gaccaccgtg  720
aaggtgccca tgatgaagcg gctgggcatg ttcaacatcc agcactgcaa gaagctgagc  780
agctgggtgc tgctgatgaa atacctgggc aacgccaccg ccatcttctt cctgcccgac  840
gaggggaaac tacagcacct ggaaaacgaa ctcacccacg acatcatcac caagttcctg  900
gaaaacgaag acagaaggag cgccagcctg cacctgccca aactgagcat caccggaacc  960
tacgacctga agtccgtgct gggccaactg ggcatcacca aggtcttcag caacggggcc  1020
gacctcagcg gggtcacaga ggaggcaccc ctgaagctca gcaaggccgt gcacaaggcc  1080
gtgctgacca tcgacgagaa agggaccgaa gccgccgggg ccatgttcct ggaggccata  1140
cccatgagca tccccccga ggtcaagttc aacaaaccct tcgtcttcct gatgatcgaa  1200
caaaacacca agagccccct cttcatggga aaagtggtga accccaccca aaaataa     1257
```

```
SEQ ID NO: 91          moltype = DNA  length = 1257
FEATURE                Location/Qualifiers
misc_feature           1..1257
                       note = Description of Artificial Sequence:
                        Syntheticpolynucleotide
source                 1..1257
                       mol_type = other DNA
                       organism = synthetic construct
SEQUENCE: 91
atgccgtctt ctgtctcgtg gggcatcctc ctgctggcag gcctgtgctg cctggtccct  60
gtctccctgg ctgaggatcc ccagggagat gctgcccaga agacagatac atcccaccat  120
gatcaggatc acccaacctt caacaagatc acccccaacc tggctgagtt cgccttcagc  180
ctataccgcc agctggcaca ccagtccaac agcaccaata tcttcttctc cccagtgagc  240
atcgctacag cctttgcaat gctctccctg gggaccaagg ctgacactca cgatgaaatc  300
ctggagggcc tgaacttcaa cctcacggag atcccggagg cccagatcca cgaaggcttc  360
caggaactcc tccggaccct caaccagcca gacagccagc tccagctgac caccggcaac  420
ggcctgttcc tcagcgaggg cctgaagcta gtggacaagt tcctggagga cgtgaaaaag  480
ctgtaccaca gcgaagcctt caccgtcaac ttcggggaca ccgaagaggc caagaaacag  540
atcaacgact acgtggagaa gggcacccaa gggaaaatcg tggacctggt caaggagctg  600
gacagagaca cagtgttcgc cctggtgaac tacatcttct tcaaaggcaa atgggagaga  660
cccttcgaag tcaaggacac cgaggaagag gacttccacg tggaccaggt gaccaccgtg  720
aaggtgccca tgatgaagcg gctgggcatg ttcaacatcc agcactgcaa gaagctgagc  780
agctgggtgc tgctgatgaa atacctgggc aacgccaccg ccatcttctt cctgcccgac  840
gaggggaaac tacagcacct ggaaaacgaa ctcacccacg acatcatcac caagttcctg  900
gaaaacgaag acagaaggag cgccagcctg cacctgccca aactgagcat caccggaacc  960
tacgacctga agtccgtgct gggccaactg ggcatcacca aggtcttcag caacggggcc  1020
gacctcagcg gggtcacaga ggaggcaccc ctgaagctca gcaaggccgt gcacaaggcc  1080
gtgctgacca tcgacgagaa agggaccgaa gccgccgggg ccatgttcct ggaggccata  1140
cccatgagca tcccccccga ggtcaagttc aacaaaccct tcgtcttcct gatgatcgaa  1200
caaaacacca agagccccct cttcatggga aaagtggtga accccaccca aaaataa     1257

SEQ ID NO: 92          moltype = DNA  length = 1257
FEATURE                Location/Qualifiers
misc_feature           1..1257
                       note = Description of Artificial Sequence:
                        Syntheticpolynucleotide
source                 1..1257
                       mol_type = other DNA
                       organism = synthetic construct
SEQUENCE: 92
atgccgtctt ctgtctcgtg gggcatcctc ctgctggcag gcctgtgctg cctggtccct  60
gtctccctgg ctgaggatcc ccagggagat gctgcccaga agacagatac atcccaccat  120
gatcaggatc acccaacctt caacaagatc acccccaacc tggctgagtt cgccttcagc  180
ctataccgcc agctggcaca ccagtccaac agcaccaata tcttcttctc cccagtgagc  240
atcgctacag cctttgcaat gctctccctg gggaccaagg ctgacactca cgatgaaatc  300
ctggagggcc tgaatttcaa cctcacggag attccggagg ctcagatcca tgaaggcttc  360
caggaactcc tccgtaccct caaccagcca gacagccagc tccagctgac caccggcaat  420
ggcctgttcc tcagcgaggg cctgaagcta gtggataagt tttggagga tgttaaaaag  480
ttgtaccact cagaagcctt cactgtcaac ttcggggaca ccgaagaggc caagaaacag  540
atcaacgatt acgtggagaa gggtactcaa gggaaaattg tggatttggt caaggagctt  600
gacagagaca cagtttttgc tctggtgaat tacatcttct tcaaaggcaa atgggagaga  660
cccttcgaag tcaaggacac cgaggaagag gacttccacg tggaccaggt gaccaccgtg  720
aaggtgccca tgatgaagcg gctgggcatg ttcaacatcc agcactgcaa gaagctgagc  780
agctgggtgc tgctgatgaa atacctgggc aacgccaccg ccatcttctt cctgcccgac  840
gaggggaaac tacagcacct ggaaaacgaa ctcacccacg acatcatcac caagttcctg  900
gaaaacgaag acagaaggag cgccagcctg cacctgccca aactgagcat caccggaacc  960
tacgacctga agtccgtgct gggccaactg ggcatcacca aggtcttcag caacggggcc  1020
gacctcagcg gggtcacaga ggaggcaccc ctgaagctca gcaaggccgt gcacaaggcc  1080
gtgctgacca tcgacgagaa agggaccgaa gccgccgggg ccatgttcct ggaggccata  1140
cccatgagca tcccccccga ggtcaagttc aacaaaccct tcgtcttcct gatgatcgaa  1200
caaaacacca agagccccct cttcatggga aaagtggtga accccaccca aaaataa     1257

SEQ ID NO: 93          moltype = DNA  length = 1257
FEATURE                Location/Qualifiers
misc_feature           1..1257
                       note = Description of Artificial Sequence:
                        Syntheticpolynucleotide
source                 1..1257
                       mol_type = other DNA
                       organism = synthetic construct
SEQUENCE: 93
atgccgtctt ctgtctcgtg gggcatcctc ctgctggcag gcctgtgctg cctggtccct  60
gtctccctgg ctgaggatcc ccagggagat gctgcccaga agacagatac atcccaccat  120
gatcaggatc acccaacctt caacaagatc acccccaacc tggctgagtt cgccttcagc  180
ctataccgcc agctggcaca ccagtccaac agcaccaata tcttcttctc cccagtgagc  240
atcgctacag cctttgcaat gctctccctg gggaccaagg ctgacactca cgatgaaatc  300
ctggagggcc tgaatttcaa cctcacggag attccggagg ctcagatcca tgaaggcttc  360
caggaactcc tccgtaccct caaccagcca gacagccagc tccagctgac caccggcaat  420
ggcctgttcc tcagcgaggg cctgaagcta gtggataagt tttggagga tgttaaaaag  480
```

```
ttgtaccact cagaagcctt cactgtcaac ttcggggaca ccgaagaggc caagaaacag  540
atcaacgatt acgtggagaa gggtactcaa gggaaaattg tggatttggt caaggagctt  600
gacagagaca cagtttttgc tctggtgaat tacatcttct ttaaaggcaa atgggagaga  660
ccctttgaag tcaaggacac cgaggaagag gacttccacg tggaccaggt gaccaccgtg  720
aaggtgccta tgatgaagcg tttaggcatg tttaacatcc agcactgtaa gaagctgtcc  780
agctgggtgc tgctgatgaa atacctgggc aatgccaccg ccatcttctt cctgcctgat  840
gaggggaaac tacagcacct ggaaaatgaa ctcacccacg atatcatcac caagttcctg  900
gaaaatgaag acagaaggtc tgccagctta catttaccca aactgtccat tactggaacc  960
tatgatctga agtccgtgct gggtcaactg ggcatcacca aggtcttcag caacggggcc  1020
gacctcagcg gggtcacaga ggaggcaccc ctgaagctca gcaaggccgt gcacaaggcc  1080
gtgctgacca tcgacgagaa agggaccgaa gccgccgggg ccatgttcct ggaggccata  1140
cccatgagca tcccccccga ggtcaagttc aacaaaccct tcgtcttcct gatgatcgaa  1200
caaaacacca agagccccct cttcatggga aaagtggtga accccaccca aaaataa     1257

SEQ ID NO: 94           moltype = DNA  length = 1257
FEATURE                 Location/Qualifiers
misc_feature            1..1257
                        note = Description of Artificial Sequence:
                         Syntheticpolynucleotide
source                  1..1257
                        mol_type = other DNA
                        organism = synthetic construct
SEQUENCE: 94
atgccgagca gcgtcagctg ggcatcctc ctgctggcag gcctgtgctg cctggtcccc  60
gtcagcctgg ccgaggaccc ccagggagac gccgcccaga agacagacac aagccaccac  120
gaccaggacc acccaacctt caacaagatc acccccaacc tggccgagtt cgccttcagc  180
ctataccgcc agctggcaca ccagagcaac agcaccaaca tcttcttcag cccagtgagc  240
atcgccacag ccttcgcaat gctcagcctg gggaccaagg ccgacaccca cgacgaaatc  300
ctggagggcc tgaacttcaa cctcacggag atcccggagg cccagatcca cgaaggcttc  360
caggaactcc tccggaccct caaccagcca gacagccagc tccagctgac caccggcaac  420
ggcctgttcc tcagcgaggg cctgaagcta gtggacaagt tcctggagga cgtgaaaaag  480
ctgtaccaca gcgaagcctt caccgtcaac ttcggggaca ccgaagaggc caagaaacag  540
atcaacgact acgtggagaa gggcacccaa gggaaaatcg tggacctggt caaggagctg  600
gacagagaca cagtgttcgc cctggtgaac tacatcttct tcaaaggcaa atgggagaga  660
cccttcgaag tcaaggacac cgaggaagag gacttccacg tggaccaggt gaccaccgtg  720
aaggtgccca tgatgaagcg gctgggcatg ttcaacatcc agcactgcaa gaagctgagc  780
agctgggtgc tgctgatgaa atacctgggc aacgccaccg ccatcttctt cctgcccgac  840
gaggggaaac tacagcacct ggaaaacgaa ctcacccacg acatcatcac caagttcctg  900
gaaaacgaag acagaaggag cgccagcctg cacctgccca aactgagcat tactggaacc  960
tatgatctga agtccgtgct gggtcaactg ggcatcacta aggtcttcag caatggggct  1020
gacctctccg gggtcacaga ggaggcaccc ctgaagctct ccaaggccgt gcataaggct  1080
gtgctgacca tcgacgagaa agggactgaa gctgctgggg ccatgttttt agaggccata  1140
cccatgtcta tcccccccga ggtcaagttc aacaaaccct ttgtcttctt aatgattgaa  1200
caaaatacca agtctcccct cttcatggga aaagtggtga atcccaccca aaaataa     1257

SEQ ID NO: 95           moltype = DNA  length = 1257
FEATURE                 Location/Qualifiers
misc_feature            1..1257
                        note = Description of Artificial Sequence:
                         Syntheticpolynucleotide
source                  1..1257
                        mol_type = other DNA
                        organism = synthetic construct
SEQUENCE: 95
atgccgagca gcgtcagctg ggcatcctc ctgctggcag gcctgtgctg cctggtcccc  60
gtcagcctgg ccgaggaccc ccagggagac gccgcccaga agacagacac aagccaccac  120
gaccaggacc acccaacctt caacaagatc acccccaacc tggccgagtt cgccttcagc  180
ctataccgcc agctggcaca ccagagcaac agcaccaaca tcttcttcag cccagtgagc  240
atcgccacag ccttcgcaat gctcagcctg gggaccaagg ccgacaccca cgacgaaatc  300
ctggagggcc tgaacttcaa cctcacggag atcccggagg cccagatcca cgaaggcttc  360
caggaactcc tccggaccct caaccagcca gacagccagc tccagctgac caccggcaac  420
ggcctgttcc tcagcgaggg cctgaagcta gtggacaagt tcctggagga cgtgaaaaag  480
ctgtaccaca gcgaagcctt caccgtcaac ttcggggaca ccgaagaggc caagaaacag  540
atcaacgact acgtggagaa gggcacccaa gggaaaatcg tggacctggt caaggagctt  600
gacagagaca cagtttttgc tctggtgaat tacatcttct ttaaaggcaa atgggagaga  660
ccctttgaag tcaaggacac cgaggaagag gacttccacg tggaccaggt gaccaccgtg  720
aaggtgccta tgatgaagcg tttaggcatg tttaacatcc agcactgtaa gaagctgtcc  780
agctgggtgc tgctgatgaa atacctgggc aatgccaccg ccatcttctt cctgcctgat  840
gaggggaaac tacagcacct ggaaaatgaa ctcacccacg atatcatcac caagttcctg  900
gaaaatgaag acagaaggtc tgccagctta catttaccca aactgtccat tactggaacc  960
tatgatctga agtccgtgct gggtcaactg ggcatcacta aggtcttcag caatggggct  1020
gacctctccg gggtcacaga ggaggcaccc ctgaagctct ccaaggccgt gcataaggct  1080
gtgctgacca tcgacgagaa agggactgaa gctgctgggg ccatgttttt agaggccata  1140
cccatgtcta tcccccccga ggtcaagttc aacaaaccct ttgtcttctt aatgattgaa  1200
caaaatacca agtctcccct cttcatggga aaagtggtga atcccaccca aaaataa     1257

SEQ ID NO: 96           moltype = DNA  length = 1257
FEATURE                 Location/Qualifiers
misc_feature            1..1257
```

```
                          note = Description of Artificial Sequence:
                           Syntheticpolynucleotide
source                    1..1257
                          mol_type = other DNA
                          organism = synthetic construct
SEQUENCE: 96
atgccgagca gcgtcagctg gggcatcctc ctgctggcag gcctgtgctg cctggtcccc  60
gtcagcctgg ccgaggaccc ccagggagac gccgcccaga agacagacac aagccaccac  120
gaccaggacc acccaacctt caacaagatc acccccaacc tggccgagtt cgccttcagc  180
ctataccgcc agctggcaca ccagagcaac agcaccaaca tcttcttcag cccagtgagc  240
atcgccacag cctttgcaat gctctccctg gggaccaagg ctgacactca cgatgaaatc  300
ctggagggcc tgaatttcaa cctcacggag attccggagg ctcagatcca tgaaggcttc  360
caggaactcc tccgtaccct caaccagcca gacagccagc tccagctgac caccggcaat  420
ggcctgttcc tcagcgaggg cctgaagcta gtggataagt tttggagga tgttaaaaag  480
ttgtaccact cagaagcctt cactgtcaac ttcggggaca ccgaagaggc caagaaacag  540
atcaacgatt acgtggagaa gggtactcaa gggaaaattg tggatttggt caaggagctt  600
gacagagaca cagtttttgc tctggtgaat tacatcttct ttaaaggcaa atgggagaga  660
ccctttgaag tcaaggacac cgaggaagag gacttccacg tggaccaggt gaccaccgtg  720
aaggtgccta tgatgaagcg tttaggcatg tttaacatcc agcactgtaa gaagctgtcc  780
agctgggtgc tgctgatgaa atacctgggc aatgccaccg ccatcttctt cctgcctgat  840
gaggggaaac tacagcacct ggaaaatgaa ctcacccacg atatcatcac caagttcctg  900
gaaaatgaag acagaaggtc tgccagctta catttaccca aactgtccat tactggaacc  960
tatgatctga agtccgtgct gggtcaactg ggcatcacta aggtcttcag caatggggct  1020
gacctctccg gggtcacaga ggaggcaccc ctgaagctct ccaaggccgt gcataaggct  1080
gtgctgacca tcgacgagaa agggactgaa gctgctgggg ccatgttttt agaggccata  1140
cccatgtcta tcccccccga ggtcaagttc aacaaaccct ttgtcttctt aatgattgaa  1200
caaaatacca agtctcccct cttcatggga aaagtggtga atcccaccca aaaataa     1257

SEQ ID NO: 97             moltype = DNA  length = 1257
FEATURE                   Location/Qualifiers
misc_feature              1..1257
                          note = Description of Artificial Sequence:
                           Syntheticpolynucleotide
source                    1..1257
                          mol_type = other DNA
                          organism = synthetic construct
SEQUENCE: 97
atgccgagca gcgtctcgtg gggcatcctc ctgctggcag gcctgtgctg cctggtcccc  60
gtcagcctgg ccgaggaccc ccagggagat gctgcccaga agacagacac atcccaccac  120
gaccaggacc acccaacctt caacaagatc acccccaacc tggctgagtt cgccttcagc  180
ctataccgcc agctggcaca ccagagcaac agcaccaata tcttcttcag cccagtgagc  240
atcgctacag ccttcgcaat gctcagcctg gggaccaagg ccgacaccca cgatgaaatc  300
ctggagggcc tgaatttcaa cctcacggag atcccggagg ctcagatcca cgaaggcttc  360
caggaactcc tccggaccct caaccagcca gacagccagc tccagctgac caccggcaac  420
ggcctgttcc tcagcgaggg cctgaagcta gtggacaagt tcctggagga cgttaaaaag  480
ctgtaccaca gcgaagcctt caccgtcaac ttcggggaca ccgaagaggc caagaaacag  540
atcaacgatt acgtggagaa gggcacccaa gggaaaatcg tggacctggt caaggagctt  600
gacagagaca cagtgtttgc cctggtgaac tacatcttct tcaaaggcaa atgggagaga  660
cccttcgaag tcaaggacac cgaggaagag gacttccacg tggaccaggt gaccaccgtg  720
aaggtgccca tgatgaagcg gttaggcatg ttcaacatcc agcactgcaa gaagctgagc  780
agctgggtgc tgctgatgaa atacctgggc aacgccaccg ccatcttctt cctgcccgac  840
gaggggaaac tacagcacct ggaaaacgaa ctcacccacg acatcatcac caagttcctg  900
gaaaacgaag acagaaggag cgccagcctg catctgccca aactgagcat tactggaacc  960
tacgatctga agtccgtgct gggtcaactg ggcatcacca aggtcttcag caatggggcc  1020
gacctcagcg gggtcacaga ggaggcaccc ctgaagctca gcaaggccgt gcacaaggct  1080
gtgctgacca tcgacgagaa agggaccgaa gccgctgggg ccatgttcct ggaggccata  1140
cccatgagca tcccccccga ggtcaagttc aacaaaccct ttgtcttcct gatgatcgaa  1200
caaaacacca agtctcccct cttcatggga aaagtggtga accccaccca aaaataa     1257

SEQ ID NO: 98             moltype = DNA  length = 1257
FEATURE                   Location/Qualifiers
misc_feature              1..1257
                          note = Description of Artificial Sequence:
                           Syntheticpolynucleotide
source                    1..1257
                          mol_type = other DNA
                          organism = synthetic construct
SEQUENCE: 98
atgccgtctt ctgtctcgtg gggcatcctc ctgctggcag gcctgtgctg cctggtcccc  60
gtctccctgg ctgaggaccc ccagggagat gccgcccaga agacagacac atcccaccat  120
gaccaggacc acccaacctt caacaagatc acccccaacc tggccgagtt cgccttcagc  180
ctataccgcc agctggcaca ccagagcaac agcaccaaca tcttcttctc cccagtgagc  240
atcgccacag cctttgcaat gctctccctg gggaccaagg ccgacaccca cgacgaaatc  300
ctggagggcc tgaatttcaa cctcacggag atcccggagg ctcagatcca tgaaggcttc  360
caggaactcc tccggaccct caaccagcca gacagccagc tccagctgac caccggcaat  420
ggcctgttcc tcagcgaggg cctgaagcta gtggataagt tcctggagga tgttaaaaag  480
ctgtaccaca gcgaagcctt caccgtcaac ttcggggaca ccgaagaggc caagaaacag  540
atcaacgatt acgtggagaa gggcacccaa gggaaaatcg tggacctggt caaggagctt  600
gacagagaca cagtgtttgc tctggtgaat tacatcttct ttaaaggcaa atgggagaga  660
```

```
ccctttgaag tcaaggacac cgaggaagag gacttccacg tggaccaggt gaccaccgtg  720
aaggtgccta tgatgaagcg gttaggcatg tttaacatcc agcactgcaa gaagctgagc  780
agctgggtgc tgctgatgaa atacctgggc aatgccaccg ccatcttctt cctgcctgat  840
gaggggaaac tacagcacct ggaaaacgaa ctcacccacg acatcatcac caagttcctg  900
gaaaatgaag acagaaggtc tgccagctta cacttaccca aactgagcat tactggaacc  960
tacgatctga agtccgtgct gggccaactg ggcatcacta aggtcttcag caacggggct  1020
gacctctccg ggtcacagga ggaggcaccc ctgaagctca gcaaggccgt gcacaaggct  1080
gtgctgacca tcgacgagaa agggaccgaa gctgccgggg ccatgtttct ggaggccata  1140
cccatgtcta tccccccccga ggtcaagttc aacaaaccct ttgtcttcct gatgatcgaa  1200
caaaatacca agagcccccct cttcatggga aaagtggtga accccaccca aaaataa     1257
```

```
SEQ ID NO: 99          moltype = DNA  length = 1257
FEATURE                Location/Qualifiers
misc_feature           1..1257
                       note = Description of Artificial Sequence:
                        Syntheticpolynucleotide
source                 1..1257
                       mol_type = other DNA
                       organism = synthetic construct
SEQUENCE: 99
atgccgagca gcgtcagctg gggcatcctc ctgctggcag gcctgtgctg cctggtccct  60
gtctccctgg ctgaggatcc ccagggagat gctgcccaga agacagatac atcccaccat  120
gatcaggatc acccaacctt caacaagatc acccccaacc tggctgagtt cgccttcagc  180
ctataccgcc agctggcaca ccagtccaac agcaccaata tcttcttctc cccagtgagc  240
atcgctacag ccttcgcaat gctctccctg gggaccaagg ctgacactca cgatgaaatc  300
ctggagggcc tgaatttcaa cctcacggag attccggagg cccagatcca tgaaggcttc  360
caggaactcc tccgtaccct caaccagcca gacagccagc tccagctgac caccggcaat  420
ggcctgttcc tcagcgaggg cctgaagcta gtggataagt ttttggagga tgttaaaaag  480
ctgtaccaca gcgaagcctt cactgtcaac ttcggggaca ccgaagaggc caagaaacag  540
atcaacgatt acgtggagaa gggtactcaa gggaaaattg tggatttggt caaggagctt  600
gacagagaca cagtttttgc tctggtgaat tacatcttct tcaaaggcaa atgggagaga  660
ccctttgaag tcaaggacac cgaggaagag gacttccacg tggaccaggt gaccaccgtg  720
aaggtgccta tgatgaagcg gttaggcatg ttcaacatcc agcactgtaa gaagctgtcc  780
agctgggtgc tgctgatgaa atacctgggc aatgccaccg ccatcttctt cctgcctgat  840
gaggggaaac tacagcacct ggaaaatgaa ctcacccacg atatcatcac caagttcctg  900
gaaaatgaag acagaaggag cgccagctta catttaccca aactgagcat tactggaacc  960
tacgatctga agtccgtgct gggtcaactg ggcatcacta aggtcttcag caacggggct  1020
gacctctccg ggtcacagga ggaggcaccc ctgaagctct ccaaggccgt gcataaggct  1080
gtgctgacca tcgacgagaa agggactgaa gctgctgggg ccatgttttt agaggccata  1140
cccatgtcta tccccccccga ggtcaagttc aacaaaccct ttgtcttcct gatgatcgaa  1200
caaaatacca agagcccccct cttcatggga aaagtggtga atcccaccca aaaataa     1257
```

```
SEQ ID NO: 100         moltype = DNA  length = 1689
FEATURE                Location/Qualifiers
misc_feature           1..1689
                       note = Description of Artificial Sequence:
                        Syntheticpolynucleotide
source                 1..1689
                       mol_type = other DNA
                       organism = synthetic construct
SEQUENCE: 100
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtcag ctggggcatc ctcctgctgg  180
caggcctgtg ctgcctggtc cccgtcagcc tggccgagga cccccaggga gacgccgccc  240
agaagacaga cacaagccac cacgaccagg accacccaac cttcaacaag atcacccccca  300
acctggccga gttcgccttc agcctatacc gccagctggc acaccagagc aacagcacca  360
acatcttctt cagcccagtg agcatcgcca cagccttcgc aatgctcagc ctggggacca  420
aggccgacac ccacgacgaa atcctggagg gcctgaactt caacctcacg gagatcccgg  480
aggcccagat ccacgaaggc ttccaggaac tcctccggac cctcaaccag ccagacagcc  540
agctccagct gaccaccggc aacggcctgt tcctcagcga gggcctgaag ctagtggaca  600
agttcctgga ggacgtgaaa aagctgtacc acagcgaagc cttcaccgtc aacttcgggg  660
acaccgaaga ggccaagaaa cagatcaacg actacgtgga gaagggcacc caagggaaaa  720
tcgtggacct ggtcaaggag ctggacagag acacagtgtt cgccctggtg aactacatct  780
tcttcaaagg caaatgggag agacccttcg aagtcaagga caccgaggaa gaggacttcc  840
acgtggacca ggtgaccacc gtgaaggtgc ccatgatgaa gcggctgggc atgttcaaca  900
tccagcactg caagaagctg agcagctggg tgctgctgat gaaatacctg ggcaacgcca  960
ccgccatctt cttcctgccc gacgagggga aactacagca cctggaaaac gaactcaccc  1020
acgacatcat caccaagttc ctggaaaacg aagacagaag gagcgccagc ctgcacctgc  1080
ccaaactgag catcaccgga acctacgacc tgaagtccgt gctgggccaa ctgggcatca  1140
ccaaggtctt cagcaacggg gccgacctca gcggggtcac agaggaggca cccctgaagc  1200
tcagcaaggc cgtgcacaag gccgtgctga ccatcgacga gaaagggacc gaagccgccg  1260
gggccatgtt cctggaggcc atacccatga gcatcccccc cgaggtcaag ttcaacaaac  1320
ccttcgtctt cctgatgatc gaacaaaaca ccaagagccc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
```

```
aaaaaaaaa                                                         1689

SEQ ID NO: 101          moltype = DNA  length = 1689
FEATURE                 Location/Qualifiers
misc_feature            1..1689
                        note = Description of Artificial Sequence:
                         Syntheticpolynucleotide
source                  1..1689
                        mol_type = other DNA
                        organism = synthetic construct
SEQUENCE: 101
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccgt cttctgtctc gtggggcatc ctcctgctgg  180
caggcctgtg ctgcctggtc cctgtctccc tggctgagga tccccaggga gatgctgccc  240
agaagacaga tacatcccac catgatcagg atcacccaac cttcaacaag atcaccccca  300
acctggctga gttcgccttc agcctatacc gccagctggc acaccagtcc aacagcacca  360
atatcttctt ctccccagtg agcatcgcta cagcctttgc aatgctctcc ctggggacca  420
aggctgacac tcacgatgaa atcctggagg gcctgaactt caacctcacg gagatcccgg  480
aggcccagat ccacgaaggc ttccaggaac tcctccggac cctcaaccag ccagacagcc  540
agctccagct gaccaccggc aacggcctgt tcctcagcga gggcctgaag ctagtggaca  600
agttcctgga ggacgtgaaa aagctgtacc acagcgaagc cttcaccgtc aacttcgggg  660
acaccgaaga ggccaagaaa cagatcaacg actacgtgga gaagggcacc caagggaaaa  720
tcgtggacct ggtcaaggag ctggacagag acacagtgtt cgccctggtg aactacatct  780
tcttcaaagg caaatgggag agacccttcg aagtcaagga caccgaggaa gaggacttcc  840
acgtggacca ggtgaccacc gtgaaggtgc ccatgatgaa gcggctgggc atgttcaaca  900
tccagcactg caagaagctg agcagctggg tgctgctgat gaaatacctg ggcaacgcca  960
ccgccatctt cttcctgccc gacgagggga aactacagca cctggaaaac gaactcaccc  1020
acgacatcat caccaagttc ctggaaaacg aagacagaag gagcgccagc ctgcacctgc  1080
ccaaactgag catcaccgga acctacgacc tgaagtccgt gctgggccaa ctgggcatca  1140
ccaaggtctt cagcaacggg gccgacctca gcggggtcac agaggaggca cccctgaagc  1200
tcagcaaggc cgtgcacaag gccgtgctga ccatcgacga gaaagggacc gaagccgccg  1260
gggccatgtt cctggaggcc atacccatga gcatcccccc cgaggtcaag ttcaacaaac  1320
ccttcgtctt cctgatgatc gaacaaaaca ccaagagccc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                         1689

SEQ ID NO: 102          moltype = DNA  length = 1689
FEATURE                 Location/Qualifiers
misc_feature            1..1689
                        note = Description of Artificial Sequence:
                         Syntheticpolynucleotide
source                  1..1689
                        mol_type = other DNA
                        organism = synthetic construct
SEQUENCE: 102
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccgt cttctgtctc gtggggcatc ctcctgctgg  180
caggcctgtg ctgcctggtc cctgtctccc tggctgagga tccccaggga gatgctgccc  240
agaagacaga tacatcccac catgatcagg atcacccaac cttcaacaag atcaccccca  300
acctggctga gttcgccttc agcctatacc gccagctggc acaccagtcc aacagcacca  360
atatcttctt ctccccagtg agcatcgcta cagcctttgc aatgctctcc ctggggacca  420
aggctgacac tcacgatgaa atcctggagg gcctgaattt caacctcacg gagattccgg  480
aggctcagat ccatgaaggc ttccaggaac tcctccgtac cctcaaccag ccagacagcc  540
agctccagct gaccaccggc aatggcctgt tcctcagcga gggcctgaag ctagtggata  600
agtttttgga ggatgttaaa aagttgtacc actcagaagc cttcactgtc aacttcgggg  660
acaccgaaga ggccaagaaa cagatcaacg attacgtgga gaagggtact caagggaaaa  720
ttgtggattt ggtcaaggag cttgacagag acacagtttt tgctctggtg aattacatct  780
tcttcaaagg caaatgggag agacccttcg aagtcaagga caccgaggaa gaggacttcc  840
acgtggacca ggtgaccacc gtgaaggtgc ccatgatgaa gcggctgggc atgttcaaca  900
tccagcactg caagaagctg agcagctggg tgctgctgat gaaatacctg ggcaacgcca  960
ccgccatctt cttcctgccc gacgagggga aactacagca cctggaaaac gaactcaccc  1020
acgacatcat caccaagttc ctggaaaacg aagacagaag gagcgccagc ctgcacctgc  1080
ccaaactgag catcaccgga acctacgacc tgaagtccgt gctgggccaa ctgggcatca  1140
ccaaggtctt cagcaacggg gccgacctca gcggggtcac agaggaggca cccctgaagc  1200
tcagcaaggc cgtgcacaag gccgtgctga ccatcgacga gaaagggacc gaagccgccg  1260
gggccatgtt cctggaggcc atacccatga gcatcccccc cgaggtcaag ttcaacaaac  1320
ccttcgtctt cctgatgatc gaacaaaaca ccaagagccc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                         1689
```

```
SEQ ID NO: 103          moltype = DNA  length = 1689
FEATURE                 Location/Qualifiers
misc_feature            1..1689
                        note = Description of Artificial Sequence:
                         Syntheticpolynucleotide
source                  1..1689
                        mol_type = other DNA
                        organism = synthetic construct
SEQUENCE: 103
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccgt cttctgtctc gtggggcatc ctcctgctgg  180
caggcctgtg ctgcctggtc cctgtctccc tggctgagga tccccaggga gatgctgccc  240
agaagacaga tacatcccac catgatcagg atcacccaac cttcaacaag atcaccccca  300
acctggctga gttcgccttc agcctatacc gccagctggc acaccagtcc aacagcacca  360
atatcttctt ctccccagtg agcatcgcta cagcctttgc aatgctctcc ctggggacca  420
aggctgacac tcacgatgaa atcctggagg gcctgaattt caacctcacg gagattccgg  480
aggctcagat ccatgaaggc ttccaggaac tcctccgtac cctcaaccag ccagacagcc  540
agctccagct gaccaccggc aatggcctgt tcctcagcga gggcctgaag ctagtggata  600
agtttttgga ggatgttaaa aagttgtacc actcagaagc cttcactgtc aacttcgggg  660
acaccgaaga ggccaagaaa cagatcaacg attacgtgga gaagggtact caagggaaaa  720
ttgtggattt ggtcaaggag cttgacagag acacagtttt tgctctggtg aattacatct  780
tctttaaagg caaatgggag agaccctttg aagtcaagga caccgaggaa gaggacttcc  840
acgtggacca ggtgaccacc gtgaaggtgc ctatgatgaa gcgtttaggc atgtttaaca  900
tccagcactg taagaagctg tccagctggg tgctgctgat gaaatacctg ggcaatgcca  960
ccgccatctt cttcctgcct gatgagggga aactacagca cctggaaaat gaactcaccc  1020
acgatatcat caccaagttc ctggaaaatg aagacagaag gtctgccagc ttacatttac  1080
ccaaactgtc cattactgga acctatgatc tgaagtccgt gctgggtcaa ctgggcatca  1140
ccaaggtctt cagcaacggg gccgacctca gcggggtcac agaggaggca cccctgaagc  1200
tcagcaaggc cgtgcacaag gccgtgctga ccatcgacga gaaagggacc gaagccgccg  1260
gggccatgtt cctggaggcc atacccatga gcatcccccc cgaggtcaag ttcaacaaac  1320
ccttcgtctt cctgatgatc gaacaaaaca ccaagagccc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 104          moltype = DNA  length = 1689
FEATURE                 Location/Qualifiers
misc_feature            1..1689
                        note = Description of Artificial Sequence:
                         Syntheticpolynucleotide
source                  1..1689
                        mol_type = other DNA
                        organism = synthetic construct
SEQUENCE: 104
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtcag ctggggcatc ctcctgctgg  180
caggcctgtg ctgcctggtc cccgtcagcc tggccgagga cccccaggga gacgccgccc  240
agaagacaga cacaagccac cacgaccagg accacccaac cttcaacaag atcaccccca  300
acctggccga gttcgccttc agcctatacc gccagctggc acaccagagc aacagcacca  360
acatcttctt cagcccagtg agcatcgcca cagccttcgc aatgctcagc ctggggacca  420
aggccgacac ccacgacgaa atcctggagg gcctgaactt caacctcacg gagatcccgg  480
aggcccagat ccacgaaggc ttccaggaac tcctccggac cctcaaccag ccagacagcc  540
agctccagct gaccaccggc aacggcctgt tcctcagcga gggcctgaag ctagtggaca  600
agttcctgga ggacgtgaaa aagctgtacc acagcgaagc cttcaccgtc aacttcgggg  660
acaccgaaga ggccaagaaa cagatcaacg actacgtgga gaagggcacc caagggaaaa  720
tcgtggacct ggtcaaggag ctggacagag acacagtgtt cgccctggtg aactacatct  780
tcttcaaagg caaatgggag agacccttcg aagtcaagga caccgaggaa gaggacttcc  840
acgtggacca ggtgaccacc gtgaaggtgc ccatgatgaa gcggctgggc atgttcaaca  900
tccagcactg caagaagctg agcagctggg tgctgctgat gaaatacctg ggcaacgcca  960
ccgccatctt cttcctgccc gacgagggga aactacagca cctggaaaac gaactcaccc  1020
acgacatcat caccaagttc ctggaaaacg aagacagaag gagcgccagc ctgcacctgc  1080
ccaaactgag cattactgga acctatgatc tgaagtccgt gctgggtcaa ctgggcatca  1140
ctaaggtctt cagcaatggg gctgacctct ccggggtcac agaggaggca cccctgaagc  1200
tctccaaggc cgtgcataag gctgtgctga ccatcgacga gaaagggact gaagctgctg  1260
gggccatgtt tttagaggcc atacccatgt ctatcccccc cgaggtcaag ttcaacaaac  1320
cctttgtctt cttaatgatt gaacaaaata ccaagtctcc cctcttcatg ggaaaagtgg  1380
tgaatcccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689
```

-continued

```
SEQ ID NO: 105          moltype = DNA  length = 1689
FEATURE                 Location/Qualifiers
misc_feature            1..1689
                        note = Description of Artificial Sequence:
                         Syntheticpolynucleotide
source                  1..1689
                        mol_type = other DNA
                        organism = synthetic construct
SEQUENCE: 105
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtcag ctggggcatc ctcctgctgg  180
caggcctgtg ctgcctggtc cccgtcagcc tggccgagga cccccaggga gacgccgccc  240
agaagacaga cacaagccac cacgaccagg accacccaac cttcaacaag atcaccccca  300
acctggccga gttcgccttc agcctatacc gccagctggc acaccagagc aacagcacca  360
acatcttctt cagcccagtg agcatcgcca cagccttcgc aatgctcagc ctggggacca  420
aggccgacac ccacgacgaa atcctggagg gcctgaactt caacctcacg gagatcccgg  480
aggcccagat ccacgaaggc ttccaggaac tcctccggac cctcaaccag ccagacagcc  540
agctccagct gaccaccggc aacggcctgt tcctcagcga gggcctgaag ctagtggaca  600
agttcctgga ggacgtgaaa aagctgtacc acagcgaagc cttcaccgtc aacttcgggg  660
acaccgaaga ggccaagaaa cagatcaacg actacgtgga gaagggcacc caagggaaaa  720
tcgtggacct ggtcaaggag cttgacagag acacagtttt tgctctggtg aattacatct  780
tctttaaagg caaatgggag agaccctttg aagtcaagga caccgaggaa gaggacttcc  840
acgtggacca ggtgaccacc gtgaaggtgc ctatgatgaa gcgtttaggc atgtttaaca  900
tccagcactg taagaagctg tccagctggg tgctgctgat gaaatacctg ggcaatgcca  960
ccgccatctt cttcctgcct gatgagggga aactacagca cctggaaaat gaactcaccc  1020
acgatatcat caccaagttc ctggaaaatg aagacagaag gtctgccagc ttacatttac  1080
ccaaactgtc cattactgga acctatgatc tgaagtccgt gctgggtcaa ctgggcatca  1140
ctaaggtctt cagcaatggg gctgacctct ccggggtcac agaggaggca cccctgaagc  1200
tctccaaggc cgtgcataag gctgtgctga ccatcgacga gaaagggact gaagctgctg  1260
gggccatgtt tttagaggcc atacccatgt ctatcccccc cgaggtcaag ttcaacaaac  1320
cctttgtctt cttaatgatt gaacaaaata ccaagtctcc cctcttcatg ggaaaagtgg  1380
tgaatcccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 106          moltype = DNA  length = 1689
FEATURE                 Location/Qualifiers
misc_feature            1..1689
                        note = Description of Artificial Sequence:
                         Syntheticpolynucleotide
source                  1..1689
                        mol_type = other DNA
                        organism = synthetic construct
SEQUENCE: 106
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtcag ctggggcatc ctcctgctgg  180
caggcctgtg ctgcctggtc cccgtcagcc tggccgagga cccccaggga gacgccgccc  240
agaagacaga cacaagccac cacgaccagg accacccaac cttcaacaag atcaccccca  300
acctggccga gttcgccttc agcctatacc gccagctggc acaccagagc aacagcacca  360
acatcttctt cagcccagtg agcatcgcca cagcctttgc aatgctctcc ctggggacca  420
aggctgacac tcacgatgaa atcctggagg gcctgaattt caacctcacg gagattccgg  480
aggctcagat ccatgaaggc ttccaggaac tcctccgtac cctcaaccag ccagacagcc  540
agctccagct gaccaccggc aatggcctgt tcctcagcga gggcctgaag ctagtggata  600
agtttttgga ggatgttaaa aagttgtacc actcagaagc cttcactgtc aacttcgggg  660
acaccgaaga ggccaagaaa cagatcaacg attacgtgga gaagggtact caagggaaaa  720
ttgtggattt ggtcaaggag cttgacagag acacagtttt tgctctggtg aattacatct  780
tctttaaagg caaatgggag agaccctttg aagtcaagga caccgaggaa gaggacttcc  840
acgtggacca ggtgaccacc gtgaaggtgc ctatgatgaa gcgtttaggc atgtttaaca  900
tccagcactg taagaagctg tccagctggg tgctgctgat gaaatacctg ggcaatgcca  960
ccgccatctt cttcctgcct gatgagggga aactacagca cctggaaaat gaactcaccc  1020
acgatatcat caccaagttc ctggaaaatg aagacagaag gtctgccagc ttacatttac  1080
ccaaactgtc cattactgga acctatgatc tgaagtccgt gctgggtcaa ctgggcatca  1140
ctaaggtctt cagcaatggg gctgacctct ccggggtcac agaggaggca cccctgaagc  1200
tctccaaggc cgtgcataag gctgtgctga ccatcgacga gaaagggact gaagctgctg  1260
gggccatgtt tttagaggcc atacccatgt ctatcccccc cgaggtcaag ttcaacaaac  1320
cctttgtctt cttaatgatt gaacaaaata ccaagtctcc cctcttcatg ggaaaagtgg  1380
tgaatcccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 107          moltype = DNA  length = 1689
```

-continued

```
FEATURE                Location/Qualifiers
misc_feature           1..1689
                       note = Description of Artificial Sequence:
                        Syntheticpolynucleotide
source                 1..1689
                       mol_type = other DNA
                       organism = synthetic construct
SEQUENCE: 107
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtctc gtggggcatc ctcctgctgg  180
caggcctgtg ctgcctggtc cccgtcagcc tggccgagga cccccaggga gatgctgccc  240
agaagacaga cacatcccac cacgaccagg accacccaac cttcaacaag atcaccccca  300
acctggctga gttcgccttc agcctatacc gccagctggc acaccagagc aacagcacca  360
atatcttctt cagcccagtg agcatcgcta cagccttcgc aatgctcagc ctggggacca  420
aggccgacac ccacgatgaa atcctggagg gcctgaattt caacctcacg gagatcccgg  480
aggctcagat ccacgaaggc ttccaggaac tcctccggac cctcaaccag ccagacagcc  540
agctccagct gaccaccggc aacggcctgt tcctcagcga gggcctgaag ctagtggaca  600
agttcctgga ggacgttaaa aagctgtacc acagcgaagc cttcaccgtc aacttcgggg  660
acaccgaaga ggccaagaaa cagatcaacg attacgtgga gaagggcacc caagggaaaa  720
tcgtggacct ggtcaaggag cttgacagag acacagtgtt tgccctggtg aactacatct  780
tcttcaaagg caaatgggag agacccttcg aagtcaagga caccgaggaa gaggacttcc  840
acgtggacca ggtgaccacc gtgaaggtgc ccatgatgaa gcggttaggc atgttcaaca  900
tccagcactg caagaagctg agcagctggg tgctgctgat gaaatacctg ggcaacgcca  960
ccgccatctt cttcctgccc gacgagggga aactacagca cctggaaaac gaactcaccc  1020
acgacatcat caccaagttc ctggaaaacg aagacagaag gagcgccagc ctgcatctgc  1080
ccaaactgag cattactgga acctacgatc tgaagtccgt gctgggtcaa ctgggcatca  1140
ccaaggtctt cagcaatggg gccgacctca gcggggtcac agaggaggca cccctgaagc  1200
tcagcaaggc cgtgcacaag gctgtgctga ccatcgacga gaaagggacc gaagccgctg  1260
gggccatgtt cctggaggcc atacccatga gcatcccccc cgaggtcaag ttcaacaaac  1320
cctttgtctt cctgatgatc gaacaaaaca ccaagtctcc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                         1689

SEQ ID NO: 108         moltype = DNA  length = 1689
FEATURE                Location/Qualifiers
misc_feature           1..1689
                       note = Description of Artificial Sequence:
                        Syntheticpolynucleotide
source                 1..1689
                       mol_type = other DNA
                       organism = synthetic construct
SEQUENCE: 108
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccgt cttctgtctc gtggggcatc ctcctgctgg  180
caggcctgtg ctgcctggtc cccgtctccc tggctgagga cccccaggga gatgccgccc  240
agaagacaga cacatcccac catgaccagg accacccaac cttcaacaag atcaccccca  300
acctggccga gttcgccttc agcctatacc gccagctggc acaccagagc aacagcacca  360
acatcttctt ctccccagtg agcatcgcca cagcctttgc aatgctctcc ctggggacca  420
aggccgacac ccacgacgaa atcctggagg gcctgaattt caacctcacg gagatcccgg  480
aggctcagat ccatgaaggc ttccaggaac tcctccggac cctcaaccag ccagacagcc  540
agctccagct gaccaccggc aatggcctgt tcctcagcga gggcctgaag ctagtggata  600
agttcctgga ggatgttaaa aagctgtacc acagcgaagc cttcaccgtc aacttcgggg  660
acaccgaaga ggccaagaaa cagatcaacg attacgtgga gaagggcacc caagggaaaa  720
tcgtggacct ggtcaaggag cttgacagag acacagtgtt tgctctggtg aattacatct  780
tctttaaagg caaatgggag agaccctttg aagtcaagga caccgaggaa gaggacttcc  840
acgtggacca ggtgaccacc gtgaaggtgc ctatgatgaa gcggttaggc atgtttaaca  900
tccagcactg caagaagctg agcagctggg tgctgctgat gaaatacctg ggcaatgcca  960
ccgccatctt cttcctgcct gatgagggga aactacagca cctggaaaac gaactcaccc  1020
acgacatcat caccaagttc ctggaaaatg aagacagaag gtctgccagc ttacacttac  1080
ccaaactgag cattactgga acctacgatc tgaagtccgt gctgggccaa ctgggcatca  1140
ctaaggtctt cagcaacggg gctgacctct ccggggtcac agaggaggca cccctgaagc  1200
tcagcaaggc cgtgcacaag gctgtgctga ccatcgacga gaaagggacc gaagctgccg  1260
gggccatgtt tctggaggcc atacccatgt ctatcccccc cgaggtcaag ttcaacaaac  1320
cctttgtctt cctgatgatc gaacaaaata ccaagagccc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                         1689

SEQ ID NO: 109         moltype = DNA  length = 1689
FEATURE                Location/Qualifiers
```

```
misc_feature            1..1689
                        note = Description of Artificial Sequence:
                         Syntheticpolynucleotide
source                  1..1689
                        mol_type = other DNA
                        organism = synthetic construct
SEQUENCE: 109
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtcag ctggggcatc ctcctgctgg  180
caggcctgtg ctgcctggtc cctgtctccc tggctgagga tccccaggga gatgctgccc  240
agaagacaga tacatcccac catgatcagg atcacccaac cttcaacaag atcaccccca  300
acctggctga gttcgccttc agcctatacc gccagctggc acaccagtcc aacagcacca  360
atatcttctt ctccccagtg agcatcgcta cagccttcgc aatgctctcc ctggggacca  420
aggctgacac tcacgatgaa atcctggagg gcctgaattt caacctcacg gagattccgg  480
aggcccagat ccatgaaggc ttccaggaac tcctccgtac cctcaaccag ccagacagcc  540
agctccagct gaccaccggc aatggcctgt tcctcagcga gggcctgaag ctagtggata  600
agtttttgga ggatgttaaa aagctgtacc acagcgaagc cttcactgtc aacttcgggg  660
acaccgaaga ggccaagaaa cagatcaacg attacgtgga gaagggtact caagggaaaa  720
ttgtggattt ggtcaaggag cttgacagag acacagtttt tgctctggtg aattacatct  780
tcttcaaagg caaatgggag agaccctttg aagtcaagga caccgaggaa gaggacttcc  840
acgtggacca ggtgaccacc gtgaaggtgc ctatgatgaa gcggttaggc atgttcaaca  900
tccagcactg taagaagctg tccagctggg tgctgctgat gaaatacctg ggcaatgcca  960
ccgccatctt cttcctgcct gatgagggga aactacagca cctggaaaat gaactcaccc  1020
acgatatcat caccaagttc ctggaaaatg aagacagaag gagcgccagc ttacatttac  1080
ccaaactgag cattactgga acctacgatc tgaagtccgt gctgggtcaa ctgggcatca  1140
ctaaggtctt cagcaacggg gctgacctct ccggggtcac agaggaggca cccctgaagc  1200
tctccaaggc cgtgcataag gctgtgctga ccatcgacga gaaagggact gaagctgctg  1260
gggccatgtt tttagaggcc atacccatgt ctatcccccc cgaggtcaag ttcaacaaac  1320
cctttgtctt cctgatgatc gaacaaaata ccaagagccc cctcttcatg ggaaaagtgg  1380
tgaatcccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 110          moltype = RNA  length = 1689
FEATURE                 Location/Qualifiers
misc_feature            1..1689
                        note = Description of Artificial Sequence:
                         Syntheticpolynucleotide
source                  1..1689
                        mol_type = other RNA
                        organism = synthetic construct
SEQUENCE: 110
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtcag ctggggcatc ctcctgctgg  180
caggcctgtg ctgcctggtc cccgtcagcc tggccgagga cccccaggga gacgccgccc  240
agaagacaga cacaagccac cacgaccagg accacccaac cttcaacaag atcaccccca  300
acctggccga gttcgccttc agcctatacc gccagctggc acaccagagc aacagcacca  360
acatcttctt cagcccagtg agcatcgcca cagccttcgc aatgctcagc ctggggacca  420
aggccgacac ccacgacgaa atcctggagg gcctgaactt caacctcacg gagatcccgg  480
aggcccagat ccacgaaggc ttccaggaac tcctccggac cctcaaccag ccagacagcc  540
agctccagct gaccaccggc aacggcctgt tcctcagcga gggcctgaag ctagtggaca  600
agttcctgga ggacgtgaaa aagctgtacc acagcgaagc cttcaccgtc aacttcgggg  660
acaccgaaga ggccaagaaa cagatcaacg actacgtgga gaagggcacc caagggaaaa  720
tcgtggacct ggtcaaggag ctggacagag acacagtgtt cgccctggtg aactacatct  780
tcttcaaagg caaatgggag agacccttcg aagtcaagga caccgaggaa gaggacttcc  840
acgtggacca ggtgaccacc gtgaaggtgc ccatgatgaa gcggctgggc atgttcaaca  900
tccagcactg caagaagctg agcagctggg tgctgctgat gaaatacctg ggcaacgcca  960
ccgccatctt cttcctgccc gacgagggga aactacagca cctggaaaac gaactcaccc  1020
acgacatcat caccaagttc ctggaaaacg aagacagaag gagcgccagc ctgcacctgc  1080
ccaaactgag catcaccgga acctacgacc tgaagtccgt gctgggccaa ctgggcatca  1140
ccaaggtctt cagcaacggg gccgacctca gcggggtcac agaggaggca cccctgaagc  1200
tcagcaaggc cgtgcacaag gccgtgctga ccatcgacga gaaagggacc gaagccgccg  1260
gggccatgtt cctggaggcc atacccatga gcatcccccc cgaggtcaag ttcaacaaac  1320
ccttcgtctt cctgatgatc gaacaaaaca ccaagagccc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 111          moltype = RNA  length = 1689
FEATURE                 Location/Qualifiers
misc_feature            1..1689
```

```
                        note = Description of Artificial Sequence:
                         Syntheticpolynucleotide
source                  1..1689
                        mol_type = other RNA
                        organism = synthetic construct
SEQUENCE: 111
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccgt cttctgtctc gtggggcatc ctcctgctgg  180
caggcctgtg ctgcctggtc cctgtctccc tggctgagga tccccaggga gatgctgccc  240
agaagacaga tacatcccac catgatcagg atcacccaac cttcaacaag atcaccccca  300
acctggctga gttcgccttc agcctatacc gccagctggc acaccagtcc aacagcacca  360
atatcttctt ctccccagtg agcatcgcta cagcctttgc aatgctctcc ctggggacca  420
aggctgacac tcacgatgaa atcctggagg gcctgaactt caacctcacg gagatcccgg  480
aggcccagat ccacgaaggc ttccaggaac tcctccggac cctcaaccag ccagacagcc  540
agctccagct gaccaccggc aacggcctgt tcctcagcga gggcctgaag ctagtggaca  600
agttcctgga ggacgtgaaa aagctgtacc acagcgaagc cttcaccgtc aacttcgggg  660
acaccgaaga ggccaagaaa cagatcaacg actacgtgga gaagggcacc caagggaaaa  720
tcgtggacct ggtcaaggag ctggacagag acacagtgtt cgccctggtg aactacatct  780
tcttcaaagg caaatgggag agacccttcg aagtcaagga caccgaggaa gaggacttcc  840
acgtggacca ggtgaccacc gtgaaggtgc ccatgatgaa gcggctgggc atgttcaaca  900
tccagcactg caagaagctg agcagctggg tgctgctgat gaaatacctg ggcaacgcca  960
ccgccatctt cttcctgccc gacgagggga aactacagca cctggaaaac gaactcaccc  1020
acgacatcat caccaagttc ctggaaaacg aagacagaag gagcgccagc ctgcacctgc  1080
ccaaactgag catcaccgga acctacgacc tgaagtccgt gctgggccaa ctgggcatca  1140
ccaaggtctt cagcaacggg gccgacctca gcggggtcac agaggaggca cccctgaagc  1200
tcagcaaggc cgtgcacaag gccgtgctga ccatcgacga gaaagggacc gaagccgccg  1260
gggccatgtt cctggaggcc atacccatga gcatcccccc cgaggtcaag ttcaacaaac  1320
ccttcgtctt cctgatgatc gaacaaaaca ccaagagccc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 112          moltype = RNA  length = 1689
FEATURE                 Location/Qualifiers
misc_feature            1..1689
                        note = Description of Artificial Sequence:
                         Syntheticpolynucleotide
source                  1..1689
                        mol_type = other RNA
                        organism = synthetic construct
SEQUENCE: 112
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccgt cttctgtctc gtggggcatc ctcctgctgg  180
caggcctgtg ctgcctggtc cctgtctccc tggctgagga tccccaggga gatgctgccc  240
agaagacaga tacatcccac catgatcagg atcacccaac cttcaacaag atcaccccca  300
acctggctga gttcgccttc agcctatacc gccagctggc acaccagtcc aacagcacca  360
atatcttctt ctccccagtg agcatcgcta cagcctttgc aatgctctcc ctggggacca  420
aggctgacac tcacgatgaa atcctggagg gcctgaattt caacctcacg gagattccgg  480
aggctcagat ccatgaaggc ttccaggaac tcctccgtac cctcaaccag ccagacagcc  540
agctccagct gaccaccggc aatggcctgt tcctcagcga gggcctgaag ctagtggata  600
agtttttgga ggatgttaaa aagttgtacc actcagaagc cttcactgtc aacttcgggg  660
acaccgaaga ggccaagaaa cagatcaacg attacgtgga gaagggtact caagggaaaa  720
ttgtggattt ggtcaaggag cttgacagag acacagtttt tgctctggtg aattacatct  780
tcttcaaagg caaatgggag agacccttcg aagtcaagga caccgaggaa gaggacttcc  840
acgtggacca ggtgaccacc gtgaaggtgc ccatgatgaa gcggctgggc atgttcaaca  900
tccagcactg caagaagctg agcagctggg tgctgctgat gaaatacctg ggcaacgcca  960
ccgccatctt cttcctgccc gacgagggga aactacagca cctggaaaac gaactcaccc  1020
acgacatcat caccaagttc ctggaaaacg aagacagaag gagcgccagc ctgcacctgc  1080
ccaaactgag catcaccgga acctacgacc tgaagtccgt gctgggccaa ctgggcatca  1140
ccaaggtctt cagcaacggg gccgacctca gcggggtcac agaggaggca cccctgaagc  1200
tcagcaaggc cgtgcacaag gccgtgctga ccatcgacga gaaagggacc gaagccgccg  1260
gggccatgtt cctggaggcc atacccatga gcatcccccc cgaggtcaag ttcaacaaac  1320
ccttcgtctt cctgatgatc gaacaaaaca ccaagagccc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 113          moltype = RNA  length = 1689
FEATURE                 Location/Qualifiers
misc_feature            1..1689
                        note = Description of Artificial Sequence:
```

```
                         Syntheticpolynucleotide
source                  1..1689
                        mol_type = other RNA
                        organism = synthetic construct
SEQUENCE: 113
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccgt cttctgtctc gtggggcatc ctcctgctgg  180
caggcctgtg ctgcctggtc cctgtctccc tggctgagga tccccaggga gatgctgccc  240
agaagacaga tacatcccac catgatcagg atcacccaac cttcaacaag atcacccccca 300
acctggctga gttcgccttc agcctatacc gccagctggc acaccagtcc aacagcacca  360
atatcttctt ctccccagtg agcatcgcta cagcctttgc aatgctctcc ctggggacca  420
aggctgacac tcacgatgaa atcctggagg gcctgaattt caacctcacg gagattccgg  480
aggctcagat ccatgaaggc ttccaggaac tcctccgtac cctcaaccag ccagacagcc  540
agctccagct gaccaccggc aatggcctgt tcctcagcga gggcctgaag ctagtggata  600
agtttttgga ggatgttaaa aagttgtacc actcagaagc cttcactgtc aacttcgggg  660
acaccgaaga ggccaagaaa cagatcaacg attacgtgga gaagggtact caagggaaaa  720
ttgtggattt ggtcaaggag cttgacagag acacagtttt tgctctggtg aattacatct  780
tctttaaagg caaatgggag agacccttttg aagtcaagga caccgaggaa gaggacttcc 840
acgtggacca ggtgaccacc gtgaaggtgc ctatgatgaa gcgtttaggc atgtttaaca  900
tccagcactg taagaagctg tccagctggg tgctgctgat gaaatacctg ggcaatgcca  960
ccgccatctt cttcctgcct gatgagggga aactacagca cctggaaaat gaactcaccc  1020
acgatatcat caccaagttc ctggaaaatg aagacagaag gtctgccagc ttacatttac  1080
ccaaactgtc cattactgga acctatgatc tgaagtccgt gctgggtcaa ctgggcatca  1140
ccaaggtctt cagcaacggg gccgacctca gcggggtcac agaggaggca cccctgaagc  1200
tcagcaaggc cgtgcacaag gccgtgctga ccatcgacga gaaagggacc gaagccgccg  1260
gggccatgtt cctggaggcc atacccatga gcatcccccc cgaggtcaag ttcaacaaac  1320
ccttcgtctt cctgatgatc gaacaaaaca ccaagagccc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                         1689

SEQ ID NO: 114          moltype = RNA  length = 1689
FEATURE                 Location/Qualifiers
misc_feature            1..1689
                        note = Description of Artificial Sequence:
                         Syntheticpolynucleotide
source                  1..1689
                        mol_type = other RNA
                        organism = synthetic construct
SEQUENCE: 114
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtcag ctggggcatc ctcctgctgg  180
caggcctgtg ctgcctggtc cccgtcagcc tggccgagga cccccaggga gacgccgccc  240
agaagacaga cacaagccac cacgaccagg accacccaac cttcaacaag atcacccccca 300
acctggccga gttcgccttc agcctatacc gccagctggc acaccagagc aacagcacca  360
acatcttctt cagcccagtg agcatcgcca cagccttcgc aatgctcagc ctggggacca  420
aggccgacac ccacgacgaa atcctggagg gcctgaactt caacctcacg gagatcccgg  480
aggcccagat ccacgaaggc ttccaggaac tcctccggac cctcaaccag ccagacagcc  540
agctccagct gaccaccggc aacggcctgt tcctcagcga gggcctgaag ctagtggaca  600
agttcctgga ggacgtgaaa aagctgtacc acagcgaagc cttcaccgtc aacttcgggg  660
acaccgaaga ggccaagaaa cagatcaacg actacgtgga gaagggcacc caagggaaaa  720
tcgtggacct ggtcaaggag ctggacagag acacagtgtt cgccctggtg aactacatct  780
tcttcaaagg caaatgggag agacccttcg aagtcaagga caccgaggaa gaggacttcc  840
acgtggacca ggtgaccacc gtgaaggtgc ccatgatgaa gcggctgggc atgttcaaca  900
tccagcactg caagaagctg agcagctggg tgctgctgat gaaatacctg ggcaacgcca  960
ccgccatctt cttcctgccc gacgagggga aactacagca cctggaaaac gaactcaccc  1020
acgacatcat caccaagttc ctggaaaacg aagacagaag gagcgccagc ctgcacctgc  1080
ccaaactgag cattactgga acctatgatc tgaagtccgt gctgggtcaa ctgggcatca  1140
ctaaggtctt cagcaatggg gctgacctct ccggggtcac agaggaggca cccctgaagc  1200
tctccaaggc cgtgcataag gctgtgctga ccatcgacga gaaagggact gaagctgctg  1260
gggccatgtt tttagaggcc atacccatgt ctatcccccc cgaggtcaag ttcaacaaac  1320
cctttgtctt cttaatgatt gaacaaaata ccaagtctcc cctcttcatg ggaaaagtgg  1380
tgaatcccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                         1689

SEQ ID NO: 115          moltype = RNA  length = 1689
FEATURE                 Location/Qualifiers
misc_feature            1..1689
                        note = Description of Artificial Sequence:
                         Syntheticpolynucleotide
```

```
source                  1..1689
                        mol_type = other RNA
                        organism = synthetic construct
SEQUENCE: 115
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtcag ctggggcatc ctcctgctgg  180
caggcctgtg ctgcctggtc cccgtcagcc tggccgagga cccccaggga gacgccgccc  240
agaagacaga cacaagccac cacgaccagg accacccaac cttcaacaag atcacccccca  300
acctggccga gttcgccttc agcctatacc gccagctggc acaccagagc aacagcacca  360
acatcttctt cagcccagtg agcatcgcca cagccttcgc aatgctcagc ctggggacca  420
aggccgacac ccacgacgaa atcctggagg gcctgaactt caacctcacg gagatcccgg  480
aggcccagat ccacgaaggc ttccaggaac tcctccggac cctcaaccag ccagacagcc  540
agctccagct gaccaccggc aacggcctgt tcctcagcga gggcctgaag ctagtggaca  600
agttcctgga ggacgtgaaa aagctgtacc acagcgaagc cttcaccgtc aacttcgggg  660
acaccgaaga ggccaagaaa cagatcaacg actacgtgga gaagggcacc caagggaaaa  720
tcgtggacct ggtcaaggag cttgacagag acacagtttt tgctctggtg aattacatct  780
tctttaaagg caaatgggag agaccctttg aagtcaagga caccgaggaa gaggacttcc  840
acgtggacca ggtgaccacc gtgaaggtgc ctatgatgaa gcgtttaggc atgtttaaca  900
tccagcactg taagaagctg tccagctggg tgctgctgat gaaatacctg ggcaatgcca  960
ccgccatctt cttcctgcct gatgagggga aactacagca cctggaaaat gaactcaccc  1020
acgatatcat caccaagttc ctggaaaatg aagacagaag gtctgccagc ttacatttac  1080
ccaaactgtc cattactgga acctatgatc tgaagtccgt gctgggtcaa ctgggcatca  1140
ctaaggtctt cagcaatggg gctgacctct ccggggtcac agaggaggca cccctgaagc  1200
tctccaaggc cgtgcataag gctgtgctga ccatcgacga gaaagggact gaagctgctg  1260
gggccatgtt tttagaggcc atacccatgt ctatcccccc cgaggtcaag ttcaacaaac  1320
cctttgtctt cttaatgatt gaacaaaata ccaagtctcc cctcttcatg ggaaaagtgg  1380
tgaatcccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 116          moltype = RNA  length = 1689
FEATURE                 Location/Qualifiers
misc_feature            1..1689
                        note = Description of Artificial Sequence:
                         Syntheticpolynucleotide
source                  1..1689
                        mol_type = other RNA
                        organism = synthetic construct
SEQUENCE: 116
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtcag ctggggcatc ctcctgctgg  180
caggcctgtg ctgcctggtc cccgtcagcc tggccgagga cccccaggga gacgccgccc  240
agaagacaga cacaagccac cacgaccagg accacccaac cttcaacaag atcacccccca  300
acctggccga gttcgccttc agcctatacc gccagctggc acaccagagc aacagcacca  360
acatcttctt cagcccagtg agcatcgcca cagcctttgc aatgctctcc ctggggacca  420
aggctgacac tcacgatgaa atcctggagg gcctgaattt caacctcacg gagattccgg  480
aggctcagat ccatgaaggc ttccaggaac tcctccgtac cctcaaccag ccagacagcc  540
agctccagct gaccaccggc aatggcctgt tcctcagcga gggcctgaag ctagtggata  600
agtttttgga ggatgttaaa aagttgtacc actcagaagc cttcactgtc aacttcgggg  660
acaccgaaga ggccaagaaa cagatcaacg attacgtgga gaagggtact caagggaaaa  720
ttgtggattt ggtcaaggag cttgacagag acacagtttt tgctctggtg aattacatct  780
tctttaaagg caaatgggag agaccctttg aagtcaagga caccgaggaa gaggacttcc  840
acgtggacca ggtgaccacc gtgaaggtgc ctatgatgaa gcgtttaggc atgtttaaca  900
tccagcactg taagaagctg tccagctggg tgctgctgat gaaatacctg ggcaatgcca  960
ccgccatctt cttcctgcct gatgagggga aactacagca cctggaaaat gaactcaccc  1020
acgatatcat caccaagttc ctggaaaatg aagacagaag gtctgccagc ttacatttac  1080
ccaaactgtc cattactgga acctatgatc tgaagtccgt gctgggtcaa ctgggcatca  1140
ctaaggtctt cagcaatggg gctgacctct ccggggtcac agaggaggca cccctgaagc  1200
tctccaaggc cgtgcataag gctgtgctga ccatcgacga gaaagggact gaagctgctg  1260
gggccatgtt tttagaggcc atacccatgt ctatcccccc cgaggtcaag ttcaacaaac  1320
cctttgtctt cttaatgatt gaacaaaata ccaagtctcc cctcttcatg ggaaaagtgg  1380
tgaatcccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 117          moltype = RNA  length = 1689
FEATURE                 Location/Qualifiers
misc_feature            1..1689
                        note = Description of Artificial Sequence:
                         Syntheticpolynucleotide
source                  1..1689
```

```
                        mol_type = other RNA
                        organism = synthetic construct
SEQUENCE: 117
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtctc gtggggcatc ctcctgctgg  180
caggcctgtg ctgcctggtc cccgtcagcc tggccgagga cccccaggga gatgctgccc  240
agaagacaga cacatcccac cacgaccagg accacccaac cttcaacaag atcaccccca  300
acctggctga gttcgccttc agcctatacc gccagctggc acaccagagc aacagcacca  360
atatcttctt cagcccagtg agcatcgcta cagccttcgc aatgctcagc ctggggacca  420
aggccgacac ccacgatgaa atcctggagg gcctgaattt caacctcacg gagatcccgg  480
aggctcagat ccacgaaggc ttccaggaac tcctccggac cctcaaccag ccagacagcc  540
agctccagct gaccaccggc aacggcctgt tcctcagcga gggcctgaag ctagtggaca  600
agttcctgga ggacgttaaa aagctgtacc acagcgaagc cttcaccgtc aacttcgggg  660
acaccgaaga ggccaagaaa cagatcaacg attacgtgga gaagggcacc caagggaaaa  720
tcgtggacct ggtcaaggag cttgacagag acacagtgtt tgccctggtg aactacatct  780
tcttcaaagg caaatgggag agacccttcg aagtcaagga caccgaggaa gaggacttcc  840
acgtggacca ggtgaccacc gtgaaggtgc ccatgatgaa gcggttaggc atgttcaaca  900
tccagcactg caagaagctg agcagctggg tgctgctgat gaaatacctg ggcaacgcca  960
ccgccatctt cttcctgccc gacgagggga aactacagca cctggaaaac gaactcaccc  1020
acgacatcat caccaagttc ctggaaaacg aagacagaag gagcgccagc ctgcatctgc  1080
ccaaactgag cattactgga acctacgatc tgaagtccgt gctgggtcaa ctgggcatca  1140
ccaaggtctt cagcaatggg gccgacctca gcggggtcac agaggaggca cccctgaagc  1200
tcagcaaggc cgtgcacaag gctgtgctga ccatcgacga gaaagggacc gaagccgctg  1260
gggccatgtt cctggaggcc atacccatga gcatcccccc cgaggtcaag ttcaacaaac  1320
cctttgtctt cctgatgatc gaacaaaaca ccaagtctcc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 118          moltype = RNA  length = 1689
FEATURE                 Location/Qualifiers
misc_feature            1..1689
                        note = Description of Artificial Sequence:
                         Syntheticpolynucleotide
source                  1..1689
                        mol_type = other RNA
                        organism = synthetic construct
SEQUENCE: 118
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccgt cttctgtctc gtggggcatc ctcctgctgg  180
caggcctgtg ctgcctggtc cccgtctccc tggctgagga cccccaggga gatgccgccc  240
agaagacaga cacatcccac catgaccagg accacccaac cttcaacaag atcaccccca  300
acctggccga gttcgccttc agcctatacc gccagctggc acaccagagc aacagcacca  360
acatcttctt ctccccagtg agcatcgcca cagcctttgc aatgctctcc ctggggacca  420
aggccgacac ccacgacgaa atcctggagg gcctgaattt caacctcacg gagatcccgg  480
aggctcagat ccatgaaggc ttccaggaac tcctccggac cctcaaccag ccagacagcc  540
agctccagct gaccaccggc aatggcctgt tcctcagcga gggcctgaag ctagtggata  600
agttcctgga ggatgttaaa aagctgtacc acagcgaagc cttcaccgtc aacttcgggg  660
acaccgaaga ggccaagaaa cagatcaacg attacgtgga gaagggcacc caagggaaaa  720
tcgtggacct ggtcaaggag cttgacagag acacagtgtt tgctctggtg aattacatct  780
tctttaaagg caaatgggag agaccctttg aagtcaagga caccgaggaa gaggacttcc  840
acgtggacca ggtgaccacc gtgaaggtgc ctatgatgaa gcggttaggc atgtttaaca  900
tccagcactg caagaagctg agcagctggg tgctgctgat gaaatacctg ggcaatgcca  960
ccgccatctt cttcctgcct gatgagggga aactacagca cctggaaaac gaactcaccc  1020
acgacatcat caccaagttc ctggaaaatg aagacagaag gtctgccagc ttacacttac  1080
ccaaactgag cattactgga acctacgatc tgaagtccgt gctgggccaa ctgggcatca  1140
ctaaggtctt cagcaacggg gctgacctct ccggggtcac agaggaggca cccctgaagc  1200
tcagcaaggc cgtgcacaag gctgtgctga ccatcgacga gaaagggacc gaagctgccg  1260
gggccatgtt tctggaggcc atacccatgt ctatcccccc cgaggtcaag ttcaacaaac  1320
cctttgtctt cctgatgatc gaacaaaata ccaagagccc cctcttcatg ggaaaagtgg  1380
tgaaccccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 119          moltype = RNA  length = 1689
FEATURE                 Location/Qualifiers
misc_feature            1..1689
                        note = Description of Artificial Sequence:
                         Syntheticpolynucleotide
source                  1..1689
                        mol_type = other RNA
```

```
                          organism = synthetic construct
SEQUENCE: 119
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgccga gcagcgtcag ctggggcatc ctcctgctgg  180
caggcctgtg ctgcctggtc cctgtctccc tggctgagga tccccaggga gatgctgccc  240
agaagacaga tacatcccac catgatcagg atcacccaac cttcaacaag atcacccccca  300
acctggctga gttcgccttc agcctatacc gccagctggc acaccagtcc aacagcacca  360
atatcttctt ctccccagtg agcatcgcta cagccttcgc aatgctctcc ctggggacca  420
aggctgacac tcacgatgaa atcctggagg gcctgaattt caacctcacg gagattccgg  480
aggcccagat ccatgaaggc ttccaggaac tcctccgtac cctcaaccag ccagacagcc  540
agctccagct gaccaccggc aatggcctgt tcctcagcga gggcctgaag ctagtggata  600
agtttttgga ggatgttaaa aagctgtacc acagcgaagc cttcactgtc aacttcgggg  660
acaccgaaga ggccaagaaa cagatcaacg attacgtgga gaagggtact caagggaaaa  720
ttgtggattt ggtcaaggag cttgacagag acacagtttt tgctctggtg aattacatct  780
tcttcaaagg caaatgggag agaccctttg aagtcaagga caccgaggaa gaggacttcc  840
acgtggacca ggtgaccacc gtgaaggtgc ctatgatgaa gcggttaggc atgttcaaca  900
tccagcactg taagaagctg tccagctggg tgctgctgat gaaatacctg ggcaatgcca  960
ccgccatctt cttcctgcct gatgagggga aactacagca cctggaaaat gaactcaccc  1020
acgatatcat caccaagttc ctggaaaatg aagacagaag gagcgccagc ttacatttac  1080
ccaaactgag cattactgga acctacgatc tgaagtccgt gctgggtcaa ctgggcatca  1140
ctaaggtctt cagcaacggg gctgacctct ccggggtcac agaggaggca cccctgaagc  1200
tctccaaggc cgtgcataag gctgtgctga ccatcgacga gaaagggact gaagctgctg  1260
gggccatgtt tttagaggcc atacccatgt ctatcccccc cgaggtcaag ttcaacaaac  1320
cctttgtctt cctgatgatc gaacaaaata ccaagagccc cctcttcatg ggaaaagtgg  1380
tgaatcccac ccaaaaataa ctcgagctag tgactgacta ggatctggtt accactaaac  1440
cagcctcaag aacacccgaa tggagtctct aagctacata ataccaactt acacttacaa  1500
aatgttgtcc cccaaaatgt agccattcgt atctgctcct aataaaaaga aagtttcttc  1560
acattctaga aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaa                                                          1689

SEQ ID NO: 120          moltype = DNA  length = 735
FEATURE                 Location/Qualifiers
source                  1..735
                        mol_type = genomic DNA
                        organism = Homo sapiens
SEQUENCE: 120
atgctgttgc tgggagctgt tctactgcta ttagctctgc ccggtcatga ccaggaaacc  60
acgactcaag ggcccggagt cctgcttccc ctgcccaagg gggcctgcac aggttggatg  120
gcgggcatcc cagggcatcc gggccataat ggggccccag gccgtgatgg cagagatggc  180
acccctggtg agaagggtga gaaaggagat ccaggtctta ttggtcctaa gggagacatc  240
ggtgaaaccg gagtacccgg ggctgaaggt ccccgaggct ttccgggaat ccaaggcagg  300
aaaggagaac ctggagaagg tgcctatgta taccgctcag cattcagtgt gggattggag  360
acttacgtta ctatccccaa catgcccatt cgctttacca agatcttcta caatcagcaa  420
aaccactatg atggctccac tggtaaattc cactgcaaca ttcctgggct gtactacttt  480
gcctaccaca tcacagtcta tatgaaggat gtgaaggtca gcctcttcaa gaaggacaag  540
gctatgctct tcacctatga tcagtaccag gaaaataatg tggaccaggc ctccggctct  600
gtgctcctgc atctggaggt gggcgaccaa gtctggctcc aggtgtatgg ggaaggagag  660
cgtaatggac tctatgctga taatgacaat gactccacct tcacaggctt tcttctctac  720
catgacacca actga                                                   735

SEQ ID NO: 121          moltype = DNA  length = 735
FEATURE                 Location/Qualifiers
misc_feature            1..735
                        note = Description of Artificial Sequence:
                         Syntheticpolynucleotide
source                  1..735
                        mol_type = other DNA
                        organism = synthetic construct
SEQUENCE: 121
atgctgctgc tgggagccgt gctactgcta ctggccctgc ccggccacga ccaggaaacc  60
acgacccaag ggcccggagt cctgctgccc ctgcccaagg gggcctgcac aggctggatg  120
gcgggcatcc cagggcaccc gggccacaac ggggccccag gccgggacgg cagagacggc  180
acccccggcg agaagggcga gaaaggagac ccaggcctga tcggccccaa gggagacatc  240
ggcgaaaccg gagtacccgg ggccgaaggc ccccgaggct tcccgggaat ccaaggcagg  300
aaaggagaac ccggagaagg cgcctacgta taccgcagcg cattcagcgt gggactggag  360
acctacgtga ccatccccaa catgcccatc cgcttcacca agatcttcta caaccagcaa  420
aaccactacg acggcagcac cggcaaattc cactgcaaca tccccgggct gtactacttc  480
gcctaccaca tcacagtcta catgaaggac gtgaaggtca gcctcttcaa gaaggacaag  540
gccatgctgt tcacctacga ccagtaccag gaaaacaacg tggaccaggc cagcggcagc  600
gtgctcctgc acctggaggt gggcgaccaa gtctggctcc aggtgtacgg ggaaggagag  660
cggaacggac tctacgccga caacgacaac gacagcacct tcacaggctt cctgctctac  720
cacgacacca actga                                                   735

SEQ ID NO: 122          moltype = DNA  length = 735
FEATURE                 Location/Qualifiers
misc_feature            1..735
                        note = Description of Artificial Sequence:
```

```
                          Syntheticpolynucleotide
source                   1..735
                         mol_type = other DNA
                         organism = synthetic construct
SEQUENCE: 122
atgctgttgc tgggagctgt tctactgcta ttagctctgc ccggtcatga ccaggaaacc  60
acgactcaag ggcccggagt cctgcttccc ctgcccaagg gggcctgcac aggttggatg  120
gcgggcatcc cagggcatcc gggccataac ggggccccag gccgggacgg cagagacggc  180
acccccggcg agaagggcga gaaaggagac ccaggcctga tcggccccaa gggagacatc  240
ggcgaaaccg gagtacccgg ggccgaaggc ccccgaggct tcccgggaat ccaaggcagg  300
aaaggagaac ccggagaagg cgcctacgta taccgcagcg cattcagcgt gggactggag  360
acctacgtga ccatccccaa catgcccatc cgcttcacca agatcttcta caaccagcaa  420
aaccactacg acggcagcac cggcaaattc cactgcaaca tccccgggct gtactacttc  480
gcctaccaca tcacagtcta catgaaggac gtgaaggtca gcctcttcaa gaaggacaag  540
gccatgctgt tcacctacga ccagtaccag gaaaacaacg tggaccaggc cagcggcagc  600
gtgctcctgc acctggaggt gggcgaccaa gtctggctcc aggtgtacgg ggaaggagag  660
cggaacggac tctacgccga caacgacaac gacagcacct tcacaggctt cctgctctac  720
cacgacacca actga                                                   735

SEQ ID NO: 123           moltype = DNA  length = 735
FEATURE                  Location/Qualifiers
misc_feature             1..735
                         note = Description of Artificial Sequence:
                          Syntheticpolynucleotide
source                   1..735
                         mol_type = other DNA
                         organism = synthetic construct
SEQUENCE: 123
atgctgttgc tgggagctgt tctactgcta ttagctctgc ccggtcatga ccaggaaacc  60
acgactcaag ggcccggagt cctgcttccc ctgcccaagg gggcctgcac aggttggatg  120
gcgggcatcc cagggcatcc gggccataat ggggccccag gccgtgatgg cagagatggc  180
acccctggtg agaagggtga gaaaggagat ccaggtctta ttggtcctaa gggagacatc  240
ggtgaaaccg gagtacccgg ggctgaaggc ccccgaggct tcccgggaat ccaaggcagg  300
aaaggagaac ccggagaagg cgcctacgta taccgcagcg cattcagcgt gggactggag  360
acctacgtga ccatccccaa catgcccatc cgcttcacca agatcttcta caaccagcaa  420
aaccactacg acggcagcac cggcaaattc cactgcaaca tccccgggct gtactacttc  480
gcctaccaca tcacagtcta catgaaggac gtgaaggtca gcctcttcaa gaaggacaag  540
gccatgctgt tcacctacga ccagtaccag gaaaacaacg tggaccaggc cagcggcagc  600
gtgctcctgc acctggaggt gggcgaccaa gtctggctcc aggtgtacgg ggaaggagag  660
cggaacggac tctacgccga caacgacaac gacagcacct tcacaggctt cctgctctac  720
cacgacacca actga                                                   735

SEQ ID NO: 124           moltype = DNA  length = 735
FEATURE                  Location/Qualifiers
misc_feature             1..735
                         note = Description of Artificial Sequence:
                          Syntheticpolynucleotide
source                   1..735
                         mol_type = other DNA
                         organism = synthetic construct
SEQUENCE: 124
atgctgttgc tgggagctgt tctactgcta ttagctctgc ccggtcatga ccaggaaacc  60
acgactcaag ggcccggagt cctgcttccc ctgcccaagg gggcctgcac aggttggatg  120
gcgggcatcc cagggcatcc gggccataat ggggccccag gccgtgatgg cagagatggc  180
acccctggtg agaagggtga gaaaggagat ccaggtctta ttggtcctaa gggagacatc  240
ggtgaaaccg gagtacccgg ggctgaaggt ccccgaggct ttccgggaat ccaaggcagg  300
aaaggagaac ctggagaagg tgcctatgta taccgctcag cattcagtgt gggattggag  360
acttacgtta ctatccccaa catgcccatt cgctttacca agatcttcta caatcagcaa  420
aaccactatg acggcagcac cggcaaattc cactgcaaca tccccgggct gtactacttc  480
gcctaccaca tcacagtcta catgaaggac gtgaaggtca gcctcttcaa gaaggacaag  540
gccatgctgt tcacctacga ccagtaccag gaaaacaacg tggaccaggc cagcggcagc  600
gtgctcctgc acctggaggt gggcgaccaa gtctggctcc aggtgtacgg ggaaggagag  660
cggaacggac tctacgccga caacgacaac gacagcacct tcacaggctt cctgctctac  720
cacgacacca actga                                                   735

SEQ ID NO: 125           moltype = DNA  length = 735
FEATURE                  Location/Qualifiers
misc_feature             1..735
                         note = Description of Artificial Sequence:
                          Syntheticpolynucleotide
source                   1..735
                         mol_type = other DNA
                         organism = synthetic construct
SEQUENCE: 125
atgctgttgc tgggagctgt tctactgcta ttagctctgc ccggtcatga ccaggaaacc  60
acgactcaag ggcccggagt cctgcttccc ctgcccaagg gggcctgcac aggttggatg  120
gcgggcatcc cagggcatcc gggccataat ggggccccag gccgtgatgg cagagatggc  180
acccctggtg agaagggtga gaaaggagat ccaggtctta ttggtcctaa gggagacatc  240
ggtgaaaccg gagtacccgg ggctgaaggt ccccgaggct ttccgggaat ccaaggcagg  300
```

```
aaaggagaac ctggagaagg tgcctatgta taccgctcag cattcagtgt gggattggag  360
acttacgtta ctatccccaa catgcccatt cgctttacca agatcttcta caatcagcaa  420
aaccactatg atggctccac tggtaaattc cactgcaaca ttcctgggct gtactacttt  480
gcctaccaca tcacagtcta tatgaaggat gtgaaggtca gcctcttcaa gaaggacaag  540
gctatgctgt tcacctatga tcagtaccag gaaaataatg tggaccaggc ctccggcagc  600
gtgctcctgc acctggaggt gggcgaccaa gtctggctcc aggtgtacgg ggaaggagag  660
cggaacggac tctacgccga caacgacaac gacagcacct tcacaggctt cctgctctac  720
cacgacacca actga                                                   735

SEQ ID NO: 126         moltype = DNA  length = 735
FEATURE                Location/Qualifiers
misc_feature           1..735
                       note = Description of Artificial Sequence:
                        Syntheticpolynucleotide
source                 1..735
                       mol_type = other DNA
                       organism = synthetic construct
SEQUENCE: 126
atgctgctgc tgggagccgt gctactgcta ctggccctgc ccggccacga ccaggaaacc  60
acgacccaag ggcccggagt cctgctgccc ctgcccaagg gggcctgcac aggctggatg  120
gcgggcatcc cagggcaccc gggccacaac ggggccccag gccgggacgg cagagacggc  180
acccccggcg agaagggcga gaaaggagac ccaggcctga tcggccccaa gggagacatc  240
ggcgaaaccg gagtacccgg ggccgaaggc ccccgaggct tcccgggaat ccaaggcagg  300
aaaggagaac ccggagaagg cgcctacgta taccgcagcg cattcagcgt gggactggag  360
acctacgtga ccatccccaa catgcccatc cgcttcacca agatcttcta caaccagcaa  420
aaccactacg acggcagcac cggcaaattc cactgcaaca tccccgggct gtactacttc  480
gcctaccaca tcacagtcta catgaaggac gtgaaggtca gcctcttcaa gaaggacaag  540
gccatgctgt tcacctacga ccagtaccag gaaaacaacg tggaccaggc cagcggcagc  600
gtgctcctgc acctggaggt gggcgaccaa gtctggctcc aggtgtatgg ggaaggagag  660
cgtaatggac tctatgctga taatgacaat gactccacct tcacaggctt tcttctctac  720
catgacacca actga                                                   735

SEQ ID NO: 127         moltype = DNA  length = 735
FEATURE                Location/Qualifiers
misc_feature           1..735
                       note = Description of Artificial Sequence:
                        Syntheticpolynucleotide
source                 1..735
                       mol_type = other DNA
                       organism = synthetic construct
SEQUENCE: 127
atgctgctgc tgggagccgt gctactgcta ctggccctgc ccggccacga ccaggaaacc  60
acgacccaag ggcccggagt cctgctgccc ctgcccaagg gggcctgcac aggctggatg  120
gcgggcatcc cagggcaccc gggccacaac ggggccccag gccgggacgg cagagacggc  180
acccccggcg agaagggcga gaaaggagac ccaggcctga tcggccccaa gggagacatc  240
ggcgaaaccg gagtacccgg ggccgaaggc ccccgaggct tcccgggaat ccaaggcagg  300
aaaggagaac ccggagaagg cgcctacgta taccgcagcg cattcagcgt gggactggag  360
acctacgtga ccatccccaa catgcccatc cgcttcacca agatcttcta caaccagcaa  420
aaccactacg acggcagcac cggtaaattc cactgcaaca ttcctgggct gtactacttt  480
gcctaccaca tcacagtcta tatgaaggat gtgaaggtca gcctcttcaa gaaggacaag  540
gctatgctgt tcacctatga tcagtaccag gaaaataatg tggaccaggc ctccggctct  600
gtgctcctgc atctggaggt gggcgaccaa gtctggctcc aggtgtatgg ggaaggagag  660
cgtaatggac tctatgctga taatgacaat gactccacct tcacaggctt tcttctctac  720
catgacacca actga                                                   735

SEQ ID NO: 128         moltype = DNA  length = 735
FEATURE                Location/Qualifiers
misc_feature           1..735
                       note = Description of Artificial Sequence:
                        Syntheticpolynucleotide
source                 1..735
                       mol_type = other DNA
                       organism = synthetic construct
SEQUENCE: 128
atgctgctgc tgggagccgt gctactgcta ctggccctgc ccggccacga ccaggaaacc  60
acgacccaag ggcccggagt cctgctgccc ctgcccaagg gggcctgcac aggctggatg  120
gcgggcatcc cagggcaccc gggccacaac ggggccccag gccgggacgg cagagacggc  180
acccccggcg agaagggcga gaaaggagac ccaggcctga tcggccccaa gggagacatc  240
ggcgaaaccg gagtacccgg ggccgaaggc ccccgaggct tcccgggaat ccaaggcagg  300
aaaggagaac ccggagaagg tgcctatgta taccgctcag cattcagtgt gggattggag  360
acttacgtta ctatccccaa catgcccatt cgctttacca agatcttcta caatcagcaa  420
aaccactatg atggctccac tggtaaattc cactgcaaca ttcctgggct gtactacttt  480
gcctaccaca tcacagtcta tatgaaggat gtgaaggtca gcctcttcaa gaaggacaag  540
gctatgctgt tcacctatga tcagtaccag gaaaataatg tggaccaggc ctccggctct  600
gtgctcctgc atctggaggt gggcgaccaa gtctggctcc aggtgtatgg ggaaggagag  660
cgtaatggac tctatgctga taatgacaat gactccacct tcacaggctt tcttctctac  720
catgacacca actga                                                   735

SEQ ID NO: 129         moltype = DNA  length = 735
```

-continued

```
FEATURE                 Location/Qualifiers
misc_feature            1..735
                        note = Description of Artificial Sequence:
                         Syntheticpolynucleotide
source                  1..735
                        mol_type = other DNA
                        organism = synthetic construct
SEQUENCE: 129
atgctgctgc tgggagccgt gctactgcta ctggccctgc ccggccacga ccaggaaacc  60
acgacccaag ggcccggagt cctgctgccc ctgcccaagg gggcctgcac aggctggatg  120
gcgggcatcc cagggcaccc gggccacaac ggggccccag gccgggacgg cagagatggc  180
acccctggtg agaagggtga gaaaggagat ccaggtctta ttggtcctaa gggagacatc  240
ggtgaaaccg gagtacccgg ggctgaaggt ccccgaggct ttccgggaat ccaaggcagg  300
aaaggagaac ctggagaagg tgcctatgta taccgctcag cattcagtgt gggattggag  360
acttacgtta ctatccccaa catgcccatt cgctttacca agatcttcta caatcagcaa  420
aaccactatg atggctccac tggtaaattc cactgcaaca ttcctgggct gtactacttt  480
gcctaccaca tcacagtcta tatgaaggat gtgaaggtca gcctcttcaa gaaggacaag  540
gctatgctgt tcacctatga tcagtaccag gaaaataatg tggaccaggc ctccggctct  600
gtgctcctgc atctggaggt gggcgaccaa gtctggctcc aggtgtatgg ggaaggagag  660
cgtaatggac tctatgctga taatgacaat gactccacct tcacaggctt tcttctctac  720
catgacacca actga                                                   735

SEQ ID NO: 130          moltype = DNA  length = 735
FEATURE                 Location/Qualifiers
misc_feature            1..735
                        note = Description of Artificial Sequence:
                         Syntheticpolynucleotide
source                  1..735
                        mol_type = other DNA
                        organism = synthetic construct
SEQUENCE: 130
atgctgttgc tgggagccgt gctactgcta ctggccctgc ccggccacga ccaggaaacc  60
acgactcaag ggcccggagt cctgctgccc ctgcccaagg gggcctgcac aggttggatg  120
gcgggcatcc cagggcaccc gggccacaat ggggccccag gccgggatgg cagagacggc  180
acccccggcg agaagggcga gaaaggagat ccaggcctga tcggtcccaa gggagacatc  240
ggcgaaaccg gagtacccgg ggccgaaggc ccccgaggct tcccgggaat ccaaggcagg  300
aaaggagaac ccggagaagg cgcctatgta taccgcagcg cattcagtgt gggattggag  360
acctacgtga ccatccccaa catgcccatc cgcttcacca agatcttcta caaccagcaa  420
aaccactacg acggcagcac cggcaaattc cactgcaaca tccccgggct gtactacttt  480
gcctaccaca tcacagtcta catgaaggac gtgaaggtca gcctcttcaa gaaggacaag  540
gccatgctgt tcacctacga ccagtaccag gaaaacaacg tggaccaggc cagcggcagc  600
gtgctcctgc acctggaggt gggcgaccaa gtctggctcc aggtgtacgg ggaaggagag  660
cgtaacggac tctacgccga caacgacaac gacagcacct tcacaggctt cctgctctac  720
cacgacacca actga                                                   735

SEQ ID NO: 131          moltype = DNA  length = 735
FEATURE                 Location/Qualifiers
misc_feature            1..735
                        note = Description of Artificial Sequence:
                         Syntheticpolynucleotide
source                  1..735
                        mol_type = other DNA
                        organism = synthetic construct
SEQUENCE: 131
atgctgctgc tgggagccgt gctactgcta ctggctctgc ccggtcacga ccaggaaacc  60
acgactcaag ggcccggagt cctgctgccc ctgcccaagg gggcctgcac aggttggatg  120
gcgggcatcc cagggcatcc gggccataac ggggccccag gccgggatgg cagagacggc  180
acccctggcg agaagggtga gaaaggagac ccaggcctga tcggccctaa gggagacatc  240
ggcgaaaccg gagtacccgg ggccgaaggc ccccgaggct tcccgggaat ccaaggcagg  300
aaaggagaac ccggagaagg cgcctatgta taccgcagcg cattcagtgt gggattggag  360
acttacgtta ccatccccaa catgcccatt cgcttcacca agatcttcta caaccagcaa  420
aaccactacg acggcagcac cggtaaattc cactgcaaca tccctgggct gtactacttt  480
gcctaccaca tcacagtcta tatgaaggat gtgaaggtca gcctcttcaa gaaggacaag  540
gctatgctgt tcacctacga tcagtaccag gaaaataatg tggaccaggc cagcggcagc  600
gtgctcctgc acctggaggt gggcgaccaa gtctggctcc aggtgtacgg ggaaggagag  660
cggaacggac tctacgccga caacgacaat gacagcacct tcacaggctt cctgctctac  720
catgacacca actga                                                   735

SEQ ID NO: 132          moltype = DNA  length = 735
FEATURE                 Location/Qualifiers
misc_feature            1..735
                        note = Description of Artificial Sequence:
                         Syntheticpolynucleotide
source                  1..735
                        mol_type = other DNA
                        organism = synthetic construct
SEQUENCE: 132
atgctgttgc tgggagccgt tctactgcta ctggctctgc ccggccatga ccaggaaacc  60
acgacccaag ggcccggagt cctgcttccc ctgcccaagg gggcctgcac aggttggatg  120
```

```
gcgggcatcc cagggcaccc gggccataat ggggccccag gccgtgatgg cagagacggc  180
acccccggcg agaagggtga gaaaggagat ccaggtctga tcggtcctaa gggagacatc  240
ggcgaaaccg gagtacccgg ggctgaaggt ccccgaggct ttccgggaat ccaaggcagg  300
aaaggagaac ctggagaagg cgcctacgta taccgcagcg cattcagcgt gggactggag  360
acctacgtga ccatccccaa catgcccatc cgctttacca agatcttcta caatcagcaa  420
aaccactatg acggctccac tggcaaattc cactgcaaca ttcccgggct gtactacttt  480
gcctaccaca tcacagtcta tatgaaggat gtgaaggtca gcctcttcaa gaaggacaag  540
gccatgctgt tcacctacga tcagtaccag gaaaacaatg tggaccaggc cagcggctct  600
gtgctcctgc atctggaggt gggcgaccaa gtctggctcc aggtgtacgg ggaaggagag  660
cgtaacggac tctatgccga taatgacaat gactccacct tcacaggctt tcttctctac  720
catgacacca actga                                                   735
```

```
SEQ ID NO: 133          moltype = DNA  length = 735
FEATURE                 Location/Qualifiers
misc_feature            1..735
                        note = Description of Artificial Sequence:
                         Syntheticpolynucleotide
source                  1..735
                        mol_type = other DNA
                        organism = synthetic construct
SEQUENCE: 133
atgctgttgc tgggagccgt tctactgcta ttagctctgc ccggtcatga ccaggaaacc  60
acgactcaag ggcccggagt cctgctgccc ctgcccaagg gggcctgcac aggttggatg  120
gcgggcatcc cagggcatcc gggccataat ggggccccag gccgtgacgg cagagatggc  180
acccccggtg agaagggtga gaaaggagac ccaggtctta ttggccctaa gggagacatc  240
ggtgaaaccg gagtacccgg ggctgaaggc ccccgaggct ttccgggaat ccaaggcagg  300
aaaggagaac ctggagaagg cgcctatgta taccgcagcg cattcagtgt gggattggag  360
acttacgtta ctatccccaa catgcccatt cgctttacca agatcttcta caatcagcaa  420
aaccactatg atggcagcac cggtaaattc cactgcaaca tccctgggct gtactacttt  480
gcctaccaca tcacagtcta tatgaaggat gtgaaggtca gcctcttcaa gaaggacaag  540
gctatgctgt tcacctatga ccagtaccag gaaaataatg tggaccaggc ctccggctct  600
gtgctcctgc atctggaggt gggcgaccaa gtctggctcc aggtgtatgg ggaaggagag  660
cgtaatggac tctacgctga taatgacaat gactccacct tcacaggctt tctgctctac  720
catgacacca actga                                                  735
```

```
SEQ ID NO: 134          moltype = DNA  length = 1167
FEATURE                 Location/Qualifiers
misc_feature            1..1167
                        note = Description of Artificial Sequence:
                         Syntheticpolynucleotide
source                  1..1167
                        mol_type = other DNA
                        organism = synthetic construct
SEQUENCE: 134
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgc tgctgggagc cgtgctactg ctactggccc  180
tgcccggcca cgaccaggaa accacgaccc aagggcccgg agtcctgctg cccctgccca  240
agggggcctg cacaggctgg atggcgggca tcccagggca cccgggccac aacggggccc  300
caggccggga cggcagagac ggcacccccg gcgagaaggg cgagaaagga gacccaggcc  360
tgatcggccc caagggagac atcggcgaaa ccggagtacc cggggccgaa ggcccccgag  420
gcttcccggg aatccaaggc aggaaaggag aacccggaga aggcgcctac gtataccgca  480
gcgcattcag cgtgggactg gagacctacg tgaccatccc caacatgccc atccgcttca  540
ccaagatctt ctacaaccag caaaaccact acgacggcag caccggcaaa ttccactgca  600
acatccccgg gctgtactac ttcgcctacc acatcacagt ctacatgaag gacgtgaagg  660
tcagcctctt caagaaggac aaggccatgc tgttcaccta cgaccagtac caggaaaaca  720
acgtggacca ggccagcggc agcgtgctcc tgcacctgga ggtgggcgac caagtctggc  780
tccaggtgta cggggaagga gagcggaacg gactctacgc cgacaacgac aacgacagca  840
ccttcacagg cttcctgctc taccacgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167
```

```
SEQ ID NO: 135          moltype = DNA  length = 1167
FEATURE                 Location/Qualifiers
misc_feature            1..1167
                        note = Description of Artificial Sequence:
                         Syntheticpolynucleotide
source                  1..1167
                        mol_type = other DNA
                        organism = synthetic construct
SEQUENCE: 135
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc tgttctactg ctattagctc  180
tgcccggtca tgaccaggaa accacgactc aagggcccgg agtcctgctt cccctgccca  240
agggggcctg cacaggttgg atggcgggca tcccagggca tccgggccat aacggggccc  300
```

```
caggccggga cggcagagac ggcacccccg gcgagaaggg cgagaaagga gacccaggcc  360
tgatcggccc caagggagac atcggcgaaa ccggagtacc cggggccgaa ggccccccgag 420
gcttcccggg aatccaaggc aggaaaggag aacccggaga aggcgcctac gtataccgca  480
gcgcattcag cgtgggactg gagacctacg tgaccatccc caacatgccc atccgcttca  540
ccaagatctt ctacaaccag caaaaccact acgacggcag caccggcaaa ttccactgca  600
acatccccgg gctgtactac ttcgcctacc acatcacagt ctacatgaag gacgtgaagg  660
tcagcctctt caagaaggac aaggccatgc tgttcaccta cgaccagtac caggaaaaca  720
acgtggacca ggccagcggc agcgtgctcc tgcacctgga ggtgggcgac caagtctggc  780
tccaggtgta cggggaagga gagcggaacg gactctacgc cgacaacgac aacgacagca  840
ccttcacagg cttcctgctc taccacgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 136         moltype = DNA  length = 1167
FEATURE                Location/Qualifiers
misc_feature           1..1167
                       note = Description of Artificial Sequence:
                        Syntheticpolynucleotide
source                 1..1167
                       mol_type = other DNA
                       organism = synthetic construct
SEQUENCE: 136
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc tgttctactg ctattagctc  180
tgcccggtca tgaccaggaa accacgactc aagggcccgg agtcctgctt cccctgccca  240
agggggcctg cacaggttgg atggcgggca tcccagggca tccgggccat aatggggccc  300
caggccgtga tggcagagat ggcacccctg gtgagaaggg tgagaaagga gatccaggtc  360
ttattggtcc taagggagac atcggtgaaa ccggagtacc cggggctgaa ggcccccgag  420
gcttcccggg aatccaaggc aggaaaggag aacccggaga aggcgcctac gtataccgca  480
gcgcattcag cgtgggactg gagacctacg tgaccatccc caacatgccc atccgcttca  540
ccaagatctt ctacaaccag caaaaccact acgacggcag caccggcaaa ttccactgca  600
acatccccgg gctgtactac ttcgcctacc acatcacagt ctacatgaag gacgtgaagg  660
tcagcctctt caagaaggac aaggccatgc tgttcaccta cgaccagtac caggaaaaca  720
acgtggacca ggccagcggc agcgtgctcc tgcacctgga ggtgggcgac caagtctggc  780
tccaggtgta cggggaagga gagcggaacg gactctacgc cgacaacgac aacgacagca  840
ccttcacagg cttcctgctc taccacgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 137         moltype = DNA  length = 1167
FEATURE                Location/Qualifiers
misc_feature           1..1167
                       note = Description of Artificial Sequence:
                        Syntheticpolynucleotide
source                 1..1167
                       mol_type = other DNA
                       organism = synthetic construct
SEQUENCE: 137
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc tgttctactg ctattagctc  180
tgcccggtca tgaccaggaa accacgactc aagggcccgg agtcctgctt cccctgccca  240
agggggcctg cacaggttgg atggcgggca tcccagggca tccgggccat aatggggccc  300
caggccgtga tggcagagat ggcacccctg gtgagaaggg tgagaaagga gatccaggtc  360
ttattggtcc taagggagac atcggtgaaa ccggagtacc cggggctgaa ggtccccgag  420
gctttccggg aatccaaggc aggaaaggag aacctggaga aggtgcctat gtataccgct  480
cagcattcag tgtgggattg gagacttacg ttactatccc caacatgccc attcgcttta  540
ccaagatctt ctacaatcag caaaaccact atgacggcag caccggcaaa ttccactgca  600
acatccccgg gctgtactac ttcgcctacc acatcacagt ctacatgaag gacgtgaagg  660
tcagcctctt caagaaggac aaggccatgc tgttcaccta cgaccagtac caggaaaaca  720
acgtggacca ggccagcggc agcgtgctcc tgcacctgga ggtgggcgac caagtctggc  780
tccaggtgta cggggaagga gagcggaacg gactctacgc cgacaacgac aacgacagca  840
ccttcacagg cttcctgctc taccacgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 138         moltype = DNA  length = 1167
FEATURE                Location/Qualifiers
misc_feature           1..1167
```

```
                        note = Description of Artificial Sequence:
                         Syntheticpolynucleotide
source                  1..1167
                        mol_type = other DNA
                        organism = synthetic construct
SEQUENCE: 138
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc tgttctactg ctattagctc  180
tgcccggtca tgaccaggaa accacgactc aagggcccgg agtcctgctt cccctgccca  240
agggggcctg cacaggttgg atggcgggca tcccagggca tccgggccat aatggggccc  300
caggccgtga tggcagagat ggcacccctg gtgagaaggg tgagaaagga gatccaggtc  360
ttattggtcc taagggagac atcggtgaaa ccggagtacc cggggctgaa ggtccccgag  420
gctttccggg aatccaaggc aggaaaggag aacctggaga aggtgcctat gtataccgct  480
cagcattcag tgtgggattg gagacttacg ttactatccc caacatgccc attcgcttta  540
ccaagatctt ctacaatcag caaaaccact atgatggctc cactggtaaa ttccactgca  600
acattcctgg gctgtactac tttgcctacc acatcacagt ctatatgaag gatgtgaagg  660
tcagcctctt caagaaggac aaggctatgc tgttcaccta tgatcagtac caggaaaata  720
atgtggacca ggcctccggc agcgtgctcc tgcacctgga ggtgggcgac caagtctggc  780
tccaggtgta cggggaagga gagcggaacg gactctacgc cgacaacgac aacgacagca  840
ccttcacagg cttcctgctc taccacgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                     1167

SEQ ID NO: 139          moltype = DNA  length = 1167
FEATURE                 Location/Qualifiers
misc_feature            1..1167
                        note = Description of Artificial Sequence:
                         Syntheticpolynucleotide
source                  1..1167
                        mol_type = other DNA
                        organism = synthetic construct
SEQUENCE: 139
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgc tgctgggagc cgtgctactg ctactggccc  180
tgcccggcca cgaccaggaa accacgaccc aagggcccgg agtcctgctg cccctgccca  240
agggggcctg cacaggctgg atggcgggca tcccagggca cccgggccac aacggggccc  300
caggccggga cggcagagac ggcacccccg gcgagaaggg cgagaaagga gacccaggcc  360
tgatcggccc caagggagac atcggcgaaa ccggagtacc cggggccgaa ggcccccgag  420
gcttcccggg aatccaaggc aggaaaggag aacccggaga aggcgcctac gtataccgca  480
gcgcattcag cgtgggactg gagacctacg tgaccatccc caacatgccc atccgcttca  540
ccaagatctt ctacaaccag caaaaccact acgacggcag caccggcaaa ttccactgca  600
acatccccgg gctgtactac ttcgcctacc acatcacagt ctacatgaag gacgtgaagg  660
tcagcctctt caagaaggac aaggccatgc tgttcaccta cgaccagtac caggaaaaca  720
acgtggacca ggccagcggc agcgtgctcc tgcacctgga ggtgggcgac caagtctggc  780
tccaggtgta tggggaagga gagcgtaatg gactctatgc tgataatgac aatgactcca  840
ccttcacagg ctttcttctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                     1167

SEQ ID NO: 140          moltype = DNA  length = 1167
FEATURE                 Location/Qualifiers
misc_feature            1..1167
                        note = Description of Artificial Sequence:
                         Syntheticpolynucleotide
source                  1..1167
                        mol_type = other DNA
                        organism = synthetic construct
SEQUENCE: 140
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgc tgctgggagc cgtgctactg ctactggccc  180
tgcccggcca cgaccaggaa accacgaccc aagggcccgg agtcctgctg cccctgccca  240
agggggcctg cacaggctgg atggcgggca tcccagggca cccgggccac aacggggccc  300
caggccggga cggcagagac ggcacccccg gcgagaaggg cgagaaagga gacccaggcc  360
tgatcggccc caagggagac atcggcgaaa ccggagtacc cggggccgaa ggcccccgag  420
gcttcccggg aatccaaggc aggaaaggag aacccggaga aggcgcctac gtataccgca  480
gcgcattcag cgtgggactg gagacctacg tgaccatccc caacatgccc atccgcttca  540
ccaagatctt ctacaaccag caaaaccact acgacggcag caccggtaaa ttccactgca  600
acattcctgg gctgtactac tttgcctacc acatcacagt ctatatgaag gatgtgaagg  660
tcagcctctt caagaaggac aaggctatgc tgttcaccta tgatcagtac caggaaaata  720
atgtggacca ggcctccggc tctgtgctcc tgcatctgga ggtgggcgac caagtctggc  780
```

```
tccaggtgta tggggaagga gagcgtaatg gactctatgc tgataatgac aatgactcca  840
ccttcacagg ctttcttctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 141          moltype = DNA  length = 1167
FEATURE                 Location/Qualifiers
misc_feature            1..1167
                        note = Description of Artificial Sequence:
                         Syntheticpolynucleotide
source                  1..1167
                        mol_type = other DNA
                        organism = synthetic construct
SEQUENCE: 141
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgc tgctgggagc cgtgctactg ctactggccc  180
tgcccggcca cgaccaggaa accacgaccc aagggcccgg agtcctgctg cccctgccca  240
agggggcctg cacaggctgg atggcgggca tcccagggca cccgggccac aacggggccc  300
caggccggga cggcagagac ggcacccccg gcgagaaggg cgagaaagga gacccaggcc  360
tgatcggccc caagggagac atcggcgaaa ccggagtacc cggggccgaa ggcccccgag  420
gcttcccggg aatccaaggc aggaaaggag aacccggaga aggtgcctat gtataccgct  480
cagcattcag tgtgggattg gagacttacg ttactatccc caacatgccc attcgcttta  540
ccaagatctt ctacaatcag caaaaccact atgatggctc cactggtaaa ttccactgca  600
acattcctgg gctgtactac tttgcctacc acatcacagt ctatatgaag gatgtgaagg  660
tcagcctctt caagaaggac aaggctatgc tgttcaccta tgatcagtac caggaaaata  720
atgtggacca ggcctccggc tctgtgctcc tgcatctgga ggtgggcgac caagtctggc  780
tccaggtgta tggggaagga gagcgtaatg gactctatgc tgataatgac aatgactcca  840
ccttcacagg ctttcttctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 142          moltype = DNA  length = 1167
FEATURE                 Location/Qualifiers
misc_feature            1..1167
                        note = Description of Artificial Sequence:
                         Syntheticpolynucleotide
source                  1..1167
                        mol_type = other DNA
                        organism = synthetic construct
SEQUENCE: 142
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgc tgctgggagc cgtgctactg ctactggccc  180
tgcccggcca cgaccaggaa accacgaccc aagggcccgg agtcctgctg cccctgccca  240
agggggcctg cacaggctgg atggcgggca tcccagggca cccgggccac aacggggccc  300
caggccggga cggcagagat ggcacccctg gtgagaaggg tgagaaagga gatccaggtc  360
ttattggtcc taagggagac atcggtgaaa ccggagtacc cggggctgaa ggtccccgag  420
gctttccggg aatccaaggc aggaaaggag aacctggaga aggtgcctat gtataccgct  480
cagcattcag tgtgggattg gagacttacg ttactatccc caacatgccc attcgcttta  540
ccaagatctt ctacaatcag caaaaccact atgatggctc cactggtaaa ttccactgca  600
acattcctgg gctgtactac tttgcctacc acatcacagt ctatatgaag gatgtgaagg  660
tcagcctctt caagaaggac aaggctatgc tgttcaccta tgatcagtac caggaaaata  720
atgtggacca ggcctccggc tctgtgctcc tgcatctgga ggtgggcgac caagtctggc  780
tccaggtgta tggggaagga gagcgtaatg gactctatgc tgataatgac aatgactcca  840
ccttcacagg ctttcttctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 143          moltype = DNA  length = 1167
FEATURE                 Location/Qualifiers
misc_feature            1..1167
                        note = Description of Artificial Sequence:
                         Syntheticpolynucleotide
source                  1..1167
                        mol_type = other DNA
                        organism = synthetic construct
SEQUENCE: 143
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
```

```
ttcaccattt acgaacgata gccatgctgt tgctgggagc cgtgctactg ctactggccc  180
tgcccggcca cgaccaggaa accacgactc aagggcccgg agtcctgctg cccctgccca  240
agggggcctg cacaggttgg atggcgggca tcccagggca cccgggccac aatgggggccc  300
caggccggga tggcagagac ggcacccccg gcgagaaggg cgagaaagga gatccaggcc  360
tgatcggtcc caagggagac atcggcgaaa ccggagtacc cggggccgaa ggccccccgag  420
gcttcccggg aatccaaggc aggaaaggag aacccggaga aggcgcctat gtataccgca  480
gcgcattcag tgtgggattg gagacctacg tgaccatccc caacatgccc atccgcttca  540
ccaagatctt ctacaaccag caaaaccact acgacggcag caccggcaaa ttccactgca  600
acatccccgg gctgtactac tttgcctacc acatcacagt ctacatgaag gacgtgaagg  660
tcagcctctt caagaaggac aaggccatgc tgttcaccta cgaccagtac caggaaaaca  720
acgtggacca ggccagcggc agcgtgctcc tgcacctgga ggtgggcgac caagtctggc  780
tccaggtgta cggggaagga gagcgtaacg gactctacgc cgacaacgac aacgacagca  840
ccttcacagg cttcctgctc taccacgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 144          moltype = DNA  length = 1167
FEATURE                 Location/Qualifiers
misc_feature            1..1167
                        note = Description of Artificial Sequence:
                         Syntheticpolynucleotide
source                  1..1167
                        mol_type = other DNA
                        organism = synthetic construct
SEQUENCE: 144
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgc tgctgggagc cgtgctactg ctactggctc  180
tgcccggtca cgaccaggaa accacgactc aagggcccgg agtcctgctg cccctgccca  240
agggggcctg cacaggttgg atggcgggca tcccagggca tccgggccat aacgggggccc  300
caggccggga tggcagagac ggcacccctg gcgagaaggg tgagaaagga gacccaggcc  360
tgatcggccc taagggagac atcggcgaaa ccggagtacc cggggccgaa ggccccccgag  420
gcttcccggg aatccaaggc aggaaaggag aacccggaga aggcgcctat gtataccgca  480
gcgcattcag tgtgggattg gagacttacg ttaccatccc caacatgccc attcgcttca  540
ccaagatctt ctacaaccag caaaaccact acgacggcag caccggtaaa ttccactgca  600
acatccctgg gctgtactac tttgcctacc acatcacagt ctatatgaag gatgtgaagg  660
tcagcctctt caagaaggac aaggctatgc tgttcaccta cgatcagtac caggaaaata  720
atgtggacca ggccagcggc agcgtgctcc tgcacctgga ggtgggcgac caagtctggc  780
tccaggtgta cggggaagga gagcggaacg gactctacgc cgacaacgac aatgacagca  840
ccttcacagg cttcctgctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 145          moltype = DNA  length = 1167
FEATURE                 Location/Qualifiers
misc_feature            1..1167
                        note = Description of Artificial Sequence:
                         Syntheticpolynucleotide
source                  1..1167
                        mol_type = other DNA
                        organism = synthetic construct
SEQUENCE: 145
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc cgttctactg ctactggctc  180
tgcccggcca tgaccaggaa accacgaccc aagggcccgg agtcctgctt cccctgccca  240
agggggcctg cacaggttgg atggcgggca tcccagggca cccgggccat aatggggccc  300
caggccgtga tggcagagac ggcacccccg gcgagaaggg tgagaaagga gatccaggtc  360
tgatcggtcc taagggagac atcggcgaaa ccggagtacc cggggctgaa ggtccccgag  420
gctttccggg aatccaaggc aggaaaggag aacctggaga aggcgcctac gtataccgca  480
gcgcattcag cgtgggactg gagacctacg tgaccatccc caacatgccc atccgcttta  540
ccaagatctt ctacaatcag caaaaccact atgacggctc cactggcaaa ttccactgca  600
acattcccgg gctgtactac tttgcctacc acatcacagt ctatatgaag gatgtgaagg  660
tcagcctctt caagaaggac aaggccatgc tgttcaccta cgatcagtac caggaaaaca  720
atgtggacca ggccagcggc tctgtgctcc tgcatctgga ggtgggcgac caagtctggc  780
tccaggtgta cggggaagga gagcgtaacg gactctatgc cgataatgac aatgactcca  840
ccttcacagg ctttcttctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167
```

-continued

```
SEQ ID NO: 146          moltype = DNA  length = 1167
FEATURE                 Location/Qualifiers
misc_feature            1..1167
                        note = Description of Artificial Sequence:
                         Syntheticpolynucleotide
source                  1..1167
                        mol_type = other DNA
                        organism = synthetic construct
SEQUENCE: 146
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc cgttctactg ctattagctc  180
tgcccggtca tgaccaggaa accacgactc aagggcccgg agtcctgctg cccctgccca  240
agggggcctg cacaggttgg atggcgggca tcccagggca tccgggccat aatggggccc  300
caggccgtga cggcagagat ggcacccccg gtgagaaggg tgagaaagga gacccaggtc  360
ttattggccc taagggagac atcggtgaaa ccggagtacc cggggctgaa ggcccccgag  420
gctttccggg aatccaaggc aggaaaggag aacctggaga aggcgcctat gtataccgca  480
gcgcattcag tgtgggattg gagacttacg ttactatccc caacatgccc attcgcttta  540
ccaagatctt ctacaatcag caaaaccact atgatggcag caccggtaaa ttccactgca  600
acatccctgg gctgtactac tttgcctacc acatcacagt ctatatgaag gatgtgaagg  660
tcagcctctt caagaaggac aaggctatgc tgttcaccta tgaccagtac caggaaaata  720
atgtggacca ggcctccggc tctgtgctcc tgcatctgga ggtgggcgac caagtctggc  780
tccaggtgta tggggaagga gagcgtaatg gactctacgc tgataatgac aatgactcca  840
ccttcacagg ctttctgctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                     1167

SEQ ID NO: 147          moltype = RNA  length = 1167
FEATURE                 Location/Qualifiers
misc_feature            1..1167
                        note = Description of Artificial Sequence:
                         Syntheticpolynucleotide
source                  1..1167
                        mol_type = other RNA
                        organism = synthetic construct
SEQUENCE: 147
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgc tgctgggagc cgtgctactg ctactggccc  180
tgcccggcca cgaccaggaa accacgaccc aagggcccgg agtcctgctg cccctgccca  240
agggggcctg cacaggctgg atggcgggca tcccagggca cccgggccac aacggggccc  300
caggccggga cggcagagac ggcacccccg gcgagaaggg cgagaaagga gacccaggcc  360
tgatcggccc caagggagac atcggcgaaa ccggagtacc cggggccgaa ggcccccgag  420
gcttcccggg aatccaaggc aggaaaggag aacccggaga aggcgcctac gtataccgca  480
gcgcattcag cgtgggactg gagacctacg tgaccatccc caacatgccc atccgcttca  540
ccaagatctt ctacaaccag caaaaccact acgacggcag caccggcaaa ttccactgca  600
acatccccgg gctgtactac ttcgcctacc acatcacagt ctacatgaag gacgtgaagg  660
tcagcctctt caagaaggac aaggccatgc tgttcaccta cgaccagtac caggaaaaca  720
acgtggacca ggccagcggc agcgtgctcc tgcacctgga ggtgggcgac caagtctggc  780
tccaggtgta cggggaagga gagcggaacg gactctacgc cgacaacgac aacgacagca  840
ccttcacagg cttcctgctc taccacgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                     1167

SEQ ID NO: 148          moltype = RNA  length = 1167
FEATURE                 Location/Qualifiers
misc_feature            1..1167
                        note = Description of Artificial Sequence:
                         Syntheticpolynucleotide
source                  1..1167
                        mol_type = other RNA
                        organism = synthetic construct
SEQUENCE: 148
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc tgttctactg ctattagctc  180
tgcccggtca tgaccaggaa accacgactc aagggcccgg agtcctgctt cccctgccca  240
agggggcctg cacaggttgg atggcgggca tcccagggca tccgggccat aacggggccc  300
caggccggga cggcagagac ggcacccccg gcgagaaggg cgagaaagga gacccaggcc  360
tgatcggccc caagggagac atcggcgaaa ccggagtacc cggggccgaa ggcccccgag  420
gcttcccggg aatccaaggc aggaaaggag aacccggaga aggcgcctac gtataccgca  480
gcgcattcag cgtgggactg gagacctacg tgaccatccc caacatgccc atccgcttca  540
ccaagatctt ctacaaccag caaaaccact acgacggcag caccggcaaa ttccactgca  600
```

```
acatccccgg gctgtactac ttcgcctacc acatcacagt ctacatgaag gacgtgaagg  660
tcagcctctt caagaaggac aaggccatgc tgttcaccta cgaccagtac caggaaaaca  720
acgtggacca ggccagcggc agcgtgctcc tgcacctgga ggtgggcgac caagtctggc  780
tccaggtgta cggggaagga gagcggaacg gactctacgc cgacaacgac aacgacagca  840
ccttcacagg cttcctgctc taccacgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 149         moltype = RNA  length = 1167
FEATURE                Location/Qualifiers
misc_feature           1..1167
                       note = Description of Artificial Sequence:
                        Syntheticpolynucleotide
source                 1..1167
                       mol_type = other RNA
                       organism = synthetic construct
SEQUENCE: 149
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc tgttctactg ctattagctc  180
tgcccggtca tgaccaggaa accacgactc aagggcccgg agtcctgctt cccctgccca  240
agggggcctg cacaggttgg atggcgggca tcccagggca tccgggccat aatggggccc  300
caggccgtga tggcagagat ggcacccctg gtgagaaggg tgagaaagga gatccaggtc  360
ttattggtcc taagggagac atcggtgaaa ccggagtacc cggggctgaa ggcccccgag  420
gcttcccggg aatccaaggc aggaaaggag aacccggaga aggcgcctac gtataccgca  480
gcgcattcag cgtgggactg gagacctacg tgaccatccc caacatgccc atccgcttca  540
ccaagatctt ctacaaccag caaaaccact acgacggcag caccggcaaa ttccactgca  600
acatccccgg gctgtactac ttcgcctacc acatcacagt ctacatgaag gacgtgaagg  660
tcagcctctt caagaaggac aaggccatgc tgttcaccta cgaccagtac caggaaaaca  720
acgtggacca ggccagcggc agcgtgctcc tgcacctgga ggtgggcgac caagtctggc  780
tccaggtgta cggggaagga gagcggaacg gactctacgc cgacaacgac aacgacagca  840
ccttcacagg cttcctgctc taccacgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 150         moltype = RNA  length = 1167
FEATURE                Location/Qualifiers
misc_feature           1..1167
                       note = Description of Artificial Sequence:
                        Syntheticpolynucleotide
source                 1..1167
                       mol_type = other RNA
                       organism = synthetic construct
SEQUENCE: 150
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc tgttctactg ctattagctc  180
tgcccggtca tgaccaggaa accacgactc aagggcccgg agtcctgctt cccctgccca  240
agggggcctg cacaggttgg atggcgggca tcccagggca tccgggccat aatggggccc  300
caggccgtga tggcagagat ggcacccctg gtgagaaggg tgagaaagga gatccaggtc  360
ttattggtcc taagggagac atcggtgaaa ccggagtacc cggggctgaa ggtccccgag  420
gctttccggg aatccaaggc aggaaaggag aacctggaga aggtgcctat gtataccgct  480
cagcattcag tgtgggattg gagacttacg ttactatccc caacatgccc attcgcttta  540
ccaagatctt ctacaatcag caaaaccact atgacggcag caccggcaaa ttccactgca  600
acatccccgg gctgtactac ttcgcctacc acatcacagt ctacatgaag gacgtgaagg  660
tcagcctctt caagaaggac aaggccatgc tgttcaccta cgaccagtac caggaaaaca  720
acgtggacca ggccagcggc agcgtgctcc tgcacctgga ggtgggcgac caagtctggc  780
tccaggtgta cggggaagga gagcggaacg gactctacgc cgacaacgac aacgacagca  840
ccttcacagg cttcctgctc taccacgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 151         moltype = RNA  length = 1167
FEATURE                Location/Qualifiers
misc_feature           1..1167
                       note = Description of Artificial Sequence:
                        Syntheticpolynucleotide
source                 1..1167
                       mol_type = other RNA
                       organism = synthetic construct
```

SEQUENCE: 151
aggaaactta agtcaacaca acatatacaa aacaaacgaa tctcaagcaa tcaagcattc 60
tacttctatt gcagcaattt aaatcatttc ttttaaagca aaagcaattt tctgaaaatt 120
ttcaccattt acgaacgata gccatgctgt tgctgggagc tgttctactg ctattagctc 180
tgcccggtca tgaccaggaa accacgactc aagggcccgg agtcctgctt cccctgccca 240
agggggcctg cacaggttgg atggcgggca tcccagggca tccgggccat aatggggccc 300
caggccgtga tggcagagat ggcacccctg gtgagaaggg tgagaaagga gatccaggtc 360
ttattggtcc taagggagac atcggtgaaa ccggagtacc cggggctgaa ggtccccgag 420
gctttccggg aatccaaggc aggaaaggag aacctggaga aggtgcctat gtataccgct 480
cagcattcag tgtgggattg gagacttacg ttactatccc caacatgccc attcgcttta 540
ccaagatctt ctacaatcag caaaaccact atgatggctc cactggtaaa ttccactgca 600
acattcctgg gctgtactac tttgcctacc acatcacagt ctatatgaag gatgtgaagg 660
tcagcctctt caagaaggac aaggctatgc tgttcaccta tgatcagtac caggaaaata 720
atgtggacca ggcctccggc agcgtgctcc tgcacctgga ggtgggcgac caagtctggc 780
tccaggtgta cggggaagga gagcggaacg gactctacgc cgacaacgac aacgacagca 840
ccttcacagg cttcctgctc taccacgaca ccaactgact cgagctagtg actgactagg 900
atctggttac cactaaacca gcctcaagaa cacccgaatg gagtctctaa gctacataat 960
accaacttac acttacaaaa tgttgtcccc caaaatgtag ccattcgtat ctgctcctaa 1020
taaaaagaaa gtttcttcac attctagaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaa 1167

SEQ ID NO: 152 moltype = RNA length = 1167
FEATURE Location/Qualifiers
misc_feature 1..1167
note = Description of Artificial Sequence:
Syntheticpolynucleotide
source 1..1167
mol_type = other RNA
organism = synthetic construct
SEQUENCE: 152
aggaaactta agtcaacaca acatatacaa aacaaacgaa tctcaagcaa tcaagcattc 60
tacttctatt gcagcaattt aaatcatttc ttttaaagca aaagcaattt tctgaaaatt 120
ttcaccattt acgaacgata gccatgctgc tgctgggagc cgtgctactg ctactggccc 180
tgcccggcca cgaccaggaa accacgaccc aagggcccgg agtcctgctg cccctgccca 240
agggggcctg cacaggctgg atggcgggca tcccagggca cccgggccac aacggggccc 300
caggccggga cggcagagac ggcacccccg gcgagaaggg cgagaaagga gacccaggcc 360
tgatcggccc caagggagac atcggcgaaa ccggagtacc cggggccgaa ggcccccgag 420
gcttcccggg aatccaaggc aggaaaggag aacccggaga aggcgcctac gtataccgca 480
gcgcattcag cgtgggactg gagacctacg tgaccatccc caacatgccc atccgcttca 540
ccaagatctt ctacaaccag caaaaccact acgacggcag caccggcaaa ttccactgca 600
acatccccgg gctgtactac ttcgcctacc acatcacagt ctacatgaag gacgtgaagg 660
tcagcctctt caagaaggac aaggccatgc tgttcaccta cgaccagtac caggaaaaca 720
acgtggacca ggccagcggc agcgtgctcc tgcacctgga ggtgggcgac caagtctggc 780
tccaggtgta tggggaagga gagcgtaatg gactctatgc tgataatgac aatgactcca 840
ccttcacagg ctttcttctc taccatgaca ccaactgact cgagctagtg actgactagg 900
atctggttac cactaaacca gcctcaagaa cacccgaatg gagtctctaa gctacataat 960
accaacttac acttacaaaa tgttgtcccc caaaatgtag ccattcgtat ctgctcctaa 1020
taaaaagaaa gtttcttcac attctagaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaa 1167

SEQ ID NO: 153 moltype = RNA length = 1167
FEATURE Location/Qualifiers
misc_feature 1..1167
note = Description of Artificial Sequence:
Syntheticpolynucleotide
source 1..1167
mol_type = other RNA
organism = synthetic construct
SEQUENCE: 153
aggaaactta agtcaacaca acatatacaa aacaaacgaa tctcaagcaa tcaagcattc 60
tacttctatt gcagcaattt aaatcatttc ttttaaagca aaagcaattt tctgaaaatt 120
ttcaccattt acgaacgata gccatgctgc tgctgggagc cgtgctactg ctactggccc 180
tgcccggcca cgaccaggaa accacgaccc aagggcccgg agtcctgctg cccctgccca 240
agggggcctg cacaggctgg atggcgggca tcccagggca cccgggccac aacggggccc 300
caggccggga cggcagagac ggcacccccg gcgagaaggg cgagaaagga gacccaggcc 360
tgatcggccc caagggagac atcggcgaaa ccggagtacc cggggccgaa ggcccccgag 420
gcttcccggg aatccaaggc aggaaaggag aacccggaga aggcgcctac gtataccgca 480
gcgcattcag cgtgggactg gagacctacg tgaccatccc caacatgccc atccgcttca 540
ccaagatctt ctacaaccag caaaaccact acgacggcag caccggtaaa ttccactgca 600
acattcctgg gctgtactac tttgcctacc acatcacagt ctatatgaag gatgtgaagg 660
tcagcctctt caagaaggac aaggctatgc tgttcaccta tgatcagtac caggaaaata 720
atgtggacca ggcctccggc tctgtgctcc tgcatctgga ggtgggcgac caagtctggc 780
tccaggtgta tggggaagga gagcgtaatg gactctatgc tgataatgac aatgactcca 840
ccttcacagg ctttcttctc taccatgaca ccaactgact cgagctagtg actgactagg 900
atctggttac cactaaacca gcctcaagaa cacccgaatg gagtctctaa gctacataat 960
accaacttac acttacaaaa tgttgtcccc caaaatgtag ccattcgtat ctgctcctaa 1020
taaaaagaaa gtttcttcac attctagaaa aaaaaaaaaa aaaaaaaaaa aaaaaaaaaa 1080

```
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 154         moltype = RNA  length = 1167
FEATURE                Location/Qualifiers
misc_feature           1..1167
                       note = Description of Artificial Sequence:
                        Syntheticpolynucleotide
source                 1..1167
                       mol_type = other RNA
                       organism = synthetic construct
SEQUENCE: 154
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgc tgctgggagc cgtgctactg ctactggccc  180
tgcccggcca cgaccaggaa accacgaccc aagggcccgg agtcctgctg cccctgccca  240
agggggcctg cacaggctgg atggcgggca tcccagggca cccgggccac aacggggccc  300
caggccggga cggcagagac ggcacccccg gcgagaaggg cgagaaagga gacccaggcc  360
tgatcggccc caagggagac atcggcgaaa ccggagtacc cggggccgaa ggcccccgag  420
gcttcccggg aatccaaggc aggaaaggag aacccggaga aggtgcctat gtataccgct  480
cagcattcag tgtgggattg gagacttacg ttactatccc caacatgccc attcgcttta  540
ccaagatctt ctacaatcag caaaaccact atgatggctc cactggtaaa ttccactgca  600
acattcctgg gctgtactac tttgcctacc acatcacagt ctatatgaag gatgtgaagg  660
tcagcctctt caagaaggac aaggctatgc tgttcaccta tgatcagtac caggaaaata  720
atgtggacca ggcctccggc tctgtgctcc tgcatctgga ggtgggcgac caagtctggc  780
tccaggtgta tggggaagga gagcgtaatg gactctatgc tgataatgac aatgactcca  840
ccttcacagg ctttcttctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 155         moltype = RNA  length = 1167
FEATURE                Location/Qualifiers
misc_feature           1..1167
                       note = Description of Artificial Sequence:
                        Syntheticpolynucleotide
source                 1..1167
                       mol_type = other RNA
                       organism = synthetic construct
SEQUENCE: 155
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgc tgctgggagc cgtgctactg ctactggccc  180
tgcccggcca cgaccaggaa accacgaccc aagggcccgg agtcctgctg cccctgccca  240
agggggcctg cacaggctgg atggcgggca tcccagggca cccgggccac aacggggccc  300
caggccggga cggcagagat ggcacccctg gtgagaaggg tgagaaagga gatccaggtc  360
ttattggtcc taagggagac atcggtgaaa ccggagtacc cggggctgaa ggtccccgag  420
gctttccggg aatccaaggc aggaaaggag aacctggaga aggtgcctat gtataccgct  480
cagcattcag tgtgggattg gagacttacg ttactatccc caacatgccc attcgcttta  540
ccaagatctt ctacaatcag caaaaccact atgatggctc cactggtaaa ttccactgca  600
acattcctgg gctgtactac tttgcctacc acatcacagt ctatatgaag gatgtgaagg  660
tcagcctctt caagaaggac aaggctatgc tgttcaccta tgatcagtac caggaaaata  720
atgtggacca ggcctccggc tctgtgctcc tgcatctgga ggtgggcgac caagtctggc  780
tccaggtgta tggggaagga gagcgtaatg gactctatgc tgataatgac aatgactcca  840
ccttcacagg ctttcttctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 156         moltype = RNA  length = 1167
FEATURE                Location/Qualifiers
misc_feature           1..1167
                       note = Description of Artificial Sequence:
                        Syntheticpolynucleotide
source                 1..1167
                       mol_type = other RNA
                       organism = synthetic construct
SEQUENCE: 156
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc cgtgctactg ctactggccc  180
tgcccggcca cgaccaggaa accacgactc aagggcccgg agtcctgctg cccctgccca  240
agggggcctg cacaggttgg atggcgggca tcccagggca cccgggccac aatggggccc  300
caggccggga tggcagagac ggcacccccg gcgagaaggg cgagaaagga gatccaggcc  360
tgatcggtcc caagggagac atcggcgaaa ccggagtacc cggggccgaa ggcccccgag  420
```

```
gcttcccggg aatccaaggc aggaaaggag aacccggaga aggcgcctat gtataccgca  480
gcgcattcag tgtgggattg gagacctacg tgaccatccc caacatgccc atccgcttca  540
ccaagatctt ctacaaccag caaaaccact acgacggcag caccggcaaa ttccactgca  600
acatccccgg gctgtactac tttgcctacc acatcacagt ctacatgaag gacgtgaagg  660
tcagcctctt caagaaggac aaggccatgc tgttcaccta cgaccagtac caggaaaaca  720
acgtggacca ggccagcggc agcgtgctcc tgcacctgga ggtgggcgac caagtctggc  780
tccaggtgta cggggaagga gagcgtaacg gactctacgc cgacaacgac aacgacagca  840
ccttcacagg cttcctgctc taccacgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 157          moltype = RNA  length = 1167
FEATURE                 Location/Qualifiers
misc_feature            1..1167
                        note = Description of Artificial Sequence:
                         Syntheticpolynucleotide
source                  1..1167
                        mol_type = other RNA
                        organism = synthetic construct
SEQUENCE: 157
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgc tgctgggagc cgtgctactg ctactggctc  180
tgcccggtca cgaccaggaa accacgactc aagggcccgg agtcctgctg cccctgccca  240
agggggcctg cacaggttgg atggcgggca tcccagggca tccgggccat aacggggccc  300
caggccggga tggcagagac ggcacccctg gcgagaaggg tgagaaagga gacccaggcc  360
tgatcggccc taagggagac atcggcgaaa ccggagtacc cggggccgaa ggcccccgag  420
gcttcccggg aatccaaggc aggaaaggag aacccggaga aggcgcctat gtataccgca  480
gcgcattcag tgtgggattg gagacttacg ttaccatccc caacatgccc attcgcttca  540
ccaagatctt ctacaaccag caaaaccact acgacggcag caccggtaaa ttccactgca  600
acatccctgg gctgtactac tttgcctacc acatcacagt ctatatgaag gatgtgaagg  660
tcagcctctt caagaaggac aaggctatgc tgttcaccta cgatcagtac caggaaaata  720
atgtggacca ggccagcggc agcgtgctcc tgcacctgga ggtgggcgac caagtctggc  780
tccaggtgta cggggaagga gagcggaacg gactctacgc cgacaacgac aatgacagca  840
ccttcacagg cttcctgctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 158          moltype = RNA  length = 1167
FEATURE                 Location/Qualifiers
misc_feature            1..1167
                        note = Description of Artificial Sequence:
                         Syntheticpolynucleotide
source                  1..1167
                        mol_type = other RNA
                        organism = synthetic construct
SEQUENCE: 158
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc cgttctactg ctactggctc  180
tgcccggcca tgaccaggaa accacgaccc aagggcccgg agtcctgctt cccctgccca  240
agggggcctg cacaggttgg atggcgggca tcccagggca cccgggccat aatggggccc  300
caggccgtga tggcagagac ggcacccccg gcgagaaggg tgagaaagga gatccaggtc  360
tgatcggtcc taagggagac atcggcgaaa ccggagtacc cggggctgaa ggtccccgag  420
gctttccggg aatccaaggc aggaaaggag aacctggaga aggcgcctac gtataccgca  480
gcgcattcag cgtgggactg gagacctacg tgaccatccc caacatgccc atccgcttta  540
ccaagatctt ctacaatcag caaaaccact atgacggctc cactggcaaa ttccactgca  600
acattcccgg gctgtactac tttgcctacc acatcacagt ctatatgaag gatgtgaagg  660
tcagcctctt caagaaggac aaggccatgc tgttcaccta cgatcagtac caggaaaaca  720
atgtggacca ggccagcggc tctgtgctcc tgcatctgga ggtgggcgac caagtctggc  780
tccaggtgta cggggaagga gagcgtaacg gactctatgc cgataatgac aatgactcca  840
ccttcacagg ctttcttctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                      1167

SEQ ID NO: 159          moltype = RNA  length = 1167
FEATURE                 Location/Qualifiers
misc_feature            1..1167
                        note = Description of Artificial Sequence:
                         Syntheticpolynucleotide
```

```
source                  1..1167
                        mol_type = other RNA
                        organism = synthetic construct
SEQUENCE: 159
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatgctgt tgctgggagc cgttctactg ctattagctc  180
tgcccggtca tgaccaggaa accacgactc aagggcccgg agtcctgctg cccctgccca  240
agggggcctg cacaggttgg atggcgggca tcccagggca tccgggccat aatggggccc  300
caggccgtga cggcagagat ggcacccccg gtgagaaggg tgagaaagga gacccaggtc  360
ttattggccc taagggagac atcggtgaaa ccggagtacc cggggctgaa ggcccccgag  420
gctttccggg aatccaaggc aggaaaggag aacctggaga aggcgcctat gtataccgca  480
gcgcattcag tgtgggattg gagacttacg ttactatccc caacatgccc attcgcttta  540
ccaagatctt ctacaatcag caaaaccact atgatggcag caccggtaaa ttccactgca  600
acatccctgg gctgtactac tttgcctacc acatcacagt ctatatgaag gatgtgaagg  660
tcagcctctt caagaaggac aaggctatgc tgttcaccta tgaccagtac caggaaaata  720
atgtggacca ggcctccggc tctgtgctcc tgcatctgga ggtgggcgac caagtctggc  780
tccaggtgta tggggaagga gagcgtaatg gactctacgc tgataatgac aatgactcca  840
ccttcacagg ctttctgctc taccatgaca ccaactgact cgagctagtg actgactagg  900
atctggttac cactaaacca gcctcaagaa cacccgaatg gagtctctaa gctacataat  960
accaacttac acttacaaaa tgttgtcccc caaaatgtag ccattcgtat ctgctcctaa  1020
taaaaagaaa gtttcttcac attctagaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaa                                     1167

SEQ ID NO: 160          moltype = DNA  length = 579
FEATURE                 Location/Qualifiers
source                  1..579
                        mol_type = genomic DNA
                        organism = Macaca fascicularis
SEQUENCE: 160
atgggggtgc acgaatgtcc tgcctggctg tggcttctcc tgtctctgct gtcgctccct  60
ctgggcctcc cagtcccggg cgccccacca cgcctcatct gtgacagccg agtcctggag  120
aggtacctct tggaggccaa ggaggccgag aatgtcacga tgggctgttc cgaaagctgc  180
agcttgaatg agaatatcac cgtcccagac accaaagtta acttctatgc ctggaagagg  240
atggaggtcg ggcagcaggc tgtagaagtc tggcagggcc tggccctgct ctcagaagct  300
gtcctgcggg gccaggccgt gttggccaac tcttcccagc ctttcgagcc cctgcagctg  360
cacatggata aagccatcag tggccttcgc agcatcacca ctctgcttcg ggcgctggga  420
gcccaggaag ccatctccct cccagatgcg gcctcggctg ctccactccg aaccatcact  480
gctgacactt tctgcaaact cttccgagtc tactccaatt tcctccgggg aaagctgaag  540
ctgtacacgg gggaggcctg caggagaggg gacagatga                        579

SEQ ID NO: 161          moltype = DNA  length = 579
FEATURE                 Location/Qualifiers
misc_feature            1..579
                        note = Description of Artificial Sequence:
                         Syntheticpolynucleotide
source                  1..579
                        mol_type = other DNA
                        organism = synthetic construct
SEQUENCE: 161
atgggggtgc acgaatgccc cgcctggctg tggctgctcc tgagcctgct gagcctcccc  60
ctgggcctcc cagtcccggg cgccccacca cgcctcatct gcgacagccg agtcctggag  120
aggtacctcc tggaggccaa ggaggccgag aacgtcacga tgggctgcag cgaaagctgc  180
agcctgaacg agaacatcac cgtcccagac accaaagtga acttctacgc ctggaagagg  240
atggaggtcg ggcagcaggc cgtagaagtc tggcagggcc tggccctgct cagcgaagcc  300
gtcctgcggg gccaggccgt gctggccaac agcagccagc ccttcgagcc cctgcagctg  360
cacatggaca aagccatcag cggcctgcgc agcatcacca ccctgctgcg ggcgctggga  420
gcccaggaag ccatcagcct cccagacgcg gccagcgccg ccccactccg aaccatcacc  480
gccgacacct tctgcaaact cttccgagtc tacagcaact tcctccgggg aaagctgaag  540
ctgtacacgg gggaggcctg caggagaggg gacagatga                        579

SEQ ID NO: 162          moltype = DNA  length = 579
FEATURE                 Location/Qualifiers
misc_feature            1..579
                        note = Description of Artificial Sequence:
                         Syntheticpolynucleotide
source                  1..579
                        mol_type = other DNA
                        organism = synthetic construct
SEQUENCE: 162
atgggggtgc acgaatgtcc tgcctggctg tggcttctcc tgagcctgct gagcctcccc  60
ctgggcctcc cagtcccggg cgccccacca cgcctcatct gcgacagccg agtcctggag  120
aggtacctcc tggaggccaa ggaggccgag aacgtcacga tgggctgcag cgaaagctgc  180
agcctgaacg agaacatcac cgtcccagac accaaagtga acttctacgc ctggaagagg  240
atggaggtcg ggcagcaggc cgtagaagtc tggcagggcc tggccctgct cagcgaagcc  300
gtcctgcggg gccaggccgt gctggccaac agcagccagc ccttcgagcc cctgcagctg  360
cacatggaca aagccatcag cggcctgcgc agcatcacca ccctgctgcg ggcgctggga  420
gcccaggaag ccatcagcct cccagacgcg gccagcgccg ccccactccg aaccatcacc  480
```

```
gccgacacct tctgcaaact cttccgagtc tacagcaact tcctccgggg aaagctgaag  540
ctgtacacgg gggaggcctg caggagaggg gacagatga                         579

SEQ ID NO: 163         moltype = DNA  length = 579
FEATURE                Location/Qualifiers
misc_feature           1..579
                       note = Description of Artificial Sequence:
                        Syntheticpolynucleotide
source                 1..579
                       mol_type = other DNA
                       organism = synthetic construct
SEQUENCE: 163
atgggggtgc acgaatgtcc tgcctggctg tggcttctcc tgtctctgct gtcgctccct  60
ctgggcctcc cagtcccggg cgccccacca cgcctcatct gtgacagccg agtcctggag  120
aggtacctct tggaggccaa ggaggccgag aatgtcacga tgggctgttc cgaaagctgc  180
agcttgaatg agaacatcac cgtcccagac accaaagtga acttctacgc ctggaagagg  240
atggaggtcg ggcagcaggc cgtagaagtc tggcagggcc tggccctgct cagcgaagcc  300
gtcctgcggg gccaggccgt gctggccaac agcagccagc ccttcgagcc cctgcagctg  360
cacatggaca aagccatcag cggcctgcgc agcatcacca ccctgctgcg ggcgctggga  420
gcccaggaag ccatcagcct cccagacgcg gccagcgccg ccccactccg aaccatcacc  480
gccgacacct tctgcaaact cttccgagtc tacagcaact tcctccgggg aaagctgaag  540
ctgtacacgg gggaggcctg caggagaggg gacagatga                         579

SEQ ID NO: 164         moltype = DNA  length = 579
FEATURE                Location/Qualifiers
misc_feature           1..579
                       note = Description of Artificial Sequence:
                        Syntheticpolynucleotide
source                 1..579
                       mol_type = other DNA
                       organism = synthetic construct
SEQUENCE: 164
atgggggtgc acgaatgtcc tgcctggctg tggcttctcc tgtctctgct gtcgctccct  60
ctgggcctcc cagtcccggg cgccccacca cgcctcatct gtgacagccg agtcctggag  120
aggtacctct tggaggccaa ggaggccgag aatgtcacga tgggctgttc cgaaagctgc  180
agcttgaatg agaatatcac cgtcccagac accaaagtta acttctatgc ctggaagagg  240
atggaggtcg ggcagcaggc tgtagaagtc tggcagggcc tggccctgct ctcagaagct  300
gtcctgcggg gccaggccgt gttggccaac tcttcccagc ctttcgagcc cctgcagctg  360
cacatggata aagccatcag cggcctgcgc agcatcacca ccctgctgcg ggcgctggga  420
gcccaggaag ccatcagcct cccagacgcg gccagcgccg ccccactccg aaccatcacc  480
gccgacacct tctgcaaact cttccgagtc tacagcaact tcctccgggg aaagctgaag  540
ctgtacacgg gggaggcctg caggagaggg gacagatga                         579

SEQ ID NO: 165         moltype = DNA  length = 579
FEATURE                Location/Qualifiers
misc_feature           1..579
                       note = Description of Artificial Sequence:
                        Syntheticpolynucleotide
source                 1..579
                       mol_type = other DNA
                       organism = synthetic construct
SEQUENCE: 165
atgggggtgc acgaatgtcc tgcctggctg tggcttctcc tgtctctgct gtcgctccct  60
ctgggcctcc cagtcccggg cgccccacca cgcctcatct gtgacagccg agtcctggag  120
aggtacctct tggaggccaa ggaggccgag aatgtcacga tgggctgttc cgaaagctgc  180
agcttgaatg agaatatcac cgtcccagac accaaagtta acttctatgc ctggaagagg  240
atggaggtcg ggcagcaggc tgtagaagtc tggcagggcc tggccctgct ctcagaagct  300
gtcctgcggg gccaggccgt gttggccaac tcttcccagc ctttcgagcc cctgcagctg  360
cacatggata aagccatcag tggccttcgc agcatcacca ctctgcttcg ggcgctggga  420
gcccaggaag ccatctccct cccagatgcg gcctcggctg ctccactccg aaccatcact  480
gctgacacct tctgcaaact cttccgagtc tacagcaact tcctccgggg aaagctgaag  540
ctgtacacgg gggaggcctg caggagaggg gacagatga                         579

SEQ ID NO: 166         moltype = DNA  length = 579
FEATURE                Location/Qualifiers
misc_feature           1..579
                       note = Description of Artificial Sequence:
                        Syntheticpolynucleotide
source                 1..579
                       mol_type = other DNA
                       organism = synthetic construct
SEQUENCE: 166
atgggggtgc acgaatgccc cgcctggctg tggctgctcc tgagcctgct gagcctcccc  60
ctgggcctcc cagtcccggg cgccccacca cgcctcatct gcgacagccg agtcctggag  120
aggtacctcc tggaggccaa ggaggccgag aacgtcacga tgggctgcag cgaaagctgc  180
agcctgaacg agaacatcac cgtcccagac accaaagtga acttctacgc ctggaagagg  240
atggaggtcg ggcagcaggc cgtagaagtc tggcagggcc tggccctgct cagcgaagcc  300
gtcctgcggg gccaggccgt gctggccaac agcagccagc ccttcgagcc cctgcagctg  360
cacatggaca aagccatcag cggcctgcgc agcatcacca ccctgctgcg ggcgctggga  420
```

```
gcccaggaag ccatcagcct cccagacgcg gccagcgccg ccccactccg aaccatcacc  480
gccgacactt tctgcaaact cttccgagtc tactccaatt tcctccgggg aaagctgaag  540
ctgtacacgg gggaggcctg caggagaggg gacagatga                          579

SEQ ID NO: 167          moltype = DNA  length = 579
FEATURE                 Location/Qualifiers
misc_feature            1..579
                        note = Description of Artificial Sequence:
                         Syntheticpolynucleotide
source                  1..579
                        mol_type = other DNA
                        organism = synthetic construct
SEQUENCE: 167
atgggggtgc acgaatgccc cgcctggctg tggctgctcc tgagcctgct gagcctcccc  60
ctgggcctcc cagtcccggg cgccccacca cgcctcatct gcgacagccg agtcctggag  120
aggtacctcc tggaggccaa ggaggccgag aacgtcacga tgggctgcag cgaaagctgc  180
agcctgaacg agaacatcac cgtcccagac accaaagtga acttctacgc ctggaagagg  240
atggaggtcg ggcagcaggc cgtagaagtc tggcagggcc tggccctgct cagcgaagcc  300
gtcctgcggg gccaggccgt gctggccaac agcagccagc ccttcgagcc cctgcagctg  360
cacatggaca aagccatcag tggccttcgc agcatcacca ctctgcttcg ggcgctggga  420
gcccaggaag ccatctccct cccagatgcg gcctcggctg ctccactccg aaccatcact  480
gctgacactt tctgcaaact cttccgagtc tactccaatt tcctccgggg aaagctgaag  540
ctgtacacgg gggaggcctg caggagaggg gacagatga                          579

SEQ ID NO: 168          moltype = DNA  length = 579
FEATURE                 Location/Qualifiers
misc_feature            1..579
                        note = Description of Artificial Sequence:
                         Syntheticpolynucleotide
source                  1..579
                        mol_type = other DNA
                        organism = synthetic construct
SEQUENCE: 168
atgggggtgc acgaatgccc cgcctggctg tggctgctcc tgagcctgct gagcctcccc  60
ctgggcctcc cagtcccggg cgccccacca cgcctcatct gcgacagccg agtcctggag  120
aggtacctcc tggaggccaa ggaggccgag aacgtcacga tgggctgcag cgaaagctgc  180
agcctgaacg agaatatcac cgtcccagac accaaagtta acttctatgc ctggaagagg  240
atggaggtcg ggcagcaggc tgtagaagtc tggcagggcc tggccctgct ctcagaagct  300
gtcctgcggg gccaggccgt gttggccaac tcttcccagc ctttcgagcc cctgcagctg  360
cacatggata aagccatcag tggccttcgc agcatcacca ctctgcttcg ggcgctggga  420
gcccaggaag ccatctccct cccagatgcg gcctcggctg ctccactccg aaccatcact  480
gctgacactt tctgcaaact cttccgagtc tactccaatt tcctccgggg aaagctgaag  540
ctgtacacgg gggaggcctg caggagaggg gacagatga                          579

SEQ ID NO: 169          moltype = DNA  length = 579
FEATURE                 Location/Qualifiers
misc_feature            1..579
                        note = Description of Artificial Sequence:
                         Syntheticpolynucleotide
source                  1..579
                        mol_type = other DNA
                        organism = synthetic construct
SEQUENCE: 169
atgggggtgc acgaatgccc cgcctggctg tggctgctcc tgtctctgct gtcgctccct  60
ctgggcctcc cagtcccggg cgccccacca cgcctcatct gtgacagccg agtcctggag  120
aggtacctct tggaggccaa ggaggccgag aatgtcacga tgggctgttc cgaaagctgc  180
agcttgaatg agaatatcac cgtcccagac accaaagtta acttctatgc ctggaagagg  240
atggaggtcg ggcagcaggc tgtagaagtc tggcagggcc tggccctgct ctcagaagct  300
gtcctgcggg gccaggccgt gttggccaac tcttcccagc ctttcgagcc cctgcagctg  360
cacatggata aagccatcag tggccttcgc agcatcacca ctctgcttcg ggcgctggga  420
gcccaggaag ccatctccct cccagatgcg gcctcggctg ctccactccg aaccatcact  480
gctgacactt tctgcaaact cttccgagtc tactccaatt tcctccgggg aaagctgaag  540
ctgtacacgg gggaggcctg caggagaggg gacagatga                          579

SEQ ID NO: 170          moltype = DNA  length = 579
FEATURE                 Location/Qualifiers
misc_feature            1..579
                        note = Description of Artificial Sequence:
                         Syntheticpolynucleotide
source                  1..579
                        mol_type = other DNA
                        organism = synthetic construct
SEQUENCE: 170
atgggggtgc acgaatgccc cgcctggctg tggctgctcc tgagcctgct gagcctccct  60
ctgggcctcc cagtcccggg cgccccacca cgcctcatct gcgacagccg agtcctggag  120
aggtacctcc tggaggccaa ggaggccgag aacgtcacga tgggctgcag cgaaagctgc  180
agcctgaacg agaatatcac cgtcccagac accaaagtga acttctacgc ctggaagagg  240
atggaggtcg ggcagcaggc cgtagaagtc tggcagggcc tggccctgct cagcgaagcc  300
gtcctgcggg gccaggccgt gctggccaac agcagccagc ctttcgagcc cctgcagctg  360
```

```
cacatggaca aagccatcag cggcctgcgc agcatcacca ccctgctgcg ggcgctggga  420
gcccaggaag ccatcagcct cccagacgcg gccagcgccg ccccactccg aaccatcacc  480
gccgacacct tctgcaaact cttccgagtc tacagcaact tcctccgggg aaagctgaag  540
ctgtacacgg gggaggcctg caggagaggg gacagatga                         579

SEQ ID NO: 171         moltype = DNA  length = 579
FEATURE                Location/Qualifiers
misc_feature           1..579
                       note = Description of Artificial Sequence:
                        Syntheticpolynucleotide
source                 1..579
                       mol_type = other DNA
                       organism = synthetic construct
SEQUENCE: 171
atgggggtgc acgaatgccc cgcctggctg tggcttctcc tgagcctgct gtcgctcccc  60
ctgggcctcc cagtcccggg cgccccacca cgcctcatct gcgacagccg agtcctggag  120
aggtacctcc tggaggccaa ggaggccgag aacgtcacga tgggctgctc cgaaagctgc  180
agcttgaatg agaacatcac cgtcccagac accaaagtga acttctacgc ctggaagagg  240
atggaggtcg ggcagcaggc cgtagaagtc tggcagggcc tggccctgct ctcagaagcc  300
gtcctgcggg gccaggccgt gctggccaac agcagccagc ctttcgagcc cctgcagctg  360
cacatggata aagccatcag cggccttcgc agcatcacca ctctgctgcg ggcgctggga  420
gcccaggaag ccatctccct cccagatgcg gccagcgctg ccccactccg aaccatcact  480
gccgacacct tctgcaaact cttccgagtc tacagcaact tcctccgggg aaagctgaag  540
ctgtacacgg gggaggcctg caggagaggg gacagatga                         579

SEQ ID NO: 172         moltype = DNA  length = 579
FEATURE                Location/Qualifiers
misc_feature           1..579
                       note = Description of Artificial Sequence:
                        Syntheticpolynucleotide
source                 1..579
                       mol_type = other DNA
                       organism = synthetic construct
SEQUENCE: 172
atgggggtgc acgaatgccc cgcctggctg tggcttctcc tgtctctgct gagcctccct  60
ctgggcctcc cagtcccggg cgccccacca cgcctcatct gtgacagccg agtcctggag  120
aggtacctct tggaggccaa ggaggccgag aacgtcacga tgggctgttc cgaaagctgc  180
agcttgaacg agaatatcac cgtcccagac accaaagtga acttctatgc ctggaagagg  240
atggaggtcg ggcagcaggc tgtagaagtc tggcagggcc tggccctgct cagcgaagcc  300
gtcctgcggg gccaggccgt gttggccaac agctcccagc ccttcgagcc cctgcagctg  360
cacatggaca aagccatcag tggcctgcgc agcatcacca ctctgcttcg ggcgctggga  420
gcccaggaag ccatctccct cccagatgcg gccagcgctg ctccactccg aaccatcact  480
gctgacactt tctgcaaact cttccgagtc tactccaatt tcctccgggg aaagctgaag  540
ctgtacacgg gggaggcctg caggagaggg gacagatga                         579

SEQ ID NO: 173         moltype = DNA  length = 579
FEATURE                Location/Qualifiers
misc_feature           1..579
                       note = Description of Artificial Sequence:
                        Syntheticpolynucleotide
source                 1..579
                       mol_type = other DNA
                       organism = synthetic construct
SEQUENCE: 173
atgggggtgc acgaatgccc tgcctggctg tggcttctcc tgtctctgct gtcgctccct  60
ctgggcctcc cagtcccggg cgccccacca cgcctcatct gtgacagccg agtcctggag  120
aggtacctct tggaggccaa ggaggccgag aatgtcacga tgggctgttc cgaaagctgc  180
agcctgaatg agaatatcac cgtcccagac accaaagtta acttctatgc ctggaagagg  240
atggaggtcg ggcagcaggc tgtagaagtc tggcagggcc tggccctgct ctcagaagct  300
gtcctgcggg gccaggccgt gttggccaac tcttcccagc ctttcgagcc cctgcagctg  360
cacatggata aagccatcag tggccttcgc agcatcacca ctctgctgcg ggcgctggga  420
gcccaggaag ccatctccct cccagatgcg gcctcggctg ctccactccg aaccatcact  480
gctgacactt tctgcaaact cttccgagtc tactccaatt tcctccgggg aaagctgaag  540
ctgtacacgg gggaggcctg caggagaggg gacagatga                         579

SEQ ID NO: 174         moltype = DNA  length = 913
FEATURE                Location/Qualifiers
misc_feature           1..913
                       note = Description of Artificial Sequence:
                        Syntheticpolynucleotide
source                 1..913
                       mol_type = other DNA
                       organism = synthetic construct
SEQUENCE: 174
aggaaactta agaacttaaa aaaaaaaatc aaaatggccg ccaccatggg ggtgcacgaa  60
tgccccgcct ggctgtggct gctcctgagc ctgctgagcc tccccctggg cctcccagtc  120
ccgggcgccc caccacgcct catctgcgac agccgagtcc tggagaggta cctcctggag  180
gccaaggagg ccgagaacgt cacgatgggc tgcagcgaaa gctgcagcct gaacgagaac  240
atcaccgtcc cagacaccaa agtgaacttc tacgcctgga agaggatgga ggtcgggcag  300
```

```
caggccgtag aagtctggca gggcctggcc ctgctcagcg aagccgtcct gcggggccag  360
gccgtgctgg ccaacagcag ccagcccttc gagcccctgc agctgcacat ggacaaagcc  420
atcagcggcc tgcgcagcat caccaccctg ctgcgggcgc tgggagccca ggaagccatc  480
agcctcccag acgcggccag cgccgcccca ctccgaacca tcaccgccga caccttctgc  540
aaactcttcc gagtctacag caacttcctc cggggaaagc tgaagctgta cacgggggag  600
gcctgcagga gaggggacag atgactcgag ctagtgactg actaggatct ggttaccact  660
aaaccagcct caagaacacc cgaatggagt ctctaagcta cataatacca acttacactt  720
acaaaatgtt gtcccccaaa atgtagccat tcgtatctgc tcctaataaa aagaaagttt  780
cttcacattc tagaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaa                                                     913

SEQ ID NO: 175         moltype = DNA  length = 913
FEATURE                Location/Qualifiers
misc_feature           1..913
                       note = Description of Artificial Sequence:
                        Syntheticpolynucleotide
source                 1..913
                       mol_type = other DNA
                       organism = synthetic construct
SEQUENCE: 175
aggaaactta agaacttaaa aaaaaaaatc aaaatggccg ccaccatggg ggtgcacgaa  60
tgtcctgcct ggctgtggct tctcctgagc ctgctgagcc tccccctggg cctcccagtc  120
ccgggcgccc caccacgcct catctgcgac agccgagtcc tggagaggta cctcctggag  180
gccaaggagg ccgagaacgt cacgatgggc tgcagcgaaa gctgcagcct gaacgagaac  240
atcaccgtcc cagacaccaa agtgaacttc tacgcctgga agaggatgga ggtcgggcag  300
caggccgtag aagtctggca gggcctggcc ctgctcagcg aagccgtcct gcggggccag  360
gccgtgctgg ccaacagcag ccagcccttc gagcccctgc agctgcacat ggacaaagcc  420
atcagcggcc tgcgcagcat caccaccctg ctgcgggcgc tgggagccca ggaagccatc  480
agcctcccag acgcggccag cgccgcccca ctccgaacca tcaccgccga caccttctgc  540
aaactcttcc gagtctacag caacttcctc cggggaaagc tgaagctgta cacgggggag  600
gcctgcagga gaggggacag atgactcgag ctagtgactg actaggatct ggttaccact  660
aaaccagcct caagaacacc cgaatggagt ctctaagcta cataatacca acttacactt  720
acaaaatgtt gtcccccaaa atgtagccat tcgtatctgc tcctaataaa aagaaagttt  780
cttcacattc tagaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaa                                                     913

SEQ ID NO: 176         moltype = DNA  length = 913
FEATURE                Location/Qualifiers
misc_feature           1..913
                       note = Description of Artificial Sequence:
                        Syntheticpolynucleotide
source                 1..913
                       mol_type = other DNA
                       organism = synthetic construct
SEQUENCE: 176
aggaaactta agaacttaaa aaaaaaaatc aaaatggccg ccaccatggg ggtgcacgaa  60
tgccccgcct ggctgtggct gctcctgagc ctgctgagcc tccccctggg cctcccagtc  120
ccgggcgccc caccacgcct catctgcgac agccgagtcc tggagaggta cctcctggag  180
gccaaggagg ccgagaacgt cacgatgggc tgcagcgaaa gctgcagcct gaacgagaac  240
atcaccgtcc cagacaccaa agtgaacttc tacgcctgga agaggatgga ggtcgggcag  300
caggccgtag aagtctggca gggcctggcc ctgctcagcg aagccgtcct gcggggccag  360
gccgtgctgg ccaacagcag ccagcccttc gagcccctgc agctgcacat ggacaaagcc  420
atcagcggcc tgcgcagcat caccaccctg ctgcgggcgc tgggagccca ggaagccatc  480
agcctcccag acgcggccag cgccgcccca ctccgaacca tcaccgccga cactttctgc  540
aaactcttcc gagtctactc caatttcctc cggggaaagc tgaagctgta cacgggggag  600
gcctgcagga gaggggacag atgactcgag ctagtgactg actaggatct ggttaccact  660
aaaccagcct caagaacacc cgaatggagt ctctaagcta cataatacca acttacactt  720
acaaaatgtt gtcccccaaa atgtagccat tcgtatctgc tcctaataaa aagaaagttt  780
cttcacattc tagaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaa                                                     913

SEQ ID NO: 177         moltype = DNA  length = 913
FEATURE                Location/Qualifiers
misc_feature           1..913
                       note = Description of Artificial Sequence:
                        Syntheticpolynucleotide
source                 1..913
                       mol_type = other DNA
                       organism = synthetic construct
SEQUENCE: 177
aggaaactta agaacttaaa aaaaaaaatc aaaatggccg ccaccatggg ggtgcacgaa  60
tgccccgcct ggctgtggct gctcctgagc ctgctgagcc tccctctggg cctcccagtc  120
ccgggcgccc caccacgcct catctgcgac agccgagtcc tggagaggta cctcctggag  180
gccaaggagg ccgagaacgt cacgatgggc tgcagcgaaa gctgcagcct gaacgagaat  240
atcaccgtcc cagacaccaa agtgaacttc tacgcctgga agaggatgga ggtcgggcag  300
caggccgtag aagtctggca gggcctggcc ctgctcagcg aagccgtcct gcggggccag  360
```

```
gccgtgctgg ccaacagcag ccagcctttc gagcccctgc agctgcacat ggacaaagcc  420
atcagcggcc tgcgcagcat caccaccctg ctgcgggcgc tgggagccca ggaagccatc  480
agcctcccag acgcggccag cgccgcccca ctccgaacca tcaccgccga caccttctgc  540
aaactcttcc gagtctacag caacttcctc cggggaaagc tgaagctgta cacgggggag  600
gcctgcagga gaggggacag atgactcgag ctagtgactg actaggatct ggttaccact  660
aaaccagcct caagaacacc cgaatggagt ctctaagcta cataatacca acttacactt  720
acaaaatgtt gtcccccaaa atgtagccat tcgtatctgc tcctaataaa aagaaagttt  780
cttcacattc tagaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaa                                                      913

SEQ ID NO: 178         moltype = RNA  length = 913
FEATURE                Location/Qualifiers
misc_feature           1..913
                       note = Description of Artificial Sequence:
                        Syntheticpolynucleotide
source                 1..913
                       mol_type = other RNA
                       organism = synthetic construct
SEQUENCE: 178
aggaaactta agaacttaaa aaaaaaaatc aaaatggccg ccaccatggg ggtgcacgaa  60
tgccccgcct ggctgtggct gctcctgagc ctgctgagcc tccccctggg cctcccagtc  120
ccgggcgccc caccacgcct catctgcgac agccgagtcc tggagaggta cctcctggag  180
gccaaggagg ccgagaacgt cacgatgggc tgcagcgaaa gctgcagcct gaacgagaac  240
atcaccgtcc cagacaccaa agtgaacttc tacgcctgga agaggatgga ggtcgggcag  300
caggccgtag aagtctggca gggcctggcc ctgctcagcg aagccgtcct gcggggccag  360
gccgtgctgg ccaacagcag ccagcccttc gagcccctgc agctgcacat ggacaaagcc  420
atcagcggcc tgcgcagcat caccaccctg ctgcgggcgc tgggagccca ggaagccatc  480
agcctcccag acgcggccag cgccgcccca ctccgaacca tcaccgccga caccttctgc  540
aaactcttcc gagtctacag caacttcctc cggggaaagc tgaagctgta cacgggggag  600
gcctgcagga gaggggacag atgactcgag ctagtgactg actaggatct ggttaccact  660
aaaccagcct caagaacacc cgaatggagt ctctaagcta cataatacca acttacactt  720
acaaaatgtt gtcccccaaa atgtagccat tcgtatctgc tcctaataaa aagaaagttt  780
cttcacattc tagaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaa                                                      913

SEQ ID NO: 179         moltype = RNA  length = 913
FEATURE                Location/Qualifiers
misc_feature           1..913
                       note = Description of Artificial Sequence:
                        Syntheticpolynucleotide
source                 1..913
                       mol_type = other RNA
                       organism = synthetic construct
SEQUENCE: 179
aggaaactta agaacttaaa aaaaaaaatc aaaatggccg ccaccatggg ggtgcacgaa  60
tgtcctgcct ggctgtggct tctcctgagc ctgctgagcc tccccctggg cctcccagtc  120
ccgggcgccc caccacgcct catctgcgac agccgagtcc tggagaggta cctcctggag  180
gccaaggagg ccgagaacgt cacgatgggc tgcagcgaaa gctgcagcct gaacgagaac  240
atcaccgtcc cagacaccaa agtgaacttc tacgcctgga agaggatgga ggtcgggcag  300
caggccgtag aagtctggca gggcctggcc ctgctcagcg aagccgtcct gcggggccag  360
gccgtgctgg ccaacagcag ccagcccttc gagcccctgc agctgcacat ggacaaagcc  420
atcagcggcc tgcgcagcat caccaccctg ctgcgggcgc tgggagccca ggaagccatc  480
agcctcccag acgcggccag cgccgcccca ctccgaacca tcaccgccga caccttctgc  540
aaactcttcc gagtctacag caacttcctc cggggaaagc tgaagctgta cacgggggag  600
gcctgcagga gaggggacag atgactcgag ctagtgactg actaggatct ggttaccact  660
aaaccagcct caagaacacc cgaatggagt ctctaagcta cataatacca acttacactt  720
acaaaatgtt gtcccccaaa atgtagccat tcgtatctgc tcctaataaa aagaaagttt  780
cttcacattc tagaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaa                                                      913

SEQ ID NO: 180         moltype = RNA  length = 913
FEATURE                Location/Qualifiers
misc_feature           1..913
                       note = Description of Artificial Sequence:
                        Syntheticpolynucleotide
source                 1..913
                       mol_type = other RNA
                       organism = synthetic construct
SEQUENCE: 180
aggaaactta agaacttaaa aaaaaaaatc aaaatggccg ccaccatggg ggtgcacgaa  60
tgccccgcct ggctgtggct gctcctgagc ctgctgagcc tccccctggg cctcccagtc  120
ccgggcgccc caccacgcct catctgcgac agccgagtcc tggagaggta cctcctggag  180
gccaaggagg ccgagaacgt cacgatgggc tgcagcgaaa gctgcagcct gaacgagaac  240
atcaccgtcc cagacaccaa agtgaacttc tacgcctgga agaggatgga ggtcgggcag  300
caggccgtag aagtctggca gggcctggcc ctgctcagcg aagccgtcct gcggggccag  360
gccgtgctgg ccaacagcag ccagcccttc gagcccctgc agctgcacat ggacaaagcc  420
```

-continued

```
atcagcggcc tgcgcagcat caccaccctg ctgcgggcgc tgggagccca ggaagccatc  480
agcctcccag acgcggccag cgccgcccca ctccgaacca tcaccgccga cactttctgc  540
aaactcttcc gagtctactc caatttcctc cggggaaagc tgaagctgta cacgggggag  600
gcctgcagga gaggggacag atgactcgag ctagtgactg actaggatct ggttaccact  660
aaaccagcct caagaacacc cgaatggagt ctctaagcta cataatacca acttacactt  720
acaaaatgtt gtcccccaaa atgtagccat tcgtatctgc tcctaataaa aagaaagttt  780
cttcacattc tagaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaa                                                     913

SEQ ID NO: 181         moltype = RNA  length = 913
FEATURE                Location/Qualifiers
misc_feature           1..913
                       note = Description of Artificial Sequence:
                        Syntheticpolynucleotide
source                 1..913
                       mol_type = other RNA
                       organism = synthetic construct
SEQUENCE: 181
aggaaactta agaacttaaa aaaaaaaatc aaaatggccg ccaccatggg ggtgcacgaa  60
tgccccgcct ggctgtggct gctcctgagc ctgctgagcc tccctctggg cctcccagtc  120
ccgggcgccc caccacgcct catctgcgac agccgagtcc tggagaggta cctcctggag  180
gccaaggagg ccgagaacgt cacgatgggc tgcagcgaaa gctgcagcct gaacgagaat  240
atcaccgtcc cagacaccaa agtgaacttc tacgcctgga agaggatgga ggtcgggcag  300
caggccgtag aagtctggca gggcctggcc ctgctcagcg aagccgtcct gcggggccag  360
gccgtgctgg ccaacagcag ccagcctttc gagcccctgc agctgcacat ggacaaagcc  420
atcagcggcc tgcgcagcat caccaccctg ctgcgggcgc tgggagccca ggaagccatc  480
agcctcccag acgcggccag cgccgcccca ctccgaacca tcaccgccga caccttctgc  540
aaactcttcc gagtctacag caacttcctc cggggaaagc tgaagctgta cacgggggag  600
gcctgcagga gaggggacag atgactcgag ctagtgactg actaggatct ggttaccact  660
aaaccagcct caagaacacc cgaatggagt ctctaagcta cataatacca acttacactt  720
acaaaatgtt gtcccccaaa atgtagccat tcgtatctgc tcctaataaa aagaaagttt  780
cttcacattc tagaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaa                                                     913

SEQ ID NO: 182         moltype = DNA  length = 1011
FEATURE                Location/Qualifiers
misc_feature           1..1011
                       note = Description of Artificial Sequence:
                        Syntheticpolynucleotide
source                 1..1011
                       mol_type = other DNA
                       organism = synthetic construct
SEQUENCE: 182
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtccc gggcgcccca ccacgcctca  240
tctgcgacag ccgagtcctg gagaggtacc tcctggaggc caaggaggcc gagaacgtca  300
cgatgggctg cagcgaaagc tgcagcctga acgagaacat caccgtccca gacaccaaag  360
tgaacttcta cgcctggaag aggatggagg tcgggcagca ggccgtagaa gtctggcagg  420
gcctggccct gctcagcgaa gccgtcctgc ggggccaggc cgtgctggcc aacagcagcc  480
agcccttcga gcccctgcag ctgcacatgg acaaagccat cagcggcctg cgcagcatca  540
ccaccctgct gcgggcgctg ggagcccagg aagccatcag cctcccagac gcggccagcg  600
ccgccccact ccgaaccatc accgccgaca ccttctgcaa actcttccga gtctacagca  660
acttcctccg gggaaagctg aagctgtaca cgggggaggc ctgcaggaga ggggacagat  720
gactcgagct agtgactgac taggatctgg ttaccactaa accagcctca agaacacccg  780
aatggagtct ctaagctaca taataccaac ttacacttac aaaatgttgt cccccaaaat  840
gtagccattc gtatctgctc ctaataaaaa gaaagtttct tcacattcta gaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa a           1011

SEQ ID NO: 183         moltype = DNA  length = 1011
FEATURE                Location/Qualifiers
misc_feature           1..1011
                       note = Description of Artificial Sequence:
                        Syntheticpolynucleotide
source                 1..1011
                       mol_type = other DNA
                       organism = synthetic construct
SEQUENCE: 183
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgagcct gctgagcctc cccctgggcc tcccagtccc gggcgcccca ccacgcctca  240
tctgcgacag ccgagtcctg gagaggtacc tcctggaggc caaggaggcc gagaacgtca  300
cgatgggctg cagcgaaagc tgcagcctga acgagaacat caccgtccca gacaccaaag  360
tgaacttcta cgcctggaag aggatggagg tcgggcagca ggccgtagaa gtctggcagg  420
```

-continued

```
gcctggccct gctcagcgaa gccgtcctgc ggggccaggc cgtgctggcc aacagcagcc  480
agcccttcga gcccctgcag ctgcacatgg acaaagccat cagcggcctg cgcagcatca  540
ccaccctgct gcgggcgctg ggagcccagg aagccatcag cctcccagac gcggccagcg  600
ccgccccact ccgaaccatc accgccgaca ccttctgcaa actcttccga gtctacagca  660
acttcctccg gggaaagctg aagctgtaca cgggggaggc ctgcaggaga ggggacagat  720
gactcgagct agtgactgac taggatctgg ttaccactaa accagcctca agaacacccg  780
aatggagtct ctaagctaca taataccaac ttacacttac aaaatgttgt cccccaaaat  840
gtagccattc gtatctgctc ctaataaaaa gaaagtttct tcacattcta gaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa a           1011

SEQ ID NO: 184         moltype = DNA  length = 1011
FEATURE                Location/Qualifiers
misc_feature           1..1011
                       note = Description of Artificial Sequence:
                        Syntheticpolynucleotide
source                 1..1011
                       mol_type = other DNA
                       organism = synthetic construct
SEQUENCE: 184
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtccc gggcgcccca ccacgcctca  240
tctgcgacag ccgagtcctg gagaggtacc tcctggaggc caaggaggcc gagaacgtca  300
cgatgggctg cagcgaaagc tgcagcctga acgagaacat caccgtccca gacaccaaag  360
tgaacttcta cgcctggaag aggatggagg tcgggcagca ggccgtagaa gtctggcagg  420
gcctggccct gctcagcgaa gccgtcctgc ggggccaggc cgtgctggcc aacagcagcc  480
agcccttcga gcccctgcag ctgcacatgg acaaagccat cagcggcctg cgcagcatca  540
ccaccctgct gcgggcgctg ggagcccagg aagccatcag cctcccagac gcggccagcg  600
ccgccccact ccgaaccatc accgccgaca ctttctgcaa actcttccga gtctactcca  660
atttcctccg gggaaagctg aagctgtaca cgggggaggc ctgcaggaga ggggacagat  720
gactcgagct agtgactgac taggatctgg ttaccactaa accagcctca agaacacccg  780
aatggagtct ctaagctaca taataccaac ttacacttac aaaatgttgt cccccaaaat  840
gtagccattc gtatctgctc ctaataaaaa gaaagtttct tcacattcta gaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa a           1011

SEQ ID NO: 185         moltype = DNA  length = 1011
FEATURE                Location/Qualifiers
misc_feature           1..1011
                       note = Description of Artificial Sequence:
                        Syntheticpolynucleotide
source                 1..1011
                       mol_type = other DNA
                       organism = synthetic construct
SEQUENCE: 185
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cctctgggcc tcccagtccc gggcgcccca ccacgcctca  240
tctgcgacag ccgagtcctg gagaggtacc tcctggaggc caaggaggcc gagaacgtca  300
cgatgggctg cagcgaaagc tgcagcctga acgagaatat caccgtccca gacaccaaag  360
tgaacttcta cgcctggaag aggatggagg tcgggcagca ggccgtagaa gtctggcagg  420
gcctggccct gctcagcgaa gccgtcctgc ggggccaggc cgtgctggcc aacagcagcc  480
agcctttcga gcccctgcag ctgcacatgg acaaagccat cagcggcctg cgcagcatca  540
ccaccctgct gcgggcgctg ggagcccagg aagccatcag cctcccagac gcggccagcg  600
ccgccccact ccgaaccatc accgccgaca ccttctgcaa actcttccga gtctacagca  660
acttcctccg gggaaagctg aagctgtaca cgggggaggc ctgcaggaga ggggacagat  720
gactcgagct agtgactgac taggatctgg ttaccactaa accagcctca agaacacccg  780
aatggagtct ctaagctaca taataccaac ttacacttac aaaatgttgt cccccaaaat  840
gtagccattc gtatctgctc ctaataaaaa gaaagtttct tcacattcta gaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa a           1011

SEQ ID NO: 186         moltype = RNA  length = 1011
FEATURE                Location/Qualifiers
misc_feature           1..1011
                       note = Description of Artificial Sequence:
                        Syntheticpolynucleotide
source                 1..1011
                       mol_type = other RNA
                       organism = synthetic construct
SEQUENCE: 186
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtccc gggcgcccca ccacgcctca  240
tctgcgacag ccgagtcctg gagaggtacc tcctggaggc caaggaggcc gagaacgtca  300
```

-continued

```
cgatgggctg cagcgaaagc tgcagcctga acgagaacat caccgtccca gacaccaaag  360
tgaacttcta cgcctggaag aggatggagg tcgggcagca ggccgtagaa gtctggcagg  420
gcctggccct gctcagcgaa gccgtcctgc ggggccaggc cgtgctggcc aacagcagcc  480
agcccttcga gcccctgcag ctgcacatgg acaaagccat cagcggcctg cgcagcatca  540
ccaccctgct gcgggcgctg ggagcccagg aagccatcag cctcccagac gcggccagcg  600
ccgcccccact ccgaaccatc accgccgaca ccttctgcaa actcttccga gtctacagca  660
acttcctccg gggaaagctg aagctgtaca cgggggaggc ctgcaggaga ggggacagat  720
gactcgagct agtgactgac taggatctgg ttaccactaa accagcctca agaacacccg  780
aatggagtct ctaagctaca taataccaac ttacacttac aaaatgttgt cccccaaaat  840
gtagccattc gtatctgctc ctaataaaaa gaaagtttct tcacattcta gaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa a           1011

SEQ ID NO: 187         moltype = RNA  length = 1011
FEATURE                Location/Qualifiers
misc_feature           1..1011
                       note = Description of Artificial Sequence:
                        Syntheticpolynucleotide
source                 1..1011
                       mol_type = other RNA
                       organism = synthetic construct
SEQUENCE: 187
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg tcctgcctgg ctgtggcttc  180
tcctgagcct gctgagcctc cccctgggcc tcccagtccc gggcgcccca ccacgcctca  240
tctgcgacag ccgagtcctg gagaggtacc tcctggaggc caaggaggcc gagaacgtca  300
cgatgggctg cagcgaaagc tgcagcctga acgagaacat caccgtccca gacaccaaag  360
tgaacttcta cgcctggaag aggatggagg tcgggcagca ggccgtagaa gtctggcagg  420
gcctggccct gctcagcgaa gccgtcctgc ggggccaggc cgtgctggcc aacagcagcc  480
agcccttcga gcccctgcag ctgcacatgg acaaagccat cagcggcctg cgcagcatca  540
ccaccctgct gcgggcgctg ggagcccagg aagccatcag cctcccagac gcggccagcg  600
ccgcccccact ccgaaccatc accgccgaca ccttctgcaa actcttccga gtctacagca  660
acttcctccg gggaaagctg aagctgtaca cgggggaggc ctgcaggaga ggggacagat  720
gactcgagct agtgactgac taggatctgg ttaccactaa accagcctca agaacacccg  780
aatggagtct ctaagctaca taataccaac ttacacttac aaaatgttgt cccccaaaat  840
gtagccattc gtatctgctc ctaataaaaa gaaagtttct tcacattcta gaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa a           1011

SEQ ID NO: 188         moltype = RNA  length = 1011
FEATURE                Location/Qualifiers
misc_feature           1..1011
                       note = Description of Artificial Sequence:
                        Syntheticpolynucleotide
source                 1..1011
                       mol_type = other RNA
                       organism = synthetic construct
SEQUENCE: 188
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
tcctgagcct gctgagcctc cccctgggcc tcccagtccc gggcgcccca ccacgcctca  240
tctgcgacag ccgagtcctg gagaggtacc tcctggaggc caaggaggcc gagaacgtca  300
cgatgggctg cagcgaaagc tgcagcctga acgagaacat caccgtccca gacaccaaag  360
tgaacttcta cgcctggaag aggatggagg tcgggcagca ggccgtagaa gtctggcagg  420
gcctggccct gctcagcgaa gccgtcctgc ggggccaggc cgtgctggcc aacagcagcc  480
agcccttcga gcccctgcag ctgcacatgg acaaagccat cagcggcctg cgcagcatca  540
ccaccctgct gcgggcgctg ggagcccagg aagccatcag cctcccagac gcggccagcg  600
ccgcccccact ccgaaccatc accgccgaca ctttctgcaa actcttccga gtctactcca  660
atttcctccg gggaaagctg aagctgtaca cgggggaggc ctgcaggaga ggggacagat  720
gactcgagct agtgactgac taggatctgg ttaccactaa accagcctca agaacacccg  780
aatggagtct ctaagctaca taataccaac ttacacttac aaaatgttgt cccccaaaat  840
gtagccattc gtatctgctc ctaataaaaa gaaagtttct tcacattcta gaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa a           1011

SEQ ID NO: 189         moltype = RNA  length = 1011
FEATURE                Location/Qualifiers
misc_feature           1..1011
                       note = Description of Artificial Sequence:
                        Syntheticpolynucleotide
source                 1..1011
                       mol_type = other RNA
                       organism = synthetic construct
SEQUENCE: 189
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggggg tgcacgaatg ccccgcctgg ctgtggctgc  180
```

-continued

```
tcctgagcct gctgagcctc cctctgggcc tcccagtccc gggcgcccca ccacgcctca  240
tctgcgacag ccgagtcctg gagaggtacc tcctggaggc caaggaggcc gagaacgtca  300
cgatgggctg cagcgaaagc tgcagcctga acgagaatat caccgtccca gacaccaaag  360
tgaacttcta cgcctggaag aggatggagg tcgggcagca ggccgtagaa gtctggcagg  420
gcctggccct gctcagcgaa gccgtcctgc ggggccaggc cgtgctggcc aacagcagcc  480
agcctttcga gcccctgcag ctgcacatgg acaaagccat cagcggcctg cgcagcatca  540
ccaccctgct gcgggcgctg ggagcccagg aagccatcag cctcccagac gcggccagcg  600
ccgccccact ccgaaccatc accgccgaca ccttctgcaa actcttccga gtctacagca  660
acttcctccg gggaaagctg aagctgtaca cgggggaggc ctgcaggaga ggggacagat  720
gactcgagct agtgactgac taggatctgg ttaccactaa accagcctca agaacacccg  780
aatggagtct ctaagctaca taataccaac ttacacttac aaaatgttgt cccccaaaat  840
gtagccattc gtatctgctc ctaataaaaa gaaagtttct tcacattcta gaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa a           1011

SEQ ID NO: 190         moltype = DNA  length = 1653
FEATURE                Location/Qualifiers
misc_feature           1..1653
                       note = Description of Artificial Sequence:
                        Syntheticpolynucleotide
source                 1..1653
                       mol_type = other DNA
                       organism = synthetic construct
SEQUENCE: 190
atggaagacg ccaaaaacat aaagaaaggc ccggcgccat tctatccgct ggaagatgga  60
accgctggag agcaactgca taaggctatg aagagatacg ccctggttcc tggaacaatt  120
gcttttacag atgcacatat cgaggtggac atcacttacg ctgagtactt cgaaatgtcc  180
gttcggttgg cagaagctat gaaacgatat gggctgaata caaatcacag aatcgtcgta  240
tgcagtgaaa actctcttca attctttatg ccggtgttgg gcgcgttatt tatcggagtt  300
gcagttgcgc ccgcgaacga catttataat gaacgtgaat tgctcaacag tatgggcatt  360
tcgcagccta ccgtggtgtt cgtttccaaa aaggggttgc aaaaaatttt gaacgtgcaa  420
aaaaagctcc caatcatcca aaaaattatt atcatggatt ctaaaacgga ttaccaggga  480
tttcagtcga tgtacacgtt cgtcacatct catctacctc ccggttttaa tgaatacgat  540
tttgtgccag agtccttcga tagggacaag acaattgcac tgatcatgaa ctcctctgga  600
tctactggtc tgcctaaagg tgtcgctctg cctcatagaa ctgcctgcgt gagattctcg  660
catgccagag atcctatttt tggcaatcaa atcattccgg atactgcgat tttaagtgtt  720
gttccattcc atcacggttt tggaatgttt actacactcg gatatttgat atgtggattt  780
cgagtcgtct taatgtatag atttgaagaa gagctgtttc tgaggagcct tcaggattac  840
aagattcaaa gtgcgctgct ggtgccaacc ctattctcct tcttcgccaa aagcactctg  900
attgacaaat acgatttatc taatttacac gaaattgctt ctggtggcgc tcccctctct  960
aaggaagtcg gggaagcggt tgccaagagg ttccatctgc caggtatcag gcaaggatat  1020
gggctcactg agactacatc agctattctg attacacccg agggggatga taaaccgggc  1080
gcggtcggta aagttgttcc atttttgaa gcgaaggttg tggatctgga taccgggaaa  1140
acgctgggcg ttaatcaaag aggcgaactg tgtgtgagag gtcctatgat tatgtccggt  1200
tatgtaaaca atccggaagc gaccaacgcc ttgattgaca aggatggatg gctacattct  1260
ggagacatag cttactggga cgaagacgaa cacttcttca tcgttgaccg cctgaagtct  1320
ctgattaagt acaaaggcta tcaggtggct cccgctgaat tggaatccat cttgctccaa  1380
caccccaaca tcttcgacgc aggtgtcgca ggtcttcccg acgatgacgc cggtgaactt  1440
cccgccgccg ttgttgtttt ggagcacgga aagacgatga cggaaaaaga gatcgtggat  1500
tacgtcgcca gtcaagtaac aaccgcgaaa aagttgcgcg gaggagttgt gtttgtggac  1560
gaagtaccga aaggtcttac cggaaaactc gacgcaagaa aaatcagaga gatcctcata  1620
aaggccaaga agggcggaaa gatcgccgtg taa                                1653

SEQ ID NO: 191         moltype = DNA  length = 1653
FEATURE                Location/Qualifiers
misc_feature           1..1653
                       note = Description of Artificial Sequence:
                        Syntheticpolynucleotide
source                 1..1653
                       mol_type = other DNA
                       organism = synthetic construct
SEQUENCE: 191
atggaagacg ccaaaaacat aaagaaaggc ccggcgccat tctacccgct ggaagacgga  60
accgccggag agcaactgca caaggccatg aagagatacg ccctggtgcc cggaacaatc  120
gccttcacag acgcacacat cgaggtggac atcacctacg ccgagtactt cgaaatgagc  180
gtgcggctgg cagaagccat gaaacgatac gggctgaaca caaaccacag aatcgtcgta  240
tgcagcgaaa acagcctgca attcttcatg ccggtgctgg gcgcgctgtt catcggagtg  300
gcagtggcgc ccgcgaacga catctacaac gaacgggaac tgctcaacag catgggcatc  360
agccagccca ccgtggtgtt cgtgagcaaa aagggggctgc aaaaaatcct gaacgtgcaa  420
aaaaagctcc caatcatcca aaaaatcatc atcatggaca gcaaaacgga ctaccaggga  480
ttccagagca tgtacacgtt cgtcacaagc cacctacccc ccggcttcaa cgaatacgac  540
ttcgtgccag agagcttcga cagggacaag acaatcgcac tgatcatgaa cagcagcgga  600
agcaccggcc tgcccaaagg cgtcgccctg ccccacagaa ccgcctgcgt gagattcagc  660
cacgccagag accccatctt cggcaaccaa atcatcccgg acaccgcgat cctgagcgtg  720
gtgccattcc accacggctt cggaatgttc accacactcg gatacctgat atgcggattc  780
cgagtcgtcc tgatgtacag attcgaggag gagctgttcc tgaggagcct gcaggactac  840
aagatccaaa gcgcgctgct ggtgccaacc ctattcagct tcttcgccaa aagcaccctg  900
atcgacaaat acgacctgag caacctgcac gaaatcgcca gcggcggcgc cccccctcagc  960
aaggaagtcg gggaagcggt ggccaagagg ttccacctgc caggcatcag gcaaggatac  1020
```

-continued gggctcaccg agaccacaag cgccatcctg atcacacccg agggggacga caaaccgggc 1080
gcggtcggca aagtggtgcc attcttcgaa gcgaaggtgg tggacctgga caccgggaaa 1140
acgctgggcg tgaaccaaag aggcgaactg tgcgtgagag gccccatgat catgagcggc 1200
tacgtaaaca acccggaagc gaccaacgcc ctgatcgaca aggacggatg gctacacagc 1260
ggagacatag cctactggga cgaagacgaa cacttcttca tcgtggaccg cctgaagtcc 1320
ctgatcaagt acaaaggcta ccaggtggcc cccgccgaac tggaaagcat cctgctccaa 1380
caccccaaca tcttcgacgc aggcgtcgca ggcctgcccg acgacgacgc cggcgaactg 1440
cccgccgccg tggtggtgct ggagcacgga aagacgatga cggaaaaaga gatcgtggac 1500
tacgtcgcca gccaagtaac aaccgcgaaa aagctgcgcg gaggagtggt gttcgtggac 1560
gaagtaccga aaggcctgac cggaaaactc gacgcaagaa aaatcagaga gatcctcata 1620
aaggccaaga agggcggaaa gatcgccgtg taa 1653

SEQ ID NO: 192 moltype = DNA length = 1653
FEATURE Location/Qualifiers
misc_feature 1..1653
note = Description of Artificial Sequence:
Syntheticpolynucleotide
source 1..1653
mol_type = other DNA
organism = synthetic construct
SEQUENCE: 192
atggaagacg ccaaaaacat aaagaaaggc ccggcgccat tctatccgct ggaagatgga 60
accgctggag agcaactgca taaggctatg aagagatacg ccctggttcc tggaacaatt 120
gcttttacag atgcacatat cgaggtggac atcacttacg ctgagtactt cgaaatgtcc 180
gttcggttgg cagaagctat gaaacgatat gggctgaata caaatcacag aatcgtcgta 240
tgcagtgaaa actctcttca attctttatg ccggtgttgg gcgcgttatt tatcggagtg 300
gcagtggcgc ccgcgaacga catctacaac gaacgggaac tgctcaacag catgggcatc 360
agccagccca ccgtggtgtt cgtgagcaaa aaggggctgc aaaaaatcct gaacgtgcaa 420
aaaaagctcc caatcatcca aaaaatcatc atcatggaca gcaaaacgga ctaccaggga 480
ttccagagca tgtacacgtt cgtcacaagc cacctacccc ccggcttcaa cgaatacgac 540
ttcgtgccag agagcttcga cagggacaag acaatcgcac tgatcatgaa cagcagcgga 600
agcaccggcc tgcccaaagg cgtcgccctg ccccacagaa ccgcctgcgt gagattcagc 660
cacgccagag accccatctt cggcaaccaa atcatcccgg acaccgcgat cctgagcgtg 720
gtgccattcc accacggctt cggaatgttc accacactcg gatacctgat atgcggattc 780
cgagtcgtcc tgatgtacag attcgaggag gagctgttcc tgaggagcct gcaggactac 840
aagatccaaa gcgcgctgct ggtgccaacc ctattcagct tcttcgccaa aagcaccctg 900
atcgacaaat acgacctgag caacctgcac gaaatcgcca gcggcggcgc cccccctcagc 960
aaggaagtcg gggaagcggt ggccaagagg ttccacctgc caggcatcag gcaaggatac 1020
gggctcaccg agaccacaag cgccatcctg atcacacccg agggggacga caaaccgggc 1080
gcggtcggca aagtggtgcc attcttcgaa gcgaaggtgg tggacctgga caccgggaaa 1140
acgctgggcg tgaaccaaag aggcgaactg tgcgtgagag gccccatgat catgagcggc 1200
tacgtaaaca acccggaagc gaccaacgcc ctgatcgaca aggacggatg gctacacagc 1260
ggagacatag cctactggga cgaagacgaa cacttcttca tcgtggaccg cctgaagtcc 1320
ctgatcaagt acaaaggcta ccaggtggcc cccgccgaac tggaaagcat cctgctccaa 1380
caccccaaca tcttcgacgc aggcgtcgca ggcctgcccg acgacgacgc cggcgaactg 1440
cccgccgccg tggtggtgct ggagcacgga aagacgatga cggaaaaaga gatcgtggac 1500
tacgtcgcca gccaagtaac aaccgcgaaa aagctgcgcg gaggagtggt gttcgtggac 1560
gaagtaccga aaggcctgac cggaaaactc gacgcaagaa aaatcagaga gatcctcata 1620
aaggccaaga agggcggaaa gatcgccgtg taa 1653